(12) United States Patent
Vendeville et al.

(10) Patent No.: US 11,845,752 B2
(45) Date of Patent: *Dec. 19, 2023

(54) SUBSTITUTED IMIDAZO[1,5-A]PYRAZINES FOR THE TREATMENT OF HEPATITIS B

(71) Applicant: ALIGOS THERAPEUTICS, INC., South San Francisco, CA (US)

(72) Inventors: Sandrine Vendeville, Brussels (BE); Yannick Debing, Bilzen (BE); Antitsa Dimitrova Stoycheva, Half Moon Bay, CA (US); Pierre Jean-Marie Bernard Raboisson, Wavre (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/450,808

(22) Filed: Oct. 13, 2021

(65) Prior Publication Data

US 2022/0119395 A1 Apr. 21, 2022

Related U.S. Application Data

(60) Provisional application No. 63/092,309, filed on Oct. 15, 2020.

(51) Int. Cl.
| | | |
|---|---|---|
| *A61K 31/4985* | (2006.01) |
| *C07D 487/04* | (2006.01) |
| *A61K 45/06* | (2006.01) |
| *C07D 519/00* | (2006.01) |

(52) U.S. Cl.
CPC ............ *C07D 487/04* (2013.01); *A61K 45/06* (2013.01); *C07D 519/00* (2013.01)

(58) Field of Classification Search
CPC .......................... A61K 31/4985; C07D 487/04
USPC ........................................... 514/249; 544/350
See application file for complete search history.

(56) References Cited

U.S. PATENT DOCUMENTS

| | | |
|---|---|---|
| 2020/0147124 A1 | 5/2020 | Beigelman et al. |
| 2020/0157111 A1 | 5/2020 | Li et al. |
| 2020/0361947 A1 | 11/2020 | Vendeville et al. |
| 2022/0119395 A1 | 4/2022 | Vendeville et al. |

FOREIGN PATENT DOCUMENTS

| | | |
|---|---|---|
| WO | WO 2008/017932 | 2/2008 |
| WO | WO 2016/113273 | 7/2016 |
| WO | WO 2016/168633 | 10/2016 |
| WO | WO 2017/011552 | 1/2017 |
| WO | WO 2019/076310 | 10/2018 |
| WO | WO 2018/219356 | 12/2018 |
| WO | WO 2019/020070 | 1/2019 |
| WO | WO 2019/076310 | 4/2019 |
| WO | WO 2020/125729 | 6/2020 |
| WO | WO 2020/214728 | 10/2020 |
| WO | WO 2020/221816 | 11/2020 |

OTHER PUBLICATIONS

International Search Report and Written Opinion dated Nov. 19, 2021 for PCT Application No. PCT/US2021/054848, filed Oct. 13, 2021.
CAS Registry No. 1353500-80-7; STN Entry Date Jan. 18, 2012.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5):942-944.
Liang, "Hepatitis B: The Virus and Disease" Hepatology (2009) 49(S5):S13-S21.
CAS Registry No. 2386336-43-0; STN Entry Date Dec. 1, 2019.
International Preliminary Report on Patentability dated Apr. 13, 2013 for PCT Application No. PCT/US2021/054848, filed Oct. 13, 2021.

*Primary Examiner* — Douglas M Willis
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

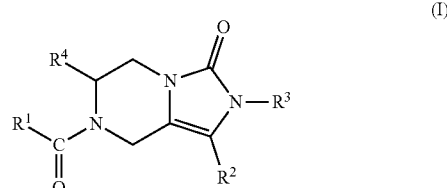

(I)

21 Claims, 1 Drawing Sheet
Specification includes a Sequence Listing.

The plate map of compound treatment

|   | 1 | 2 | 3 | 4 | 5 | 6 | 7 | 8 | 9 | 10 | 11 | 12 |
|---|---|---|---|---|---|---|---|---|---|---|---|---|
| A |   | High dose | | 4-fold dilution, 8 dilution points, duplicate | | | | | Low dose | | | |
| B | compound 1 | | | | | | | | | ETV(1µM) | 0.5%DMSO control | Blank |
| C | | | | | | | | | | | | |
| D | compound 2 | | | | | | | | | | | |
| E | | | | | | | | | | | | |
| F | compound 3 | | | | | | | | | | | |
| G | | | | | | | | | | | | |
| H |   | High dose | | 4-fold dilution, 8 dilution points, duplicate | | | | | Low dose | | | |

SUBSTITUTED IMIDAZO[1,5-A]PYRAZINES FOR THE TREATMENT OF HEPATITIS B

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 63/092,309, filed Oct. 15, 2020.

REFERENCE TO SEQUENCE LISTING

The present application is filed with a Sequence Listing in Electronic format. The Sequence Listing is provided as a file entitled ALIG056.txt, created Oct. 13, 2021, which is approximately 4 kb in size. The information in the electronic format of the sequence listing is incorporated herein by reference in its entirety.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

BRIEF DESCRIPTION OF THE DRAWINGS

FIG. 1 shows the plate map of compound treatment for the HBV-DNA Antiviral Assay described herein.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroalkyl, hydroxy, alkoxyalkyl, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH (an unsubstituted $C_{1-4}$ alkyl), —O-(an unsubstituted $C_{1-4}$ alkyl)-N(an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group

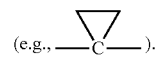

(e.g., ).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoro-2-ethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a $C_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C(=O) group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$_A$" in which R$_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$_A$, wherein R$_A$ can be an unsubstituted C$_{1-6}$ alkyl or an unsubstituted or a substituted benzyl.

A "di-substituted amine" refers to a "—NR$_A$R$_B$" in which R$_A$ and R$_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

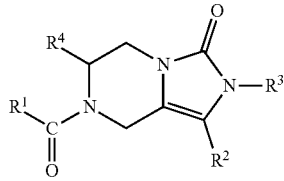

(I)

wherein: $R^1$ can be 3,4-disubstituted phenyl or trisubstituted phenyl, wherein each substitution group on the phenyl can be independently selected from fluoro, chloro, bromo, —$CHF_2$, —$CF_3$, —$CH_3$, —CN and —C≡CH; $R^2$ can be —C(=O)$R^5$; $R^3$ can be selected from a substituted phenyl, a substituted monocyclic heteroaryl and a substituted bicyclic heteroaryl; $R^4$ can be selected from —$CHF_2$, —$CH_3$, -cyclopropyl, an unsubstituted $C_{1-4}$ hydroxyalkyl, an unsubstituted or substituted benzyl-O—$CH_2$— and an unsubstituted or substituted monocyclic heterocyclyl-$CH_2$—; $R^5$ can be

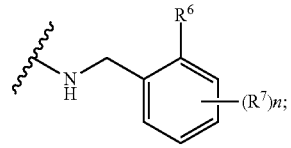

$R^6$ can be an unsubstituted or a substituted 5- or 6-membered monocyclic heteroaryl comprising 1, 2 or 3 nitrogens, and optionally 1 or 2 heteroatoms selected from oxygen and sulfur, and when $R^6$ is substituted, $R^6$ can be substituted with one or more substituents selected from halogen, an unsubstituted $C_{1-4}$ alkyl, an unsubstituted $C_{1-4}$ haloalkyl, an unsubstituted —O—$C_{1-4}$ alkyl, amino and mono- and mono-$C_{1-6}$ alkyl amine; $R^7$ can be selected from halogen, an unsubstituted $C_{1-4}$ alkyl and an unsubstituted —O—$C_{1-4}$ alkyl; and n can be 0 or 1; or $R^6$ can be halogen; n can be 1; and $R^7$ can be halogen.

Various substituted phenyl groups can be present for $R^1$. In some embodiments, $R^1$ can be 3,4-disubstituted phenyl. In other embodiments, $R^1$ can be a trisubstituted phenyl, for example, a 3,4,5-trisubstituted phenyl. The substituted phenyl can be substituted by moieties independently selected from fluoro, chloro, bromo, —$CHF_2$, —$CF_3$, —$CH_3$, —CN and —C≡CH. The moieties on the phenyl can be the same or different moieties. In some embodiments, at least one of moieties on the phenyl of $R^1$ can be bromo. In some embodiments, at least one of moieties on the phenyl of $R^1$ can be chloro. When $R^1$ is a 3,4-disubstituted phenyl, in some embodiments, one moiety on the phenyl of $R^1$ can be bromo and the other moiety on the phenyl of $R^1$ can be chloro or —$CF_3$. In some embodiments when $R^1$ is a 3,4-disubstituted phenyl, one moiety on the phenyl of $R^1$ can be bromo and the other moiety on the phenyl of $R^1$ can be fluoro, chloro, —$CHF_2$, —$CF_3$, —$CH_3$, —CN and —C≡CH. In other embodiments when $R^1$ is a 3,4-disubstituted phenyl, one moiety on the phenyl of $R^1$ can be chloro and the other moiety on the phenyl of $R^1$ can be fluoro, chloro, —$CHF_2$, —$CF_3$, —$CH_3$, —CN and —C≡CH. When $R^1$ is a trisubstituted phenyl, in some embodiments, at least moiety on the phenyl can be bromo and another moiety can be chloro. In some embodiments when $R^1$ is a trisubstituted phenyl, one moiety can be bromo, a second moiety can be chloro and a third moiety can be selected from fluoro, —$CHF_2$, —$CF_3$, —$CH_3$, —CN and —C≡CH. In other embodiments when $R^1$ is a trisubstituted phenyl, one moiety can be bromo, a second moiety can be fluoro, and a third moiety can be selected from fluoro, —$CHF_2$, —$CF_3$, —$CH_3$, —CN and —C≡CH. Examples of suitable 3,4-disubstituted phenyl for $R^1$ include the following:

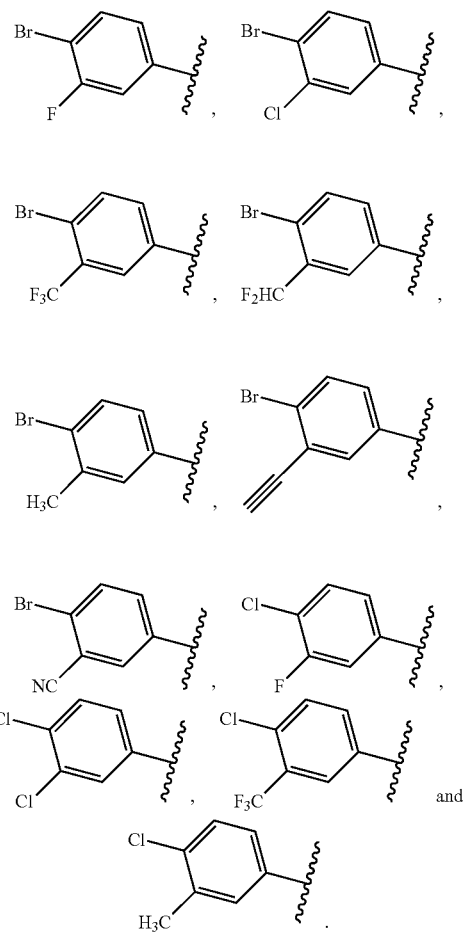

Examples of suitable trisubstituted phenyl for $R^1$ include the following:

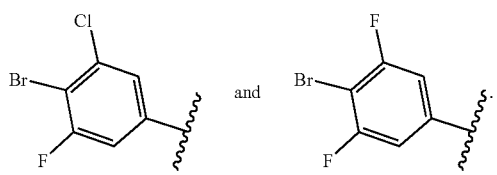 [SMILES: *c1cc(F)c(Br)c(Cl)c1 ; *c1cc(F)c(Br)c(F)c1]

As recited herein, $R^2$ with $R^5$ can be an amido group. In some embodiments, $R^2$ can be —C(═O)$R^5$, wherein $R^5$ can be

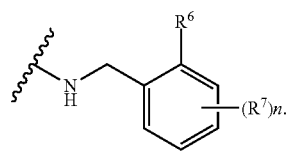

The phenyl ring of $R^5$ can be substituted $R^6$, where $R^6$ can be an unsubstituted or a substituted 5- or 6-membered monocyclic heteroaryl comprising 1, 2 or 3 nitrogens, and optionally 1 or 2 heteroatoms selected from the group consisting of oxygen and sulfur. The 5- or 6-membered monocyclic heteroaryl comprising 1, 2 or 3 nitrogens can include 1 or 2 other heteroatoms, such as O (oxygen) and S (sulfur). In some embodiments, the unsubstituted or a substituted 5- or 6-membered monocyclic heteroaryl can include 1 nitrogen. In other embodiments, the unsubstituted or a substituted 5- or 6-membered monocyclic heteroaryl can include 2 nitrogens. In still other embodiments, the unsubstituted or a substituted 5- or 6-membered monocyclic heteroaryl can include 3 nitrogens. In yet still other embodiments, the unsubstituted or a substituted 5- or 6-membered monocyclic heteroaryl can include 1 nitrogen and 1 oxygen. In some embodiments, the unsubstituted or a substituted 5- or 6-membered monocyclic heteroaryl can include 2 nitrogens and 1 oxygen. Exemplary 5- and 6-membered monocyclic heteroaryls include, but are not limited to, an unsubstituted or a substituted pyrazole, an unsubstituted or a substituted imidazole, an unsubstituted or a substituted thiazole, an unsubstituted or a substituted oxazole, an unsubstituted or a substituted 1,3,4-oxadiazole, an unsubstituted or a substituted 1,3,4-thiadiazole an unsubstituted or a substituted pyridine, an unsubstituted or a substituted pyrimidine, an unsubstituted or a substituted pyrazine, an unsubstituted or a substituted pyridazine, an unsubstituted or a substituted 1,2,4-triazine and an unsubstituted or a substituted 1,2,4-triazole.

The phenyl ring of $R^5$ can include another substitution, $R^7$. For example, when n is 1, the phenyl ring of $R^5$ can be further substituted by a halogen, an unsubstituted $C_{1-4}$ alkyl or an unsubstituted —O—$C_{1-4}$ alkyl. Examples of halogens include fluoro, chloro, bromo and iodo. In some embodiments, $R^7$ can be fluoro. Unsubstituted $C_{1-4}$ alkyls include methyl, ethyl, n-propyl, isopropyl, n-butyl, iso-butyl, sec-butyl and tert-butyl. Exemplary unsubstituted —O—$C_{1-4}$ alkyl include methoxy, ethoxy, n-propoxy, isopropoxy, n-butoxy, iso-butoxy, sec-butoxy and tert-butoxy. In some embodiments, $R^7$ can be methyl or methoxy. When n is 0, the phenyl ring of $R^5$ can be substituted with $R^6$ and not be further substituted.

The position of $R^7$ can vary. For example, $R^7$ can be positioned as shown below:

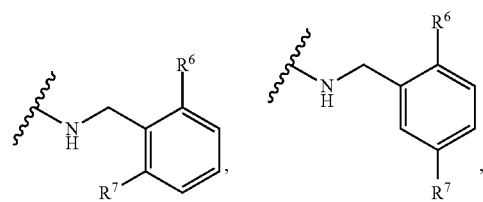

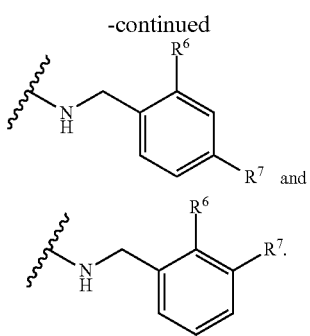

In some embodiments, $R^5$ can be selected from

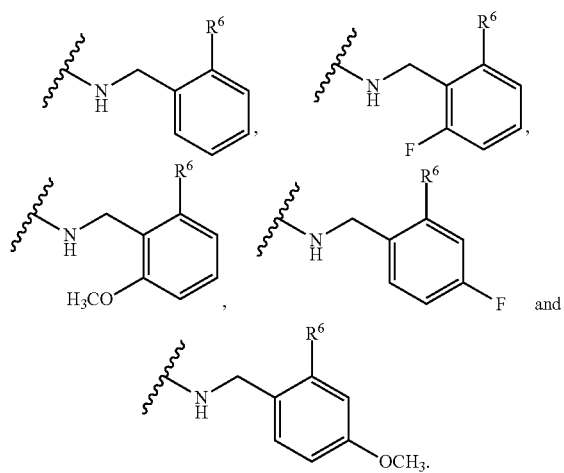

In some embodiments, $R^5$ can be selected from

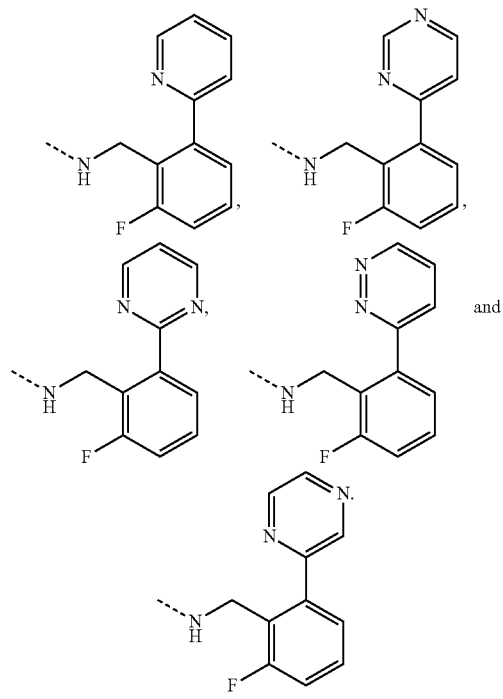

As provided herein, $R^6$ can be unsubstituted or substituted. When $R^6$ is substituted, $R^6$ can be substituted with one or more substituents selected from halogen, an unsubstituted $C_{1-4}$ alkyl, an unsubstituted $C_{1-4}$ haloalkyl, an unsubstituted —O—$C_{1-4}$ alkyl, amino and mono-$C_{1-6}$ alkyl amine. Examples of halogen, unsubstituted $C_{1-4}$ alkyls and unsubstituted —O—$C_{1-4}$ alkyls are provided herein. In some embodiments, $R^6$ can be substituted with one or more substituents selected from fluoro, chloro, bromo, iodo, methyl, ethyl, n-propyl, isopropyl, n-butyl, iso-butyl, sec-butyl, tert-butyl, —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$, —$CH_2CH_2CH_2Cl$, methoxy, ethoxy, n-propoxy, isopropoxy, n-butoxy, iso-butoxy, sec-butoxy, tert-butoxy, mono-methylamine, mono-ethylamine, mono-n-propylamine, mono-iso-propylamine, mono-n-butylamine, mono-sec-butylamine, mono-iso-butylamine, mono-pentylamine and mono-hexylamine, wherein the pentyl and hexyl of the mono-pentylamine and mono-hexylamine, respectively, can be straight-chained or branched). When $R^6$ is substituted, $R^6$ can be mono-substituted, di-substituted or tri-substituted.

Examples of $R^5$ include the following:

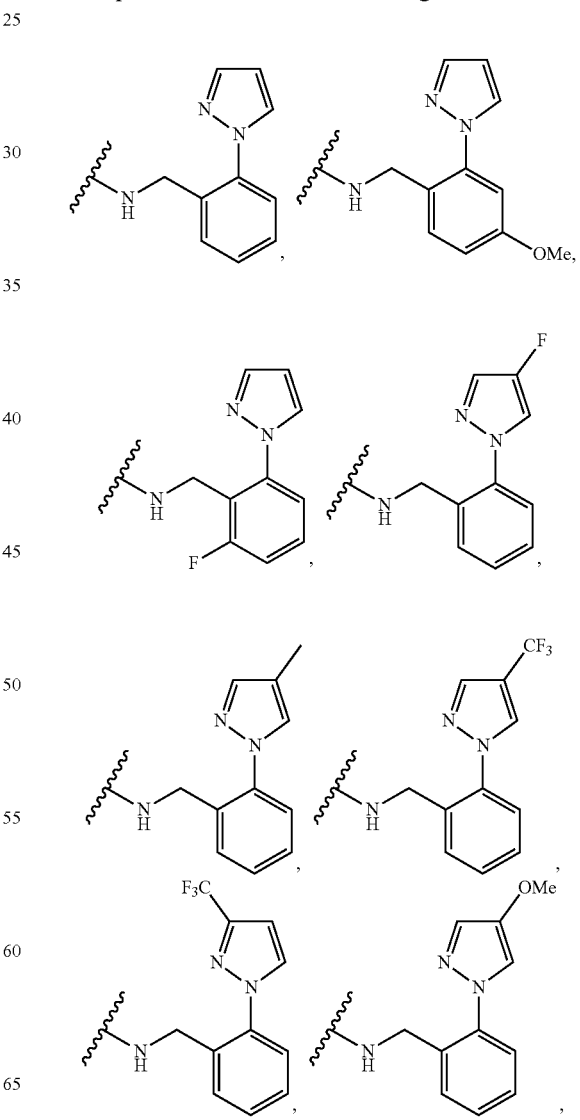

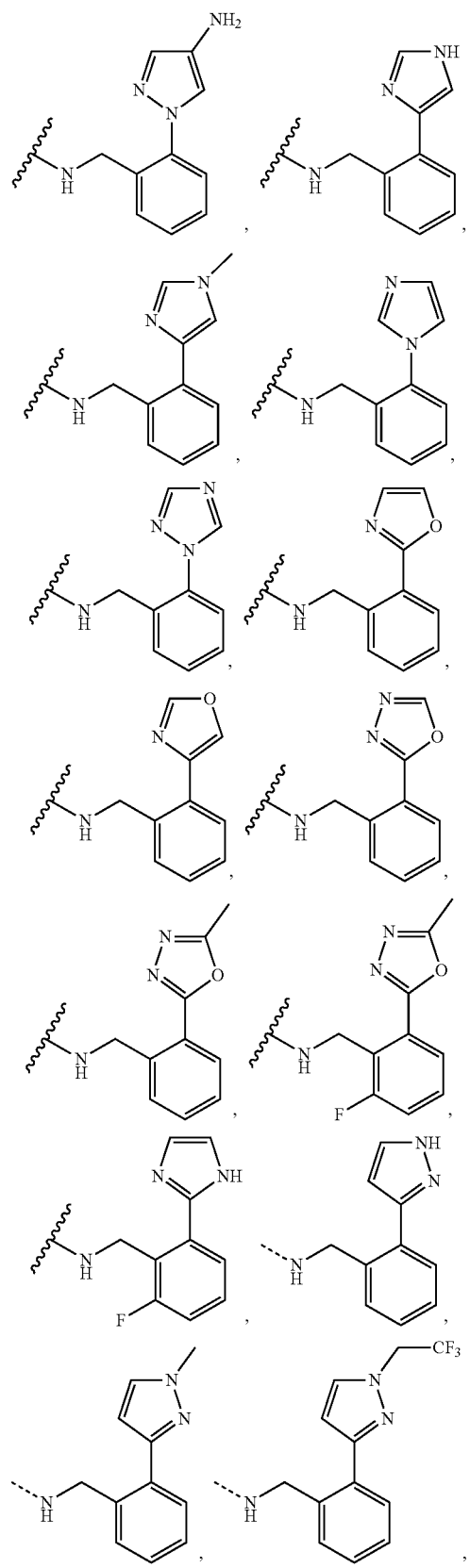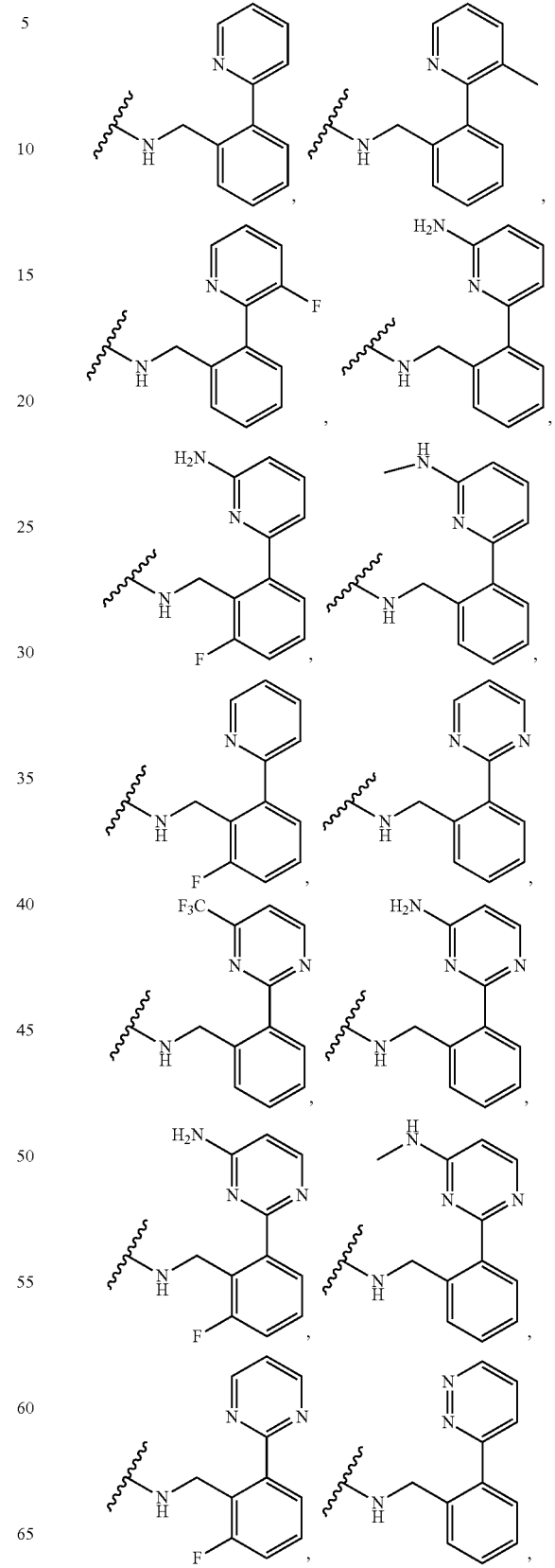

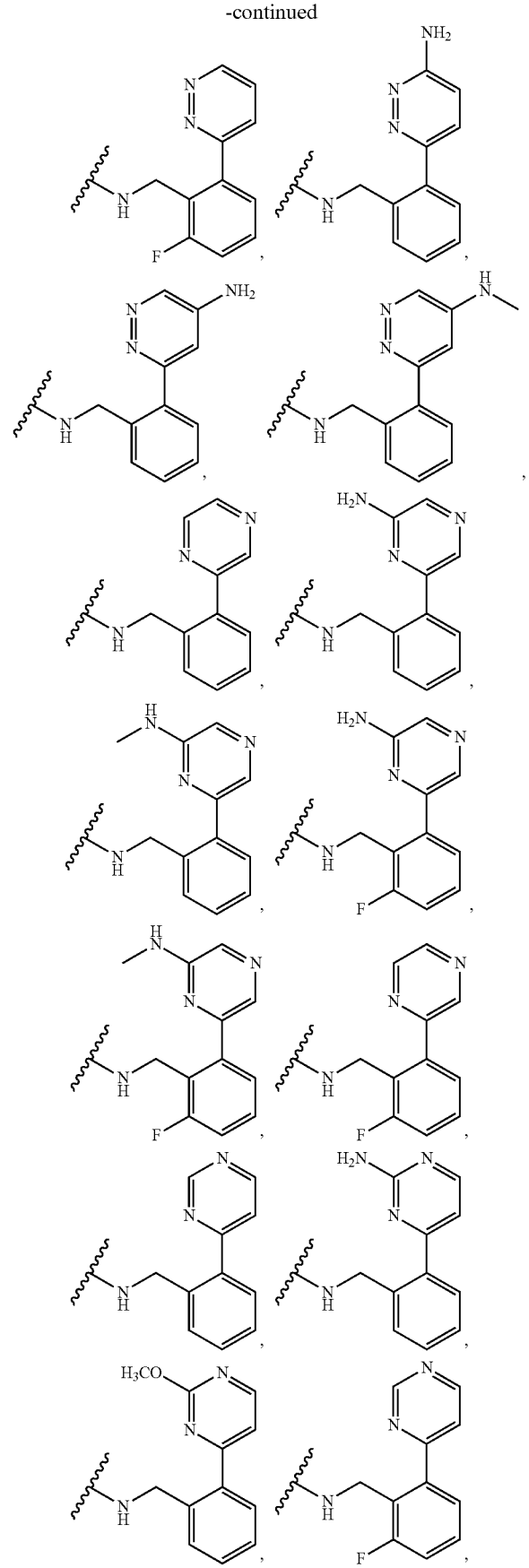
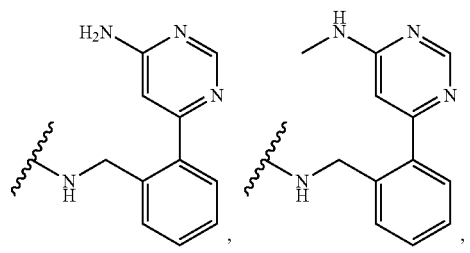
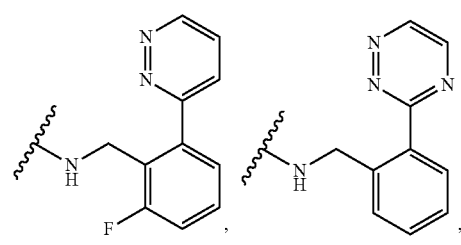
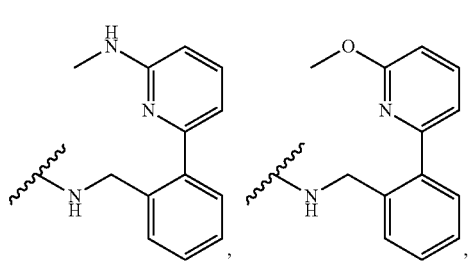
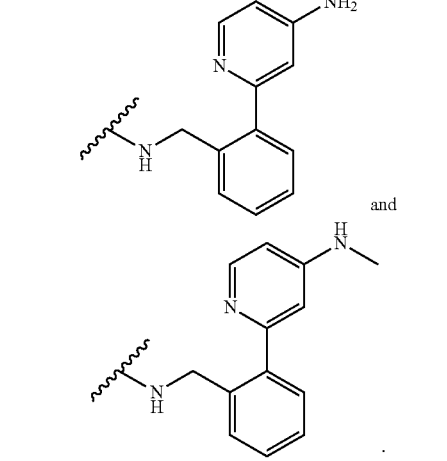
In some embodiments, when $R^6$ is a 5-membered monocyclic heteroaryl, $R^5$ can be selected from
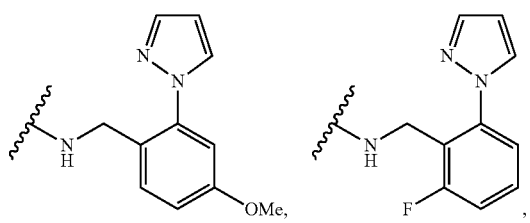

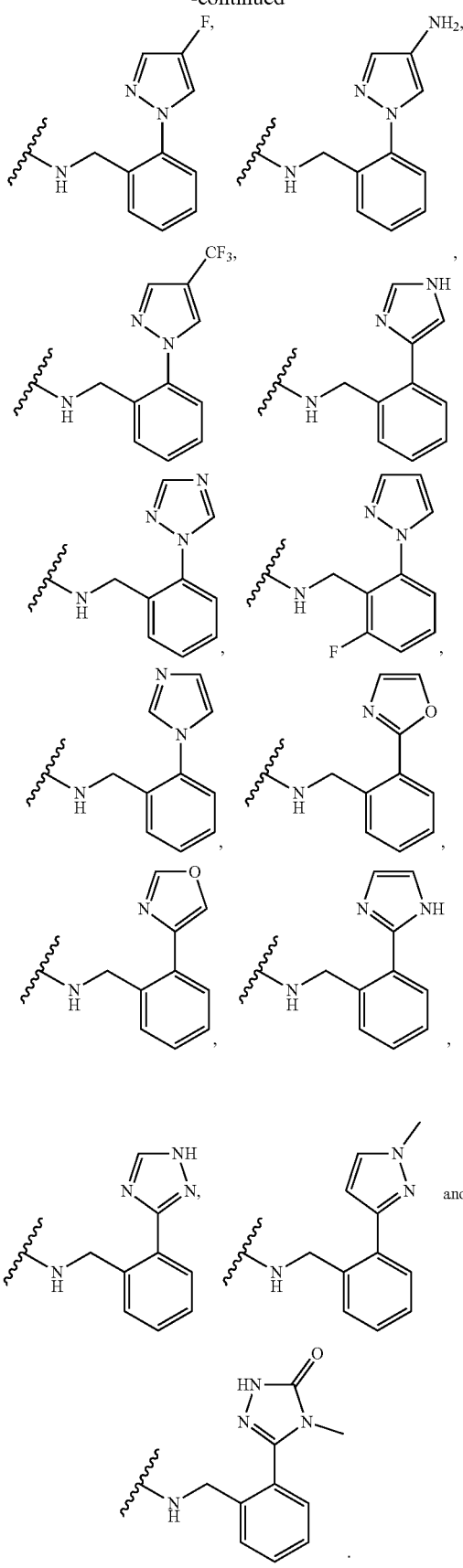
In some embodiments, when $R^6$ is a 6-membered monocyclic heteroaryl, $R^5$ can be selected from
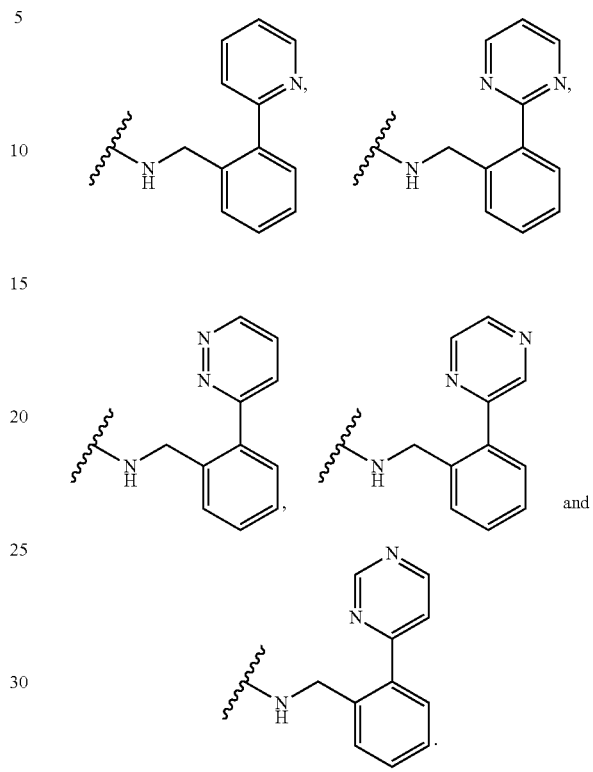
As provided herein, $R^6$ can be substituted with an amino. Exemplary $R^5$ groups with an amino-substituted $R^6$ include the following:
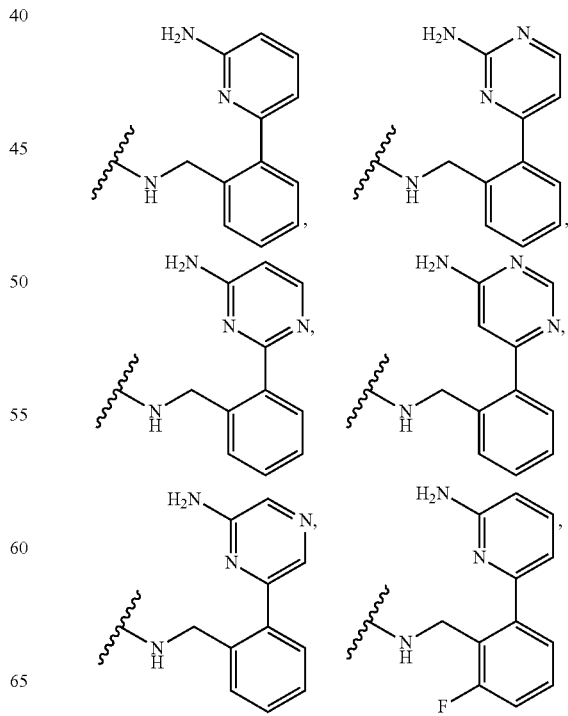

-continued

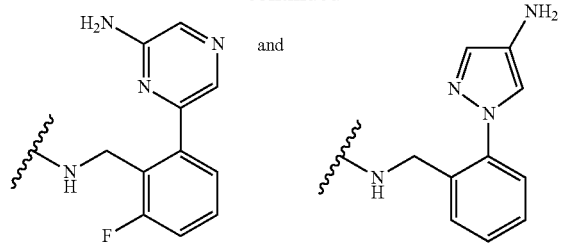

In some embodiments, $R^6$ can be halogen; n can be 1; and $R^7$ can be halogen. For example, $R^6$ can be F or Cl; n can be 1; and $R^7$ can be F or Cl. As described herein, the position of $R^7$ can vary. In some embodiments, $R^5$ can be

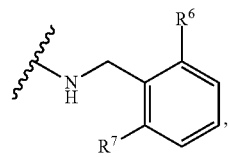

such as

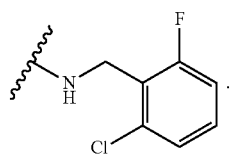 [SMILES: *NCc1c(F)cccc1Cl]

Various groups can be attached to the nitrogen of the 1,3-dihydro-2H-imidazol-2-one of Formula (I), $R^3$. The $R^3$ groups can include a phenyl substituted by an unsubstituted $C_{1-4}$ alkoxy (such as an unsubstituted —O—$C_{1-4}$ alkyl and an unsubstituted —O—$C_{3-6}$ cycloalkyl, including methoxy, ethoxy, n-propoxy, isopropoxy, n-butoxy, iso-butoxy, sec-butoxy, tert-butoxy, cyclopropoxy, cyclobutoxy, cyclopentoxy and/or cyclohexoxy), an unsubstituted $C_{1-4}$ haloalkoxy (for example, —OCHF$_2$, —OCF$_3$, —OCH$_2$F, —OCH$_2$CHF$_2$, —OCH$_2$CF$_3$ and/or —OCH$_2$CH$_2$F), hydroxy-substituted $C_{1-4}$ alkoxy (such as

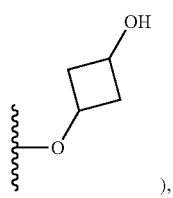 [SMILES: *OC1CC(O)C1]

a mono(an unsubstituted $C_{1-4}$ alkyl)amine-substituted $C_{1-4}$ alkoxy, (for example,

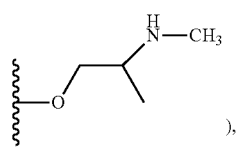 [SMILES: *OCC(C)NC]

a di(an unsubstituted $C_{1-4}$ alkyl)amine-substituted $C_{1-4}$ alkoxy (for example,

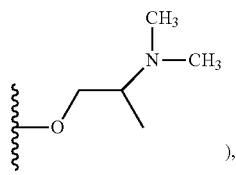 [SMILES: *OCC(C)N(C)C]

a monocyclic heterocyclyl-substituted $C_{1-4}$ alkoxy (such as

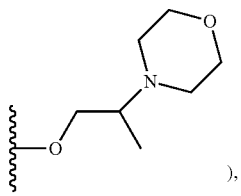 [SMILES: *OCC(C)N1CCOCC1]

hydroxy- and fluoro-substituted $C_{1-4}$ alkoxy (for example,

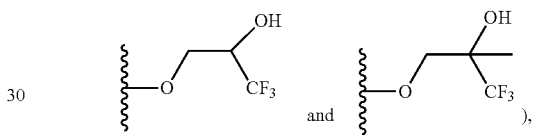

—O—CH$_2$—C(=O)-(an unsubstituted $C_{1-4}$ alkyl) (such as —O—CH$_2$—C(=O)—CH$_2$CH$_3$), an unsubstituted or a substituted monocyclic heteroaryl, an unsubstituted or a substituted monocyclic heterocyclyl and/or an unsubstituted or a substituted bicyclic heterocyclyl. In some embodiments, $R^3$ can be a phenyl that is mono-substituted, for example, a mono-substituted phenyl where the substitution is at the para-position. In some embodiments, $R^3$ can be

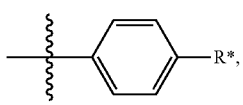

wherein R* can be a substitution described herein (such as in this paragraph and those paragraphs below).

Other examples of $R^3$ groups can include a phenyl substituted by an unsubstituted monocyclic heterocyclyl (such as an unsubstituted 4-, 5- or 6-membered heterocyclyl), a substituted monocyclic heterocyclyl (such as a substituted 4-, 5- or 6-membered heterocyclyl), an unsubstituted fused-bicyclic heterocyclyl, a substituted fused-bicyclic heterocyclyl, an unsubstituted spiro-bicyclic heterocyclyl or a substituted spiro-bicyclic heterocyclyl. In some embodiments, a heterocyclyl described herein substituted on $R^3$ can include 1, 2 or 3 heteroatoms independent selected from nitrogen (N), oxygen (O) and sulfur (S). Exemplary heterocyclyls include azetidine, pyrrolidine, morpholine, piperidine, piperazine, 2-azaspiro[3.3]heptane, 1,6-diazaspiro[3.3]heptane, 2,6-diazaspiro[3.3]heptane, 2-oxa-6-azaspiro[3.3]heptane, 2-oxa-5-azabicyclo[2.2.1]heptane, 4-oxa-7-azaspiro[2.5]octane, 2-oxa-5-azabicyclo[2.2.2]octane, 8-oxa-3-azabicyclo[3.2.1]octane, 2,6-diazaspiro[3.4]octane, 2,5-diazabicyclo

[2.2.2]octane, 3,8-diazabicyclo[3.2.1]octane and 2,7-diazaspiro[3.5]nonane. The heterocyclyls described herein substituted on a phenyl of $R^3$ can be unsubstituted or substituted. When substituted, the heterocyclyl attached to the phenyl of $R^3$ can be substituted with one or more moieties (such as 1, 2 or 3 moieties) selected from halogen (for example, F and Cl), hydroxy, an unsubstituted $C_{1-4}$ alkyl and an unsubstituted $C_{1-4}$ haloalkyl (—$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$).

Other cyclic groups that can be substituted on $R^3$ when $R^3$ is a phenyl include an unsubstituted monocyclic heteroaryl (such as an unsubstituted 4-, 5- or 6-membered heteroaryl) and a substituted monocyclic heteroaryl (such as a substituted 4-, 5- or 6-membered heterocyclyl). The monocyclic and bicyclic heteroaryl that can be substituted on a phenyl of $R^3$ can include 1, 2 or 3 heteroatoms independent selected from nitrogen (N), oxygen (O) and sulfur (S). When $R^3$ is substituted with a heteroaryl, the heteroaryl can be substituted with one or more moieties (such as 1, 2 or 3 moieties) selected from halogen (for example, F and Cl), hydroxy, an unsubstituted $C_{1-4}$ alkyl and an unsubstituted $C_{1-4}$ haloalkyl (such as those described herein). An example of a suitable unsubstituted or substituted heteroaryl that can be substituted on $R^3$ when $R^3$ is phenyl is pyrazole.

The $R^3$ group can be an unsubstituted or a substituted 5- to 6-membered monocyclic heteroaryl or an unsubstituted or a substituted 9-membered bicyclic heteroaryl, for example, an unsubstituted or a substituted 5- to 6-membered bicyclic heteroaryl or an unsubstituted or a substituted 9-membered bicyclic heteroaryl, wherein the monocyclic and/or bicyclic heteroaryl can include 1, 2 or more than 2 nitrogens. Additional examples of $R^3$ groups include pyridine, indole, indazole, benzo[d]oxazole, benzo[d]isoxazole and benzo[d][1,2,3]triazole, wherein each of the aforementioned groups can be unsubstituted or substituted.

When $R^3$ is a substituted phenyl, a substituted monocyclic heteroaryl or a substituted bicyclic heteroaryl, such as those described herein, $R^3$ can be substituted with one or more of the following moieties: halogen (for example, F or Cl), hydroxy, amino, —NH (an unsubstituted $C_{1-4}$ alkyl), —N(an unsubstituted $C_{1-4}$ alkyl)$_2$, an unsubstituted $C_{1-4}$ alkyl (such as methyl, ethyl, n-propyl, isopropyl, n-butyl, iso-butyl, sec-butyl and/or tert-butyl), an unsubstituted $C_{1-4}$ alkoxy (for example, methoxy, ethoxy, n-propoxy, isopropoxy, n-butoxy, iso-butoxy, sec-butoxy, tert-butoxy, cyclopropoxy, cyclobutoxy, cyclopentoxy and/or cyclohexoxy), an unsubstituted $C_{1-4}$ haloalkyl (for example, —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$, —$CH_2CH_2CH_2Cl$), an unsubstituted $C_{1-4}$ haloalkoxy (such as —$OCHF_2$, —$OCF_3$, —$OCH_2F$, —$OCH_2CHF_2$, —$OCH_2CF_3$ and/or —$OCH_2CH_2F$), hydroxy-substituted $C_{1-4}$ alkoxy, an unsubstituted $C_{1-4}$ hydroxyalkyl, $C_{1-4}$ alkyl substituted by hydroxy and halogen (such as F), $C_{1-4}$ alkoxy substituted by hydroxy and halogen (such as F), $C_{1-4}$ alkoxy substituted by hydroxy and —$NR^{Z1}R^{Z2}$, wherein $R^{Z1}$ and $R^{Z2}$ are independently H or an unsubstituted $C_{1-4}$ alkyl or wherein $R^{Z1}$ and $R^{Z2}$ along with the nitrogen to which $R^{Z1}$ and $R^{Z2}$ are attached are taken together to form a monocyclic heterocyclyl, —O—$CH_2$—C(=O)-(an unsubstituted $C_{1-4}$ alkyl) (such as —O—$CH_2$—C(=O)—$CH_2CH_3$), an unsubstituted monocyclic heterocyclyl, a substituted monocyclic heterocyclyl, an unsubstituted bicyclic heterocyclyl, a substituted bicyclic heterocyclyl, an unsubstituted monocyclic heteroaryl, a substituted monocyclic heteroaryl, an unsubstituted bicyclic heteroaryl and a substituted bicyclic heteroaryl.

Examples of $R^3$ groups include:

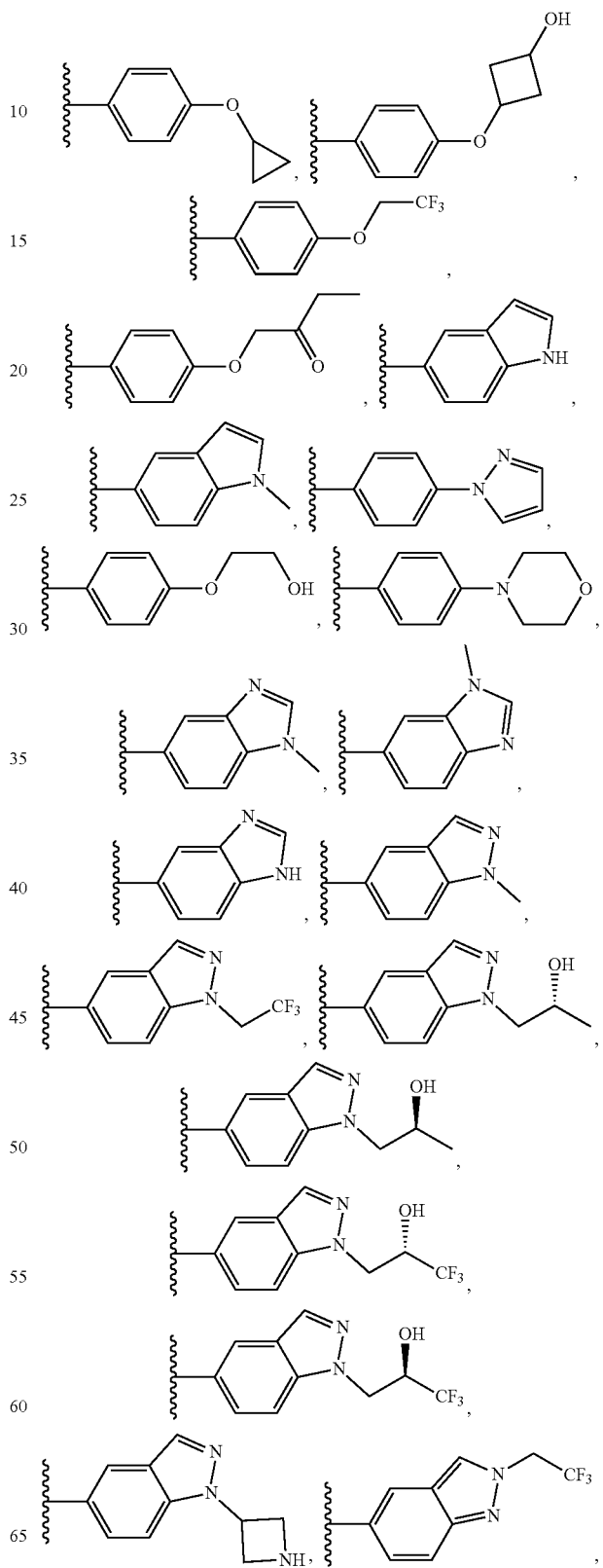

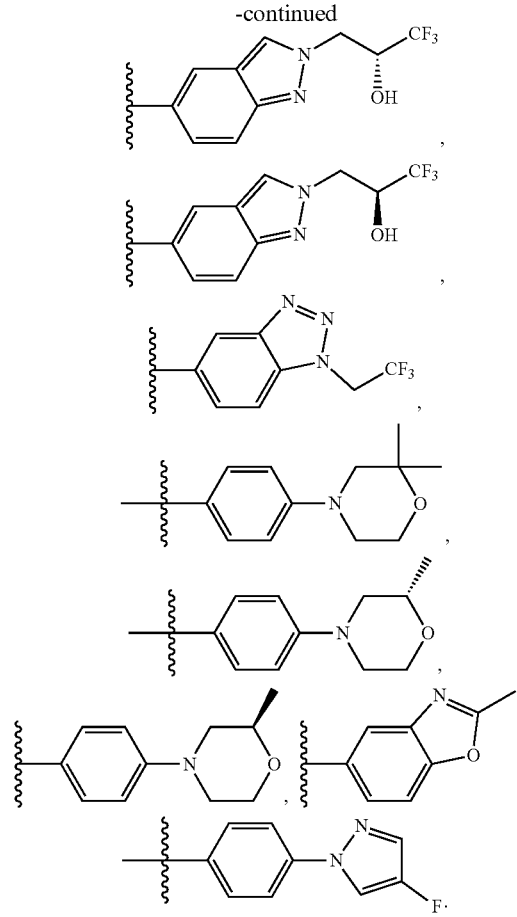
Additional examples of R³ groups include the following:
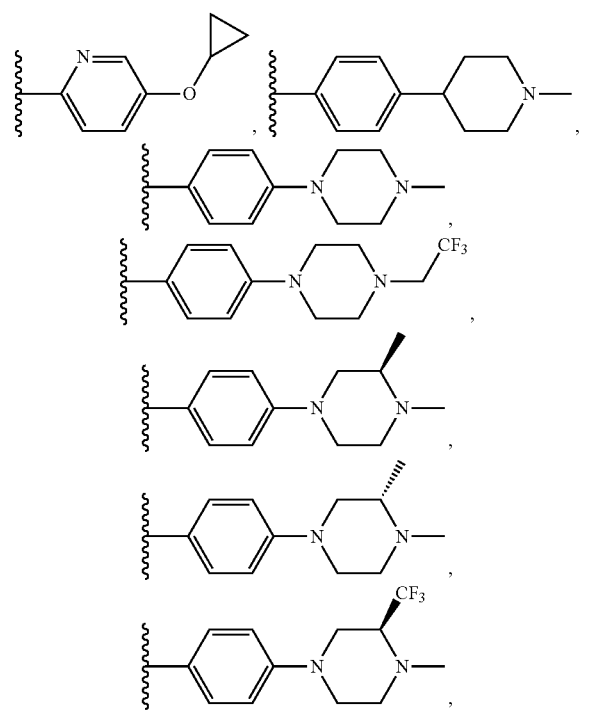
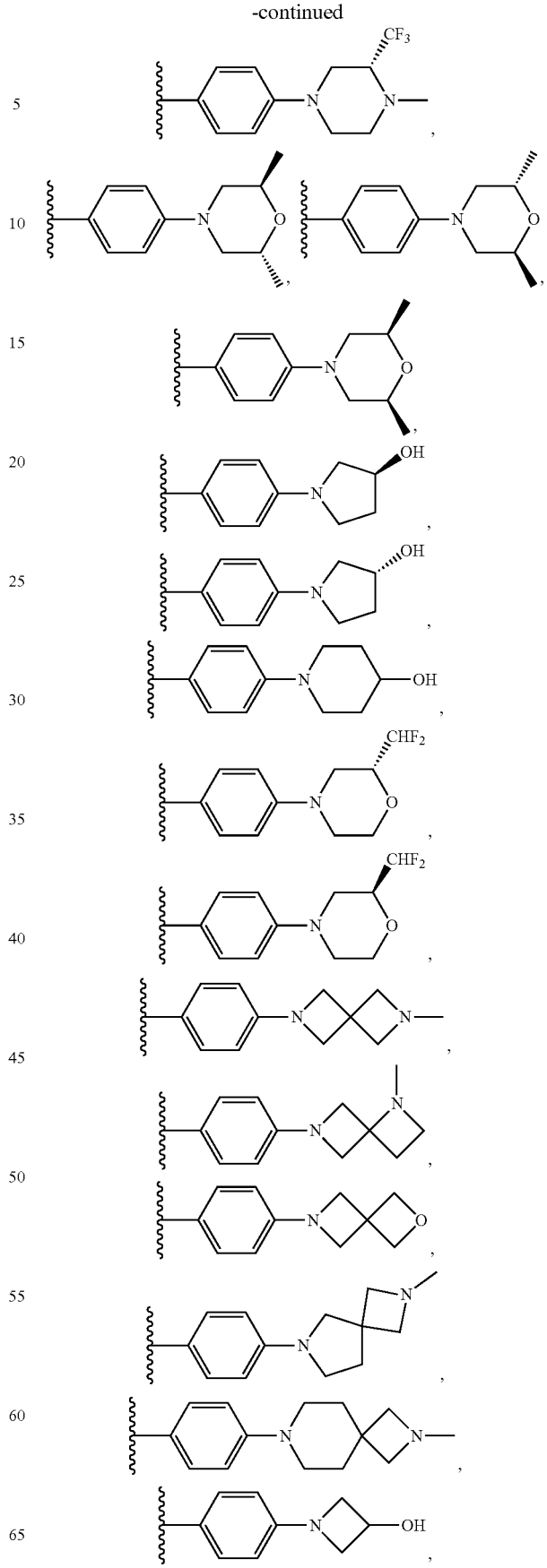

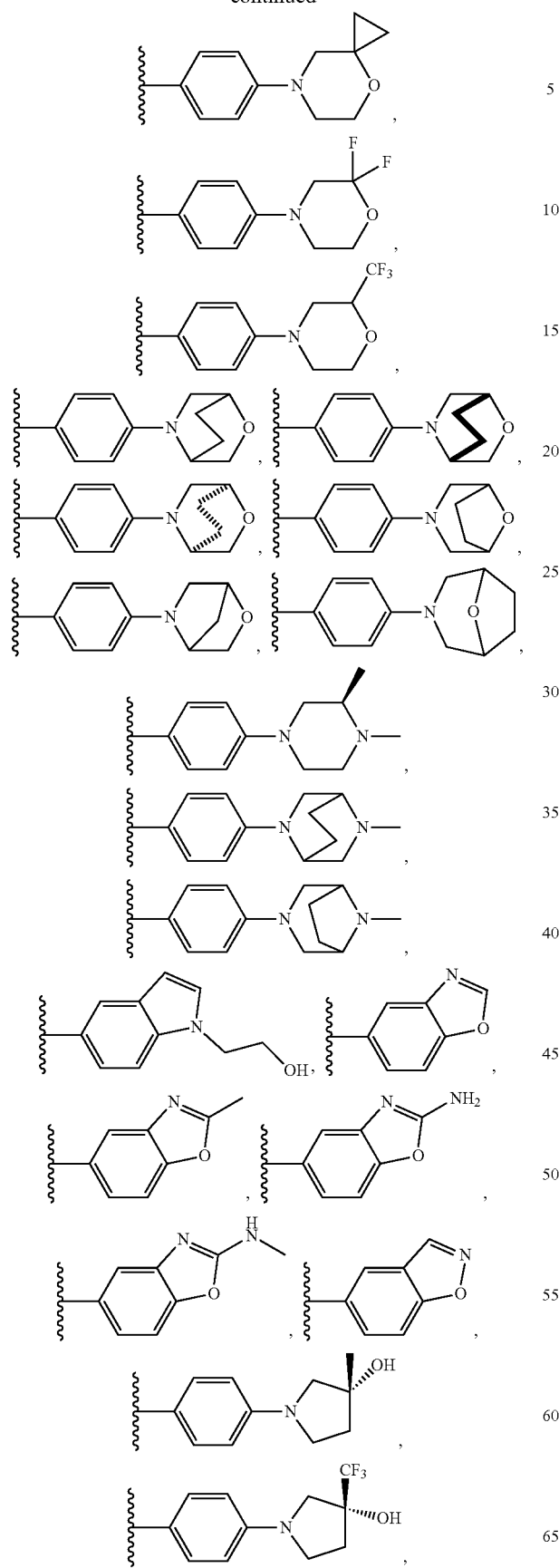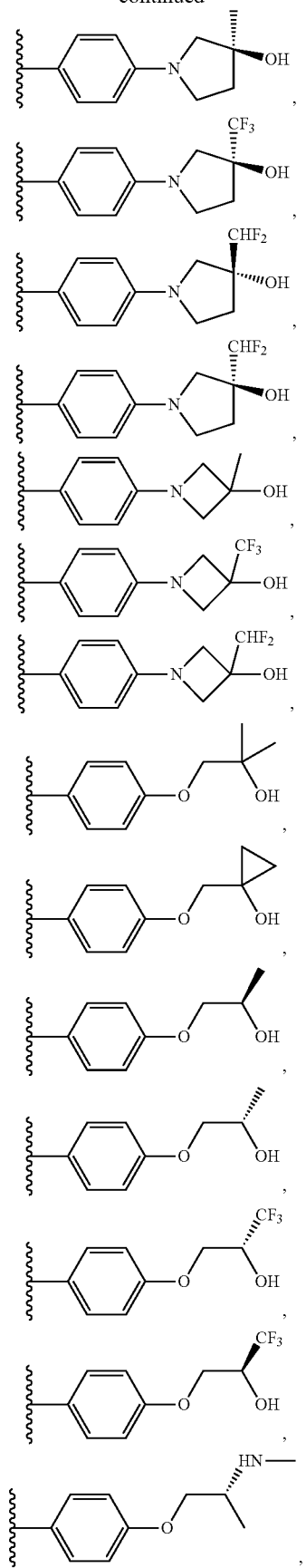

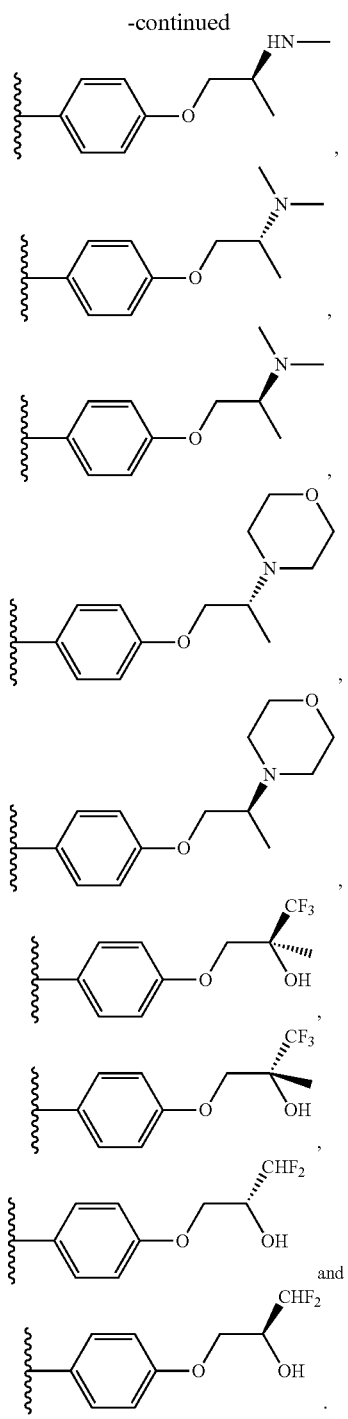

In some embodiments, $R^4$ can be —$CHF_2$. In other embodiments, $R^4$ can be —$CH_3$. In still other embodiments, $R^4$ can be -cyclopropyl. In yet still other embodiments, $R^4$ can be an unsubstituted $C_{1-4}$ hydroxyalkyl, such as —$(CH_2)_{1-4}$—OH. In some embodiments, $R^4$ can be an unsubstituted benzyl-O—$CH_2$—. In other embodiments, $R^4$ can be a substituted benzyl-O—$CH_2$—. In still other embodiments, $R^4$ can be an unsubstituted monocyclic heterocyclyl-$CH_2$—. In yet still other embodiments, $R^4$ can be a substituted monocyclic heterocyclyl-$CH_2$—. The heterocyclyl of heterocyclyl-$CH_2$— can be a 5- or 6-membered heterocyclyl that can include 1 or 2 heteroatoms selected from nitrogen (N), oxygen (O) and sulfur (S). Examples of suitable monocyclic heterocyclyls are described herein, and include an unsubstituted or a substituted morpholine.

When $R^4$ is a substituent provided herein, a stereocenter may be formed. In some embodiments, the stereocenter that is formed can be in the (R)-configuration. In other embodiments, the stereocenter that is formed can be in the (S)-configuration. Compounds of Formula (I), along with pharmaceutically acceptable salts thereof, with a stereocenter at the carbon to which $R^4$ is attached can include Formula (Ia) and Formula (Ib).

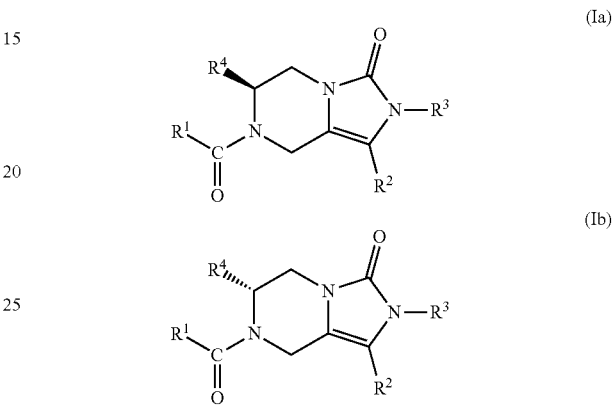

In some embodiments, a compound of Formula (I), or a pharmaceutically acceptable salt thereof, can be where $R^1$ can be 3,4-disubstituted phenyl or trisubstituted phenyl, wherein each substitution group on the phenyl can be independently selected from fluoro, chloro, bromo, —$CHF_2$, —$CF_3$, —$CH_3$, —CN and —C≡CH; $R^2$ can be —$C(=O)R^5$; $R^3$ can be selected from

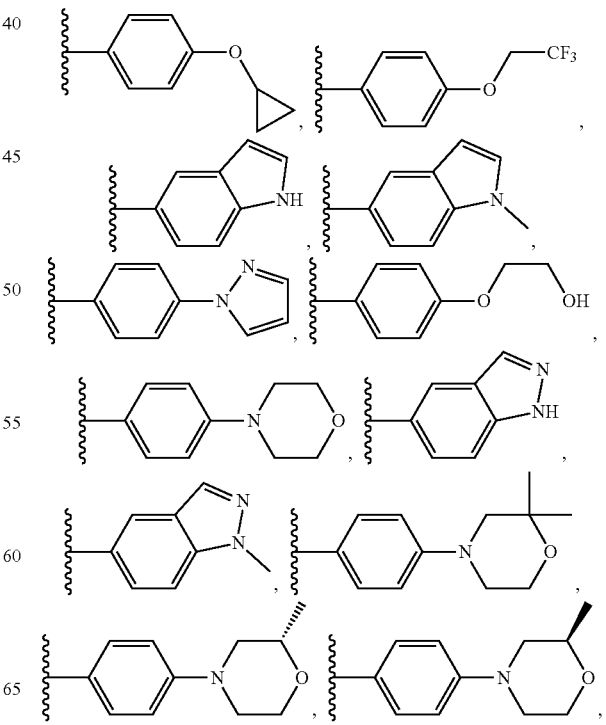

31
-continued
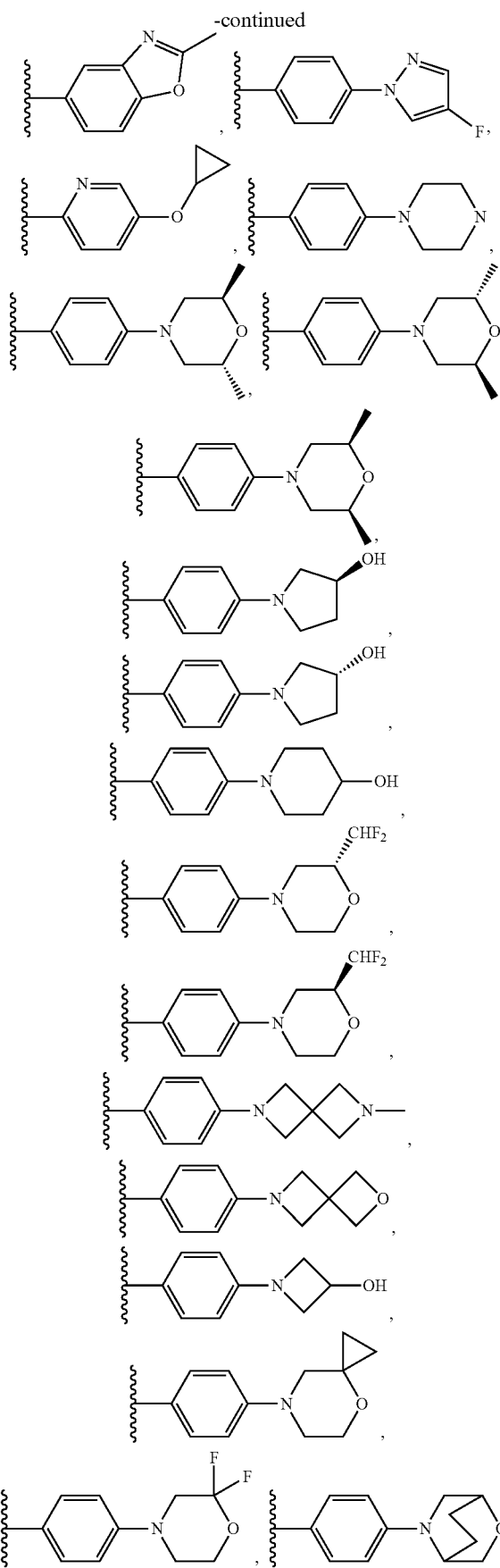
32
-continued
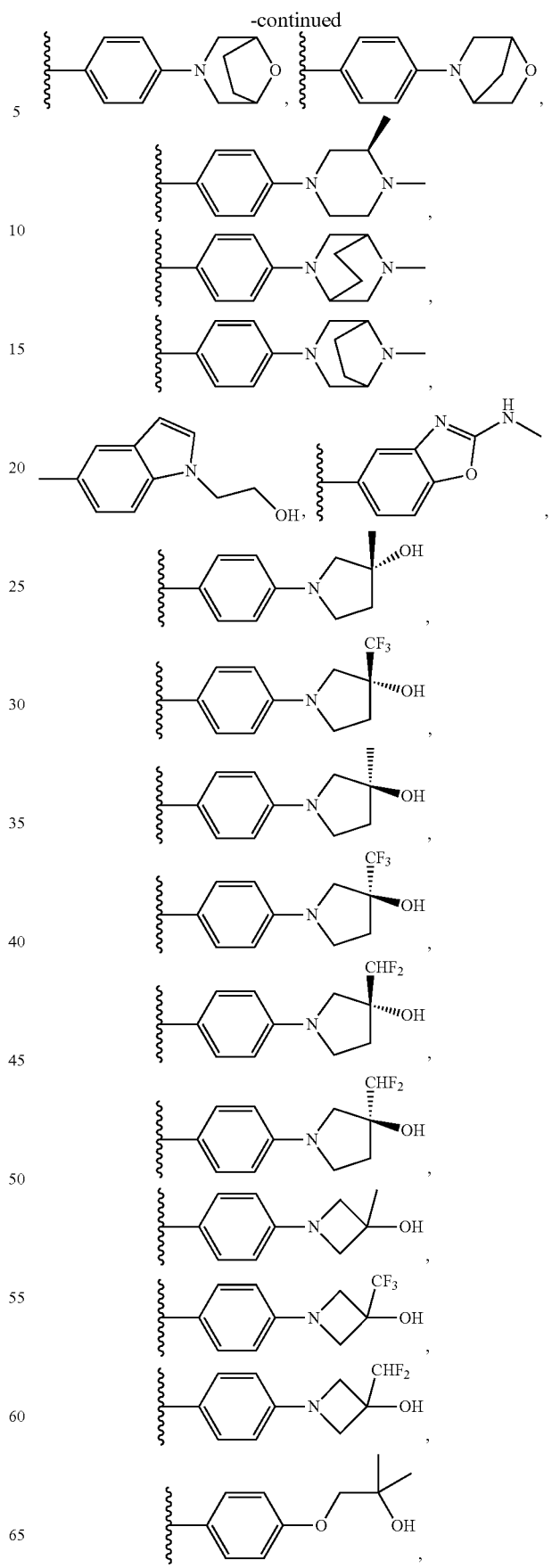

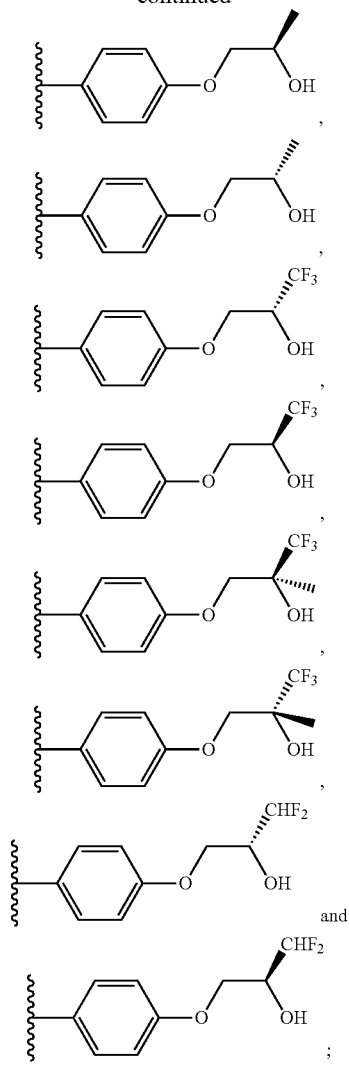

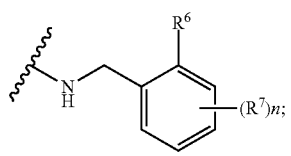

$R^4$ can be selected from —CHF$_2$, —CH$_3$ and -cyclopropyl; $R^5$ can be

$R^6$ can be an unsubstituted or a substituted 5- or 6-membered monocyclic heteroaryl comprising 1, 2 or 3 nitrogens, and optionally 1 or 2 heteroatoms selected from oxygen and sulfur, and when $R^6$ is substituted, $R^6$ can be substituted with one or more substituents selected from halogen, an unsubstituted C$_{1-4}$ alkyl, an unsubstituted —O—C$_{1-4}$ alkyl, amino and mono-C$_{1-6}$ alkyl amine; $R^7$ can be selected from halogen, an unsubstituted C$_{1-4}$ alkyl and an unsubstituted —O—C$_{1-4}$ alkyl; and n can be 0 or 1.

In some embodiments, a compound of Formula (I), or a pharmaceutically acceptable salt thereof, can be where $R^1$ can be

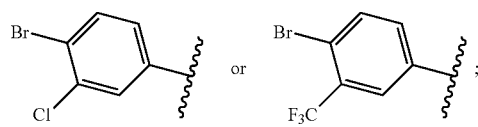 [SMILES: *c1ccc(Br)c(Cl)c1 ; *c1ccc(Br)c(C(F)(F)F)c1]

$R^2$ can be —C(=O)R$^5$, wherein $R^5$ can be selected from

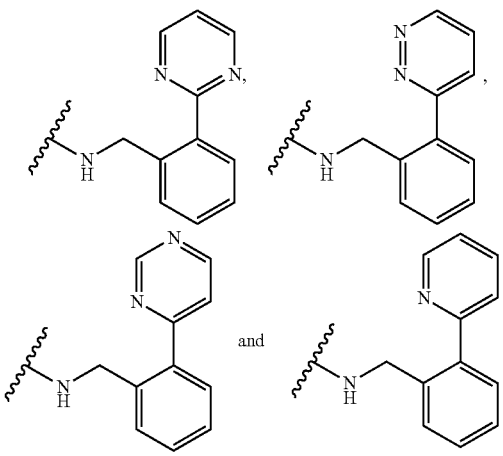

$R^3$ can be a substituted phenyl (such as and R⁴ can be —CH₃. In some embodiments, a compound of Formula (I), or a pharmaceutically acceptable salt thereof, can be where R¹ can be

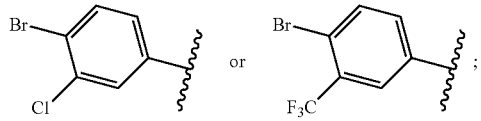

R² can be —C(=O)R⁵, wherein R⁵ can be a substituted bicyclic heteroaryl (such as those described herein); R³ can be a substituted phenyl (such as

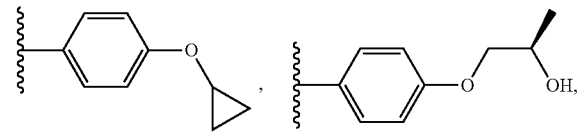

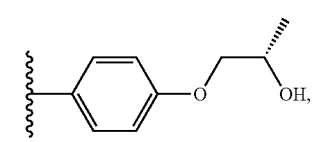

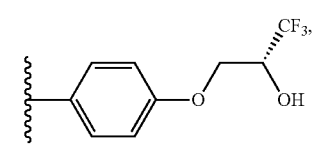

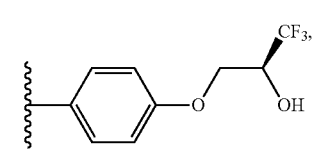

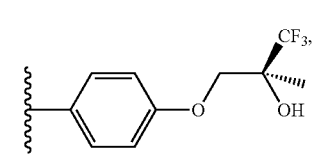

);

and R⁴ can be —CH₃.

Examples of compounds of Formula (I), including pharmaceutically acceptable salts thereof, include:

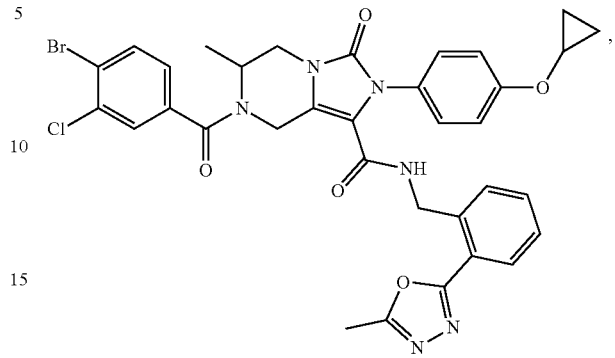

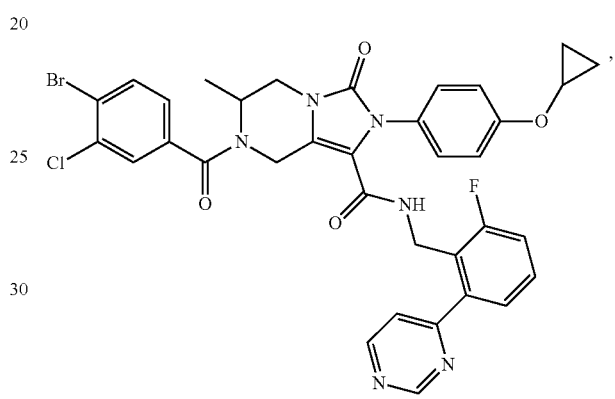

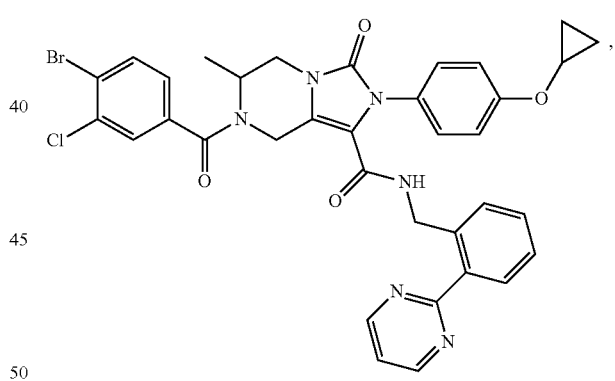

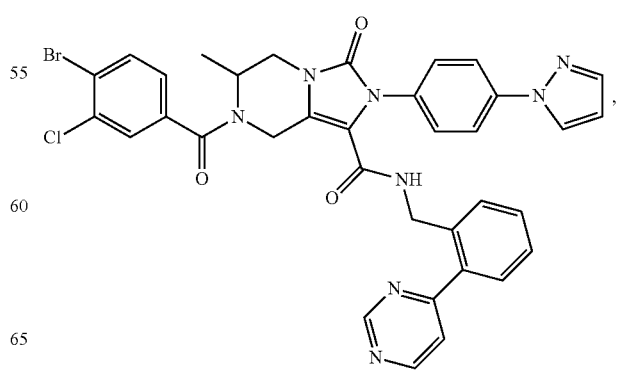

37
-continued
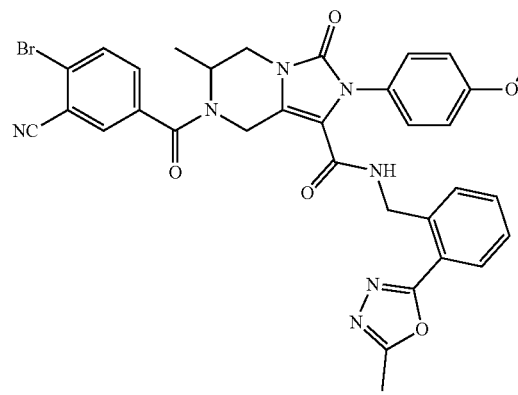
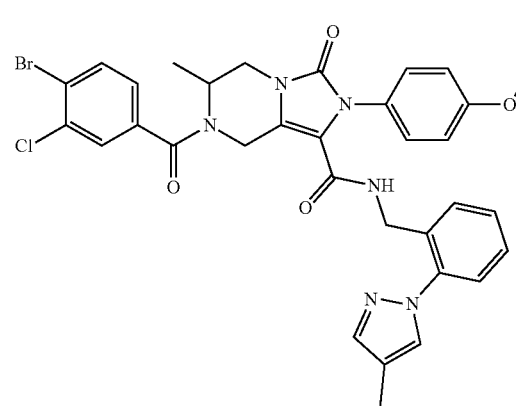
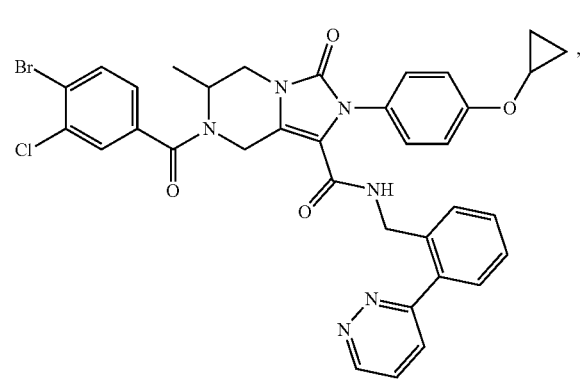
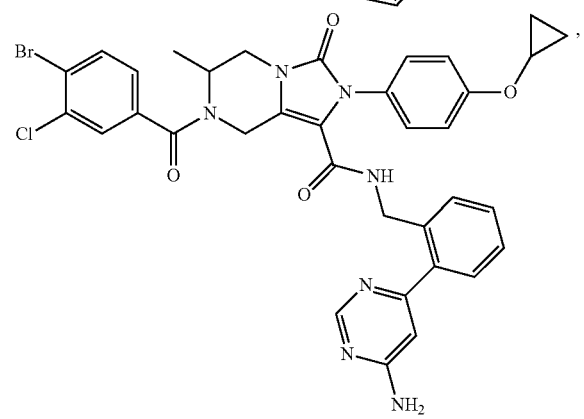
38
-continued
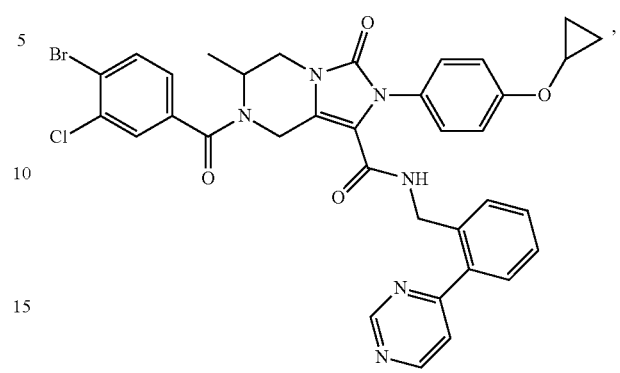
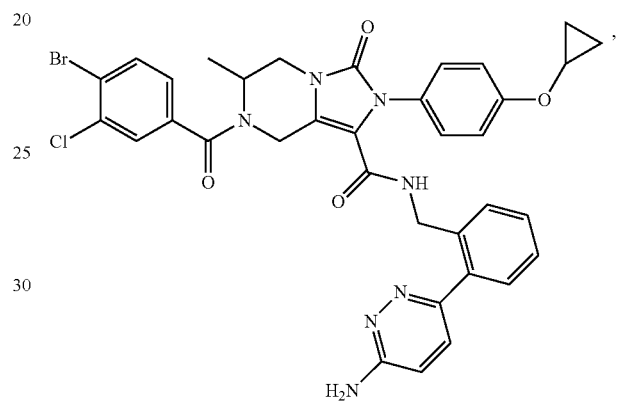
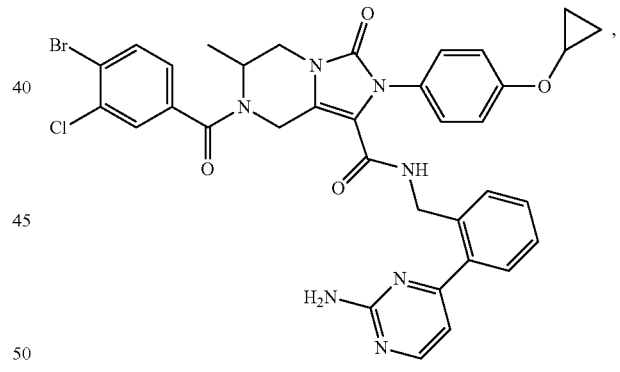
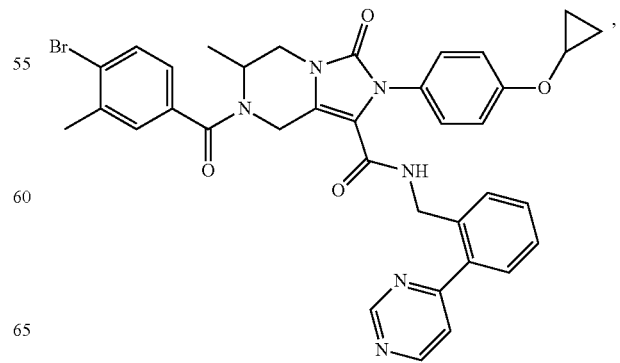

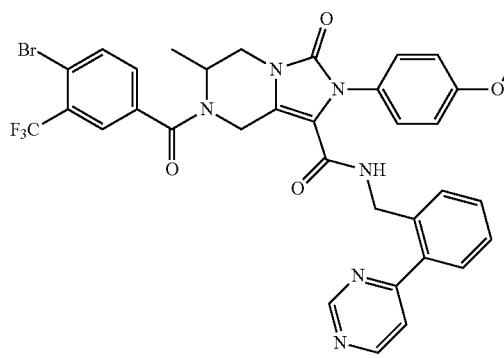
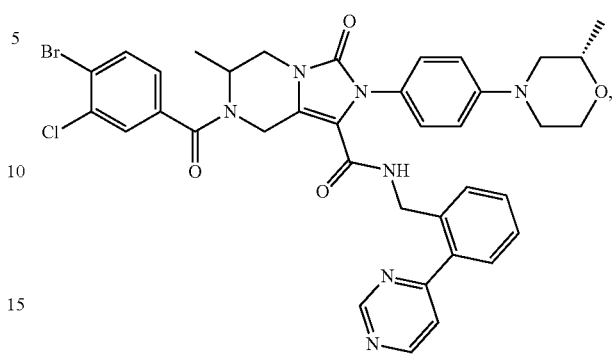
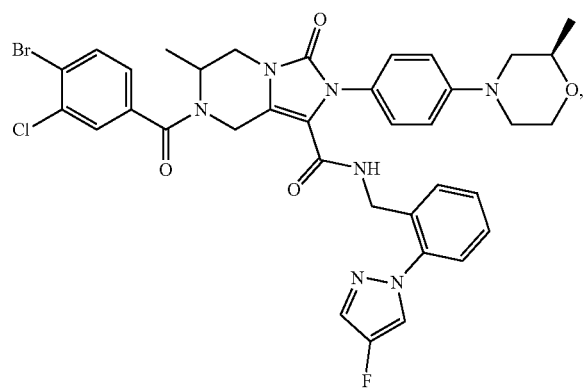
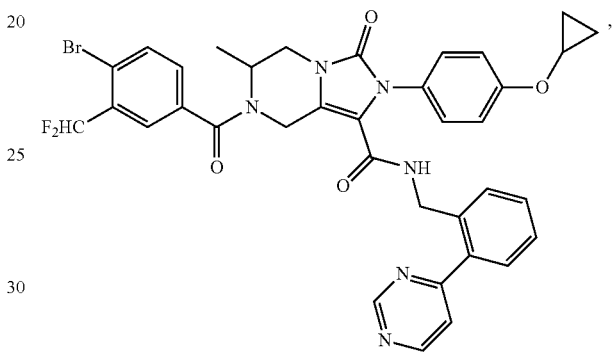
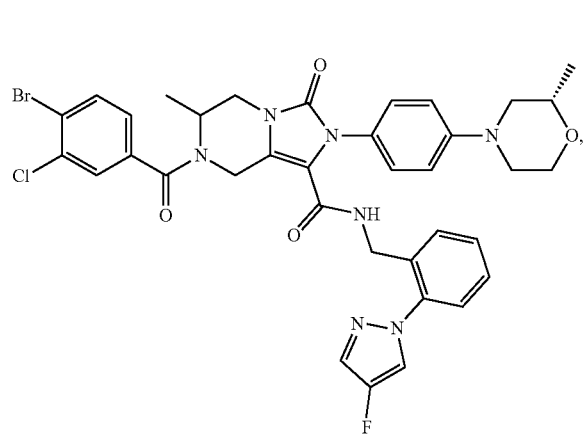
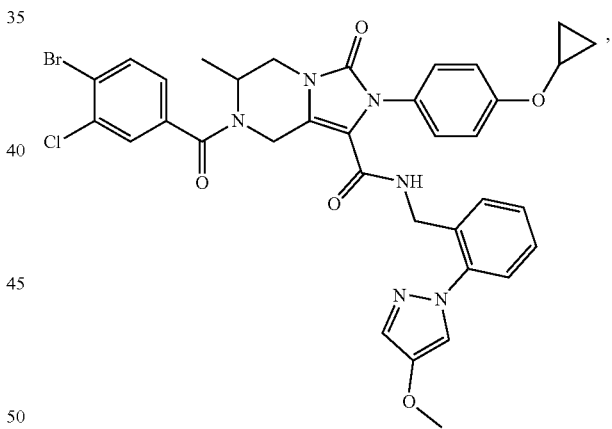
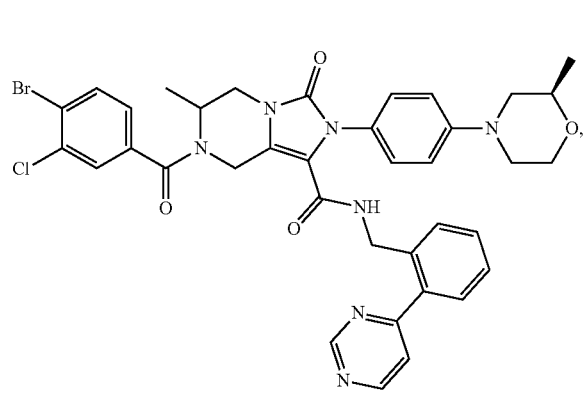
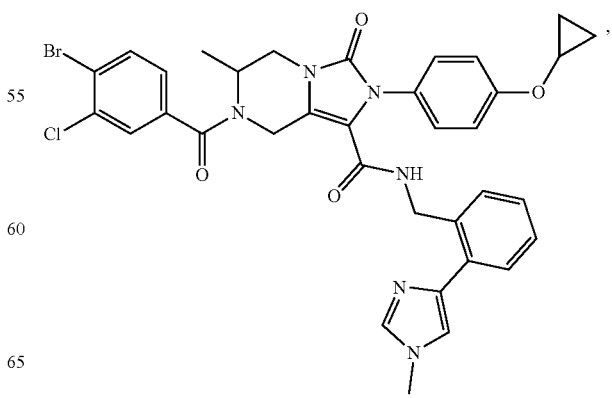

41
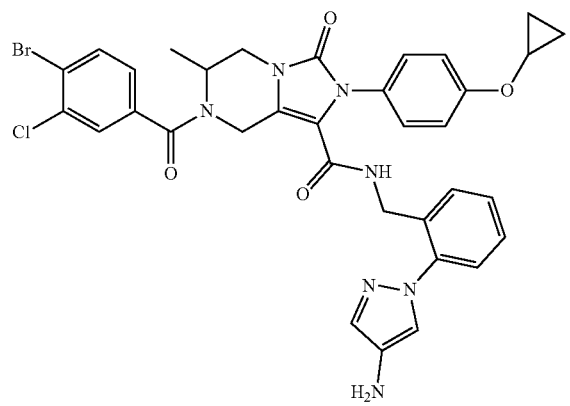
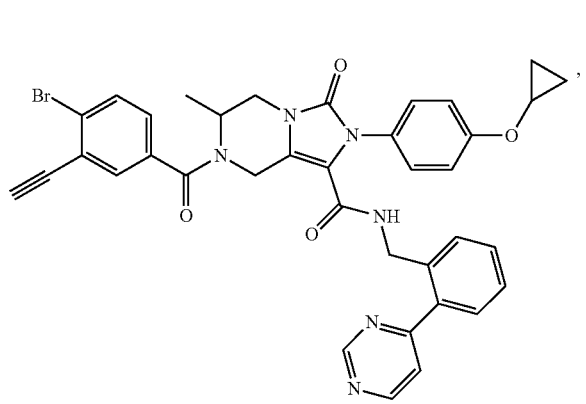
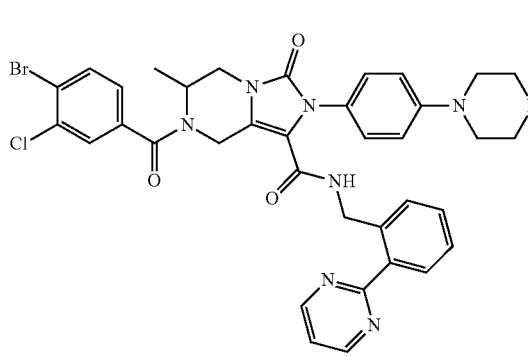
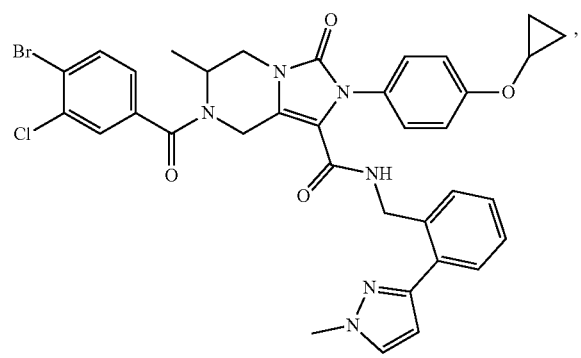
42
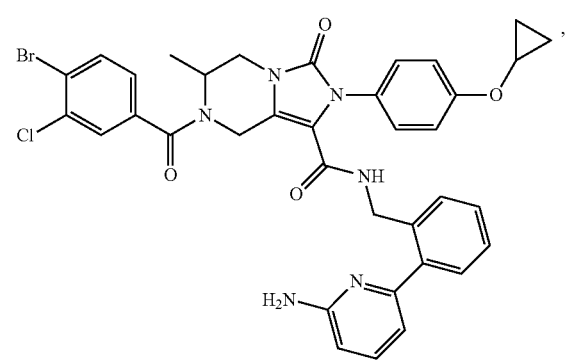
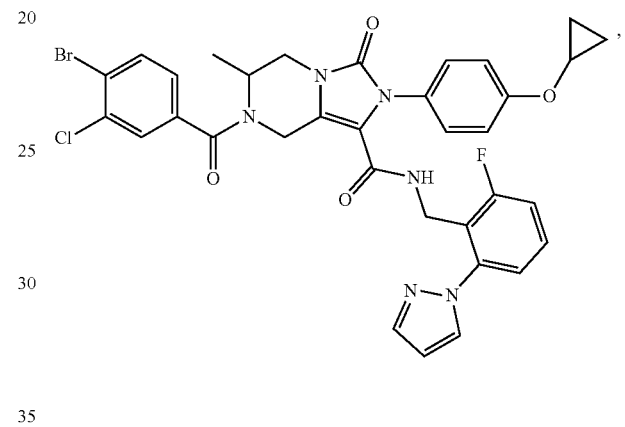
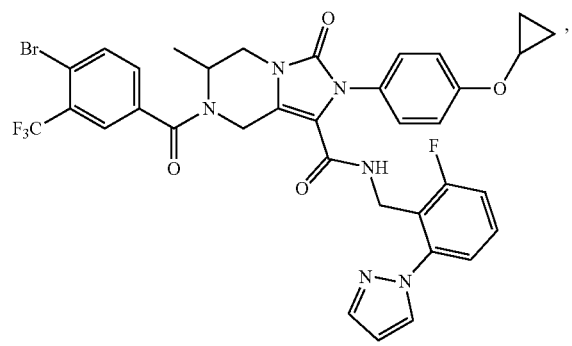
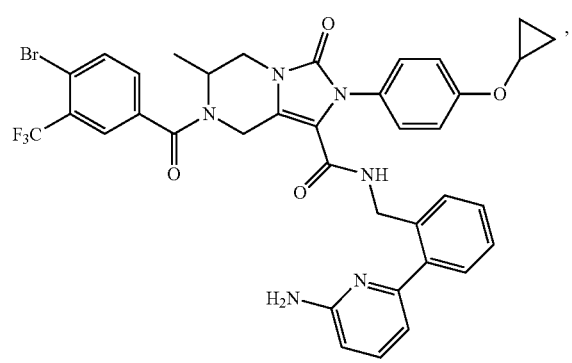

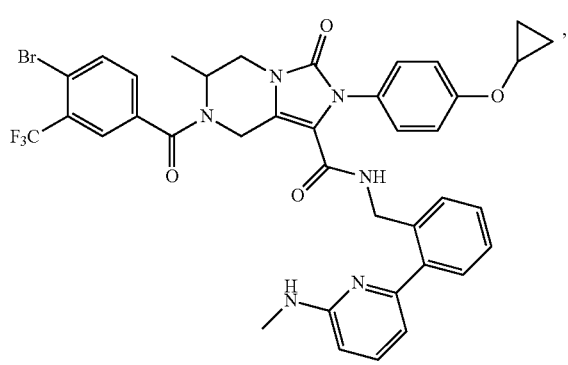
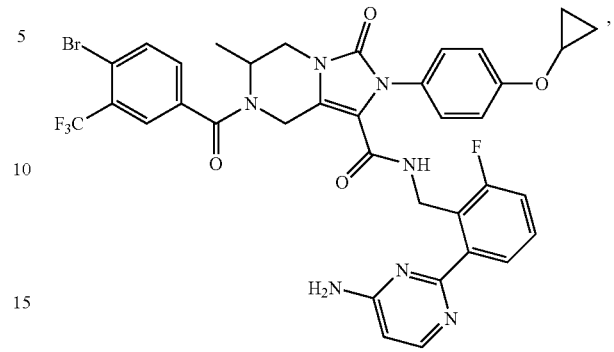
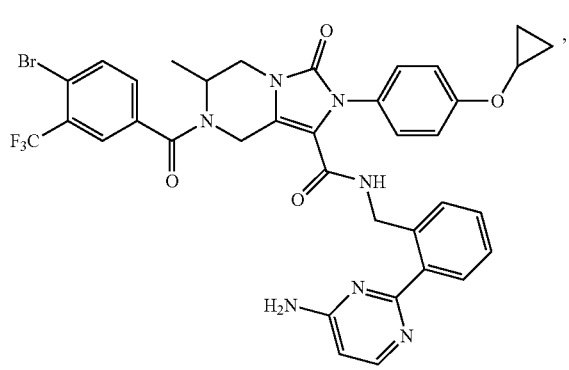
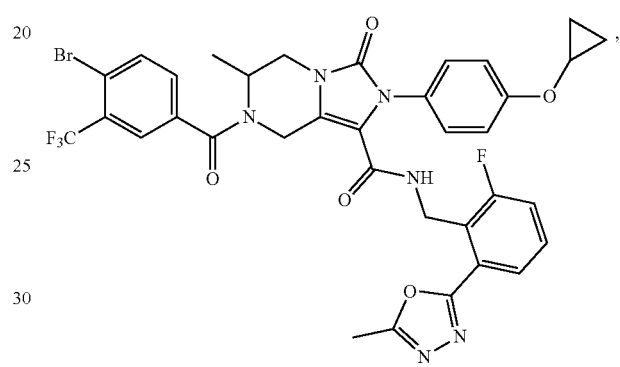
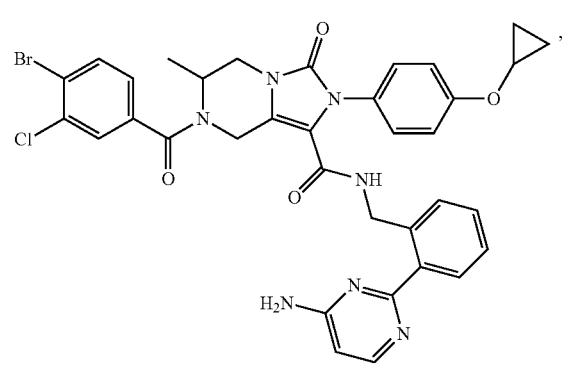
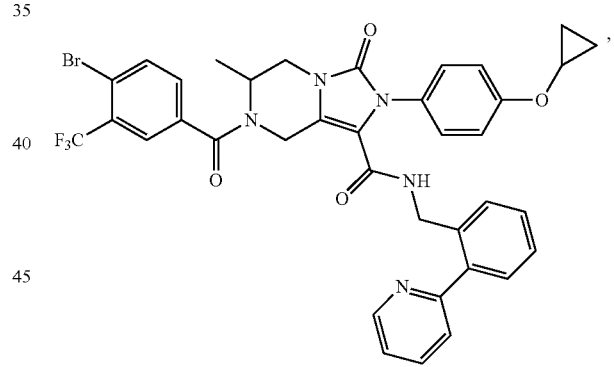
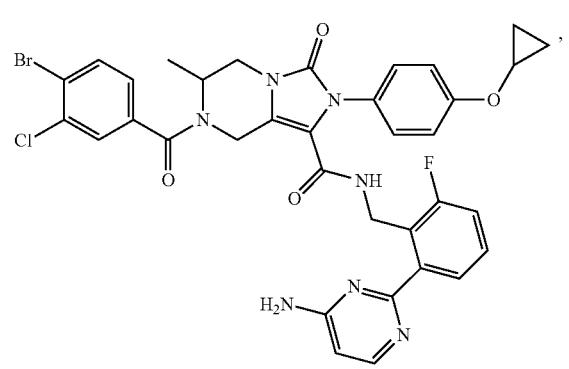
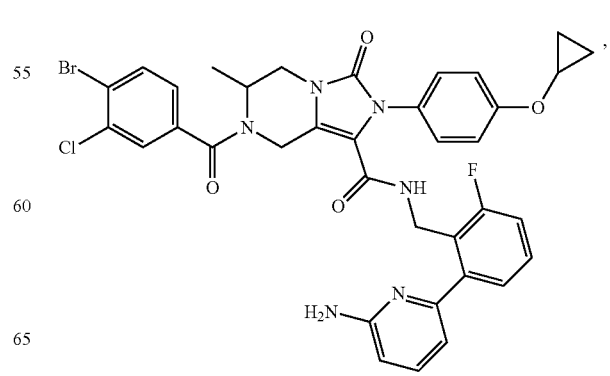

45
-continued
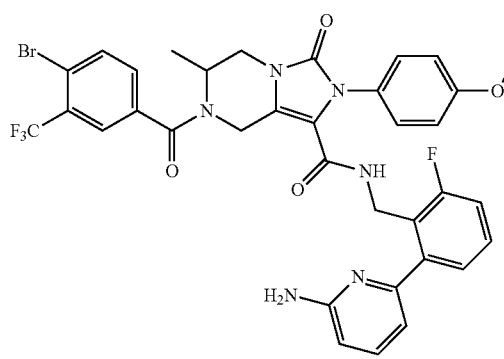
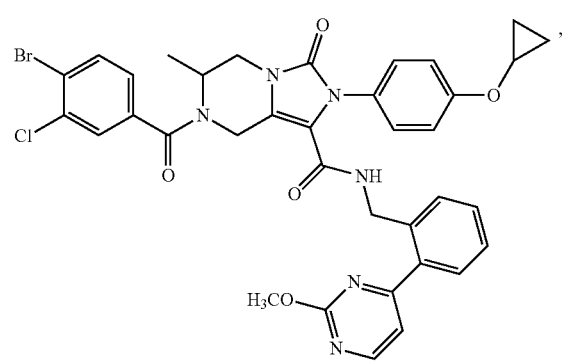
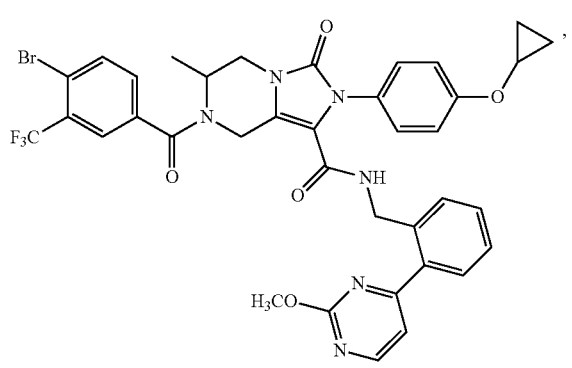
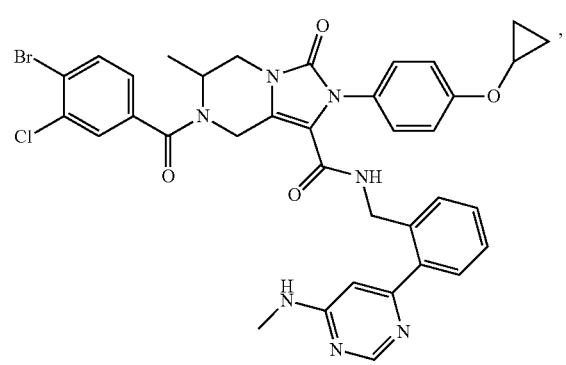
46
-continued
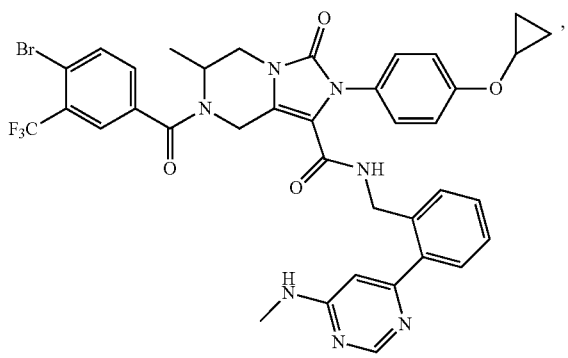
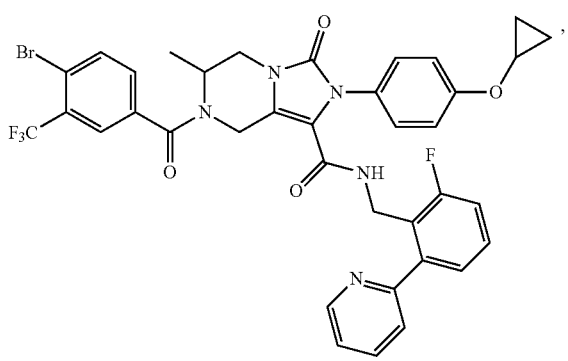
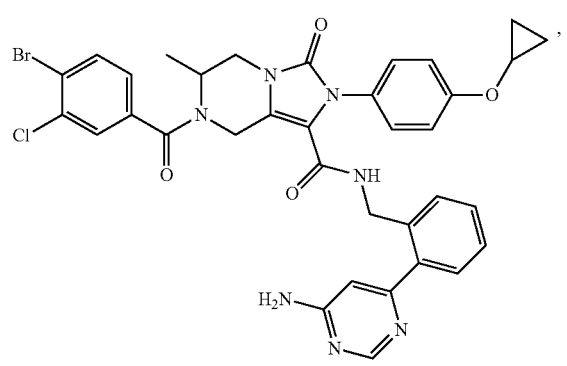
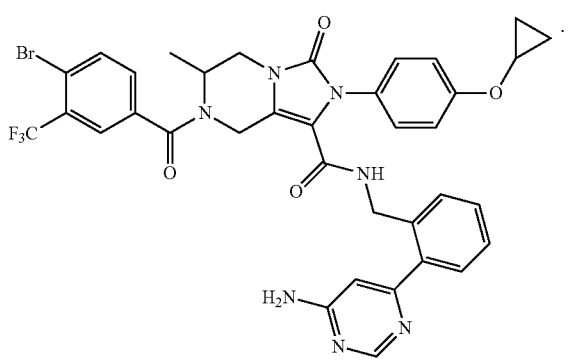

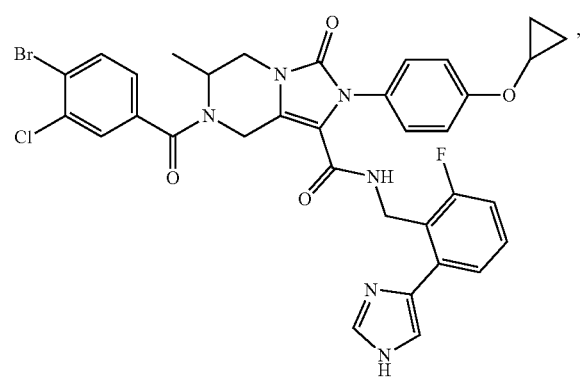
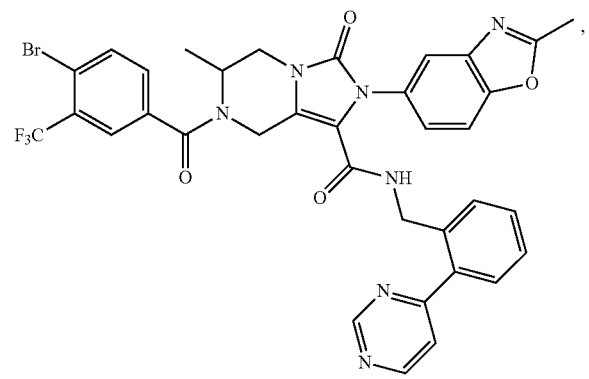
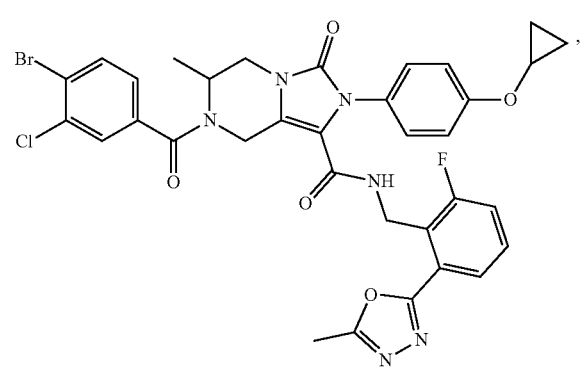
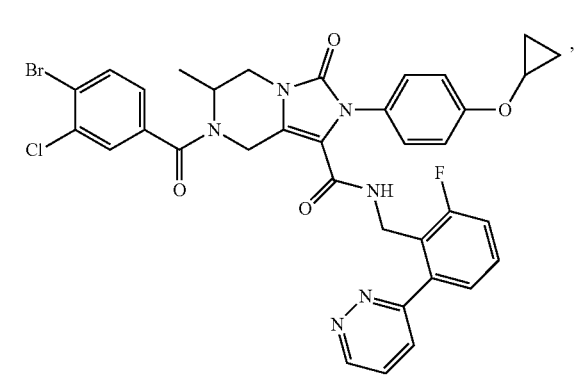
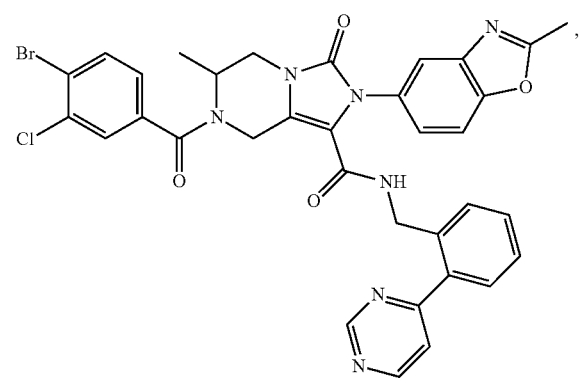
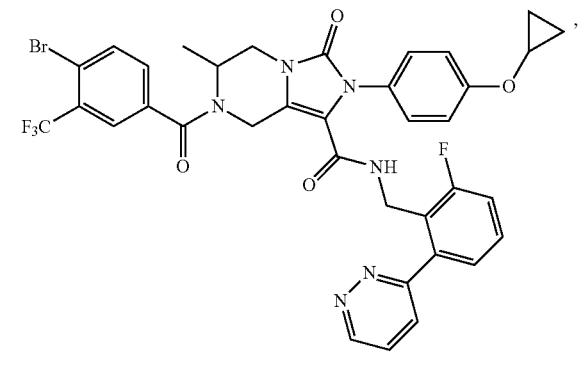
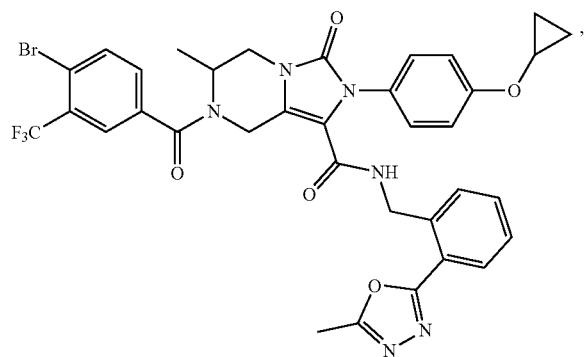
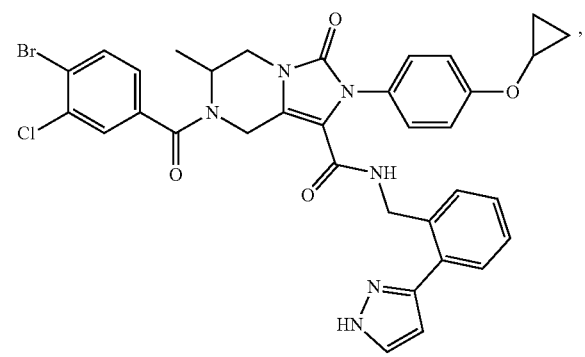

49
-continued
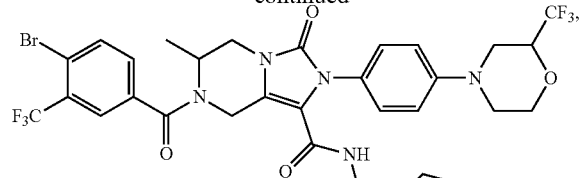
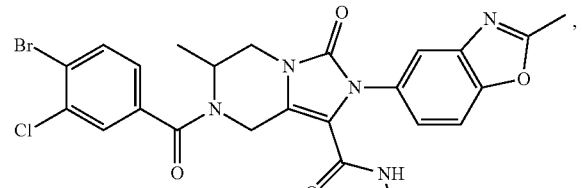
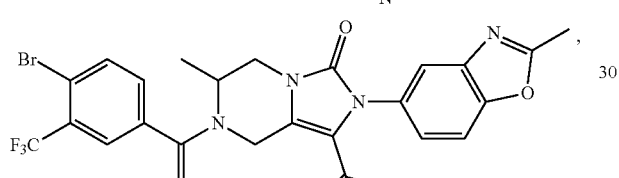
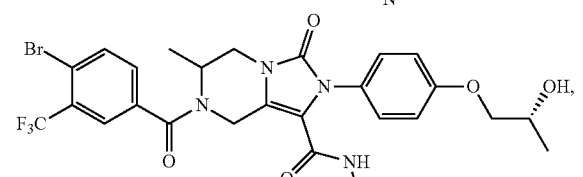
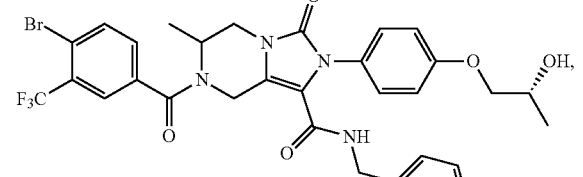
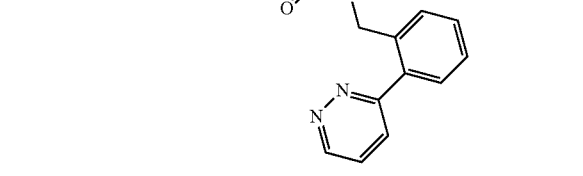
50
-continued
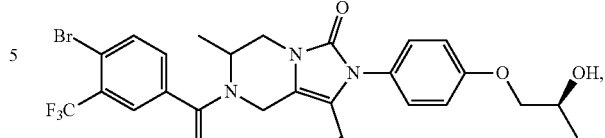
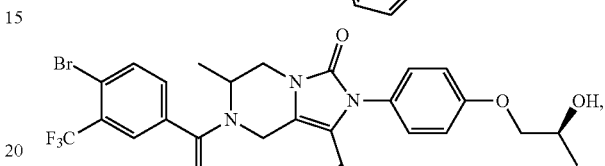
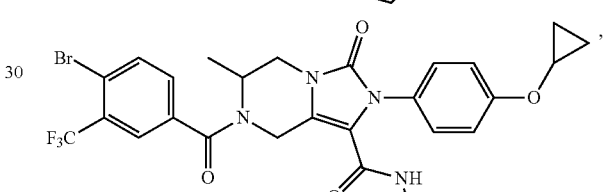
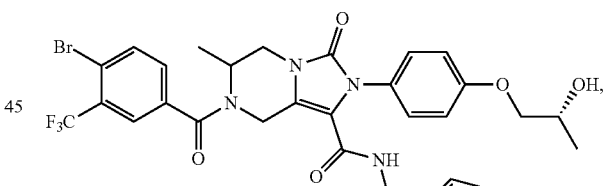
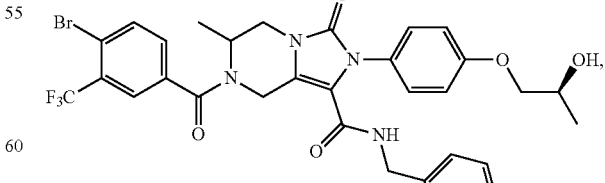
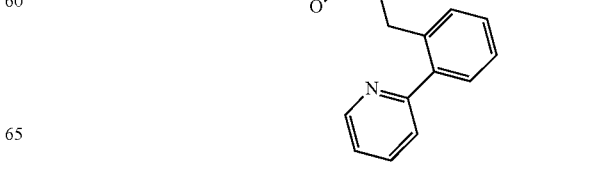

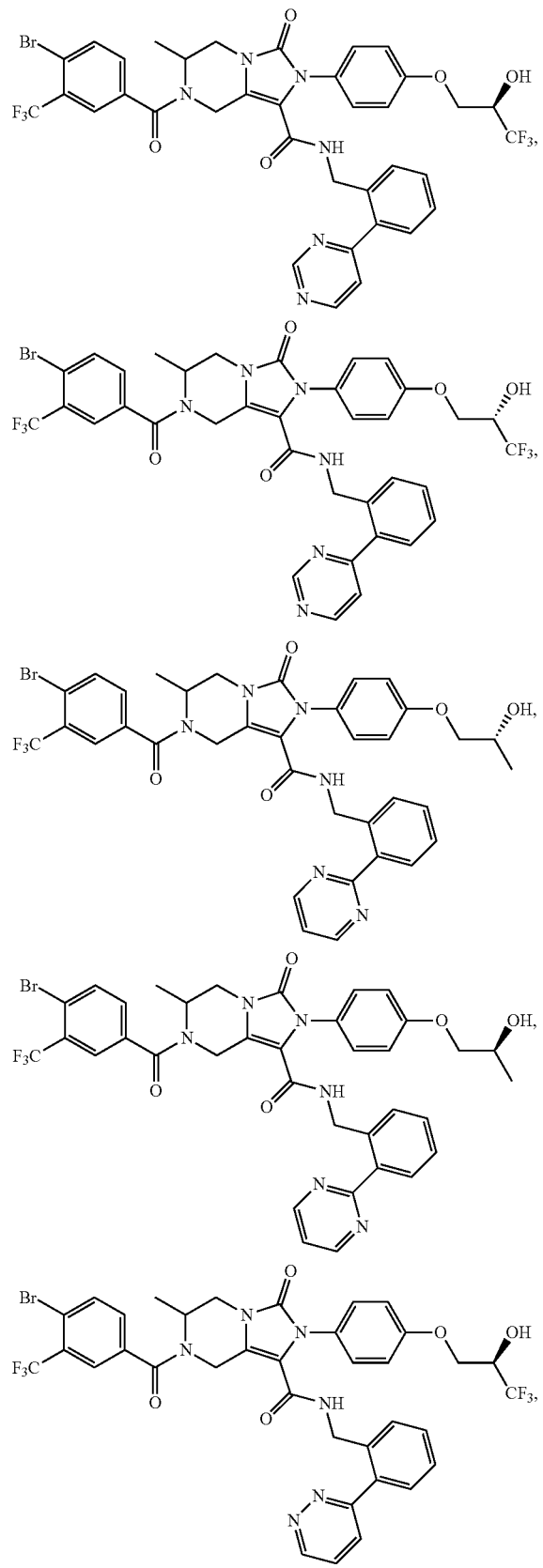
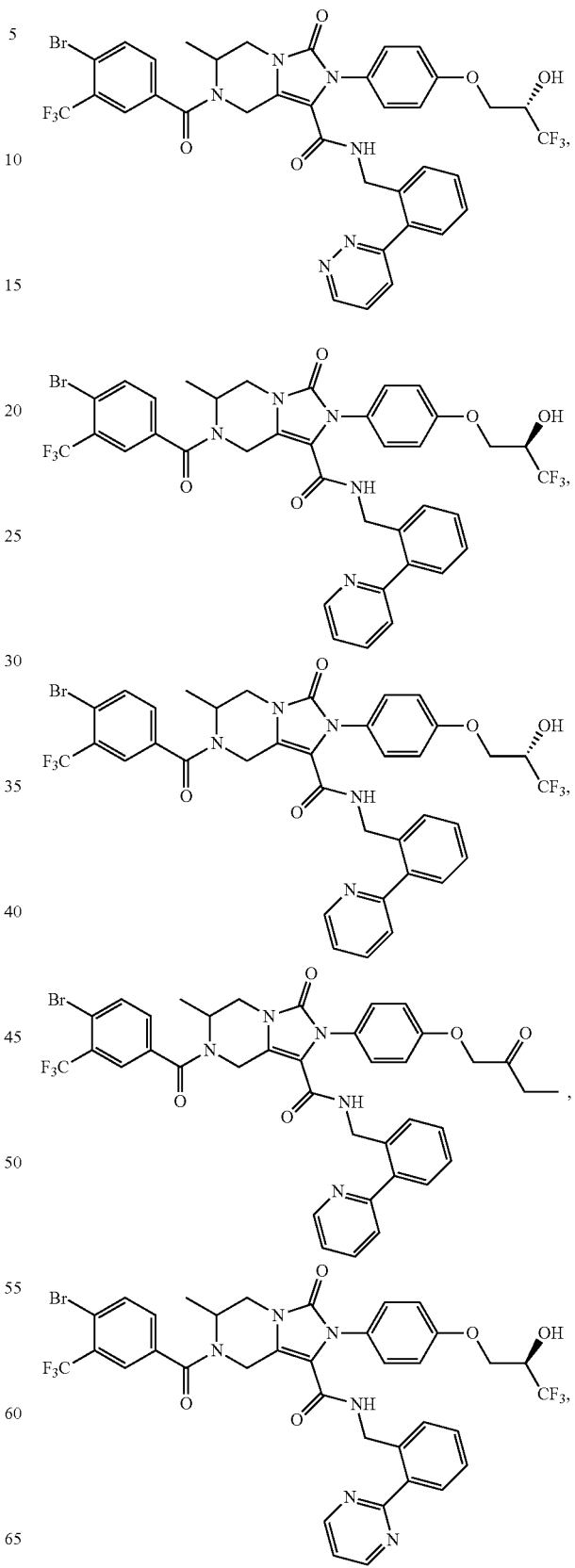

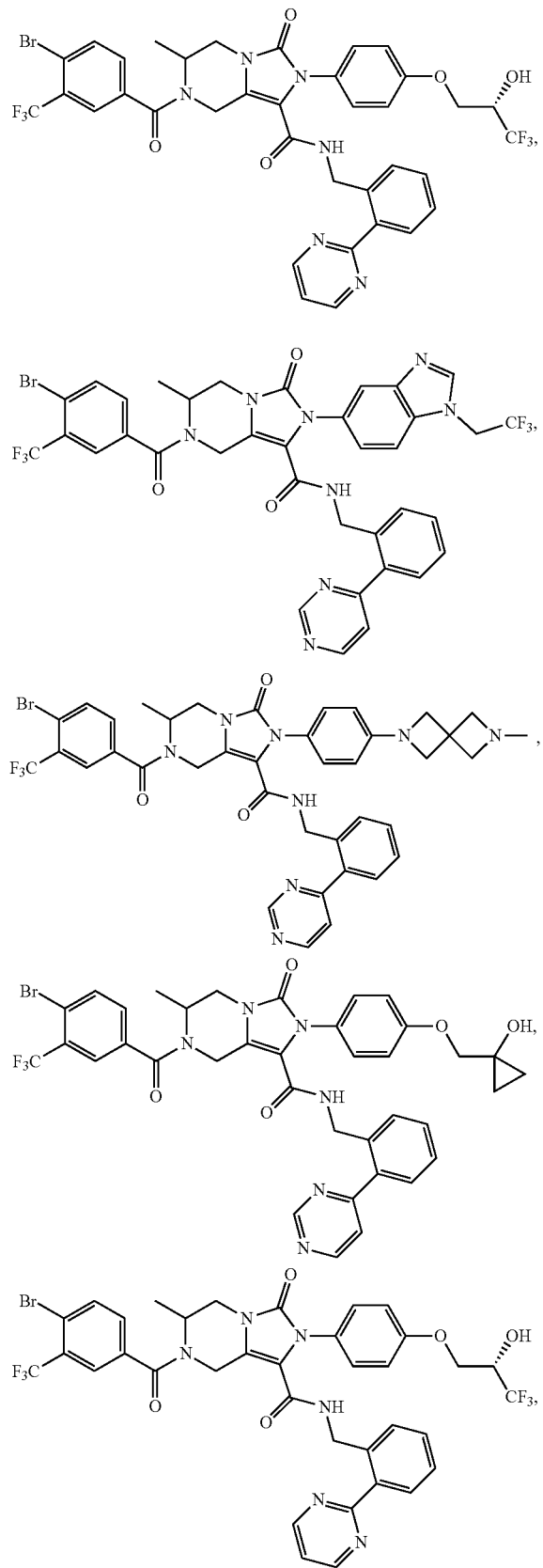
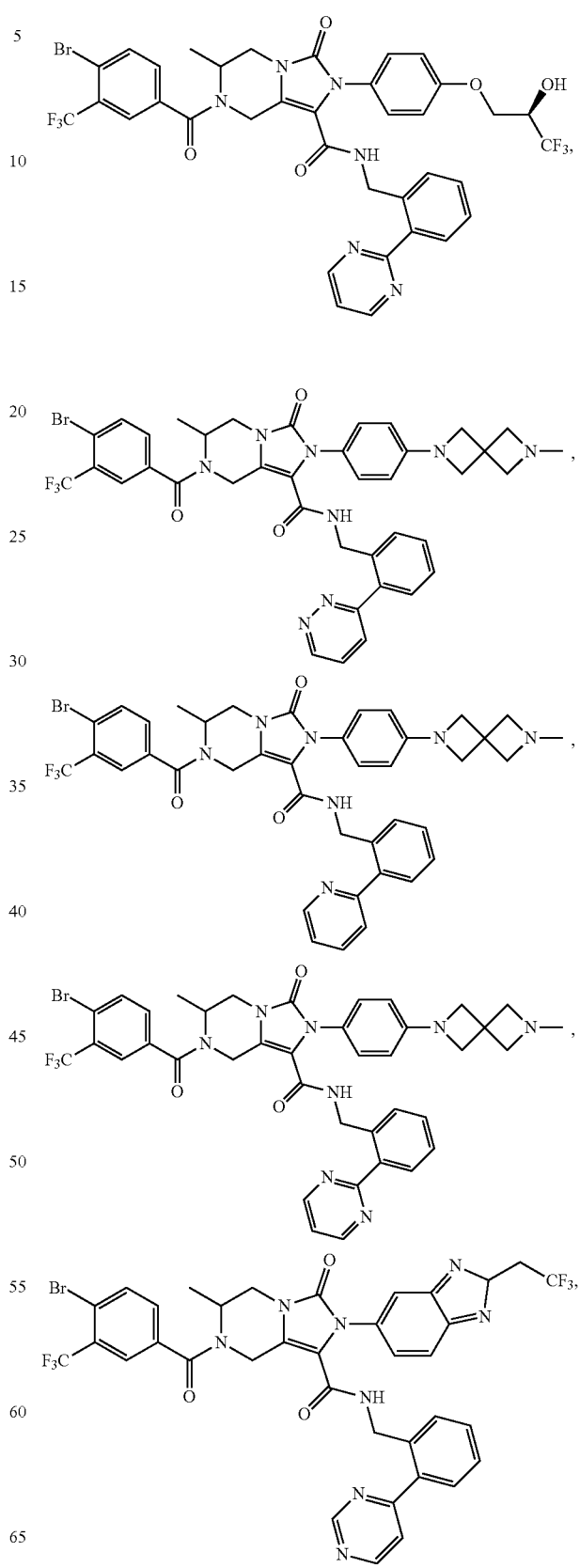

55
-continued
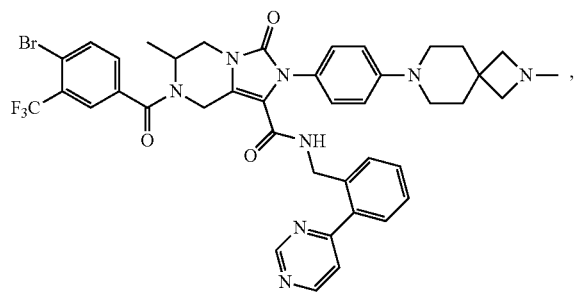
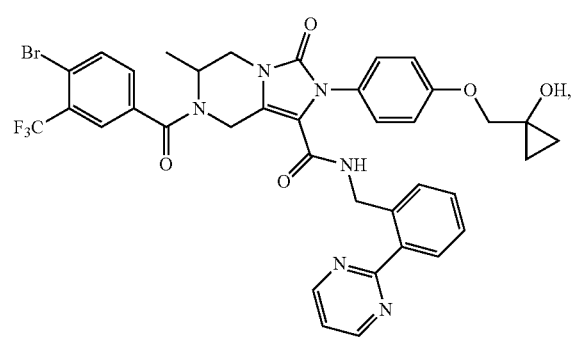
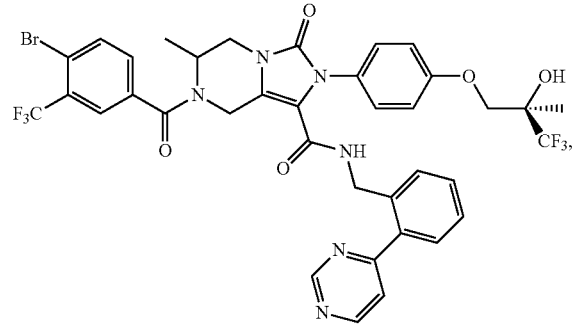
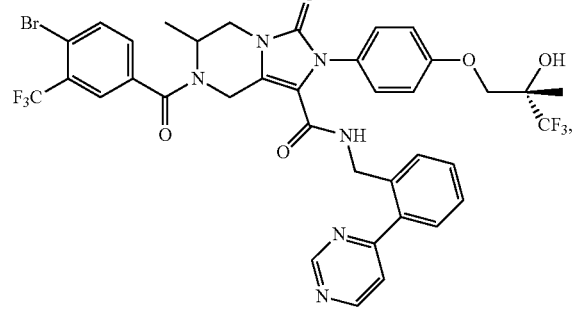
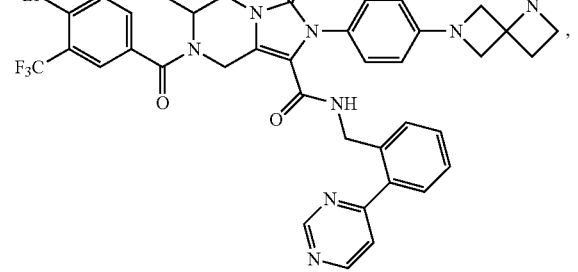
56
-continued
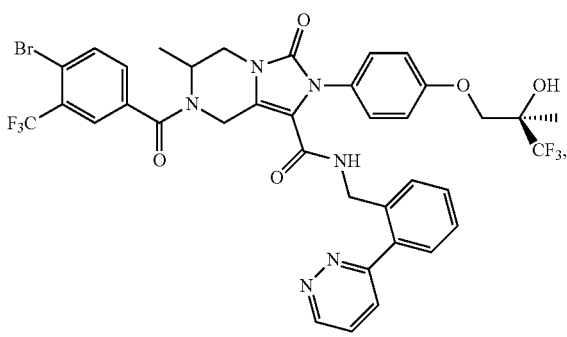
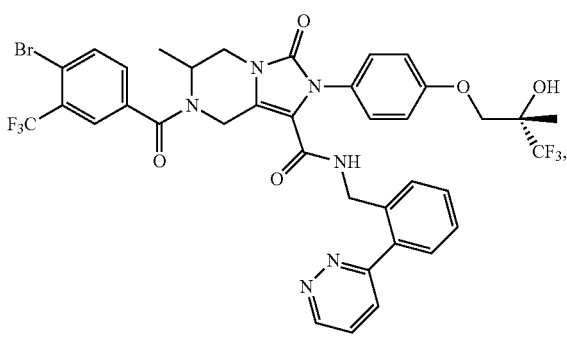
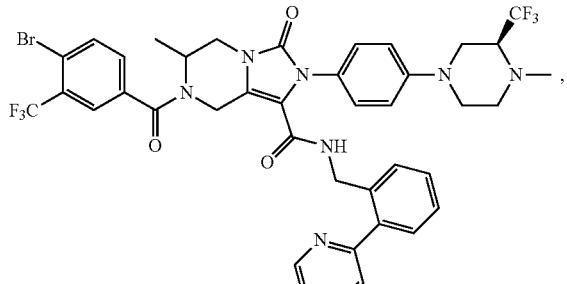
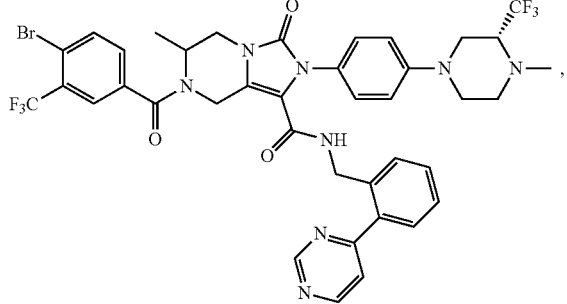
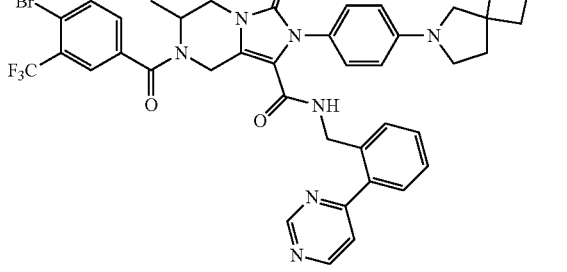

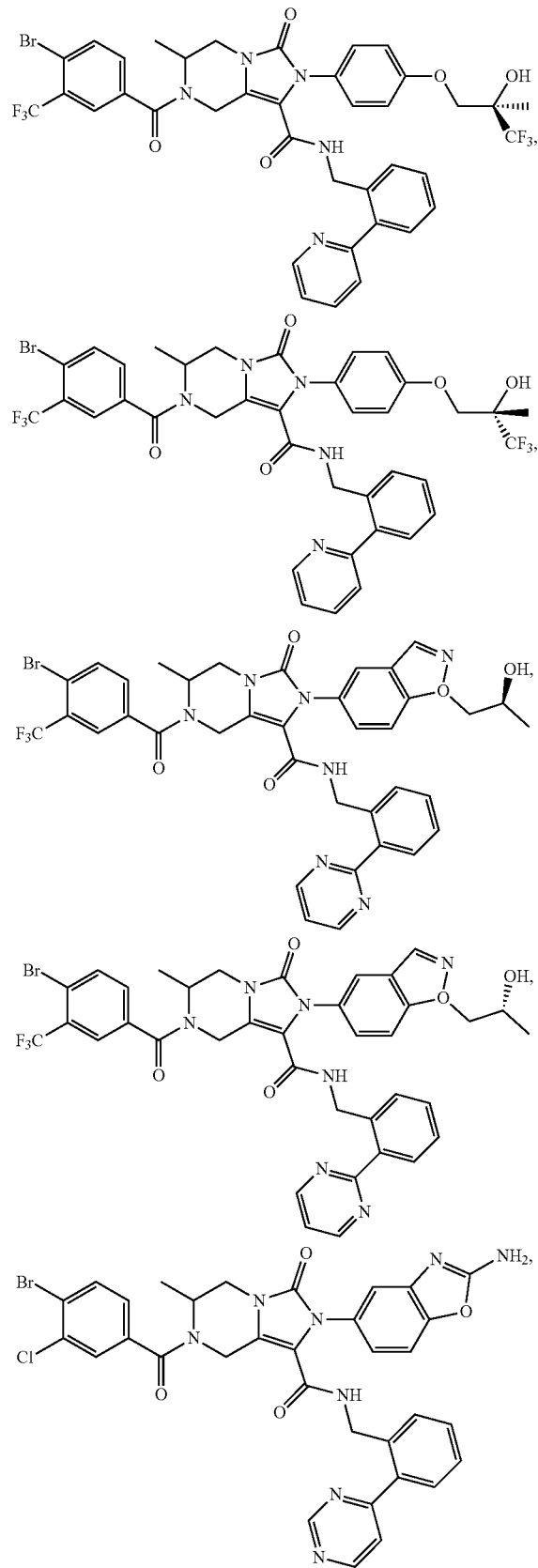
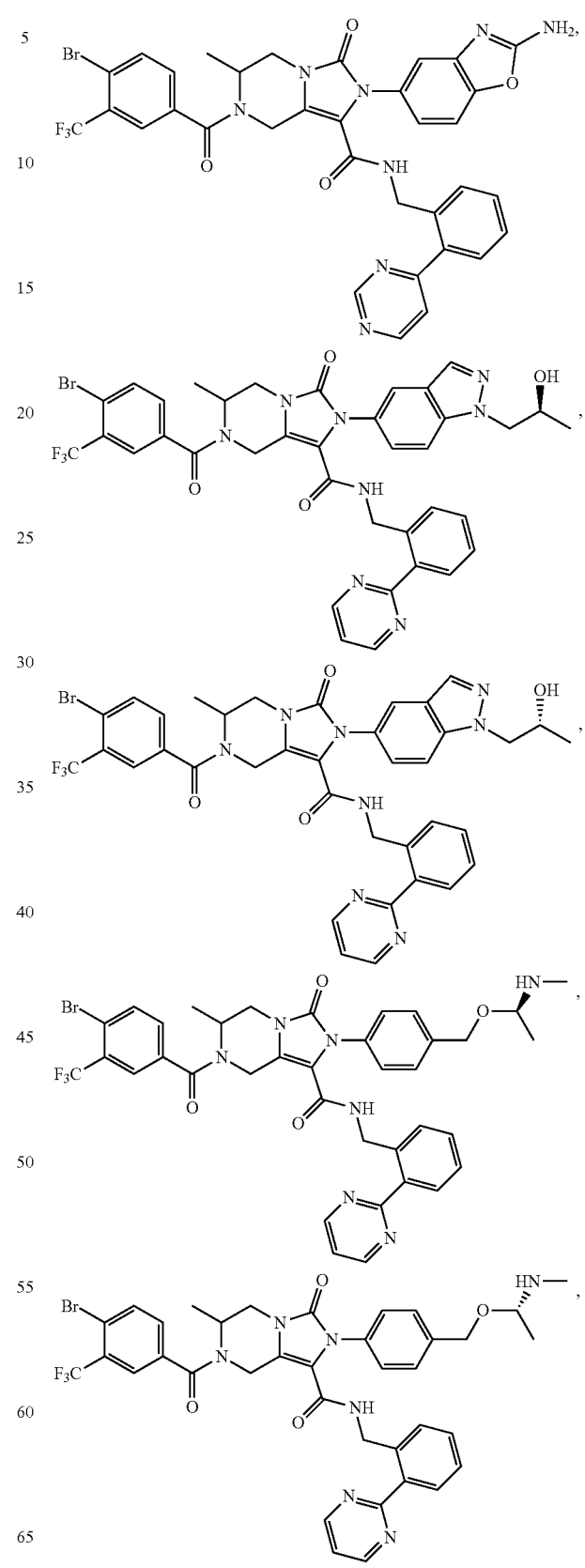

59
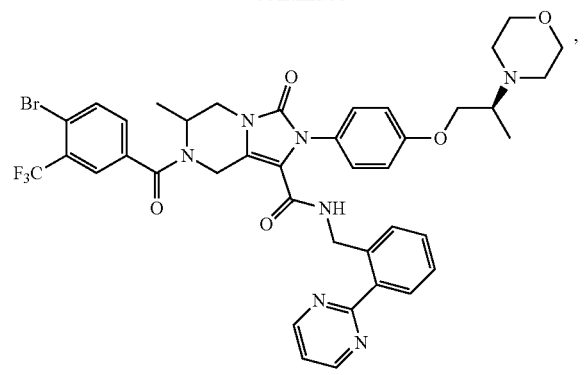
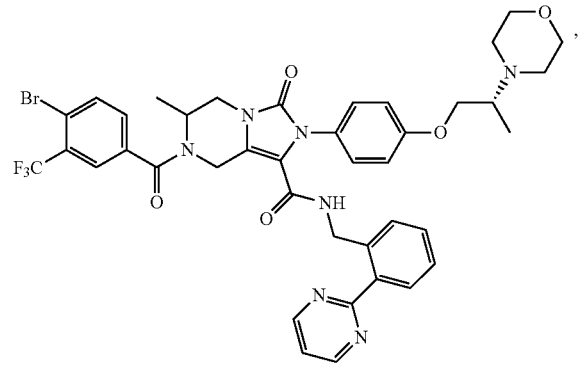
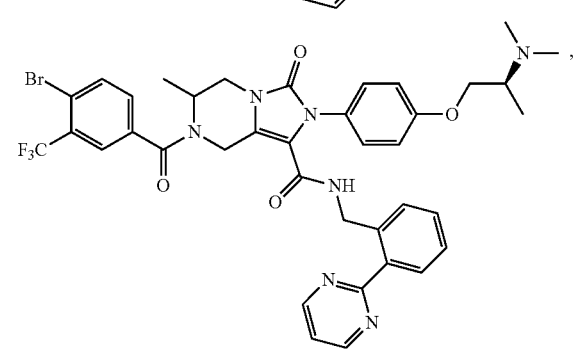
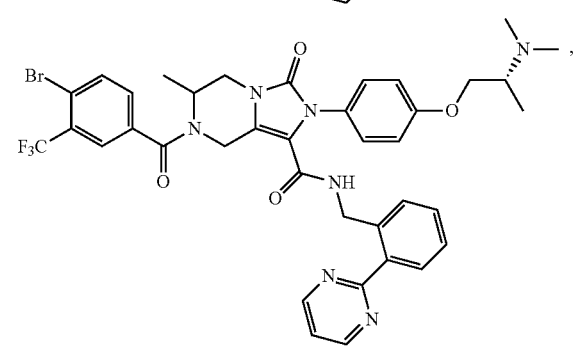
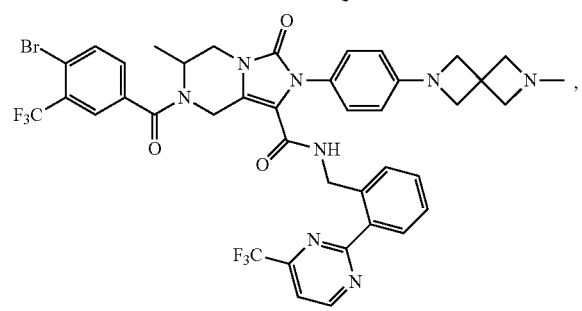
60

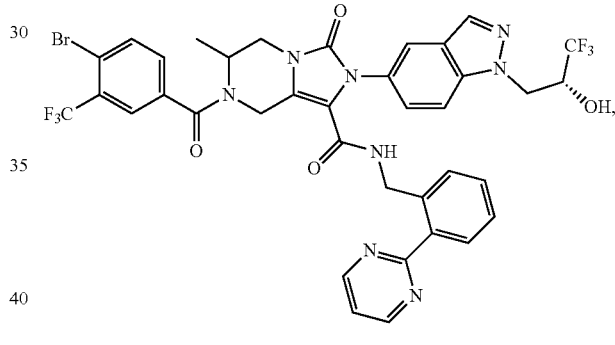
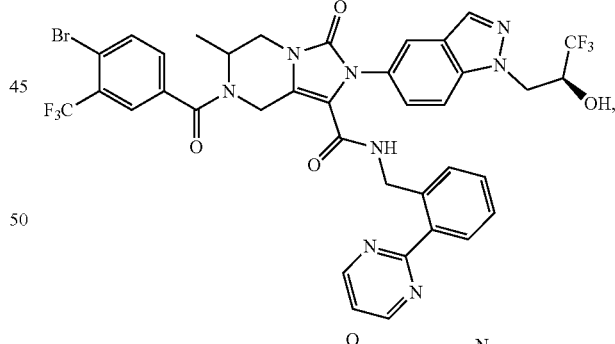
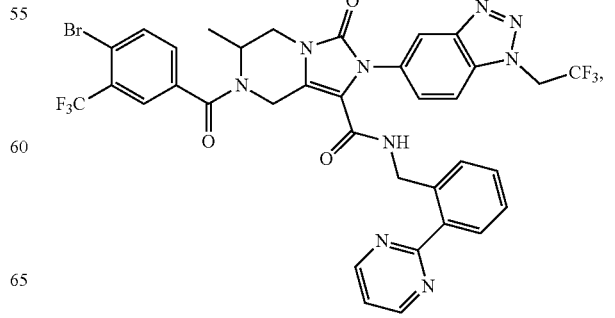

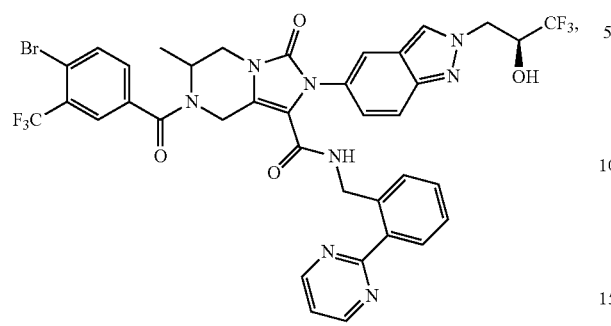
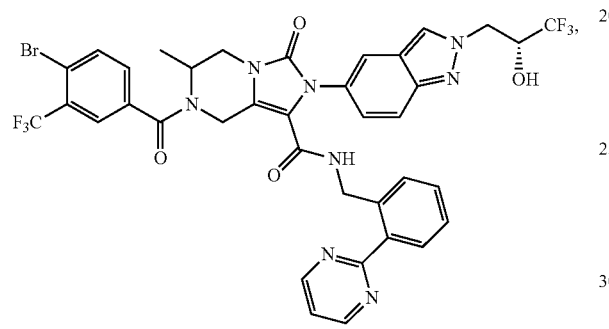
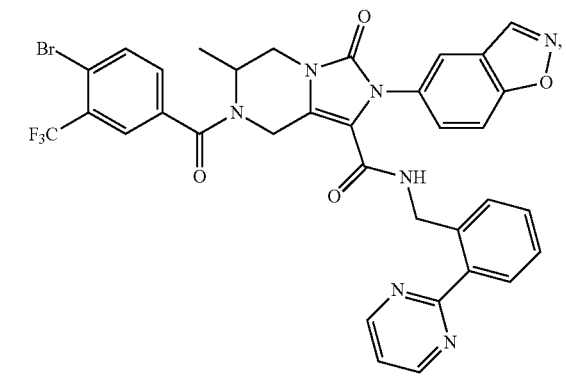
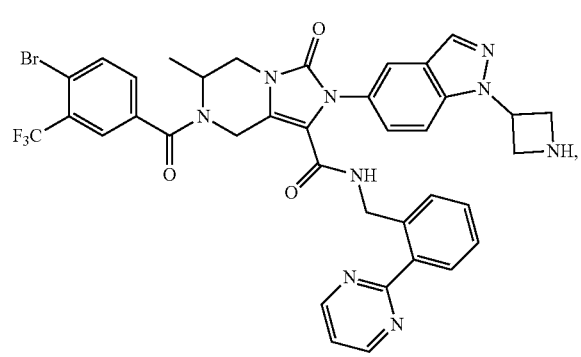
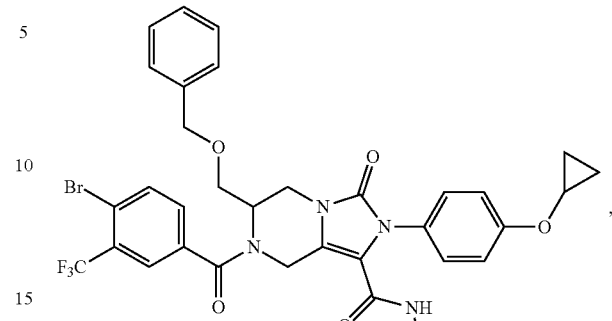
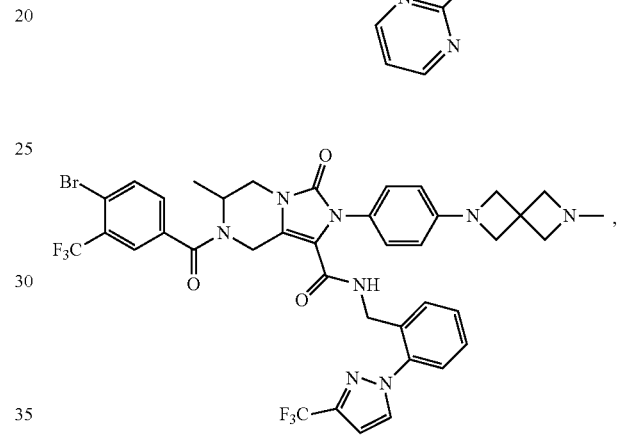
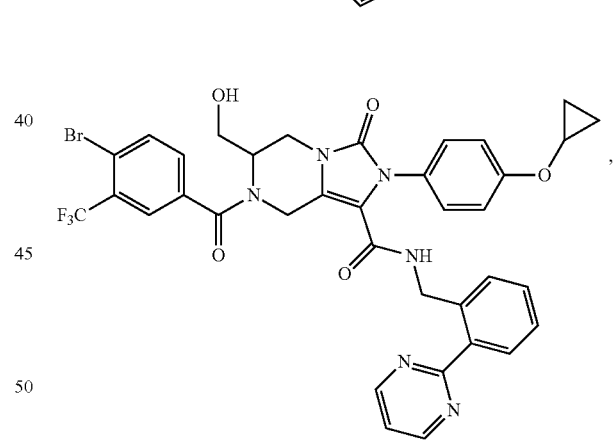
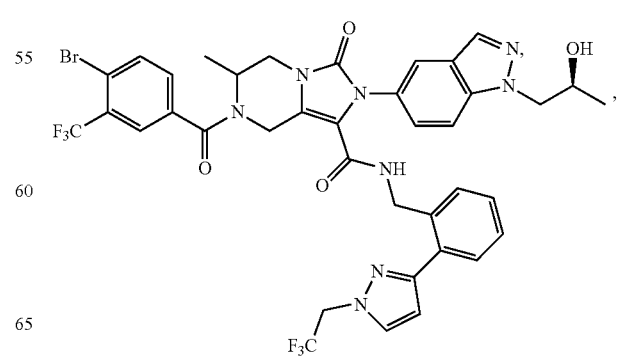

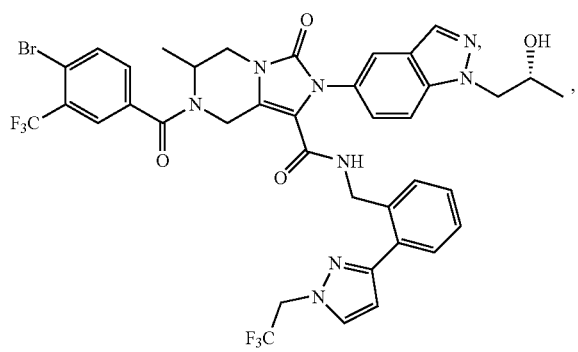
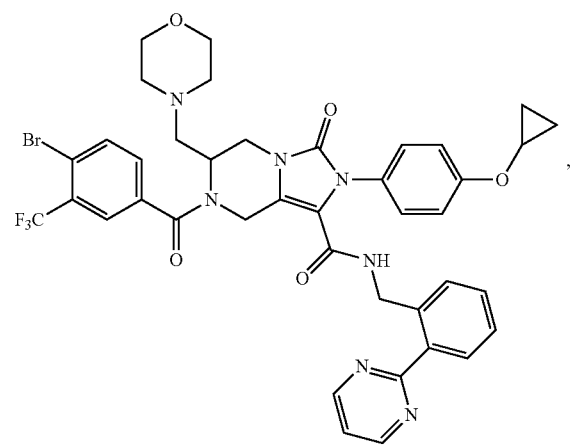
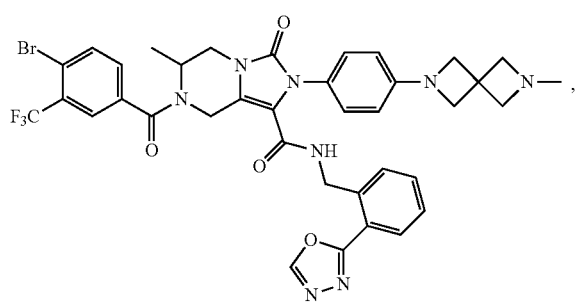
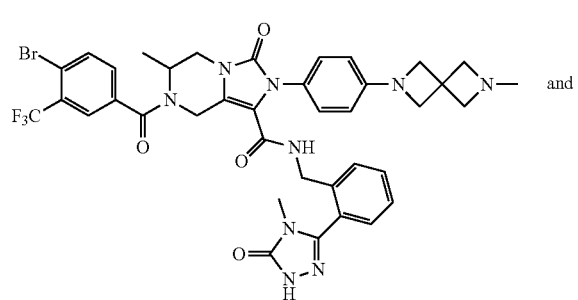
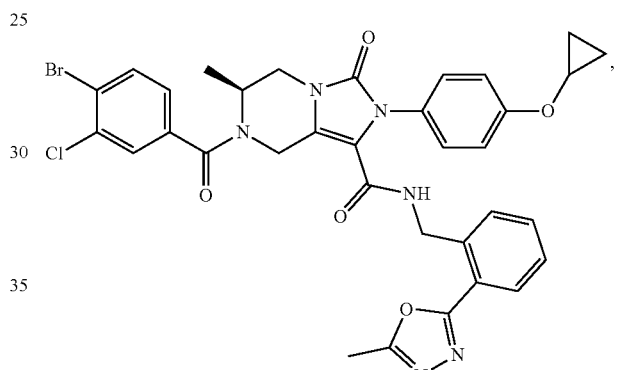
or a pharmaceutically acceptable salt of any of the foregoing.
Further examples of compounds of Formula (I), including pharmaceutically acceptable salts thereof, include the following:
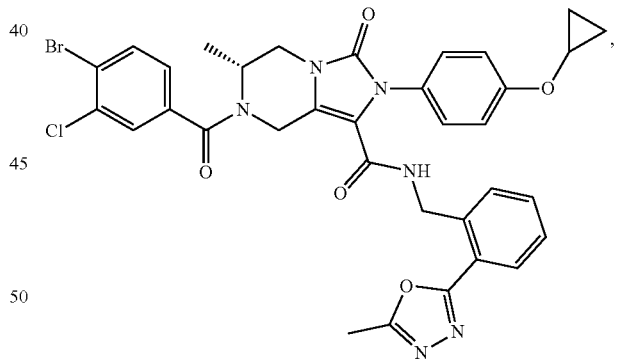
and 65
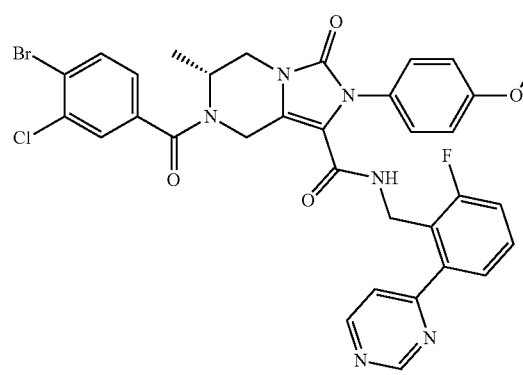
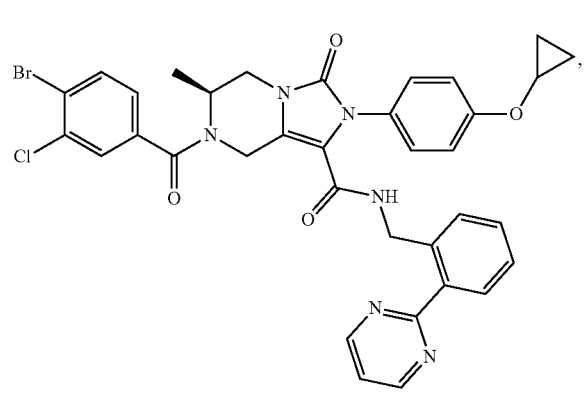
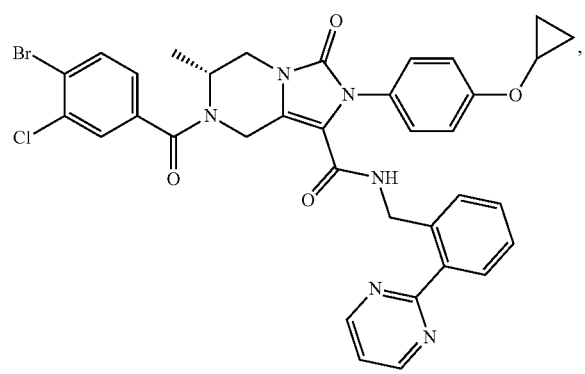
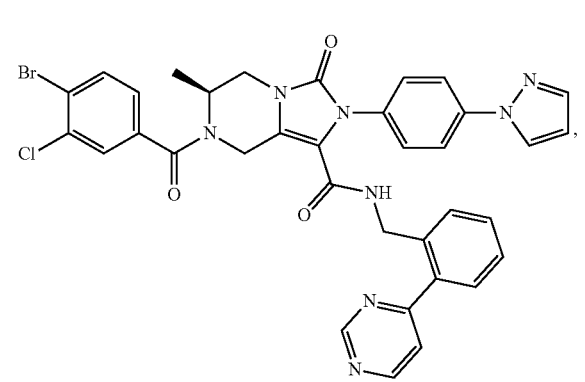
66
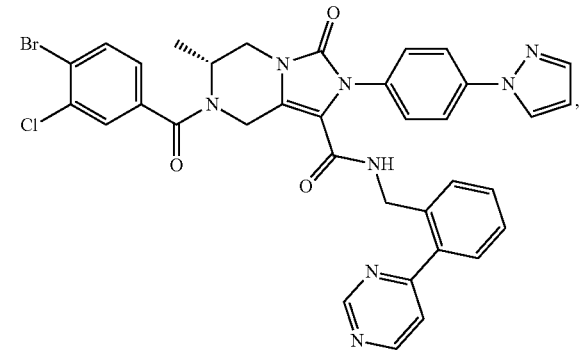
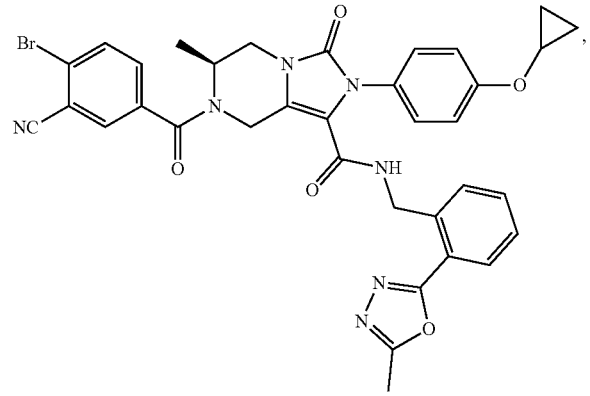
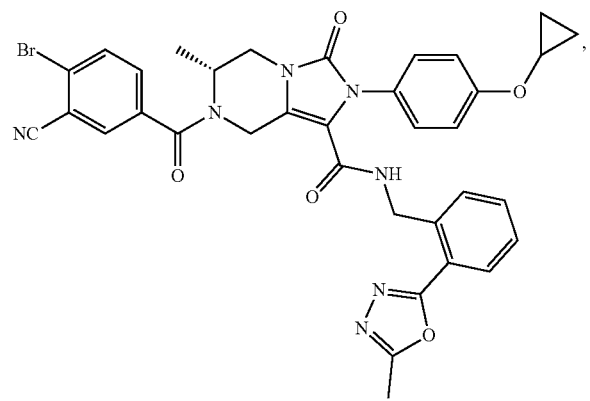
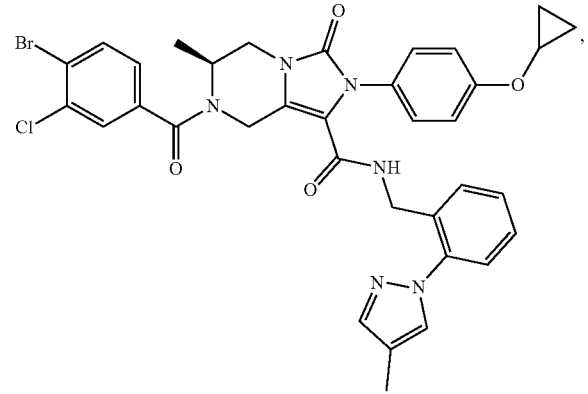

67
-continued
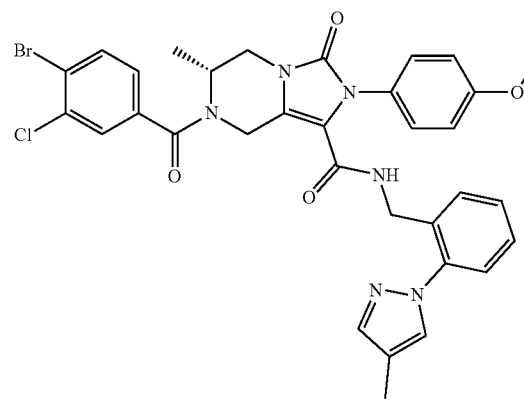
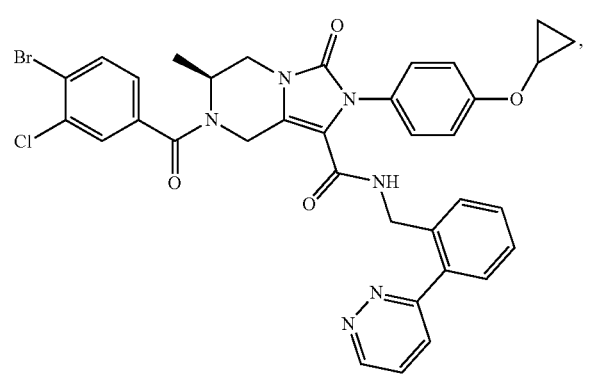
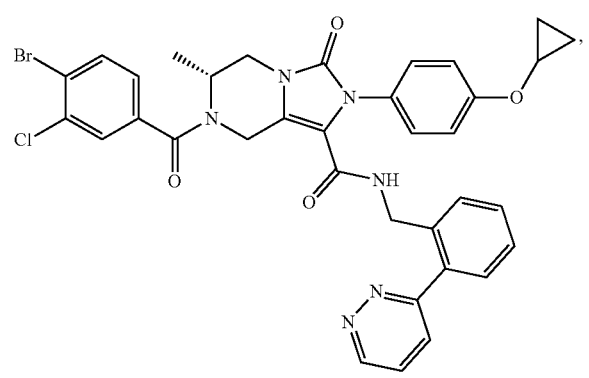
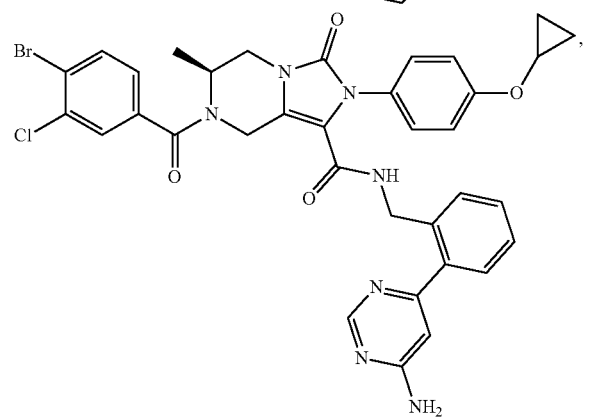
68
-continued
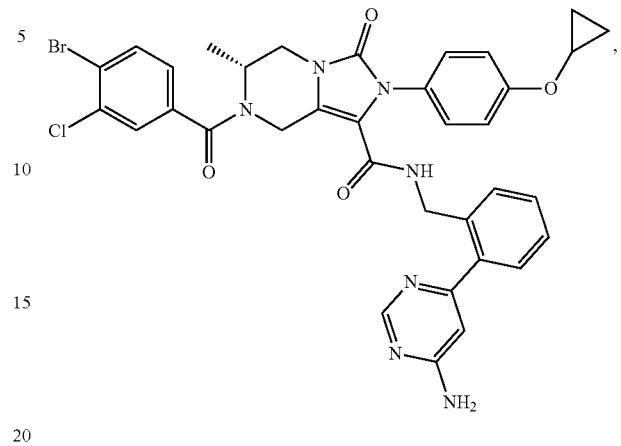
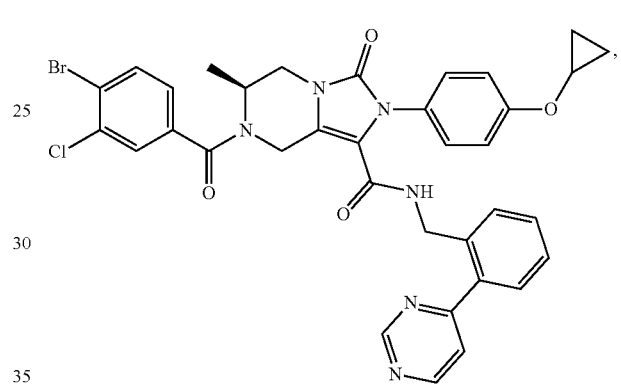
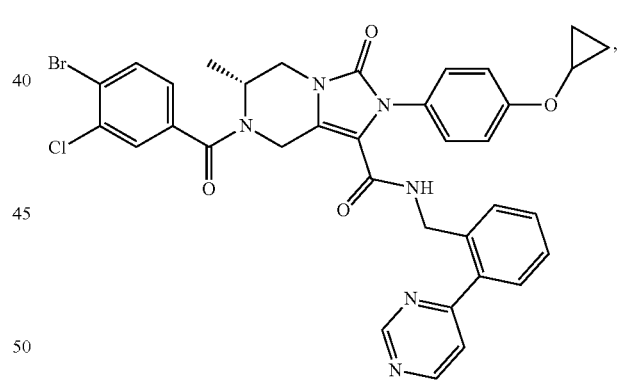
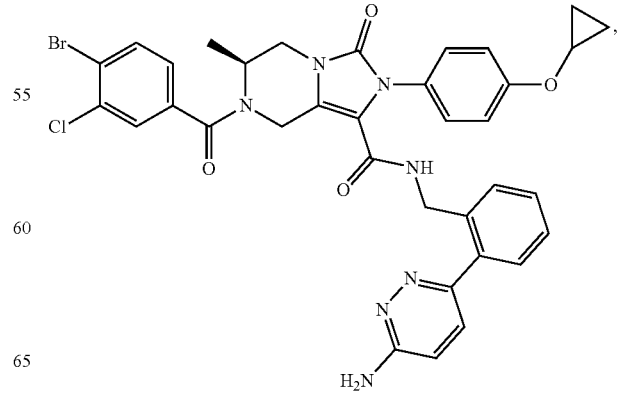

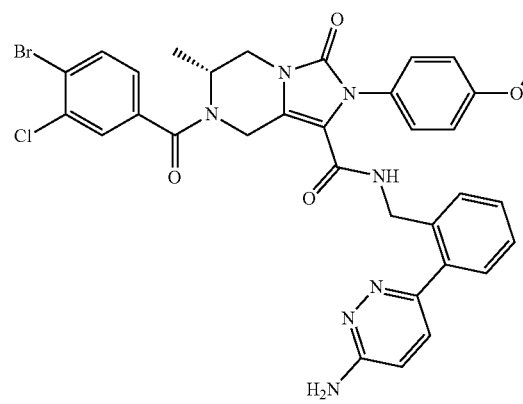
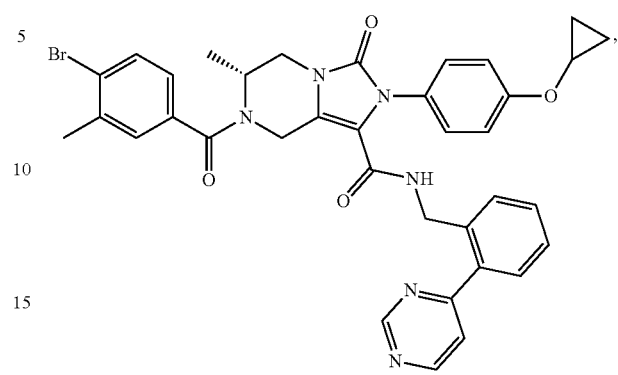
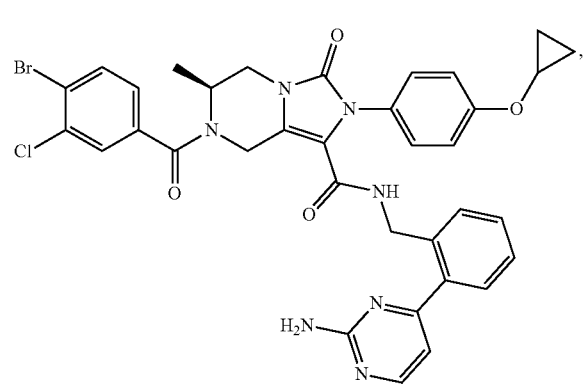
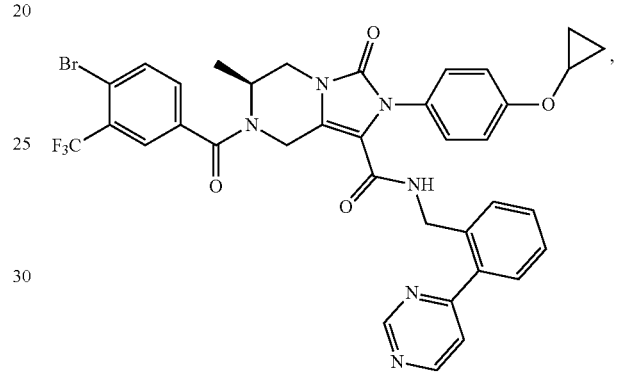
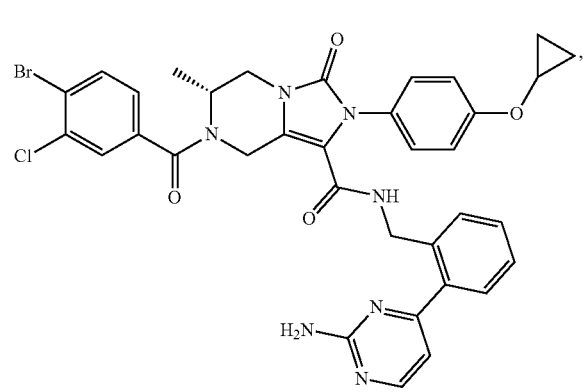
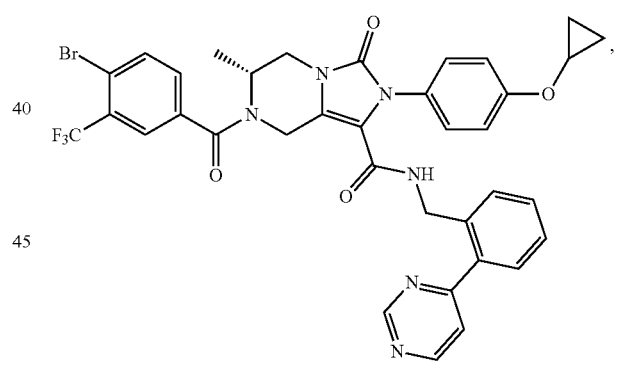
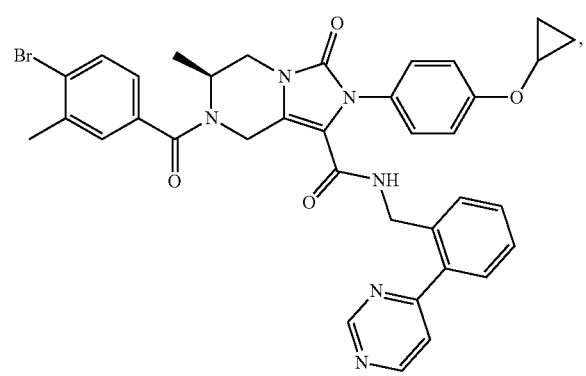
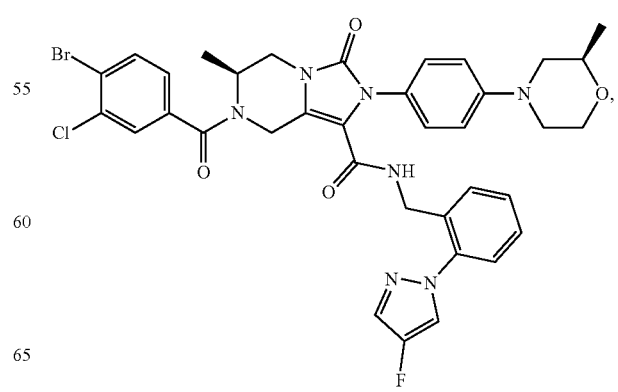

71
-continued
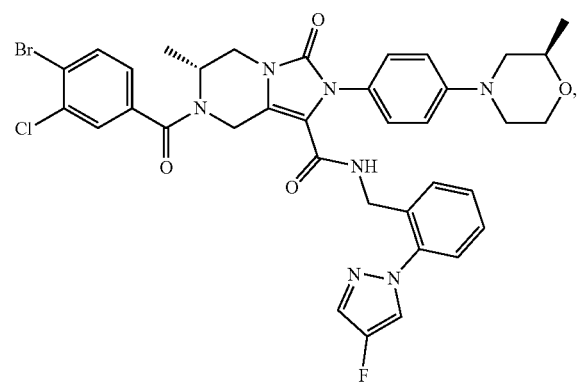
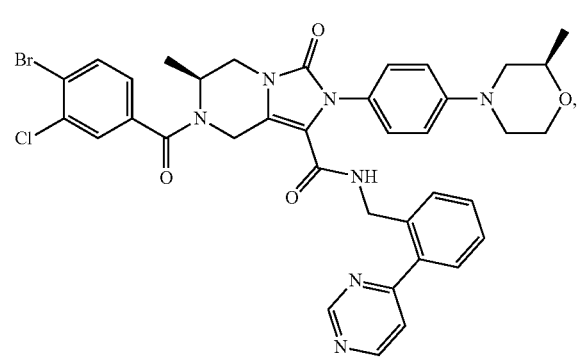
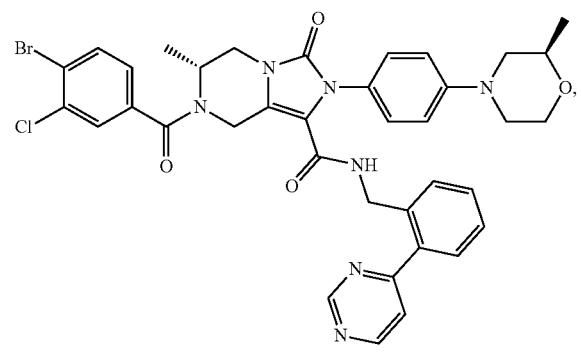
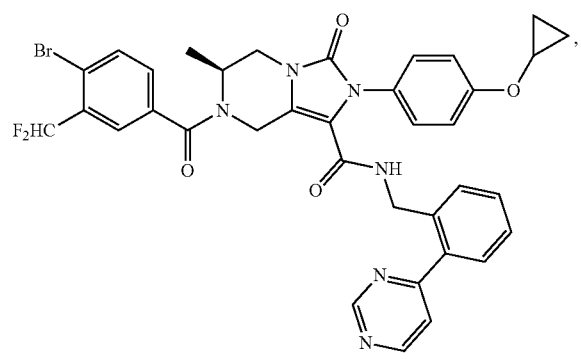
72
-continued
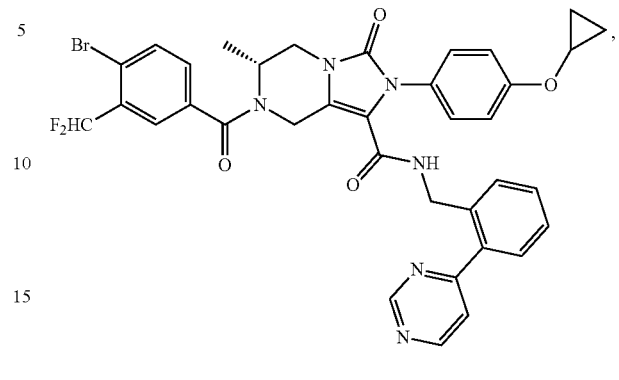
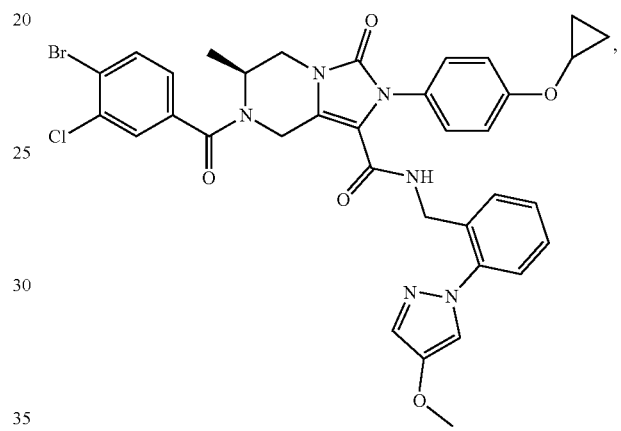
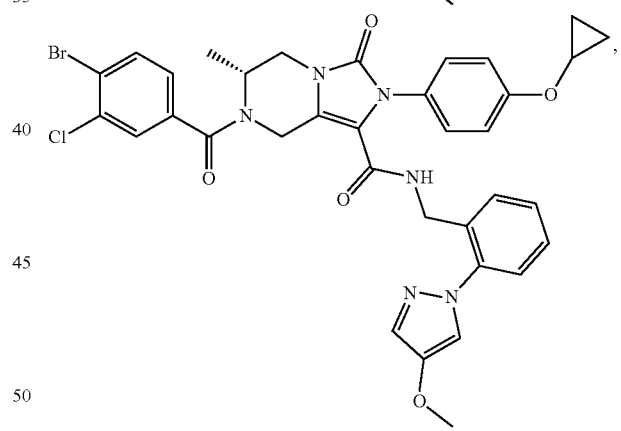
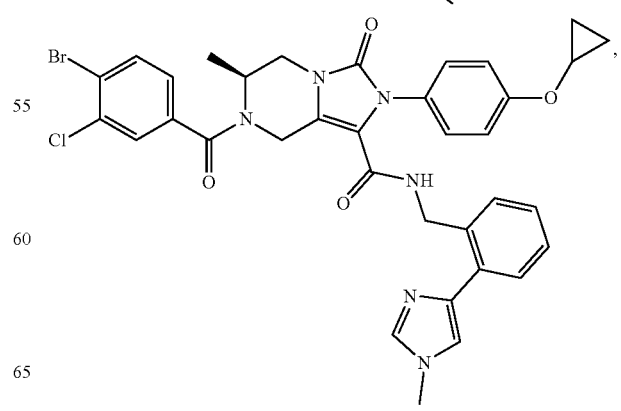

73
-continued
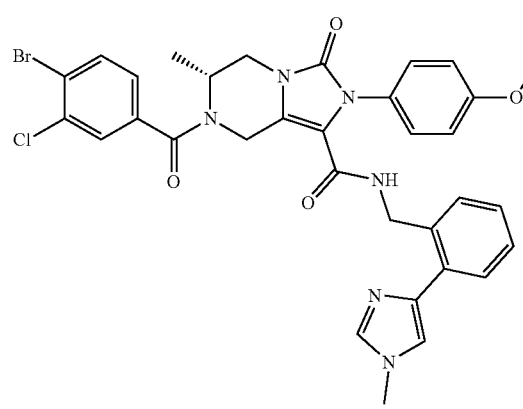
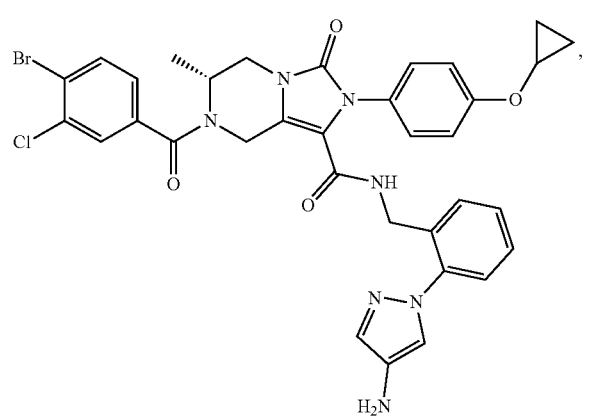
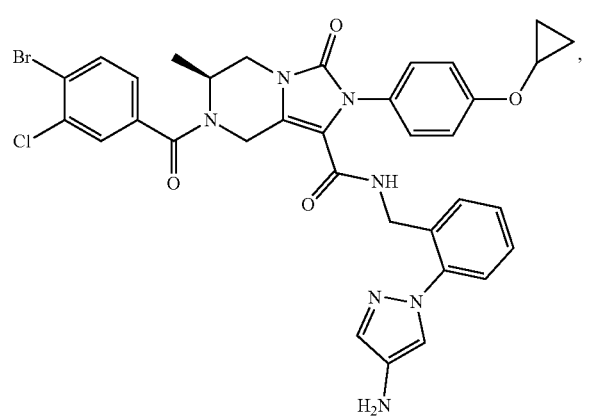
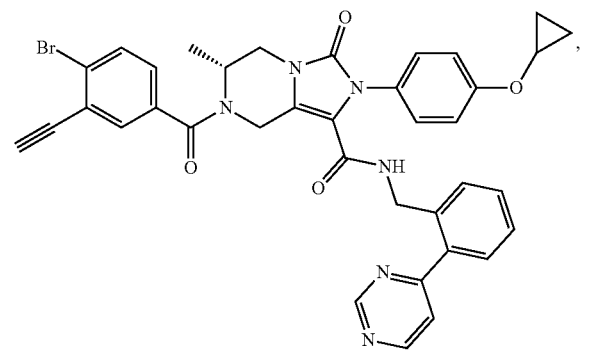
74
-continued
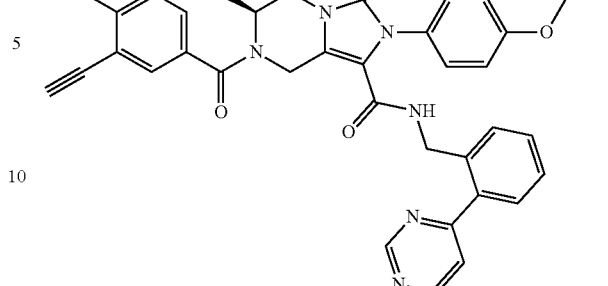
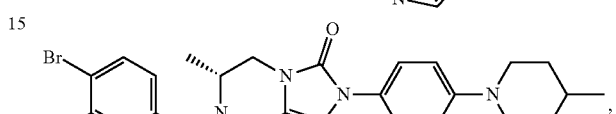
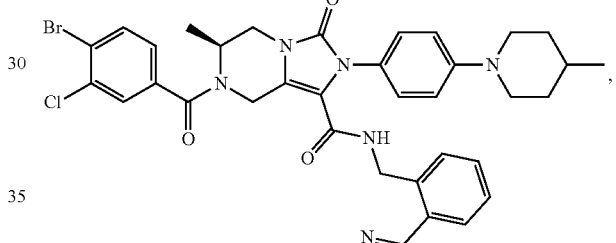
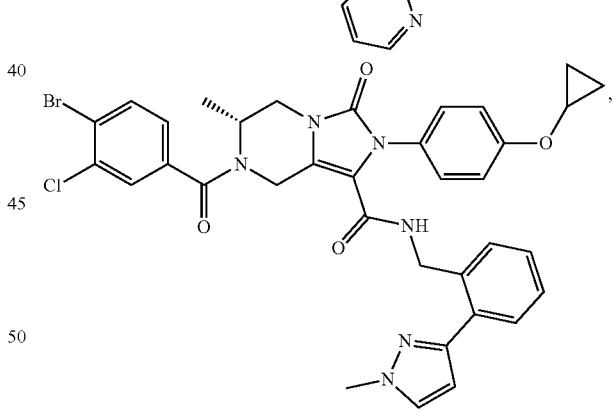
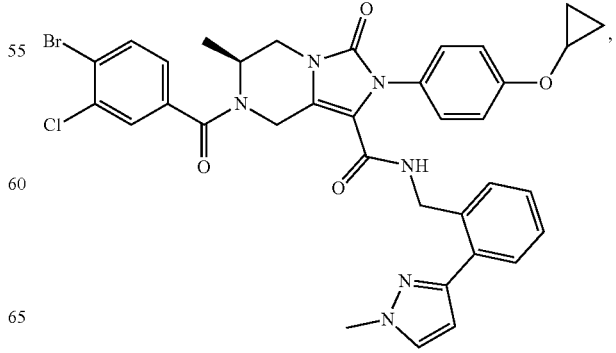

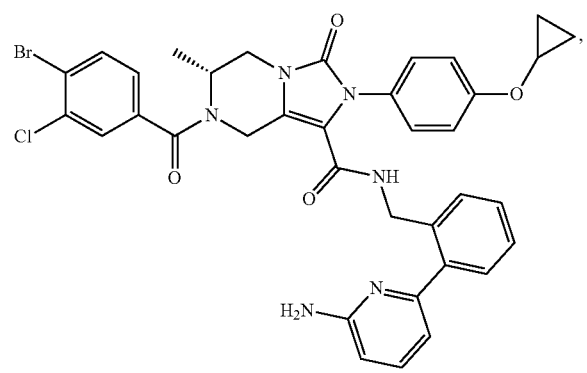
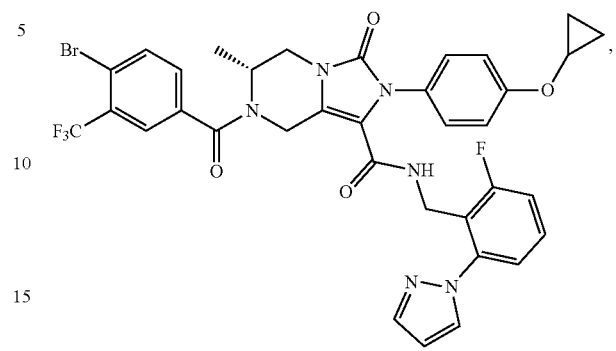
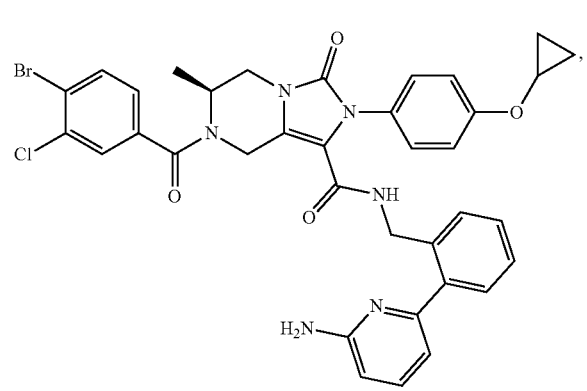
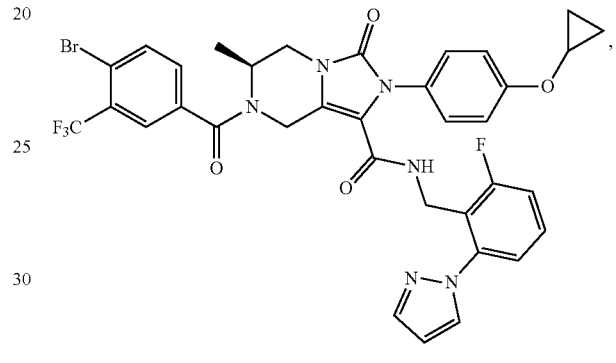
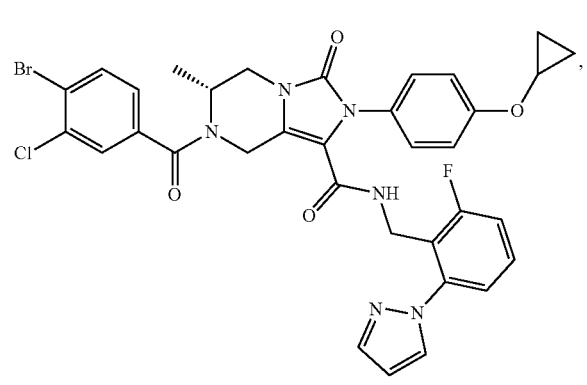
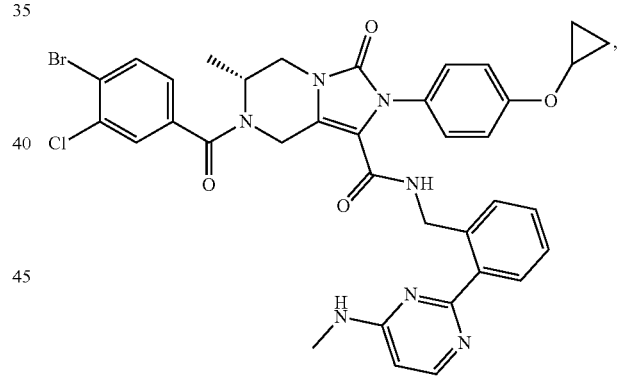
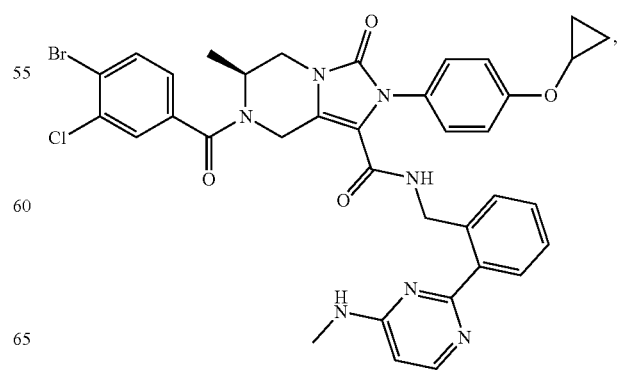

77
-continued
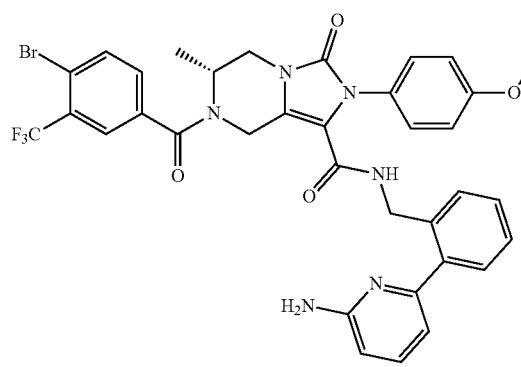
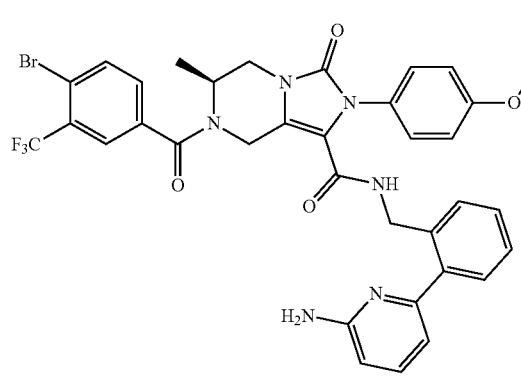
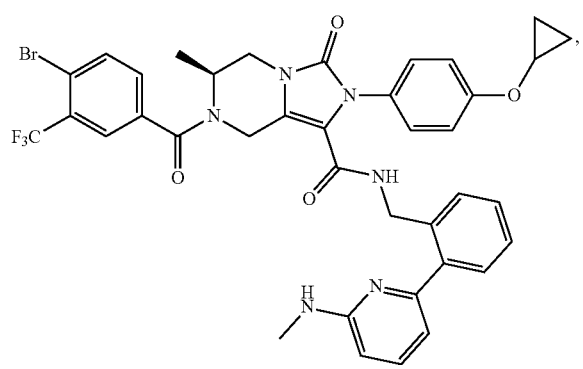
78
-continued
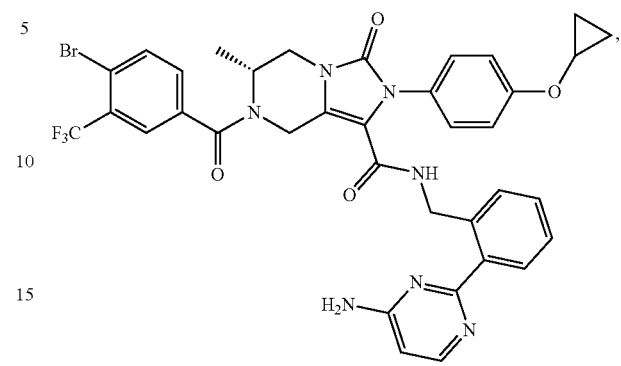
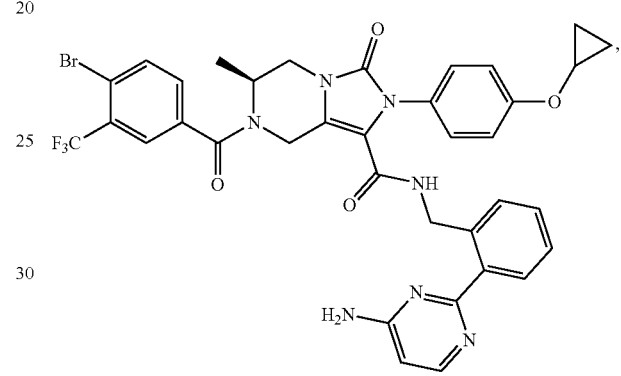
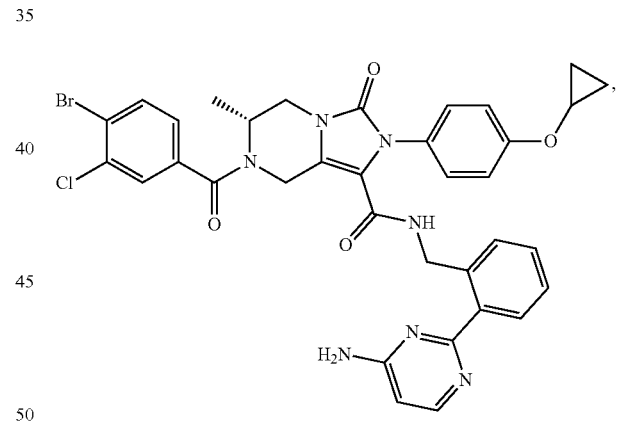
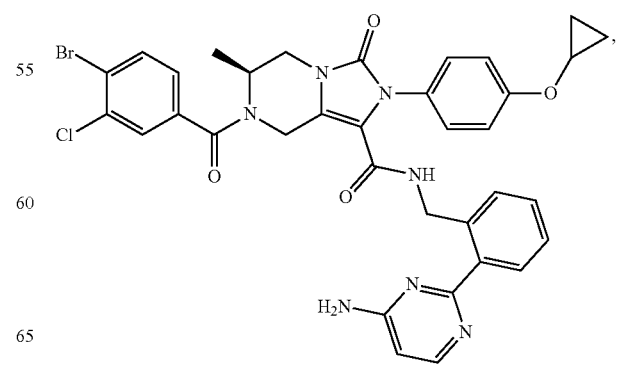

79
-continued
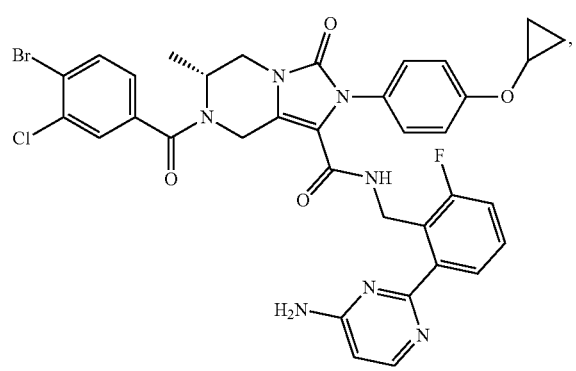
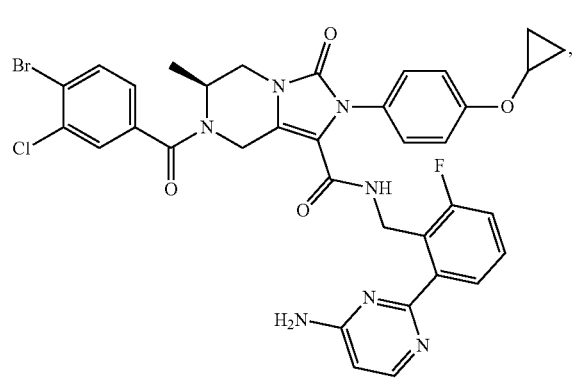
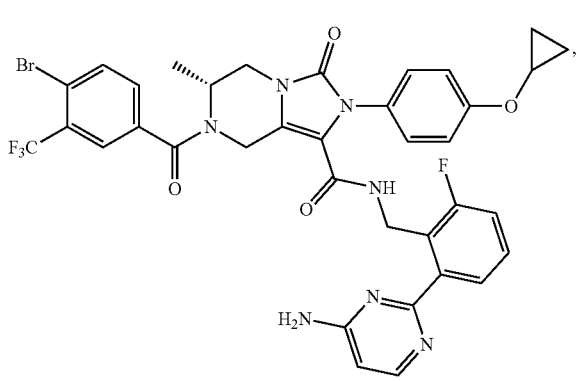
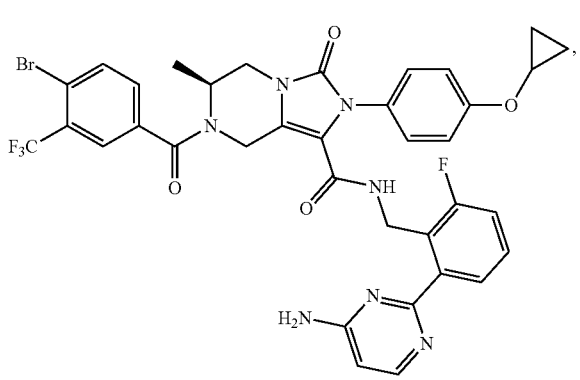
80
-continued
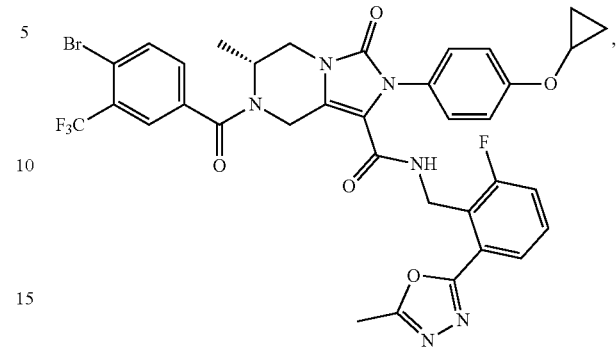
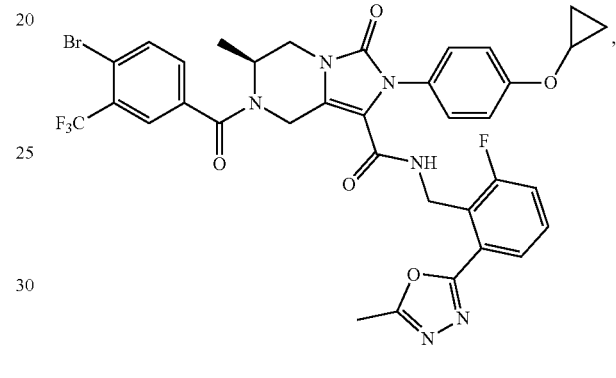
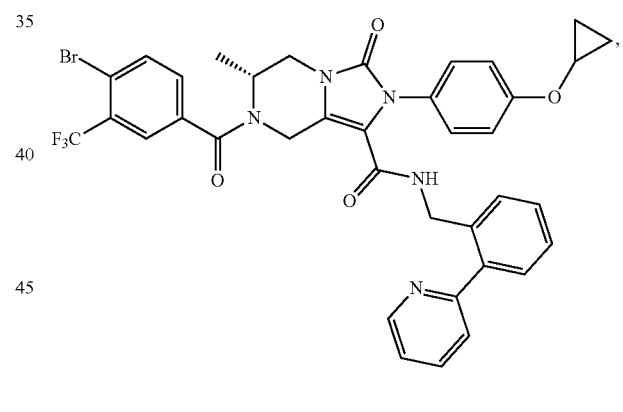

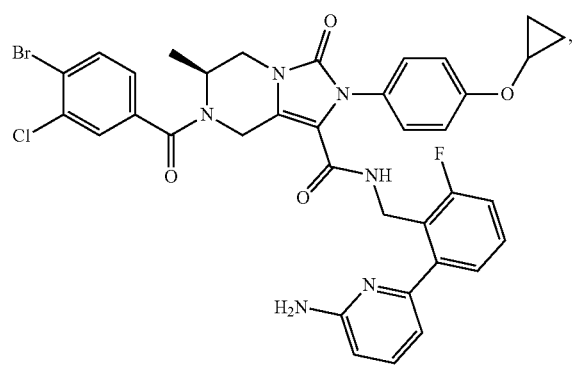
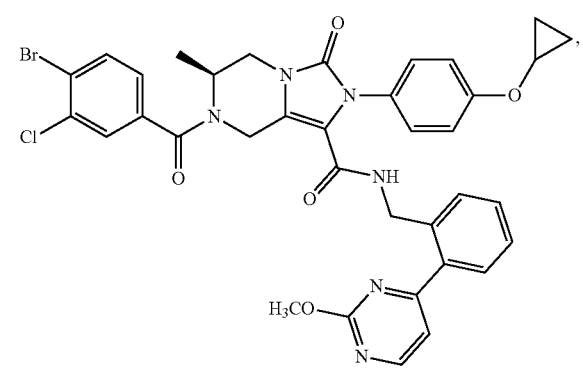
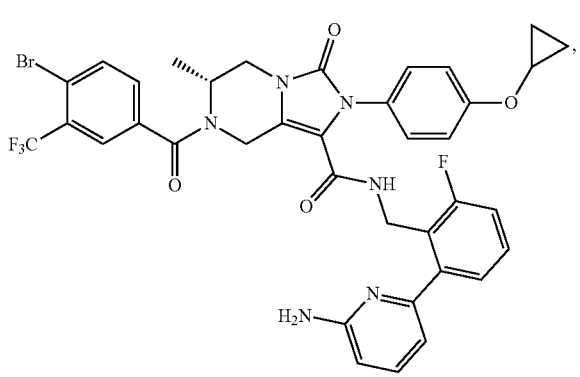
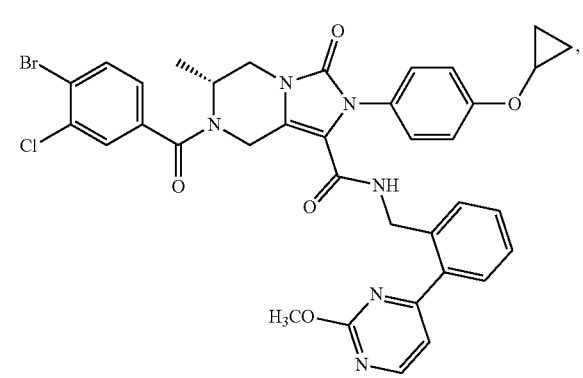
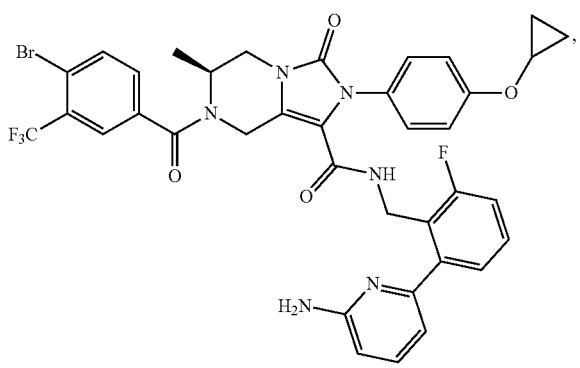
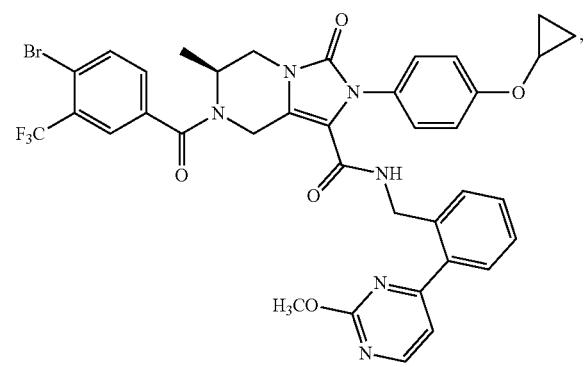
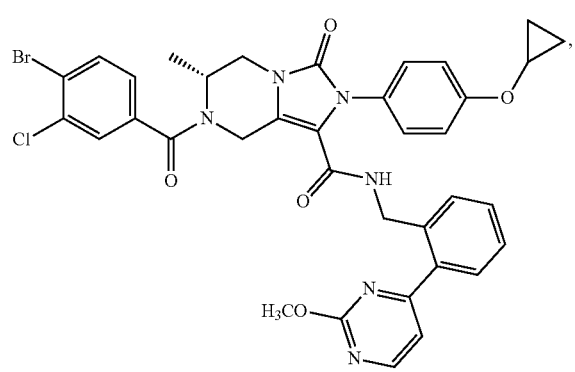
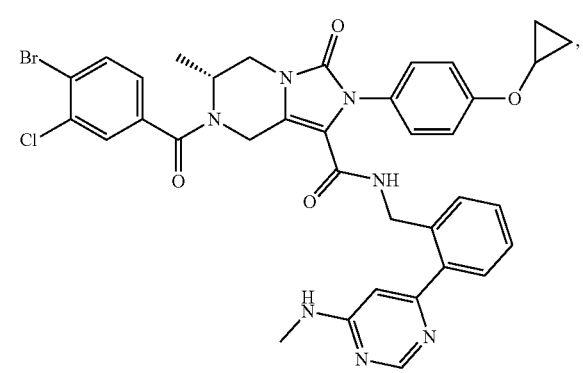

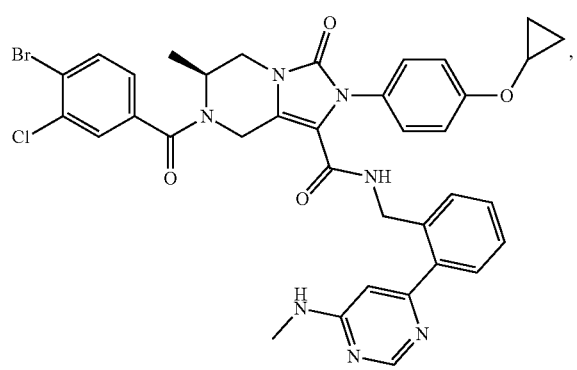
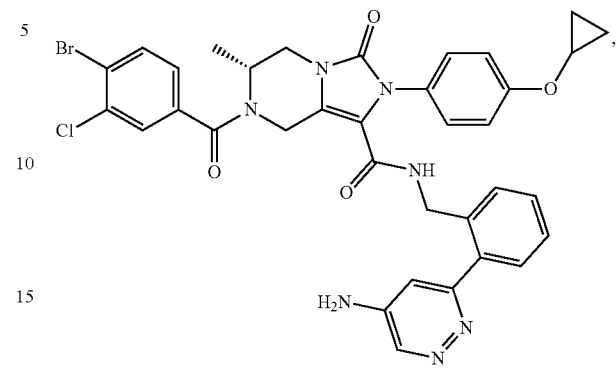
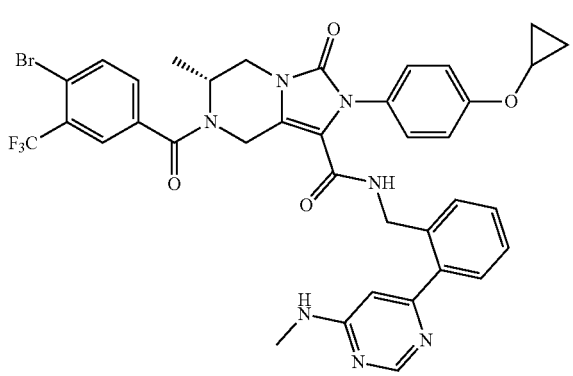
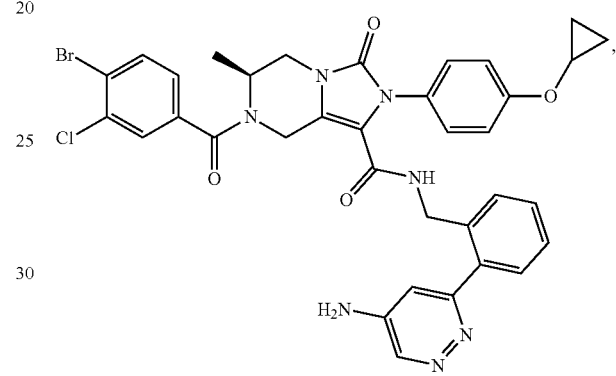
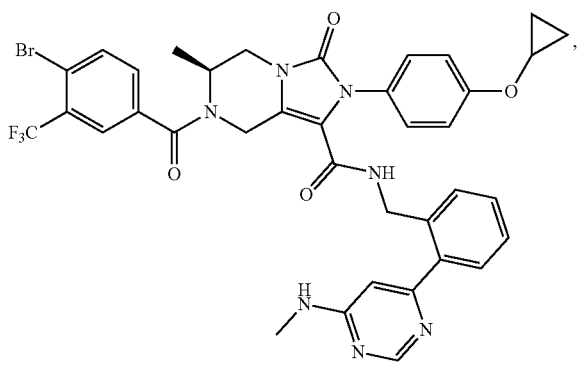
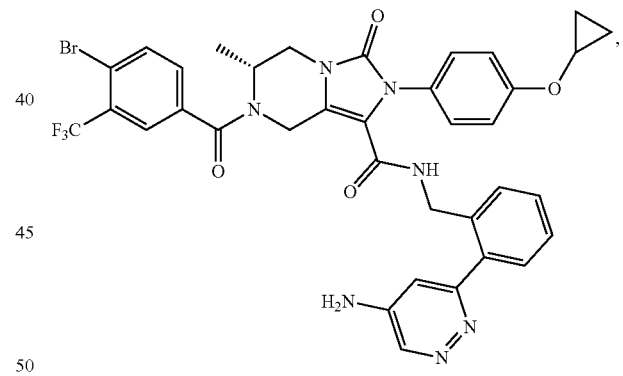
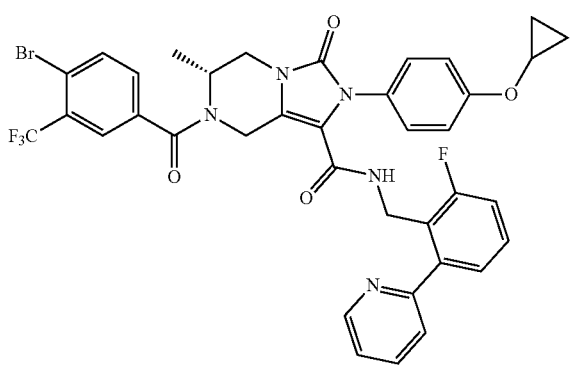

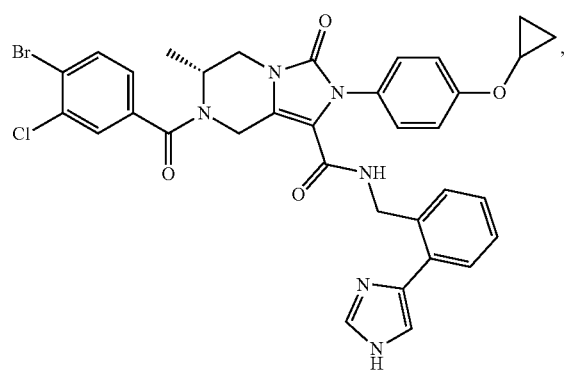
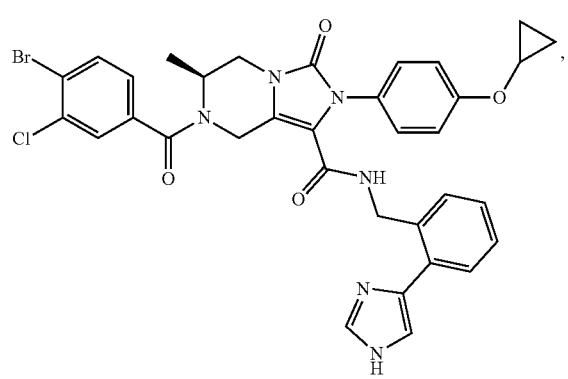
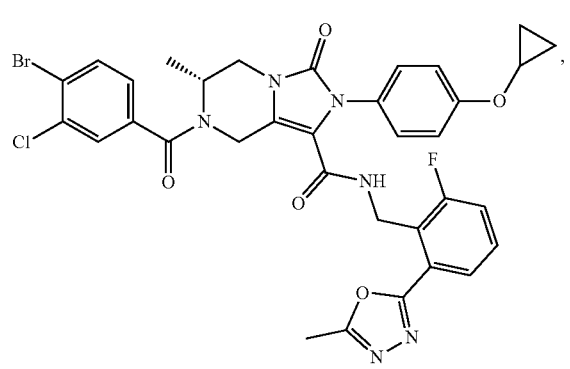
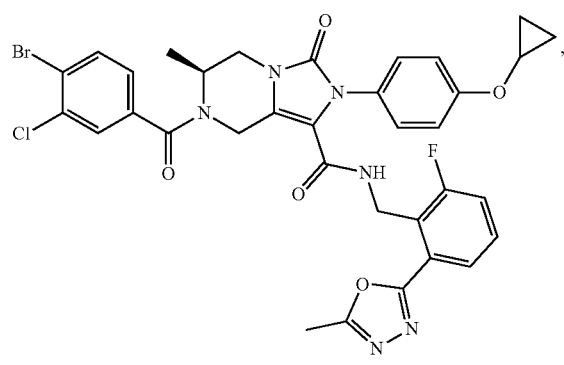
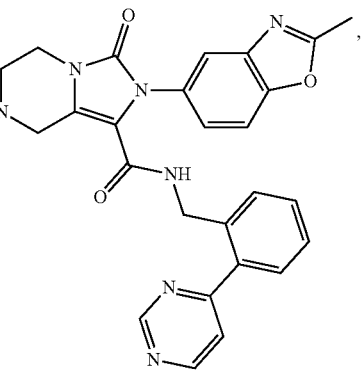
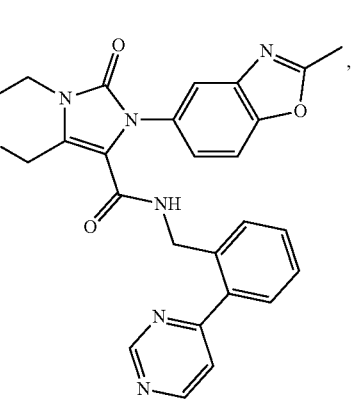
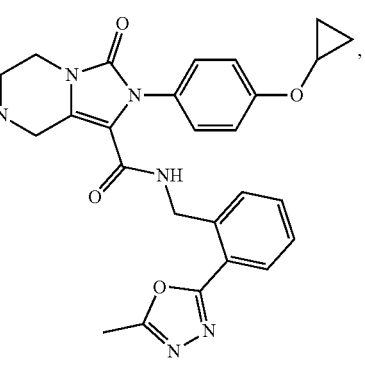
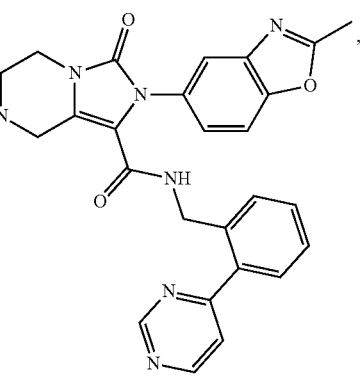

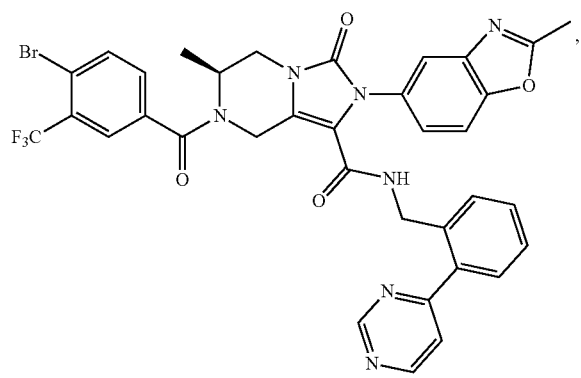
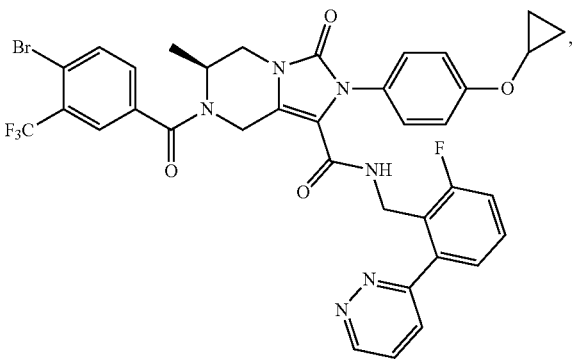

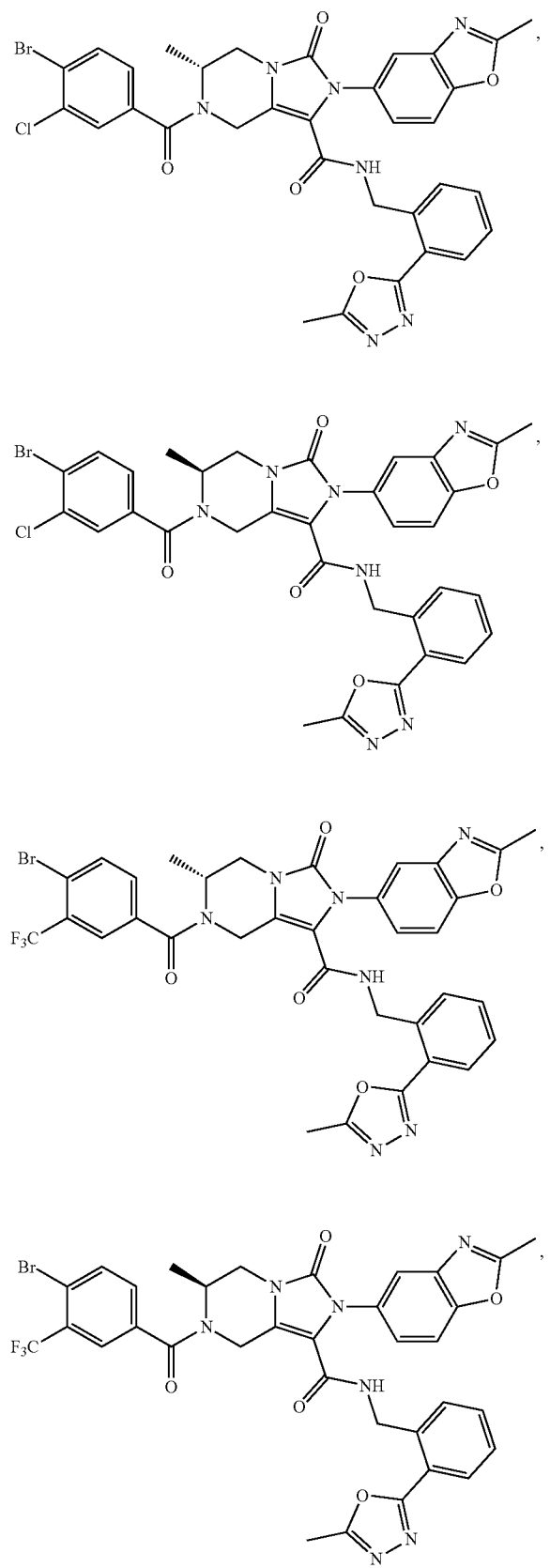
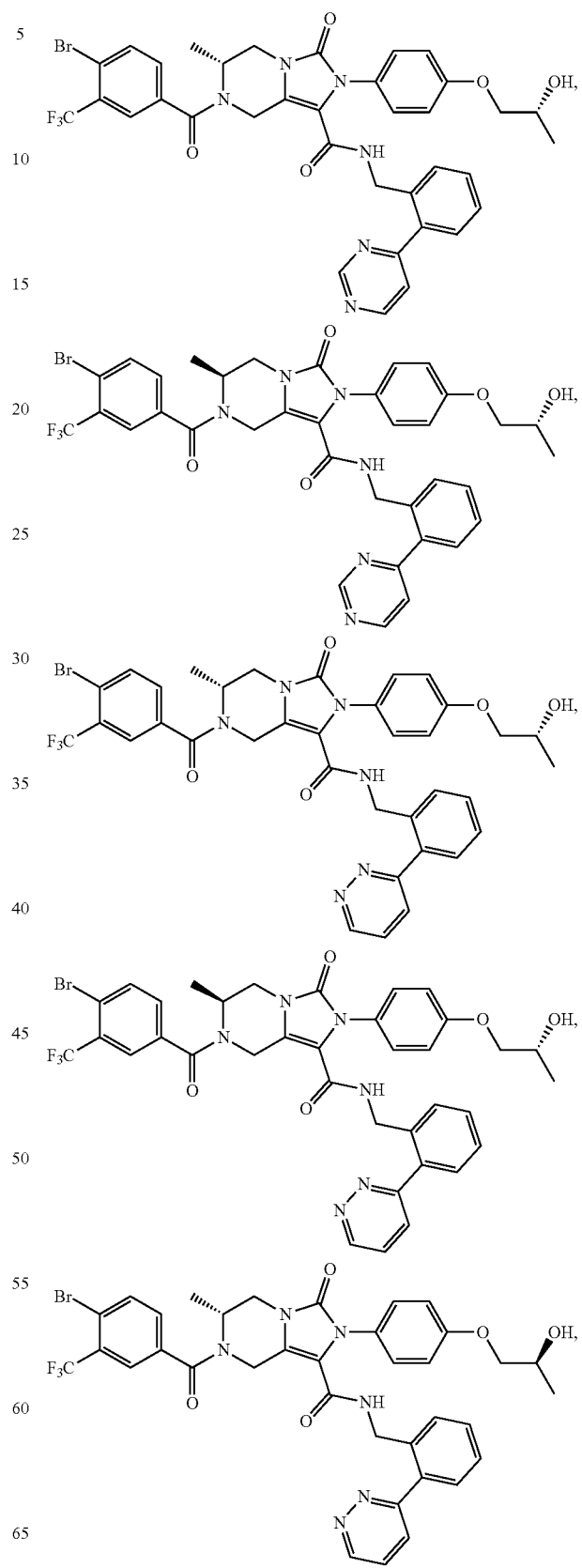

91
-continued
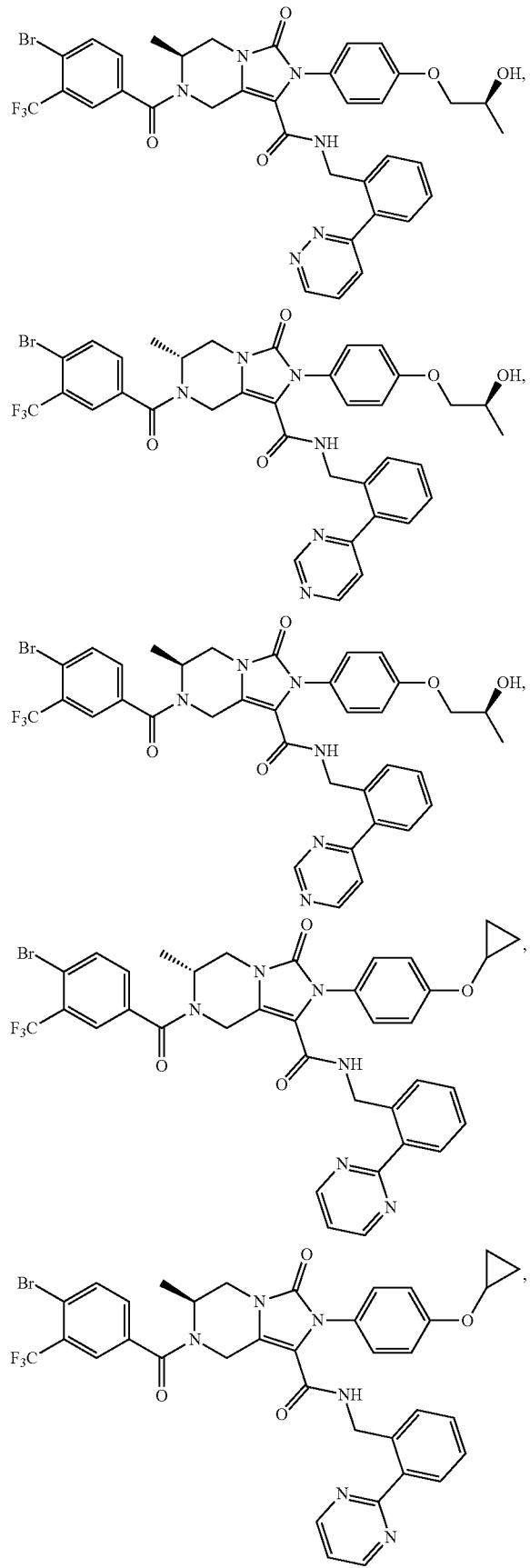
92
-continued
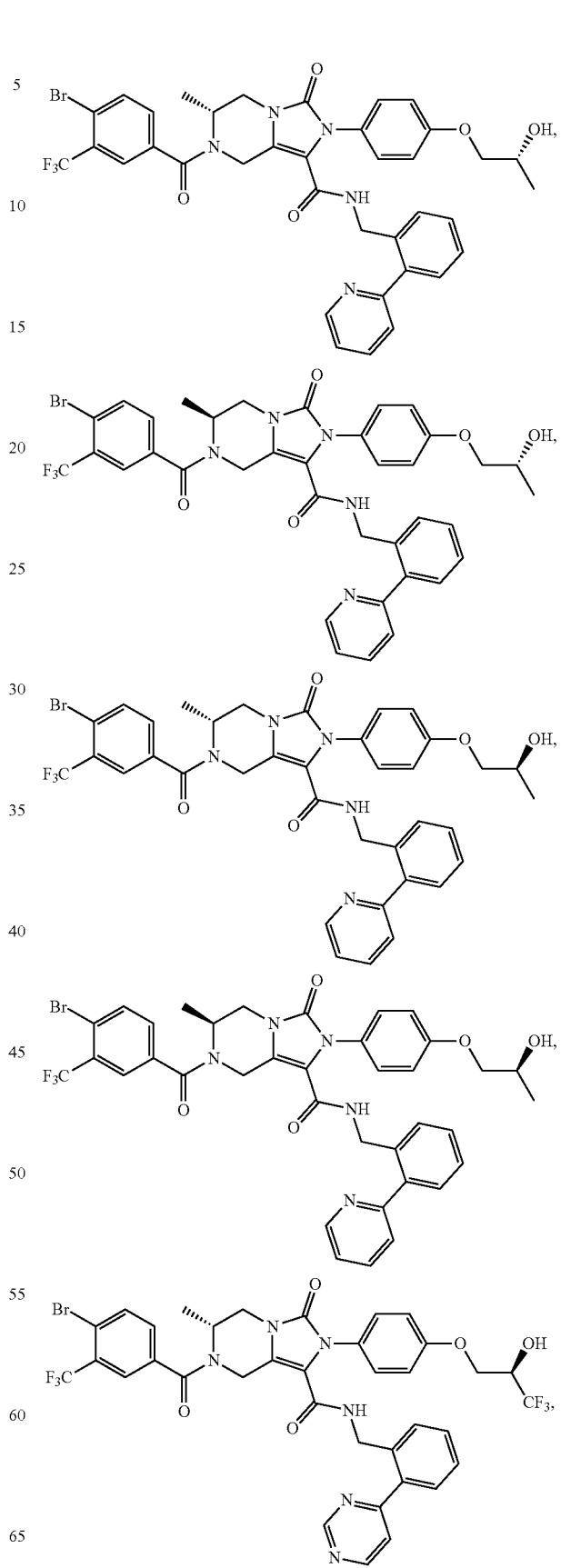

93
-continued
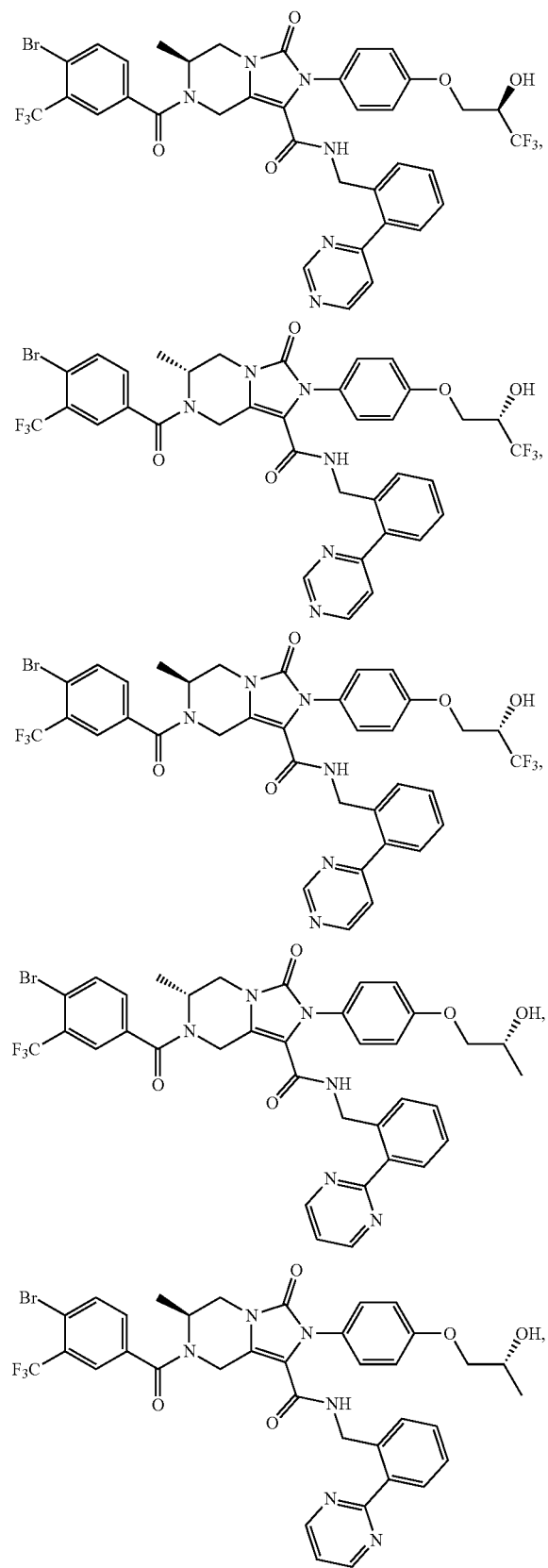
94
-continued
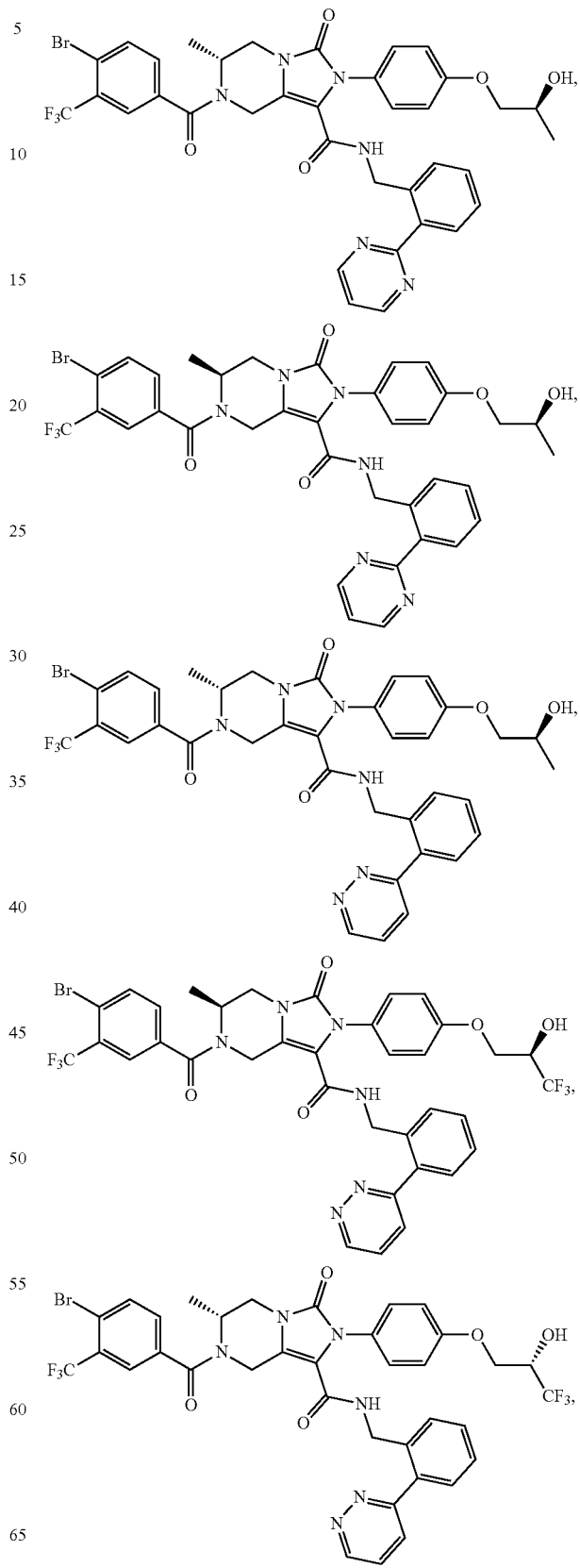

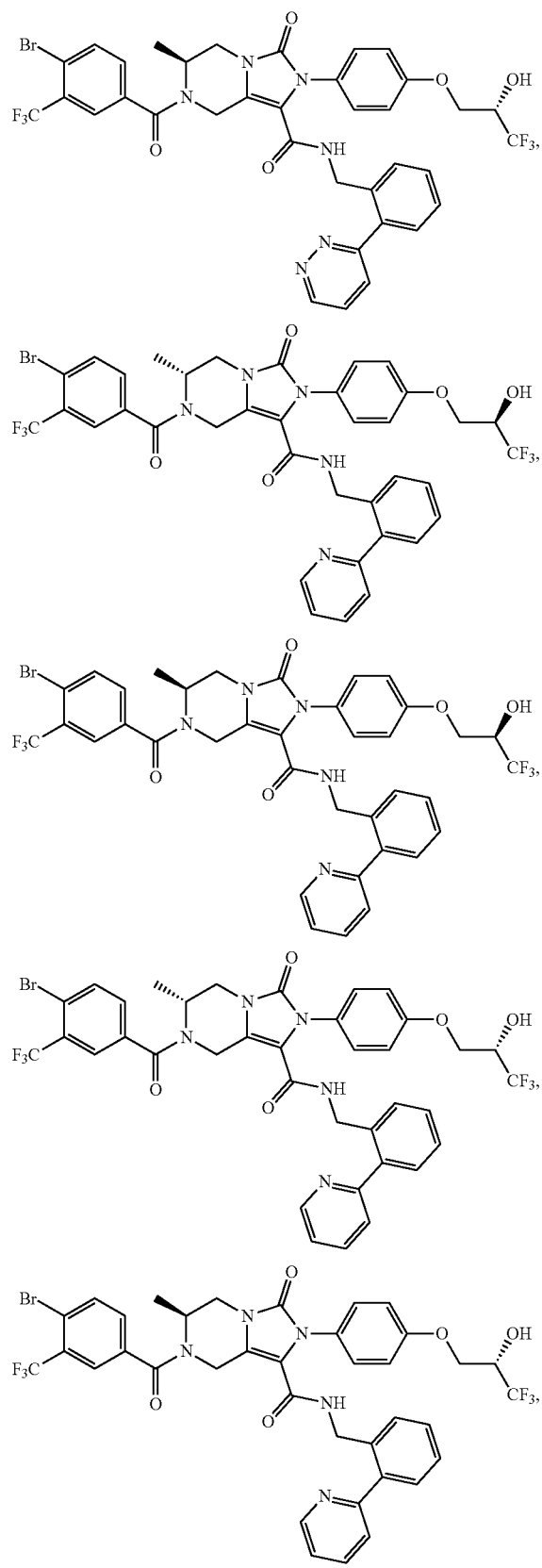
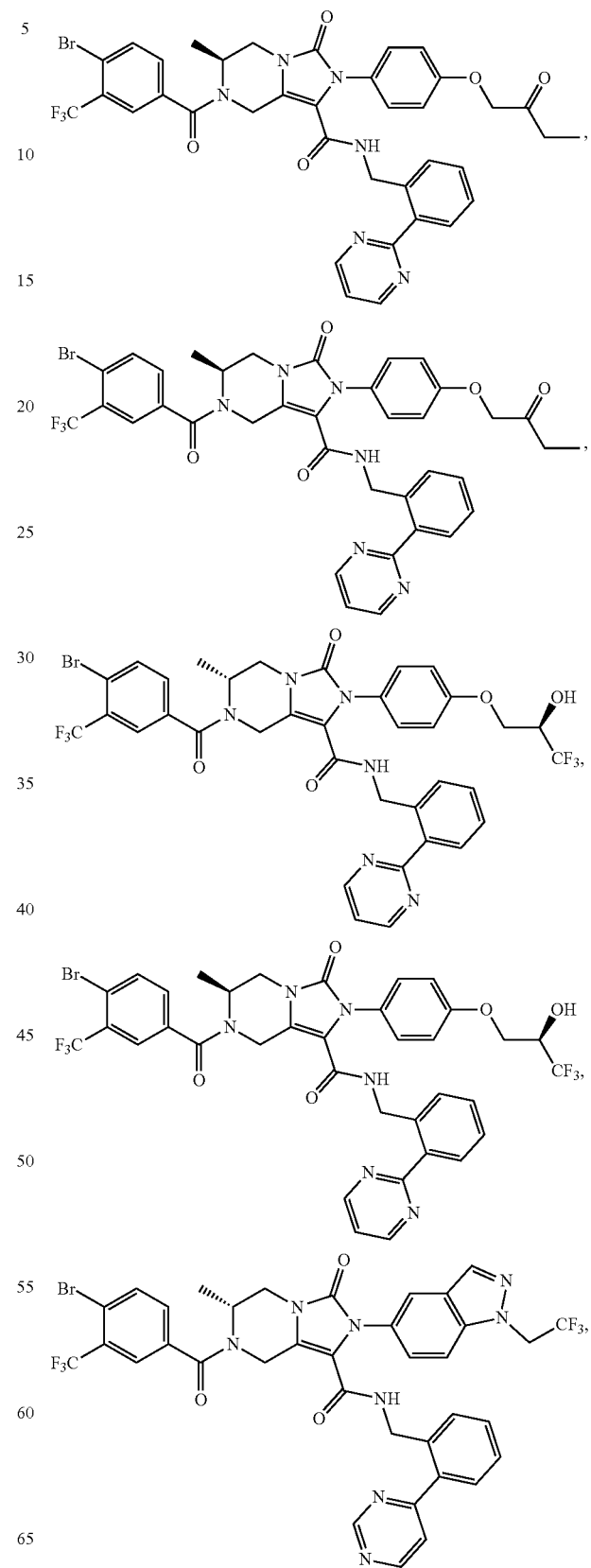

97
-continued
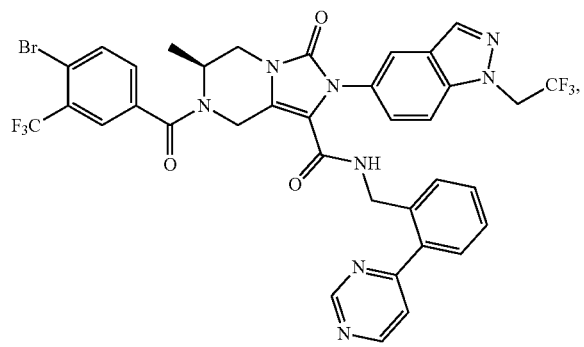
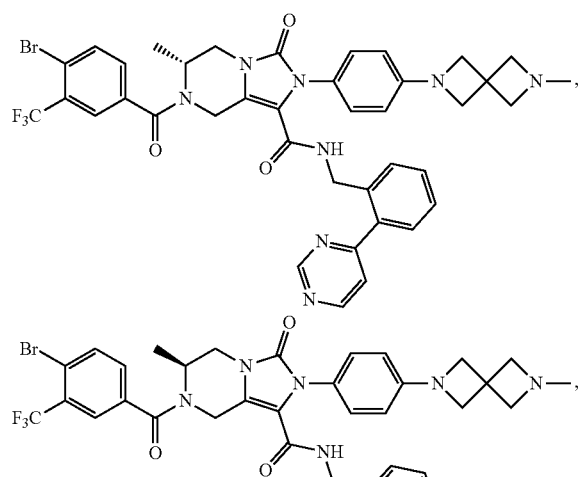
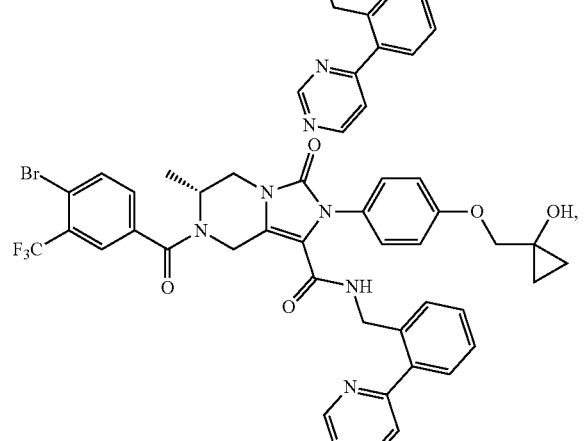
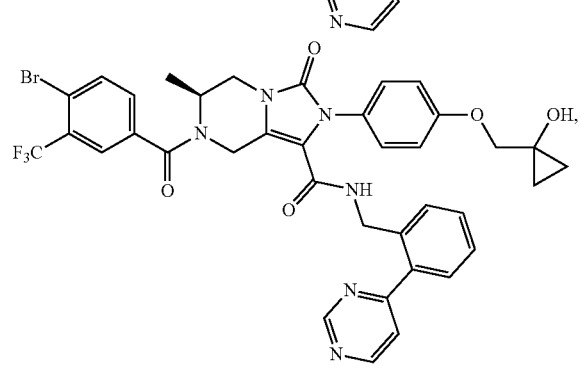
98
-continued
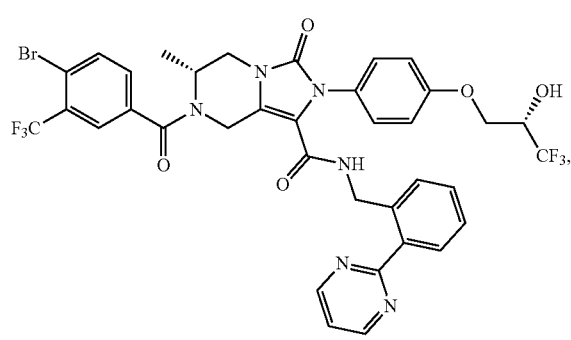
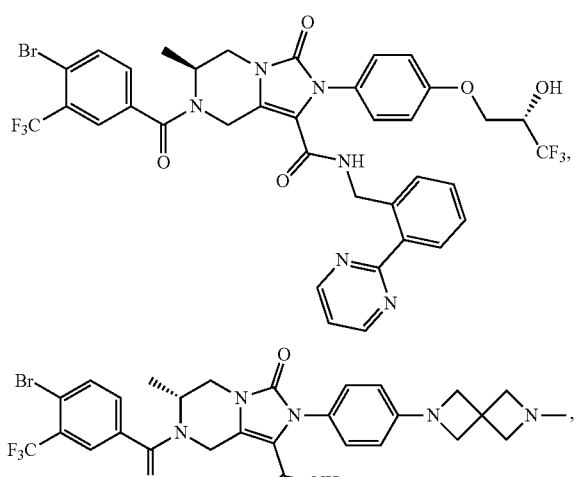
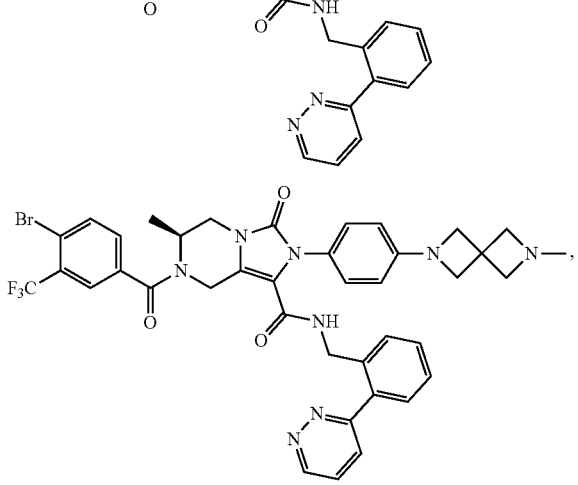
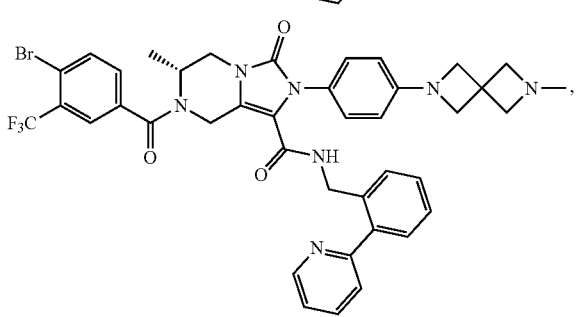

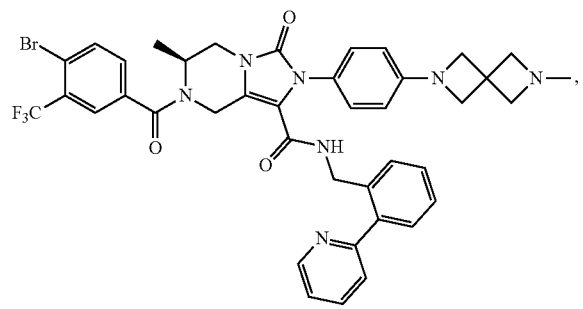
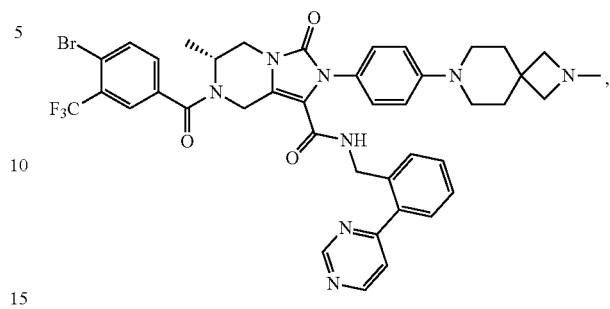
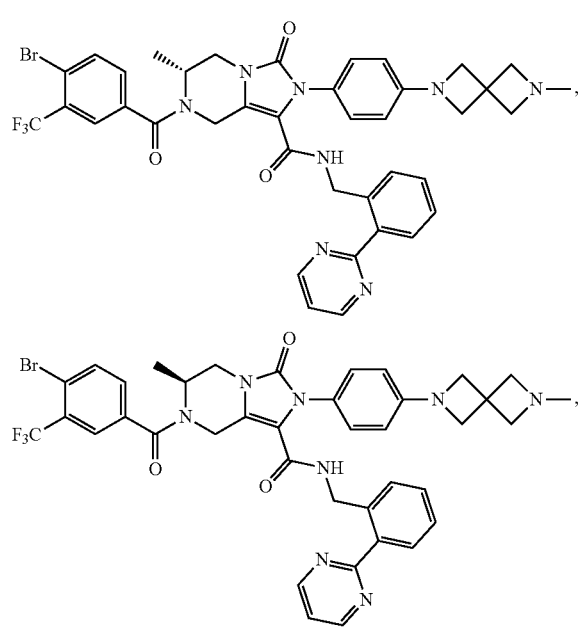
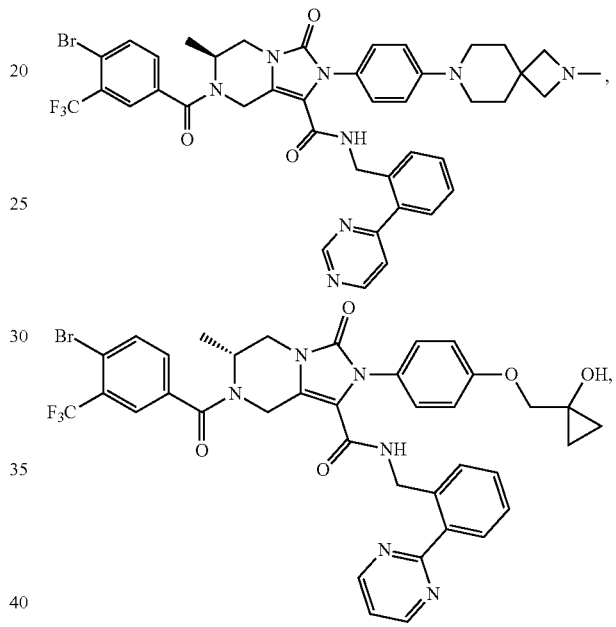
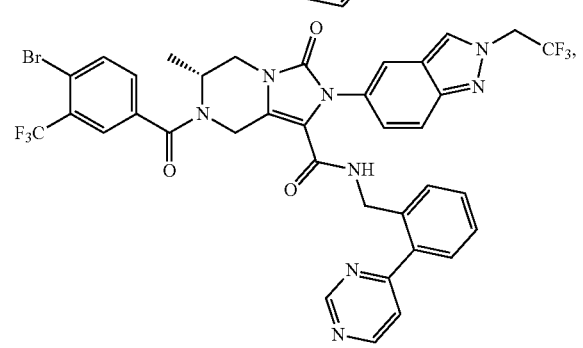
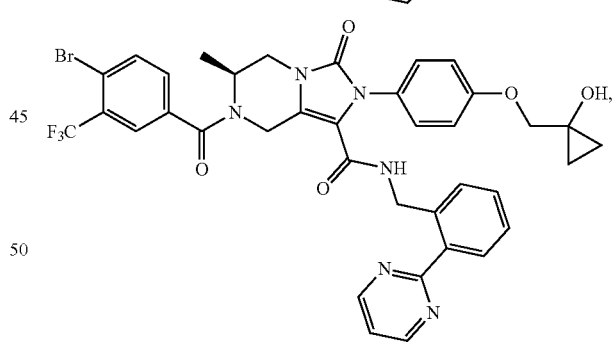
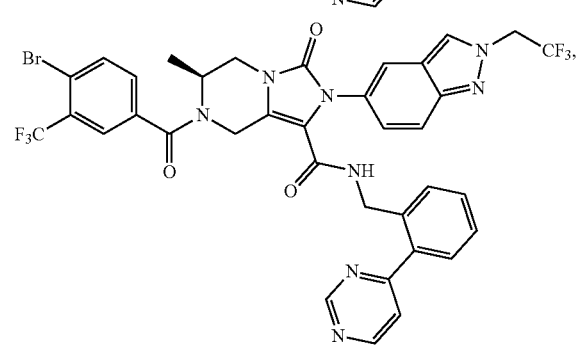
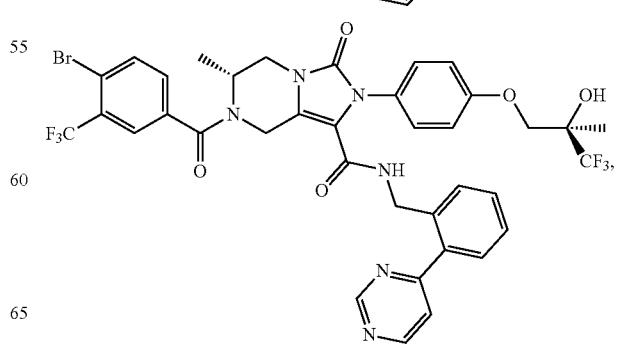

101
-continued
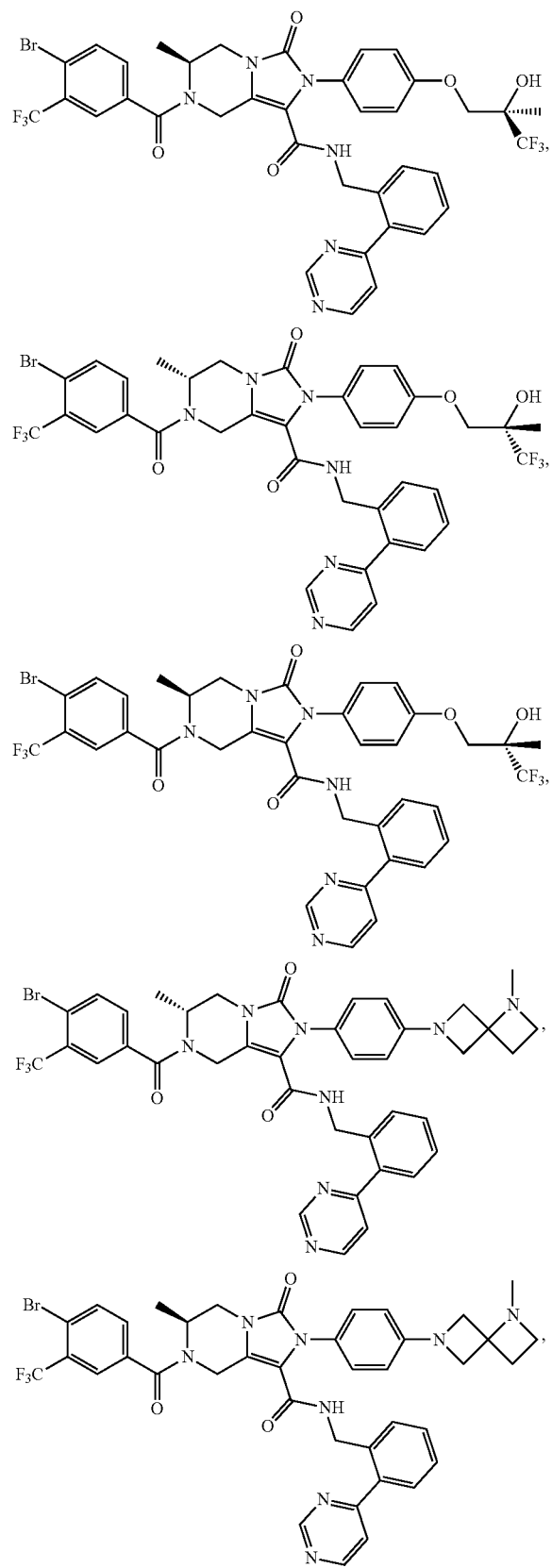
102
-continued
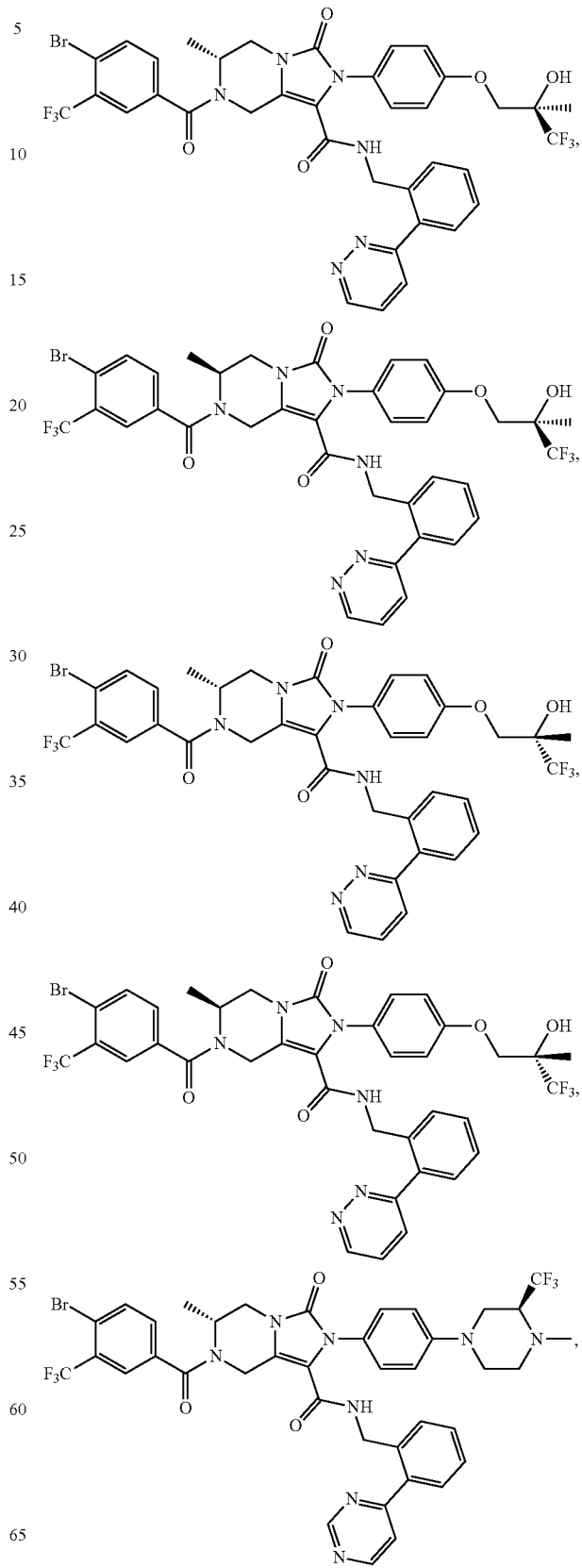

-continued
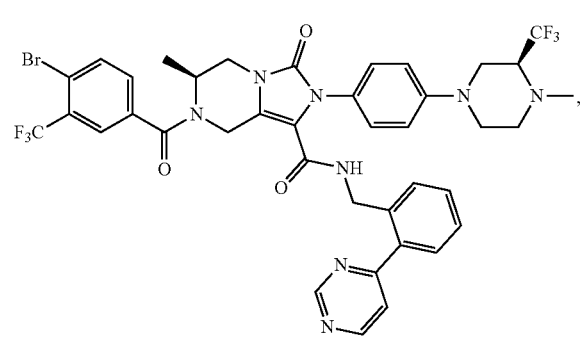
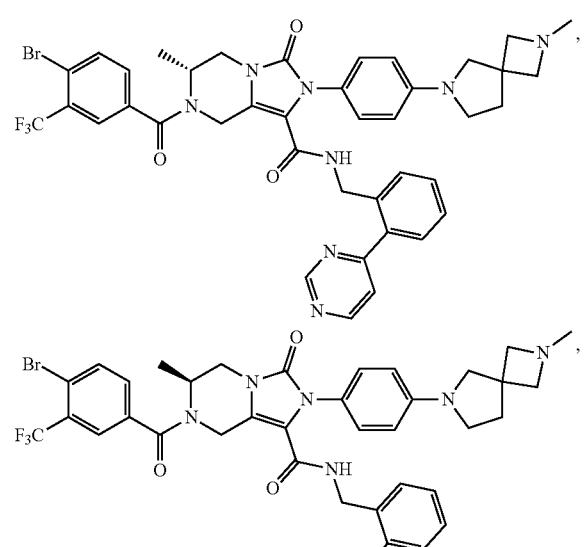
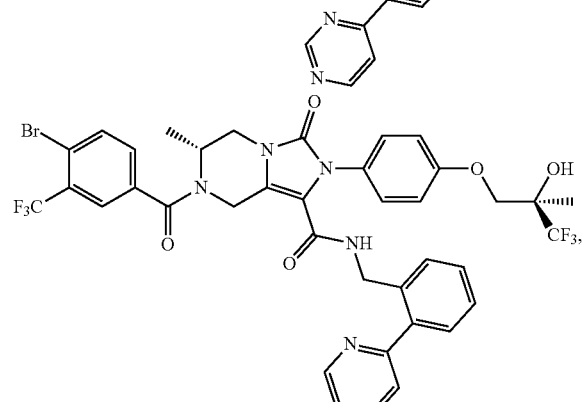
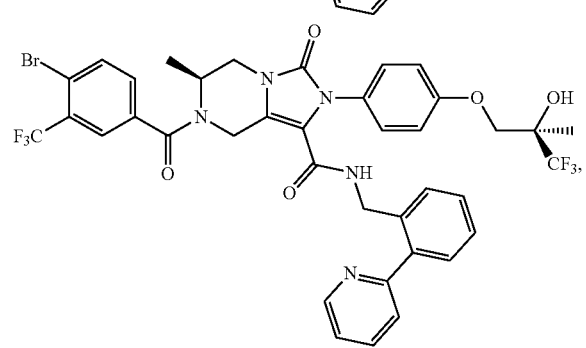
-continued
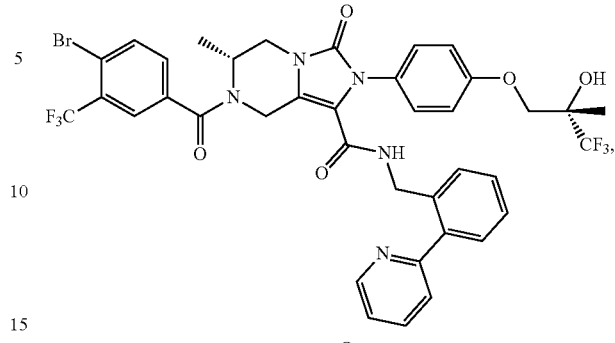
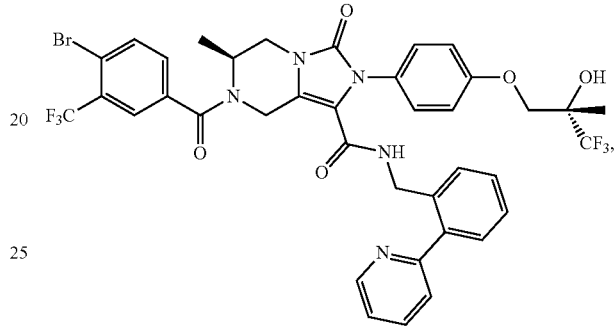

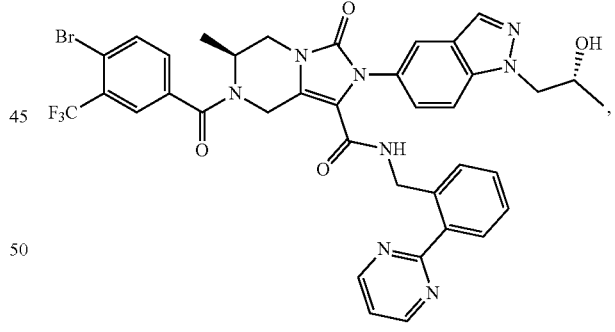
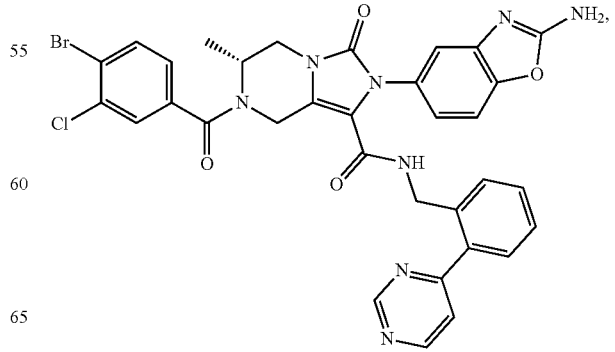

105
-continued
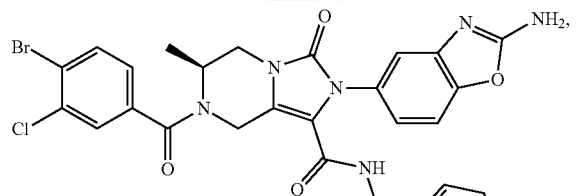
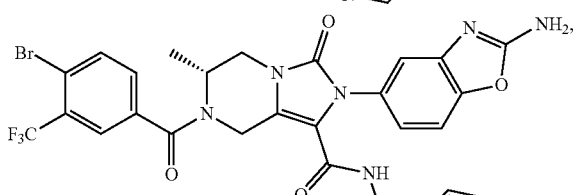
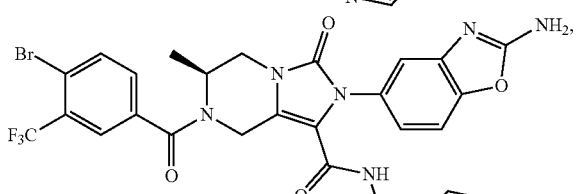
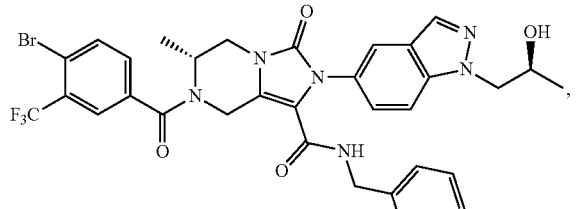
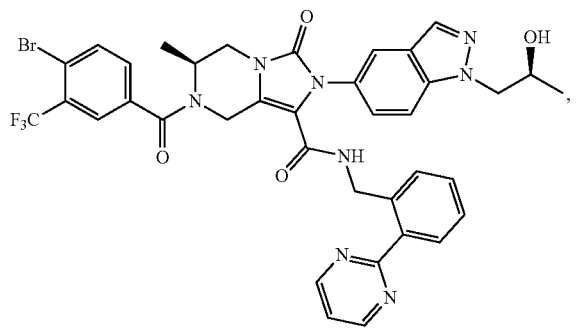
106
-continued
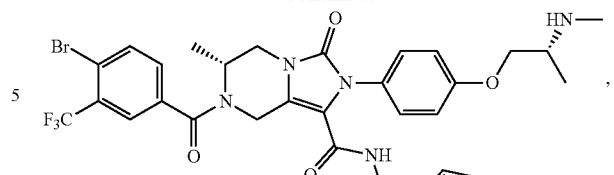
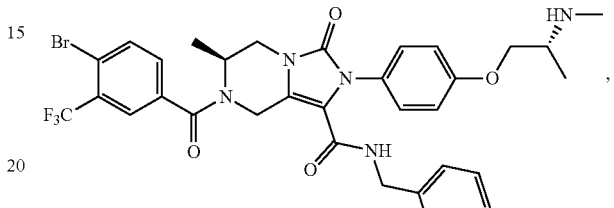
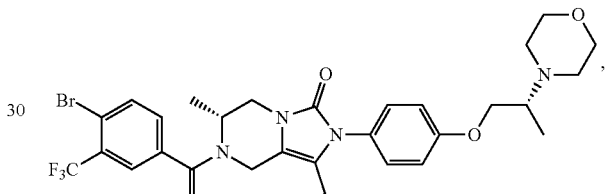
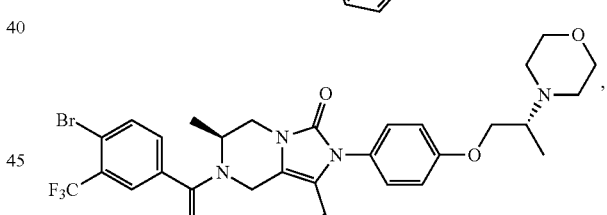
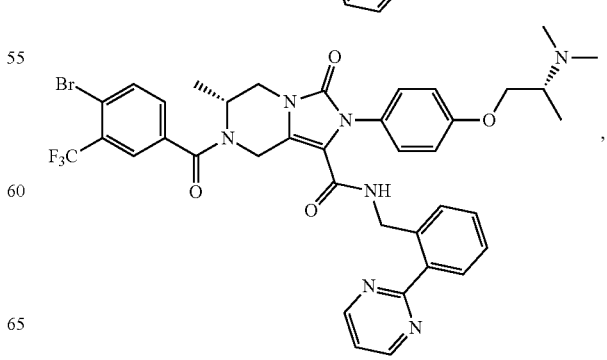

107
-continued
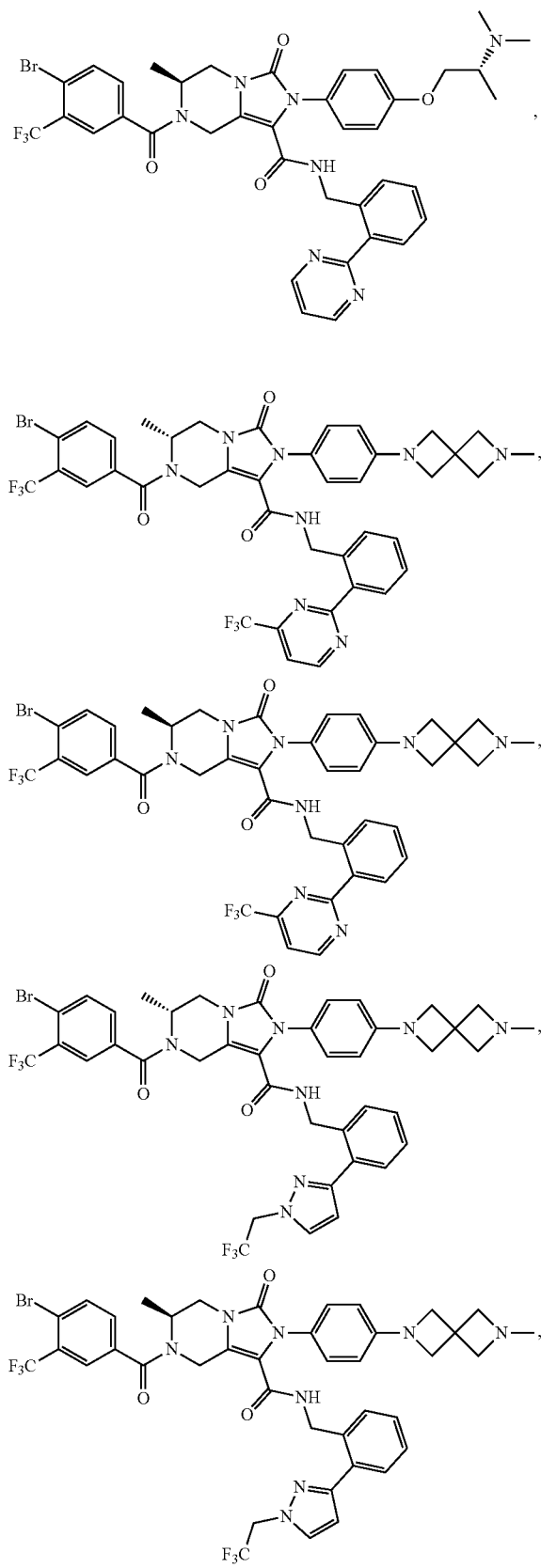
108
-continued
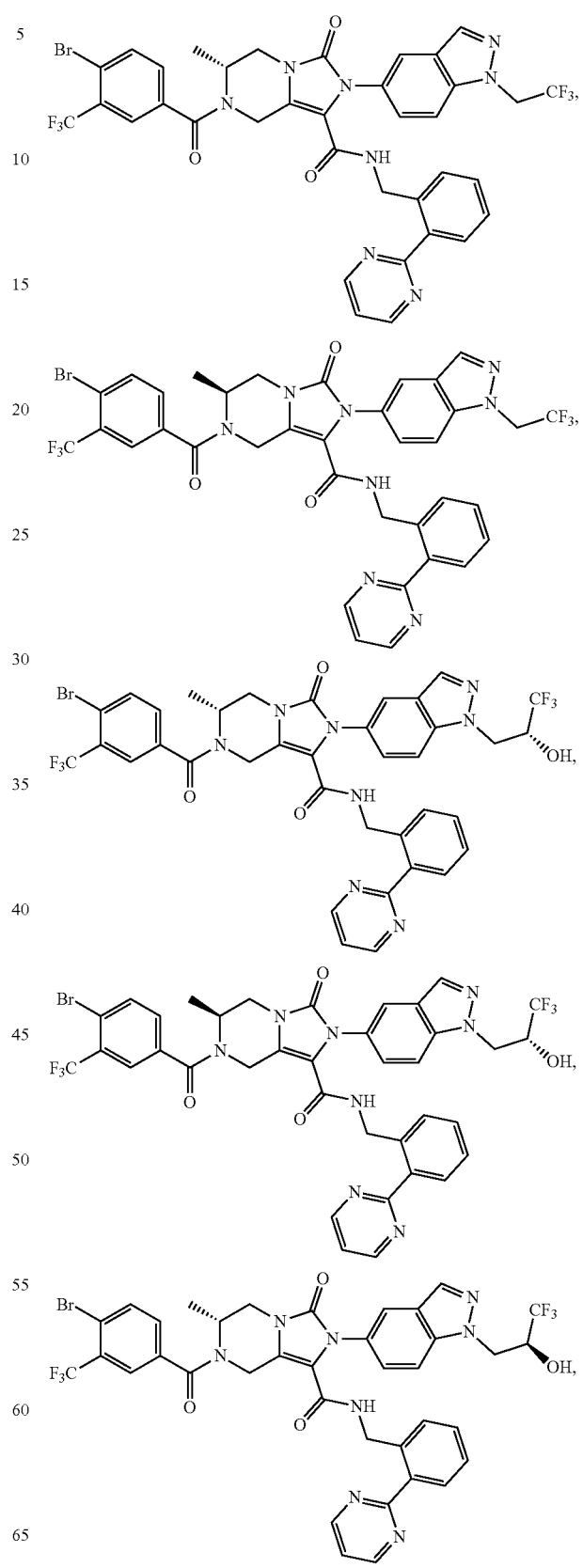

109
-continued
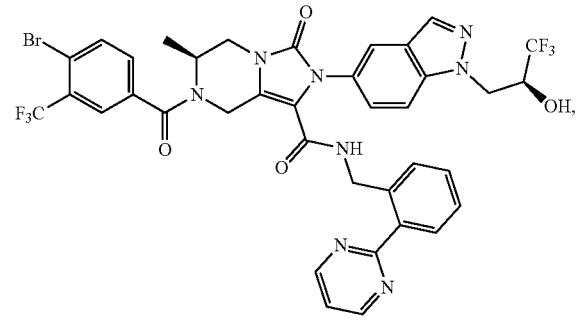
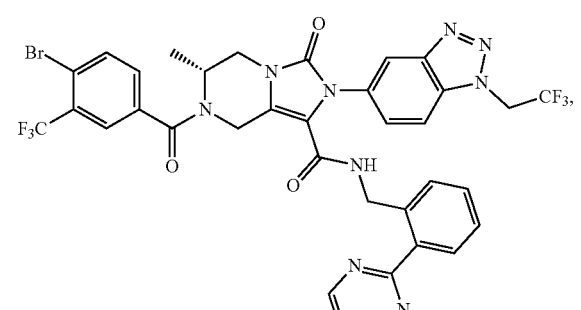
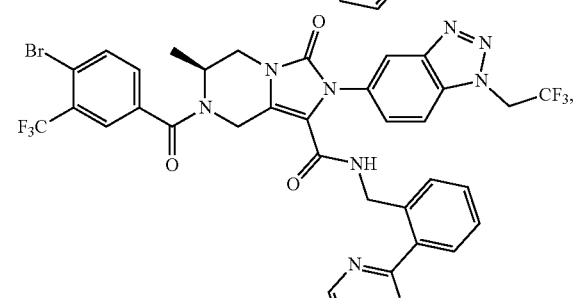
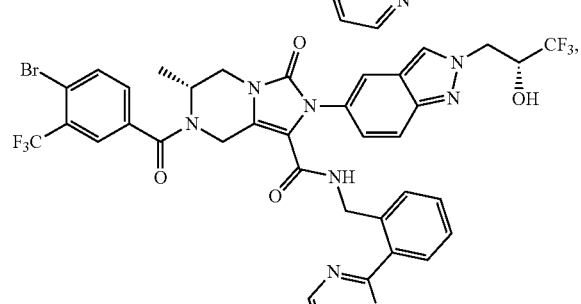
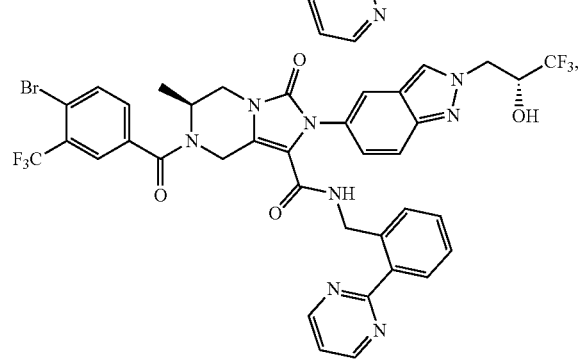
110
-continued
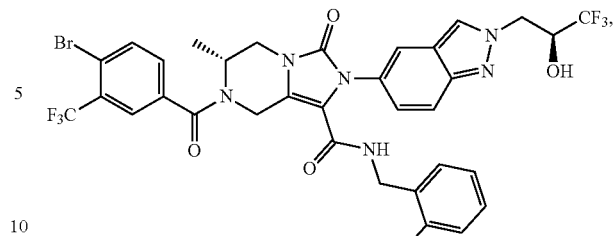
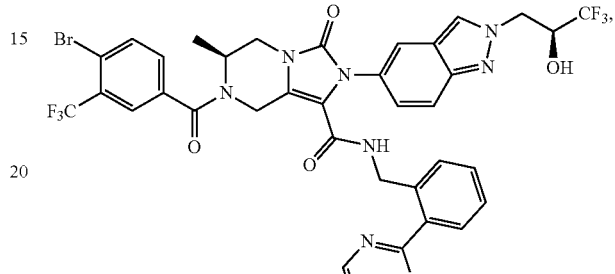
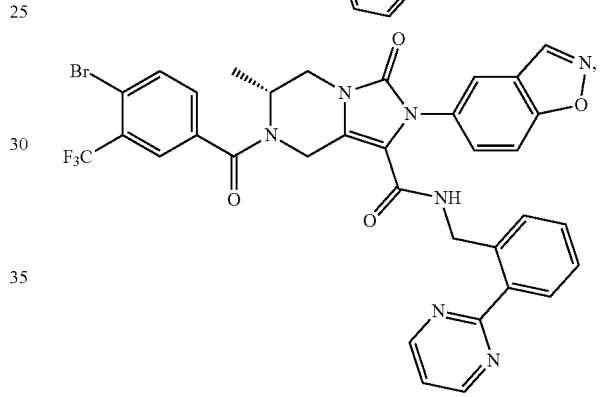
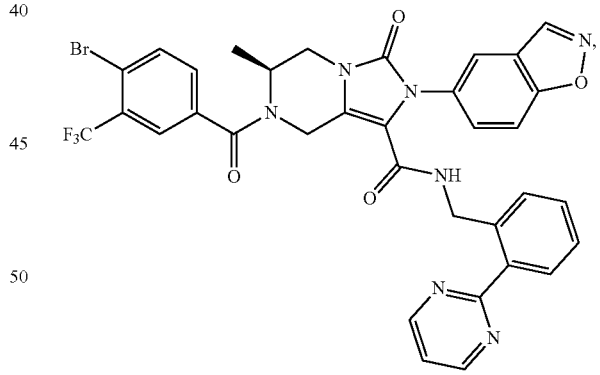
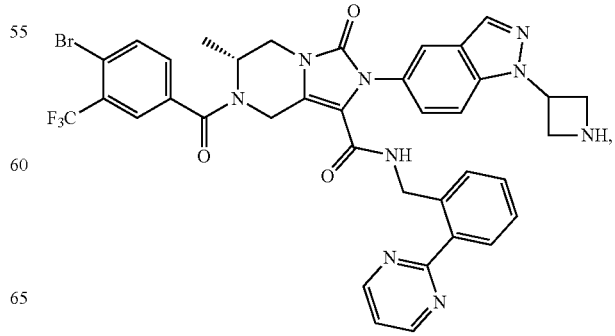

111
-continued
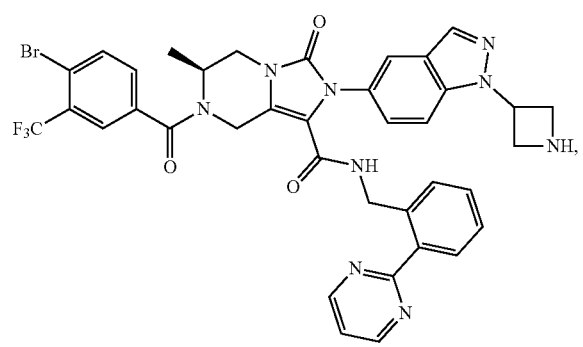
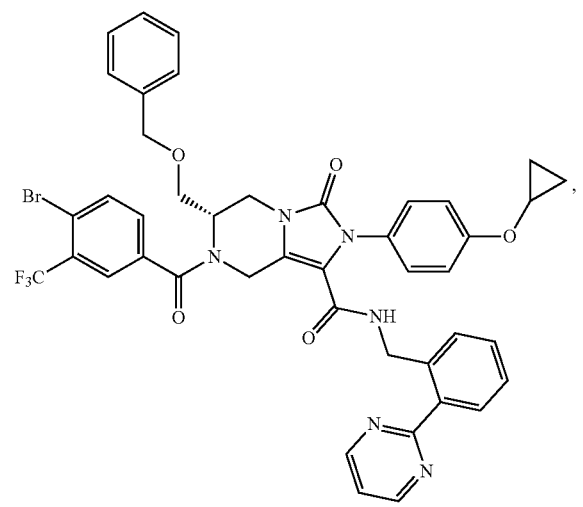
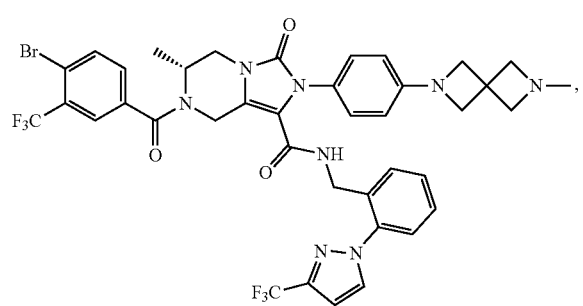
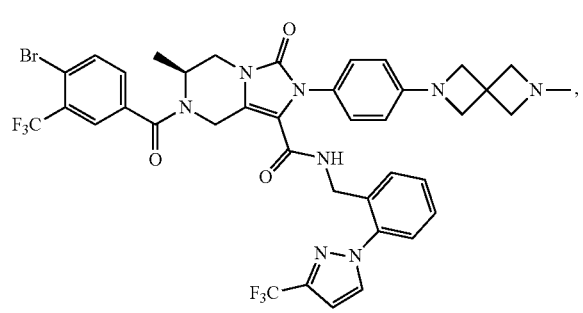
112
-continued
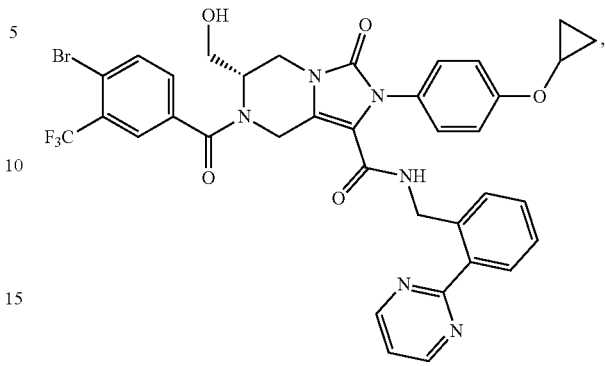
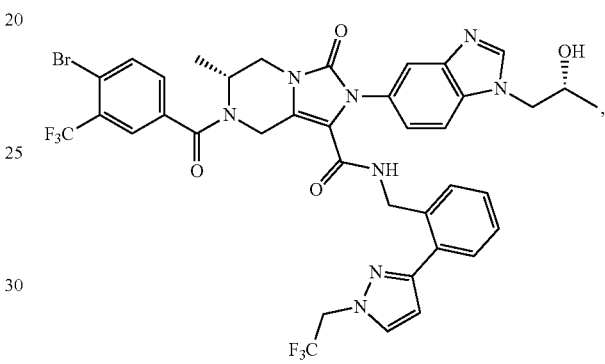
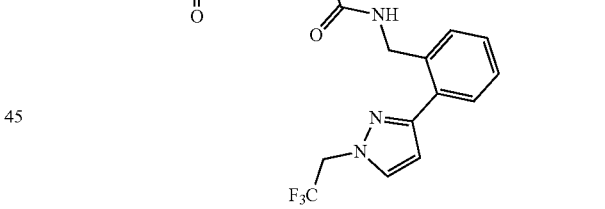
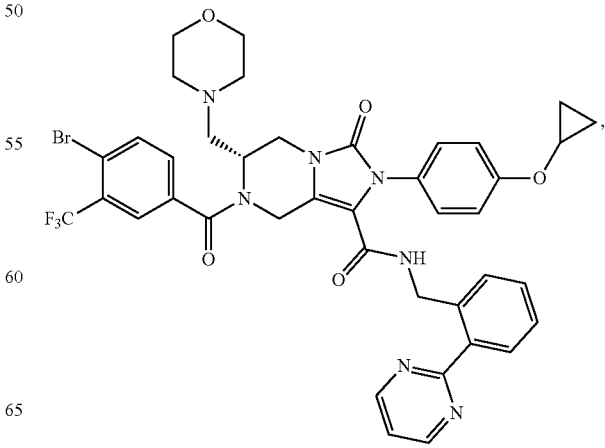

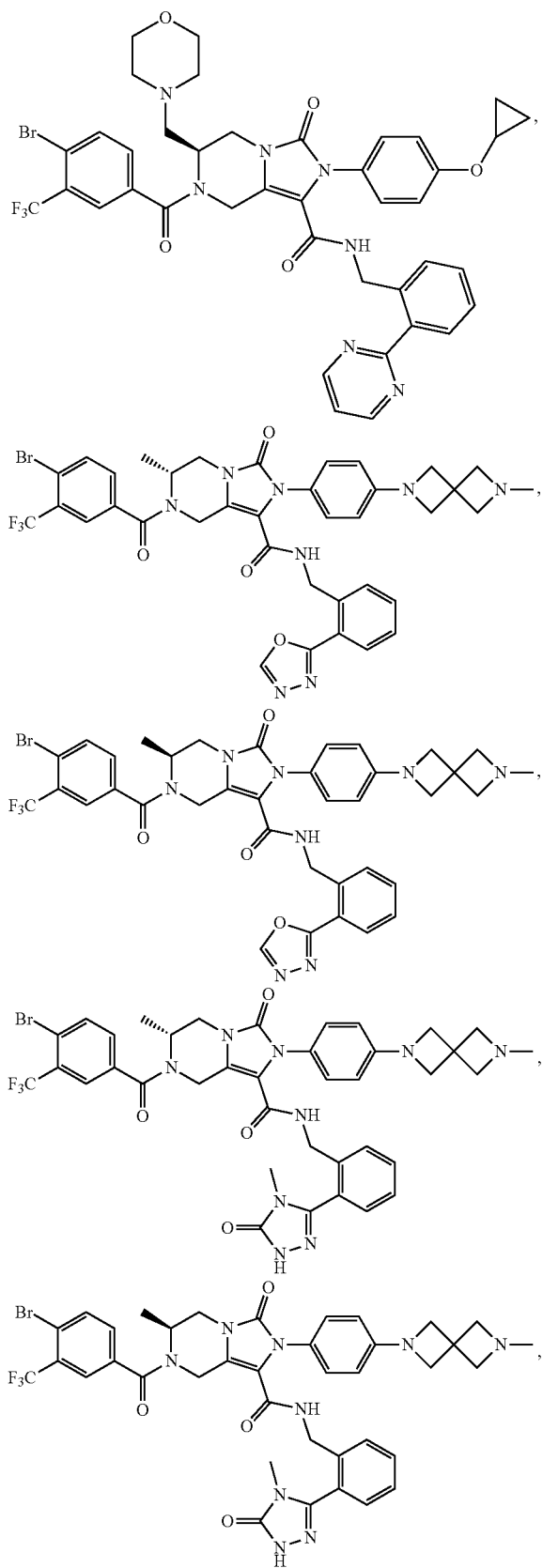
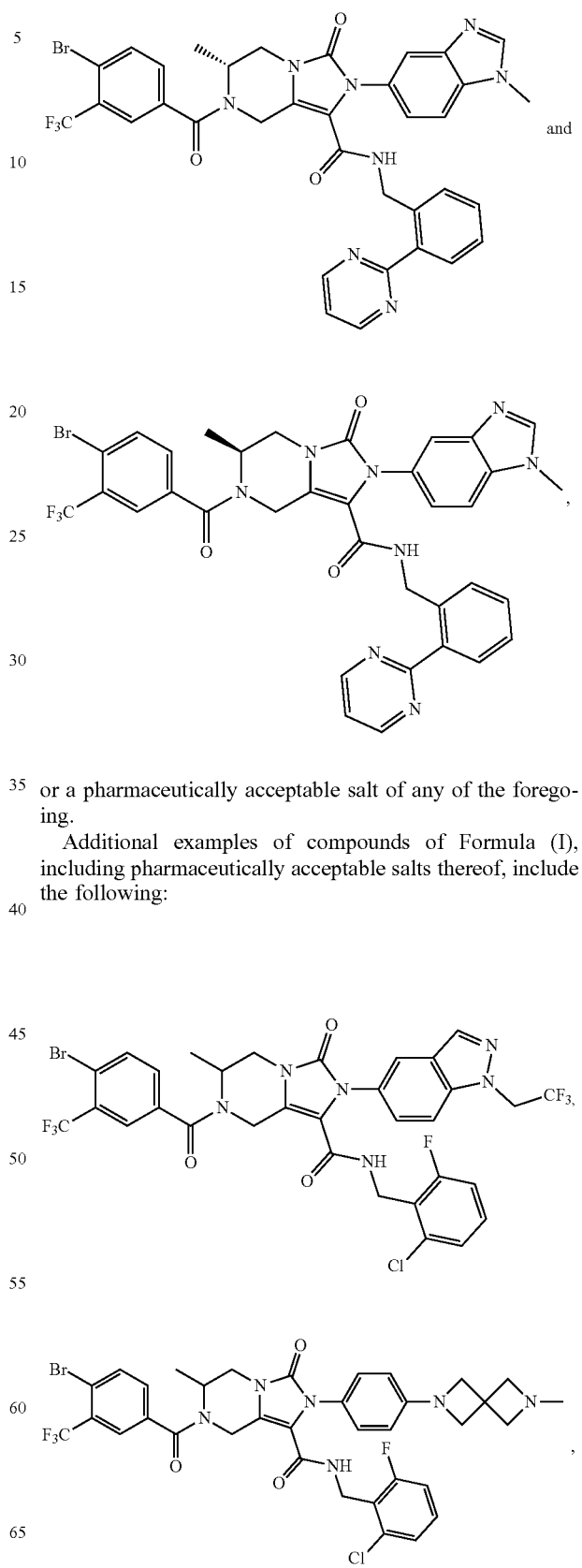
or a pharmaceutically acceptable salt of any of the foregoing.
Additional examples of compounds of Formula (I), including pharmaceutically acceptable salts thereof, include the following:

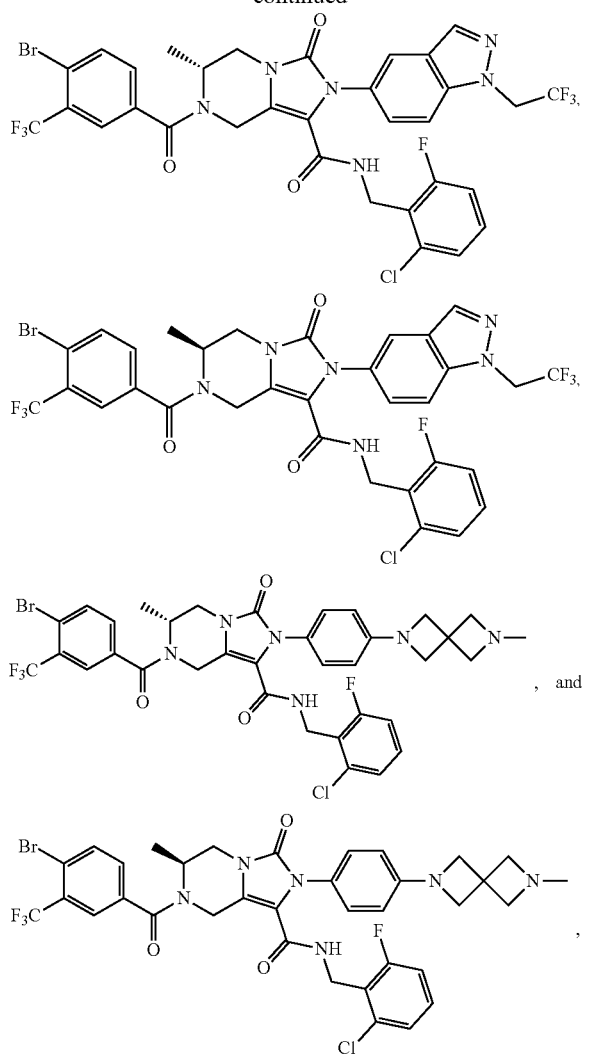
or a pharmaceutically acceptable salt of any of the foregoing.
In some embodiments, a compound can be selected from:
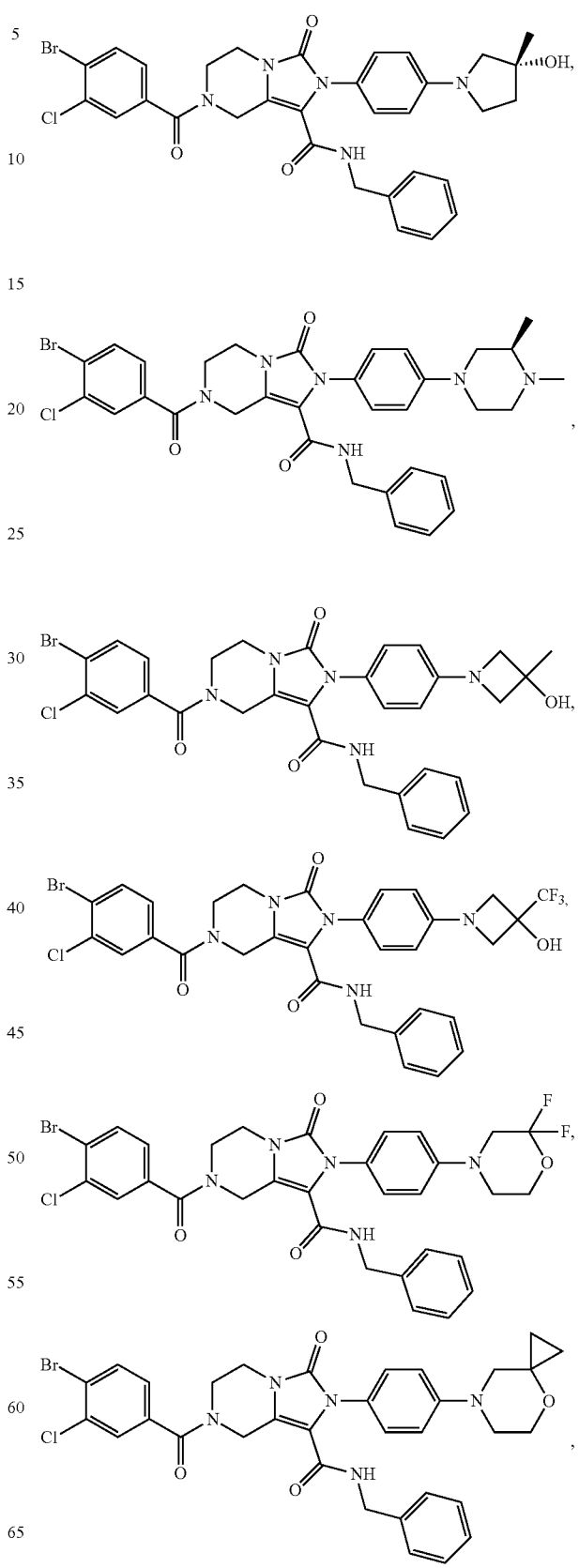

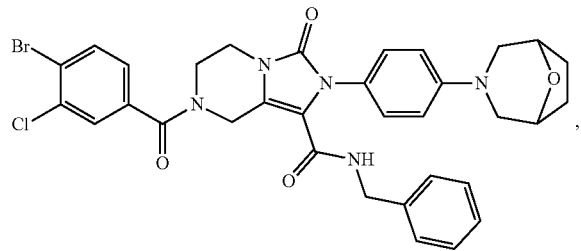

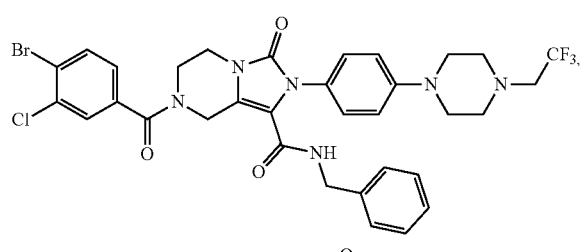

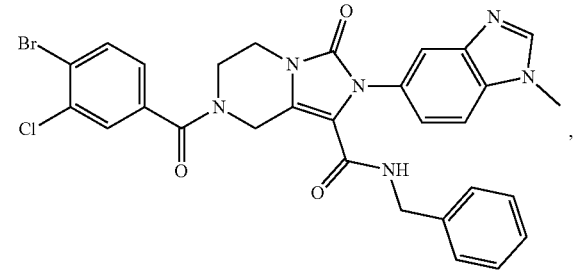

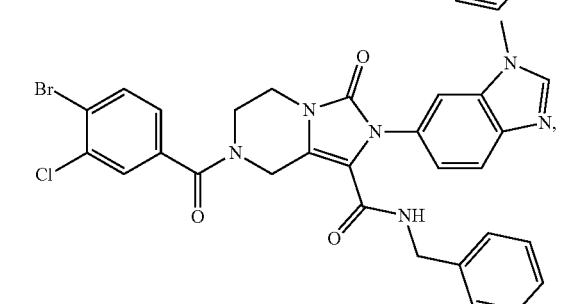

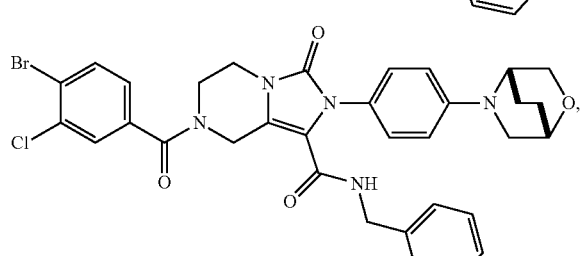

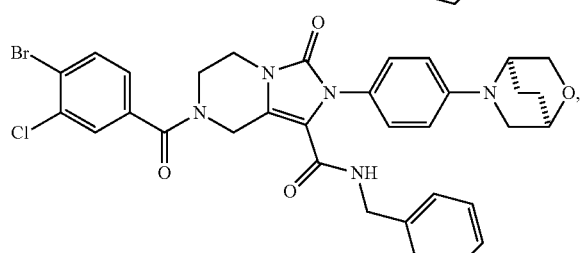

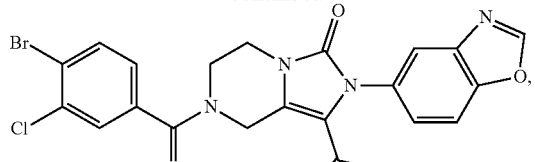

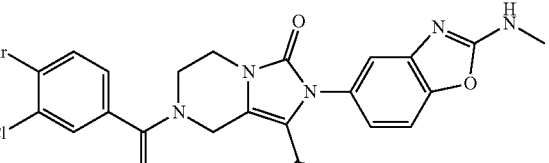

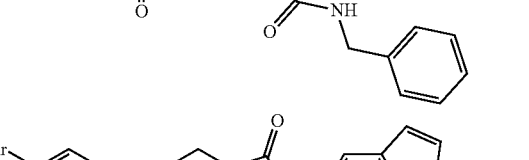

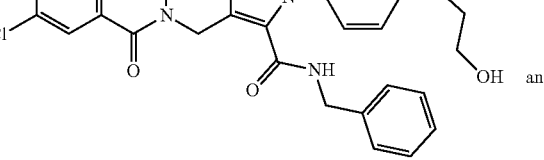

and

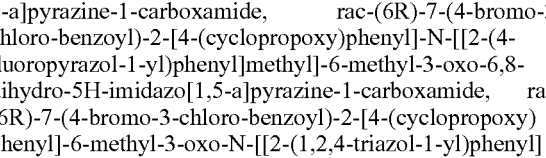

or a pharmaceutically acceptable salt of any of the foregoing.

In some embodiments, a compounds of Formula (I), or a pharmaceutically acceptable salt thereof, cannot be selected from rac-(6S)-7-(4-bromo-3-chloro-benzoyl)-2-[4-(cyclopropoxy)phenyl]-6-methyl-3-oxo-N-[(2-pyrazol-1-ylphenyl)methyl]-6,8-dihydro-5H-imidazo[1,5-a]pyrazine-1-carboxamide, rac-(6R)-7-(4-bromo-3-chloro-benzoyl)-2-[4-(cyclopropoxy)phenyl]-6-methyl-3-oxo-N-[(2-pyrazol-1-ylphenyl)methyl]-6,8-dihydro-5H-imidazo[1,5-a]pyrazine-1-carboxamide, rac-(6S)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo[1,5-a]pyrazine-1-carboxamide, rac-(6R)-7-(4-bromo-3-chloro-benzoyl)-2-[4-(cyclopropoxy)phenyl]-N-[[2-(4-fluoropyrazol-1-yl)phenyl]methyl]-6-methyl-3-oxo-6,8-dihydro-5H-imidazo[1,5-a]pyrazine-1-carboxamide, rac-(6R)-7-(4-bromo-3-chloro-benzoyl)-2-[4-(cyclopropoxy)phenyl]-6-methyl-3-oxo-N-[[2-(1,2,4-triazol-1-yl)phenyl]methyl]-6,8-dihydro-5H-imidazo[1,5-a]pyrazine-1-carboxamide, rac-(6S)-7-(4-bromo-3-chloro-benzoyl)-2-[4-(cyclopropoxy)phenyl]-6-methyl-3-oxo-N-[[2-(1,2,4-triazol-1-yl)phenyl]methyl]-6,8-dihydro-5H-imidazo[1,5-a]

pyrazine-1-carboxamide, rac-(6R)-7-(4-bromo-3-cyano-benzoyl)-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide, rac-(6S)-7-(4-bromo-3-cyano-benzoyl)-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide, rac-(6R)-7-(4-bromo-3-chloro-benzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide, rac-(6S)-7-(4-bromo-3-chloro-benzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide, rac-(6R)-7-(4-bromo-3-cyano-benzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide, and rac-(6S)-7-(4-bromo-3-cyano-benzoyl)-6-methyl-3-oxo-2-(4-pyrazol-1-ylphenyl)-N-[(2-pyrimidin-2-ylphenyl)methyl]-6,8-dihydro-5H-imidazo[1,5-a]pyrazine-1-carboxamide.

In some embodiments, a compound of Formula (I), or a pharmaceutically acceptable salt thereof, cannot be a compound or a pharmaceutically acceptable salt of a compound provided in U.S. 2020/0361947 A1, which is hereby incorporated by reference. In some embodiments, $R^1$ cannot be

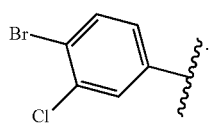

In other embodiments, $R^1$ cannot be

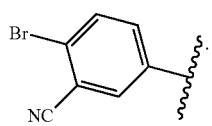

In some embodiments, $R^3$ cannot be

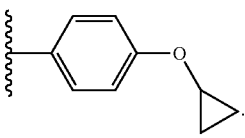 [SMILES: *c1ccc(OC2CC2)cc1]

In other embodiments, $R^3$ cannot be

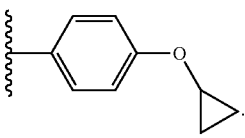 [SMILES: *c1ccc(OC2CC2)cc1]

In some embodiments, $R^5$ cannot be

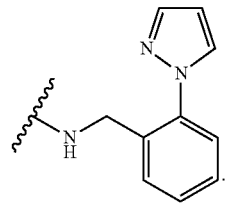 [SMILES: *NCc1ccccc1-n1cccn1]

In other embodiments, $R^5$ cannot be

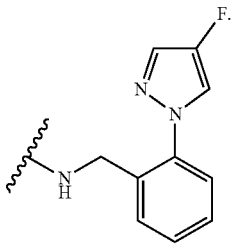 [SMILES: *NCc1ccccc1-n1cc(F)cn1]

In still other embodiments, $R^5$ cannot be

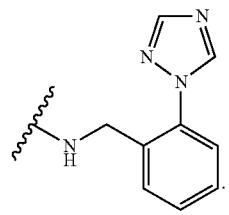 [SMILES: *NCc1ccccc1-n1cncn1]

In yet still other embodiments, $R^5$ cannot be

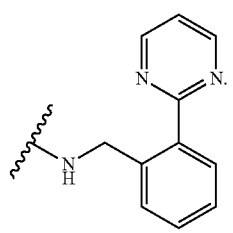 [SMILES: *NCc1ccccc1-c1ncccn1]

In some embodiments, when $R^3$ is

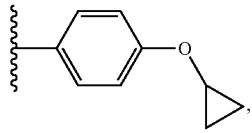 [SMILES: *c1ccc(OC2CC2)cc1]

then R⁵ cannot be
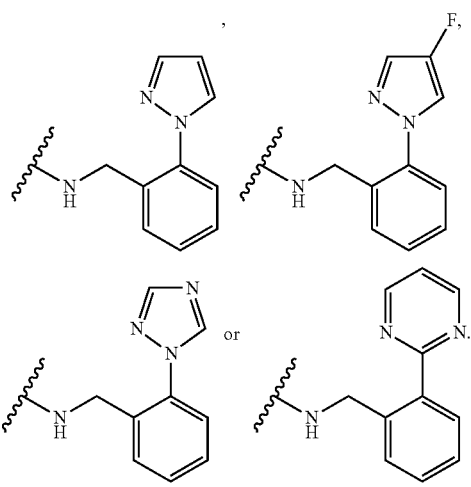
In some embodiments, when R³ is
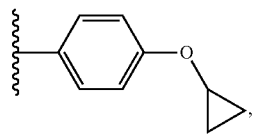
then R¹ cannot be
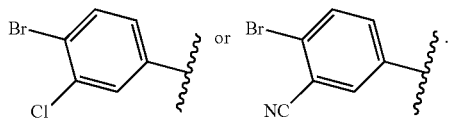 [SMILES: *c1ccc(Br)c(Cl)c1 ; *c1ccc(Br)c(C#N)c1]
In some embodiments, when R³ is
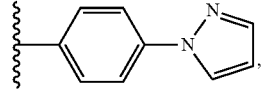
then R⁵ cannot be
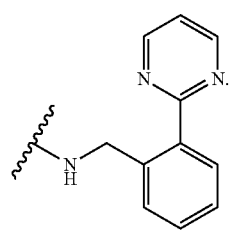
In some embodiments, when R³ is
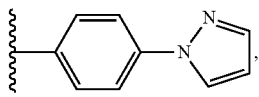
then R¹ cannot be
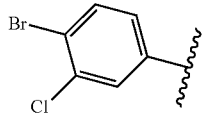
or
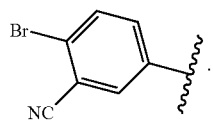 [SMILES: *c1ccc(Br)c(C#N)c1]
In some embodiments, when R³ is
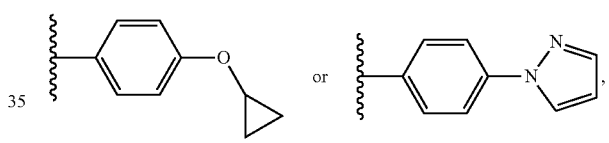
then R⁴ cannot be —CH₃. In some embodiments, when R⁵ is
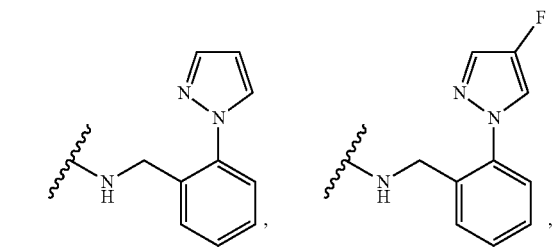
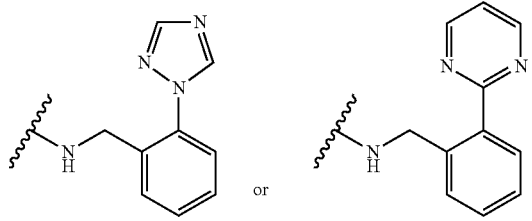

then R⁴ cannot be —CH₃. In some embodiments, when R¹ is

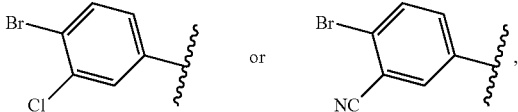 [SMILES: *c1ccc(Br)c(Cl)c1 ; *c1ccc(Br)c(C#N)c1]

or then R⁴ cannot be —CH₃.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

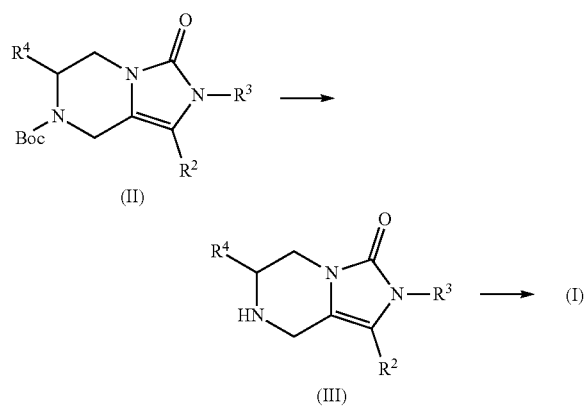

Compounds of Formula (I), along with pharmaceutically acceptable salts thereof, can be prepared from an intermediate of Formula (II) by cleaving the Boc protecting group in acidic condition, for example, by using HCl in a suitable solvent or by using cupper triflate to provide an intermediate of Formula (III). Compounds of Formula (I), and pharmaceutically acceptable salts thereof, can be obtained by methods know in the art. As an example, acyls of Formula (I) can be obtained by coupling Formula (III) with an acyl chloride, such as an acyl chloride of the general formula R¹—C(=O)—Cl, or by using an acid (such as R¹—C(=O)—OH) in presence of a suitable coupling agent (for example TCFH in presence of N-methylimidazole), in a suitable solvent, such as acetonitrile.

Scheme 2

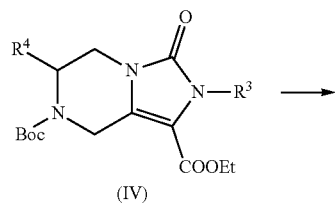

-continued

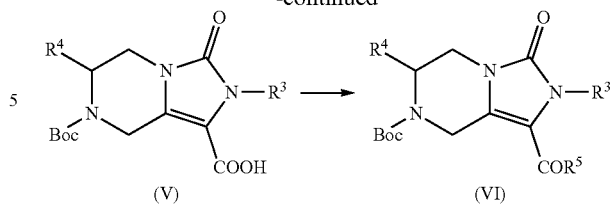

Compounds of Formula (I), along with pharmaceutically acceptable salts thereof, wherein R² can be —C(=O)R⁵ can be prepared from an intermediate of Formula (VI) whose synthesis is shown in Scheme 2. The ester of Formula (IV) can be saponified using lithium hydroxide or another suitable agent (such as sodium hydroxide) in a suitable solvent such a mixture of water in ethanol, to give an intermediate of Formula (V). The coupling of Formula (V) with an amine of general formula

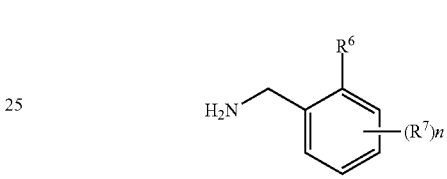

can be achieved using a coupling agent, such as EDCI/HOAT, or another suitable coupling agent (such as HATU in presence of DIPEA) in a suitable solvent to provide an intermediate of Formula (VI). The intermediate of Formula (VI) can be treated as depicted in Scheme 1 to give a compound of Formula (I), along with pharmaceutically acceptable salts thereof, where R² can be —C(=O)R⁵.

Scheme 3

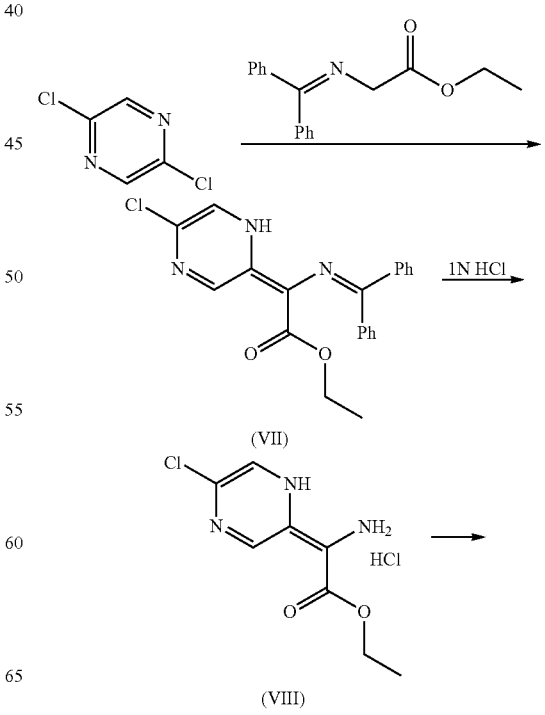

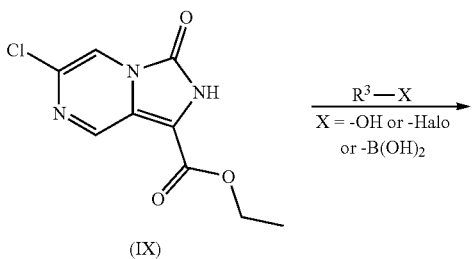

(IX)

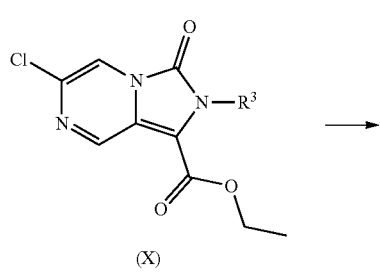

(X)

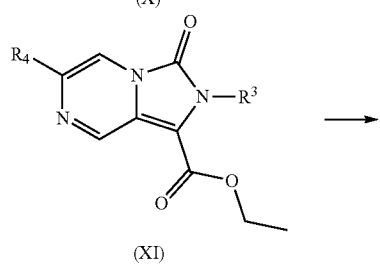

(XI)

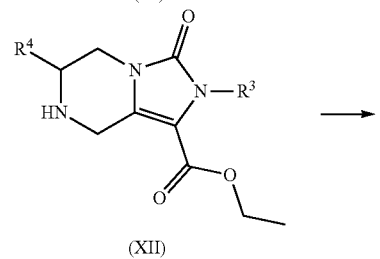

(XII)

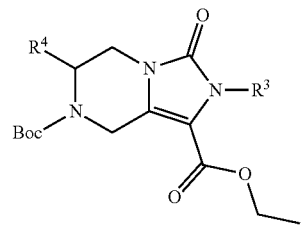

(IV)

Compounds of Formula (IV) can be obtained from 2,5-dichloropyrazine as depicted in Scheme 3. 2,5-dichloropyrazine can be reacted with N-(diphenylmethylene)glycine ethyl ester in a suitable solvent in presence of a base (for example, potassium carbonate) to provide a compound of Formula (VII). Deprotection of Formula (VII) can be accomplished under acidic conditions, for example, in presence of HCl to provide a compound of Formula (VIII). Formula (VIII) can be cyclized to a compound of Formula (IX), for example, using triphosgen in a suitable solvent (such as THF), or CDI in presence of a suitable base (such DIEA) in a suitable solvent (such as THF). Introduction of a $R^3$ substituent to a compound of Formula (IX) to give a compound of Formula (X) can be achieved by methods known to those skilled in the art. For instance, an intermediate of Formula (X) can be obtained from an intermediate of Formula (IX) by using an alkylating agent of general formula $R^3$-Halo, where Halo can be chloro, bromo or iodo, in presence of a base (for example, potassium carbonate) in a suitable solvent. Alternatively, an intermediate of Formula (X) can be obtained by a Mitsunobu reaction using an alcohol of general formula $R^3$—OH in a suitable solvent. Other compounds of Formula (X) can be prepared from Formula (IX), a boronic acid of general formula $R^3$—$B(OH)_2$, and a catalyst (such as $Cu(OTf)_2$ or $Cu(AcO)_2$), in presence of a suitable base. Other compounds of Formula (X) can be prepared from Formula (IX) using a halogenated aryl or heteroaryl $R^3$-Halo, where Halo can be iodo, bromo or chloro, in the presence of copper iodide, potassium carbonate and $N^1,N^2$-dimethylethane-1,2-diamine, in a solvent, such as DMSO, under heating conditions. Other compounds of Formula (X) can be prepared from Formula (IX) using a halogenated aryl or heteroaryl $R^3$-Halo, where Halo can be iodo, bromo or chloro, in the presence of a palladium catalyst (for example, $Pd_2dba_3$) a ligand (such as Xantphos), a base (for example, cesium carbonate) in a suitable solvent (such as dioxane) under heating conditions. Other methods known in the art to functionalize lactams can also be used.

The chloro of Formula (X) can be transformed to an alkyl or cycloalkyl, for example, methyl and cyclopropyl, using 2,4,6-trimethyl-1,3,5,2,4,6-trioxatriborinane and a cyclopropyl boronic acid, respectively, in the presence of a catalyst (for example, $Pd(dppf)Cl_2$, $K_2CO_3$ in dioxane, or $Pd(OAc)_2$ and SPhos in toluene/water). The obtained compound of Formula (XI), where $R^4$ can be methyl or cyclopropyl, can be reduced under known conditions (such as hydrogenation on Pd/C in ethanol or using sodium borohydride in ethanol) to provide a compound a Formula (XII). Protection of a compound of Formula (XII) using a Boc protecting group can be achieved using conditions known in the art, such as $Boc_2O$, in presence of TEA, in a suitable solvent (such as DCM), to give a compound a Formula (IV).

Scheme 4

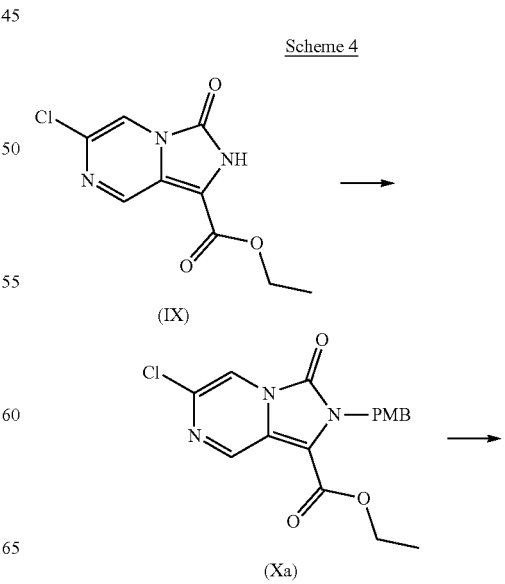

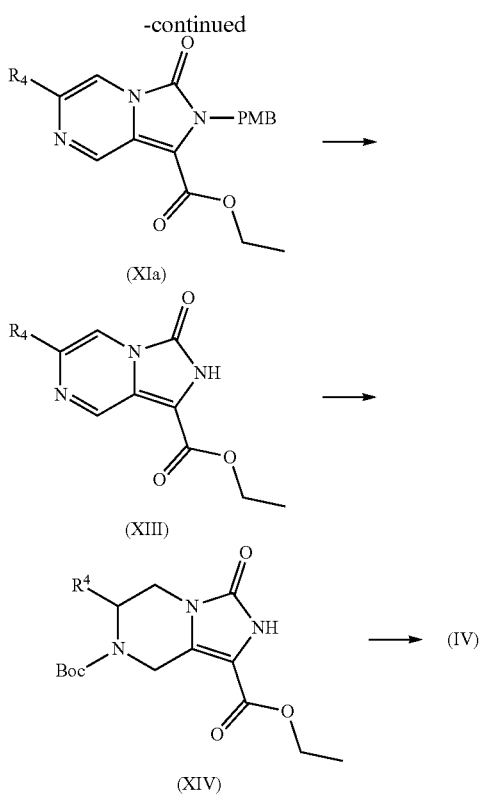

A compound of Formula (IV) can be obtained following the route depicted in Scheme 4. A compound of Formula (IX) can be protected using a PMB group, and conditions known in the art. For example, PMB-Cl can be used in presence of a suitable base (such as $K_2CO_3$) in a suitable solvent (such as DMF) to provide a compound of Formula (Xa). The chloro can be transformed to an alkyl or a cycloalkyl (for example, methyl and cyclopropyl using 2,4,6-trimethyl-1,3,5,2,4,6-trioxatriborinane and cyclopropyl boronic acid, respectively) in the presence of a catalyst (such as Pd(dppf)$Cl_2$, $K_2CO_3$ in dioxane, or Pd(OAc)$_2$ and SPhos in toluene/water) to provide a compound of Formula (XIa). A compound of Formula (XIa), where $R^4$ can be methyl or cyclopropyl, can be deprotected using conditions, such as hot TFA, to give a compound a Formula (XIII). Reduction and protection with a Boc protecting group of a compound a Formula (XIII) can be achieved in one pot under known conditions known to those skilled in the art (such as hydrogenation on Pd/C in ethanol, or using sodium borohydride in ethanol in presence of $Boc_2O$) to obtain a compound a Formula (XIV), where $R^4$ can be methyl or cyclopropyl. A $R^3$ substituent can be introduced to a compound of Formula (XIII) using the conditions depicted in Scheme 3 for the synthesis of Formula (X). For example, compounds of Formula (IV) can be obtained by reacting a compound of Formula (XIII), a boronic acid of general formula $R^3$—B(OH)$_2$, and a catalyst (such as Cu(TfO)$_2$), in presence of a suitable base (such as pyridine) and solvent (such as DMF). Other methods known in the art to functionalize lactams can also be used.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction <$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those STOPS™ compounds described in U.S. Publication No. 2020/0147124 A1, which is hereby incorporated by reference for the purpose of describing the STOPS™ compounds provided therein. In some embodiments, the additional agent can be 5'mApsln(5m)CpsmApsln(5m)CpsmApsln(5m)CpsmApsln(5m)CpsmApsln (5m)CpsrApsln(5m)CpsmApsln(5m)CpsmApsln(5m) CpsrApsln(5m)CpsmApsln(5m)CpsmApsln(5m)CpsrApsln (5m)CpsmApsln(5m)CpsmApsln(5m)CpsrApsln(5m) CpsmApsln(5m)CpsmApsln(5m)CpsrApsln(5m) CpsmApsln(5m)CpsmApsln(5m)C 3' (SEQ ID NO: 4), wherein mA is 2'-O-methyladenosine, ps is phosphorothioate, ln(5m)C is locked 5-methylcytidine, and rA is riboadenosine.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

7-tert-butyl 1-ethyl 2-(4-cyclopropoxyphenyl)-6-methyl-3-oxo-5H,6H,8H-imidazo[1,5-a]pyrazine-1,7-dicarboxylate (Intermediate 1)

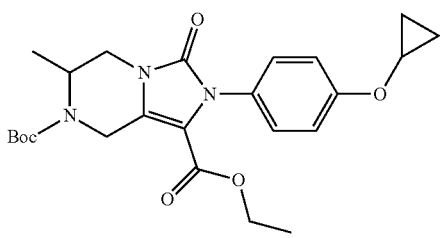 [SMILES: CCOC(=O)c1c2n(c(=O)n1-c1ccc(OC3CC3)cc1)CC(C)N(C(=O)OC(C)(C)C)C2]

Intermediate 1

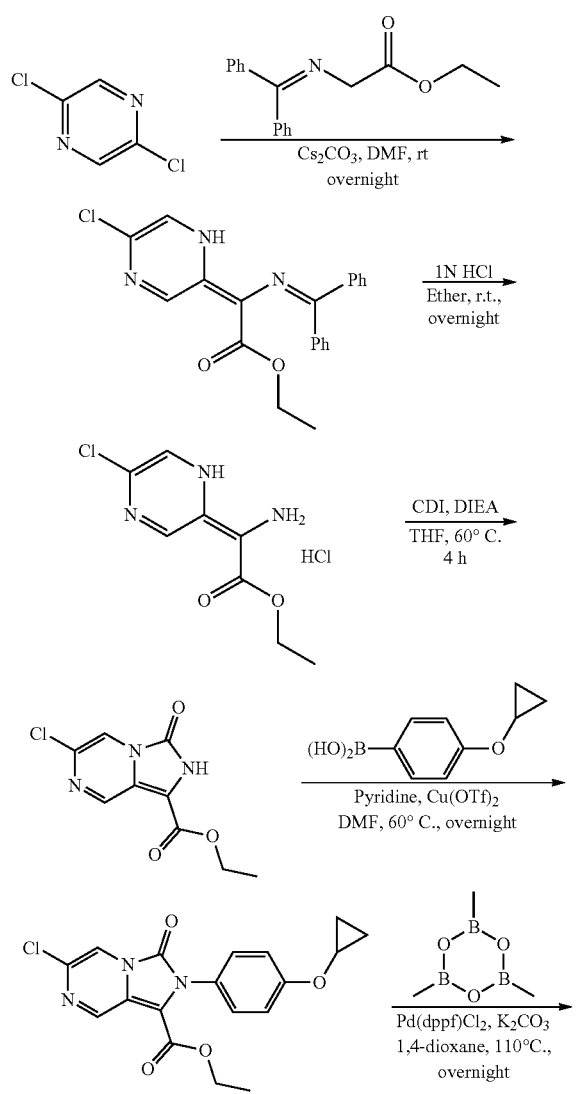

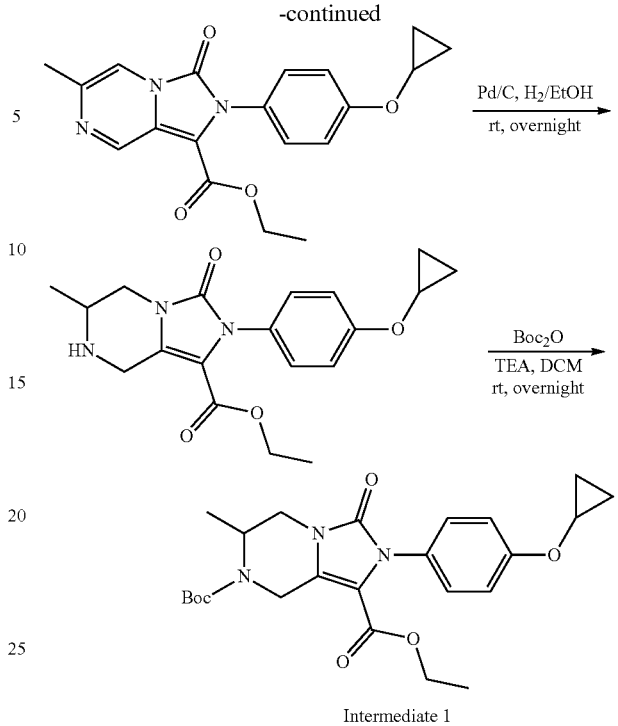

Intermediate 1

To a stirred solution of 2,5-dichloro-pyrazine (30.0 g, 201 mmol, 1.00 eq.) and ethyl 2-[(diphenylmethylidene)amino] acetate (53.8 g, 201 mmol, 1.00 eq.) in N,N-dimethylformamide (300 mL) was added cesium carbonate (65.6 g, 201 mmol, 1.00 eq.) at room temperature (rt). The mixture was stirred overnight at rt, and the reaction was quenched with water (500 mL). The mixture was extracted with ethyl acetate (3×200 mL)/The organic layers were combined, washed with water (3×100 mL), dried over anhydrous sodium sulfate, filtered and concentrated under reduced pressure. The residue was purified by silica gel column chromatography, eluted with 0-20% ethyl acetate in petroleum ether to afford ethyl 2-(5-chloropyrazin-2-yl)-2-[(diphenylmethylidene)amino]acetate (48.9 g, 64%) as a yellow solid. LCMS (ESI, m/z): 380 [M+H]+. $^1$H NMR (400 MHz, DMSO-$d_6$) δ ppm 8.75-8.73 (m, 2H), 7.64-7.62 (m, 2H), 7.57-7.55 (m, 3H), 7.48-7.50 (m, 1H), 7.42-7.45 (m, 2H), 7.20-7.22 (m, 2H), 5.31 (s, 1H), 4.11-4.07 (q, J=6.2 Hz, 2H), 1.12 (t, J=6.2 Hz, 3H).

To a stirred solution of ethyl 2-(5-chloropyrazin-2-yl)-2-[(diphenylmethylidene) amino]acetate (40.0 g, 105 mmol, 1.00 eq.) in ether (400) was added 1N hydrochloric acid (150 mL, 150 mmol, 1.42 eq.) at rt. The mixture was stirred overnight at rt and then extracted with ether (2×20 mL). The combined water layers were concentrated under reduced pressure to afford ethyl 2-amino-2-(5-chloropyrazin-2-yl) acetate hydrochloric acid salt (20.0 g, crude) as a white solid and used directly into next step without further purification. LCMS (ESI, m/z): 216 [M+H—HCl]+. $^1$H NMR (300 MHz, DMSO-$d_6$) δ ppm 9.33 (s, 3H), 8.93-8.85 (m, 2H), 5.71 (s, 1H), 4.22-4.17 (q, J=6.2 Hz, 2H), 1.15 (t, J=6.2 Hz, 3H).

To a stirred solution of ethyl 2-amino-2-(5-chloropyrazin-2-yl)acetate hydrochloric acid salt (19.0 g, 75.4 mmol, 1.00 eq.) in tetrahydrofuran (200 mL) was added N,N-diisopropylethylamine (30.8 g, 238 mmol, 3.16 eq.) and N,N'-carbonyldiimidazole (12.9 g, 79.3 mmol, 1.05 eq.) at 60° C. The mixture was stirred for 4 h at 60° C. and then concentrated under reduced pressure. The residue was purified by silica gel column chromatography, eluted with 0-5% methanol in dichloromethane to afford ethyl 6-chloro-3-oxo-2H-imidazo[1,5-a]pyrazine-1-carboxylate (11.0 g, 60%) as a yellow solid. LCMS (ESI, m/z): 242 [M+H]+. ¹H NMR (300 MHz, DMSO-d₆) δ ppm 12.49 (s, 1H), 8.82 (s, 1H), 7.95 (s, 1H), 4.33-4.27 (q, J=6.2 Hz, 2H), 1.31 (t, J=6.2 Hz, 3H).

A 250 mL of round bottom flask was charged with ethyl 6-chloro-3-oxo-2H-imidazo[1,5-a]pyrazine-1-carboxylate (3.00 g, 12.4 mmol, 1.00 eq.), 4-cyclopropoxyphenylboronic acid (2.65 g, 14.9 mmol, 1.20 eq.), pyridine (2.94 g, 37.1 mmol, 2.99 eq.), copper(II) trifluoromethanesulfonate (4.49 g, 12.4 mmol, 1.00 eq.) and N,N-dimethylformamide (100 mL). The mixture was stirred for 2 h at 60° C. under oxygen atmosphere. The mixture was added ethyl acetate (100 mL) and washed with water (3×100 mL). The organic layers were combined, dried over anhydrous sodium sulfate, filtered and concentrated under reduced pressure. The residue was purified by silica gel column chromatography, eluted with 0-50% ethyl acetate in petroleum ether to afford ethyl 6-chloro-2-(4-cyclopropoxyphenyl)-3-oxoimidazo[1,5-a]pyrazine-1-carboxylate (3.40 g, 73%) as a yellow solid. LCMS (ESI, m/z): 374 [M+H]+. ¹H NMR (400 MHz, CDCl₃) δ 9.08 (d, J=1.6 Hz, 1H), 7.75 (d, J=1.6 Hz, 1H), 7.30-7.20 (m, 2H), 7.17-7.11 (m, 2H), 4.25 (q, J=7.1 Hz, 2H), 3.76 (tt, J=4.8, 3.8 Hz, 1H), 2.95 (s, 1H), 2.88 (s, 1H), 1.24 (t, J=7.1 Hz, 3H), 0.80 (s, 2H).

A 250 mL of round bottom flask was charged with ethyl 6-chloro-2-(4-cyclopropoxyphenyl)-3-oxoimidazo[1,5-a]pyrazine-1-carboxylate (3.40 g, 9.10 mmol, 1.00 eq.), [1,1'-bis(diphenylphosphino)ferrocene] dichloropalladium(II) (0.700 g, 0.957 mmol, 0.11 eq.), potassium carbonate (3.77 g, 27.3 mmol, 3.00 eq.) and 1,4-dioxane (100 mL). Trimethyl-1,3,5,2,4,6-trioxatriborinane (4.57 g, 18.2 mmol, 2.00 eq., 50% in THF) was then added at rt under nitrogen atmosphere. The mixture was stirred overnight at 110° C. The reaction was quenched with water (100 mL). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with 0-50% ethyl acetate in petroleum ether to afford ethyl 2-(4-cyclopropoxyphenyl)-6-methyl-3-oxoimidazo[1,5-a]pyrazine-1-carboxylate (2.20 g, 68%) as a yellow solid. LCMS (ESI, m/z): 354 [M+H]+. ¹H NMR (300 MHz, CDCl₃) δ 9.23 (d, J=1.6 Hz, 1H), 7.52 (t, J=1.5 Hz, 1H), 7.30-7.24 (m, 2H), 7.19-7.13 (m, 2H), 4.27 (q, J=7.1 Hz, 2H), 4.14 (q, J=7.1 Hz, 2H), 3.85-3.72 (m, 1H), 2.41 (s, 3H), 1.27 (td, J=7.2, 2.4 Hz, 3H), 0.82 (d, J=4.5 Hz, 2H).

A 250 mL of round bottom flask was charged with ethyl 2-(4-cyclopropoxyphenyl)-6-methyl-3-oxoimidazo[1,5-a]pyrazine-1-carboxylate (2.20 g, 6.23 mmol, 1.00 eq.) and methanol (100 mL). Sodium borohydride (1.18 g, 31.2 mmol, 5.01 eq.) was added at 0° C. The mixture was stirred for 2 h at rt. The reaction was quenched with water (10 mL). To the mixture was added sodium bicarbonate (2.62 g, 31.1 mmol, 5.00 eq.) and di-tert-butyl dicarbonate (6.79 g, 31.1 mmol, 5.00 eq.) at rt. The mixture was stirred overnight at rt. The reaction was quenched with water (100 mL). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with 0-50% ethyl acetate in petroleum ether to afford 7-tert-butyl 1-ethyl 2-(4-cyclopropoxyphenyl)-6-methyl-3-oxo-5H,6H, 8H-imidazo[1,5-a]pyrazine-1,7-dicarboxylate (2.00 g, 70%) as a yellow solid. LCMS (ESI, m/z): 458 [M+H]+. ¹H NMR (400 MHz, CDCl₃) δ 7.21-7.16 (m, 2H), 7.10-7.04 (m, 2H), 5.31-5.20 (m, 1H), 4.82 (dd, J=13.6, 1.7 Hz, 1H), 4.33 (d, J=19.4 Hz, 1H), 4.21-4.08 (m, 2H), 3.85 (dd, J=12.7, 1.4 Hz, 1H), 3.76-3.70 (m, 1H), 3.63 (dd, J=12.8, 4.7 Hz, 1H), 1.51 (s, 9H), 1.26 (d, J=6.9 Hz, 3H), 1.19 (t, J=7.1 Hz, 3H), 0.87-0.84 (m, 2H), 0.78 (d, J=4.5 Hz, 2H).

Example 2

(6S*)-7-tert-butyl 1-ethyl 2-(4-cyclopropoxyphenyl)-6-methyl-3-oxo-5H,6H,8H-imidazo[1,5-a]pyrazine-1,7-dicarboxylate (Intermediate 1a) and (6R*)-7-tert-butyl 1-ethyl 2-(4-cyclopropoxyphenyl)-6-methyl-3-oxo-5H,6H,8H-imidazo[1,5-a]pyrazine-1, 7-dicarboxylate (Intermediate 1b)

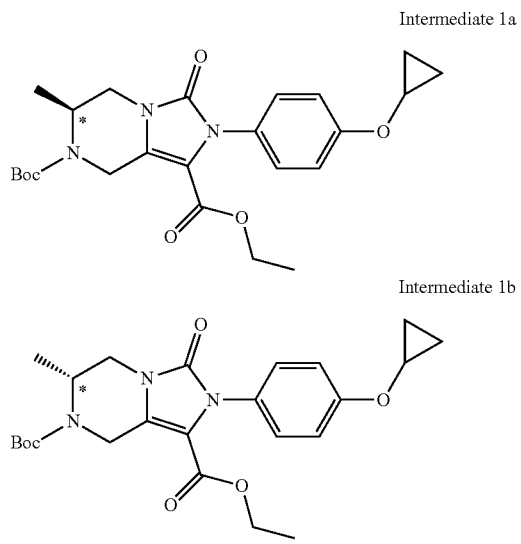

Intermediate 1a

Intermediate 1b

Intermediate 1 was dissolved in ethanol and then was separated into its two enantiomers intermediate 1a (first eluting enantiomer) and intermediate 1b (second eluting enantiomer) by SFC, using a column Lux A2 (21.2 mm×250 mm, 5 um), at 40° C., with a flow rate of 50 mL/min and 100 bar, under isochratic conditions (30:70 EtOH:CO₂ (0.2% v/v NH₃).

Example 3

7-(tert-butoxycarbonyl)-2-(4-cyclopropoxyphenyl)-6-methyl-3-oxo-2,3,5,6,7,8-hexahydroimidazo[1,5-a]pyrazine-1-carboxylic acid (Intermediate 2)

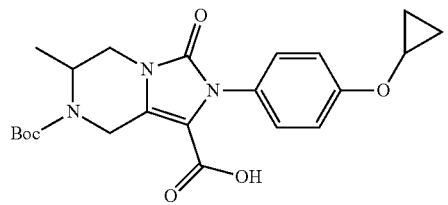 [SMILES: CC1Cn2c(c(C(=O)O)n(-c3ccc(OC4CC4)cc3)c2=O)CN1C(=O)OC(C)(C)C]

A solution of NaOH (4 eq., 357 mg, 8.92 mmol) in H₂O (1.5 mL) was added to a solution of Intermediate 1 (1 eq., 1020 mg, 2.23 mmol) in EtOH (15 mL). The mixture was stirred at rt for 3 h. The mixture was concentrated to remove ethanol. Water (15 mL) was added, and the aqueous layer was extracted with Et₂O (2×20 mL). The aqueous layer was acidified with HCl 1 N to pH 2 and extracted with DCM (3×30 mL). The combined organic layers were dried with magnesium sulfate, filtered and evaporated to dryness to afford 7-(tert-butoxycarbonyl)-2-(4-cyclopropoxyphenyl)-6-methyl-3-oxo-2,3,5,6,7,8-hexahydroimidazo[1,5-a]pyrazine-1-carboxylic acid (Intermediate 2) (830 mg, 78%).

Example 4

(6S*)-7-(tert-butoxycarbonyl)-2-(4-cyclopropoxyphenyl)-6-methyl-3-oxo-2,3,5,6,7,8-hexahydroimidazo[1,5-a]pyrazine-1-carboxylic acid (Intermediate 2a) and (6R*)-7-(tert-butoxycarbonyl)-2-(4-cyclopropoxyphenyl)-6-methyl-3-oxo-2,3,5,6,7,8-hexahydroimidazo[1,5-a]pyrazine-1-carboxylic acid (Intermediate 2b)

Intermediates 2a and 2b were synthetized according to the procedures for the synthesis of 7-(tert-butoxycarbonyl)-2-(4-cyclopropoxyphenyl)-6-methyl-3-oxo-2,3,5,6,7,8-hexahydroimidazo[1,5-a]pyrazine-1-carboxylic acid (Intermediate 2), starting from Intermediate 1a and Intermediate 1b, respectively.

Example 5

(6R*)-7-(4-bromo-3-chlorobenzoyl)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide (1b)

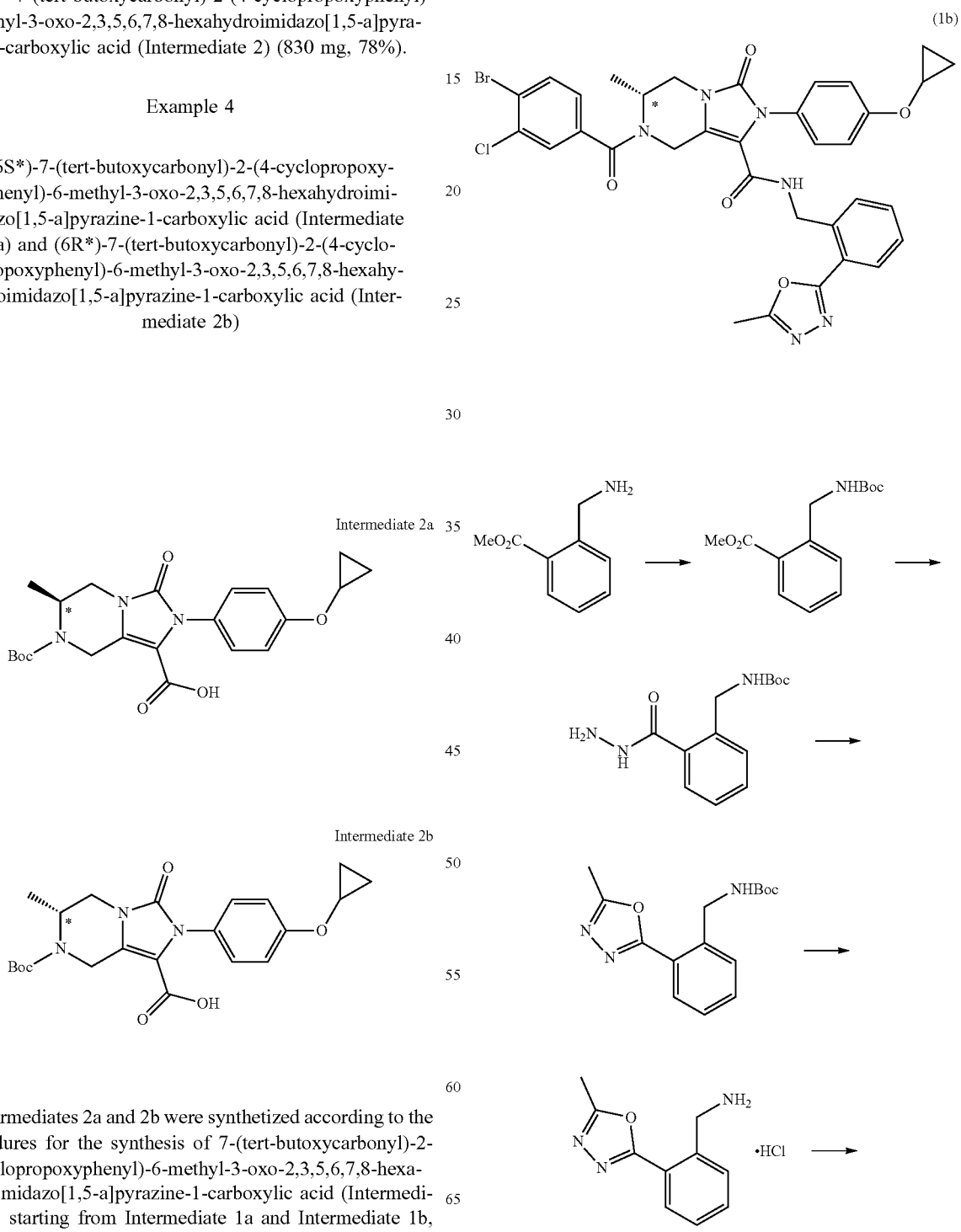

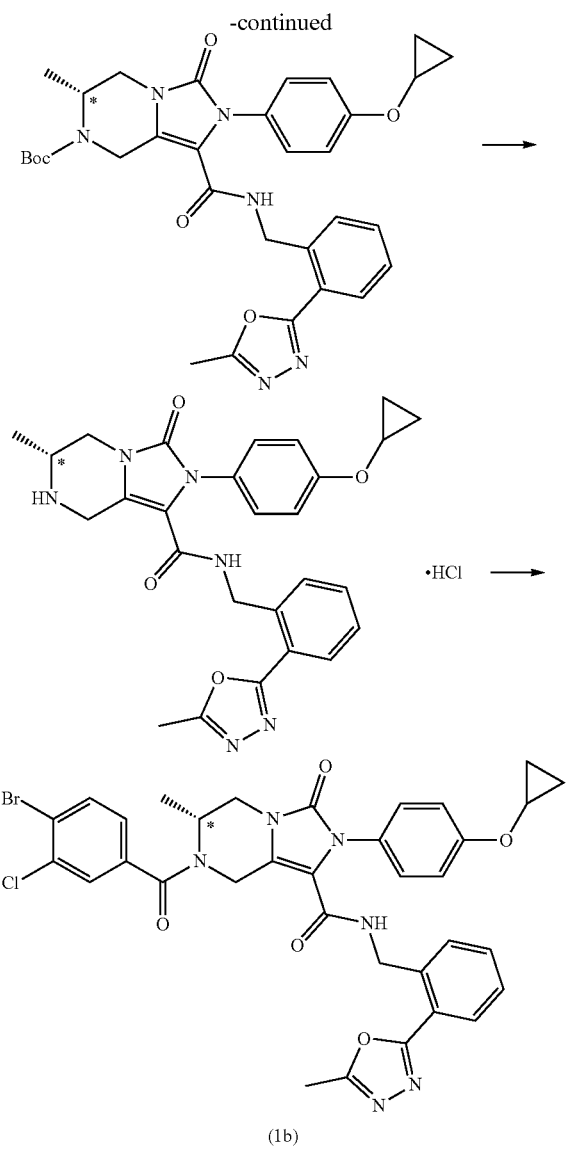

amino)methyl)benzoate (1 eq., 2.26 g, 8.52 mmol) in MeOH (58.3 mL) under N$_2$. The mixture was heated at 65° C. for 24 h. The mixture was then evaporated to dryness to afford tert-butyl (2-(hydrazinecarbonyl)benzyl)carbamate (3.78 g, quant.) as a white solid, which was used as such. LCMS (ESI, m/z): 210.1 [M-tBu+H]$^+$.

Tert-butyl (2-(5-methyl-1,3,4-oxadiazol-2-yl)benzyl) carbamate

PTSA·H$_2$O (0.1 eq., 0.18 g, 0.94 mmol) was added to a suspension of tert-butyl (2-(hydrazinecarbonyl)benzyl)carbamate (1 eq., 2.49 g, 9.38 mmol) in trimethyl orthoacetate (16.7 eq., 20 mL, 156 mmol) under N$_2$. The mixture was heated at 100° C. for 1 h. Sat. NaHCO$_3$ (10 mL) was added, and the aqueous layer was extracted with AcOEt (3×10 mL). The combined organic layers were washed with brine (30 mL), dried with magnesium sulfate, filtered and evaporated to dryness. The crude mixture was purified by flash chromatography on silica gel (from 0% to 50% of AcOEt in CyH) to give tert-butyl (2-(5-methyl-1,3,4-oxadiazol-2-yl)benzyl)carbamate (1.76 g, 65%) as a white solid. LCMS (ESI, m/z): 290.1 [M+H]$^+$. $^1$H-NMR (CDCl$_3$, 300 MHz, 25° C.) δ ppm 1.40 (s, 9H), 2.64 (s, 3H), 4.58 (d, J=6.6 Hz, 2H), 6.14 (br s, 1H), 7.39-7.44 (m, 1H), 7.46-7.51 (m, 1H), 7.63 (d, J=7.2 Hz, 1H), 7.89 (d, J=7.8 Hz, 1H).

(2-(5-methyl-1,3,4-oxadiazol-2-yl)phenyl)methanamine hydrochloride

A solution of tert-butyl (2-(5-methyl-1,3,4-oxadiazol-2-yl)benzyl)carbamate (1 eq., 400 mg, 1.38 mmol) in HCl 4N in dioxane (20 eq., 6.91 mL, 27.65 mmol) was stirred under N$_2$ at rt for 1 h. The mixture was evaporated to dryness to afford (2-(5-methyl-1,3,4-oxadiazol-2-yl)phenyl)methanamine hydrochloride (328 mg, quant.) as a white solid. LCMS (ESI, m/z): 190.1 [M+H]$^+$. $^1$H-NMR (DMSO-d6, 300 MHz, 25° C.) δ ppm 2.62 (s, 3H), 4.46 (q, J=2.4 Hz, 2H), 7.61-7.77 (m, 3H), 7.99 (d, J=6.9 Hz, 1H), 8.46 (br s, 3H).

Tert-butyl (R*)-2-(4-cyclopropoxyphenyl)-6-methyl-1-((2-(5-methyl-1,3,4-oxadiazol-2-yl)benzyl)carbamoyl)-3-oxo-2,5,6,8-tetrahydroimidazo[1,5-a]pyrazine-7(3H)-carboxylate HATU (1.2 eq., 106.2 mg, 0.28 mmol), (2-(5-methyl-1,3,4-oxadiazol-2-yl)phenyl)methanamine hydrochloride (1.1 eq., 57.8 mg, 0.26 mmol) and DIPEA (5 eq., 0.19 mL, 1.16 mmol) were added to a suspension of Intermediate 2b (1 eq., 100 mg, 0.23 mmol) in anhydrous DCM (4 mL) under N$_2$. The mixture was stirred at rt for 30 min. Sat. Na$_2$CO$_3$ (15 mL) was added to the mixture, and the aqueous phase was extracted with EtOAc (3×15 mL). The combined organic phases were washed with water (4×15 mL) and brine (15 mL), dried over MgSO$_4$, filtered and evaporated to dryness to afford the title compound (134 mg, 96%) as a brown solid, which was used without further purification. LCMS (ESI, m/z): 601.2 [M+H]$^+$.

(R*)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide hydrochloride A solution of tert-butyl (R*)-2-(4-cyclopropoxyphenyl)-6-methyl-1-((2-(5-methyl-1,3,4-oxadiazol-2-yl)benzyl)carbamoyl)-3-oxo-2,5,6,8-tetrahydroimidazo[1,5-a]pyrazine-7 (3H)-carboxylate (1 eq., 134 mg, 0.22 mmol) in HCl 4N in dioxane (20 eq., 1.12 mL, 4.46 mmol) was stirred under N₂ at rt for 1 h. The mixture was evaporated to dryness to afford the title compound (125 mg, quant.) as a red solid, which was used as such. LCMS (ESI, m/z): 501.1 [M+H]⁺.

(R*)-7-(4-bromo-3-chlorobenzoyl)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide (1b)

TCFH (1.2 eq., 89.6 mg, 0.32 mmol) and N-methylimidazole (5 eq., 0.106 mL, 1.33 mmol) were added to a suspension of (R*)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide hydrochloride (0.84 eq., 120 mg, 0.22 mmol) and 4-bromo-3-chlorobenzoic acid (1.1 eq., 69.0 mg, 0.29 mmol) in anhydrous MeCN (2.55 mL) under N₂. The mixture was stirred at rt for 1 h. Sat. Na₂CO₃ (10 mL) was added to the mixture, and the aqueous phase was extracted with EtOAc (3×15 mL). The combined organic phases were washed with water (3×15 mL), brine (20 mL), dried over MgSO₄, filtered and evaporated to dryness. The crude mixture was purified by flash chromatography on silica gel (from 0% to 10% of MeOH in DCM). The resulting solid was triturated in Et₂O to give the title compound (1b) (86 mg, 54%) as a white solid. LCMS (ESI, m/z): 716.9/718.9/720.9 [M+H]⁺. ¹H-NMR (DMSO-d6, 600 MHz, 80° C.) δ ppm 0.63-0.73 (m, 2H), 0.77-0.87 (m, 2H), 1.27 (d, J=6.9 Hz, 3H), 2.58 (s, 3H), 3.64-3.71 (m, 2H), 3.83 (hept., J=3.0 Hz, 1H), 4.50 (d, J=18.3 Hz, 1H), 4.54-4.77 (m, 3H), 5.06-5.32 (m, 1H), 6.95-7.00 (m, 2H), 7.12-7.20 (m, 3H), 7.31 (d, J=7.1 Hz, 1H), 7.37 (dd, J=8.1, 1.7 Hz, 1H), 7.45-7.51 (m, 2H), 7.73 (d, J=1.7 Hz, 1H), 7.85 (d, J=7.9 Hz, 2H).

Example 6

(S*)-7-(4-bromo-3-chlorobenzoyl)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide (1a)

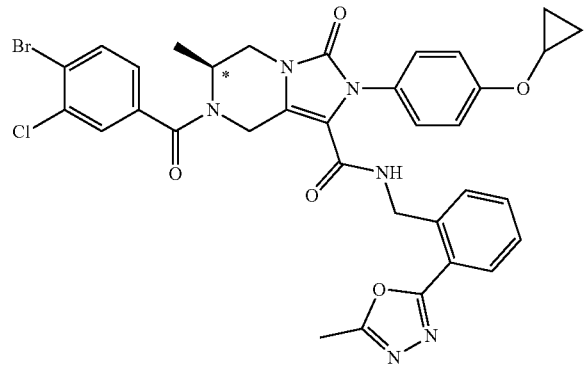

(S*)-7-(4-bromo-3-chlorobenzoyl)-2-(4-cyclopropoxyphenyl)-6-methyl-N-(2-(5-methyl-1,3,4-oxadiazol-2-yl)benzyl)-3-oxo-2,3,5,6,7,8-hexahydroimidazo[1,5-a]pyrazine-1-carboxamide (1a) was synthetized following the procedure as depicted for (1b), using Intermediate 2a in step 5 in place of Intermediate 2b. LCMS (ESI, m/z): 716.9/718.9/720.9 [M+H]⁺. ¹H-NMR (DMSO-d6, 600 MHz, 80° C.) δ ppm 0.63-0.73 (m, 2H), 0.77-0.87 (m, 2H), 1.27 (d, J=6.9 Hz, 3H), 2.58 (s, 3H), 3.64-3.71 (m, 2H), 3.83 (hept., J=3.0 Hz, 1H), 4.50 (d, J=18.3 Hz, 1H), 4.54-4.77 (m, 3H), 5.06-5.32 (m, 1H), 6.95-7.00 (m, 2H), 7.12-7.20 (m, 3H), 7.31 (d, J=7.1 Hz, 1H), 7.37 (dd, J=8.1, 1.7 Hz, 1H), 7.45-7.51 (m, 2H), 7.73 (d, J=1.7 Hz, 1H), 7.85 (d, J=7.9 Hz, 2H).

Example 7

(R*)-7-(4-bromo-3-chlorobenzoyl)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide (2b)

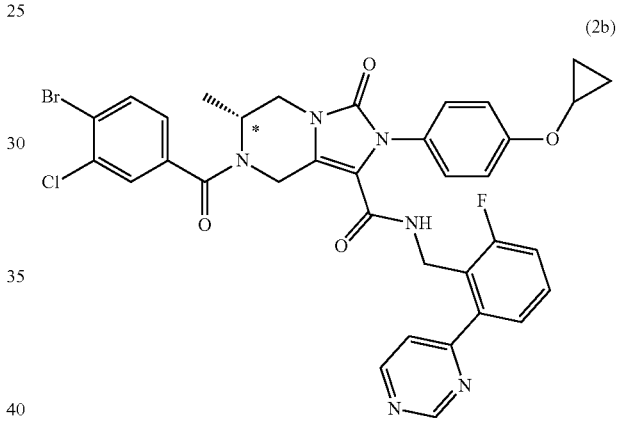

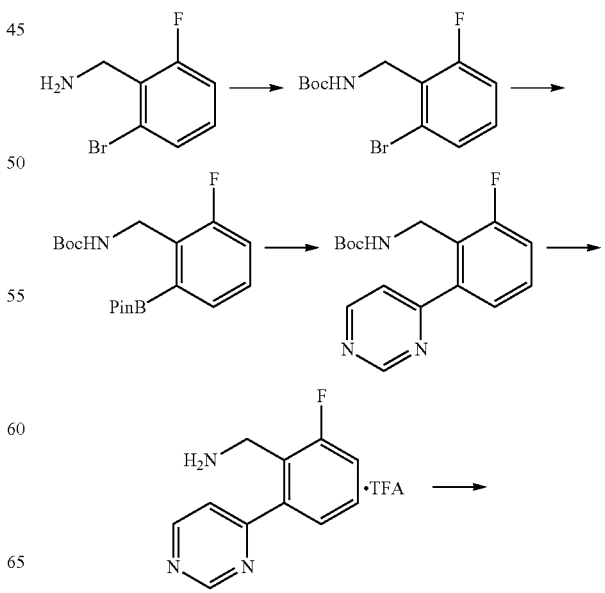

-continued

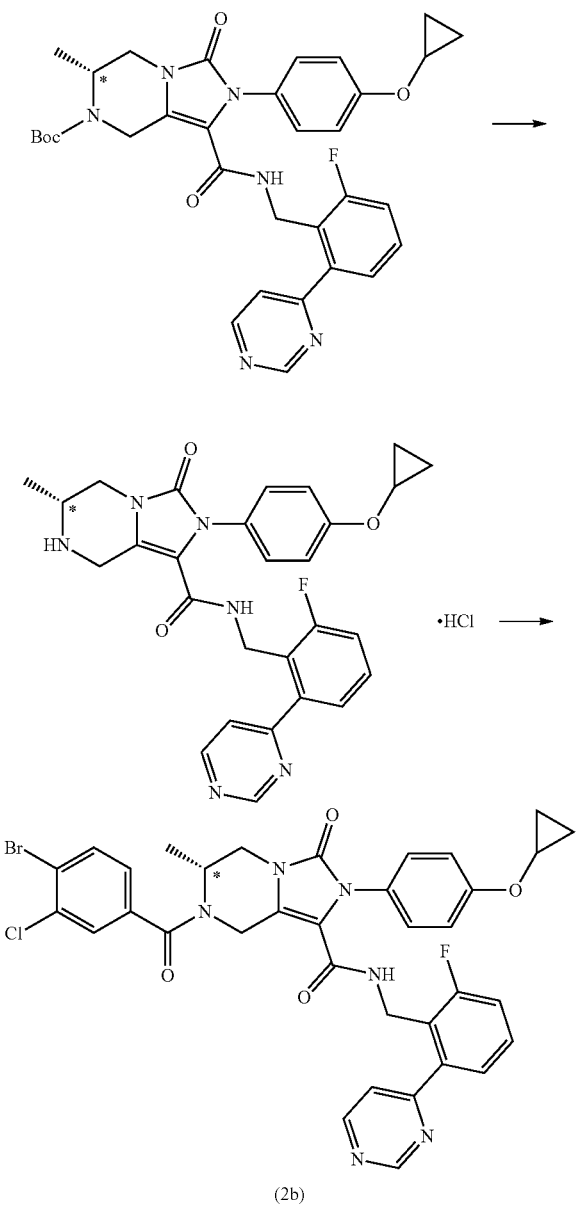

(2b)

Tert-butyl (2-bromo-6-fluorobenzyl)carbamate

A solution of Boc₂O (1.2 eq., 1.28 g, 5.88 mmol) in anhydrous DCM (5 mL) was added at 0° C. to a solution of Et₃N (1.2 eq., 0.82 mL, 5.88 mmol) and 2-bromo-6-fluorobenzylamine (1 eq., 1.0 g, 4.90 mmol) in anhydrous DCM (15 mL) under $N_2$. The mixture was stirred at rt for 1 h and evaporated to dryness. Water (50 mL) and HCl 1M (10 mL) were added. The aqueous solution was extracted with AcOEt (3×20 mL). The combined organic layers were and washed with HCl 1M (20 mL), brine (20 mL), dried over MgSO₄, filtered and evaporated to dryness to give tert-butyl (2-bromo-6-fluorobenzyl)carbamate (1.39 g, 93%) as a yellow oil, which was used without further purification. LCMS (ESI, m/z): 247.9/249.9 [M-tBu+H]⁺. ¹H-NMR (DMSO-d6, 400 MHz, 25° C.) δ ppm 1.37 (s, 9H), 4.26 (d, J=4.0 Hz, 2H), 7.14 (br s, 1H), 7.20-7.31 (m, 2H), 7.45 (d, J=8.0 Hz, 1H).

Tert-butyl (2-fluoro-6-(4,4,5,5-tetramethyl-1,3,2-dioxaborolan-2-yl)benzyl)carbamate A mixture of tert-butyl (2-bromo-6-fluorobenzyl)carbamate (1 eq., 1.1 g, 3.62 mmol), potassium acetate (2.5 eq., 0.89 g, 9.04 mmol), bis(pinacolato)diboron (1.2 eq., 1.10 g, 4.34 mmol) and Pd(dppf)Cl₂·DCM (0.1 eq., 0.3 g, 0.36 mmol) in anhydrous dioxane (11 mL) under $N_2$ was heated to 80° C. for 4 h. After cooling to rt, water (50 mL) was added. The solution was extracted with EtOAc (3×30 mL). The combined organic layers were washed with brine (50 mL), dried over MgSO₄, filtered and evaporated to dryness. The crude mixture was purified by flash chromatography on silica gel (from 0% to 30% AcOEt in CyH) to give tert-butyl (2-fluoro-6-(4,4,5,5-tetramethyl-1,3,2-dioxaborolan-2-yl)benzyl)carbamate (852 mg, 67%) as a colorless oil. LCMS (ESI, m/z): 252.1 [M-Boc+H]⁺.

Tert-butyl (2-fluoro-6-(pyrimidin-4-yl)benzyl)carbamate

A mixture of tert-butyl (2-fluoro-6-(4,4,5,5-tetramethyl-1,3,2-dioxaborolan-2-yl)benzyl)carbamate (1 eq., 883 mg, 2.52 mmol), 4-chloropyrimidine hydrochloride (1 eq., 380 mg, 2.52 mmol), sodium carbonate 2.4 M in water (5 eq., 5 mL, 12.6 mmol) and Pd(dppf)Cl₂·DCM (0.05 eq., 102.7 mg, 0.13 mmol) in dioxane (11 mL) was heated at 100° C. for 1 h. After cooling to rt, the mixture was diluted with water and extracted with AcOEt (3×70 mL). The combined organic layers were washed with brine, dried over MgSO₄, filtered and evaporated to dryness. The crude mixture was purified by flash chromatography on silica gel (from 0% to 65% AcOEt in CyH) to give tert-butyl (2-fluoro-6-(pyrimidin-4-yl)benzyl)carbamate (657 mg, 86%) as a colorless oil. LCMS (ESI, m/z): 304.1 [M+H]⁺. ¹H-NMR (DMSO-d6, 300 MHz, 25° C.) δ ppm 1.29 (s, 9H), 4.31 (d, J=4.5 Hz, 2H), 6.91 (br s, 1H), 7.31-7.39 (m, 2H), 7.45-7.52 (m, 1H), 7.73 (d, J=5.1 Hz, 1H), 8.90 (d, J=5.1 Hz, 1H), 9.26 (s, 1H).

(2-fluoro-6-(pyrimidin-4-yl)phenyl)methanamine·TFA

TFA (20 eq., 1.62 mL, 21.8 mmol) was added to a solution of tert-butyl (2-fluoro-6-(pyrimidin-4-yl)benzyl)carbamate (1 eq., 330 mg, 1.09 mmol) in DCM (7 mL) under $N_2$. The mixture was stirred at rt for 1 h. The mixture was evaporated to dryness and the residue was triturated in Et₂O to give (2-fluoro-6-(pyrimidin-4-yl)phenyl)methanamine·TFA (227 mg, 66%) as a black solid. LCMS (ESI, m/z): 204.1 [M+H]⁺.

Tert-butyl (R*)-2-(4-cyclopropoxyphenyl)-1-((2-fluoro-6-(pyrimidin-4-yl)benzyl)carbamoyl)-6-methyl-3-oxo-2,5,6,8-tetrahydroimidazo[1,5-a]pyrazine-7(3H)-carboxylate A solution of Intermediate 2b (1 eq., 108.3 mg, 0.25 mmol), (2-fluoro-6-(pyrimidin-4-yl)phenyl)methanamine·TFA (1.1 eq., 88 mg, 0.28 mmol), HATU (1.2 eq., 115 mg, 0.303 mmol) and DIPEA (10 eq., 0.42 mL, 2.52 mmol) in anhydrous DCM (3.8 mL) was stirred at rt under $N_2$ for 1 h. Sat. Na₂CO₃ (20 mL) was added to the mixture, and the aqueous phase was extracted with EtOAc (3×30 mL). The combined organic layers were washed with water (3×15 mL), brine (30 mL), dried over MgSO$_4$, filtered and evaporated to dryness. The crude product was purified by flash chromatography on silica gel (from 0% to 10% MeOH in DCM) to give the title product (117 mg, 76%) as a red oil. LCMS (ESI, m/z): 615.1 [M+H]$^+$.

(R*)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide hydrochloride A solution of tert-butyl (R*)-2-(4-cyclopropoxyphenyl)-1-((2-fluoro-6-(pyrimidin-4-yl)benzyl)carbamoyl)-6-methyl-3-oxo-2,5,6,8-tetrahydroimidazo[1,5-a]pyrazine-7(3H)-carboxylate (1 eq., 129 mg, 0.21 mmol) in HCl 4N in dioxane (20 eq., 1.05 mL, 4.2 mmol) was stirred at rt under N$_2$ for 1 h. The mixture was evaporated to dryness to afford the title compound (129 mg, quant.) as a dark red sticky solid, which was used as such. LCMS (ESI, m/z): 515.1 [M+H]$^+$.

(R*)-7-(4-bromo-3-chlorobenzoyl)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide (2b)

TCFH (1.2 eq., 35.69 mg, 0.13 mmol) and N-methylimidazole (5 eq., 0.042 mL, 0.53 mmol) were added to a suspension of (R*)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide hydrochloride (1 eq., 61 mg, 0.11 mmol) and 4-bromo-3-chlorobenzoic acid (1.1 eq., 27.45 mg, 0.12 mmol) in anhydrous MeCN (0.5 mL) under N$_2$. The mixture was stirred at rt for 2 h. Sat. Na$_2$CO$_3$ (10 mL) was added to the mixture, and the aqueous phase was extracted with EtOAc (3×20 mL). The combined organic layers were washed with water (3×10 mL), brine (30 mL), dried over MgSO$_4$, filtered and evaporated to dryness. The crude mixture was purified by flash chromatography on silica gel (from 0% to 10% MeOH in DCM). The resulting solid was purified by reverse phase flash chromatography (from 0% to 100% MeCN in water+0.1% TFA). The tubes containing the product were combined and MeCN was evaporated. The resulting aqueous solution was neutralized with sat. NaHCO$_3$ and extracted with EtOAc (4×10 mL). The combined organic layers were washed with water (20 mL), dried over MgSO$_4$, filtered and evaporated to dryness to give (2b) (31 mg, 36 mg) as a tan solid. LCMS (ESI, m/z): 728.9/730.9/732.9 [M+H]$^+$. $^1$H-NMR (DMSO-d6, 600 MHz, 80° C.) δ ppm 0.52-0.59 (m, 2H), 0.71-0.77 (m, 2H), 1.26 (d, J=6.6 Hz, 3H), 3.66 (d, J=2.9 Hz, 2H), 3.72 (hept, J=3.0 Hz, 1H), 4.32-4.42 (m, 2H), 4.47 (d, J=18.3 Hz, 1H), 4.59 (br. s, 1H), 5.08-5.21 (m, 1H), 6.86 (br. s, 1H), 6.90 (d, J=8.8 Hz, 2H), 7.13 (d, J=8.8 Hz, 2H), 7.31 (t, J=9.0 Hz, 1H), 7.35-7.37 (m, 2H), 7.48-7.54 (m, 1H), 7.65 (d, J=5.1 Hz, 1H), 7.72 (d, J=1.5 Hz, 1H), 7.84 (d, J=8.2 Hz, 1H), 8.86 (d, J=5.2 Hz, 1H), 9.11 (s, 1H).

Example 8

(S*)-7-(4-bromo-3-chlorobenzoyl)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide (2a)

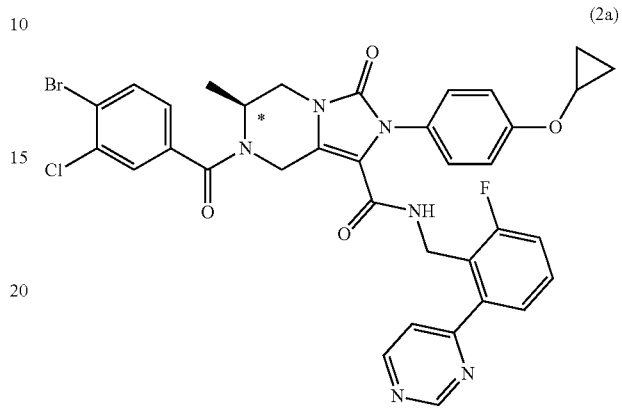

(2a)

(S*)-7-(4-bromo-3-chlorobenzoyl)-2-(4-cyclopropoxyphenyl)-N-(2-fluoro-6-(pyrimidin-4-yl)benzyl)-6-methyl-3-oxo-2,3,5,6,7,8-hexahydroimidazo[1,5-a]pyrazine-1-carboxamide (2a) was synthetized following the procedure as depicted for (2b), using Intermediate 2a in step 5, in place of Intermediate 2b. LCMS (ESI, m/z): 728.9/730.9/732.9 [M+H]$^+$. $^1$H-NMR (DMSO-d6, 600 MHz, 80° C.) δ ppm 0.52-0.59 (m, 2H), 0.71-0.77 (m, 2H), 1.26 (d, J=6.6 Hz, 3H), 3.66 (d, J=2.9 Hz, 2H), 3.72 (hept, J=3.0 Hz, 1H), 4.32-4.42 (m, 2H), 4.47 (d, J=18.3 Hz, 1H), 4.59 (br. s, 1H), 5.08-5.21 (m, 1H), 6.86 (br. s, 1H), 6.90 (d, J=8.8 Hz, 2H), 7.13 (d, J=8.8 Hz, 2H), 7.31 (t, J=9.0 Hz, 1H), 7.35-7.37 (m, 2H), 7.48-7.54 (m, 1H), 7.65 (d, J=5.1 Hz, 1H), 7.72 (d, J=1.5 Hz, 1H), 7.84 (d, J=8.2 Hz, 1H), 8.86 (d, J=5.2 Hz, 1H), 9.11 (s, 1H).

Example 9

(6S*)-7-(4-bromo-3-chloro-benzoyl)-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide (3a) and (6R*)-7-(4-bromo-3-chloro-benzoyl)-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide (3b)

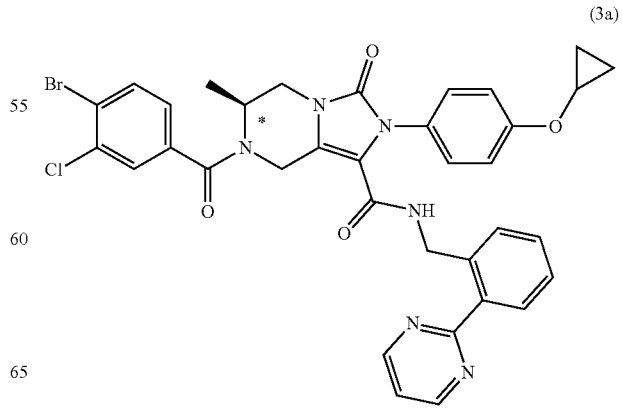

(3a)

-continued (3b)

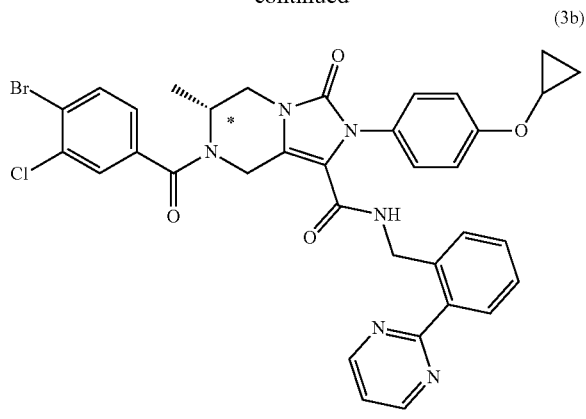

Compounds (3a) and (3b) were synthetized following the pathway described to synthetize (2b), using Intermediate 2 in place of Intermediate 2b, and (2-(pyrimidin-2-yl)phenyl)methanamine in place of (2-fluoro-6-(pyrimidin-4-yl)phenyl)methanamine in step 5. The resulting racemic compound (3) was then further separated into its two enantiomers (3a) (first eluting enantiomer) and (3b) (second eluting enantiomer) by SFC, using a column Lux C3 (20 mm×250 mm, 5 um) at 40° C., with a flow rate of 50 mL/min and 100 bar, under isochratic conditions (35:65 EtOH:$CO_2$ (0.1% v/v $NH_3$). LCMS (ESI, m/z): 713/715/717 [M+H]$^+$. $^1$H-NMR (DMSO, 600 MHz, 80° C.) δ ppm 0.57-0.61 (m, 2H), 0.73-0.79 (m, 2H), 1.28 (d, J=6.5 Hz, 3H), 3.64-3.69 (m, 2H), 3.70-3.75 (m, 1H), 4.47-4.55 (m, 3H), 4.56-4.69 (m, 1H), 5.12-5.29 (m, 1H), 6.91 (d, J=8.8 Hz, 2H), 7.09-7.18 (m, 3H), 7.26-7.30 (m, 1H), 7.38 (dd, J=8.2 Hz, 1.8 Hz, 1H), 7.39-7.45 (m, 3H), 7.73 (d, J=1.7 Hz, 1H), 7.85 (d, J=8.1 Hz, 1H), 7.95-7.99 (m, 1H), 8.81 (d, J=4.6 Hz, 2H).

Example 10

(6R*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55a) and (6S*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55b)

55a

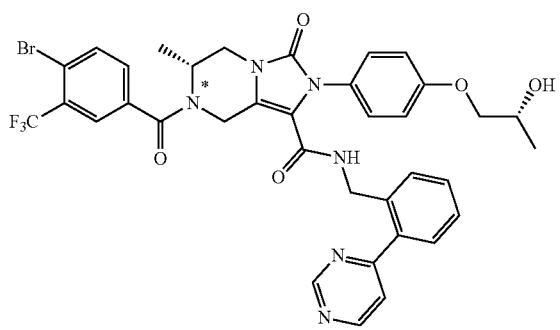

-continued

55b

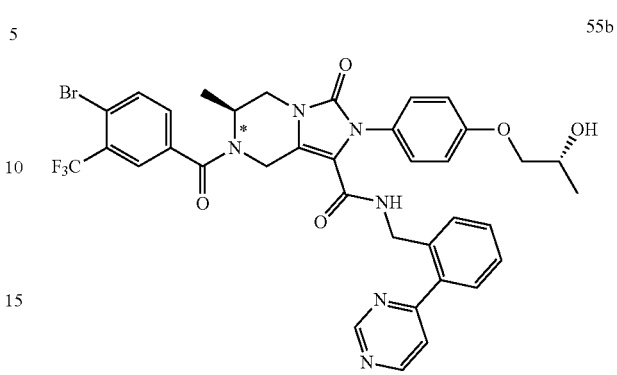

Tert-butyl (2-(pyrimidin-4-yl)benzyl)carbamate

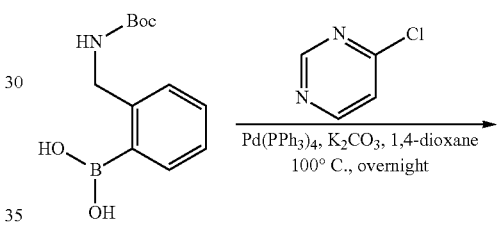

A 100 mL round bottom flask was charged with 2-{[(tert-butoxycarbonyl)amino]methyl}phenylboronic acid (5.00 g, 19.9 mmol, 1.00 eq.), 4-chloropyrimidine (2.96 g, 25.9 mmol, 1.30 eq.), $K_2CO_3$ (8.26 g, 59.7 mmol, 3.00 eq.), Pd(PPh$_3$)$_4$ (0.920 g, 0.797 mmol, 0.04 eq.) and 1,4-dioxane (100 mL). The solution was stirred overnight at 100° C. under a nitrogen atmosphere and then concentrated under reduced pressure. The reaction was quenched with water (200 mL), and the mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:5) to afford tert-butyl N-{[2-(pyrimidin-4-yl)phenyl]methyl}carbamate (5.00 g, 88% yield) as a white solid. LCMS (ESI, m/z): 286 [M+H]$^+$.

1-[2-(pyrimidin-4-yl)phenyl]methanamine hydrochloride

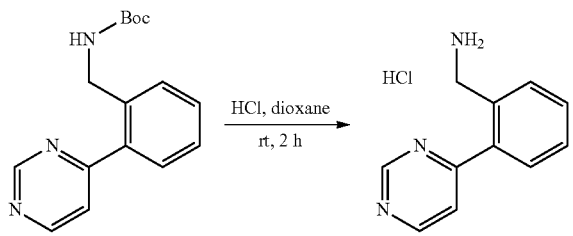 [SMILES: CC(C)(C)OC(=O)NCc1ccccc1-c1ccncn1 ; NCc1ccccc1-c1ccncn1 ; Cl]

A 100 mL round-bottom flask was charged with tert-butyl N-{[2-(pyrimidin-4-yl)phenyl]methyl}carbamate (1.50 g, 5.26 mmol, 1.00 eq.) and hydrogen chloride (20 mL, 4M in 1,4-dioxane). The mixture was stirred for 2 h at rt and then concentrated under reduced pressure to afford 1-[2-(pyrimidin-4-yl)phenyl]methanamine hydrochloride (0.85 g, crude) as an off-white solid. LCMS (ESI, m/z): 186 [M+H—HCl]$^+$.

7-tert-butyl 1-ethyl 2-{4-[(tert-butyldimethylsilyl)oxy]phenyl}-6-methyl-3-oxo-5H,6H, 8H-imidazo[1,5-a]pyrazine-1,7-dicarboxylate)

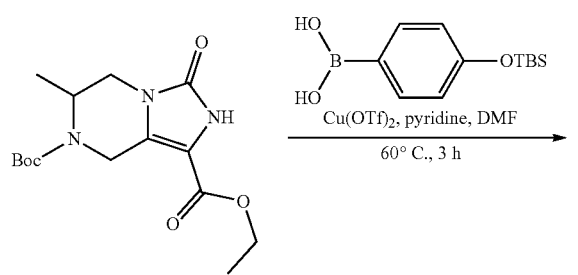

A 100 mL round-bottom flask was charged with 7-tert-butyl 1-ethyl 6-methyl-3-oxo-2H,5H,6H,8H-imidazo[1,5-a]pyrazine-1,7-dicarboxylate (3.00 g, 9.22 mmol, 1.00 eq.), 4-[(tert-butyldimethylsilyl)oxy] phenylboronic acid (2.56 g, 10.1 mmol, 1.10 eq.), Cu(OTf)$_2$ (3.33 g, 9.22 mmol, 1.00 eq.), pyridine (2.19 g, 27.660 mmol, 3.00 eq.) and DMF (30 mL). The mixture was stirred for 3 h at 60° C. under an O$_2$ atmosphere and then diluted with ethyl acetate (300 mL). The mixture was washed with water (3×100 mL), dried over anhydrous sodium sulfate, filtered and concentrated under reduced pressure. The residue was purified by silica gel column chromatography, eluted with ethyl acetate:petroleum ether (1:2) to afford to afford 7-tert-butyl 1-ethyl 2-{4-[(tert-butyldimethylsilyl) oxy]phenyl}-6-methyl-3-oxo-5H,6H,8H-imidazo[1,5-a]pyrazine-1,7-dicarboxylate (4.20 g, 87% yield) as a yellow oil. LCMS (ESI, m/z): 532 [M+H]$^+$.

7-(tert-butoxycarbonyl)-2-(4-hydroxyphenyl)-6-methyl-3-oxo-5H,6H,8H-imidazo[1,5-a]pyrazine-1-carboxylic acid

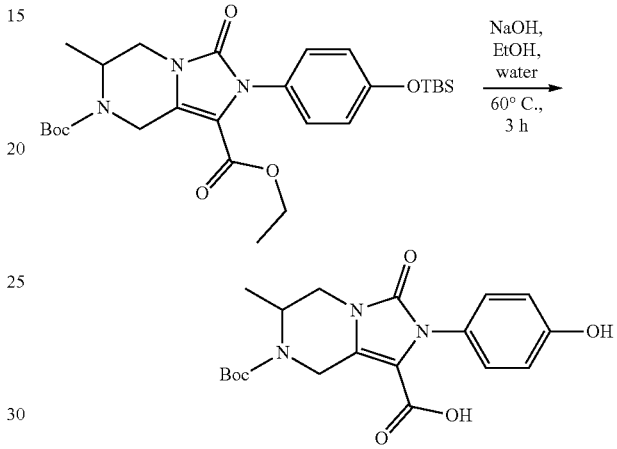

A 100 mL round-bottom flask was charged with 7-tert-butyl 1-ethyl 2-{4-[(tert-butyldimethylsilyl)oxy]phenyl}-6-methyl-3-oxo-5H,6H,8H-imidazo[1,5-a]pyrazine-1,7-dicarboxylate (4.26 g, 8.01 mmol, 1.00 eq.), NaOH (0.640 g, 16.0 mmol, 2.00 eq.), EtOH (40 mL) and water (10 mL). The mixture was stirred for 3 h at 60° C. and then concentrated under reduced pressure. The mixture was diluted with water (50 mL) and the pH value of the mixture was adjusted to about 6 with 1 mol/L HCl (aq.). The mixture was extracted with ethyl acetate (3×100 mL). The organic layers were combined, washed with water (3×100 mL), dried over anhydrous sodium sulfate, filtered and concentrated under reduced pressure to afford 7-(tert-butoxycarbonyl)-2-(4-hydroxyphenyl)-6-methyl-3-oxo-5H,6H,8H-imidazo[1,5-a]pyrazine-1-carboxylic acid (2.20 g, 71% yield) as a red solid. LCMS (ESI, m/z): 390 [M+H]$^+$.

tert-butyl 2-(4-hydroxyphenyl)-6-methyl-3-oxo-1-({[2-(pyrimidin-4-yl)phenyl]methyl} carbamoyl)-5H,6H,8H-imidazo[1,5-a]pyrazine-7-carboxylate

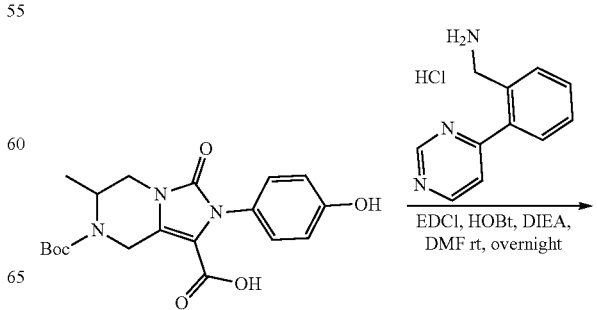

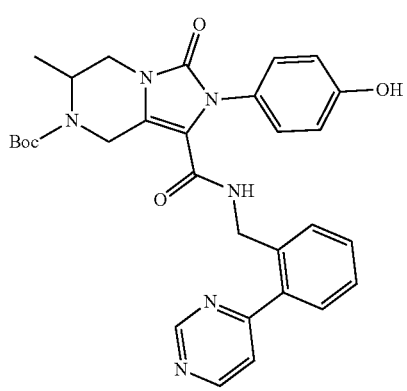
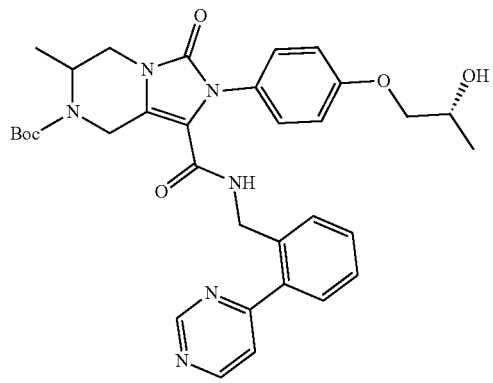

A 250 mL round-bottom flask was charged with 7-(tert-butoxycarbonyl)-2-(4-hydroxyphenyl)-6-methyl-3-oxo-5H,6H,8H-imidazo[1,5-a]pyrazine-1-carboxylic acid (500 mg, 1.28 mmol, 1.00 eq.), 1-[2-(pyrimidin-4-yl)phenyl]methanamine hydrochloride (342 mg, 1.54 mmol, 1.20 eq.), DIEA (829 mg, 6.42 mmol, 5.00 eq.), HOBT (208 mg, 1.54 mmol, 1.20 eq.), EDCI (295 mg, 1.54 mmol, 1.20 eq.) and DMF (10 mL). The mixture was stirred for overnight at rt. The reaction was quenched with water (50 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with $CH_2Cl_2$:MeOH (9:1) to afford tert-butyl 2-(4-hydroxyphenyl)-6-methyl-3-oxo-1-({[2-(pyrimidin-4-yl)phenyl]methyl}carbamyl)-5H,6H,8H-imidazo[1,5-a]pyrazine-7-carboxylate (650 mg, 91% yield) as purple oil. LCMS (ESI, m/z): 557 [M+H]$^+$.

2-{4-[(2R)-2-hydroxypropoxy]phenyl}-6-methyl-3-oxo-1-({[2-(pyrimidin-4-yl)phenyl]methyl}carbamoyl)-5H,6H,8H-imidazo[1,5-a]pyrazine-7-carboxylate A 250 mL round-bottom flask was charged with tert-butyl 2-(4-hydroxyphenyl)-6-methyl-3-oxo-1-({[2-(pyrimidin-4-yl)phenyl]methyl}carbamoyl)-5H,6H,8H-imidazo[1,5-a]pyrazine-7-carboxylate (350 mg, 0.629 mmol, 1.00 eq.), (R)-propylene oxide (2 mL), $K_2CO_3$ (260 mg, 1.88 mmol, 3.00 eq.) and $CH_3CN$ (10 mL). The mixture was stirred overnight at 80° C. and then concentrated under reduced pressure. The residue was diluted with water (30 mL). The organic layers were combined, washed with water (3×50 mL), dried over anhydrous sodium sulfate, filtered and concentrated under reduced pressure. The residue was purified by prep-TLC with $CH_2Cl_2$:MeOH (9:1) to afford tert-butyl 2-{4-[(2R)-2-hydroxypropoxyl]phenyl}-6-methyl-3-oxo-1-({[2-(pyrimidin-4-yl)phenyl]methyl}carbamoyl)-5H,6H,8H-imidazo[1,5-a]pyrazine-7-carboxylate (200 mg, 52% yield) as a yellow oil. LCMS (ESI, m/z): 615 [M+H]$^+$.

2-{4-[(2R)-2-hydroxypropoxy]phenyl}-6-methyl-3-oxo-N-{[2-(pyrimidin-4-yl)phenyl] methyl}-5H,6H,7H,8H-imidazo[1,5-a]pyrazine-1-carboxamide trifluoracetic acid salt

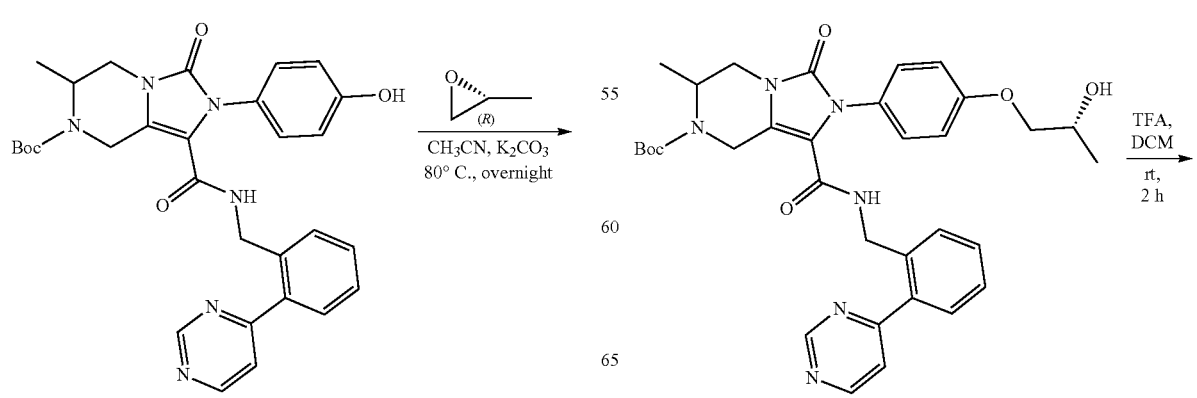

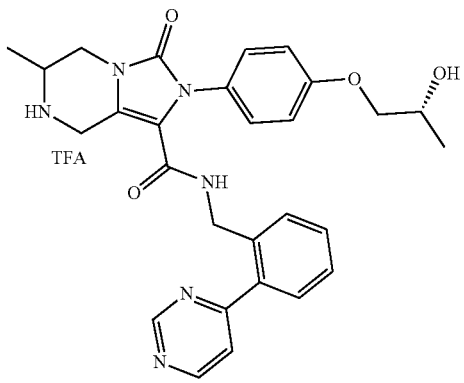

A 100 mL round-bottom flask was charged with tert-butyl 2-{4-[(2R)-2-hydroxypropoxy]phenyl}-6-methyl-3-oxo-1-({[2-(pyrimidin-4-yl)phenyl]methyl}carbamoyl)-5H,6H,8H-imidazo[1,5-a]pyrazine-7-carboxylate (200 mg, 0.325 mmol, 1.00 eq.), TFA (2 mL) and DCM (10 mL). The mixture was stirred for 2 h at rt and then concentrated under reduced pressure to afford 2-{4-[(2R)-2-hydroxypropoxy]phenyl}-6-methyl-3-oxo-N-{[2-(pyrimidin-4-yl)phenyl]methyl}-5H,6H,7H,8H-imidazo[1,5-a]pyrazine-1-carboxamide trifluoracetic acid salt (205 mg, crude) as a yellow oil. LCMS (ESI, m/z): 515 [M-TFA+H]⁺.

(6R*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55a) and (6S*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55b)

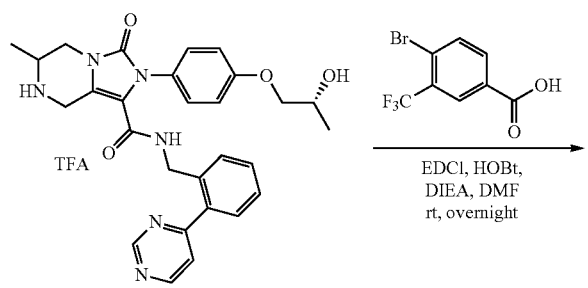

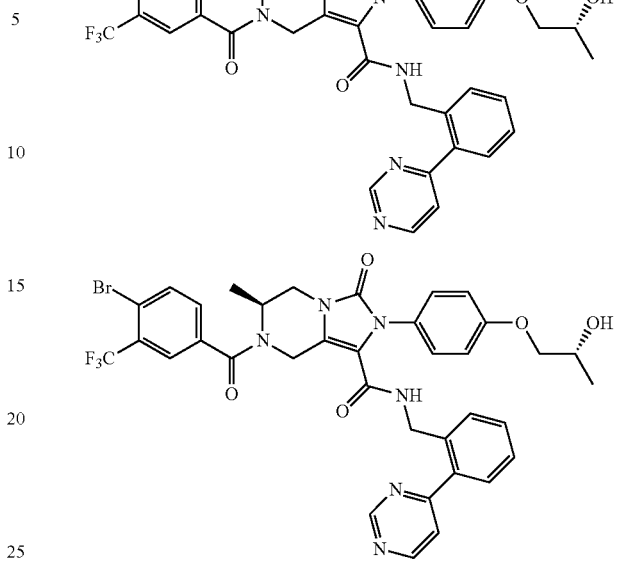

A 100 mL round bottom flask was charged with 2-{4-[(2R)-2-hydroxypropoxy]phenyl}-6-methyl-3-oxo-N-{[2-(pyrimidin-4-yl)phenyl]methyl}-5H,6H,7H,8H-imidazo[1,5-a]pyrazine-1-carboxamide trifluoroacetic acid salt (205 mg, 0.326 mmol, 1.00 eq.), 4-bromo-3-(trifluoromethyl)benzoic acid (105 mg, 0.391 mmol, 1.20 eq.), EDCI (75.1 mg, 0.391 mmol, 1.20 eq.), HOBT (52.9 mg, 0.391 mmol, 1.20 eq.), DIEA (210 mg, 1.630 mmol, 5.00 eq.) and DMF (10 mL). The mixture was stirred overnight at rt. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by prep-TLC with CH₂Cl₂:MeOH (10:1) to afford the crude product. The crude product was purified by prep-CHIRAL-HPLC with the following conditions: Column: Column: CHIRALPAK IE, 2×25 cm, 5 μm; Mobile Phase A: MtBE (0.5% 2M NH₃-MeOH)—HPLC, Mobile Phase B: EtOH-HPLC; Flow rate: 14 mL/min; Gradient: 20% B to 20% B in 30 min; Wave Length: 220/254 nm to afford the final products.

(6R*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55a) (the first eluting diastereoisomer, 31.7 mg, 13% yield) as a white solid. LCMS (ESI, m/z): 765 [M+H]⁺. ¹H NMR (400 MHz, CDCl₃) δ 8.77-8.74 (m, 2H), 7.82 (d, J=4.0 Hz, 2H), 7.54-7.41 (m, 6H), 7.15 (d, J=4.0 Hz, 2H), 6.84-6.81 (m, 1H), 6.64 (d, J=4.0 Hz, 2H), 5.23 (s, 1H), 4.65 (d, J=8.0 Hz, 1H), 4.45-4.32 (m, 2H), 4.09-3.84 (m, 2H), 3.74-3.69 (m, 2H), 3.58-3.54 (m, 1H), 2.50 (s, 1H), 1.65 (s, 1H), 1.41 (d, J=4.0 Hz, 3H), 1.26 (d, J=2.0 Hz, 3H).

(6S*)-7-[4-bromo-3-(trifluoromethyl)benzoyl]-2-{4-[(2R)-2-hydroxypropoxy]phenyl}-6-methyl-3-oxo-N-{[2-(pyrimidin-4-yl)phenyl]methyl}-5H,6H,8H-imidazo[1,5-a]pyrazine-1-carboxamide (55b) (the second eluting diastereoisomer, 39.7 mg, 16% yield) as a white solid. LCMS (ESI, m/z): 765 [M+H]⁺. ¹H NMR (400 MHz, CDCl₃) δ 8.77-8.74 (m, 2H), 7.82 (d, J=4.0 Hz, 2H), 7.54-7.41 (m, 6H), 7.15 (d, J=4.0 Hz, 2H), 6.84-6.81 (m, 1H), 6.64 (d, J=4.0 Hz, 2H), 5.23 (s, 1H), 4.65 (d, J=8.0 Hz, 1H), 4.45-4.32 (m, 2H), 4.09-3.84 (m, 2H), 3.74-3.69 (m, 2H), 3.58-3.54 (m, 1H), 1.41 (d, J=4.0 Hz, 3H), 1.26 (d, J=2.0 Hz, 3H).

Example 11

(6R*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71a) and (6S*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71b)

71a

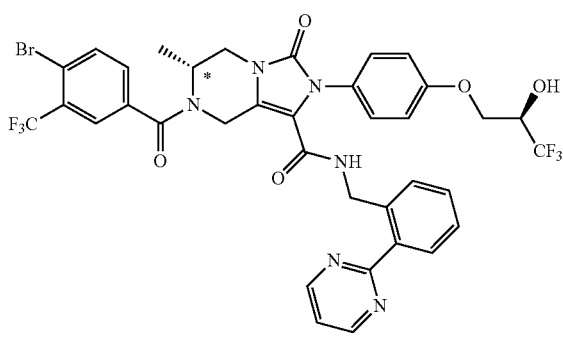

71b tert-butyl N-{[2-(pyrimidin-2-yl)phenyl]methyl}carbamate

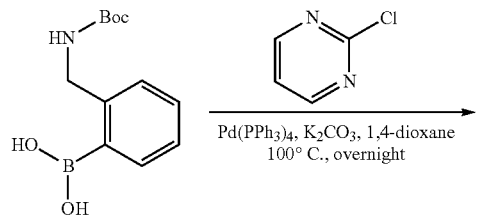

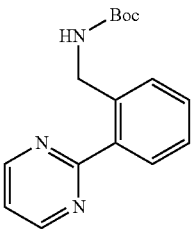

A 100 mL round bottom flask was charged with 2-{[(tert-butoxycarbonyl) amino] methyl}phenylboronic acid (3.00 g, 11.9 mmol, 1.00 eq.), 2-chloro-pyrimidine (1.64 g, 14.3 mmol, 1.20 eq.), K₂CO₃ (4.95 g, 35.8 mmol, 3.00 eq.), Pd(PPh₃)₄ (0.690 g, 0.597 mmol, 0.05 eq.) and 1,4-dioxane (20 mL). The solution was stirred overnight at 100° C. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate: petroleum ether (1:5) to afford tert-butyl N-{[2-(pyrimidin-2-yl)phenyl] methyl}carbamate (2.50 g, 73% yield) as a white solid. LCMS (ESI, m/z): 286 [M+H]⁺.

1-[2-(pyrimidin-2-yl)phenyl]methanamine hydrochloride

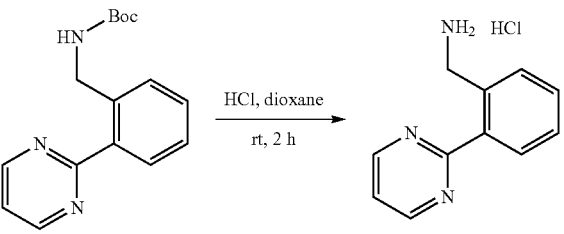 [SMILES: CC(C)(C)OC(=O)NCc1ccccc1-c1ncccn1 ; NCc1ccccc1-c1ncccn1 ; Cl]

A 100 mL round-bottom flask was charged with tert-butyl N-{[2-(pyrimidin-2-yl)phenyl]methyl}carbamate (1.00 g, 3.51 mmol, 1.00 eq.) and hydrogen chloride (20 mL, 4M in 1,4-dioxane). The solution was stirred for 2 h at rt and then concentrated under reduced pressure to afford 1-[2-(pyrimidin-2-yl)phenyl]methanamine hydrochloride (0.770 g, crude) as a white solid. LCMS (ESI, m/z): 186 [M+H—HCl]⁺.

tert-butyl 2-(4-hydroxyphenyl)-6-methyl-3-oxo-1-((2-(pyrimidin-2-yl)benzyl)carbamoyl)-2,5,6,8-tetrahydroimidazo[1,5-a]pyrazine-7(3H)-carboxylate

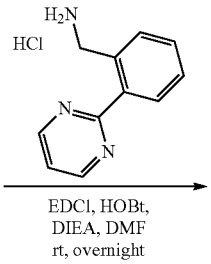

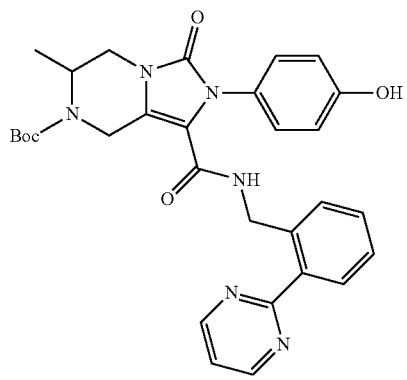
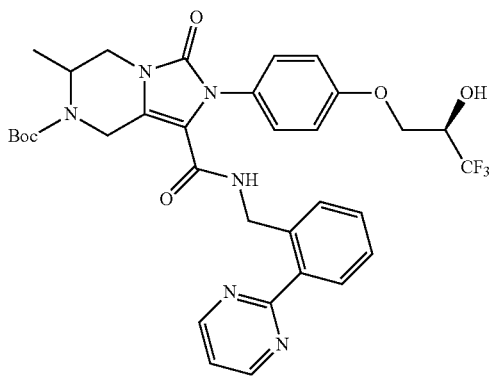

A 100 mL round-bottom flask was charged with 7-(tert-butoxycarbonyl)-2-(4-hydroxyphenyl)-6-methyl-3-oxo-5H,6H,8H-imidazo[1,5-a]pyrazine-1-carboxylic acid (500 mg, 1.28 mmol, 1.00 eq.), 1-[2-(pyrimidin-2-yl)phenyl]methanamine hydrochloride (285 mg, 1.284 mmol, 1.00 eq.), EDCI (320 mg, 1.67 mmol, 1.03 eq.), HOBT (226 mg, 1.67 mmol, 1.30 eq.), DIEA (830 mg, 6.42 mmol, 5.00 eq.) and DMF (8 mL). The mixture was stirred for overnight at rt and then diluted with ethyl acetate (150 mL). The mixture was washed with water (3×100 mL), dried over anhydrous sodium sulfate, filtered and concentrated under reduced pressure. The residue was purified by silica gel column chromatography, eluted with CH$_2$Cl$_2$:MeOH (9:1) to afford tert-butyl 2-(4-hydroxyphenyl)-6-methyl-3-oxo-1-({[2-(pyrimidin-2-yl)phenyl]methyl}carbamoyl)-5H,6H,8H-imidazo[1,5-a]pyrazine-7-carboxylate (550 mg, 77% yield) as a yellow solid. LCMS (ESI, m/z): 557 [M+H]$^+$.

tert-butyl 6-methyl-3-oxo-1-((2-(pyrimidin-2-yl)benzyl)carbamoyl)-2-(4-((R)-3,3,3-trifluoro-2-hydroxypropoxy)phenyl)-2,5,6,8-tetrahydroimidazo[1,5-a]pyrazine-7(3H)-carboxylate A 250 mL round-bottom flask was charged with tert-butyl 2-(4-hydroxyphenyl)-6-methyl-3-oxo-1-({[2-(pyrimidin-4-yl)phenyl]methyl}carbamoyl)-5H,6H,8H-imidazo[1,5-a]pyrazine-7-carboxylate (280 mg, 0.503 mmol, 1.00 eq.), (2R)-2-(trifluoromethyl)oxirane (84.6 mg, 0.754 mmol, 1.50 eq.), K$_2$CO$_3$ (208 mg, 1.51 mmol, 3.00 eq.) and CH$_3$CN (10 mL). The mixture was stirred for overnight at 80° C. and then concentrated under reduced pressure. The residue was diluted with water (30 mL). The aqueous layer was extracted with ethyl acetate (3×50 mL), dried over anhydrous sodium sulfate, filtered and concentrated under reduced pressure. The residue was purified by prep-TLC with CH$_2$Cl$_2$:MeOH (9:1) to afford tert-butyl 6-methyl-3-oxo-1-((2-(pyrimidin-2-yl)benzyl)carbamoyl)-2-(4-((R)-3,3,3-trifluoro-2-hydroxypropoxy)phenyl)-2,5,6,8-tetrahydroimidazo[1,5-a]pyrazine-7(3H)-carboxylate (230 mg, 68% yield) as a yellow solid. LCMS (ESI, m/z): 669 [M+H]$^+$.

6-methyl-3-oxo-N-(2-(pyrimidin-2-yl)benzyl)-2-(4-((R)-3,3,3-trifluoro-2-hydroxypropoxy)phenyl)-2,3,5,6,7,8-hexahydroimidazo[1,5-a]pyrazine-1-carboxamide trifluoroacetic acid salt

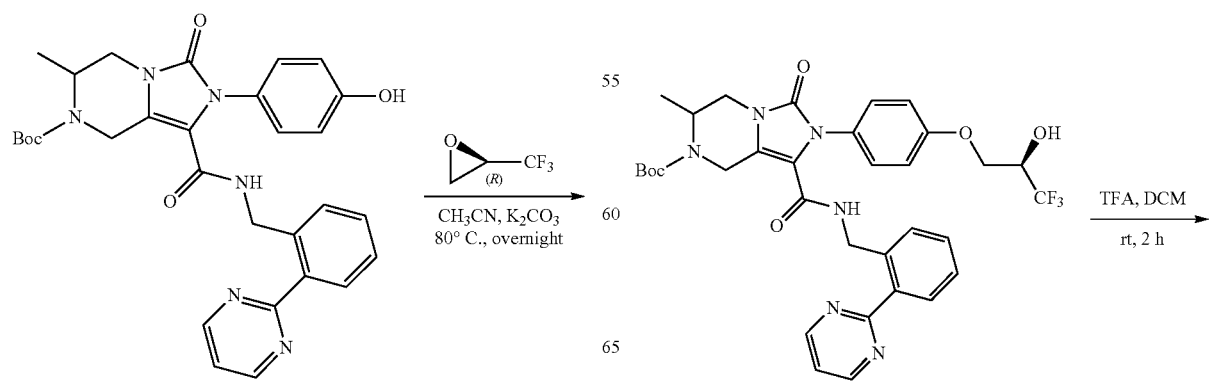

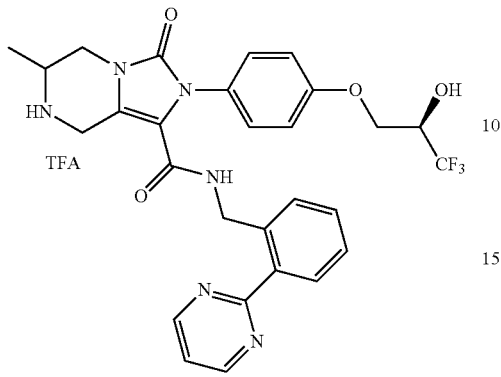

A 100 mL round-bottom flask was charged with tert-butyl 6-methyl-3-oxo-1-((2-(pyrimidin-2-yl)benzyl)carbamoyl)-2-(4-((R)-3,3,3-trifluoro-2-hydroxypropoxy)phenyl)-2,5,6,8-tetrahydroimidazo[1,5-a]pyrazine-7(3H)-carboxylate (230 mg, 0.325 mmol, 1.00 eq.), TFA (2 mL) and DCM (10 mL) at rt. The mixture was stirred for 2 h at rt under air atmosphere and then concentrated under reduced pressure to afford 6-methyl-3-oxo-N-(2-(pyrimidin-2-yl)benzyl)-2-(4-((R)-3,3,3-trifluoro-2-hydroxypropoxy)phenyl)-2,3,5,6,7,8-hexahydroimidazo[1,5-a]pyrazine-1-carboxamide trifluoroacetic acid salt (250 mg, crude) as a yellow oil. LCMS (ESI, m/z): 569 [M-TFA+H]$^+$.

(6R*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71a) and (6S*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71b)

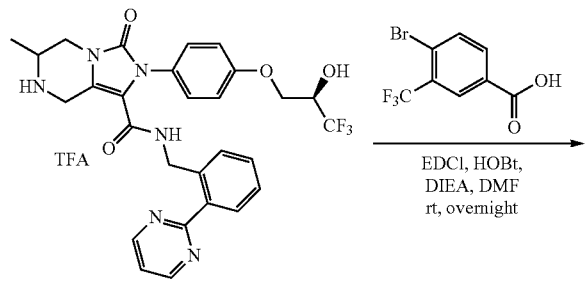

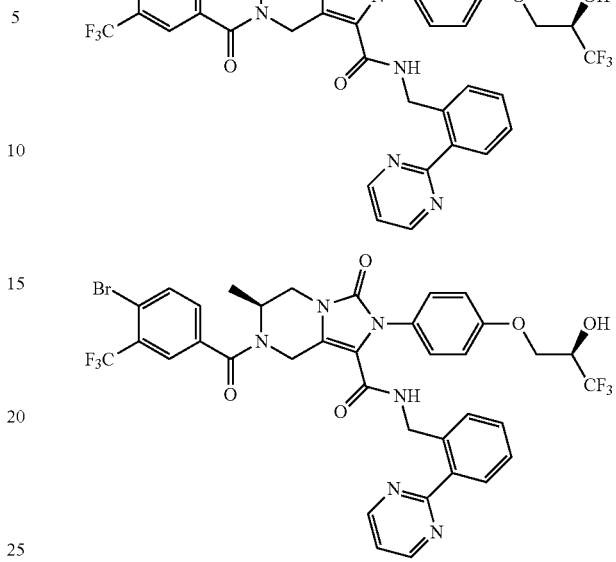

A 100 mL round-bottom flask was charged with 6-methyl-3-oxo-N-(2-(pyrimidin-2-yl)benzyl)-2-(4-((R)-3,3,3-trifluoro-2-hydroxypropoxy)phenyl)-2,3,5,6,7,8-hexahydro-imidazo[1,5-a]pyrazine-1-carboxamide trifluoroacetic acid salt (205 mg, 0.300 mmol, 1.00 eq.), 4-bromo-3-(trifluoromethyl)benzoic acid (96.9 mg, 0.360 mmol, 1.20 eq.), EDCI (69.0 mg, 0.360 mmol, 1.20 eq.), HOBT (48.7 mg, 0.360 mmol, 1.20 eq.), DIEA (194 mg, 1.500 mmol, 5.00 eq.) and DMF (5 mL). The mixture was stirred for overnight at rt. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by prep-TLC with CH$_2$Cl$_2$:MeOH (10:1) to afford the crude product. The crude product was purified by prep-CHIRAL-HPLC with the following conditions: Column: Chiral ART Cellulose-SA, 2×25 cm, 5 µm; Mobile Phase A: MtBE (0.5% 2M NH$_3$-MeOH)—HPLC, Mobile Phase B: EtOH-HPLC; Flow rate: 20 mL/min; Gradient: 13% B to 13% B in 18 min; Wave Length: 254/220 nm to afford the final products.

(6R*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71a) (the first eluting diastereoisomer, 16.7 mg, 6.8% yield) as a white solid. LCMS (ESI, m/z): 819 [M+H]$^+$. $^1$H NMR (400 MHz, CDCl$_3$) δ 8.59 (d, J=4.0 Hz, 2H), 8.16-8.12 (m, 1H), 7.84-7.82 (m, 2H), 7.52-7.43 (m, 4H), 7.18-7.16 (m, 1H), 7.05 (d, J=4.0 Hz, 2H), 6.84 (s, 1H), 6.47 (d, J=4.0 Hz, 2H), 5.34 (s, 2H), 4.68-4.56 (m, 2H), 4.48-4.46 (m, 1H) 4.26-4.18 (m, 1H), 3.94-3.90 (m, 1H), 3.85-3.81 (m, 2H), 3.71 (d, J=6.0 Hz, 1H), 3.45 (s, 1H), 1.41 (d, J=2.0 Hz, 3H).

(6S*)-7-[4-bromo-3-(trifluoromethyl)benzoyl]-6-methyl-3-oxo-N-{[2-(pyrimidin-2-yl)phenyl]methyl}-2-{4-[(2R)-3,3,3-trifluoro-2-hydroxypropoxy]phenyl}-5H,6H,8H-imidazo[1,5-a]pyrazine-1-carboxamide (71b) (the second eluting diastereoisomer, 22.3 mg, 9.1% yield). LCMS (ESI, m/z): 819 [M+H]$^+$. $^1$H NMR (400 MHz, CDCl$_3$) δ 8.59 (d, J=4.0 Hz, 2H), 8.16-8.12 (m, 1H), 7.84-7.82 (m, 2H), 7.52-7.43 (m, 4H), 7.18-7.16 (m, 1H), 7.05 (d, J=4.0 Hz, 2H), 6.84 (s, 1H), 6.47 (d, J=4.0 Hz, 2H), 5.34 (s, 2H), 4.68-4.56 (m, 2H), 4.48-4.46 (m, 1H) 4.26-4.18 (m, 1H), 3.94-3.90 (m, 1H), 3.85-3.81 (m, 2H), 3.71 (d, J=6.0 Hz, 1H), 3.45 (s, 1H), 1.41 (d, J=2.0 Hz, 3H).

Example 12

(6R*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl]methyl}-5H,6H,8H-imidazo[1,5-a]pyrazine-1-carboxamide (73a) and (6S*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl]methyl}-5H,6H,8H-imidazo[1,5-a]pyrazine-1-carboxamide (73b)

73a

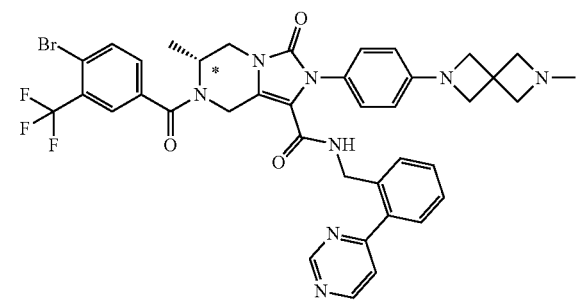

73b

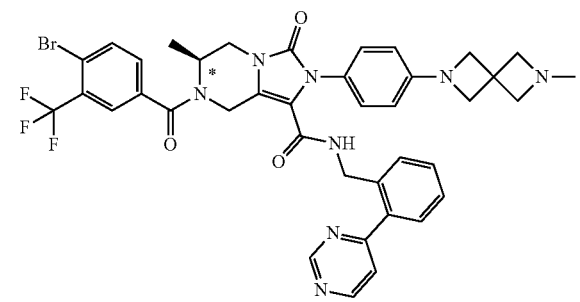

7-tert-butyl 1-ethyl 2-(4-iodophenyl)-6-methyl-3-oxo-5H,6H,8H-imidazo[1,5-a]pyrazine-1,7-dicarboxylate

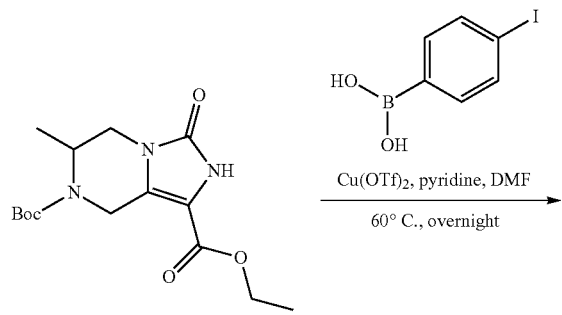

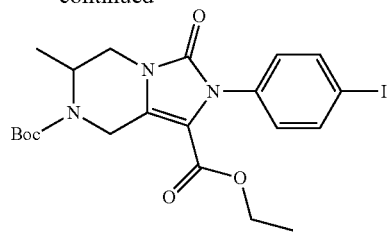

A 40 ml vial was charged with 7-tert-butyl 1-ethyl 6-methyl-3-oxo-2H,5H,6H,8H-imidazo[1,5-a]pyrazine-1,7-dicarboxylate (500 mg, 1.54 mmol, 1.00 eq.), 4-iodophenylboronic acid (457 mg, 1.84 mmol, 1.20 eq.), pyridine (267 mg, 3.38 mmol, 2.20 eq.), Cu(OTf)₂ (111 mg, 0.307 mmol, 0.200 eq.) and DMF (20 mL). The mixture was stirred overnight at 60° C. under an O₂ atmosphere. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate:petroleum ether (1:3) to afford 7-tert-butyl 1-ethyl 2-(4-iodophenyl)-6-methyl-3-oxo-5H,6H,8H-imidazo[1,5-a]pyrazine-1,7-dicarboxylate (730 mg, 90% yield) as an off-white solid. LCMS (ESI, m/z): 528 [M+H]⁺.

tert-butyl 1-(benzylcarbamoyl)-2-(4-{6-methyl-2,6-diazaspiro[3.3]heptan-2-yl}phenyl)-3-oxo-5H,6H,8H-imidazo[1,5-a]pyrazine-7-carboxylate A 250 mL round-bottom flask was charged with 7-tert-butyl 1-ethyl 2-(4-iodophenyl)-6-methyl-3-oxo-5H,6H,8H-imidazo[1,5-a]pyrazine-1,7-dicarboxylate (900 mg, 1.71 mmol, 1.00 eq.), 2-methyl-2,6-diazaspiro[3.3]heptane dihydrochloride (631 mg, 3.41 mmol, 2.00 eq.), Pd(OAc)₂ (38.3 mg, 0.171 mmol, 0.10 eq.), XPhos (163 mg, 0.341 mmol, 0.20 eq.), Cs₂CO₃ (3.34 g, 10.2 mmol, 6.00 eq.) and toluene (20 mL) The mixture was stirred for overnight at 90° C. under a nitrogen atmosphere. The reaction was quenched with water (50 mL). The mixture was extracted with ethyl acetate (3×50 mL). The organic layers were combined, washed with brine (3×50 mL), dried over anhydrous sodium sulfate, filtered and concentrated under reduced pressure. The residue was purified by silica gel column chromatography, eluted with CH$_2$Cl$_2$:MeOH (10:1) to afford tert-butyl 1-(benzylcarbamoyl)-2-(4-{6-methyl-2,6-diazaspiro[3.3]heptan-2-yl}phenyl)-3-oxo-5H,6H,8H-imidazo[1,5-a]pyrazine-7-carboxylate (660 mg, 69% yield) as a light yellow solid. LCMS (ESI, m/z): 512 [M+H]$^+$.

1-(ethoxycarbonyl)-6-methyl-2-(4-{6-methyl-2,6-diazaspiro[3.3]heptan-2-yl}phenyl)-3-oxo-5H,6H,8H-imidazo[1,5-a]pyrazine-7-carboxylic acid

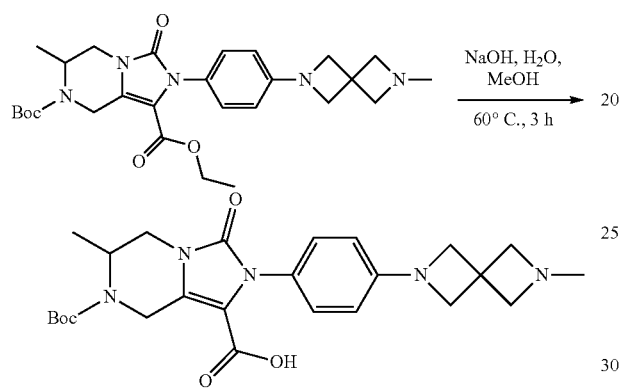

A 40 mL vial was charged with 7-tert-butyl 1-ethyl 6-methyl-2-(4-{6-methyl-2,6-diazaspiro[3.3]heptan-2-yl}phenyl)-3-oxo-5H,6H,8H-imidazo[1,5-a]pyrazine-1,7-dicarboxylate (650 mg, 1.27 mmol, 1.00 eq.), MeOH (16 mL), NaOH (102 mg, 2.55 mmol, 2.00 eq.) and water (4 mL) at rt. The mixture was stirred 3 h at 60° C. The reaction was quenched with water (20 mL). The mixture was adjusted to pH 7 with HCl (1 mol/L aq.). The mixture was extracted with ethyl acetate (3×50 mL). The organic layers were combined, washed with brine (3×50 mL), dried over anhydrous sodium sulfate, filtered and concentrated under reduced pressure to afford 1-(ethoxycarbonyl)-6-methyl-2-(4-{6-methyl-2,6-diazaspiro[3.3]heptan-2-yl}phenyl)-3-oxo-5H,6H,8H-imidazo[1,5-a]pyrazine-7-carboxylic acid (770 mg, crude) as an off-white solid. LCMS (ESI, m/z): 484 [M+H]$^+$.

tert-butyl 6-methyl-2-(4-{6-methyl-2,6-diazaspiro[3.3]heptan-2-yl}phenyl)-3-oxo-1-({[2-(pyrimidin-4-yl)phenyl]methyl}carbamoyl)-5H,6H,8H-imidazo[1,5-a]pyrazine-7-carboxylate

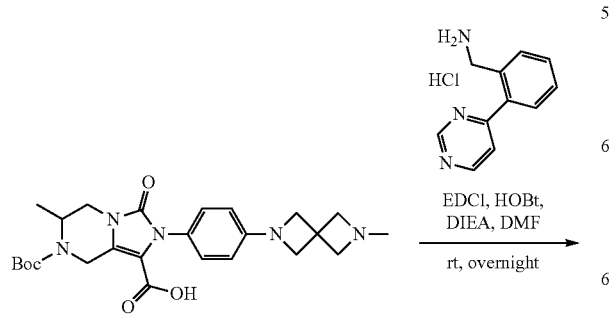

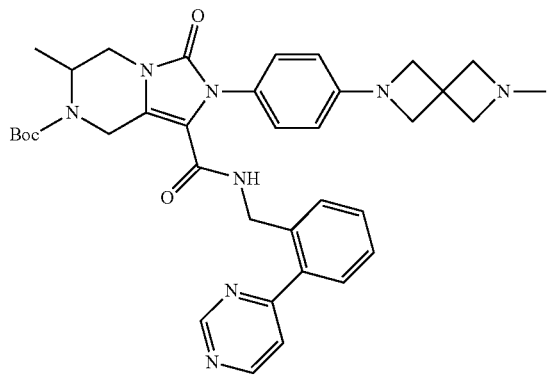

A 40 mL vial was charged with 7-(tert-butoxycarbonyl)-6-methyl-2-(4-{6-methyl-2,6-diazaspiro[3.3]heptan-2-yl}phenyl)-3-oxo-5H,6H,8H-imidazo[1,5-a]pyrazine-1-carboxylic acid (200 mg, 0.414 mmol, 1.00 eq.), 1-[2-(pyrimidin-4-yl)phenyl]methanamine hydrochloride (110 mg, 0.497 mmol, 1.20 eq.), DIEA (267 mg, 2.07 mmol, 5.00 eq.), HOBT (83.8 mg, 0.621 mmol, 1.50 eq.), EDCI (119 mg, 0.621 mmol, 1.50 eq.) and DMF (20 mL). The mixture was stirred overnight at rt. The reaction was quenched with water (20 mL). The mixture was extracted with ethyl acetate (3×50 mL). The organic layers were combined, washed with brine (3×50 mL), dried over anhydrous sodium sulfate, filtered and concentrated under reduced pressure. The residue was purified by silica gel column chromatography, eluted with CH$_2$Cl$_2$:MeOH (10:1) to afford tert-butyl 6-methyl-2-(4-{6-methyl-2,6-diazaspiro[3.3]heptan-2-yl}phenyl)-3-oxo-1-({[2-(pyrimidin-4-yl)phenyl]methyl}carbamoyl)-5H,6H,8H-imidazo[1,5-a]pyrazine-7-carboxylate (110 mg, 41% yield) as a yellow solid. LCMS (ESI, m/z): 651 [M+H]$^+$.

6-methyl-2-(4-{6-methyl-2,6-diazaspiro[3.3]heptan-2-yl}phenyl)-3-oxo-N-{[2-(pyrimidin-4-yl)phenyl]methyl}-5H,6H,7H,8H-imidazo[1,5-a]pyrazine-1-carboxamide trifluoroacetic acid salt

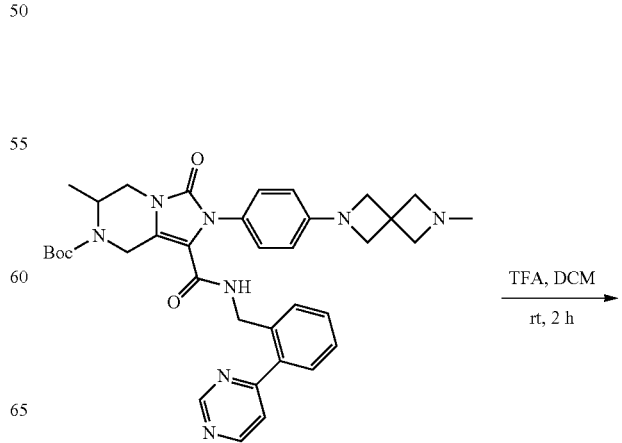

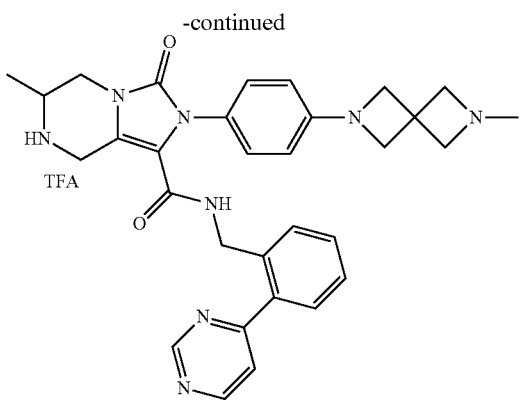

A 100 mL round-bottom flask was charged with tert-butyl 6-methyl-2-(4-{6-methyl-2,6-diazaspiro[3.3]heptan-2-yl}phenyl)-3-oxo-1-({[2-(pyrimidin-4-yl)phenyl] methyl}carbamoyl)-5H,6H,8H-imidazo[1,5-a]pyrazine-7-carboxylate (110 mg, 0.169 mmol, 1.00 eq.), TFA (4 mL) and DCM (20 mL). The mixture was stirred for 2 h at rt and then concentrated under reduced pressure to afford 6-methyl-2-(4-{6-methyl-2,6-diazaspiro[3.3]heptan-2-yl}phenyl)-3-oxo-N-{[2-(pyrimidin-4-yl)phenyl]methyl}-5H,6H,7H,8H-imidazo[1,5-a]pyrazine-1-carboxamide trifluoroacetic acid salt (118 mg, crude) as a light yellow oil. LCMS (ESI, m/z): 550 [M+H-TFA]$^+$.

(6R*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl] methyl}-5H,6H,8H-imidazo[1,5-a]pyrazine-1-carboxamide (73a) and (6S*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl]methyl}-5H,6H,8H-imidazo[1,5-a]pyrazine-1-carboxamide (73b)

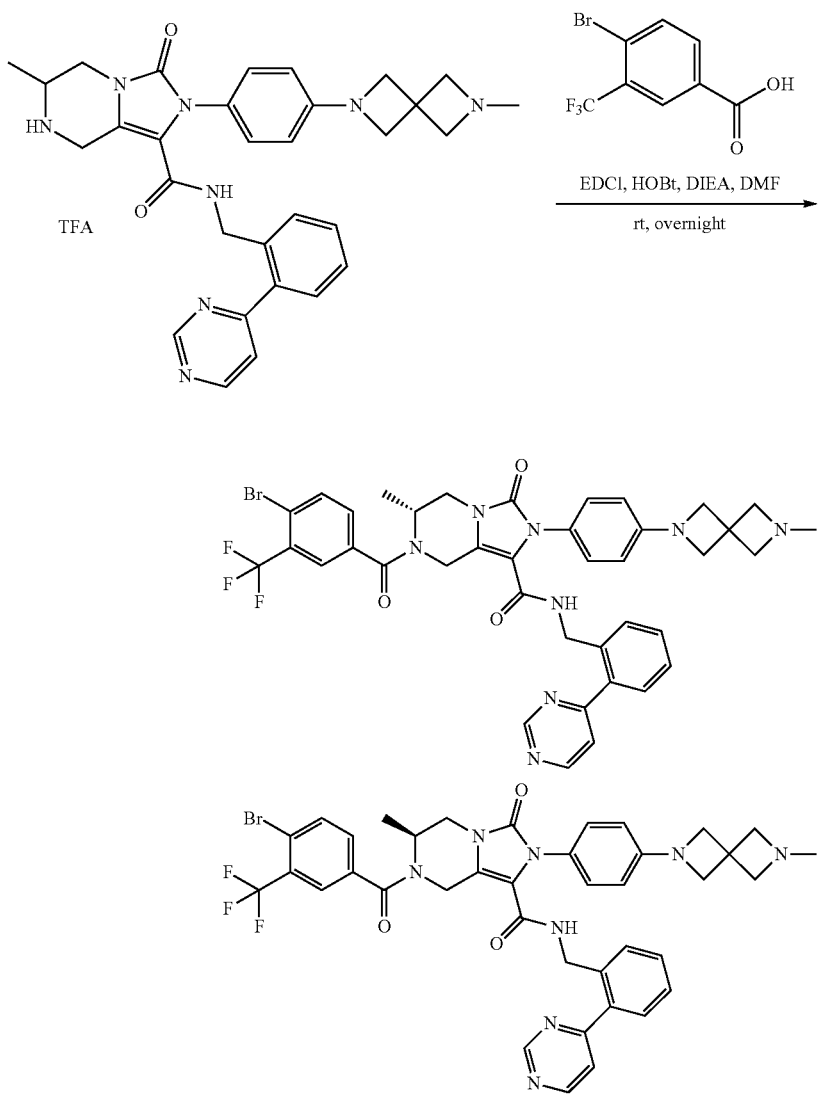

A 40 mL vial was charged with 6-methyl-2-(4-{6-methyl-2,6-diazaspiro[3.3]heptan-2-yl}phenyl)-3-oxo-N-{[2-(pyrimidin-4-yl)phenyl]methyl}-5H,6H,7H,8H-imidazo[1,5-a]pyrazine-1-carboxamide trifluoroacetic acid salt (118 mg, 0.177 mmol, 1.00 eq.), 4-bromo-3-(trifluoromethyl)benzoic acid (57.2 mg, 0.212 mmol, 1.20 eq.), EDCI (51.0 mg, 0.265 mmol, 1.50 eq.), DIEA (68.7 mg, 0.531 mmol, 3.00 eq.), HOBT (35.9 mg, 0.265 mmol, 1.50 eq.) and DMF (5 mL). The mixture was stirred for overnight at rt. The reaction was quenched with water (20 mL). The mixture was extracted with ethyl acetate (3×50 mL). The organic layers were combined, washed with brine (3×50 mL), dried over anhydrous sodium sulfate, filtered and concentrated under reduced pressure. The residue was purified by silica gel column chromatography, eluted with $CH_2Cl_2$:MeOH (8:1) to afford the crude product. The crude product was purified by purified by prep-CHIRAL-HPLC with the following conditions: Column: CHIRALPAK IE, 2×25 cm, 5 μm; Mobile Phase A: MtBE (0.5% 2M $NH_3$-MeOH)—HPLC, Mobile Phase B: MeOH-HPLC; Flow rate: 20 mL/min; Gradient: 50% B to 50% B in 18 min; Wave Length: 254/220 nm to afford the final products.

(6R*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl]methyl}-5H,6H,8H-imidazo[1,5-a]pyrazine-1-carboxamide (73a) (the first elution, 17.3 mg, 12% yield) as a white solid. LCMS (ESI, m/z): 801 $[M+H]^+$. $^1$H NMR (300 MHz, $CDCl_3$) δ 8.83 (d, J=1.4 Hz, 1H), 8.75 (d, J=5.2 Hz, 1H), 7.83 (d, J=8.2 Hz, 2H), 7.58-7.39 (m, 6H), 7.09-6.99 (m, 2H), 6.77 (t, J=6.2 Hz, 1H), 6.22-6.12 (m, 2H), 5.35 (s, 2H), 4.66 (d, J=18.9 Hz, 1H), 4.38 (qd, J=13.8, 6.2 Hz, 2H), 3.87 (d, J=12.7 Hz, 1H), 3.74 (s, 5H), 3.40 (s, 4H), 2.37 (s, 3H), 1.41 (d, J=6.9 Hz, 3H).

(6S*)-7-[4-bromo-3-(trifluoromethyl)benzoyl]-6-methyl-2-(4-{6-methyl-2,6-diazaspiro[3.3]heptan-2-yl}phenyl)-3-oxo-N-{[2-(pyrimidin-4-yl)phenyl]methyl}-5H,6H,8H-imidazo[1,5-a]pyrazine-1-carboxamide (73b) (17.2 mg, 12% yield) as a white solid. LCMS (ESI, m/z): 801 $[M+H]^+$. $^1$H NMR (300 MHz, $CDCl_3$) δ 8.83 (d, J=1.4 Hz, 1H), 8.75 (d, J=5.3 Hz, 1H), 7.83 (d, J=8.1 Hz, 2H), 7.56-7.39 (m, 6H), 7.10-7.00 (m, 2H), 6.77 (t, J=6.2 Hz, 1H), 6.17 (d, J=8.6 Hz, 2H), 5.32 (s, 1H), 4.66 (d, J=18.9 Hz, 1H), 4.38 (qd, J=13.8, 6.2 Hz, 2H), 3.87 (d, J=12.8 Hz, 1H), 3.75 (s, 5H), 3.43 (s, 4H), 2.38 (s, 3H), 1.42 (d, J=6.9 Hz, 3H).

Example 13

7-(4-bromo-3-(trifluoromethyl)benzoyl)-6-methyl-3-oxo-N-(2-(pyridazin-3-yl)benzyl)-2-(4-(3,3,3-trifluoro-2-hydroxy-2-methylpropoxy)phenyl)-2,3,5,6,7,8-hexahydroimidazo[1,5-a]pyrazine-1-carboxamide (85) and Separation into its 4 Diastereoisomers (85a), (85b), (85c) and (85d)

85

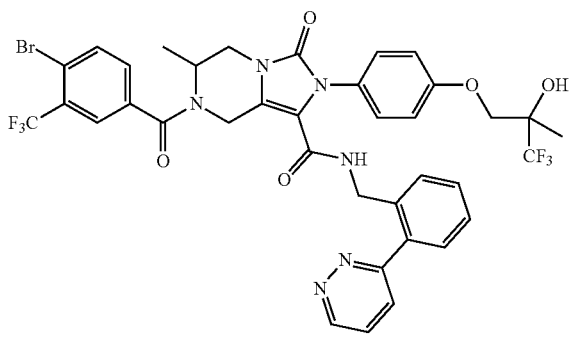

tert-butyl (2-(pyridazin-3-yl)benzyl)carbamate

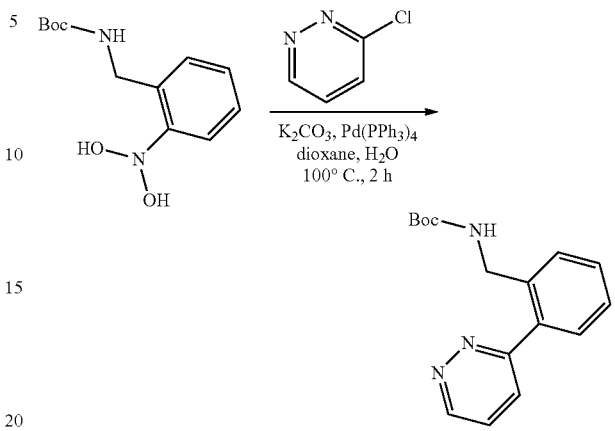

A 250 mL round-bottom flask was charged with 2-{[(tert-butoxycarbonyl)amino]methyl}phenylboronic acid (2.00 g, 7.96 mmol, 1.00 eq.), 3-chloropyridazine (1.37 g, 11.9 mmol, 1.50 eq.), $K_2CO_3$ (3.30 g, 23.9 mmol, 3.00 eq.), Pd(PPh$_3$)$_4$ (0.460 g, 0.398 mmol, 0.05 eq.), $H_2O$ (2 mL) and 1,4-dioxane (20 mL). The mixture was stirred for 2 h at 100° C. under a nitrogen atmosphere. The reaction was quenched with water (100 mL). The mixture was extracted with dichloromethane (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate to afford tert-butyl N-{[2-(pyridazin-3-yl)phenyl]methyl}carbamate (2.10 g, 92% yield) as an off-white solid. LCMS (ESI, m/z):286 $[M+H]^+$.

(2-(pyridazin-3-yl)phenyl)methanamine hydrochloride

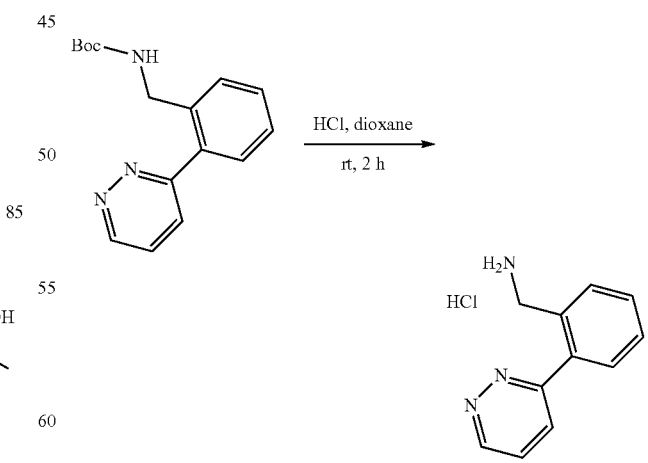

A mixture of tert-butyl N-{[2-(pyridazin-3-yl)phenyl]methyl}carbamate (2.00 g, 7.02 mmol, 1.00 eq.) and HCl (gas) (50 mL, 4M in dioxane) was stirred for 2 h at rt and then concentrated under reduced pressure to afford (2-

(pyridazin-3-yl)phenyl)methanamine hydrochloride (1.55, crude) as an off-white solid. LCMS (ESI, m/z): 186 [M+H—HCl]+.

tert-butyl 2-(4-hydroxyphenyl)-6-methyl-3-oxo-1-({[2-(pyridazin-3-yl)phenyl]methyl}carbamoyl)-5H,6H,8H-imidazo[1,5-a]pyrazine-7-carboxylate tert-butyl 6-methyl-3-oxo-1-({[2-(pyridazin-3-yl)phenyl]methyl}carbamoyl)-2-[4-(3,3,3-trifluoro-2-hydroxy-2-methylpropoxy)phenyl]-5H,6H,8H-imidazo[1,5-a]pyrazine-7-carboxylate

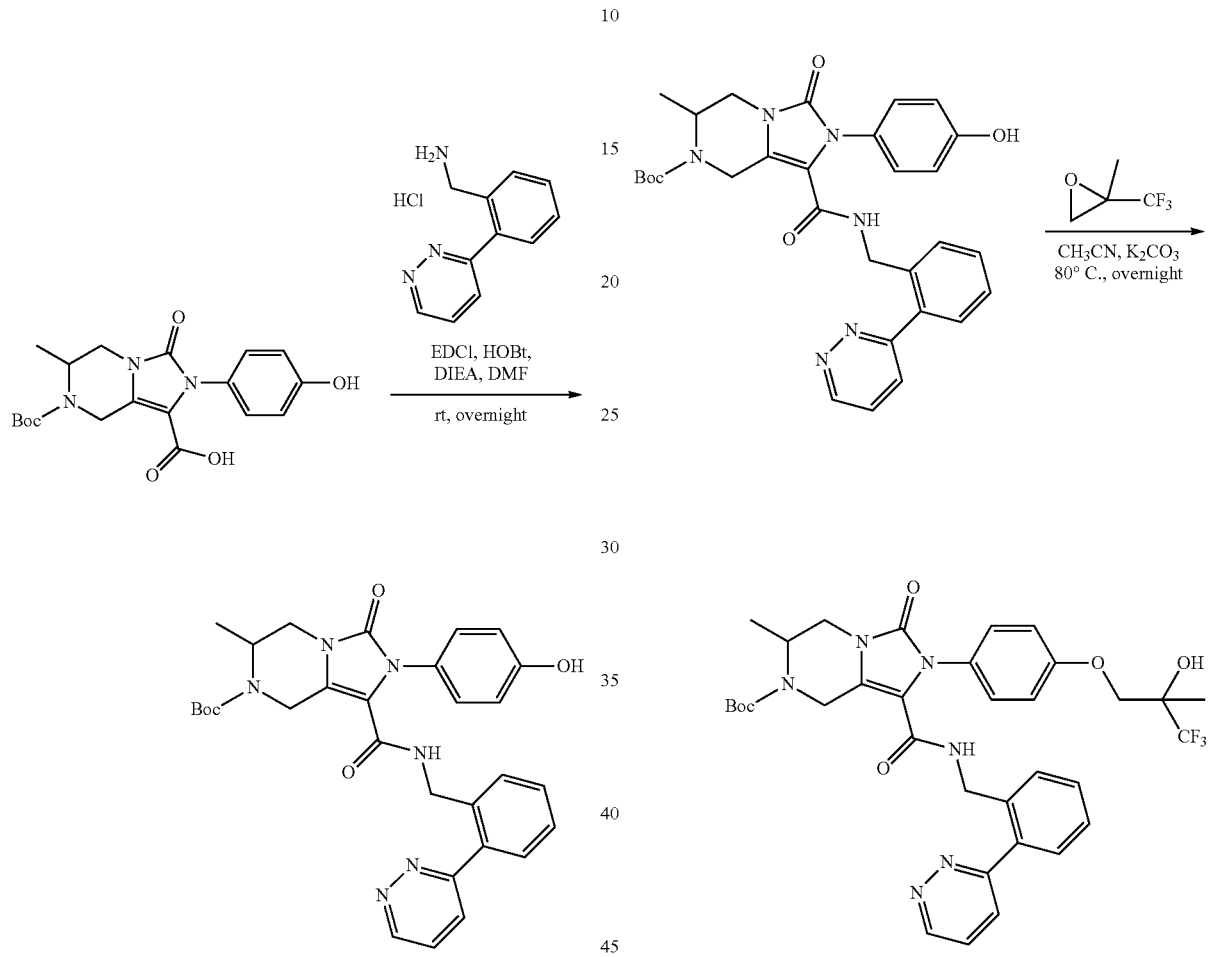

A 100 mL round-bottom flask was charged with 7-(tert-butoxycarbonyl)-2-(4-hydroxyphenyl)-6-methyl-3-oxo-5H,6H,8H-imidazo[1,5-a]pyrazine-1-carboxylic acid (0.800 g, 2.05 mmol, 1.00 eq.), (2-(pyridazin-3-yl)phenyl)methanamine hydrochloride (0.455 g, 2.05 mmol, 1.00 eq.), EDCI (0.512 g, 2.67 mmol, 1.30 eq.), HOBT (0.361 g, 2.67 mmol, 1.30 eq.), DIEA (1.33 g, 10.3 mmol, 5.00 eq.) and DMF (20 mL). The mixture was stirred for overnight at rt under a nitrogen atmosphere and then diluted with ethyl acetate (200 mL). The mixture was washed with water (3×100 mL), dried over anhydrous Na₂SO₄, filtered and concentrated under reduced pressure. The residue was purified by silica gel column chromatography, eluted with MeOH:CH₂Cl₂ (1:10) to afford tert-butyl 2-(4-hydroxyphenyl)-6-methyl-3-oxo-1-({[2-(pyridazin-3-yl)phenyl]methyl}carbamoyl)-5H,6H,8H-imidazo[1,5-a]pyrazine-7-carboxylate (400 mg, 35% yield) as a yellow solid. LCMS (ESI, m/z): 557 [M+H]+.

A 100 mL round-bottom flask was charged with tert-butyl 2-(4-hydroxyphenyl)-6-methyl-3-oxo-1-({[2-(pyridazin-3-yl)phenyl]methyl}carbamoyl)-5H,6H,8H-imidazo[1,5-a]pyrazine-7-carboxylate (400 mg, 0.719 mmol, 1.00 eq.), 2-methyl-2-(trifluoromethyl)oxirane (109 mg, 0.863 mmol, 1.20 eq.), K₂CO₃ (199 mg, 1.44 mmol, 2.00 eq.) and CH₃CN (10 mL). The mixture was stirred for overnight at 80° C. under a nitrogen atmosphere. The reaction was quenched with water (50 mL). The mixture was extracted with ethyl acetate (3×50 mL). The organic layers were combined, washed with brine (3×50 mL), dried over anhydrous sodium sulfate, filtered and concentrated under reduced pressure. The residue was purified by prep-TLC with ethyl acetate to afford tert-butyl 6-methyl-3-oxo-1-({[2-(pyridazin-3-yl)phenyl]methyl}carbamoyl)-2-[4-(3,3,3-trifluoro-2-hydroxy-2-methylpropoxy)phenyl]-5H,6H,8H-imidazo[1,5-a]pyrazine-7-carboxylate (305 mg, 62% yield) as a brown solid. LCMS (ESI, m/z): 683 [M+H]+.

6-methyl-3-oxo-N-{[2-(pyridazin-3-yl)phenyl]methyl}-2-[4-(3,3,3-trifluoro-2-hydroxy-2-methylpropoxy)phenyl]-5H,6H,7H,8H-imidazo[1,5-a]pyrazine-1-carboxamide trifluoroacetic acid salt

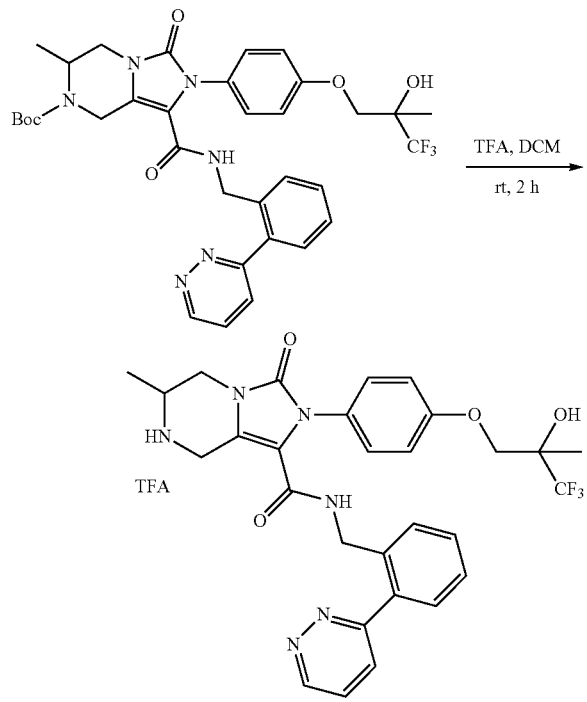

A 100 mL vial was charged with tert-butyl 6-methyl-3-oxo-1-({[2-(pyridazin-3-yl)phenyl]methyl}carbamoyl)-2-[4-(3,3,3-trifluoro-2-hydroxy-2-methylpropoxy)phenyl]-5H,6H,8H-imidazo[1,5-a]pyrazine-7-carboxylate (305 mg, 0.447 mmol, 1.00 eq.), TFA (1 mL) and DCM (5 mL). The mixture was stirred for 2 h at rt and then concentrated under reduced pressure to afford 6-methyl-3-oxo-N-{[2-(pyridazin-3-yl)phenyl]methyl}-2-[4-(3,3,3-trifluoro-2-hydroxy-2-methylpropoxy)phenyl]-5H,6H,7H,8H-imidazo[1,5-a]pyrazine-1-carboxamide trifluoroacetic acid salt (315 mg, crude) as a brown oil. LCMS (ESI, m/z): 583 [M+H-TFA]⁺.

7-(4-bromo-3-(trifluoromethyl)benzoyl)-6-methyl-3-oxo-N-(2-(pyridazin-3-yl)benzyl)-2-(4-(3,3,3-trifluoro-2-hydroxy-2-methylpropoxy)phenyl)-2,3,5,6,7,8-hexahydroimidazo[1,5-a]pyrazine-1-carboxamide (85) and Separation into its 4 Diastereoisomers (85a), (85b), (85c) and (85d)

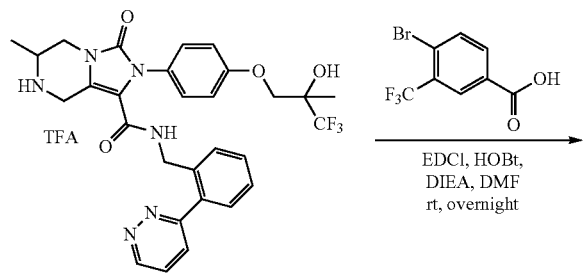

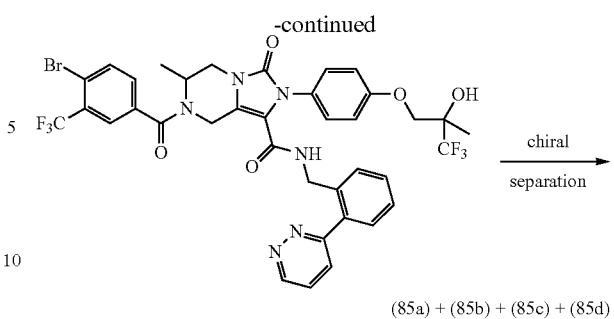

(85a) + (85b) + (85c) + (85d)

A 100 mL round-bottom flask was charged with 6-methyl-3-oxo-N-{[2-(pyridazin-3-yl)phenyl]methyl}-2-[4-(3,3,3-trifluoro-2-hydroxy-2-methylpropoxy)phenyl]-5H,6H,7H,8H-imidazo[1,5-a]pyrazine-1-carboxamide trifluoroacetic acid salt (311 mg, 0.446 mmol, 1.00 eq.), 4-bromo-3-(trifluoromethyl)benzoic acid (156 mg, 0.580 mmol, 1.30 eq.), EDCI (1110 mg, 0.580 mmol, 1.30 eq.), HOBT (78.4 mg, 0.580 mmol, 1.30 eq.), DIEA (2880 mg, 2.23 mmol, 5.00 eq.) and DMF (8 mL). The mixture was stirred for overnight at rt. The reaction was quenched with water (50 mL). The mixture was extracted with ethyl acetate (3×150 mL). The organic layers were combined, washed with brine (3×100 mL), dried over anhydrous sodium sulfate, filtered and concentrated under reduced pressure. The residue was purified by prep-TLC with $CH_2Cl_2$:MeOH (10:1) to afford the crude product. The crude product was purified by prep-Chiral-HPLC with the following conditions: Column: CHIRALPAK IF, 2×25 cm, 5 μm; Mobile Phase A: MtBE (0.5% 2M $NH_3$-MeOH)—HPLC, Mobile Phase B: EtOH-HPLC; Flow rate: 20 mL/min; Gradient: 20% B to 20% B in 16 min; Wave Length: 220/254 nm to afford the product (85-1) (the first elution) and (85-2) (the second elution). The product (85-1) was purified by Prep-Chiral-HPLC with the following conditions Column: CHIRALPAK IG, 2×25 cm, 5 μm; Mobile Phase A: Hex:DCM=3:1(0.5% 2M $NH_3$-MeOH), Mobile Phase B: EtOH; Flow rate: 20 mL/min; Gradient: 15% B to 15% B in 21 min; Wave Length: 220/254 nm to afford the final products (85a) (the first elution, 13.0 mg, 3.5% yield) as a white solid. LCMS (ESI, m/z): 833 [M+H]⁺. ¹H NMR (300 MHz, $CDCl_3$) δ 9.09 (d, J=4.8 Hz, 1H), 7.90-7.70 (m, 2H), 7.65-7.30 (m, 7H), 7.20-7.05 (m, 2H), 6.85 (d, J=5.1 Hz 1H), 6.53 (d, J=8.7 Hz 2H), 5.11 (s, 1H), 4.66 (d, J=18.6 Hz, 1H), 4.45-4.20 (m, 2H), 4.00-3.80 (m, 2H), 3.75-3.60 (m, 2H), 3.60-3.30 (m, 1H), 1.41 (d, J=4.5 Hz, 6H).

(85b) (the second elution, 13.0 mg, 3.5% yield) as a white solid. LCMS (ESI, m/z): 833 [M+H]⁺. ¹H NMR (300 MHz, $CDCl_3$) δ 9.15-8.90 (m, 1H), 7.90-7.70 (m, 2H), 7.65-7.30 (m, 7H), 7.20-7.05 (m, 2H), 6.85 (d, J=5.1 Hz 1H), 6.53 (d, J=8.7 Hz, 2H), 5.11 (s, 2H), 4.66 (d, J=18.6 Hz, 1H), 4.45-4.20 (m, 2H), 4.00-3.80 (m, 2H), 3.75-3.60 (m, 2H), 3.50-3.35 (m, 1H), 1.41 (d, J=5.4 Hz, 6H).

The product (85-2) was purified by prep-Chiral-HPLC with the following conditions Column: Lux Sum Cellulose-2, 2.12*25 cm, 5 μm; Mobile Phase A: Hex (0.5% 2M $NH_3$-MeOH)—HPLC, Mobile Phase B: MeOH:EtOH=1:1—HPLC; Flow rate: 20 mL/min; Gradient: 40% B to 40% B in 54 min; Wave Length: 220/254 nm to afford the final products.

(85c) (the first elution, 9 mg) as a white solid. LCMS (ESI, m/z): 833 [M+H]⁺. ¹H NMR (300 MHz, $CDCl_3$) δ 9.15-8.90 (m, 1H), 7.90-7.70 (m, 2H), 7.65-7.30 (m, 7H), 7.20-7.05 (m, 2H), 6.85 (d, J=5.1 Hz 1H), 6.53 (d, J=8.7 Hz 2H), 5.11 (s, 2H), 4.66 (d, J=18.6 Hz 1H), 4.45-4.20 (m, 2H), 4.00-3.80 (m, 2H), 3.75-3.60 (m, 2H), 3.50-3.20 (m, 1H), 1.41 (d, J=4.5 Hz, 6H).

(85d) (the second elution, 10.5) as a white solid. LCMS (ESI, m/z): 833 [M+H]⁺. ¹H NMR (300 MHz, CDCl₃) δ 9.15-8.90 (m, 1H), 7.90-7.70 (m, 2H), 7.65-7.30 (m, 7H), 7.20-7.05 (m, 2H), 6.85 (d, J=5.1 Hz 1H), 6.53 (d, J=8.7 Hz 2H), 5.11 (s, 2H), 4.66 (d, J=18.6 Hz 1H), 4.45-4.20 (m, 2H), 4.00-3.80 (m, 2H), 3.75-3.15 (m, 3H), 1.41 (d, J=3.6 Hz, 6H).

Example 14

(6R*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91a) and (6S*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91b)

91a

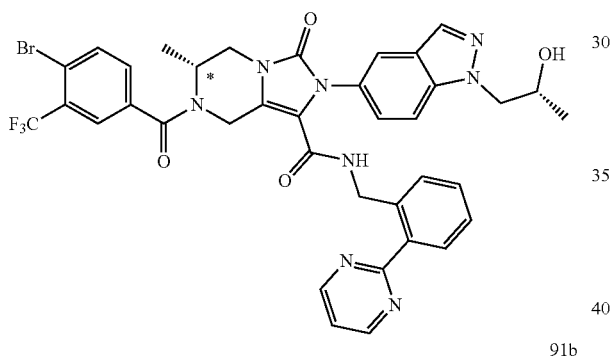

91b

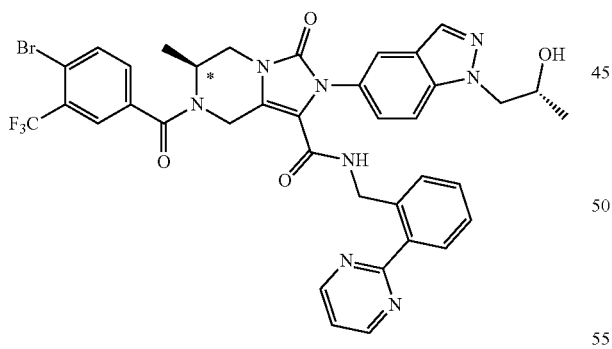

(R)-1-(5-bromo-1H-indazol-1-yl)propan-2-ol

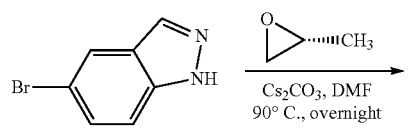

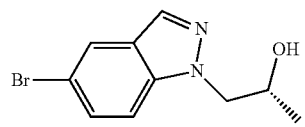

A 100 mL round-bottom flask was charged with the 5-bromo-1H-indazole (500 mg, 2.54 mmol, 1.00 eq.), (R)-2-methyloxirane (177 mg, 3.05 mmol, 1.20 eq.), Cs₂CO₃ (2.48 g, 7.61 mmol, 3.00 eq.) and DMF (10 mL). The mixture was stirred for overnight at 90° C. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford (R)-1-(5-bromo-1H-indazol-1-yl)propan-2-ol (450 mg, 69% yield) as a light yellow solid. LCMS (ESI, m/z): 255 [M+H]⁺.

(R)-1-(5-(5,5-dimethyl-1,3,2-dioxaborinan-2-yl)-1H-indazol-1-yl)propan-2-ol

A 250 mL round-bottom flask was charged with (R)-1-(5-bromo-1H-indazol-1-yl)propan-2-ol (500 mg, 1.960 mmol, 1.00 eq.), 2-(5,5-dimethyl-1,3,2-dioxaborinan-2-yl)-5,5-dimethyl-1,3,2-dioxaborinane (885 mg, 3.92 mmol, 2.00 eq.), KOAc (577 mg, 5.88 mmol, 3.00 eq.), Pd(PPh₃)₂Cl₂ (137 mg, 0.196 mmol, 0.10 eq.) and DMSO (10 mL). The mixture was stirred for overnight at 60° C. under a nitrogen atmosphere. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford (R)-1-(5-(5,5-dimethyl-1,3,2-dioxaborinan-2-yl)-1H-indazol-1-yl)propan-2-ol (570 mg, crude) as a yellow oil. LCMS (ESI, m/z): 289 [M+H]⁺.

7-(tert-butyl) 1-ethyl 2-(1-((R)-2-hydroxypropyl)-1H-indazol-5-yl)-6-methyl-3-oxo-2,5,6,8-tetrahydroimidazo[1,5-a]pyrazine-1,7(3H)-dicarboxylate

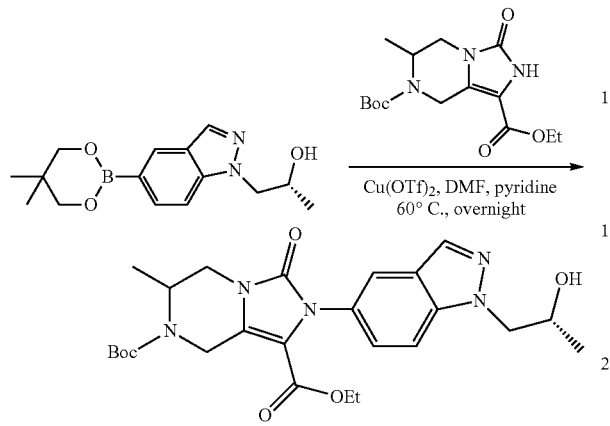

A 100 mL round-bottom flask was charged with (R)-1-(5-(5,5-dimethyl-1,3,2-dioxaborinan-2-yl)-1H-indazol-1-yl)propan-2-ol (0.570 g, 2.59 mmol, 1.00 eq.), 7-tert-butyl 1-ethyl 6-methyl-3-oxo-2H,5H,6H,8H-imidazo[1,5-a]pyrazine-1,7-dicarboxylate (1.01 g, 3.11 mmol, 1.20 eq.), Cu(OTf)$_2$ (0.940 g, 2.59 mmol, 1.00 eq.), pyridine (0.610 g, 7.77 mmol, 3.00 eq.) and DMF (10 mL). The mixture was stirred for overnight at 60° C. under an oxygen atmosphere. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with CH$_2$Cl$_2$:MeOH (10:1) to afford 7-(tert-butyl) 1-ethyl 2-(1-((R)-2-hydroxypropyl)-1H-indazol-5-yl)-6-methyl-3-oxo-2,5,6,8-tetrahydroimidazo[1,5-a]pyrazine-1,7(3H)-dicarboxylate (400 mg, 31% yield) as a light yellow solid. LCMS (ESI, m/z): 500 [M+H]$^+$.

7-(tert-butoxycarbonyl)-2-{1-[(2S)-2-hydroxypropyl]indazol-5-yl}-6-methyl-3-oxo-5H, 6H,8H-imidazo[1,5-a]pyrazine-1-carboxylic acid

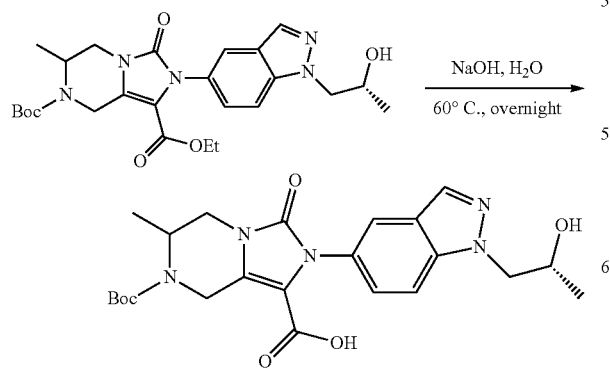

A 100 mL vial was charged with 7-(tert-butyl) 1-ethyl 2-(1-((R)-2-hydroxypropyl)-1H-indazol-5-yl)-6-methyl-3-oxo-2,5,6,8-tetrahydroimidazo[1,5-a]pyrazine-1,7(3H)-dicarboxylate (400 mg, 0.800 mmol, 1.00 eq.), NaOH (80 mg, 2.00 mmol, 2.50 eq.), H$_2$O (5 mL) and EtOH (20 mL). The mixture was stirred for overnight at 60° C. and then concentrated under reduced pressure. The mixture was diluted with water (50 mL) and neutralized to pH 7 with hydrochloric acid (1.0 mol/L). The mixture was extracted with ethyl acetate (3×300 mL). The organic layers were combined, washed with water (3×100 mL), dried over anhydrous sodium sulfate, filtered and concentrated under reduced pressure to afford 7-(tert-butoxycarbonyl)-2-(1-((R)-2-hydroxypropyl)-1H-indazol-5-yl)-6-methyl-3-oxo-2,3,5,6,7,8-hexahydroimidazo[1,5-a]pyrazine-1-carboxylic acid (350 mg, crude) as a yellow oil. LCMS (ESI, m/z): 472 [M+H]$^+$.

tert-butyl 2-{1-[(2R)-2-hydroxypropyl]indazol-5-yl}-6-methyl-3-oxo-1-({[2-(pyrimidin-2-yl)phenyl]methyl}carbamoyl)-5H,6H,8H-imidazo[1,5-a]pyrazine-7-carboxylate

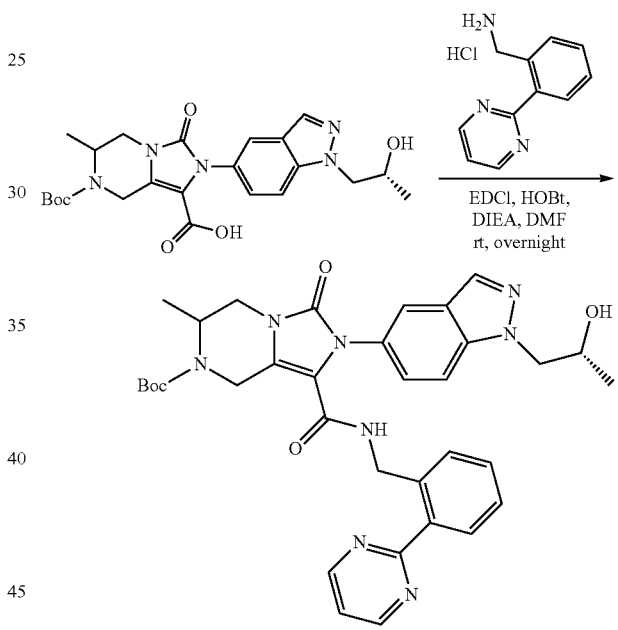

A 100 mL vial were added 7-(tert-butoxycarbonyl)-2-{1-[(2R)-2-hydroxypropyl]indazol-5-yl}-6-methyl-3-oxo-5H, 6H,8H-imidazo[1,5-a]pyrazine-1-carboxylic acid (350 mg, 0.742 mmol, 1.00 eq.), 1-[2-(pyrimidin-2-yl)phenyl]methanamine hydrochloride (198 mg, 0.890 mmol, 1.20 eq.), EDCI (171 mg, 0.890 mmol, 1.20 eq.), HOBT (120 mg, 0.890 mmol, 1.20 eq.), DIEA (480 mg, 3.71 mmol, 5.00 eq.) and DMF (20 mL). The mixture was stirred for overnight at rt. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by prep-TLC with CH$_2$Cl$_2$:MeOH (10:1) to afford tert-butyl 2-{1-[(2R)-2-hydroxypropyl]indazol-5-yl}-6-methyl-3-oxo-1-({[2-(pyrimidin-2-yl)phenyl]methyl}carbamoyl)-5H,6H,8H-imidazo[1,5-a]pyrazine-7-carboxylate (200 mg, 42% yield) as a yellow solid. LCMS (ESI, m/z): 639 [M+H]$^+$.

2-{1-[(2R)-2-hydroxypropyl]indazol-5-yl}-6-methyl-3-oxo-N-{[2-(pyrimidin-2-yl)phenyl]methyl}-5H,6H,7H,8H-imidazo[1,5-a]pyrazine-1-carboxamide trifluoroacetic acid salt

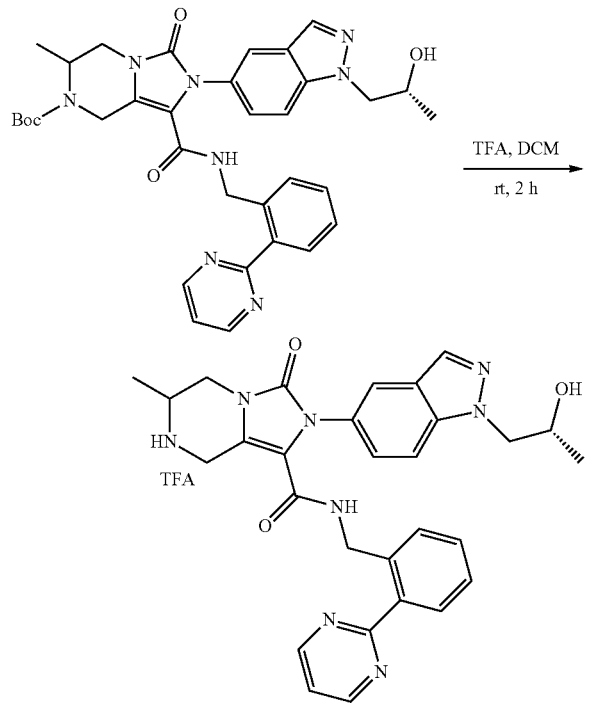

A 100 mL round bottom flask was charged with tert-butyl 2-{1-[(2R)-2-hydroxypropyl]indazol-5-yl}-6-methyl-3-oxo-1-({[2-(pyrimidin-2-yl)phenyl]methyl}carbamoyl)-5H,6H,8H-imidazo[1,5-a]pyrazine-7-carboxylate (200 mg, 0.313 mmol, 1.00 eq.), TFA (1 mL) and DCM (5 mL). The mixture was stirred for 2 h at rt under an air atmosphere and then concentrated under reduced pressure to afford 2-{1-[(2R)-2-hydroxypropyl]indazol-5-yl}-6-methyl-3-oxo-N-{[2-(pyrimidin-2-yl)phenyl]methyl}-5H,6H,7H,8H-imidazo[1,5-a]pyrazine-1-carboxamide trifluoroacetic acid salt (205 mg, crude) as a yellow oil. LCMS (ESI, m/z): 539 [M-TFA+H]$^+$.

(6R*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91a) and (6S*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91b)

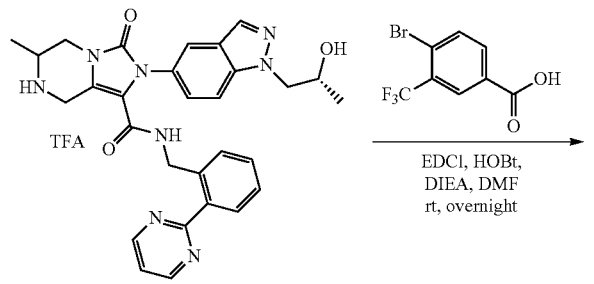

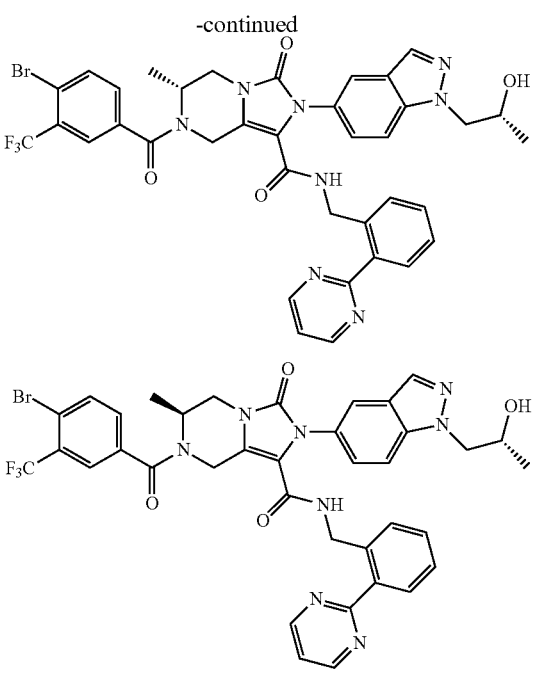

A 40 mL vial were added 2-{1-[(2R)-2-hydroxypropyl]indazol-5-yl}-6-methyl-3-oxo-N-{[2-(pyrimidin-2-yl)phenyl]methyl}-5H,6H,7H,8H-imidazo[1,5-a]pyrazine-1-carboxamide trifluoroacetic acid salt (182 mg, 0.278 mmol, 1.00 eq.), 4-bromo-3-(trifluoromethyl)benzoic acid (89.9 mg, 0.334 mmol, 1.20 eq.), EDCI (64.1 mg, 0.334 mmol, 1.20 eq.), HOBT (45.2 mg, 0.334 mmol, 1.20 eq.), DIEA (180 mg, 1.39 mmol, 5.00 eq.) and DMF (10 mL) at rt. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by prep-TLC with CH$_2$Cl$_2$:MeOH (10:1) to afford the crude product. The crude product was purified by prep-CHIRAL-HPLC with the following conditions: Column: CHIRAL-PAK IF, 2×25 cm, 5 μm; Mobile Phase A: MtBE (0.5% 2M NH$_3$-MeOH)—HPLC, Mobile Phase B: IPA-HPLC; Flow rate: 11.5 mL/min; Gradient: 50% B to 50% B in 26 min; Wave Length: 220/254 nm to afford the final products.

(6R*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91a) (the first elution, 16.0 mg, 7.3% yield) as a white solid. LCMS (ESI, m/z): 789 [M+H]$^+$. $^1$H NMR (400 MHz, CDCl$_3$) δ 8.29 (d, J=8.0 Hz, 2H), 8.03-8.01 (m, 1H), 7.90-7.83 (m, 2H), 7.75 (s, 1H), 7.65 (d, J=8.0 Hz, 1H), 7.50-7.43 (m, 4H), 6.99-6.92 (m, 4H), 5.22 (s, 1H), 4.70 (d, J=8.0 Hz, 1H), 4.53 (s, 1H), 4.36 (d, J=6.0 Hz, 1H), 4.22-4.12 (m, 2H), 4.03-3.97 (m, 1H), 3.87 (d, J=6.0 Hz, 1H), 3.74 (d, J=4.0 Hz, 1H), 2.33 (s, 1H), 1.43 (d, J=4.0 Hz, 3H), 1.28-1.24 (m, 3H).

(6S*)-7-[4-bromo-3-(trifluoromethyl)benzoyl]-2-{1-[(2R)-2-hydroxypropyl]indazol-5-yl}-6-methyl-3-oxo-N-{[2-(pyrimidin-2-yl)phenyl]methyl}-5H,6H,8H-imidazo[1,5-a]pyrazine-1-carboxamide (91b) (the second elution, 19.7 mg, 9.0% yield) as a white solid. LCMS (ESI, m/z): 789 [M+H]$^+$. $^1$H NMR (400 MHz, CDCl$_3$) δ 8.29 (d, J=8.0 Hz, 2H), 8.03-8.01 (m, 1H), 7.90-7.83 (m, 2H), 7.75 (s, 1H), 7.65 (d, J=8.0 Hz, 1H), 7.50-7.43 (m, 4H), 6.99-6.92 (m, 4H), 5.22 (s, 1H), 4.70 (d, J=8.0 Hz, 1H), 4.53 (s, 1H), 4.36 (d, J=6.0 Hz, 1H), 4.22-4.12 (m, 2H), 4.03-3.97 (m, 1H), 3.87 (d, J=6.0 Hz, 1H), 3.74 (d, J=4.0 Hz, 1H), 2.33 (s, 1H), 1.43 (d, J=4.0 Hz, 3H), 1.28-1.24 (m, 3H).

Example 15

(6R*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93a) and (6S*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93b)

93a

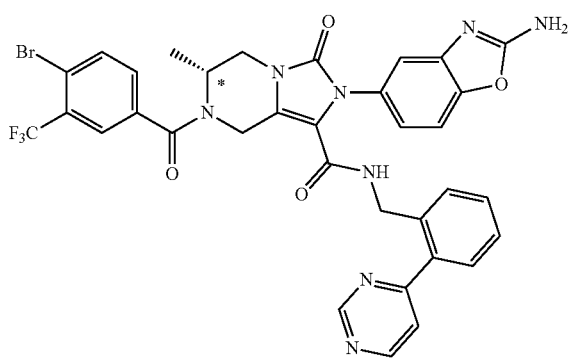

93b

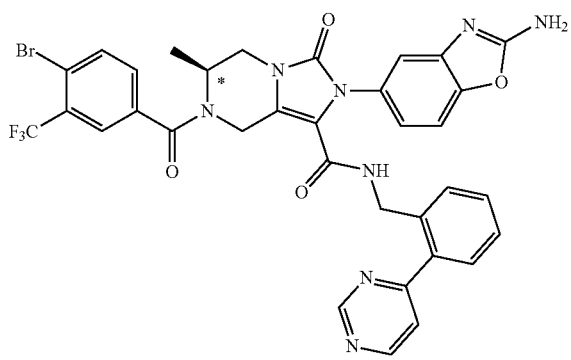

benzyl N-(5-bromo-2-hydroxyphenyl)carbamate

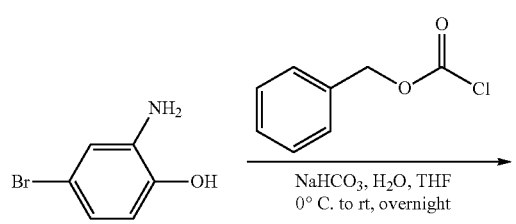

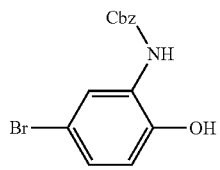

A 250 mL round-bottom flask was charged with 2-amino-4-bromophenol (5.00 g, 26.6 mmol, 1.00 eq.), benzyl chloroformate (5.44 g, 31.9 mmol, 1.20 eq.), sodium bicarbonate (6.70 g, 79.8 mmol, 3.00 eq.), water (50 mL) and tetrahydrofuran (100 mL) at 0° C. The mixture was stirred for overnight at rt. The reaction was quenched with water (150 mL). The mixture was extracted with ethyl acetate (3×250 mL). The organic layers were combined, washed with saturated sodium chloride solution (3×100 mL), dried over anhydrous sodium sulfate, filtered and concentrated under reduced pressure. The residue was purified by silica gel column chromatography, eluted with ethyl acetate:petroleum ether (1:5) to afford benzyl N-(5-bromo-2-hydroxyphenyl)carbamate (5.11 g, 60% yield) as a pink solid. LCMS (ESI, m/z): 322 [M+H]+.

benzyl N-[2-(benzyloxy)-5-bromophenyl]carbamate

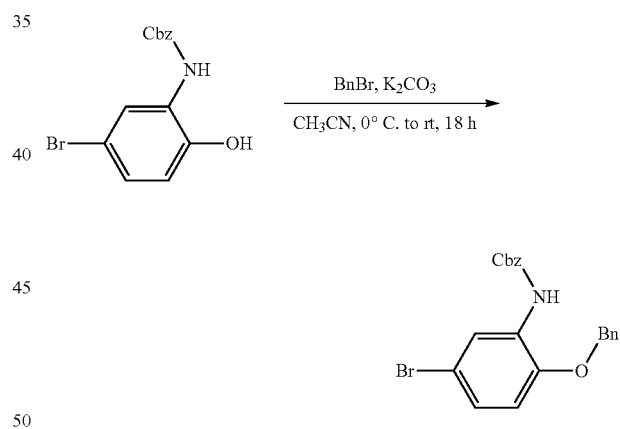

A 250 mL round-bottom flask was charged with benzyl N-(5-bromo-2-hydroxyphenyl)carbamate (5.00 g, 15.5 mmol, 1.00 eq.), BnBr (3.19 g, 18.6 mmol, 1.20 eq.), potassium carbonate (6.43 g, 46.6 mmol, 3.00 eq.) and acetonitrile (130 mL) at 0° C. The mixture was stirred for 18 h at rt and then concentrated under reduced pressure. The reaction was quenched with water (150 mL). The mixture was extracted with ethyl acetate (3×250 mL). The organic layers were combined, washed with saturated sodium chloride solution (3×100 mL), dried over anhydrous sodium sulfate, filtered and concentrated under reduced pressure. The residue was purified by silica gel column chromatography, eluted with ethyl acetate:petroleum ether (1:6) to afford benzyl N-[2-(benzyloxy)-5-bromophenyl]carbamate (4.79 g, 75% yield) as a pink solid. LCMS (ESI, m/z): 412 [M+H]+.

4-(benzyloxy)-3-{[(benzyloxy)carbonyl]amino}phenylboronic acid

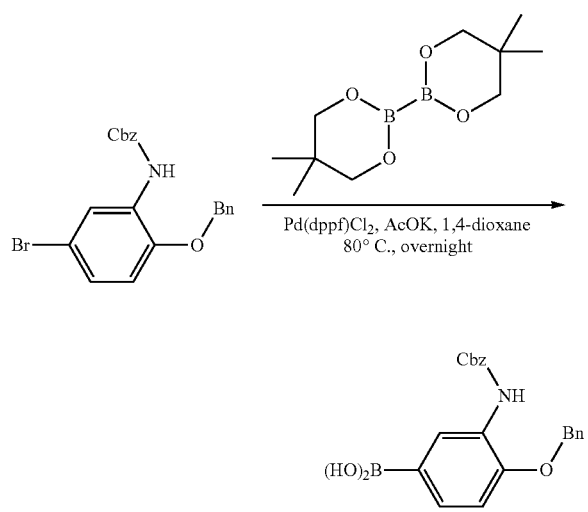

A 250 mL round bottom flask was charged with benzyl N-[2-(benzyloxy)-5-bromophenyl]carbamate (5.00 g, 12.1 mmol, 1.00 eq.), 2-(5,5-dimethyl-1,3,2-dioxaborinan-2-yl)-5,5-dimethyl-1,3,2-dioxaborinane (5.48 g, 24.3 mmol, 2.00 eq.), Pd(dppf)Cl₂ (0.890 g, 1.21 mmol, 0.10 eq.), potassium acetate (3.57 g, 36.4 mmol, 3.00 eq.) and 1,4-dioxane (150 mL). The mixture was stirred for overnight at 80° C., concentrated under reduced pressure and diluted with water (150 mL). The mixture was extracted with ethyl acetate (3×250 mL). The organic layers were combined, washed with saturated sodium chloride solution (3×100 mL), dried over anhydrous sodium sulfate, filtered and concentrated under reduced pressure. The residue was purified by reverse phase chromatography with following condition: Column: Agela C18 Column, 120 g; Mobile Phase A: Water (0.05% TFA), Mobile Phase B: ACN; Flow rate: 40 mL/min; Gradient: 0% B to 100% B in 40 min; Wave Length: 220 nm to afford 4-(benzyloxy)-3-{[(benzyloxy)carbonyl]amino}phenylboronic acid (2.11 g, 46% yield) as a white solid. LCMS (ESI, m/z): 378 [M+H]⁺.

7-tert-butyl 1-ethyl 2-[4-(benzyloxy)-3-{[(benzyloxy)carbonyl]amino}phenyl]-6-methyl-3-oxo-5H,6H,8H-imidazo[1,5-a]pyrazine-1,7-dicarboxylate

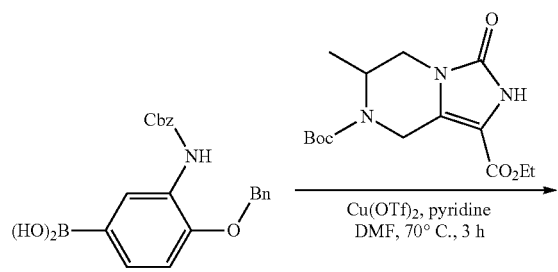

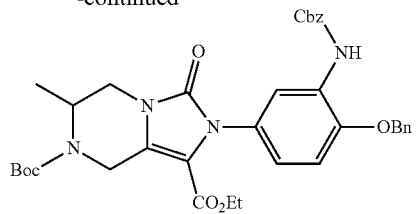

A 100 mL round bottom flask was charged with 7-tert-butyl 1-ethyl 6-methyl-3-oxo-2H,5H,6H,8H-imidazo[1,5-a]pyrazine-1,7-dicarboxylate (1.00 g, 3.07 mmol, 1.00 eq.), 4-(benzyloxy)-3-{[(benzyloxy)carbonyl]amino}phenylboronic acid (1.39 g, 3.69 mmol, 1.20 eq.), Cu(OTf)₂ (1.11 g, 3.07 mmol, 1.00 eq.), pyridine (0.729 g, 9.22 mmol, 3.00 eq.) and DMF (50 mL). The mixture was stirred for 3 h at 70° C. under an oxygen atmosphere. The reaction was quenched with water (100 mL). The mixture was extracted with ethyl acetate (3×150 mL). The organic layers were combined, washed with saturated sodium chloride solution (3×50 mL), dried over anhydrous sodium sulfate, filtered and concentrated under reduced pressure. The residue was purified by silica gel column chromatography, eluted with ethyl acetate:petroleum ether (1:1) to afford 7-tert-butyl 1-ethyl 2-[4-(benzyloxy)-3-{[(benzyloxy)carbonyl]amino}phenyl]-6-methyl-3-oxo-5H,6H,8H-imidazo[1,5-a]pyrazine-1,7-dicarboxylate (1.34 g, 66% yield) as a pink solid. LCMS (ESI, m/z): 657 [M+H]⁺.

2-[4-(benzyloxy)-3-{[(benzyloxy)carbonyl]amino}phenyl]-7-(tert-butoxycarbonyl)-6-methyl-3-oxo-5H,6H,8H-imidazo[1,5-a]pyrazine-1-carboxylic acid

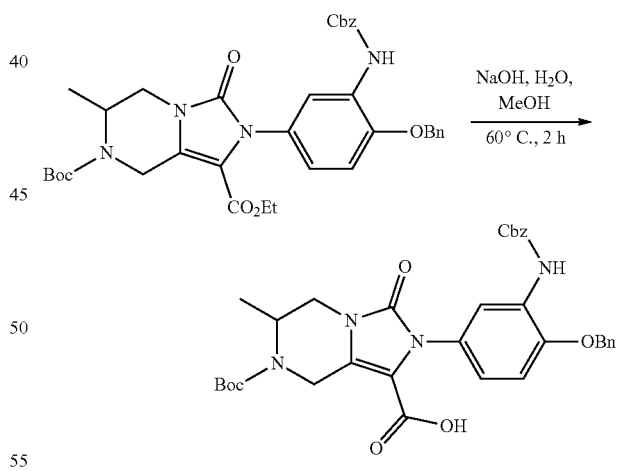

A 100 mL round bottom flask was charged with 7-tert-butyl 1-ethyl 2-[4-(benzyloxy)-3-{[(benzyloxy)carbonyl]amino}phenyl]-6-methyl-3-oxo-5H,6H,8H-imidazo[1,5-a]pyrazine-1,7-dicarboxylate (1.00 g, 1.52 mmol, 1.00 eq.), sodium hydroxide (0.120 g, 3.05 mmol, 2.00 eq.), water (20 mL) and MeOH (40 mL) at rt. The mixture was stirred for 2 h at 60° C. and acidified to pH 6 with a hydrochloric acid aqueous solution (1 mol/L). The precipitated solids were collected by filtration and washed with water (3×50 mL). The resulting solid was dried to afford 2-[4-(benzyloxy)-3-{[(benzyloxy)carbonyl]amino}phenyl]-7-(tert-butoxycarbonyl)-6-methyl-3-oxo-5H,6H, 8H-imidazo[1,5-a]pyrazine-1-carboxylic acid (312 mg, 33% yield) as an orange solid. LCMS (ESI, m/z): 629 [M+H]+.

tert-butyl 2-[4-(benzyloxy)-3-{[(benzyloxy)carbonyl]amino}phenyl]-6-methyl-3-oxo-1-({[2-(pyrimidin-4-yl)phenyl]methyl}carbamoyl)-5H,6H,8H-imidazo[1,5-a]pyrazine-7-carboxylate

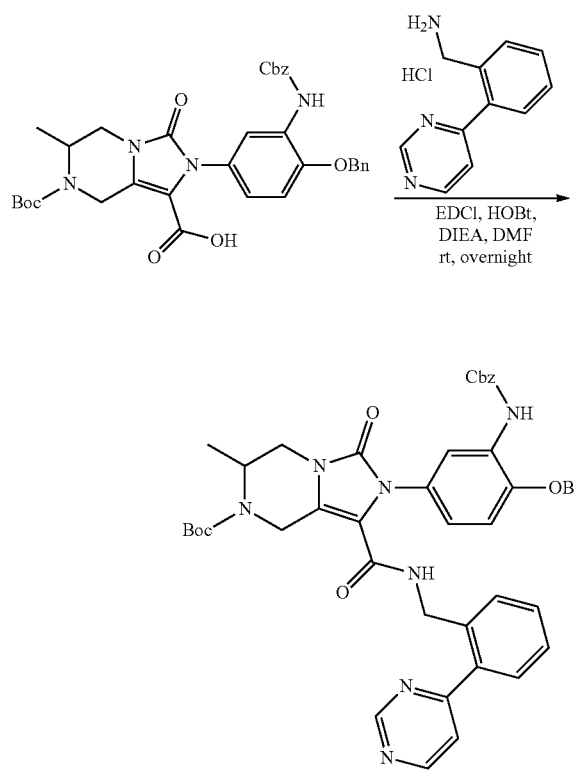

A 100 mL round bottom flask was charged with 2-[4-(benzyloxy)-3-{[(benzyloxy)carbonyl]amino}phenyl]-7-(tert-butoxycarbonyl)-6-methyl-3-oxo-5H,6H, 8H-imidazo[1,5-a]pyrazine-1-carboxylic acid (1.00 g, 1.59 mmol, 1.00 eq.), 1-[2-(pyrimidin-4-yl)phenyl]methanamine hydrochloride (424 mg, 1.91 mmol, 1.20 eq.), EDCI (457 mg, 2.39 mmol, 1.50 eq.), HOBT (322 mg, 2.39 mmol, 1.50 eq.), DIEA (1.03 g, 7.96 mmol, 5.00 eq.) and DMF (40 mL). The mixture was stirred for overnight at rt. The reaction was quenched with water (100 mL). The mixture was extracted with ethyl acetate (3×150 mL). The organic layers were combined, washed with saturated sodium chloride solution (3×50 mL), dried over anhydrous sodium sulfate, filtered and concentrated under reduced pressure. The residue was purified by silica gel column chromatography, eluted with ethyl acetate:petroleum ether (3:2) to afford tert-butyl 2-[4-(benzyloxy)-3-{[(benzyloxy)carbonyl]amino}phenyl]-6-methyl-3-oxo-1-({[2-(pyrimidin-4-yl)phenyl]methyl}carbamoyl)-5H,6H,8H-imidazo[1,5-a]pyrazine-7-carboxylate (605 mg, 48% yield) as a brown solid. LCMS (ESI, m/z): 796 [M+H]+.

tert-butyl 2-(3-amino-4-hydroxyphenyl)-6-methyl-3-oxo-1-({[2-(pyrimidin-4-yl)phenyl]methyl}carbamoyl)-5H,6H,8H-imidazo[1,5-a]pyrazine-7-carboxylate

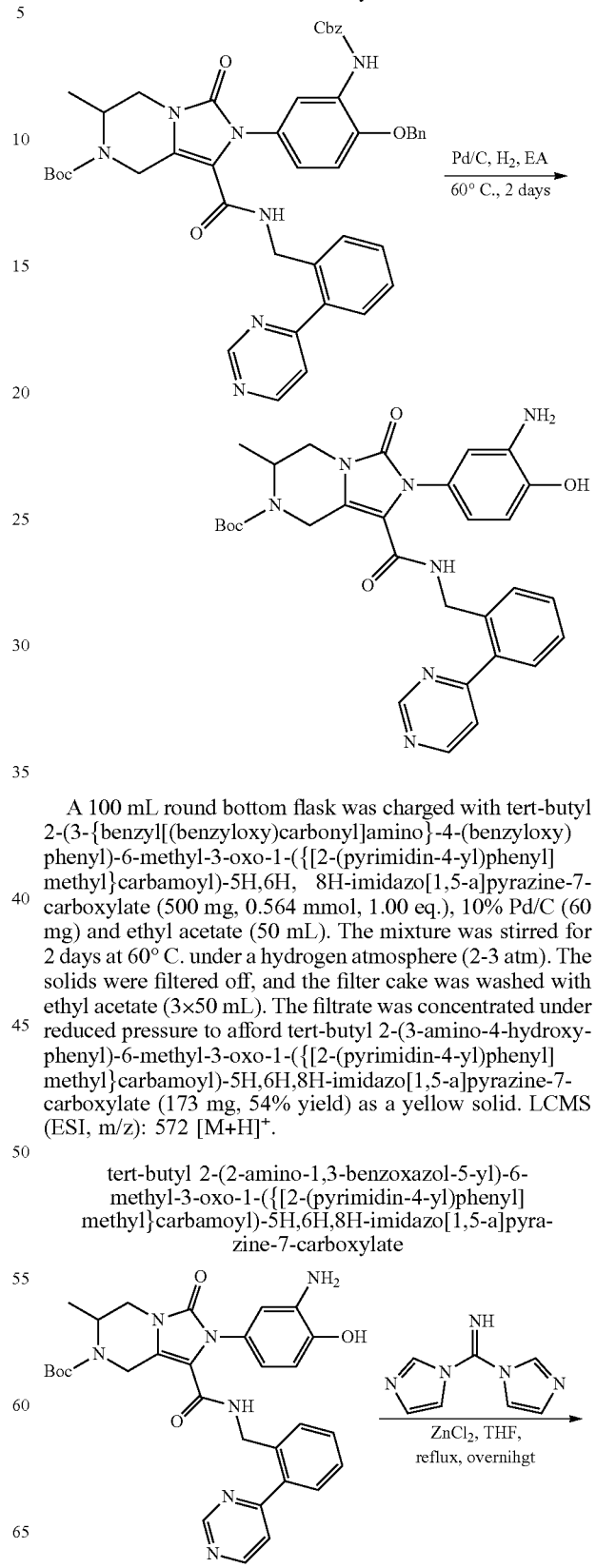

A 100 mL round bottom flask was charged with tert-butyl 2-(3-{benzyl[(benzyloxy)carbonyl]amino}-4-(benzyloxy)phenyl)-6-methyl-3-oxo-1-({[2-(pyrimidin-4-yl)phenyl]methyl}carbamoyl)-5H,6H, 8H-imidazo[1,5-a]pyrazine-7-carboxylate (500 mg, 0.564 mmol, 1.00 eq.), 10% Pd/C (60 mg) and ethyl acetate (50 mL). The mixture was stirred for 2 days at 60° C. under a hydrogen atmosphere (2-3 atm). The solids were filtered off, and the filter cake was washed with ethyl acetate (3×50 mL). The filtrate was concentrated under reduced pressure to afford tert-butyl 2-(3-amino-4-hydroxyphenyl)-6-methyl-3-oxo-1-({[2-(pyrimidin-4-yl)phenyl]methyl}carbamoyl)-5H,6H,8H-imidazo[1,5-a]pyrazine-7-carboxylate (173 mg, 54% yield) as a yellow solid. LCMS (ESI, m/z): 572 [M+H]+.

tert-butyl 2-(2-amino-1,3-benzoxazol-5-yl)-6-methyl-3-oxo-1-({[2-(pyrimidin-4-yl)phenyl]methyl}carbamoyl)-5H,6H,8H-imidazo[1,5-a]pyrazine-7-carboxylate

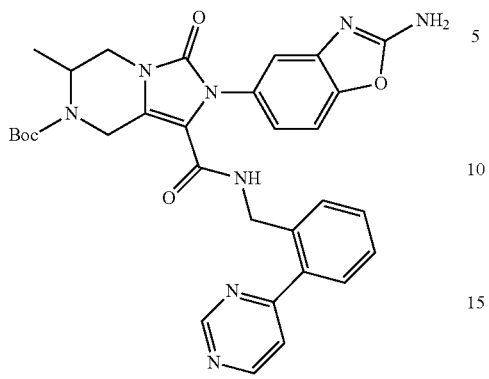

A 100 mL round bottom flask was charged with tert-butyl 2-(3-amino-4-hydroxyphenyl)-6-methyl-3-oxo-1-({[2-(pyrimidin-4-yl)phenyl]methyl}carbamoyl)-5H,6H,8H-imidazo[1,5-a]pyrazine-7-carboxylate (110 mg, 0.192 mmol, 1.00 eq.), 1-(imidazole-1-carboximidoyl)imidazole (62.0 mg, 0.384 mmol, 2.00 eq.), $ZnCl_2$ (13.1 mg, 0.10 mmol, 0.50 eq.) and tetrahydrofuran (50 mL). The solution was refluxed overnight under a nitrogen atmosphere. The reaction was quenched with water (10 mL). The mixture was concentrated under reduced pressure and then diluted with water (100 mL). The mixture was extracted with ethyl acetate (3×150 mL). The organic layers were combined, washed with saturated sodium chloride solution (3×50 mL), dried over anhydrous sodium sulfate, filtered and concentrated under reduced pressure. The residue was purified by prep-TLC with dichloromethane:methyl alcohol (10:1) to afford tert-butyl 2-(2-amino-1,3-benzoxazol-5-yl)-6-methyl-3-oxo-1-({[2-(pyrimidin-4-yl)phenyl]methyl}carbamoyl)-5H,6H,8H-imidazo[1,5-a]pyrazine-7-carboxylate (83.0 mg, 72% yield) as a yellow solid. LCMS (ESI, m/z): 597 [M+H]$^+$.

2-(2-amino-1,3-benzoxazol-5-yl)-6-methyl-3-oxo-N-{[2-(pyrimidin-4-yl)phenyl]methyl}-5H,6H,7H,8H-imidazo[1,5-a]pyrazine-1-carboxamide trifluoroacetic acid salt

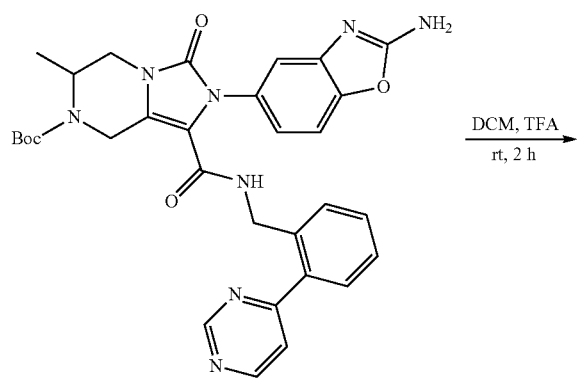

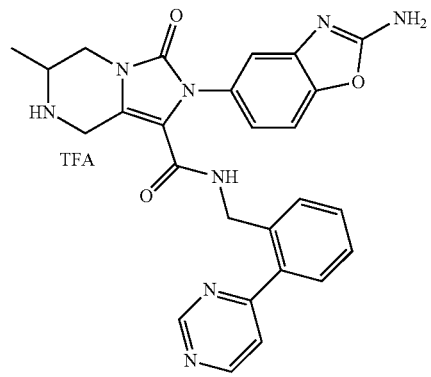

A 100 mL round bottom flask was charged with tert-butyl 2-(2-amino-1,3-benzoxazol-5-yl)-6-methyl-3-oxo-1-({[2-(pyrimidin-4-yl)phenyl]methyl}carbamoyl)-5H,6H,8H-imidazo[1,5-a]pyrazine-7-carboxylate (83.0 mg, 0.139 mmol, 1.00 eq.), dichloromethane (30 mL) and trifluoroacetic acid (6 mL). The solution was stirred for 2 h at rt and then concentrated under reduced pressure to afford 2-(2-amino-1,3-benzoxazol-5-yl)-6-methyl-3-oxo-N-{[2-(pyrimidin-4-yl)phenyl]methyl}-5H,6H,7H,8H-imidazo[1,5-a]pyrazine-1-carboxamide trifluoroacetic acid salt (88.6 mg, crude) as a yellow oil. LCMS (ESI, m/z): 497 [M+H-TFA]$^+$.

(6R*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93a) and (6S*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93b)

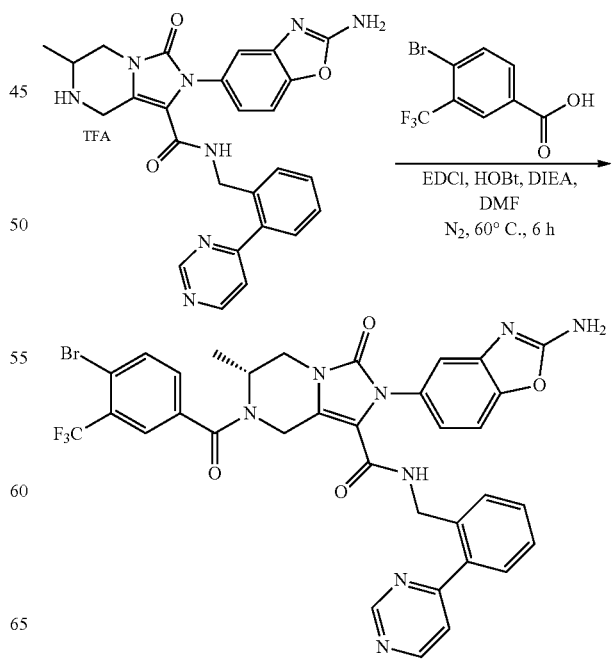

-continued

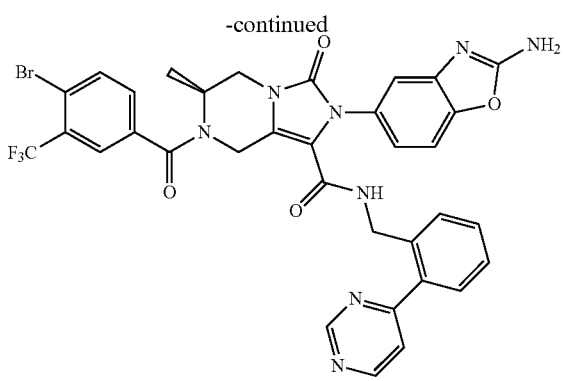

A 100 mL round bottom flask was charged with 2-(2-amino-1,3-benzoxazol-5-yl)-6-methyl-3-oxo-N-{[2-(pyrimidin-4-yl)phenyl]methyl}-5H,6H,7H,8H-imidazo[1,5-a]pyrazine-1-carboxamide trifluoroacetic acid salt (88.6 mg, 0.145 mmol, 1.00 eq.), 4-bromo-3-(trifluoromethyl)benzoic acid (46.8 mg, 0.174 mmol, 1.20 eq.), EDCI (41.7 mg, 0.217 mmol, 1.50 eq.), HOBT (29.4 mg, 0.217 mmol, 1.50 eq.), DIEA (93.7 mg, 0.725 mmol, 5.00 eq.) and DMF (20 mL). The mixture was stirred for overnight at 60° C. The reaction was quenched with water (60 mL). The mixture was extracted with ethyl acetate (3×100 mL). The organic layers were combined, washed with saturated sodium chloride solution (3×30 mL), dried over anhydrous sodium sulfate, filtered and concentrated under reduced pressure. The residue was purified by silica gel column chromatography, eluted with ethyl acetate:petroleum ether (9:1) to afford the crude product. The product was separated by prep-CHIRAL HPLC: Column: Column: CHIRALPAK IF, 2×25 cm, 5 μm; Mobile Phase A: MtBE (0.5% 2M $NH_3$-MeOH)—HPLC, Mobile Phase B: EtOH-HPLC; Flow rate: 11 mL/min; Gradient: 50% B to 50% B in 32 min; Wave Length: 220/254 nm to afford the final products.

(6R*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93a) (the first elution, 5.9 mg, 5.5% yield) as a brown solid. LCMS (ESI, m/z): 747 [M+H]$^+$. $^1$H NMR (300 MHz, $CDCl_3$) δ 8.77-8.62 (m, 2H), 7.82 (d, J=8.0 Hz, 2H), 7.55-7.34 (m, 6H), 7.22 (d, J=1.7 Hz, 1H), 6.88 (q, J=8.5 Hz, 2H), 6.71 (s, 1H), 5.71 (s, 2H), 5.34 (s, 1H), 4.66 (d, J=19.1 Hz, 1H), 4.14-4.22 (m, 2H), 3.87 (d, J=12.8 Hz, 1H), 3.73 (d, J=12.9 Hz, 1H), 1.43 (d, J=6.9 Hz, 3H).

(6S*)-2-(2-amino-1,3-benzoxazol-5-yl)-7-[4-bromo-3-(trifluoromethyl)benzoyl]-6-methyl-3-oxo-N-{[2-(pyrimidin-4-yl)phenyl]methyl}-5H,6H,8H-imidazo[1,5-a]pyrazine-1-carboxamide (93b) (the second elution, 4.7 mg, 4.3% yield) as a brown solid. LCMS (ESI, m/z): 747 [M+H]$^+$. $^1$H NMR (300 MHz, $CDCl_3$) δ 8.78-8.63 (m, 2H), 7.82 (d, J=8.0 Hz, 2H), 7.56-7.33 (m, 6H), 7.22 (s, 1H), 7.01-6.81 (m, 2H), 6.71 (s, 1H), 5.74 (s, 2H), 5.76 (s, 1H), 4.66 (d, J=18.8 Hz, 1H), 4.29 (td, J=14.0, 6.1 Hz, 2H), 3.87 (d, J=12.9 Hz, 1H), 3.73 (d, J=12.3 Hz, 1H), 1.43 (d, J=6.9 Hz, 3H).

Example 16

6-(benzyloxymethyl)-7-[4-bromo-3-(trifluoromethyl)benzoyl]-2-[4-(cyclopropoxy)phenyl]-3-oxo-N-[(2-pyrimidin-2-ylphenyl)methyl]-6,8-dihydro-5H-imidazo[1,5-a]pyrazine-1-carboxamide (130)

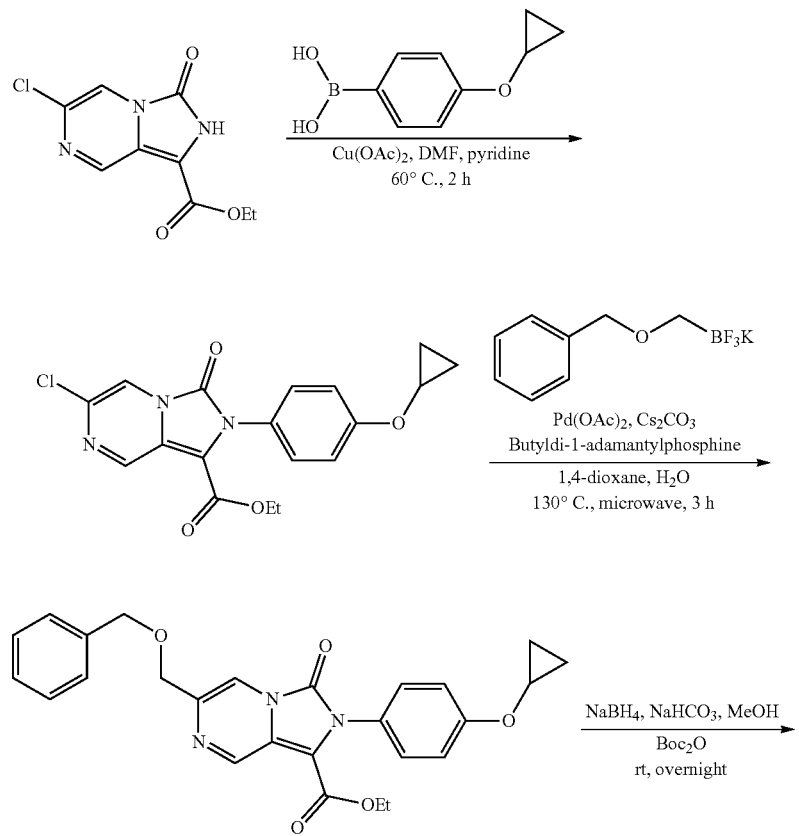

-continued
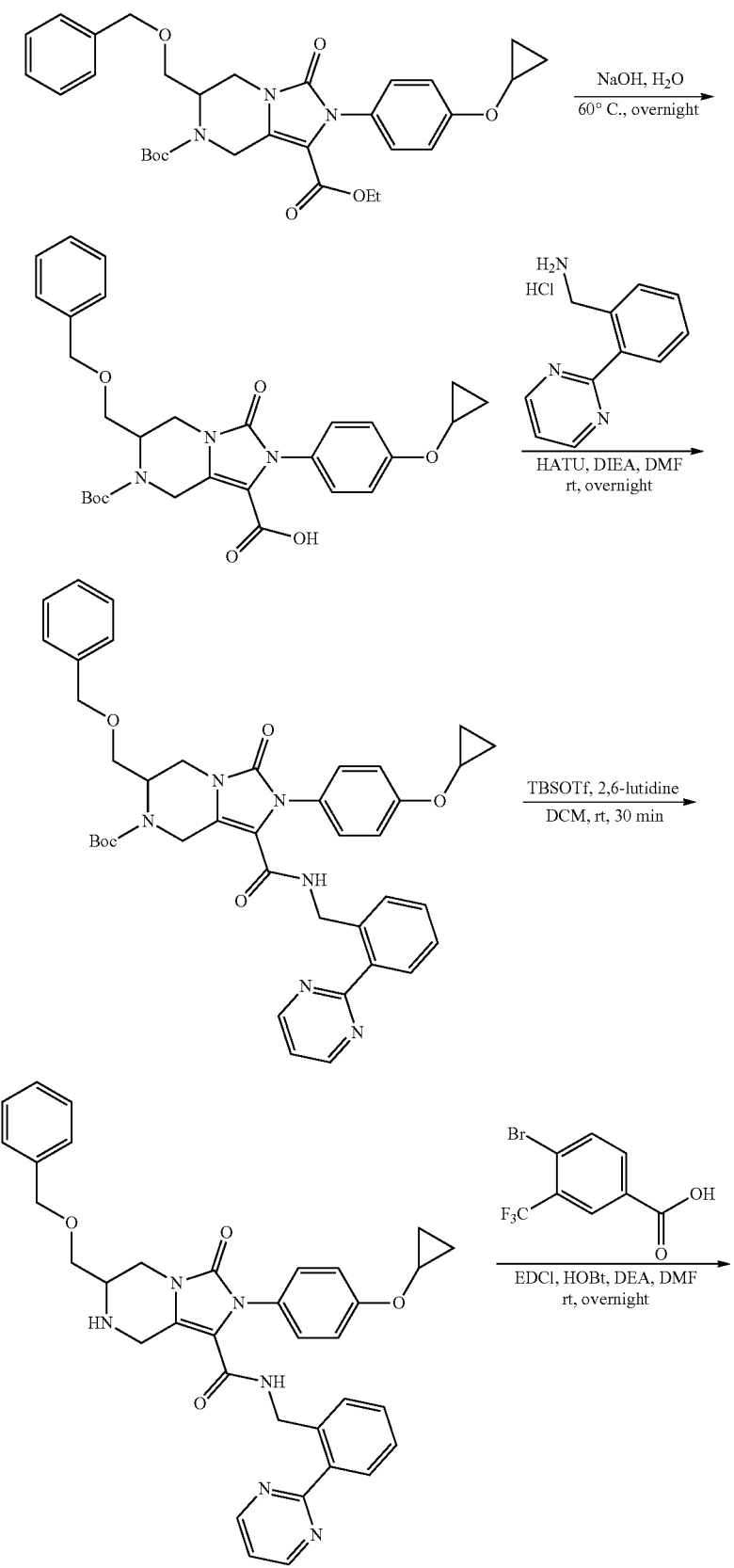

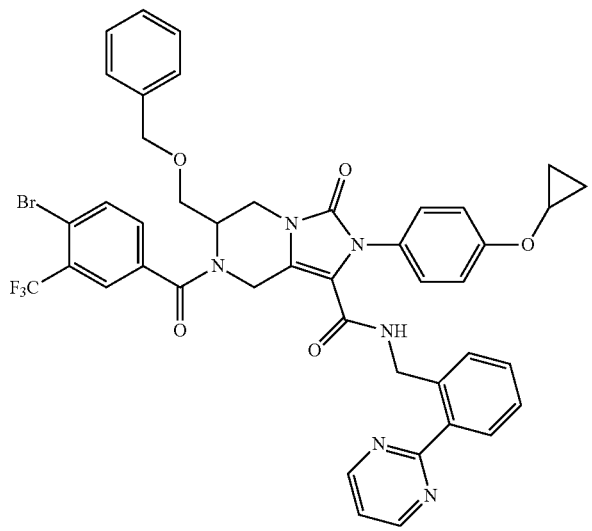

Ethyl 6-chloro-2-(4-cyclopropoxyphenyl)-3-oxoimidazo[1,5-a]pyrazine-1-carboxylate A mixture of ethyl 6-chloro-3-oxo-2H-imidazo[1,5-a]pyrazine-1-carboxylate (5.00 g, 20.7 mmol, 1.00 eq.), 4-cyclopropoxyphenylboronic acid (3.68 g, 20.7 mmol, 1.00 eq.), pyridine (8.18 g, 103 mmol, 5.00 eq.) and Cu(OAc)$_2$ (3.76 g, 20.7 mmol, 1.00 eq.) in DMF (50 mL) was stirred for 2 h at 60° C. under an O$_2$ atmosphere. The reaction was quenched with water (500 mL). The mixture was extracted with ethyl acetate (3×200 mL). The organic layers were combined, washed with water (3×200 mL), dried over anhydrous sodium sulfate, filtered and concentrated under reduced pressure. The residue was purified by silica gel column chromatography, eluted with ethyl acetate:petroleum ether (1:1) to afford ethyl 6-chloro-2-(4-cyclopropoxyphenyl)-3-oxoimidazo[1,5-a]pyrazine-1-carboxylate (2.1 g, 27% yield) as a yellow solid. LCMS (ESI, m/z): 374 [M+H]$^+$.

Ethyl 6-[(benzyloxy)methyl]-2-(4-cyclopropoxyphenyl)-3-oxoimidazo[1,5-a]pyrazine-1-carboxylate A mixture of ethyl 6-chloro-2-(4-cyclopropoxyphenyl)-3-oxoimidazo[1,5-a]pyrazine-1-carboxylate (1.60 g, 4.28 mmol, 1.00 eq.), [(benzyloxy)methyl]trifluoro-λ4-borane potassium (1.27 g, 5.56 mmol, 1.30 eq.), bis(adamantan-1-yl)(butyl)phosphane (0.310 g, 0.856 mmol, 0.20 eq.), Pd(OAc)$_2$ (0.190 g, 0.856 mmol, 0.20 eq.), Cs$_2$CO$_3$ (4.18 g, 12.8 mmol, 3.00 eq.), H$_2$O (3 mL) and 1,4-dioxane (15 mL) was irradiated with microwave radiation for 3 h at 130° C. under a nitrogen atmosphere and then concentrated under reduced pressure. The residue was purified by silica gel column chromatography, eluted with CH$_2$Cl$_2$:MeOH (10:1) to afford ethyl 6-[(benzyloxy)methyl]-2-(4-cyclopropoxyphenyl)-3-oxoimidazo[1,5-a]pyrazine-1-carboxylate (330 mg, 17% yield) as a yellow solid. LCMS (ESI, m/z): 460 [M+H]$^+$.

7-tert-butyl 1-ethyl 6-[(benzyloxy)methyl]-2-(4-cyclopropoxyphenyl)-3-oxo-5H,6H,8H-imidazo[1,5-a]pyrazine-1,7-dicarboxylate To a stirred mixture of ethyl 6-[(benzyloxy)methyl]-2-(4-cyclopropoxyphenyl)-3-oxoimidazo[1,5-a]pyrazine-1-carboxylate (330 mg, 0.718 mmol, 1.00 eq.) in MeOH (10 mL) was added NaBH$_4$ (272 mg, 7.18 mmol, 10.0 eq.) in portions at 0° C. under a nitrogen atmosphere. The mixture was stirred for overnight at rt. To the mixture was added NaHCO$_3$ (302 mg, 3.59 mmol, 5.00 eq.) and (Boc)$_2$O (784 mg, 3.59 mmol, 5.00 eq.). The mixture was stirred overnight at rt and then concentrated under reduced pressure. The residue was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by prep-TLC (ethyl acetate:petroleum ether=2:3) to afford 7-tert-butyl 1-ethyl 6-[(benzyloxy)methyl]-2-(4-cyclopropoxyphenyl)-3-oxo-5H,6H,8H-imidazo[1,5-a]pyrazine-1,7-dicarboxylate (200 mg, 49% yield) as a yellow solid. LCMS (ESI, m/z): 564 [M+H]$^+$.

6-[(benzyloxy)methyl]-7-(tert-butoxycarbonyl)-2-(4-cyclopropoxyphenyl)-3-oxo-5H,6H,8H-imidazo[1,5-a]pyrazine-1-carboxylic acid A 100 mL round-bottom flask was charged with 7-tert-butyl 1-ethyl 6-[(benzyloxy)methyl]-2-(4-cyclopropoxyphenyl)-3-oxo-5H,6H,8H-imidazo[1,5-a]pyrazine-1,7-dicarboxylate (200 mg, 0.355 mmol, 1.00 eq.), H$_2$O (10 mL) and NaOH (28.4 mg, 0.710 mmol, 2.00 eq.) at rt. The mixture was stirred for overnight at 60° C. The mixture was acidified to pH 4 with acetic acid. The mixture was extracted with ethyl acetate (3×20 mL). The organic layers were combined, washed with water (3×50 mL), dried over anhydrous sodium sulfate, filtered and concentrated under reduced pressure. The residue was purified by prep-TLC (ethyl acetate:petroleum ether=1:1) to afford 6-[(benzyloxy)methyl]-7-(tert-butoxycarbonyl)-2-(4-cyclopropoxyphenyl)-3-oxo-5H,6H,8H- imidazo[1,5-a]pyrazine-1-carboxylic acid (150 mg, 79% yield) as a yellow solid. LCMS (ESI, m/z): 536 [M+H]⁺.

tert-butyl 6-[(benzyloxy)methyl]-2-(4-cyclopropoxyphenyl)-3-oxo-1-({[2-(pyrimidin-2-yl)phenyl]methyl}carbamoyl)-5H,6H,8H-imidazo[1,5-a]pyrazine-7-carboxylate A 50 mL round-bottom flask was charged with 6-[(benzyloxy)methyl]-7-(tert-butoxycarbonyl)-2-(4-cyclopropoxyphenyl)-3-oxo-5H,6H,8H-imidazo[1,5-a]pyrazine-1-carboxylic acid (150 mg, 0.280 mmol, 1.00 eq.), 1-[2-(pyrimidin-2-yl)phenyl]methanamine hydrochloride (62.1 mg, 0.280 mmol, 1.00 eq.), EDCI (69.9 mg, 0.364 mmol, 1.30 eq.), HOBT (49.2 mg, 0.364 mmol, 1.30 eq.), DIEA (109 mg, 0.841 mmol, 3.00 eq.) and DMF (5 mL). The mixture was stirred for overnight at rt. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by prep-TLC (CH₂Cl₂:MeOH=10:1) to afford tert-butyl 6-[(benzyloxy)methyl]-2-(4-cyclopropoxyphenyl)-3-oxo-1-({[2-(pyrimidin-2-yl)phenyl]methyl}carbamoyl)-5H,6H, 8H-imidazo[1,5-a]pyrazine-7-carboxylate (122 mg, 62% yield) as a white solid. LCMS (ESI, m/z): 703 [M+H]⁺.

6-[(benzyloxy)methyl]-2-(4-cyclopropoxyphenyl)-3-oxo-N-{[2-(pyrimidin-2-yl)phenyl]methyl}-5H,6H,7H,8H-imidazo[1,5-a]pyrazine-1-carboxamide A 40 mL vial was charged with tert-butyl 6-[(benzyloxy)methyl]-2-(4-cyclopropoxyphenyl)-3-oxo-1-({[2-(pyrimidin-2-yl)phenyl]methyl}carbamoyl)-5H,6H,8H-imidazo[1,5-a]pyrazine-7-carboxylate (122 mg, 0.174 mmol, 1.00 eq.), TBSOTf (459 mg, 1.74 mmol, 10.0 eq.), 2,6-lutidine (186 mg, 1.74 mmol, 10.0 eq.) and DCM (5 mL) at rt. The mixture was stirred for 30 min at rt and then concentrated under reduced pressure. The residue was purified by silica gel column chromatography, eluted with CH₂Cl₂:MeOH (10:1) to afford 6-[(benzyloxy)methyl]-2-(4-cyclopropoxyphenyl)-3-oxo-N-{[2-(pyrimidin-2-yl)phenyl]methyl}-5H,6H,7H,8H-imidazo[1,5-a]pyrazine-1-carboxamide (90 mg, 86% yield) as a yellow solid. LCMS (ESI, m/z): 603 [M+H]⁺.

6-[(benzyloxy)methyl]-2-(4-cyclopropoxyphenyl)-3-oxo-N-{[2-(pyrimidin-2-yl)phenyl]methyl}-5H,6H,7H,8H-imidazo[1,5-a]pyrazine-1-carboxamide A mixture of 6-[(benzyloxy)methyl]-2-(4-cyclopropoxyphenyl)-3-oxo-N-{[2-(pyrimidin-2-yl)phenyl]methyl}-5H,6H,7H,8H-imidazo[1,5-a]pyrazine-1-carboxamide (90.0 mg, 0.149 mmol, 1.00 eq.), 4-bromo-3-(trifluoromethyl) benzoic acid (48.2 mg, 0.179 mmol, 1.20 eq.), HATU (68.1 mg, 0.179 mmol, 1.20 eq.) and DIEA (57.9 mg, 0.447 mmol, 3.00 eq.) in DMF (5 mL) was stirred for overnight at rt. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The crude product was purified by prep-HPLC with the following conditions: Column: XBridge Prep Phenyl OBD Column, 19×150 mm, 5 μm; Mobile Phase A: Water (10 mmol/L NH₄HCO₃+0.1% NH₃·H₂O), Mobile Phase B: ACN; Flow rate: 25 mL/min; Gradient: 55% B to 68% B in 7 min; Wave Length: 220 nm to afford 6-[(benzyloxy)methyl]-7-[4-bromo-3-(trifluoromethyl)benzoyl]-2-(4-cyclopropoxyphenyl)-3-oxo-N-{[2-(pyrimidin-2-yl)phenyl]methyl}-5H,6H,8H-imidazo[1,5-a]pyrazine-1-carboxamide (42.0 mg, 33% yield) as a white solid. LCMS (ESI, m/z): 853 [M+H]⁺. ¹H NMR (300 MHz, CDCl₃) δ 8.59 (s, 2H), 8.10 (d, J=4.2 Hz, 1H), 7.84-7.70 (m, 2H), 7.43 (d, J=8.3 Hz, 4H), 7.31 (t, J=8.4 Hz, 4H), 7.18 (d, J=5.0 Hz, 1H), 7.05 (d, J=8.4 Hz, 3H), 6.72 (d, J=8.4 Hz, 2H), 4.64-4.36 (m, 6H), 3.98-3.43 (m, 6H), 0.71 (d, J=6.0 Hz, 2H), 0.58 (s, 2H).

Example 17

7-[4-bromo-3-(trifluoromethyl)benzoyl]-2-[4-(cyclopropoxy)phenyl]-6-(hydroxymethyl)-3-oxo-N-[(2-pyrimidin-2-ylphenyl)methyl]-6,8-dihydro-5H-imidazo[1,5-a]pyrazine-1-carboxamide (131)

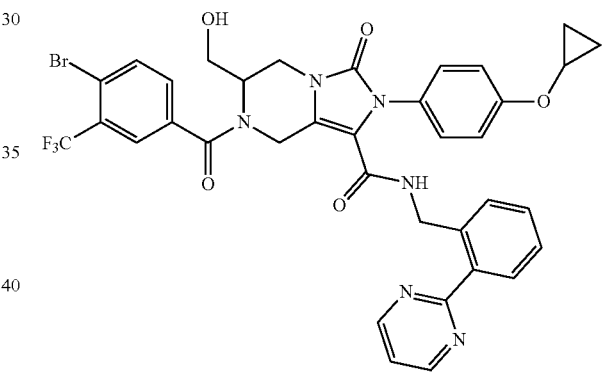

A mixture of 6-[(benzyloxy)methyl]-7-[4-bromo-3-(trifluoromethyl)benzoyl]-2-(4-cyclopropoxyphenyl)-3-oxo-N-{[2-(pyrimidin-2-yl)phenyl]methyl}-5H,6H,8H-imidazo[1,5-a]pyrazine-1-carboxamide (130) (13.0 mg, 0.0150 mmol, 1.00 eq.) and CF₃COOH (1 mL) was stirred for overnight at 60° C. and then concentrated under reduced pressure. The crude product was purified by prep-HPLC with the following conditions: Column: XSelect CSH Prep C18 OBD Column, 19×250 mm, 5 μm; Mobile Phase A: Water (10 mmol/L NH₄HCO₃), Mobile Phase B: ACN; Flow rate: 25 mL/min; Gradient: 55% B to 68% B in 10 min; Wave Length: 254 nm to afford 7-[4-bromo-3-(trifluoromethyl) benzoyl]-2-(4-cyclopropoxyphenyl)-6-(hydroxymethyl)-3-oxo-N-{[2-(pyrimidin-2-yl)phenyl]methyl}-5H,6H,8H-imidazo[1,5-a]pyrazine-1-carboxamide (131) (4.40 mg, 37% yield) as a white solid. LCMS (ESI, m/z): 763 [M+H]⁺. ¹H NMR (300 MHz, CDCl₃) δ 8.64-8.51 (m, 2H), 8.09 (s, 1H), 7.89-7.73 (m, 2H), 7.85-7.79 (m, 4H), 7.16 (t, J=4.8 Hz, 2H), 7.06 (d, J=8.6 Hz, 4H), 6.70 (d, J=8.5 Hz, 2H), 4.51-4.39 (m, 4H), 3.98-3.43 (m, 9H), 1.25 (s, 5H), 0.88 (s, 1H), 0.71-0.69 (m, 2H), 0.57 (s, 2H).

Example 18

7-[4-bromo-3-(trifluoromethyl)benzoyl]-2-[4-(cyclopropoxy)phenyl]-6-(morpholinomethyl)-3-oxo-N-[(2-pyrimidin-2-ylphenyl)methyl]-6,8-dihydro-5H-imidazo[1,5-a]pyrazine-1-carboxamide (132) and Separation into its Enantiomers rac-(6S)-7-[4-bromo-3-(trifluoromethyl)benzoyl]-2-[4-(cyclopropoxy)phenyl]-6-(morpholinomethyl)-3-oxo-N-[(2-pyrimidin-2-ylphenyl)methyl]-6,8-dihydro-5H-imidazo[1,5-a]pyrazine-1-carboxamide (132a) and rac-(6R)-7-[4-bromo-3-(trifluoromethyl)benzoyl]-2-[4-(cyclopropoxy)phenyl]-6-(morpholinomethyl)-3-oxo-N-[(2-pyrimidin-2-ylphenyl)methyl]-6,8-dihydro-5H-imidazo[1,5-a]pyrazine-1-carboxamide (132b)

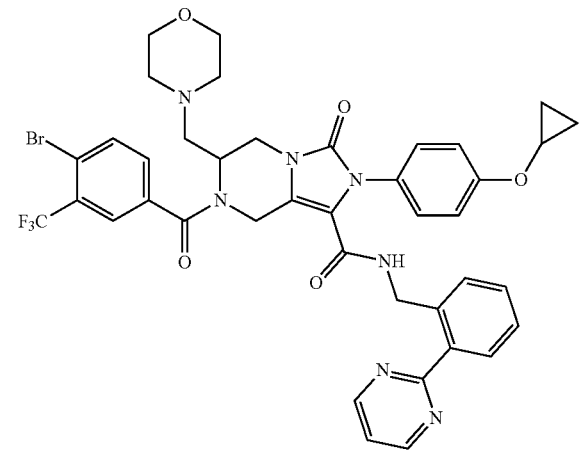

132

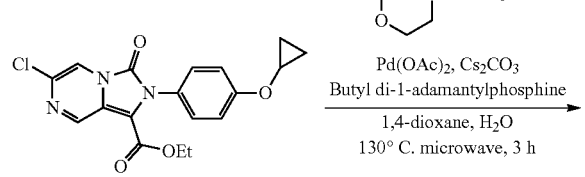

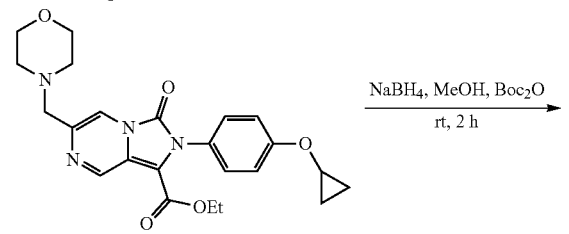

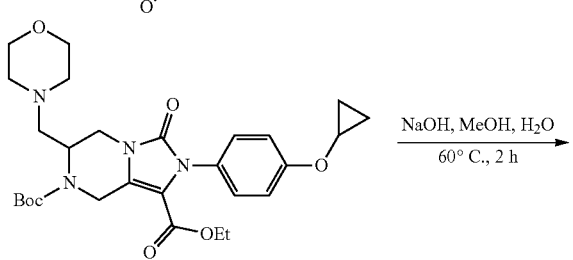

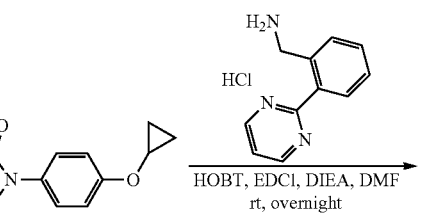

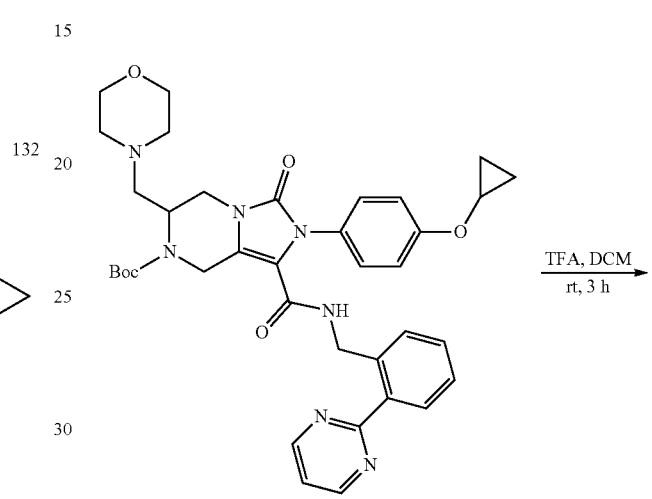

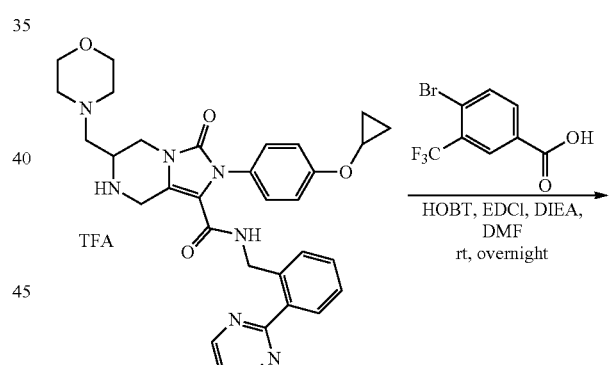

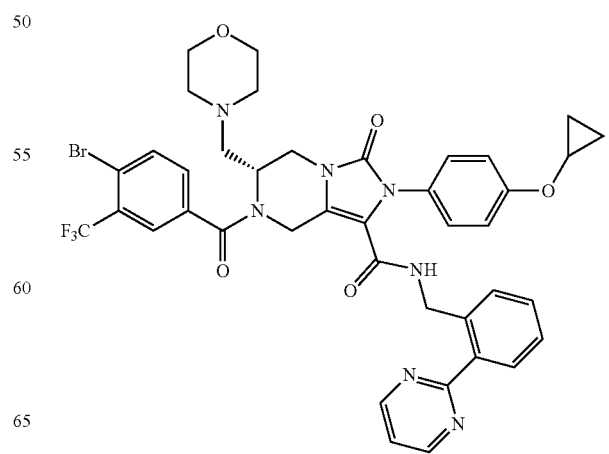

-continued

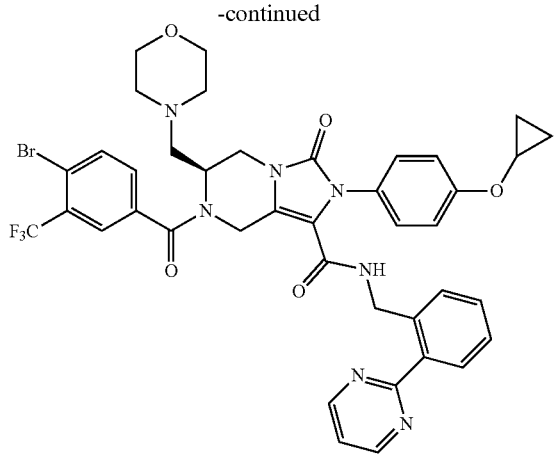

7-tert-butyl 1-ethyl 2-(4-cyclopropoxyphenyl)-6-(morpholin-4-ylmethyl)-3-oxo-5H,6H,8H-imidazo[1,5-a]pyrazine-1,7-dicarboxylate A 100 mL microwave tube was charged with ethyl 6-chloro-2-(4-cyclopropoxyphenyl)-3-oxoimidazo[1,5-a]pyrazine-1-carboxylate (600 mg, 1.60 mmol, 1.00 eq.), 4-[(trifluoro-λ4-boranyl)methyl] morpholine potassium (664 mg, 3.21 mmol, 2.00 eq.), 1,4-dioxane (30 mL), $Cs_2CO_3$ (1046 mg, 3.21 mmol, 2.00 eq.), Pd(OAc)$_2$ (18.0 mg, 0.0800 mmol, 0.05 eq.), water (10 mL) and bis(adamantan-1-yl)(butyl)phosphane (57.6 mg, 0.161 mmol, 0.10 eq.) under nitrogen. The mixture was irradiated with microwave radiation for 3 h at 130° C. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford ethyl 2-(4-cyclopropoxyphenyl)-6-(morpholin-4-ylmethyl)-3-oxoimidazo[1,5-a]pyrazine-1-carboxylate (300 mg, 42% yield) as a yellow solid. LCMS (ESI, m/z): 439 [M+H]$^+$.

7-tert-butyl 1-ethyl 2-(4-cyclopropoxyphenyl)-6-(morpholin-4-ylmethyl)-3-oxo-5H,6H,8H-imidazo[1,5-a]pyrazine-1,7-dicarboxylate A 100 mL round bottom flask was charged with ethyl 2-(4-cyclopropoxyphenyl)-6-(morpholin-4-ylmethyl)-3-oxoimidazo[1,5-a]pyrazine-1-carboxylate (300 mg, 0.684 mmol, 1.00 eq.), Boc$_2$O (298 mg, 1.37 mmol, 2.00 eq.) and methanol (50 mL). NaBH$_4$ (77.7 mg, 2.05 mmol, 3.00 eq.) was added in portions at 0° C. The solution was stirred for 2 h at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford 7-tert-butyl 1-ethyl 2-(4-cyclopropoxyphenyl)-6-(morpholin-4-ylmethyl)-3-oxo-5H,6H, 8H-imidazo[1,5-a]pyrazine-1,7-dicarboxylate (200 mg, 53% yield) as a white solid. LCMS (ESI, m/z): 543 [M+H]$^+$.

7-(tert-butoxycarbonyl)-2-(4-cyclopropoxyphenyl)-6-(morpholin-4-ylmethyl)-3-oxo-5H,6H,8H-imidazo[1,5-a]pyrazine-1-carboxylic acid A 40 mL vial was charged with 7-tert-butyl 1-ethyl 2-(4-cyclopropoxyphenyl)-6-(morpholin-4-ylmethyl)-3-oxo-5H,6H, 8H-imidazo[1,5-a]pyrazine-1,7-dicarboxylate (200 mg, 0.369 mmol, 1.00 eq.), NaOH (29.5 mg, 0.738 mmol, 2.00 eq.), water (10 mL) and methanol (10 mL). The solution was stirred for 2 h at 60° C. and then diluted with water (50 mL). The pH value of the mixture was adjusted to 4 with HCl (aq. 1 mol/L). The aqueous phase was extracted with ethyl acetate (3×50 mL). The organic layers were combined, dried over anhydrous sodium sulfate, filtered and concentrated under reduced pressure to afford 7-(tert-butoxycarbonyl)-2-(4-cyclopropoxyphenyl)-6-(morpholin-4-ylmethyl)-3-oxo-5H,6H,8H-imidazo[1,5-a]pyrazine-1-carboxylic acid (150 mg, crude) as a white solid. LCMS (ESI, m/z): 515 [M+H]$^+$.

tert-butyl 2-(4-cyclopropoxyphenyl)-6-(morpholin-4-ylmethyl)-3-oxo-1-({[2-(pyrimidin-2-yl)phenyl]methyl}carbamoyl)-5H,6H,8H-imidazo[1,5-a]pyrazine-7-carboxylate A 40 mL vial was charged with 7-(tert-butoxycarbonyl)-2-(4-cyclopropoxyphenyl)-6-(morpholin-4-ylmethyl)-3-oxo-5H,6H,8H-imidazo[1,5-a]pyrazine-1-carboxylic acid (150 mg, 0.292 mmol, 1.00 eq.), 1-[2-(pyrimidin-2-yl)phenyl]methanamine hydrochloride (71.1 mg, 0.321 mmol, 1.10 eq.), HOBT (59.1 mg, 0.438 mmol, 1.50 eq.), EDCI (83.8 mg, 0.438 mmol, 1.50 eq.), DIEA (151 mg, 1.17 mmol, 4.00 eq.) and DMF (10 mL). The solution was stirred for overnight at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford tert-butyl 2-(4-cyclopropoxyphenyl)-6-(morpholin-4-ylmethyl)-3-oxo-1-({[2-(pyrimidin-2-yl)phenyl]methyl}carbamoyl)-5H,6H, 8H-imidazo[1,5-a]pyrazine-7-carboxylate (100 mg, 50% yield) as a white solid. LCMS (ESI, m/z): 682 [M+H]$^+$.

2-(4-cyclopropoxyphenyl)-6-(morpholin-4-ylmethyl)-3-oxo-N-{[2-(pyrimidin-2-yl)phenyl]methyl}-5H,6H,7H,8H-imidazo[1,5-a]pyrazine-1-carboxamide trifluoroacetic acid salt A 100 mL round bottom flask was charged with tert-butyl 2-(4-cyclopropoxyphenyl)-6-(morpholin-4-ylmethyl)-3-oxo-1-({[2-(pyrimidin-2-yl)phenyl]methyl}carbamoyl)-5H,6H,8H-imidazo[1,5-a]pyrazine-7-carboxylate (100 mg, 0.147 mmol, 1.00 eq.), dichloromethane (20 mL) and trifluoroacetic acid (5 mL). The solution was stirred for 3 h at rt and then concentrated under reduced pressure to afford 2-(4-cyclopropoxyphenyl)-6-(morpholin-4-ylmethyl)-3-oxo-N-{[2-(pyrimidin-2-yl)phenyl]methyl}-5H,6H,7H,8H-imidazo[1,5-a]pyrazine-1-carboxamide trifluoroacetic acid salt (100 mg, crude) as a light yellow solid. LCMS (ESI, m/z): 582 [M+H-TFA]$^+$.

rac-(6R)-7-[4-bromo-3-(trifluoromethyl)benzoyl]-2-(4-cyclopropoxyphenyl)-6-(morpholin-4-ylmethyl)-3-oxo-N-{[2-(pyrimidin-2-yl)phenyl]methyl}-5H,6H,8H-imidazo[1,5-a]pyrazine-1-carboxamide and
rac-(6S)-7-[4-bromo-3-(trifluoromethyl)benzoyl]-2-(4-cyclopropoxyphenyl)-6-(morpholin-4-ylmethyl)-3-oxo-N-{[2-(pyrimidin-2-yl)phenyl]methyl}-5H,6H,8H-imidazo[1,5-a]pyrazine-1-carboxamide A 40 mL vial was charged with 2-(4-cyclopropoxyphenyl)-6-(morpholin-4-ylmethyl)-3-oxo-N-{[2-(pyrimidin-2-yl)phenyl]methyl}-5H,6H,7H,8H-imidazo[1,5-a]pyrazine-1-carboxamide trifluoroacetic acid salt (100 mg, 0.144 mmol, 1.00 eq.), 4-bromo-3-(trifluoromethyl)benzoic acid (47.5 mg, 0.176 mmol, 1.22 eq.), HOBT (23.9 mg, 0.176 mmol, 1.22 eq.), EDCI (33.8 mg, 0.176 mmol, 1.22 eq.), DIEA (76.0 mg, 0.588 mmol, 4.08 eq.) and DMF (10 mL). The solution was stirred for overnight at rt. The reaction was quenched with water (100 mL). The mixture was extracted with EA (3×100 mL). The organic layers were combined, washed with water (3×100 mL), dried over anhydrous sodium sulfate, filtered and concentrated under reduced pressure. The residue was purified by prep-TLC (ethyl acetate:petroleum ether=3:1) to afford the crude product. The crude product was purified by prep-HPLC with the following conditions: Column: CHIRAL ART Amylose-SA, 2×25 cm, 5 μm; Mobile Phase A: MtBE (0.5% 2M NH$_3$-MeOH)—HPLC, Mobile Phase B: EtOH-HPLC; Flow rate: 20 mL/min; Gradient: 25% B to 25% B in 16 min; Wave Length: 220/254 nm to afford rac-(6R)-7-[4-bromo-3-(trifluoromethyl)benzoyl]-2-(4-cyclopropoxyphenyl)-6-(morpholin-4-ylmethyl)-3-oxo-N-{[2-(pyrimidin-2-yl)phenyl]methyl}-5H,6H,8H-imidazo[1,5-a]pyrazine-1-carboxamide (132a) (the first elution, 22.5 mg, 18% yield) as a light yellow solid. LCMS (ESI, m/z): 832 [M+H]$^+$. $^1$H NMR (400 MHz, CDCl$_3$) δ 8.59 (d, J=4.8 Hz, 2H), 8.18-8.06 (m, 1H), 7.98-7.80 (m, 2H), 7.45 (d, J=4.2 Hz, 4H), 7.17 (t, J=4.9 Hz, 1H), 7.13-6.93 (m, 3H), 6.70 (d, J=8.3 Hz, 2H), 5.50 (s, 1H), 5.13 (s, 1H), 4.47 (m 3H), 3.98 (d, J=13.1 Hz, 1H), 3.71 (s, 5H), 3.43 (s, 1H), 2.70-2.50 (m, 5H), 0.71 (d, J=6.3 Hz, 2H), 0.57 (s, 2H).

rac-(6S)-7-[4-bromo-3-(trifluoromethyl)benzoyl]-2-(4-cyclopropoxyphenyl)-6-(morpholin-4-ylmethyl)-3-oxo-N-{[2-(pyrimidin-2-yl)phenyl]methyl}-5H,6H,8H-imidazo[1,5-a]pyrazine-1-carboxamide (132b) (the second elution, 23.8 mg, 19% yield) as a white solid. LCMS (ESI, m/z): 832 [M+H]$^+$. $^1$H NMR (400 MHz, CDCl$_3$) δ 8.59 (d, J=4.8 Hz, 2H), 8.18-8.05 (m, 1H), 7.96-7.78 (m, 2H), 7.45 (d, J=3.8 Hz, 4H), 7.17 (t, J=4.9 Hz, 1H), 7.13-6.90 (m, 3H), 6.70 (d, J=8.4 Hz, 2H), 5.53 (s, 1H), 5.12 (s, 1H), 4.87-4.32 (m, 3H), 3.98 (d, J=13.0 Hz, 1H), 3.75 (s, 5H), 3.43 (s, 1H), 3.02-2.33 (m, 5H), 0.71 (d, J=6.4 Hz, 2H), 0.58 (s, 2H).

Example 19

Intermediates I-1 to I-8

Synthesis of Intermediate I-1

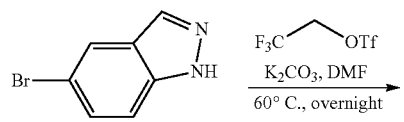

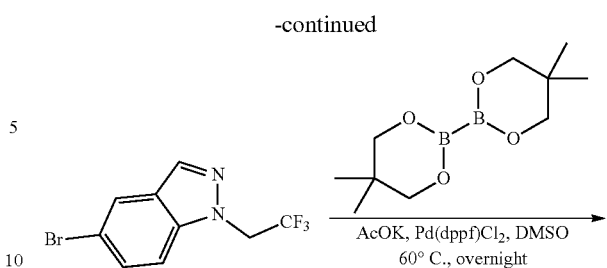

A 40 mL vial was charged with 5-bromo-1H-indazole (500 mg, 2.54 mmol, 1.00 eq.), 2,2,2-trifluoroethyl trifluoromethanesulfonate (706 mg, 3.05 mmol, 1.20 eq.), K$_2$CO$_3$ (701 mg, 5.08 mmol, 2.00 eq.) and DMF (20 mL). The mixture was stirred for overnight at 60° C. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate:petroleum ether (1:9) to afford 5-bromo-1-(2,2,2-trifluoroethyl) indazole (520 mg, 73% yield) as a white solid. LCMS (ESI, m/z): 279 [M+H]$^+$.

A 40 mL vial was charged with 5-bromo-1-(2,2,2-trifluoroethyl)indazole (400 mg, 1.43 mmol, 1.00 eq.), 2-(5,5-dimethyl-1,3,2-dioxaborinan-2-yl)-5,5-dimethyl-1,3,2-dioxaborinane (971 mg, 4.30 mmol, 3.00 eq.), Pd(dppf)Cl$_2$ (105 mg, 0.143 mmol, 0.100 eq.), DMSO (20 mL) and AcOK (422 mg, 4.30 mmol, 3.00 eq.). The mixture was stirred for overnight at 60° C. under a nitrogen atmosphere. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate:petroleum ether (1:8) to afford 5-(5,5-dimethyl-1,3,2-dioxaborinan-2-yl)-1-(2,2,2-trifluoroethyl)indazole (280 mg, 63% yield) as a white solid. LCMS (ESI, m/z): 313 [M+H]$^+$.

Synthesis of Intermediate I-2

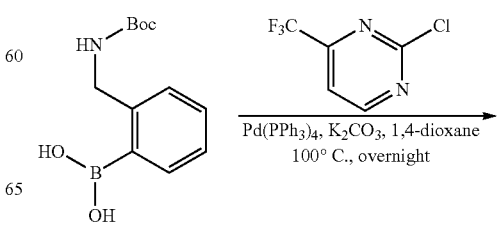

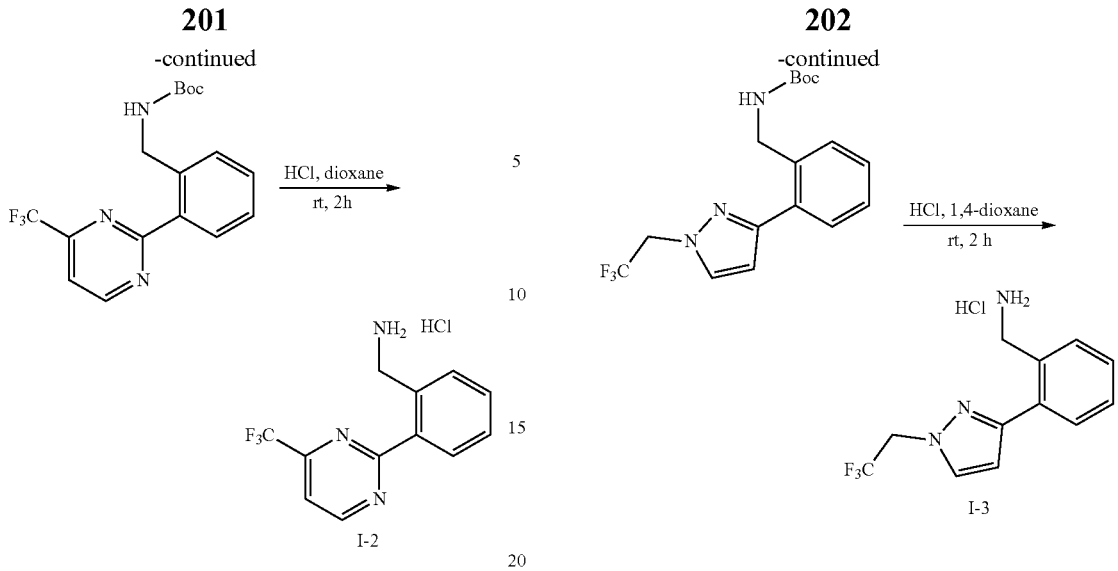

A 250 mL round-bottom flask was charged with 2-{[(tert-butoxycarbonyl)amino]methyl}phenylboronic acid (3.00 g, 11.9 mmol, 1.00 eq.), 2-chloro-4-(trifluoromethyl)pyrimidine (3.27 g, 17.9 mmol, 1.50 eq.), Pd(PPh$_3$)$_4$ (0.69 g, 0.597 mmol, 0.05 eq.), potassium carbonate (3.30 g, 23.9 mmol, 2.00 eq.) and 1,4-dioxane (150 mL). The mixture was stirred for overnight at 100° C. under a nitrogen atmosphere and then concentrated under reduced pressure. The reaction was quenched with water (100 mL) and extracted with ethyl acetate (3×150 mL). The organic layers were combined, washed with brine (3×50 mL), dried over anhydrous sodium sulfate, filtered and concentrated under reduced pressure. The residue was purified by silica gel column chromatography, eluted with ethyl acetate:petroleum ether (1:5) to afford tert-butyl N-({2-[4-(trifluoromethyl)pyrimidin-2-yl]phenyl}methyl)carbamate (1.80 g, 42% yield) as a white solid. LCMS (ESI, m/z): 354 [M+H]$^+$.

A 100 mL round-bottom flask was charged with tert-butyl N-({2-[4-(trifluoromethyl)pyrimidin-2-yl]phenyl}methyl)carbamate (1.80 g, 5.09 mmol, 1.00 eq.), hydrogen chloride solution 4.0 M in 1,4-diethylene oxide (60 mL). The solution was stirred for 2 h at rt and then concentrated under reduced pressure to afford 1-{2-[4-(trifluoromethyl)pyrimidin-2-yl]phenyl}methanamine hydrochloride (1.45 g, crude) as a white solid. LCMS (ESI, m/z): 254 [M+H—HCl]$^+$.

Synthesis of Intermediate I-3

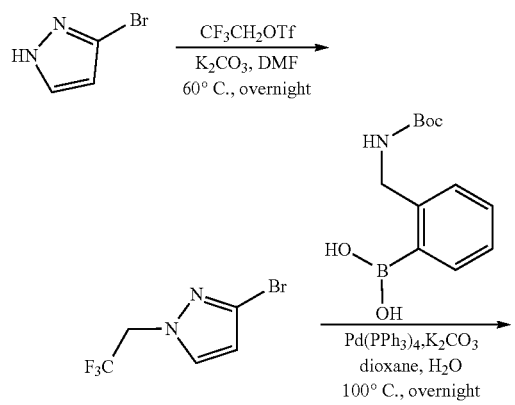

A mixture of 3-bromo-1H-pyrazole (5.00 g, 34.0 mmol, 1.00 eq.), 2,2,2-trifluoroethyl trifluoromethanesulfonate (11.8 g, 51.0 mmol, 1.50 eq.) and potassium carbonate (9.40 g, 68.0 mmol, 2.00 eq.) in DMF (50 mL) was stirred for overnight at 60° C. The reaction was quenched with water (300 mL). The mixture was extracted with dichloromethane (3×200 mL). The organic layers were combined, washed with brine (3×100 mL), dried over anhydrous sodium sulfate, filtered and concentrated under reduced pressure. The residue was purified by silica gel column chromatography, eluted with dichloromethane:methanol (5:1) to afford 3-bromo-1-(2,2,2-trifluoroethyl) pyrazole (3.80 g, 49% yield) as a light yellow oil. LCMS (ESI, m/z): 229 [M+H]$^+$.

A 100 mL round-bottom flask 3-bromo-1-(2,2,2-trifluoroethyl)pyrazole (3.80 g, 16.6 mmol, 1.50 eq.), 2-{[(tert-butoxycarbonyl)amino]methyl}phenylboronic acid (2.78 g, 11.1 mmol, 1.00 eq.), Pd(PPh$_3$)$_4$ (1.28 g, 1.11 mmol, 0.100 eq.) and K$_2$CO$_3$ (3.06 g, 22.1 mmol, 2.00 eq.), 1,4-dioxane (20 mL) and water (1 mL). The mixture was stirred for overnight at 100° C. under a nitrogen atmosphere. The reaction was quenched with water (80 mL). The mixture was extracted with dichloromethane (3×200 mL). The organic layers were combined, washed with brine (3×100 mL), dried over anhydrous sodium sulfate, filtered and concentrated under reduced pressure. The residue was purified by silica gel column chromatography, eluted with dichloromethane:methanol (5:1) to afford tert-butyl N-({2-[1-(2,2,2-trifluoroethyl)pyrazol-3-yl]phenyl}methyl)carbamate (3.08 g, 78% yield) as a yellow oil. LCMS (ESI, m/z): 356 [M+H]$^+$.

A mixture of tert-butyl N-({2-[1-(2,2,2-trifluoroethyl)pyrazol-3-yl]phenyl}methyl)carbamate (980 mg, 0.844 mmol, 1.00 eq.) and HCl (gas) (10 mL, 4M in 1,4-dioxane) was stirred for 2 h at rt and then concentrated under reduced pressure to afford 1-{2-[1-(2,2,2-trifluoroethyl)pyrazol-3-yl]phenyl}methanamine hydrochloride (1.06 g, crude) as a light yellow oil. LCMS (ESI, m/z): 256 [M+H—HCl]$^+$.

Synthesis of Intermediate I-4

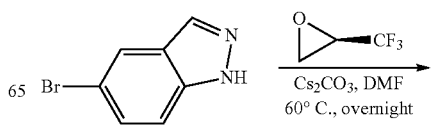

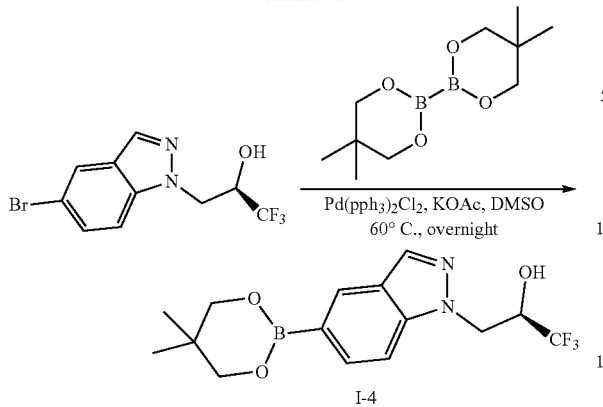

I-4

A 100 mL round-bottom flask was charged with 5-bromo-1H-indazole (880 mg, 4.47 mmol, 1.00 eq.), (2R)-2-(trifluoromethyl)oxirane (500 mg, 4.47 mmol, 1.00 eq.), K₂CO₃ (1.85 g, 13.4 mmol, 3.00 eq.) and DMF (20 mL). The mixture was stirred for overnight at 90° C. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford (2R)-3-(5-bromoindazol-1-yl)-1,1,1-trifluoropropan-2-ol (750 mg, 54% yield) as a light yellow solid. LCMS (ESI, m/z): 309 [M+H]⁺.

A 250 mL round-bottom flask was charged with (2R)-3-(5-bromoindazol-1-yl)-1,1,1-trifluoropropan-2-ol (550 mg, 1.78 mmol, 1.00 eq.), 2-(5,5-dimethyl-1,3,2-dioxaborinan-2-yl)-5,5-dimethyl-1,3,2-dioxaborinane (804 mg, 3.56 mmol, 2.00 eq.), Pd(pph₃)₂Cl₂ (125 mg, 0.178 mmol, 0.10 eq.), KOAc (524 mg, 5.34 mmol, 3.0 eq.) and DMSO (10 mL). The mixture was stirred for overnight at 60° C. under a nitrogen atmosphere. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford (R)-3-(5-(5,5-dimethyl-1,3,2-dioxaborinan-2-yl)-1H-indazol-1-yl)-1,1,1-trifluoropropan-2-ol (450 mg, 74% yield) as a yellow oil. LCMS (ESI, m/z): 343 [M+H]⁺.

Synthesis of Intermediate I-5

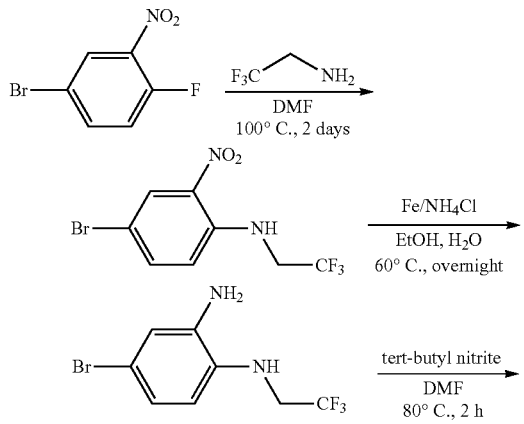

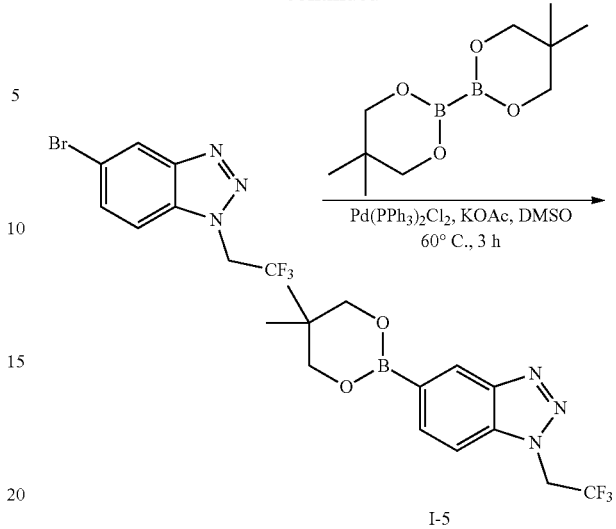

I-5

A 100 mL round-bottom flask was charged with 4-bromo-1-fluoro-2-nitrobenzene (6.00 g, 27.2 mmol, 1.00 eq.), DMF (24 mL) and 2,2,2-trifluoroethylamine (8.10 g, 81.7 mmol, 3.00 eq.) at rt. The mixture was stirred for 2 days at 100° C. The reaction was quenched with water (100 mL). The mixture was extracted with ethyl acetate (3×50 mL). The combined organic layers were washed with water (3×10 mL), dried over anhydrous sodium sulfate, filtered and concentrated under reduced pressure. The residue was purified by silica gel column chromatography, eluted with ethyl acetate:petroleum ether (1:1) to afford 4-bromo-2-nitro-N-(2,2,2-trifluoroethyl)aniline (8.00 g, 98% yield) as a yellow solid. LCMS (ESI, m/z): 299 [M+H]⁺.

A mixture of 4-bromo-2-nitro-N-(2,2,2-trifluoroethyl)aniline (8.00 g, 26.7 mmol, 1.00 eq.), iron (14.9 g, 267 mmol, 10.0 eq.) and ammonium chloride (5.72 g, 107 mmol, 4.00 eq.) in EtOH (80 mL) and water (10 mL) was stirred for overnight at 80° C. and then concentrated under reduced pressure. The residue was purified by reverse flash chromatography with the following conditions: column, Agela C18 Column, 120 g; mobile phase, acetonitrile in water, 0% to 100% gradient in 50 min; detector, UV 254 nm to afford 4-bromo-N1-(2,2,2-trifluoroethyl)benzene-1,2-diamine (6.50 g, 90% yield) as a yellow solid. LCMS (ESI, m/z): 269 [M+H]⁺.

To a stirred mixture of 4-bromo-N1-(2,2,2-trifluoroethyl)benzene-1,2-diamine (4.50 g, 16.7 mmol, 1.00 eq.) in DMF (50 mL) was added tert-butyl nitrite (3.45 g, 33.4 mmol, 2.00 eq.) at 0° C. The mixture was stirred for 2 h at 80° C. The reaction was quenched with water (250 mL). The mixture was extracted with ethyl acetate (3×250 mL). The combined organic layers were washed with water (3×200 mL), dried over anhydrous sodium sulfate, filtered and concentrated under reduced pressure. The residue was purified by silica gel column chromatography, eluted with methanol:dichloromethane (1:10) to afford 5-bromo-1-(2,2,2-trifluoroethyl)-1,2,3-benzotriazole (3.20 g, 68% yield) as a yellow solid. LCMS (ESI, m/z): 280 [M+H]⁺.

A mixture of 5-bromo-1-(2,2,2-trifluoroethyl)-1,2,3-benzotriazole (3.20 g, 11.4 mmol, 1.00 eq.), 2-(5,5-dimethyl-1,3,2-dioxaborinan-2-yl)-5,5-dimethyl-1,3,2-dioxaborinane (12.9 g, 57.2 mmol, 5.00 eq.), Pd(PPh₃)₂Cl₂ (0.800 g, 1.14 mmol, 0.10 eq.), potassium acetate (3.36 g, 34.2 mmol, 3.00 eq.) and DMSO (100 mL) was stirred for overnight at 60° C.

under a nitrogen atmosphere. The reaction was quenched with water (500 mL). The mixture was extracted with ethyl acetate (3×500 mL). The combined organic layers were washed with water (3×200 mL), dried over anhydrous sodium sulfate, filtered and concentrated under reduced pressure. The residue was purified by silica gel column chromatography, eluted with dichloromethane:methanol (10:1) to afford 5-(5,5-dimethyl-1,3,2-dioxaborinan-2-yl)-1-(2,2,2-trifluoroethyl)-1H-benzo[d][1,2,3]triazole (2.10 g, 58% yield) as a white solid. LCMS (ESI, m/z): 314 [M+H]$^+$.

Synthesis of Intermediate I-6

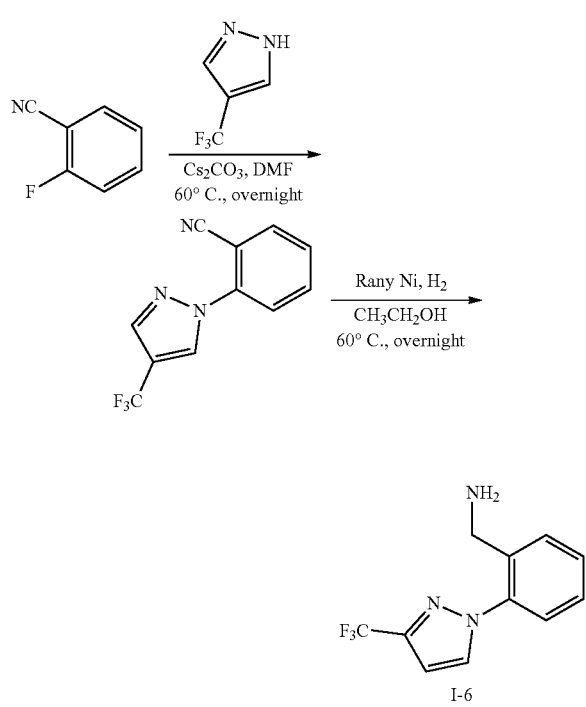

Synthesis of Intermediate I-7

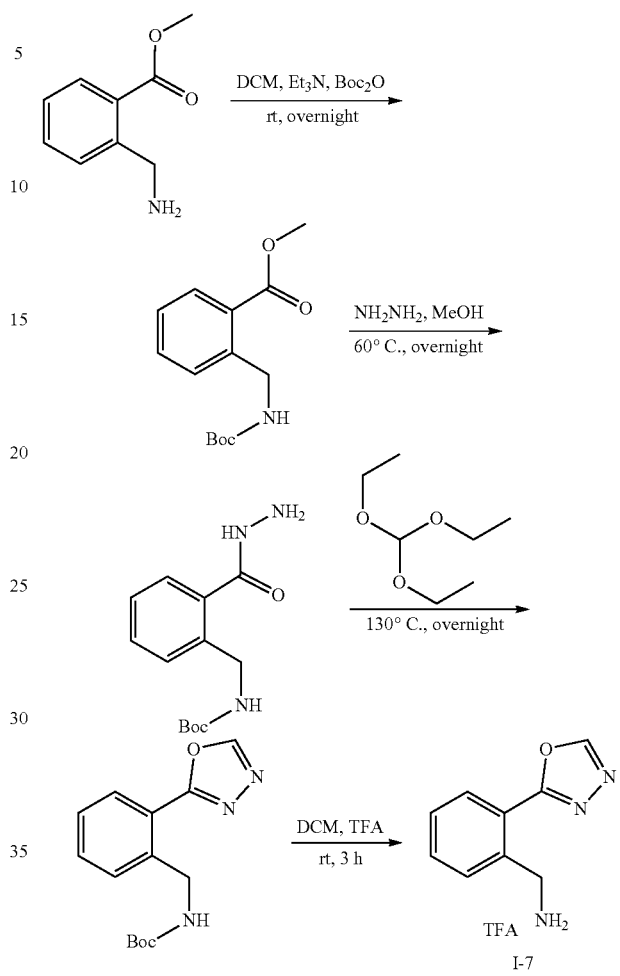

A 100 mL round-bottom flask was charged with 2-fluorobenzonitrile (1.00 g, 8.26 mmol, 1.00 eq.), 4-(trifluoromethyl)-1H-pyrazole (1.12 g, 8.26 mmol, 1.00 eq.), cesium carbonate (5.38 g, 16.5 mmol, 2.00 eq.) and DMF (10 mL). The mixture was stirred for overnight at 60° C. The reaction was quenched with water (50 mL). The mixture was extracted with ethyl acetate (3×150 mL). The organic layers were combined, washed with water (3×100 mL), dried over anhydrous sodium sulfate, filtered and concentrated under reduced pressure. The residue was purified by silica gel column chromatography, eluted with petroleum ether:ethyl acetate (1:1) to afford 2-(4-(trifluoromethyl)-1H-pyrazol-1-yl)benzonitrile (1.50 g, 76% yield) as a white solid. LCMS (ESI, m/z): 238 [M+H]$^+$.

A 100 mL round-bottom flask was charged with 2-[3-(trifluoromethyl)pyrazol-1-yl]benzonitrile (1.10 g, 4.64 mmol, 1.00 eq.), Rany Ni (100 mg) and EtOH (50 mL) at rt. The mixture was stirred for overnight at 60° C. under a hydrogen atmosphere (2-3 atm). The solids were filtered off, and the filter cake was washed with EtOH (3×50 mL). The filtrate was concentrated under reduced pressure to afford (2-(3-(trifluoromethyl)-1H-pyrazol-1-yl)phenyl)methanamine (1.00 g, 89% yield) as a colorless oil. LCMS (ESI, m/z): 242 [M+H]$^+$.

A 100 mL round-bottom flask was charged with methyl 2-(aminomethyl)benzoate (2.00 g, 12.1 mmol, 1.00 eq.), Et$_3$N (2.45 g, 24.2 mmol, 2.00 eq.), Boc$_2$O (5.28 g, 24.2 mmol, 2.00 eq.) and DCM (20 mL). The mixture was stirred for overnight at rt. The reaction was quenched with water (100 mL). The mixture was extracted with EtOAc (3×100 mL). The combined organic layers were washed with water (3×50 mL), dried over anhydrous Na$_2$SO$_4$, filtered and concentrated under reduced pressure. The residue was purified by silica gel column chromatography, eluted with ethyl acetate:petroleum ether (1:5) to afford methyl 2-{[(tert-butoxycarbonyl)amino]methyl}benzoate (1.02 g, 32% yield) as a white solid. LCMS (ESI, m/z): 266 [M+H]$^+$.

A 100 mL round-bottom flask was charged with methyl 2-{[(tert-butoxycarbonyl)amino]methyl} benzoate (1.50 g, 5.65 mmol, 1.00 eq.), hydrazine hydrate (0.448 g, 8.96 mmol, 1.58 eq.) and MeOH (10 mL). The mixture was stirred for overnight at 60° C. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate:petroleum ether (1:2) afford tert-butyl N-{[2-(hydrazinecarbonyl) phenyl]methyl} carbamate (1.02 g, 67% yield) as a colorless oil. LCMS (ESI, m/z): 266 [M+H]$^+$.

A 100 mL round-bottom flask was charged with tert-butyl N-{[2-(hydrazinecarbonyl)phenyl]methyl} carbamate (1.10 g, 4.15 mmol, 1.00 eq.) and diethoxy(methoxy)methane (5 mL). The mixture was stirred for overnight at 130° C. The reaction was quenched with water (20 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with ethyl acetate:petroleum ether (1:2) afford tert-butyl N-{[2-(1,3,4-oxadiazol-2-yl)phenyl]methyl}carbamate (500 mg, 44% yield) as a colorless oil. LCMS (ESI, m/z): 276 [M+H]$^+$.

A 100 mL round-bottom flask were added tert-butyl N-{[2-(1,3,4-oxadiazol-2-yl)phenyl]methyl} carbamate (300 mg, 1.09 mmol, 1.00 eq.), TFA (4 mL) and DCM (20 mL) at rt. The mixture was stirred for 3 h at rt and then concentrated under reduced pressure to afford 1-[2-(1,3,4-oxadiazol-2-yl)phenyl]methanamine trifluoroacetic acid salt (310 mg, crude) as a colorless oil. LCMS (ESI, m/z): 266 [M+H-TFA]$^+$.

Synthesis of Intermediate I-8

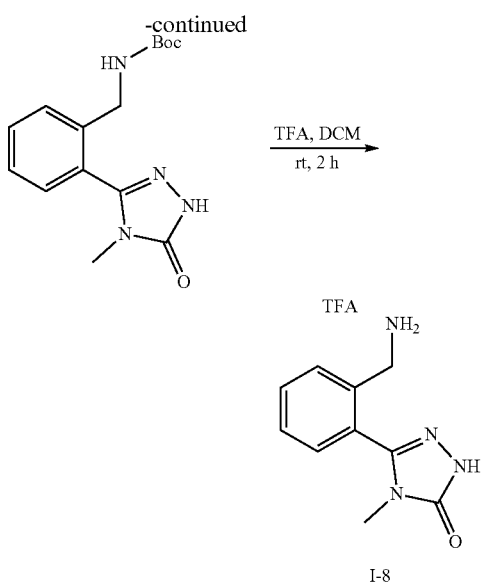

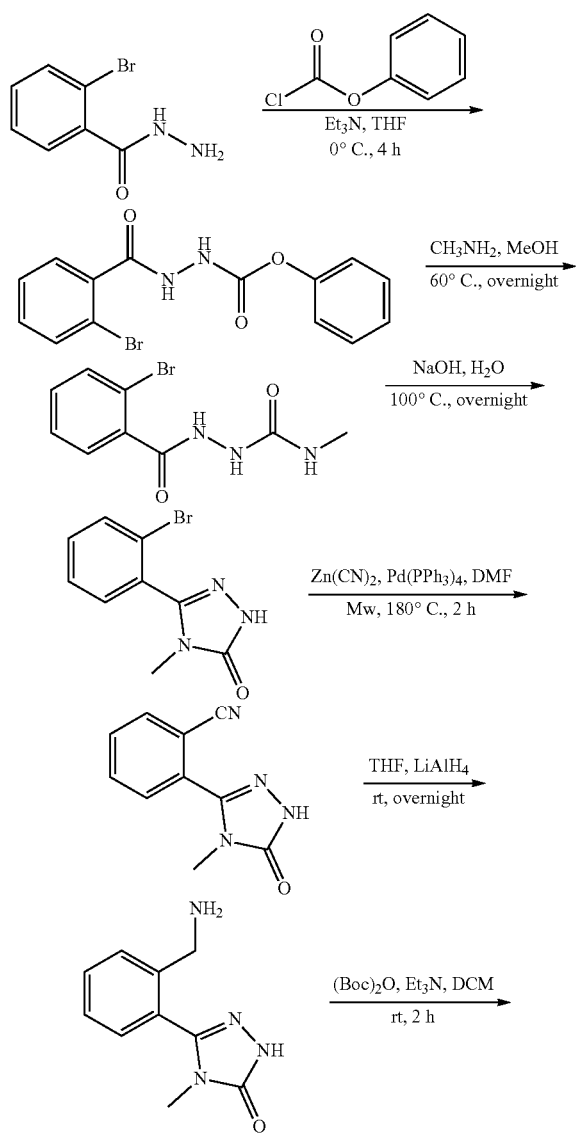

A 100 mL round-bottom flask was charged with 2-bromobenzoylhydrazine (10.0 g, 46.5 mmol, 1.00 eq.), phenyl chloroformate (10.9 g, 69.8 mmol, 1.50 eq.), Et$_3$N (9.42 g, 93.0 mmol, 2.00 eq.) and THF (100 mL) at rt. The mixture was stirred for 4 h at 0° C. and then concentrated under reduced pressure. The reaction was quenched with water (100 mL). The mixture was extracted with ethyl acetate (3×500 mL). The combined organic layers were washed with water (3×200 mL), dried over anhydrous sodium sulfate, filtered and concentrated under reduced pressure. The residue was purified by silica gel column chromatography, eluted with ethyl acetate:petroleum ether (1:1) to afford N'-(2-bromobenzoyl)-1-phenoxyformohydrazide (15.0 g, 96% yield) as a yellow solid. LCMS (ESI, m/z): 335 [M+H]$^+$.

A 250 mL round-bottom flask was charged with N'-(2-bromobenzoyl)-1-phenoxyformohydrazide (15.0 g, 44.8 mmol, 1.00 eq.), CH$_3$NH$_2$ (16.8 g, 179 mmol, 4.00 eq., 33% w/w in MeOH) and MeOH (50 mL). The mixture was stirred for overnight at 60° C. and then concentrated under reduced pressure. The reaction was quenched with water (200 mL). The mixture was extracted with ethyl acetate (3×200 mL). The combined organic layers were washed with water (3×200 mL), dried over anhydrous sodium sulfate, filtered and concentrated under reduced pressure. The residue was purified by silica gel column chromatography, eluted with ethyl acetate:petroleum ether (1:1) to afford 2-bromo-N-[(methylcarbamoyl)amino]benzamide (4.60 g, 38% yield) as a white solid. LCMS (ESI, m/z): 272 [M+H]$^+$.

A 250 mL round-bottom flask was charged with 2-bromo-N-[(methylcarbamoyl)amino]benzamide (4.60 g, 16.8 mmol, 1.00 eq.), NaOH (1.34 g, 33.6 mmol, 2.00 eq.) and H$_2$O (50 mL). The mixture was stirred for overnight at 100° C. and then concentrated under reduced pressure. The residue was purified by silica gel column chromatography, eluted with ethyl acetate:petroleum ether (1:1) to afford 5-(2-bromophenyl)-4-methyl-2H-1,2,4-triazol-3-one (3.80 g, 88% yield) as a white solid. LCMS (ESI, m/z): 254 [M+H]$^+$.

A 100 mL vial was charged with 5-(2-bromophenyl)-4-methyl-2H-1,2,4-triazol-3-one (3.80 g, 15.0 mmol, 1.00 eq.), Pd(PPh$_3$)$_4$ (867 mg, 0.75 mmol, 0.05 eq.), Zn(CN)$_2$ (3.51 g, 30.0 mmol, 2.00 eq.) and DMF (10 mL). The mixture was irradiated with microwave radiation for 2 h at 180° C. The reaction was quenched with water (100 mL). The mixture was extracted with ethyl acetate (3×500 mL). The combined organic layers were washed with water (3×200 mL), dried over anhydrous sodium sulfate, filtered and concentrated under reduced pressure. The residue was purified by silica gel column chromatography, eluted with $CH_2Cl_2$:MeOH (10:1) to afford 2-(4-methyl-5-oxo-1H-1,2,4-triazol-3-yl)benzonitrile (1.01 g, 34% yield) as a white solid. LCMS (ESI, m/z): 201 [M+H]$^+$.

A 250 mL round-bottom flask was charged with 2-(4-methyl-5-oxo-1H-1,2,4-triazol-3-yl)benzonitrile (1.01 g, 5.05 mmol, 1.00 eq.), LiAlH$_4$ (960 mg, 25.3 mmol, 5.00 eq.) and THF (100 mL) at rt. The mixture was stirred for overnight at rt. The reaction was quenched with ice/water (960 mg), 30% NaOH (aq., 2.88 g) and water (960 mg). The solids were filtered off, and the filter cake was washed with THF (3×100 mL). The filtrate was concentrated under reduced pressure to afford 5-[2-(aminomethyl)phenyl]-4-methyl-2H-1,2,4-triazol-3-one (600 mg, crude) as a white solid. LCMS (ESI, m/z): 205 [M+H]$^+$.

A 100 mL round-bottom flask was charged with 5-[2-(aminomethyl)phenyl]-4-methyl-2H-1,2,4-triazol-3-one (600 mg, 2.94 mmol, 1.00 eq.), (Boc)$_2$O (1.28 g, 5.88 mmol, 2.00 eq.), Et$_3$N (595 mg, 5.88 mmol, 2.00 eq.) and DCM (50 mL). The mixture was stirred for 2 h at rt. The reaction was quenched with water (50 mL). The mixture was extracted with DCM (3×200 mL). The combined organic layers were washed with water (3×200 mL), dried over anhydrous sodium sulfate, filtered and concentrated under reduced pressure. The residue was purified by silica gel column chromatography, eluted with ethyl acetate:petroleum ether (3:1) to afford tert-butyl N-{[2-(4-methyl-5-oxo-1H-1,2,4-triazol-3-yl)phenyl]methyl}carbamate (300 mg, 34% yield) as a white solid. LCMS (ESI, m/z): 305 [M+H]$^+$.

A 100 mL round bottom flask was charged with tert-butyl N-{[2-(4-methyl-5-oxo-1H-1,2,4-triazol-3-yl)phenyl]methyl}carbamate (300 mg, 0.984 mmol, 1.00 eq.), TFA (5 mL) and DCM (20 mL). The mixture was stirred for 2 h at rt under an air atmosphere and then concentrated under reduced pressure to provide 5-[2-(aminomethyl)phenyl]-4-methyl-2H-1,2,4-triazol-3-one trifluoroacetic acid salt (310 mg, crude) as a yellow oil. LCMS (ESI, m/z): 205 [M-TFA+H]$^+$.

Example 20

Compounds 4-18 provided in Table A were synthetized using the intermediates and/or protocols of Examples 1-9, using methods and conditions known to those skilled in the art. Enantiomers were obtained from racemic mixtures by preparative chiral HPLC using conditions C1 to C14 described in table B. Enantiomer (a) is the first eluting enantiomer, enantiomer (b) is the second eluting compound.

TABLE A

| Cmpd | Structure | Name | LCMS [M + H]$^+$ | $^1$H NMR |
|---|---|---|---|---|
| 4 | 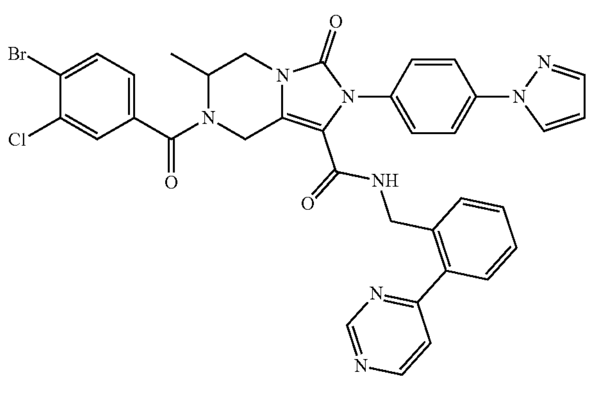 [SMILES: CC1Cn2c(c(C(=O)NCc3ccccc3-c3ccncn3)n(-c3ccc(-n4cccn4)cc3)c2=O)CN1C(=O)c1ccc(Br)c(Cl)c1] | 7-(4-bromo-3-chloro-benzoyl)-6-methyl-3-oxo-2-(4-pyrazol-1-ylphenyl)-N-[(2-pyrimidin-4-ylphenyl)methyl]-6,8-dihydro-5H-imidazo[1,5-a]pyrazine-1-carboxamide | 725.1 | (300 MHz, CDCl$_3$) δ 8.82 (s, 1H), 8.61 (s, 1H), 7.77-7.64 (m, 3H), 7.61-7.31 (m, 8H), 7.28-7.19 (m, 3H), 7.10 (s, 1H), 6.51-6.37 (m, 1H), 5.37 (s, 2H), 4.65 (d, J = 19.0 Hz, 1H), 4.53-4.28 (m, 2H), 3.88 (d, J = 12.7 Hz, 1H), 3.79-3.65 (m, 1H), 1.43 (d, J = 7.0 Hz, 3H) |
| 5a | 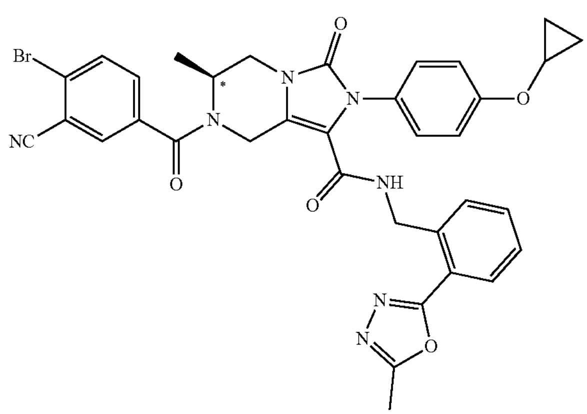 [SMILES: Cc1nnc(-c2ccccc2CNC(=O)c2c3n(c(=O)n2-c2ccc(OC4CC4)cc2)C[C@H](C)N(C(=O)c2ccc(Br)c(C#N)c2)C3)o1] | (6S*)-7-(4-bromo-3-cyano-benzoyl)-2-[4-(cyclopropoxy)phenyl]-6-methyl-N-[[2-(5-methyl-1,3,4-oxadiazol-2-yl)phenyl]methyl]-3-oxo-6,8-dihydro-5H-imidazo[1,5-a]pyrazine-1-carboxamide | 710 | (DMSO-d$_6$, 600 MHz, 80° C.) δ ppm 0.65-0.70 (m, 2H), 0.78-0.83 (m, 2H), 1.27 (d, J = 6.8 Hz, 3H), 2.58 (s, 3H), 3.62-3.73 (m, 2H), 3.83 (hept, J = 3.0 Hz, 1H), 4.41-4.68 (m, 4H), 5.16 (brs, 1H), 6.95-7.02 (m, 2H), 7.09-7.20 (m, 3H), 7.31 (d, J = 7.0 Hz, 1H), 7.44-7.52 (m, 2H), 7.72 (dd, J = 8.0, 1.9 Hz, 1H), 7.82-7.88 (m, 1H), 7.96 (d, J = 8.5 Hz, 1H), 8.05 (d, J = 1.9 Hz, 1H) |

TABLE A-continued

| Cmpd | Structure | Name | LCMS [M + H]+ | 1H NMR |
|---|---|---|---|---|
| 6 | 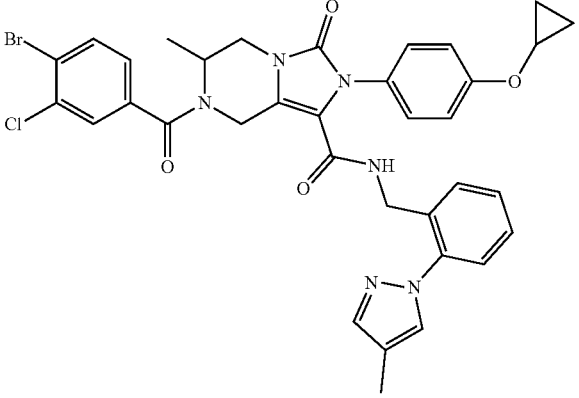 [SMILES: Cc1cnn(-c2ccccc2CNC(=O)c2c3n(c(=O)n2-c2ccc(OC4CC4)cc2)CC(C)N(C(=O)c2ccc(Br)c(Cl)c2)C3)c1] | 7-(4-bromo-3-chloro-benzoyl)-2-[4-(cyclopropoxy)phenyl]-6-methyl-N-[[2-(4-methylpyrazol-1-yl)phenyl]methyl]-3-oxo-6,8-dihydro-5H-imidazo[1,5-a]pyrazine-1-carboxamide | 716.95 | (300 MHz, CDCl$_3$) δ 7.71 (d, J = 8.1 Hz 1H), 7.65-7.56 (m, 1H), 7.49 (d, J = 7.5 Hz 1H), 7.42-7.30 (m, 3H), 7.26-7.12 (m, 5H), 6.99 (d, J = 9.0 Hz 2H), 6.78 (t, J = 5.7 Hz 1H), 5.86-4.79 (m, 2H), 4.60 (d, J = 18.0 Hz 1H), 4.23 (d, J = 6.0 Hz 2H), 3.86 (d, J = 12.3 Hz 1H), 3.79-3.60 (m, 2H), 2.14 (s, 3H), 1.39 (t, J = 9.15 Hz 3H), 0.86-0.68 (m, 4H). |
| 7 | 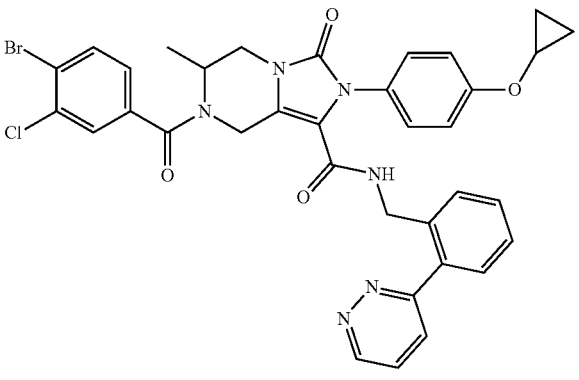 [SMILES: CC1Cn2c(c(C(=O)NCc3ccccc3-c3cccnn3)n(-c3ccc(OC4CC4)cc3)c2=O)CN1C(=O)c1ccc(Br)c(Cl)c1] | 7-(4-bromo-3-chloro-benzoyl)-2-[4-(cyclopropoxy)phenyl]-6-methyl-3-oxo-N-[(2-pyridazin-3-ylphenyl)methyl]-6,8-dihydro-5H-imidazo[1,5-a]pyrazine-1-carboxamide | 715.2 | (300 MHz, CDCl$_3$) δ 9.15 (d, J = 4.8 Hz, 1H), 7.74-7.54 (m, 4H), 7.52-7.36 (m, 4H), 7.24-7.09 (m, 3H), 6.85 (s, 1H), 6.74 (d, J = 8.8 Hz, 2H), 5.65-4.90 (m, 2H), 4.65 (d, J = 18.9 Hz, 1H), 4.33 (q, J = 8.6, 7.9 Hz, 2H), 3.88 (d, J = 12.8 Hz, 1H), 3.79-3.63 (m, 1H), 3.47 (dq, J = 6.1, 3.0 Hz, 1H), 1.41 (d, J = 7.0 Hz, 3H), 0.77-0.64 (m, 2H), 0.62-0.51 (m, 2H) |
| 8 | 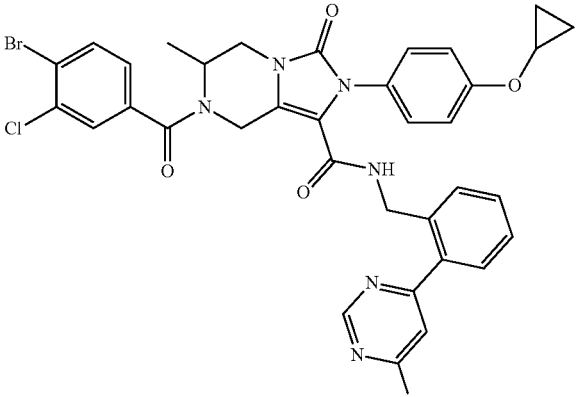 | N-[[2-(6-amino-pyrimidin-4-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | 729.95 | (300 MHz, CDCl$_3$) δ 8.20 (s, 1H), 7.71 (d, J = 8.1 Hz 1H), 7.58 (d, J = 1.8 Hz 1H), 7.50-7.35 (m, 4H), 7.24-7.04 (m, 4H), 6.84 (d, J = 8.7 Hz 2H), 6.54 (s, 1H), 5.62-5.15 (m, 1H), 5.00 (s, 2H), 4.62 (d, J = 19.2 Hz 1H), 4.44-4.20 (m, 2H), 3.86 (d, J = 12.9 Hz 1H), 3.80-3.65 (m, 1H), 3.65-3.50 (m, 1H), 1.40 (d, J = 6.9 Hz 3H), 0.80-0.60 (m, 4H) |
| 9 | 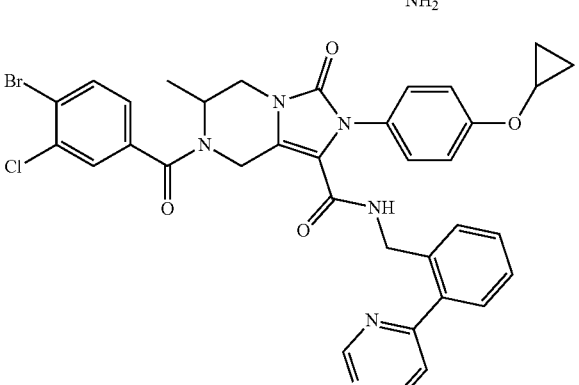 | 7-(4-bromo-3-chloro-benzoyl)-2-[4-(cyclopropoxy)phenyl]-6-methyl-3-oxo-N-[(2-pyrimidin-4-ylphenyl)methyl]-6,8-dihydro-5H-imidazo[1,5-a]pyrazine-1-carboxamide | 715.25 | (400 MHz, CDCl$_3$) δ 8.89-8.72 (m, 2H), 7.71 (d, J = 8.2 Hz, 1H), 7.60-7.40 (m, 6H), 7.22-7.08 (m, 3H), 6.90-6.75 (m, 3H), 6.29-4.88 (m, 2H), 4.75-4.55 (m, 1H), 4.50-4.30 (m, 2H), 3.84 (d, J = 12.7 Hz, 1H), 3.78-3.64 (m, 1H), 3.59-3.40 (m, 1H), 1.39 (d, J = 6.9 Hz, 3H), 0.80-0.68 (m, 2H), 0.61-0.50 (m, 2H) |

TABLE A-continued

| Cmpd | Structure | Name | LCMS [M + H]+ | 1H NMR |
|------|-----------|------|---------------|--------|
| 10 | 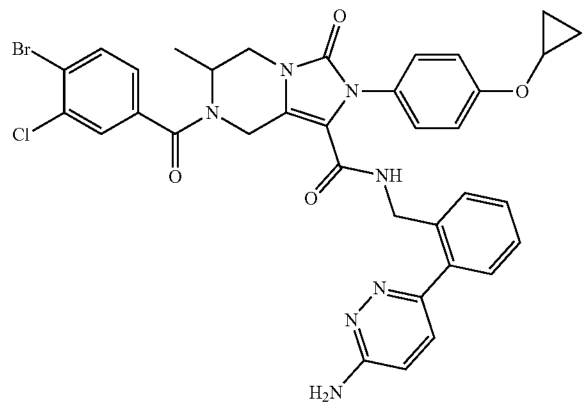 [SMILES: CC1Cn2c(c(C(=O)NCc3ccccc3-c3ccc(N)nn3)n(-c3ccc(OC4CC4)cc3)c2=O)CN1C(=O)c1ccc(Br)c(Cl)c1] | N-[[2-(6-amino-pyridazin-3-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | 730.2 | (300 MHz, CDCl$_3$) δ 7.67 (d, J = 8.2 Hz, 1H), 7.58 (d, J = 2.0 Hz, 1H), 7.46-7.30 (m, 5H), 7.23-7.08 (m, 3H), 6.90 (q, J = 9.3, 8.1 Hz, 2H), 6.76 (d, J = 8.8 Hz, 2H), 5.60-4.88 (m, 4H), 4.63 (d, J = 18.6 Hz, 1H), 4.33 (d, J = 5.9 Hz, 2H), 3.87 (d, J = 12.8 Hz, 1H), 3.71 (dd, J = 13.0, 4.4 Hz, 1H), 3.53 (tt, J = 6.2, 2.9 Hz, 1H), 1.40 (d, J = 7.0 Hz, 3H), 0.79-0.52 (m, 4H) |
| 11 | 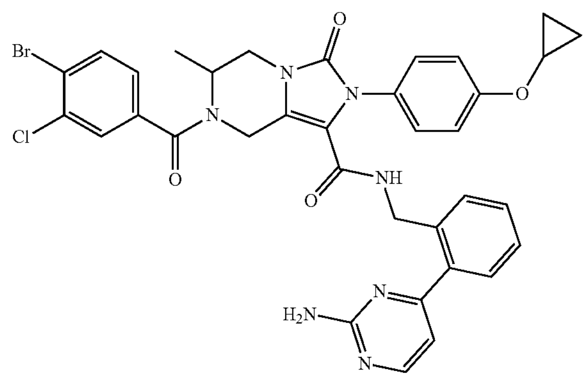 [SMILES: CC1Cn2c(c(C(=O)NCc3ccccc3-c3ccnc(N)n3)n(-c3ccc(OC4CC4)cc3)c2=O)CN1C(=O)c1ccc(Br)c(Cl)c1] | N-[[2-(2-amino-pyrimidin-4-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | 730.1 | (300 MHz, CDCl$_3$) δ 8.32 (s, 1H), 7.74 (d, J = 8.4 Hz 1H), 7.60 (d, J = 1.8 Hz 1H), 7.50-7.31 (m, 4H), 7.29-7.20 (m, 1H), 7.10 (t, J = 4.3 Hz 2H), 6.77 (t, J = 4.5 Hz 3H), 6.31 (t, J = 5.7 Hz 1H), 5.70-5.10 (m, 1H), 4.90 (s, 2H), 4.75-4.32 (m, 3H), 3.86 (d, J = 12.9 Hz 1H), 3.80-3.62 (m, 1H), 3.59-3.46 (m, 1H), 1.42 (d, J = 7.2 Hz 3H), 0.80-0.54 (m, 4H). |
| 12 | 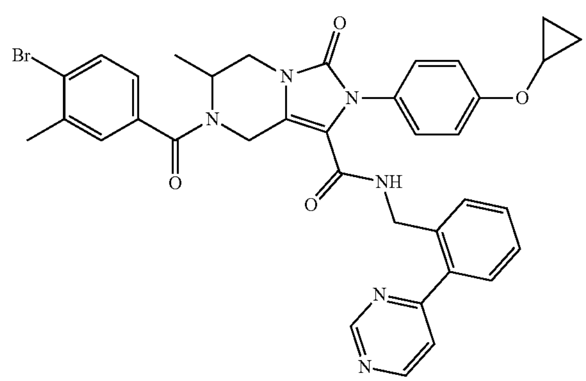 [SMILES: Cc1cc(C(=O)N2Cc3c(C(=O)NCc4ccccc4-c4ccncn4)n(-c4ccc(OC5CC5)cc4)c(=O)n3CC2C)ccc1Br] | 7-(4-bromo-3-methyl-benzoyl)-2-[4-(cyclopropoxy)phenyl]-6-methyl-3-oxo-N-[(2-pyrimidin-4-ylphenyl)methyl]-6,8-dihydro-5H-imidazo[1,5-a]pyrazine-1-carboxamide | 695.15 | (400 MHz, CDCl$_3$) δ 8.77 (t, J = 11.1 Hz 2H), 7.60 (d, J = 8.1 Hz 1H), 7.59-7.40 (m, 5H), 7.34 (d, J = 1.4 Hz 1H), 7.20-7.10 (m, 3H), 6.90-6.70 (m, 3H), 6.20-4.80 (m, 2H), 4.60 (d, J = 17.5 Hz, 1H), 4.45-4.21 (m, 2H), 3.83 (d, J = 12.6 Hz 1H), 3.69 (t, J = 6.5 Hz 1H), 3.60-3.40 (m, 1H), 2.44 (s, 3H), 1.38 (d, J = 6.8 Hz 3H), 0.80-0.50 (m, 4H). |
| 13 | 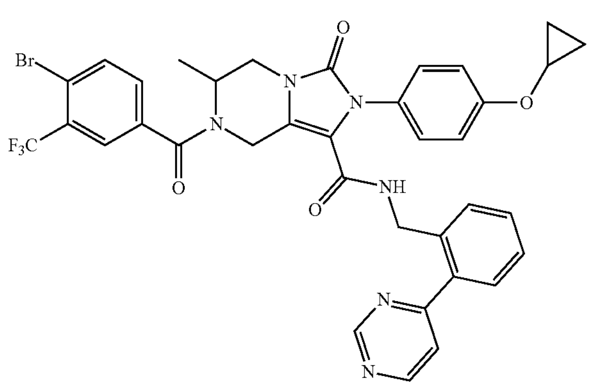 [SMILES: CC1Cn2c(c(C(=O)NCc3ccccc3-c3ccncn3)n(-c3ccc(OC4CC4)cc3)c2=O)CN1C(=O)c1ccc(Br)c(C(F)(F)F)c1] | 7-[4-bromo-3-(trifluoromethyl)benzoyl]-2-[4-(cyclopropoxy)phenyl]-6-methyl-3-oxo-N-[(2-pyrimidin-4-ylphenyl)methyl]-6,8-dihydro-5H-imidazo[1,5-a]pyrazine-1-carboxamide | 748.95 | (300 MHz, CDCl$_3$) δ 8.77 (t, J = 6.0 Hz 2H), 7.82 (d, J = 7.8 Hz 2H), 7.60-7.40 (m, 6H), 7.12 (d, J = 8.7 Hz 2H), 6.87 (t, J = 6.0 Hz 1H), 6.78 (d, J = 9.0 Hz 2H), 5.74-4.80 (m, 2H), 4.65 (d, J = 18.9 Hz 1H), 4.60-4.26 (m, 2H), 3.86 (d, J = 12.9 Hz 1H), 3.78-3.68 (m, 1H), 3.52-3.40 (m, 1H), 1.41 (d, J = 6.9 Hz 3H), 0.76-0.66 (m, 2H), 0.62-0.50 (m, 2H) |

TABLE A-continued

| Cmpd | Structure | Name | LCMS [M + H]+ | 1H NMR |
|---|---|---|---|---|
| 14a | 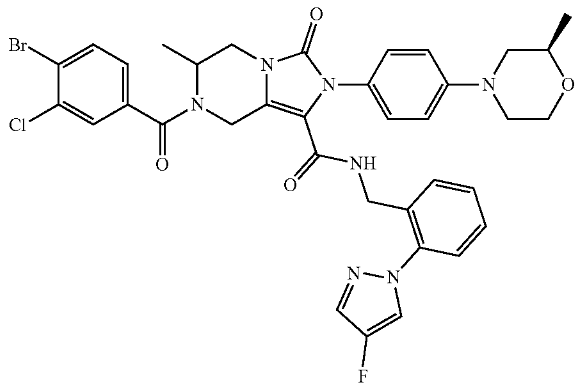 [SMILES: CC1Cn2c(c(C(=O)NCc3ccccc3-n3cc(F)cn3)n(-c3ccc(N4CCO[C@H](C)C4)cc3)c2=O)CN1C(=O)c1ccc(Br)c(Cl)c1] | (6R*)-7-(4-bromo-3-chloro-benzoyl)-N-[[2-(4-fluoropyrazol-1-yl)phenyl]methyl]-6-methyl-2-[4-[(2R)-2-methyl-morpholin-4-yl]phenyl]-3-oxo-6,8-dihydro-5H-imidazo[1,5-a]pyrazine-1-carboxamide | 764.3 | (300 MHz, CDCl$_3$) δ 7.72 (d, J = 8.2 Hz, 1H), 7.59 (d, J = 2.0 Hz, 1H), 7.56-7.45 (m, 2H), 7.42-7.33 (m, 2H), 7.30 (s, 1H), 7.25 C 7.11 (m, 4H), 6.82 (d, J = 8.9 Hz, 2H), 6.40 (d, J = 6.6 Hz, 1H), 5.37 (s, 1H), 4.61 (d, J = 19.0 Hz, 1H), 4.25 (d, J = 6.2 Hz, 2H), 4.05 (dd, J = 11.7, 2.6 Hz, 1H), 3.93-3.57 (m, 4H), 3.49-3.25 (m, 2H), 2.80 (td, J = 11.8, 3.4 Hz, 1H), 2.53-2.34 (m, 1H), 1.40 (d, J = 7.0 Hz, 3H), 1.29 (d, J = 6.2 Hz, 3H) |
| 14b | | (6S*)-7-(4-bromo-3-chloro-benzoyl)-N-[[2-(4-fluoropyrazol-1-yl)phenyl]methyl]-6-methyl-2-[4-[(2R)-2-methyl-morpholin-4-yl]phenyl]-3-oxo-6,8-dihydro-5H-imidazo[1,5-a]pyrazine-1-carboxamide | 764.1 | (300 MHz, CDCl$_3$) δ 7.72 (d, J = 8.2 Hz, 1H), 7.58 (d, J = 1.9 Hz, 1H), 7.55-7.45 (m, 2H), 7.42-7.31 (m, 2H), 7.30 (s, 1H), 7.25-7.12 (m, 4H), 6.82 (d, J = 8.9 Hz, 2H), 6.41 (t, J = 6.2 Hz, 1H), 5.37 (s, 1H), 4.61 (d, J = 19.1 Hz, 1H), 4.25 (d, J = 6.2 Hz, 2H), 4.05 (dd, J = 11.2, 3.0 Hz, 1H), 3.96-3.58 (m, 4H), 3.58-3.29 (m, 2H), 2.80 (td, J = 11.8, 3.5 Hz, 1H), 2.45 (dd, J = 11.7, 10.4 Hz, 1H), 1.40 (d, J = 7.0 Hz, 3H), 1.28 (d, J = 6.2 Hz, 3H) |
| 15a | 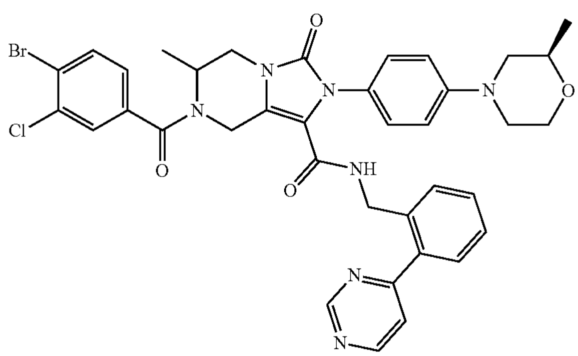 [SMILES: CC1Cn2c(c(C(=O)NCc3ccccc3-c3ccncn3)n(-c3ccc(N4CCO[C@H](C)C4)cc3)c2=O)CN1C(=O)c1ccc(Br)c(Cl)c1] | (6R*)-7-(4-bromo-3-chloro-benzoyl)-6-methyl-2-[4-[(2R)-2-methyl-morpholin-4-yl]phenyl]-3-oxo-N-[(2-pyrimidin-4-ylphenyl)methyl]-6,8-dihydro-5H-imidazo[1,5-a]pyrazine-1-carboxamide | 758.25 | (300 MHz, , CDCl$_3$) δ 8.84 (s, 1H), 8.77 (d, J = 5.3 Hz, 1H), 7.73 (d, J = 8.2 Hz, 1H), 7.62-7.43 (m, 6H), 7.22 (dd, J = 8.2, 2.0 Hz, 1H), 7.11 (d, J = 8.9 Hz, 2H), 6.89 (t, J = 6.2 Hz, 1H), 6.60 (d, J = 8.8 Hz, 2H), 4.65 (d, J = 19.0 Hz, 1H), 5.82-4.89 (s, 2H), 4.53-4.22 (m, 2H), 4.10-3.79 (m, 2H), 3.67 (td, J = 16.1, 15.3, 6.4 Hz, 3H), 3.19 (t, J = 13.3 Hz, 2H), 2.55 (td, J = 11.8, 3.5 Hz, 1H), 2.28-2.12 (m, 1H), 1.41 (d, J = 7.0 Hz, 3H), 1.24 (d, J = 6.2 Hz, 3H) |
| 15b | | (6S*)-7-(4-bromo-3-chloro-benzoyl)-6-methyl-2-[4-[(2R)-2-methyl-morpholin-4-yl]phenyl]-3-oxo-N-[(2-pyrimidin-4-ylphenyl)methyl]-6,8-dihydro-5H-imidazo[1,5-a]pyrazine-1-carboxamide | 758.25 | (300 MHz, , CDCl$_3$) δ 8.84 (s, 1H), 8.77 (d, J = 5.3 Hz, 1H), 7.73 (d, J = 8.2 Hz, 1H), 7.62-7.40 (m, 6H), 7.22 (dd, J = 8.2, 2.0 Hz, 1H), 7.11 (d, J = 8.8 Hz, 2H), 6.89 (t, J = 6.2 Hz, 1H), 6.61 (d, J = 8.7 Hz, 2H), 4.65 (d, J = 18.9 Hz, 1H), 5.57-5.12 (s, 2H), 4.49-4.27 (m, 2H), 4.01-3.93 (m, 1H), 3.87 (d, J = 12.8 Hz, 1H), 3.68 (t, J = 11.4 Hz, 3H), 3.27-3.12 (m, 2H), 2.64-2.50 (m, 1H), 2.25-2.14 (m, 1H), 1.41 (d, J = 7.0 Hz, 3H), 1.23 (d, J = 6.2 Hz, 3H) |

TABLE A-continued

| Cmpd | Structure | Name | LCMS [M + H]+ | 1H NMR |
|---|---|---|---|---|
| 16 | 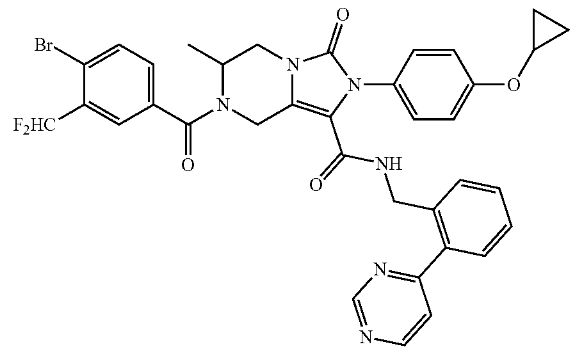 [SMILES: CC1Cn2c(c(C(=O)NCc3ccccc3-c3ccncn3)n(-c3ccc(OC4CC4)cc3)c2=O)CN1C(=O)c1ccc(Br)c(C(F)F)c1] | 7-[4-bromo-3-(difluoro-methyl)benzoyl]-2-[4-(cyclo-propoxy)phenyl]-6-methyl-3-oxo-N-[(2-pyrimidin-4-ylphenyl)methyl]-6,8-dihydro-5H-imidazo[1,5-a]pyrazine-1-carboxamide | 730.95 | (400 MHz, , CDCl$_3$) δ 8.77 (t, J = 11.2 Hz 2H), 7.73 (t, J = 12.2 Hz 2H), 7.60-7.40 (m, 6H), 7.13 (d, J = 8.8 Hz 2H), 7.09-6.74 (m, 4H), 6.20-4.76 (m, 2H), 4.64 (d, J = 19.6 Hz 1H), 4.50-4.26 (m, 2H), 3.85 (d, J = 12.5 Hz 1H), 3.70 (t, J = 6.5 Hz 1H), 3.58-3.40 (m, 1H), 1.40 (d, J = 6.9 Hz 3H), 0.80-0.68 (m, 2H), 0.64-0.55 (m, 2H) |
| 17 | 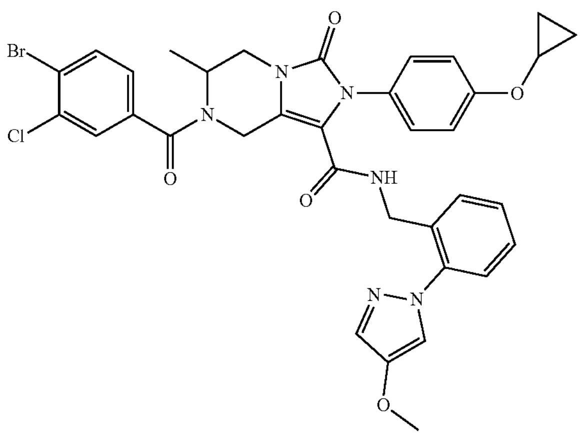 [SMILES: COc1cnn(-c2ccccc2CNC(=O)c2c3n(c(=O)n2-c2ccc(OC4CC4)cc2)CC(C)N(C(=O)c2ccc(Br)c(Cl)c2)C3)c1] | 7-(4-bromo-3-chloro-benzoyl)-2-[4-(cyclo-propoxy)phenyl]-N-[[2-(4-methoxy-pyrazol-1-yl)phenyl]methyl]-6-methyl-3-oxo-6,8-dihydro-5H-imidazo[1,5-a]pyrazine-1-carboxamide | 733.15 | (400 MHz, , CDCl$_3$) δ 7.69 (d, J = 8.2 Hz 1H), 7.56 (d, J = 1.9 Hz 1H), 7.48 (d, J = 6.5 Hz 1H), 7.38-7.29 (m, 3H), 7.24-7.16 (m, 4H), 7.11 (s, 1H), 6.98 (t, J = 6.0 Hz 2H), 6.62 (t, J = 6.0 Hz 1H), 5.95-4.88 (m, 2H), 4.59 (d, J = 18.6 Hz 1H), 4.23 (d, J = 5.8 Hz 2H), 3.90-3.74 (m, 4H), 3.72-3.52 (m, 2H), 1.38 (d, J = 6.9 Hz 3H), 0.85-0.60 (m, 4H) |
| 18 | 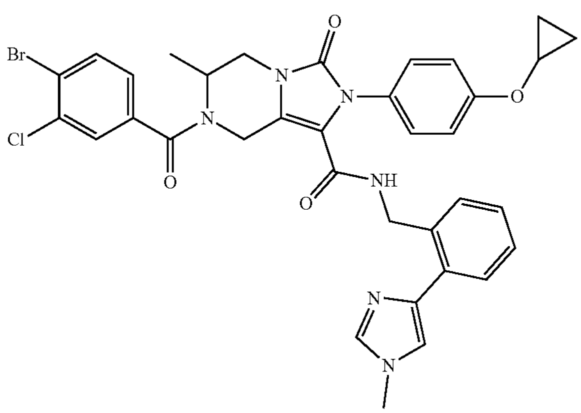 [SMILES: CC1Cn2c(c(C(=O)NCc3ccccc3-c3cn(C)cn3)n(-c3ccc(OC4CC4)cc3)c2=O)CN1C(=O)c1ccc(Br)c(Cl)c1] | 7-(4-bromo-3-chloro-benzoyl)-2-[4-(cyclo-propoxy)phenyl]-6-methyl-N-[[2-(1-methylimidazol-4-yl)phenyl]methyl]-3-oxo-6,8-dihydro-5H-imidazo[1,5-a]pyrazine-1-carboxamide | 717.1 | (300 MHz, , CDCl$_3$) δ 7.71 C 7.56 (m, 2H), 7.39 (dd, J = 7.0, 2.1 Hz, 2H), 7.31 (d, J = 1.6 Hz, 1H), 7.27 C 7.10 (m, 6H), 7.07 C 6.88 (m, 3H), 5.54 C 5.01 (m, 1H), 4.59 (d, J = 18.8 Hz, 1H), 4.41 (d, J = 6.1 Hz, 2H), 3.90 C 3.57 (m, 6H), 1.38 (d, J = 6.9 Hz, 3H), 0.84 C 0.65 (m, 4H) |

TABLE B

Conditions used for the chiral separation of racemic mixtures

| Compound | Method Name | Method Description | Retention time |
|---|---|---|---|
| 4a | C1 | Column: CHIRALPAK IG, 2*25 cm, 5 μm, Mobile Phase A: Hex:DCM = 1:1 (0.5% 2M NH$_3$-MeOH)--HPLC, Mobile Phase B: EtOH--HPLC; Flow rate: 20 mL/min; Gradient: 20 B to 20 B in 30 min | RT1: 16.8 |
| 4b | | | RT2: 24.3 |

TABLE B-continued

Conditions used for the chiral separation of racemic mixtures

| Compound | Method Name | Method Description | Retention time |
|---|---|---|---|
| 6a<br>6b | C2 | Column: CHIRALPAK IE, 2*25 cm, 5 μm; Mobile Phase A: MTBE (0.5% 2M NH₃-MeOH)--HPLC, Mobile Phase B:EtOH--HPLC; Flow rate: 18 mL/min; Gradient: 50 B to 50 B in 18 min | RT1: 12.078<br>RT2: 15.939 |
| 7a<br>7b | C3 | Column: CHIRALPAK IA, 2*25 cm, 5 μm; Mobile Phase A: Hex:DCM = 3.1 (0.5% 2M NH₃-MeOH)--HPLC, Mobile Phase B: EtOH--HPLC; Flow rate: 18 mL/min; Gradient: 10 B to 10 B in 15 min | RT1: 10.156<br>RT2: 12.623 |
| 8a<br>8b | C4 | Column: CHIRALPAK ID, 3*25 cm, 5 μm; Mobile Phase A: Hex:DCM = 1.1 (0.5% 2M NH₃-MeOH)--HPLC, Mobile Phase B: EtOH--HPLC; Flow rate: 35 mL/min; Gradient: 50 B to 50 B in 14 min | RT1: 9.8<br>RT2: 12.2 |
| 9a<br>9b | C5 | Column: CHIRALPAK ID, 2*25 cm, 5 μm; Mobile Phase A: Hex:DCM = 3:1 (0.5% 2M NH₃-MeOH)--HPLC, Mobile Phase B: EtOH; Flow rate: 18 mL/min; Gradient: 50 B to 50 B in 15 min | |
| 10a<br>10b | C6 | Column: CHIRALPAK IF, 5*25 cm, 5 μm; Mobile Phase A: MTBE (0.5% 2M NH₃-MeOH)--HPLC, Mobile Phase B: EtOH--HPLC; Flow rate: 15 mL/min; Gradient: 25 B to 25 B in 44 min | RT1: 18.568<br>RT2: 25.367; |
| 11a<br>11b | C7 | Column: CHIRAL ART Cellulose-SB, 2*25 cm, 5 μm; Mobile Phase A: MTBE (0.5% 2M NH₃-MeOH)--HPLC, Mobile Phase B: MeOH--HPLC; Flow rate: 20 mL/min; Gradient: 50 B to 50 B in 10 min | RT1: 7.116<br>RT2: 8.048; |
| 12a<br>12b | C8 | Column: CHIRALPAK IA, 2*25 cm, 5 μm; Mobile Phase A: MTBE (0.5% 2M NH₃-MeOH)--HPLC, Mobile Phase B: EtOH--HPLC; Flow rate: 18 mL/min; Gradient: 50 B to 50 B in 15 min | RT1: 10.941<br>RT2: 13.071 |
| 13a<br>13b | C9 | Column: CHIRALPAK IF, 2*25 cm, 5 μm; Mobile Phase A: MTBE (0.5% 2M NH₃-MeOH)--HPLC, Mobile Phase .B: EtOH--HPLC; Flow rate: 16 mL/mm; Gradient: 30 B to 30 B in 17 min | RT1: 11.516<br>RT2: 14.745 |
| 14a<br>14b | C10 | Column: CHIRALPAK ID, 3*25 cm, 5 μm; Mobile Phase A: Hex:DCM = 1.1 (0.5% 2M NH₃-MeOH)--HPLC, Mobile Phase B: EtOH--HPLC; Flow rate: 40 mL/min; Gradient: 50 B to 50 B in 16 min | RT1: 9.5<br>RT2: 12.8 |
| 15a<br>15b | C11 | Column: CHIRALPAK ID, 3*25 cm, 5 μm; Mobile Phase A: Hex:DCM = 1.1 (0.5% 2M NH₃-MeOH)--HPLC, Mobile Phase B: EtOH--HPLC; Flow rate: 29 mL/min; Gradient: 50 B to 50 B in 25 min | RT1: 16.093<br>RT2: 21.392 |
| 16a<br>16b | C12 | Column: CHIRALPAK ID, 2*25 cm, 5 μm; Mobile Phase A: MTBE (0.5% 2M NH₃-MeOH)--HPLC, Mobile Phase B: EtOH--HPLC; Flow rate: 14 mL/mm; Gradient: 50 B to 50 B in 21 min | RT1: 13.89<br>RT2: 19.413 |
| 17a<br>17b | C13 | Column: CHIRALPAK ID, 2*25 cm, 5 μm; Mobile Phase A: Hex:DCM = 1.1 (0.5% 2M NH₃-MeOH)--HPLC, Mobile Phase B: EtOH--HPLC; Flow rate: 17 mL/min; Gradient: 50 B to 50 B in 14 min | RT1: 7.634<br>RT2: 10.997 |
| 18a<br>18b | C14 | Column: CHIRALPAK IF, 2*25 cm, 5 μm; Mobile Phase A: MTBE (0.5% 2M NH₃-MeOH)--HPLC, Mobile Phase B: EtOH--HPLC; Flow rate: 20 mL/min; Gradient: 40 B to 40 B in 20 min | RT1: 14.095<br>RT2: 18.279 |

Example 17

Compounds 19-54, 56-70, 72, 74-84, 86-90, 92 and 94-129 provided in Tables C and D were synthetized using the intermediates and/or protocols of Examples 1-16, using methods and conditions known to those skilled in the art. Enantiomers were obtained from racemic mixtures by preparative chiral HPLC or SFC using conditions provided in Table C. Enantiomer (a) is the first eluting enantiomer, enantiomer (b) is the second eluting compound. The chiral centers referred to as rac-(R) or rac-(S) in the compound name have been chosen arbitrarily.

TABLE C

| Compound | Name | ¹H NMR | [M + H]⁺ | Separation Method |
|---|---|---|---|---|
| 114 | N-benzyl-7-(4-bromo-3-chloro-benzoyl)-2-[4-(2-hydroxy-2-methyl-propoxy)phenyl]-3-oxo-6,8-dihydro-5H-imidazo[1,5-a]pyrazine-1-carboxamide | (DMSO-$d_6$, 600 MHz, 80° C.) δ 1.25 (s, 6H), 3.68-3.70 (m, 2H), 3.76 (s, 2H), 3.84 (br s, 2H), 4.26 (d, J = 5.4 Hz, 2H), 4.37 (s, 1H), 4.86 (s, 2H), 6.97 (d, J = 8.4 Hz, 2H), 7.04 (d, J = 6.6 Hz, 2H), 7.19 (d, J = 9.0 Hz, 2H), 7.20-7.26 (m, 4H), 7.40 (dd, J = 7.8, 1.8 Hz, 1H), 7.75 (d, J = 1.8 Hz, 1H), 7.86 (d, J = 7.8 Hz, 1H). | 655 | NA |
| 115a | N-benzyl-7-(4-bromo-3-chloro-benzoyl)-3-oxo-2-[4-[rac-(3S)-3-hydroxy-3-methyl-pyrrolidin-1-yl]phenyl]-6,8-dihydro-5H-imidazo[1,5-a]pyrazine-1-carboxamide | (DMSO $d_6$, 600 MHz, 80° C.) δ 1.40 (s, 3H), 1.91-1.96 (m, 1H), 1.99-2.03 (m, 1H), 2.20 (dd, J = 13.2, 9.6 Hz, 2H), 3.30 (td, J = 8.4, 3.6 Hz, 1H), 3.41 (dd, J = 16.2, 8.4 Hz, 1H), 3.67-3.69 (m, 2H), 3.84 (br s, 2H), 4.23 (d, J = 4.8 Hz, 2H) 4.60 (s, 1H), 4.87 (s, 2H), 6.48 (d, J = 9.0 Hz, 2H), 6.70 (br s, 1H), 6.99 (d, J = 6.6 Hz, 2H), 7.07 (d, J = 9.0 Hz, 2H), 7.19-7.24 (m, 3H), 7.40 (dd, J = 8.4, 1.8 Hz, 1H), 7.75 (d, J = 1.8 Hz, 1H), 7.86 (d, J = 8.4 Hz, 1H). | 665 | SFC column: chiral ART 21.2 mm × 250 mm, 5 μm; isochratic conditions 50; 50 EtOH:$CO_2$, 40° C., 50 mL/min, 100 bar, Wave Length: 210 nm |
| 115b | N-benzyl-7-(4-bromo-3-chloro-benzoyl)-3-oxo-2-[4-[rac-(3R)-3-hydroxy-3-methyl-pyrrolidin-1-yl]phenyl]-6,8-dihydro-5H-imidazo[1,5-a]pyrazine-1-carboxamide | (DMSO-$d_6$, 600 MHz, 80° C.) δ 1.40 (s, 3H), 1.91-1.96 (m, 1H), 1.99-2.03 (m, 1H), 2.20 (dd, J = 13.2, 9.6 Hz, 2H), 3.30 (td, J = 8.4, 3.6 Hz, 1H), 3.41 (dd, J = 16.2, 8.4 Hz, 1H), 3.67-3.69 (m, 2H), 3.84 (br s, 2H), 4.23 (d, J = 4.8 Hz, 2H) 4.60 (s, 1H), 4.87 (s, 2H), 6.48 (d, J = 9.0 Hz, 2H), 6.70 (br s, 1H), 6.99 (d, J = 6.6 Hz, 2H), 7.07 (d, J = 9.0 Hz, 2H), 7.19-7.24 (m, 3H), 7.40 (dd, J = 8.4, 1.8 Hz, 1H), 7.75 (d, J = 1.8 Hz, 1H), 7.86 (d, J = 8.4 Hz, 1H). | 665 | SFC column: chiral ART 21.2 mm × 250 mm, 5 μm; isochratic conditions 50; 50 EtOH:$CO_2$, 40° C., 50 mL/min, 100 bar, Wave Length: 210 nm |
| 19a | rac-(6R)-N-[[2-(4-aminopyrazol-1-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl3) δ 7.69 (d, J = 4.0 Hz, 1H), 7.57 (d, J = 2.0 Hz, 1H), 7.46 (d, J = 4.0 Hz, 1H), 7.34-7.28 (m, 2H), 7.25-7.14 (m, 4H), 7.13(d, J = 2.0 Hz, 1H) 7.04 (s, 1H), 6.96 (d, J = 4.0 Hz, 2H), 6.69 (s, 1H), 5.31 (s, 2H), 4.58 (d, J = 8.0 Hz, 1H), 4.23 (d, J = 4.0 Hz, 2H), 3.85-3.82 (m, 1H), 3.68-3.63 (m, 2H), 3.01 (s, 2H), 1.38 (d, J = 4.0 Hz, 3H), 0.80-0.69 (m, 4H). | 716 | Column: CHIRALPAK IF, 2*25 cm, 5 μm; Mobile Phase A: MTBE(0.5% 2M $NH_3$-MeOH)--HPLC, Mobile Phase B: EtOH--HPLC; Flow rate: 12 mL/min; Gradient: 60% B to 60% B in 25 min; Wave Length: 220/254 nm |
| 19b | rac-(6S)-N-[[2-(4-aminopyrazol-1-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl3) δ 7.69 (d, J = 4.0 Hz, 1H), 7.57 (d, J = 2.0 Hz, 1H), 7.46 (d, J = 4.0 Hz, 1H), 7.34-7.28 (m, 2H), 7.25-7.14 (m, 4H), 7.13(d, J = 2.0 Hz, 1H) 7.04 (s, 1H), 6.96 (d, J = 4.0 Hz, 2H), 6.69 (s, 1H), 5.31 (s, 2H), 4.58 (d, J = 8.0 Hz, 1H), 4.23 (d, J = 4.0 Hz, 2H), 3.85-3.82 (m, 1H), 3.68-3.63 (m, 2H), 3.01 (s, 2H), 1.38 (d, J = 4.0 Hz, 3H), 0.80-0.69 (m, 4H). | 716 | Column: CHIRALPAK IF, 2*25 cm, 5 μm; Mobile Phase A: MTBE(0.5% 2M $NH_3$-MeOH)--HPLC, Mobile Phase B: EtOH--HPLC; Flow rate: 12 mL/min; Gradient: 60% B to 60% B in 25 min; Wave Length: 220/254 nm |
| 116 | N-benzyl-7-(4-bromo-3-chloro-benzoyl)-3-oxo-2-[4-[(3R)-3,4-dimethylpiperazin-1-yl]phenyl]-6,8-dihydro-5H-imidazo[1,5-a]pyrazine-1-carboxamide | (DMSO-$d_6$, 600 MHz, 80° C.) δ 1.07 (d, J = 6.2 Hz, 3H), 2.15-2.21 (m, 1H), 2.24 (s, 3H), 2.25-2.31 (m, 1H), 2.43-2.48 (m, 1H), 2.79-2.87 (m, 2H), 3.45-3.56 (m, 2H), 3.65-3.70 (m, 2H), 3.83 (br. s, 2H), 4.21-4.28 (m, 2H), 4.86 (s, 2H), 6.91 (d, J = 9.0 Hz, 2H), 6.94 (br. s, 1H), 7.01 (d, J = 6.6 Hz, 2H), 7.11 (d, J = 9.0 Hz, 2H), 7.18-7.27 (m, 3H), 7.39 (dd, J = 8.2 Hz, 1.8 Hz, 1H), 7.74 (d, J = 1.8 Hz, 1H), 7.85 (d, J = 8.3 Hz, 1H). | 677 | NA |
| 117 | N-benzyl-7-(4-bromo-3-chloro-benzoyl)-2-[4-(3-hydroxy-3-methyl-azetidin-1-yl)phenyl]-3-oxo-6,8-dihydro-5H-imidazo[1,5-a]pyrazine-1-carboxamide | (DMSO-$d_6$, 600 MHz, 80° C.) δ 1.48 (s, 3H), 3.64-3.69 (m, 4H), 3.76 (d, J = 7.4 Hz, 2H), 3.83 (br. s., 2H), 4.23 (d, J = 5.9 Hz, 2H), 4.85 (br. s., 2H), 5.30 (s, 1H), 6.42 (d, J = 8.4 Hz, 2H), 6.87 (br. s, 1H), 7.02 (d, J = 6.9 Hz, 2H), 7.06 (d, J = 7.9 Hz, 2H), 7.18-7.27 (m, 3H), 7.39 (dd, J = 8.0 Hz, 2.0 Hz, 1H), 7.74 (d, J = 1.7 Hz, 1H), 7.85 (d, J = 8.4 Hz, 1H). | 650 | NA |

TABLE C-continued

| Compound | Name | $^1$H NMR | [M + H]$^+$ | Separation Method |
|---|---|---|---|---|
| 118 | N-benzyl-7-(4-bromo-3-chloro-benzoyl)-2-[4-[3-hydroxy-3-(trifluoromethyl)azetidin-1-yl]phenyl]-3-oxo-6,8-dihydro-5H-imidazo[1,5-a]pyrazine-1-carboxamide | (DMSO-d$_6$, 600 MHz, 80° C.) δ 3.63-3.71 (m, 2H), 3.83 (br. s, 2H), 3.86 (d, J = 9.0 Hz, 2H), 4.16 (d, J = 9.0 Hz, 2H), 4.24 (d, J = 5.5 Hz, 2H), 4.85 (s, 2H), 6.51 (d, J = 8.8 Hz, 2H), 6.92-7.07 (m, 3H), 7.11 (m, 3H), 7.18-7.29 (m, 3H), 7.39 (dd, J = 8.1 Hz, 1.8 Hz, 1H), 7.74 (d, J = 1.8 Hz, 1H), 7.85 (d, J = 8.2 Hz, 1H). | 704 | NA |
| 20a | rac-(6R)-7-(4-bromo-3-ethynyl-benzoyl)-2-[4-(cyclopropoxy)phenyl]-6-methyl-3-oxo-N-[(2-pyrimidin-4-ylphenyl)methyl]-6,8-dihydro-5H-imidazo[1,5-a]pyrazine-1-carboxamide | (300 MHz, CDCl3) δ 8.77 (t, J = 8.1 Hz 2H), 7.75-7.60 (m, 2H), 7.58-7.40 (m, 5H),7.29 (d, J = 2.1 Hz 1H), 7.13 (d, J = 8.7 Hz 2H), 6.90-6.70 (m, 3H), 5.80-4.70 (m, 2H), 4.60 (d, J = 17.4 Hz 1H), 4.48-4.24 (m, 2H), 3.84 (d, J = 12.3 Hz 1H), 3.76-3.60 (m, 1H), 3.50-3.30 (m, 2H), 1.38 (t, J = 12.4 Hz 3H), 0.80-0.50 (m, 4H). | 703 | Column: CHIRALPAK ID, 2*25 cm, 5 μm; Mobile Phase A: Hex: DCM = 1: 1(0.5% 2M NH$_3$-MeOH)--HPLC, Mobile Phase B: EtOH--HPLC; Flow rate: 16 mL/min; Gradient: 50% B to 50% B in 15 min; Wave Length: 220/254 nm |
| 20b | rac-(6S)-7-(4-bromo-3-ethynyl-benzoyl)-2-[4-(cyclopropoxy)phenyl]-6-methyl-3-oxo-N-[(2-pyrimidin-4-ylphenyl)methyl]-6,8-dihydro-5H-imidazo[1,5-a]pyrazine-1-carboxamide | (300 MHz, CDCl3) δ 8.77 (t, J = 8.1 Hz 2H), 7.70-7.60 (m, 2H), 7.60-7.40 (m, 5H), 7.29 (d, J = 2.1 Hz 1H), 7.13 (d, J = 9.0 Hz 2H), 6.95-6.70 (m, 3H), 5.90-4.70 (m, 2H), 4.60 (d, J = 19.8 Hz 1H), 4.48-4.24 (m, 2H), 3.84 (d, J = 12.9 Hz 1H), 3.75-3.60 (m, 1H), 3.50-3.35 (m, 2H), 1.38 (t, J = 6.9 Hz 3H), 0.78-0.50 (m, 4H). | 703 | Column: CHIRALPAK ID, 2*25 cm, 5 μm; Mobile Phase A: Hex: DCM=1: 1(0.5% 2M NH$_3$-MeOH)--HPLC, Mobile Phase B: EtOH--HPLC; Flow rate: 16 mL/min; Gradient: 50% B to 50% B in 15 min; Wave Length: 220/254 nm |
| 119 | N-benzyl-7-(4-bromo-3-chloro-benzoyl)-2-[4-(2,2-difluoromorpholin-4-yl)phenyl]-3-oxo-6,8-dihydro-5H-imidazo[1,5-a]pyrazine-1-carboxamide | (DMSO-d$_6$, 600 MHz, 80° C.) δ 3.37-3.39 (m, 2H), 3.62 (t, J = 8.4 Hz, 2H), 3.68-3.70 (m, 2H), 3.84 (br s, 2H), 4.20-4.22 (m, 2H), 4.25 (d, J = 5.4 Hz, 2H), 4.86 (s, 2H), 7.00 (d, J = 9.0 Hz, 2H), 7.03-7.06 (m, 2H), 7.16 (br s, 1 H), 7.17 (d, J = 9.0 Hz, 2H), 7.20-7.26 (m, 3H), 7.40 (dd, J = 7.8, 1.8 Hz, 1H), 7.7 | 688 | NA |
| 120 | N-benzyl-7-(4-bromo-3-chloro-benzoyl)-2-[4-(4-oxa-7-azaspiro[2.5]octan-7-yl)phenyl]-3-oxo-6,8-dihydro-5H-imidazo[1,5-a]pyrazine-1-carboxamide | (DMSO-d$_6$, 600 MHz, 80° C.) δ 0.61-0.68 (m, 2H), 0.74-0.81 (m, 2H), 3.14 (s, 2H), 3.21-3.25 (m, 2H), 3.66-3.71 (m, 2H), 3.78-3.91 (m, 4H), 4.25 (d, J = 5.3 Hz, 2H), 4.86 (s, 2H), 6.92 (d, J = 9.0 Hz, 2H), 6.95-7.07 (m, 3H), 7.13 (d, J = 9.0 Hz, 2H), 7.19-7.28 (m, 3H), 7.40 (dd, J = 8.1 Hz, 1.8 Hz, 1H), 7.75 (d, J = 1.8 Hz, 1H), 7.86 (J = 8.1 Hz, 1H). | 676 | NA |
| 21a | rac-(6S)-7-(4-bromo-3-chloro-benzoyl)-6-methyl-2-[4-(4-methylpiperazin-1-yl)phenyl]-3-oxo-N-[(2-pyrimidin-2-ylphenyl)methyl]-6,8-dihydro-5H-imidazo[1,5-a]pyrazine-1-carboxamide | (DMSO-d$_6$, 600 MHz, 80° C.) δ 1.27 (d, J = 6.6 Hz, 3H), 2.80 (br s, 4H), 3.15 (br s, 4H), 3.67 (d, J = 3.3 Hz, 2H), 4.50 (d, J = 5.6 Hz, 2H), 4.52 (br s, 1H), 4.61 (br s, 1H), 5.22 (br s, 1H), 6.71 (d, J = 9.0 Hz, 2H), 6.98-7.02 (m, 3H), 7.27-7.31 (m, 1H), 7.37-7.43 (m, 4H), 7.73 (d, J= 1.9 Hz, 1H), 7.85 (d, J = 8.2 Hz, 1H), 7.98-8.01 (m, 1H), 8.78 (d, J = 4.8 Hz, 2H). | 757 | SFC column: Lux C3 21.2 mm × 250 mm, 5 μm; isochratic conditions 25:75 EtOH:CO$_2$ (0.2% v/v NH$_3$), 40° C., 50 mL/min, 125 bar, Wave Length: 210 nm |
| 21b | rac-(6R)-7-(4-bromo-3-chloro-benzoyl)-6-methyl-2-[4-(4-methylpiperazin-1-yl)phenyl]-3-oxo-N-[(2-pyrimidin-2-ylphenyl)methyl]-6,8-dihydro-5H-imidazo[1,5-a]pyrazine-1-carboxamide | (DMSO-d$_6$, 600 MHz, 80° C.) δ 1.27 (d, J = 6.6 Hz, 3H), 2.82 (s, 3H), 2.50-2.53 (m, 4H), 3.04-3.08 (m, 4H), 3.67 (d, J = 3.3 Hz, 2H), 4.50 (d, J = 5.6 Hz, 2H), 4.52 (br s, 1H), 4.61 (br s, 1H), 5.22 (br s, 1H), 6.71 (d, J = 9.0 Hz, 2H), 6.98-7.02 (m, 3H), 7.27-7.31 (m, 1H), 7.37-7.43 (m, 4H), 7.73 (d, J = 1.9 Hz, 1H), 7.85 (d, J = 8.2 Hz, 1H), 7.98-8.01 (m, 1H), 8.78 (d, J = 4.8 Hz, 2H). | 757 | SFC column: Lux C3 21.2 mm × 250 mm, 5 μm; isochratic conditions 25:75 EtOH:CO$_2$ (0.2% v/v NH$_3$), 40° C., 50 mL/min, 125 bar, Wave Length: 210 nm |
| 121 | N-benzyl-7-(4-bromo-3-chloro-benzoyl)-2-[4-(8-oxa-3-azabicyclo[3.2.1]octan-3-yl)phenyl]-3-oxo-6,8-dihydro-5H-imidazo[1,5-a]pyrazine-1-carboxamide | (DMSO-d$_6$, 600 MHz, 80° C.) δ 1.81-1.92 (m, 4H), 2.86 (dd, J = 11.2 Hz, 2.9 Hz, 2H), 3.39 (d, J = 12.0 Hz, 2H), 3.67 (t, J = 5.9 Hz, 2H), 3.83 (s, 2H), 4.24 (d, J = 5.4 Hz, 2H), 4.45 (s, 2H), 4.85 (s, 2H), 6.83 (d, J = 9.8 Hz, 2H), 6.96 (s, 1H), 7.0 (d, J = 6.3 Hz, 2H), 7.1 (d, J = 8.9 Hz, 2H), 7.18-7.25 (m, 3H), 7.39 (dd, J = 8.0 Hz, 2.1 Hz, 1H), 7.74 (d, J = 1.9 Hz, 1H), 7.85 (d, J = 7.9 Hz, 1H). | 678 | NA |

TABLE C-continued

| Compound | Name | ¹H NMR | [M + H]⁺ | Separation Method |
|---|---|---|---|---|
| 22a | rac-(6R)-7-(4-bromo-3-chloro-benzoyl)-2-[4-(cyclopropoxy)phenyl]-6-methyl-N-[[2-(1-methylpyrazol-3-yl)phenyl]methyl]-3-oxo-6,8-dihydro-5H-imidazo[1,5-a]pyrazine-1-carboxamide | (400 MHz, DMSO-$d_6$) δ 7.87 (d, J = 4.0 Hz, 1H), 7.78-7.72 (m, 2H), 7.53-7.38 (m, 3H), 7.28-7.31 (m, 1H), 7.30-6.94 (m, 6H), 6.49 (s, 1H), 5.48 (s, 1H), 4.48 (d, J = 4.0 Hz, 4H), 3.84 (s, 3H), 3.78-3.75 (m, 1H), 3.65 (s, 2H), 1.24 (s, 3H), 0.78-0.75 (m, 2H), 0.64 (s, 2H). | 715 | Column: CHIRALPAK IF, 2*25 cm, 5 μm; Mobile Phase A: MTBE(0.5% 2M NH₃-MeOH)--HPLC, Mobile Phase B: EtOH--HPLC; Flow rate: 20 mL/min; Gradient: 20% B to 20% B in 21 min; Wave Length: 220/254 nm |
| 22b | rac-(6S)-7-(4-bromo-3-chloro-benzoyl)-2-[4-(cyclopropoxy)phenyl]-6-methyl-N-[[2-(1-methylpyrazol-3-yl)phenyl]methyl]-3-oxo-6,8-dihydro-5H-imidazo[1,5-a]pyrazine-1-carboxamide | (400 MHz, DMSO-$d_6$) δ 7.87 (d, J = 4.0 Hz, 1H), 7.78-7.72 (m, 2H), 7.53-7.38 (m, 3H), 7.28-7.31 (m, 1H), 7.30-6.94 (m, 6H), 6.49 (s, 1H), 5.48 (s, 1H), 4.48 (d, J = 4.0 Hz, 4H), 3.84 (s, 3H), 3.78-3.75 (m, 1H), 3.65 (s, 2H), 1.24 (s, 3H), 0.78-0.75 (m, 2H), 0.64 (s, 2H). | 715 | Column: CHIRALPAK IF, 2*25 cm, 5 μm; Mobile Phase A: MTBE(0.5% 2M NH₃-MeOH)--HPLC, Mobile Phase B: EtOH--HPLC; Flow rate: 20 mL/min; Gradient: 20% B to 20% B in 21 min; Wave Length: 220/254 nm |
| 23a | rac-(6R)-N-[[2-(6-amino-2-pyridyl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (300 MHz, CDCl₃) δ 7.70 (d, J = 8.1 Hz 1H), 7.60-7.50 (m, 2H), 7.50-7.30 (m, 3H), 7.24-7.04 (m, 4H), 6.90-6.76 (m, 2H), 6.70 (d, J = 7.5 Hz 1H), 6.60-6.35 (m, 2H), 5.62-4.82 (m, 2H), 4.80-4.55 (m, 1H), 4.50-4.30 (m, 2H), 4.00-3.70 (m, 1H), 3.67 (d, J = 4.2 Hz 1H), 3.53 (d, J = 3.0 Hz 1H), 1.40 (d, J = 6.9 Hz 3H), 0.80-0.50 (m, 4H). | 727 | Column: CHIRAL ART Cellulose-SC, 2*25 cm, 5 μm; Mobile Phase A: MTBE(0.5% 2M NH₃-MeOH)--HPLC, Mobile Phase B: EtOH--HPLC; Flow rate: 20 mL/min; Gradient: 50% B to 50% B in 18 min; Wave Length: 220/254 nm |
| 23b | rac-(6S)-N-[[2-(6-amino-2-pyridyl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (300 MHz, CDCl₃) δ 7.70 (t, J = 8.4 Hz 1H), 7.60-7.50 (m, 1H), 7.48 (t, J = 7.8 Hz 1H), 7.40-7.30 (m, 3H), 7.28-7.18 (m, 2H), 7.16-7.05 (m, 2H), 6.82-6.65 (m, 3H), 6.60-6.40 (m, 2H), 5.60-4.95 (m, 1H), 4.70-4.20 (m, 4H), 3.90-3.60 (m, 2H), 3.58-3.40 (m, 1H), 1.40 (d, J = 7.5 Hz, 3H), 0.75-0.55 (m, 4H). | 727 | Column: CHIRAL ART Cellulose-SC, 2*25 cm, 5 μm; Mobile Phase A: MTBE(0.5% 2M NH₃-MeOH)--HPLC, Mobile Phase B: EtOH--HPLC; Flow rate: 20 mL/min; Gradient: 50% B to 50% B in 18 min; Wave Length: 220/254 nm |
| 24a | rac-(6R)-7-(4-bromo-3-chloro-benzoyl)-2-[4-(cyclopropoxy)phenyl]-N-[(2-fluoro-6-pyrazol-1-yl-phenyl)methyl]-6-methyl-3-oxo-6,8-dihydro-5H-imidazo[1,5-a]pyrazine-1-carboxamide | (400 MHz, CDCl₃) δ 7.72 (d, J = 8.1 Hz, 1H), 7.68-7.56 (m, 2H), 7.46 (s, 1H), 7.37 (dt, J = 8.8, 6.4 Hz, 1H), 7.25-7.16 (m, 3H), 7.04 (d, J = 8.0 Hz, 1H), 6.87 (d, J = 8.4 Hz, 2H), 6.49 (t, J = 5.9 Hz, 1H), 6.42 (d, J = 2.1 Hz, 1H), 5.27 (s, 2H), 4.65 (d, J = 18.9 Hz, 1H), 4.44 (dd, J = 13.7, 6.2 Hz, 1H), 4.23 (d, J = 13.2 Hz, 1H), 3.87 (d, J = 12.8 Hz, 1H), 3.71 (d, J = 12.8 Hz, 1H), 3.57 (d, J = 6.1 Hz, 1H), 1.41 (d, J = 7.0 Hz, 3H), 0.73 (t, J = 6.0 Hz, 2H), 0.68-0.52 (m, 2H). | 719 | Column: CHIRALPAK ID, 2*25 cm, 5 μm; Mobile Phase A: Hex: DCM = 3: 1(0.5% 2M NH3-MeOH)--HPLC, Mobile Phase B: EtOH--HPLC; Flow rate: 20 mL/min; Gradient: 50% B to 50% B in 20 min; Wave Length: 254/220 nm |
| 24b | rac-(6S)-7-(4-bromo-3-chloro-benzoyl)-2-[4-(cyclopropoxy)phenyl]-N-[(2-fluoro-6-pyrazol-1-yl-phenyl)methyl]-6-methyl-3-oxo-6,8-dihydro-5H-imidazo[1,5-a]pyrazine-1-carboxamide | (400 MHz, CDCl₃) δ 7.72 (d, J = 8.1 Hz, 1H), 7.64 (d, J = 2.4 Hz, 1H), 7.59 (d, J = 2.0 Hz, 1H), 7.46 (s, 1H), 7.41-7.32 (m, 1H), 7.25-7.17 (m, 3H), 7.16-7.08 (m, 1H), 7.04 (d, J = 8.0 Hz, 1H), 6.87 (d, J = 8.8 Hz, 2H), 6.49 (t, J = 6.0 Hz, 1H), 6.42 (t, J = 2.2 Hz, 1H), 5.20 (s, 2H), 4.65 (d, J = 18.9 Hz, 1H), 4.44 (dd, J = 14.0, 6.3 Hz, 1H), 4.23 (dd, J = 13.7, 5.3 Hz, 1H), 3.87 (d, J = 12.9 Hz, 1H), 3.71 (d, J = 10.3 Hz, 1H), 3.60-3.52 (m, 1H), 1.41 (d, J = 7.0 Hz, 3H), 0.85-0.55 (m, 4H). | 719 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 20 min; Wave Length: 254/220 nm |
| 25a | rac-(6R)-7-[4-bromo-3-(trifluoromethyl)benzoyl]-2-[4-(cyclopropoxy)phenyl]-N-[(2-fluoro-6-pyrazol-1-yl-phenyl)methyl]-6-methyl-3-oxo-6,8-dihydro-5H-imidazo[1,5-a]pyrazine-1-carboxamide | (400 MHz, CDCl₃) δ 7.91-7.74 (m, 2H), 7.64 (s, 1H), 7.57-7.42 (m, 2H), 7.37 (td, J = 8.7, 8.2, 6.0 Hz, 1H), 7.24-7.15 (m, 2H), 7.12 (t, J = 8.6 Hz, 1H), 7.04 (d, J = 8.0 Hz, 1H), 6.87 (d, J = 8.3 Hz, 2H), 6.56-6.35 (m, 2H), 5.26 (s, 2H), 4.68 (d, J = 18.8 Hz, 1H), 4.43 (d, J = 14.7 Hz, 1H), 4.28-4.16 (m, 1H), 3.88 (d, J = 12.8 Hz, 1H), 3.73 (d, J = 12.0 Hz, 1H), 3.57 (d, J = 7.5 Hz, 1H), 1.43 (d, J = 7.0 Hz, 3H), 0.87-0.49 (m, 4H). | 753 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 25 min; Wave Length: 254/220 nm |

TABLE C-continued

| Compound | Name | ¹H NMR | [M + H]⁺ | Separation Method |
|---|---|---|---|---|
| 25b | rac-(6S)-7-[4-bromo-3-(trifluoromethyl)benzoyl]-2-[4-(cyclopropoxy)phenyl]-N-[(2-fluoro-6-pyrazol-1-yl-phenyl)methyl]-6-methyl-3-oxo-6,8-dihydro-5H-imidazo[1,5-a]pyrazine-1-carboxamide | (400 MHz, CDCl₃) δ 7.99-7.76 (m, 2H), 7.64 (d, J = 2.6 Hz, 1H), 7.55-7.42 (m, 2H), 7.36 (td, J = 8.2, 5.8 Hz, 1H), 7.18 (d, J = 2.0 Hz, 2H), 7.16-6.99 (m, 2H), 6.87 (d, J = 9.2 Hz, 2H), 6.50 (s, 1H), 6.47-6.38 (m, 1H), 5.29 (s, 2H), 4.68 (d, J = 18.7 Hz, 1H), 4.42 (s, 1H), 4.23 (d, J = 14.3 Hz, 1H), 3.88 (d, J = 12.6 Hz, 1H), 3.74 (s, 1H), 3.56 (dd, J = 7.5, 4.6 Hz, 1H), 1.43 (d, J = 6.6 Hz, 3H), 0.82-0.52 (m, 4H). | 753 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 25 min; Wave Length: 254/220 nm |
| 26a | rac-(6R)-7-(4-bromo-3-chloro-benzoyl)-2[4-(cyclopropoxy)phenyl]-6-methyl-N-[[2-[4-(methylamino)pyrimidin-2-yl]phenyl]methyl]-3-oxo-6,8-dihydro-5H-imidazo[1,5-a]pyrazine-1-carboxamide | (400 MHz, CDCl₃) δ 8.10-8.00 (m, 1H), 8.00-7.89 (m, 1H), 7.70 (d, J = 8.4 Hz, 1H), 7.57 (d, J = 2.1 Hz, 1H), 7.42-7.31 (m, 3H), 7.21-7.18 (m, 1H), 7.18-7.10 (m, 1H), 7.04 (d, J = 9.0 Hz, 2H), 6.72 (d, J = 9.0 Hz, 2H), 6.20 (d, J = 6.0 Hz, 1H), 5.55-5.25 (m, 1H), 5.18-4.89 (m, 1H), 4.75-4.23 (m, 3H), 3.83 (d, J = 12.6 Hz, 1H), 3.75-3.60 (m, 1H), 3.58-3.41 (m, 1H), 2.96 (d, J = 5.1 Hz, 3H), 1.38 (d, J = 6.9 Hz, 3H), 0.79-0.51 (m, 4H). | 742 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 13 min; Wave Length: 254/220 nm |
| 26b | (4rac-(6S)-7-(4-bromo-3-chloro-benzoyl)-2[4-(cyclopropoxy)phenyl]-6-methyl-N-[[2-[4-(methylamino)pyrimidin-2-yl]phenyl]methyl]-3-oxo-6,8-dihydro-5H-imidazo[1,5-a]pyrazine-1-carboxamide | (400 MHz, CDCl₃) δ 8.11-8.00 (m, 1H), 8.00-7.90 (m, 1H), 7.71 (d, J = 8.1 Hz, 1H), 7.57 (d, J = 1.8 Hz, 1H), 7.45-7.31 (m, 3H), 7.21-7.18 (m, 1H), 7.18-7.10 (m, 1H), 7.05 (d, J = 9.0 Hz, 2H), 6.72 (d, J = 8.7 Hz, 2H), 6.20 (d, J = 5.7 Hz, 1H), 5.50-5.18 (m, 1H), 5.12-4.91 (m, 1H), 4.72-4.30 (m, 3H), 3.83 (d, J = 12.6 Hz, 1H), 3.76-3.60 (m, 1H), 3.59-3.43 (m, 1H), 2.96 (d, J = 5.1 Hz, 3H), 1.38 (d, J = 6.9 Hz, 3H), 0.79-0.55 (m, 4H). | 742 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 13 min; Wave Length: 254/220 nm |
| 122 | N-benzyl-7-(4-bromo-3-chloro-benzoyl)-3-oxo-2-[4-[4-(2,2,2-trifluoroethyl)piperazin-1-yl]phenyl]-6,8-dihydro-5H-imidazo[1,5-a]pyrazine-1-carboxamide | (DMSO-d₆, 600 MHz, 80° C.) δ 2.79-2.81 (m, 4H), 3.19-3.21 (m, 4H), 3.24 (q, J = 10.2 Hz, 2H), 3.68-3.70 (m, 2H), 3.84 (br s, 2H), 4.25 (d, J = 5.4 Hz, 2H), 4.86 (s, 2H), 6.94 (d, J = 9.0 Hz, 2H), 7.02-7.04 (m, 2H), 7.12 (d, J = 9.0 Hz, 2H), 7.21-7.26 (m, 3H), 7.40 (dd, J = 7.8, 1.8 Hz, 1H), 7.75 (d, J = 1.8 Hz, 1H), 7.86 (d, J = 7.8 Hz, 1H). | 733 | NA |
| 123 | N-benzyl-7-(4-bromo-3-chloro-benzoyl)-2-(1-methylbenzimidazol-5-yl)-3-oxo-6,8-dihydro-5H-imidazo[1,5-a]pyrazine-1-carboxamide | (DMSO-d₆, 600 MHz, 80° C.) δ 3.71 (m, 2H), 3.85 (br. s., 2H), 3.87 (s, 3H), 4.19 (d, J = 5.4 Hz, 2H), 4.88 (s, 2H), 6.92 (d, J = 7.0 Hz, 2H), 7.04-7.19 (m, 5H), 7.41 (dd, J = 8.6 Hz, 1.6 Hz, 1H), 7.55 (d, J = 8.6 Hz, 1H), 7.59 (d, J = 1.6 Hz, 1H), 7.76 (d, J = 1.8 Hz, 1H), 7.86 (d, J = 8.3 Hz, 1H), 8.21 (s, 1H). | 620 | NA |
| 124 | N-benzyl-7-(4-bromo-3-chloro-benzoyl)-2-(3-methylbenzimidazol-5-yl)-3-oxo-6,8-dihydro-5H-imidazo[1,5-a]pyrazine-1-carboxamide | (DMSO-d₆, 600 MHz, 80° C.) δ 3.71 (m, 2H), 3.77 (s, 3H), 3.88 (br. s, 2H), 4.20 (d, J = 5.5 Hz, 2H), 4.90 (s, 2H), 6.91 (d, J = 7.2 Hz, 2H), 7.04 (br. s., 1H), 7.07-7.19 (m, 4H), 7.41 (dd, J = 8.3 Hz, 1.9 Hz, 1H), 7.49 (d, J = 1.8 Hz, 1H), 7.66 (d, J = 8.5 Hz, 1H), 7.76 (d, J = 1.8 Hz, 1H), 7.86 (d, J = 8.1 Hz, 1H), 8.20 (s, 1H) | 620 | NA |
| 125a | N-benzyl-7-(4-bromo-3-chloro-benzoyl)-3-oxo-2-[4-[rac-(1S,4S)-2-oxa-5-azabicyclo[2.2.2]octan-5-yl]phenyl]-6,8-dihydro-5H-imidazo[1,5-a]pyrazine-1-carboxamide | (DMSO-d₆, 600 MHz, 80° C.) δ 1.67-1.75 (m, 1H), 1.89-1.99 (m, 2H), 2.03-2.10 (m, 1H), 3.34 (m, J = 10.1 Hz, 1H), 3.64-3.71 (m, 3H), 3.84 (br. s, 2H), 3.91-4.05 (m, 4H), 4.24 (d, J = 5.5 Hz, 2H), 4.87 (s, 2H), 6.66 (d, J = 9.0 Hz, 2H), 6.78 (br. s, 1H), 7.01 (d, J = 7.0 Hz, 2H), 7.09 (d, J = 9.0 Hz, 2H), 7.14-7.28 (m, 3H), 7.40 (dd, J = 8.1 Hz, 2.0 Hz, 1H), 7.74 (d, J = 2.0 Hz, 1H), 7.85 (d, J = 8.1 Hz, 1H). | 676 | SFC column: Lux C3 20 mm × 250 mm, 5 μm; isochratic conditions 20:80 EtOH:CO₂ (0.2% v/v NH₃), 40° C., 50 mL/min, 100 bar, Wave Length: 210 nm |

TABLE C-continued

| Compound | Name | ¹H NMR | [M + H]⁺ | Separation Method |
|---|---|---|---|---|
| 125b | N-benzyl-7-(4-bromo-3-chloro-benzoyl)-3-oxo-2-[4-[rac-(1R,4R)-2-oxa-5-azabicyclo[2.2.2]octan-5-yl]phenyl]-6,8-dihydro-5H-imidazo[1,5-a]pyrazine-1-carboxamide | (DMSO-d₆, 600 MHz, 80° C.) δ 1.67-1.76 (m, 1H), 1.88-1.99 (m, 2H), 2.02-2.14 (m, 1H), 3.33 (d, J = 10.1 Hz, 1H), 3.63-3.72 (m, 3H), 3.83 (br. s, 2H), 3.92-4.03 (m, 4H), 4.24 (d, J = 5.5 Hz, 2H), 4.86 (s, 2H), 6.66 (d, J = 9.0 Hz, 2H), 6.78 (br. s, 1H), 7.01 (d, J = 7.0 Hz, 2H), 7.09 (d, J = 9.0 Hz, 2H), 7.17-7.27 (m, 3H), 7.40 (dd, J = 8.1 Hz, 2.0 Hz, 1H), 7.74 (d, J = 2.0 Hz, 1H), 7.86 (d, J = 8.1 Hz, 1H). | 676 | SFC column: Lux C3 20 mm × 250 mm, 5 µm; isochratic conditions 20:80 EtOH:CO₂ (0.2% v/v NH₃), 40° C., 50 mL/min, 100 bar, Wave Length: 210 nm |
| 27a | rac-(6R)-N-[[2-(6-amino-2-pyridyl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (300 MHz, CDCl₃) δ 7.80 (t, J = 6.9 Hz 2H), 7.54 (t, J = 12.9 Hz 1H), 7.50-7.40 (m, 1H), 7.40-7.30 (m, 3H), 7.25-7.10 (m, 3H), 6.84 (t, J = 13.9 Hz 2H), 6.70 (t, J = 11.7 Hz 2H), 6.51 (d, J = 6.9 Hz 1H), 5.70-4.92 (m, 2H), 4.70 (d, J = 18.0 Hz 2H), 4.50-4.38 (m, 1H), 4.38-4.20 (m, 1H), 3.86 (d, J = 12.3 Hz 1H), 3.73 (t, J = 6.5 Hz 1H), 3.54 (s, 1H), 1.42 (d, J = 6.9 Hz 3H), 0.80-0.65 (m, 2H), 0.62 (s, 2H). | 761 | Column: CHIRALPAK ID, 2*25 cm, 5 µm; Mobile Phase A: Hex: DCM = 3: 1(0.5% 2M NH₃-MeOH)--HPLC, Mobile Phase B: EtOH--HPLC; Flow rate: 20 mL/min; Gradient: 20% B to 20% B in 17 min; Wave Length: 220/254 nm |
| 27b | rac-(6S)-N-[[2-(6-amino-2-pyridyl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (300 MHz, CDCl₃) δ 7.80 (d, J = 10.5 Hz 2H), 7.55-7.42 (m, 2H), 7.40-7.28 (m, 3H), 7.25-7.18 (m, 1H), 7.11 (d, J = 8.7 Hz 2H), 6.88-6.62 (m, 3H), 6.52-6.32 (m, 2H), 6.40-4.80 (m, 2H), 4.70-4.22 (m, 4H), 3.88 (t, J = 11.3 Hz 1H), 3.69 (t, J = 6.5 Hz 1H), 3.51 (t, J = 4.2 Hz 1H), 1.50-1.30 (m, 3H), 0.75-0.50 (m, 4H). | 761 | Column: CHIRALPAK ID, 2*25 cm, 5 µm; Mobile Phase A: Hex: DCM = 3: 1(0.5% 2M NH₃-MeOH)--HPLC, Mobile Phase B: EtOH--HPLC; Flow rate: 20 mL/min; Gradient: 20% B to 20% B in 17 min; Wave Length: 220/254 nm |
| 28a | rac-(6R)-7-[4-bromo-3-(trifluoromethyl)benzoyl]-2-[4-(cyclopropoxy)phenyl]-6-methyl-N-[[2-[4-(methylamino)pyrimidin-2-yl]phenyl]methyl]-3-oxo-6,8-dihydro-5H-imidazo[1,5-a]pyrazine-1-carboxamide | (300 MHz, CDCl₃) δ 8.10-7.99 (m, 1H), 7.99-7.88 (m, 1H), 7.88-7.72 (m, 2H), 7.52-7.43 (m, 1H), 7.42-7.30 (m, 3H), 7.20-7.10 (m, 1H), 7.05 (d, J = 8.7 Hz, 2H), 6.73 (d, J = 8.7 Hz, 2H), 6.20 (d, J = 6.0 Hz, 1H), 5.62-5.22 (m, 1H), 5.22-4.85 (m, 1H), 4.65 (d, J = 18.6 Hz, 1H), 4.59-4.31 (m, 2H), 3.84 (d, J = 12.3 Hz, 1H), 3.79-3.60 (m, 1H), 3.60-3.41 (m, 1H), 2.96 (d, J = 5.1 Hz, 3H), 1.40 (d, J = 6.9 Hz, 3H), 0.80-0.66 (m, 2H), 0.66-0.50 (m, 2H). | 776 | Column: CHIRALPAK ID, 2*25 cm, 5 µm; Mobile Phase A: Hex: DCM = 3: 1(0.5% 2M NH₃-MeOH)--HPLC, Mobile Phase B: IPA--HPLC; Flow rate: 20 mL/min; Gradient: 20% B to 20% B in 19 min; Wave Length: 254/220 nm |
| 28b | rac-(6S)-7-[4-bromo-3-(trifluoromethyl)benzoyl]-2-[4-(cyclopropoxy)phenyl]-6-methyl-N-[[2-[4-(methylamino)pyrimidin-2-yl]phenyl]methyl]-3-oxo-6,8-dihydro-5H-imidazo[1,5-a]pyrazine-1-carboxamide | (300 MHz, CDCl₃) δ 8.09-7.98 (m, 1H), 7.98-7.86 (m, 1H), 7.86-7.73 (m, 2H), 7.55-7.41 (m, 1H), 7.41-7.30 (m, 3H), 7.21-7.10 (m, 1H), 7.05 (d, J = 8.7 Hz, 2H), 6.72 (d, J = 8.7 Hz, 2H), 6.19 (d, J = 6.0 Hz, 1H), 5.68-5.15 (m, 1H), 5.15-4.85 (m, 1H), 4.65 (d, J = 18.0 Hz, 1H), 4.59-4.30 (m, 2H), 3.84 (d, J = 12.3 Hz, 1H), 3.78-3.60 (m, 1H), 3.55-3.41 (m, 1H), 2.96 (d, J = 4.8 Hz, 3H), 1.40 (d, J = 6.9 Hz, 3H), 0.80-0.65 (m, 2H), 0.65-0.51 (m, 2H). | 776 | Column: CHIRALPAK ID, 2*25 cm, 5 µm; Mobile Phase A: Hex: DCM = 3: 1(0.5% 2M NH₃-MeOH)--HPLC, Mobile Phase B: IPA--HPLC; Flow rate: 20 mL/min; Gradient: 20% B to 20% B in 19 min; Wave Length: 254/220 nm |
| 29a | rac-(6R)-N-[[2-(4-aminopyrimidin-2-yl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 7.99-7.95 (m, 2H), 7.81 (d, J = 4.0 Hz, 2H), 7.52-7.31 (m, 4H), 7.10 (d, J = 4.0 Hz, 2H), 6.99-6.84 (m, 4H), 5.33 (s, 2H), 4.66-4.45 (m, 1H), 3.84 (d, J = 6.0 Hz, 1H), 3.70 (d, J = 4.0 Hz, 1H), 3.58 (s, 1H), 1.40 (d, J = 4.0 Hz, 3H), 0.75-0.66 (m, 4H). | 762 | Column: CHIRALPAK IE, 2*25 cm, 5 µm; Mobile Phase A: MTBE(0.5% 2M NH₃-MeOH)--HPLC, Mobile Phase B: EtOH--HPLC; Flow rate: 20 mL/min; Gradient: 80% B to 80% B in 12 min; Wave Length: 220/254 nm |
| 29b | rac-(6S)-N-[[2-(4-aminopyrimidin-2-yl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 7.99-7.95 (m, 2H), 7.81 (d, J = 4.0 Hz, 2H), 7.52-7.31 (m, 4H), 7.10 (d, J = 4.0 Hz, 2H), 6.82 (s, 3H), 6.54 (s, 1H), 5.33 (s, 2H), 4.67-4.62 (m, 1H), 4.46 (s, 2H), 3.84 (d, J = 6.0 Hz, 1H), 3.70 (d, J = 4.0 Hz, 2H), 1.40 (d, J = 4.0 Hz, 3H), 0.75-0.66 (m, 4H). | 762 | Column: CHIRALPAK IE, 2*25 cm, 5 µm; Mobile Phase A: MTBE(0.5% 2M NH₃-MeOH)--HPLC, Mobile Phase B: EtOH--HPLC; Flow rate: 20 mL/min; Gradient: 80% B to 80% B in 12 min; Wave Length: 220/254 nm |

TABLE C-continued

| Compound | Name | ¹H NMR | [M + H]⁺ | Separation Method |
|---|---|---|---|---|
| 30a | rac-(6R)-N-[[2-(4-aminopyrimidin-2-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 7.99-7.96 (m, 2H), 7.72-7.69 (m, 1H), 7.57-7.52 (m, 1H), 7.41-7.36 (m, 3H), 7.19 (d, J = 2.0 Hz, 1H), 7.07 (d, J = 4.0 Hz, 2H), 6.95 (s, 1H), 6.76 (d, J = 4.0 Hz, 2H), 6.39 (s, 1H), 5.38-5.18 (m, 3H), 4.63 (d, J = 6.0 Hz, 1H), 4.52-4.47 (m, 2H), 3.83 (d, J = 6.0 Hz, 1H), 3.68 (d, J = 4.0 Hz, 1H), 3.53 (s, 1H), 1.38 (d, J = 4.0 Hz, 3H), 0.77-0.60 (m, 4H). | 726 | Column: CHIRALPAK ID, 2*25 cm, 5 n; Mobile Phase A: Hex:DCM = 3:1(0.5% 2M NH₃-MeOH)--HPLC, Mobile Phase B: EtOH--HPLC; Flow rate: 16 mL/min; Gradient: 50% B to 50% B in 17 min; Wave Length: 220/254 nm |
| 30b | rac-(6S)-N-[[2-(4-aminopyrimidin-2-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 7.99-7.96 (m, 2H), 7.72-7.69 (m, 1H), 7.57-7.52 (m, 1H), 7.41-7.36 (m, 3H), 7.19 (d, J = 2.0 Hz, 1H), 7.07 (d, J = 4.0 Hz, 2H), 6.95 (s, 1H), 6.76 (d, J = 4.0 Hz, 2H), 6.39 (s, 1H), 5.38-5.18 (m, 3H), 4.63 (d, J = 6.0 Hz, 1H), 4.52-4.47 (m, 2H), 3.83 (d, J = 6.0 Hz, 1H), 3.68 (d, J = 4.0 Hz, 1H), 3.53 (s, 1H), 1.38 (d, J = 4.0 Hz, 3H), 0.77-0.60 (m, 4H). | 726 | Column: CHIRALPAK ID, 2*25 cm, 5 μm; Mobile Phase A: Hex:DCM = 3:1(0.5% 2M NH₃-MeOH)--HPLC, Mobile Phase B: EtOH--HPLC; Flow rate: 16 mL/min; Gradient: 50% B to 50% B in 17 min; Wave Length: 220/254 nm |
| 31a | rac-(6R)-N-[[2-(4-aminopyrimidin-2-yl)-6-fluoro-phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.07 (d, J = 4.0 Hz, 1H), 7.74-7.69 (m, 2H), 7.58 (d, J = 2.0 Hz, 1H), 7.36-7.33 (m, 1H), 7.26-7.19 (m, 1H), 7.15-7.06 (m, 3H), 6.69-6.62 (m, 3H), 6.33 (d, J = 2.0 Hz, 1H), 5.10-5.90 (m, 2H), 4.98 (s, 2H), 4.69 (d, J = 2.0 Hz, 2H), 4.47 (d, J = 6.0 Hz, 1H), 3.85 (d, J = 6.0 Hz, 1H), 3.69 (d, J = 4.0 Hz, 1H), 3.49-3.46 (m, 1H), 1.39 (d, J = 4.0 Hz, 3H), 0.73-0.70 (m, 2H), 0.69-0.56 (m, 2H). | 746 | Column: CHIRALPAK ID, 2*25 cm, 5 μm; Mobile Phase A: Hex:DCM = 3:1(0.5% 2M NH₃-MeOH)--HPLC, Mobile Phase B: EtOH--HPLC; Flow rate: 20 mL/min; Gradient: 20% B to 20% B in 20 min; Wave Length: 220/254 nm |
| 31b | rac-(6S)-N-[[2-(4-aminopyrimidin-2-yl)-6-fluoro-phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.07 (d, J = 2.0 Hz, 1H), 7.75-7.70 (m, 2H), 7.57 (d, J = 2.0 Hz, 1H), 7.37-7.32 (m, 1H), 7.22-7.19 (m, 1H), 7.15-7.06 (m, 3H), 6.69-6.62 (m, 3H), 6.33 (d, J = 4.0 Hz, 1H), 5.93-5.10 (m, 2H), 4.97 (s, 2H), 4.69 (d, J = 4.0 Hz, 2H), 4.48 (d, J = 6.0 Hz, 1H), 3.86 (d, J = 6.0 Hz, 1H), 3.69 (d, J = 4.0 Hz, 1H), 3.49-3.46 (m, 1H), 1.39 (d, J = 4.0 Hz, 3H), 0.69-0.63 (m, 2H), 0.60-0.56 (m, 2H). | 746 | Column: CHIRALPAK ID, 2*25 cm, 5 μm; Mobile Phase A: Hex:DCM = 3:1(0.5% 2M NH₃-MeOH)--HPLC, Mobile Phase B: EtOH--HPLC; Flow rate: 20 mL/min; Gradient: 20% B to 20% B in 20 min; Wave Length: 220/254 nm |
| 32a | rac-(6R)-N-[[2-(4-aminopyrimidin-2-yl)-6-fluoro-phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.05 (d, J = 4.0 Hz, 1H), 7.82 (d, J = 6.0 Hz, 2H), 7.74 (d, J = 4.0 Hz, 1H), 7.49-7.45 (m, 1H), 7.32 (m, 1H), 7.25-6.90 (m, 3H), 6.74 (d, J = 4.0 Hz, 3H), 6.33 (d, J = 4.0 Hz, 1H), 5.80-5.17 (m, 2H), 4.96 (s, 2H), 4.70-4.67 (m, 2H), 4.46 (d, J = 6.0 Hz, 1H), 3.86 (d, J = 6.0 Hz, 1H), 3.70 (d, J = 4.0 Hz, 1H), 3.48-3.45 (m, 1H), 1.41 (d, J = 4.0 Hz, 3H), 0.74-0.70 (m, 2H), 0.69-0.55 (m, 2H). | 780 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 13.5 min; Wave Length: 220/254 nm |
| 32b | rac-(6S)-N-[[2-(4-aminopyrimidin-2-yl)-6-fluoro-phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.05 (d, J = 4.0 Hz, 1H), 7.82 (d, J = 6.0 Hz, 2H), 7.74 (d, J = 4.0 Hz, 1H), 7.52-7.45 (m, 1H), 7.37-7.32 (m, 1H), 7.15-7.05 (m, 3H), 6.68 (d, J = 4.0 Hz, 3H), 6.33 (d, J = 4.0 Hz, 1H), 5.79-5.18 (m, 2H), 4.96 (s, 2H), 4.86-4.67 (m, 2H), 4.46 (d, J = 6.0 Hz, 1H), 3.86 (d, J = 6.0 Hz, 1H), 3.71 (d, J = 6.0 Hz, 1H), 3.48-3.45 (m, 1H), 1.41 (d, J = 4.0 Hz, 3H), 0.73-0.69 (m, 2H), 0.67-0.55 (m, 2H). | 780 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 13.5 min; Wave Length: 220/254 nm |
| 33a | rac-(6R)-7-[4-bromo-3-(trifluoromethyl)benzoyl]-2-[4-(cyclopropoxy)phenyl]-N-[[2-fluoro-6-(5-methyl-1,3,4-oxadiazol-2-yl)phenyl]methyl]-6-methyl-3-oxo-6,8-dihydro-5H-imidazo[1,5-a]pyrazine-1-carboxamide | (300 MHz, CDCl₃) δ 7.81 (d, J = 7.5 Hz 2H), 7.64 (d, J = 7.8 Hz 1H), 7.50-7.39 (m, 2H), 7.25 (s, 1H), 7.02 (d, J = 9.0 Hz 2H), 6.74 (t, J = 9.0 Hz 2H), 6.60 (d, J = 5.4 Hz 1H), 5.68-4.90 (m, 2H), 4.90-4.78 (m, 1H), 4.75-4.55 (m, 1H), 3.84 (d, J = 12.9 Hz 1H), 3.72-3.50 (m, 2H), 2.63 (s, 3H), 1.38 (d, J = 7.2 Hz 3H), 0.80-0.70 (m, 4H). | 769 | Column: CHIRALPAK IF, 2*25 cm, 5 μm Mobile Phase A: Hex:DCM = 3:1(0.5% 2M NH₃-MeOH)--HPLC, Mobile Phase B: EtOH--HPLC; Flow rate: 20 mL/min; Gradient: 30% B to 30% B in 16 min; Wave Length: 220/254 nm |

TABLE C-continued

| Compound | Name | ¹H NMR | [M + H]⁺ | Separation Method |
|---|---|---|---|---|
| 33b | rac-(6S)-7-[4-bromo-3-(trifluoromethyl)benzoyl]-2-[4-(cyclopropoxy)phenyl]-N-[[2-fluoro-6-(5-methyl-1,3,4-oxadiazol-2-yl)phenyl]methyl]-6-methyl-3-oxo-6,8-dihydro-5H-imidazo[1,5-a]pyrazine-1-carboxamide | (300 MHz, CDCl$_3$) δ 7.81 (d, J = 7.5 Hz 2H), 7.64 (d, J = 7.8 Hz 1H), 7.50-7.32 (m, 2H), 7.25 (s, 1H), 7.03 (d, J = 9.0 Hz 2H), 6.80-6.52 (m, 3H), 5.82-4.90 (m, 2H), 4.90-4.75 (m, 1H), 4.72-4.52 (m, 2H), 3.90-3.52 (m, 2H), 2.63 (s, 3H), 1.38 (d, J = 6.9 Hz 3H), 0.80-0.69 (m, 4H). | 769 | Column: CHIRALPAK IF, 2*25 cm, 5 μm; Mobile Phase A: Hex: DCM = 3: 1(0.5% 2M NH$_3$-MeOH)--HPLC, Mobile Phase B: EtOH--HPLC; Flow rate: 20 mL/min; Gradient: 30% B to 30% B in 16 min; Wave Length: 220/254 nm |
| 34a | rac-(6R)-7-[4-bromo-3-(trifluoromethyl)benzoyl]-2-[4-(cyclopropoxy)phenyl]-6-methyl-3-oxo-N-[[2-(2-pyridyl)phenyl]methyl]-6,8-dihydro-5H-imidazo[1,5-a]pyrazine-1-carboxamide | (DMSO-d$_6$, 600 MHz, 80° C.) δ 0.57-0.63 (m, 2H), 0.74-0.79 (m, 2H), 1.28 (d, J = 6.8 Hz, 3H), 3.64-3.72 (m, 2H), 3.74-3.79 (m, 1H), 4.30 (d, J = 6.0 Hz, 2H), 4.47-4.69 (m, 2H), 5.19 (br. s., 1H), 6.95-7.00 (m, 2H), 7.12-7.19 (m, 3H), 7.21 (d, J = 7.2 Hz, 1H), 7.30-7.39 (m, 3H), 7.41 (dd, J = 7.8 Hz, 1.7 Hz, 1H), 7.50 (d, J = 7.9 Hz, 1H), 7.69 (dd, J = 8.2 Hz, 1.8 Hz, 1H), 7.86 (td, J = 7.7 Hz, 1.9 Hz, 1H), 7.91 (d, J = 1.6 Hz, 1H), 7.95 (d, J = 8.0 Hz, 1H), 8.49 (d, J = 5.0 Hz, 1H). | 746 | NA |
| 35a | rac-(6R)-N-[[2-(6-amino-2-pyridyl)-6-fluoro-phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl$_3$) δ 7.72-7.70 (m, 1H), 7.58 (d, J = 2.0 Hz, 1H), 7.49-7.45 (m, 1H), 7.33-7.28 (m, 1H), 7.20-7.21 (m, 1H), 7.19-7.11 (m, 3H), 7.07-7.03 (m, 1H), 6.74-6.68 (m, 3H), 6.46 (d, J = 4.0 Hz, 1H), 6.14 (s, 1H), 5.80-4.85 (m, 2H), 4.68-4.26 (m, 5H), 3.86 (d, J = 6.0 Hz, 1H), 3.70 (d, J = 4.0 Hz, 1H), 3.50 (d, J = 2.0 Hz, 1H), 1.40 (d, J = 4.0 Hz, 3H), 0.72-0.62 (m, 2H), 0.59-0.53 (m, 2H). | 745 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 30% B to 30% B in 11 min; Wave Length: 220/254 nm |
| 35b | rac-(6S)-N-[[2-(6-amino-2-pyridyl)-6-fluoro-phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl$_3$) δ 7.72-7.70 (m, 1H), 7.57 (d, J = 2.0 Hz, 1H), 7.50-7.46 (m, 1H), 7.34-7.28 (m, 1H), 7.21-7.19 (m, 1H), 7.17-7.11 (m, 3H), 7.08-7.03 (m, 1H), 6.75-6.69 (m, 3H), 6.46 (d, J = 4.0 Hz, 1H), 6.14 (s, 1H), 5.80-4.85 (m, 2H), 4.68-4.26 (m, 5H), 3.85 (d, J = 6.0 Hz, 1H), 3.70 (d, J = 4.0 Hz, 1H), 3.49 (s, 1H), 1.40 (d, J = 4.0 Hz, 3H), 0.72-0.66 (m, 2H), 0.65-0.53 (m, 2H). | 745 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 30% B to 30% B in 11 min; Wave Length: 220/254 nm |
| 36a | rac-(6R)-N-[[2-(6-amino-2-pyridyl)-6-fluoro-phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl$_3$) δ 7.81 (d, J = 4.0 Hz, 2H), 7.52-7.45 (m, 2H), 7.33-7.28 (m, 1H), 7.16-7.11 (m, 3H), 7.07-7.03 (m, 1H), 6.74-6.69 (m, 3H), 6.45 (d, J = 4.0 Hz, 1H), 6.15 (s, 1H), 5.80-4.95 (m, 2H), 4.71-4.21 (m, 5H), 3.87 (d, J = 6.0 Hz, 1H), 3.72 (d, J = 4.0 Hz, 1H), 3.48 (s, 1H), 1.42 (d, J = 4.0 Hz, 3H), 0.73-0.64 (m, 2H), 0.61-0.52 (m, 2H). | 779 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 30% B to 30% B in 10 min; Wave Length: 220/254 nm |
| 36b | rac-(6S)-N-[[2-(6-amino-2-pyridyl)-6-fluoro-phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl$_3$) δ 7.81 (d, J = 4.0 Hz, 2H), 7.52-7.45 (m, 2H), 7.33-7.28 (m, 1H), 7.16-7.10 (m, 3H), 7.08-7.03 (m, 1H), 6.74-6.69 (m, 3H), 6.46 (d, J = 4.0 Hz, 1H), 6.15 (s, 1H), 5.68-4.87 (m, 2H), 4.71-4.25 (m, 5H), 3.87 (d, J = 6.0 Hz, 1H), 3.72 (d, J = 4.0 Hz, 1H), 3.49 (d, J = 1.0 Hz, 1H), 1.42 (d, J = 4.0 Hz, 3H), 0.73-0.64 (m, 2H), 0.62-0.52 (m, 2H). | 779 | Column: CHIRALPAK IE, 2*25 cm, 5 μm Mobile Phase A: MtBE(0.5% 2M NH$_3$-MeOH)--HPLC, Mobile Phase B: EtOH--HPLC; Flow rate: 20 mL/min; Gradient: 30% B to 30% B in 10 min; Wave Length: 220/254 nm |
| 37a | rac-(6R)-7-(4-bromo-3-chloro-benzoyl)-2-[4-(cyclopropoxy)phenyl]-N-[[2-(2-methoxypyrimidin-4-yl)phenyl]methyl]-6-methyl-3-oxo-6,8-dihydro-5H-imidazo[1,5-a]pyrazine-1-carboxamide | (300 MHz, CDCl$_3$) δ 8.54 (d, J = 5.1 Hz 1H), 7.67 (d, J = 8.1 Hz 1H), 7.60-7.50 (m, 2H), 7.50-7.30 (m, 3H), 7.20-7.00 (m, 4H), 6.79 (t, J = 5.9 Hz 1H), 6.70-6.50 (m, 2H), 5.80-4.80 (m, 2H), 4.72-4.45 (m, 2H), 4.42-4.22 (m, 1H), 3.99 (s, 3H), 3.85 (d, J = 12.9 Hz 1H), 3.78-3.60 (m, 1H), 3.55-3.30 (m, 1H), 1.40 (s, 3H), 0.80-0.40 (m, 4H) | 743 | Column: CHIRALPAK ID, 2*25 cm, 5 μm; Mobile Phase A: Hex: DCM = 3: 1(0.5% 2M NH$_3$-MeOH)--HPLC, Mobile Phase B: EtOH--HPLC; Flow rate: 18 mL/min; Gradient: 50% B to 50% B in 38 min; Wave Length: 220/254 nm |

TABLE C-continued

| Compound | Name | ¹H NMR | [M + H]⁺ | Separation Method |
|---|---|---|---|---|
| 37b | rac-(6S)-7-(4-bromo-3-chloro-benzoyl)-2-[4-(cyclopropoxy)phenyl]-N-[[2-(2-methoxypyrimidin-4-yl)phenyl]methyl]-6-methyl-3-oxo-6,8-dihydro-5H-imidazo[1,5-a]pyrazine-1-carboxamide | (300 MHz, CDCl₃) δ 8.54 (d, J = 5.1 Hz 1H), 7.67 (d, J = 8.4 Hz 1H), 7.60-7.45 (m, 2H), 7.45-7.30 (m, 3H), 7.20-7.10 (m, 2H), 7.04 (d, J = 8.7 Hz 2H), 6.78 (t, J = 5.7 Hz 1H), 6.65 (d, J = 8.7 Hz 2H) 5.70-4.80 (m, 2H), 4.70-4.40 (m, 2H), 4.40-4.20 (m, 1H), 3.99 (s, 3H), 3.85 (d, J = 12.6 Hz 1H), 3.78-3.60 (m, 1H), 3.50-3.30 (m, 1H), 1.40 (d, J = 6.9 Hz 3H), 0.78-0.50 (m, 4H). | 743 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 18 mL/min; Gradient: 50% B to 50% B in 38 min; Wave Length: 220/254 nm |
| 38a | rac-(6R)-7-[4-bromo-3-(trifluoromethyl)benzoyl]-2-[4-(cyclopropoxy)phenyl]-N-[[2-(2-methoxypyrimidin-4-yl)phenyl]methyl]-6-methyl-3-oxo-6,8-dihydro-5H-imidazo[1,5-a]pyrazine-1-carboxamide | (300 MHz, CDCl₃) δ 8.53 (d, J = 5.1 Hz 1H), 7.90-7.72 (m, 2H), 7.52-7.35 (m, 5H), 7.22-6.95 (m, 2H), 6.82-6.60 (m, 3H), 5.60-4.80 (m, 2H), 4.72-4.42 (m, 2H), 4.40-4.20 (m, 1H), 3.99 (s, 3H), 3.90-3.70 (m, 2H), 3.55-3.25 (m, 1H), 1.42 (d, J = 7.2 Hz 3H), 0.72-0.60 (m, 2H), 0.60-0.50 (m, 2H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 17 mL/min; Gradient: 30% B to 30% B in 18.5 min; Wave Length: 254/220 nm |
| 38b | rac-(6S)-7-[4-bromo-3-(trifluoromethyl)benzoyl]-2-[4-(cyclopropoxy)phenyl]-N-[[2-(2-methoxypyrimidin-4-yl)phenyl]methyl]-6-methyl-3-oxo-6,8-dihydro-5H-imidazo[1,5-a]pyrazine-1-carboxamide | (300 MHz, CDCl₃) δ 8.53 (d, J = 5.1 Hz 1H), 7.90-7.70 (m, 2H), 7.60-7.30 (m, 5H), 7.10-7.00 (m, 3H), 6.78 (t, J = 5.9 Hz 1H), 6.64 (d, J = 9.0 Hz 2H), 5.60-4.85 (m, 2H), 4.75-4.40 (m, 2H), 4.40-4.24 (m, 1H), 3.99 (s, 3H), 3.86 (d, J = 12.9 Hz 1H), 3.80-3.60 (m, 1H), 3.50-3.38 (m, 1H), 1.42 (d, J = 7.2 Hz 3H), 0.70-0.50 (m, 4H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 17 mL/min; Gradient: 30% B to 30% B in 18.5 min; Wave Length: 254/220 nm |
| 39a | rac-(6R)-7-(4-bromo-3-chloro-benzoyl)-2-[4-(cyclopropoxy)phenyl]-(methylamino)pyrimidin-4-6-methyl-N-[[246-yl]phenyl]methyl]-3-oxo-6,8-dihydro-5H-imidazo[1,5-a]pyrazine-1-carboxamide | (400 MHz, CDCl₃) δ 8.15 (s, 1H), 7.69 (d, J = 4.0, 1H), 7.56 (s, 1H), 7.52-7.27 (m, 4H),7.25-7.09 (m, 4H), 6.83 (d, J = 6.0 Hz, 2H), 6.41 (s, 1H), 5.38-5.08 (m, 2H), 4.61 (d, J = 10.0 Hz, 1H), 4.32-4.24 (m, 2H), 3.84 (d, J = 8.0 Hz, 1H), 3.69 (d, J = 6.0 Hz, 1H), 3.57 (d, J = 2.0 Hz, 1H), 2.99 (d, J = 4.0 Hz, 3H), 1.38 (d, J = 4.0 Hz, 3H), 0.75-0.64 (m, 4H). | 742 | Column: CHIRALPAK IA, 2*25 cm, 5 μm; Mobile Phase A: MtBE(0.5% 2M NH₃-MeOH)--HPLC, Mobile Phase B: IPA--HPLC; Flow rate: 20 mL/min; Gradient: 30% B to 30% B in 12.5 min; Wave Length: 220/254 nm |
| 39b | rac-(6S)-7-(4-bromo-3-chloro-benzoyl)-2-[4-(cyclopropoxy)phenyl]-6-methyl-N-[[246-(methylamino)pyrimidin-4-yl]phenyl]methyl]-3-oxo-6,8-dihydro-5H-imidazo[1,5-a]pyrazine-1-carboxamide | (400 MHz, CDCl₃) δ 8.15 (s, 1H), 7.69 (d, J = 4.0, 1H), 7.56 (s, 1H), 7.52-7.27 (m, 4H),7.25-7.09 (m, 4H), 6.83 (d, J = 6.0 Hz, 2H), 6.41 (s, 1H), 5.38-5.08 (m, 2H), 4.61 (d, J = 10.0 Hz, 1H), 4.32-4.24 (m, 2H), 3.84 (d, J = 8.0 Hz, 1H), 3.69 (d, J = 6.0 Hz, 1H), 3.57 (d, J = 2.0 Hz, 1H), 2.99 (d, J = 4.0 Hz, 3H), 1.38 (d, J = 4.0 Hz, 3H), 0.75-0.64 (m, 4H). | 742 | Column: CHIRALPAK IA, 2*25 cm, 5 μm; Mobile Phase A: MtBE(0.5% 2M NH₃-MeOH)--HPLC, Mobile Phase B: IPA--HPLC; Flow rate: 20 mL/min; Gradient: 30% B to 30% B in 12.5 min; Wave Length: 220/254 nm |
| 40a | rac-(6R)-7-[4-bromo-3-(trifluoromethyl)benzoyl]-2-[4-(cyclopropoxy)phenyl]-6-methyl-N-[[2-[6-(methylamino)pyrimidin-4-yl]phenyl]methyl]-3-oxo-6,8-dihydro-5H-imidazo[1,5-a]pyrazine-1-carboxamide | (400 MHz, CDCl₃) δ 8.15 (s, 1H), 7.79 (d, J = 4.0, 2H), 7.52-7.34 (m, 5H),7.25-7.12 (m, 3H), 6.83 (d, J = 6.0 Hz, 2H), 6.41 (s, 1H), 5.35-5.07 (m, 2H), 4.61 (d, J = 10.0 Hz, 1H), 4.32-4.24 (m, 2H), 3.84 (d, J = 8.0 Hz, 1H), 3.69 (d, J = 6.0 Hz, 1H), 3.57 (d, J = 2.0 Hz, 1H), 2.98 (d, J = 8.0 Hz, 3H), 1.40 (d, J = 4.0 Hz, 3H), 0.75-0.64 (m, 4H). | 776 | Column: CHIRALPAK IF, 2*25 cm, 5 μm; Mobile Phase A: MtBE(0.5% 2M NH₃-MeOH)--HPLC, Mobile Phase B: IPA--HPLC; Flow rate: 14 mL/min; Gradient: 25% B to 25% B in 29 min; Wave Length: 220/254 nm |
| 40b | rac-(6S)-7-[4-bromo-3-(trifluoromethyl)benzoyl]-2-[4-(cyclopropoxy)phenyl]-6-methyl-N-[[2-[6-(methylamino)pyrimidin-4-yl]phenyl]methyl]-3-oxo-6,8-dihydro-5H-imidazo[1,5-a]pyrazine-1-carboxamide | (400 MHz, CDCl₃) δ 8.15 (s, 1H), 7.79 (d, J = 4.0, 2H), 7.52-7.34 (m, 5H),7.25-7.12 (m, 3H), 6.83 (d, J = 6.0 Hz, 2H), 6.41 (s, 1H), 5.35-5.07 (m, 2H), 4.61 (d, J = 10.0 Hz, 1H), 4.32-4.24 (m, 2H), 3.84 (d, J = 8.0 Hz, 1H), 3.69 (d, J = 6.0 Hz, 1H), 3.57 (d, J = 2.0 Hz, 1H), 2.98 (d, J = 8.0 Hz, 3H), 1.40 (d, J = 4.0 Hz, 3H), 0.75-0.64 (m, 4H). | 776 | Column: CHIRALPAK IF, 2*25 cm, 5 μm Mobile Phase A: MtBE(0.5% 2M NH₃-MeOH)--HPLC, Mobile Phase B: IPA--HPLC; Flow rate: 14 mL/min; Gradient: 25% B to 25% B in 29 min; Wave Length: 220/254 nm; RT1(min): 18.62; RT2(min): 26.85; Sample Solvent: EtOH--HPLC; Injection Volume: 1.2 mL; Number Of Runs: 4 |

TABLE C-continued

| Compound | Name | ¹H NMR | [M + H]⁺ | Separation Method |
|---|---|---|---|---|
| 41a | rac-(6R)-7-[4-bromo-3-(trifluoromethyl)benzoyl]-2-[4-(cyclopropoxy)phenyl]-N-[[2-fluoro-6-(2-pyridyl)phenyl]methyl]-6-methyl-3-oxo-6,8-dihydro-5H-imidazo[1,5-a]pyrazine-1-carboxamide | (DMSO-$d_6$, 600 MHz, 80° C.) δ 0.48-0.65 (m, 2H), 0.66-0.79 (m, 2H), 1.29 (d, J = 6.4 Hz, 3H), 3.58-3.81 (m, 3H), 4.21-4.38 (m, 2H), 4.51 (d, J = 18.2 Hz, 1H), 4.61 (br. s, 1H), 5.19 (br. s, 1H), 6.88 (d, J = 7.9 Hz, 2H), 7.14 (d, J = 8.3 Hz, 2H)' 7.18-7.25 (m, 1H), 7.27 (d, J = 7.5 Hz, 1H), 7.33-7.42 (m, 1H), 7.42-7.48 (m, 1H), 7.52 (d, J = 7.5 Hz, 2H), 7.70 (d, J = 7.7 Hz, 2H), 7.80-7.90 (m, 1H), 7.92 (s, 1H), 7.96 (d, J = 7.9 Hz, 1H), 8.52 (s, 1H). | 764 | NA |
| 126 | 2-(1,3-benzoxazol-5-yl)-N-benzyl-7-(4-bromo-3-chloro-benzoyl)-3-oxo-6,8-dihydro-5H-imidazo[1,5-a]pyrazine-1-carboxamide | (DMSO-$d_6$, 600 MHz, 80° C.) δ 3.72 (t, J = 5.6 Hz, 2H), 3.85 (s, 2H), 4.24 (d, J = 5.4 Hz, 2H), 4.88 (s, 2H), 7.01 (s, 2H), 7.14-7.20 (m, 3H), 7.32 (dd, J = 9.0 Hz, 2.0 Hz, 1H), 7.41 (dd, J = 8.6 Hz, 2.0 Hz, 1H), 7.53 (s, 1H), 7.7 (d, J = 2.0 Hz, 1H), 7.76 (dd, J = 5.9 Hz, 3.1 Hz, 2H), 7.86 (d, J = 8.6 Hz, 1H), 8.73 (s, 1H). | 605 | NA |
| 42a | rac-(6R)-N-[[2-(5-aminopyridazin-3-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.53 (d, J = 2.8 Hz, 1H), 7.72-7.48 (m, 2H), 7.41-7.29 (m, 4H), 7.22-7.08 (m, 4H), 6.85-6.68 (m, 3H), 6.01-4.39 (m, 5H), 4.39-4.20 (m, 2H), 3.85 (d, J = 12.7 Hz, 1H), 3.79-3.59 (m, 1H), 3.59-3.48 (m, 1H), 1.38 (d, J = 6.9 Hz, 3H), 0.75-0.65 (m, 2H), 0.65-0.58 (m, 2H). | 728 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 15 mL/min; Gradient: 25% B to 25% B in 27.5 min; Wave Length: 220/254 nm |
| 42b | rac-(6S)-N-[[2-(5-aminopyridazin-3-yl)phenyl]methyl]-7-(4-bromo-3-chloro-benzoyl)-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.53 (d, J = 2.8 Hz, 1H), 7.71-7.49 (m, 2H), 7.49-7.30 (m, 4H), 7.22-7.04 (m, 4H), 6.85-6.60 (m, 3H), 5.95-4.38 (m, 5H), 4.38-4.20 (m, 2H), 3.85 (d, J = 12.8 Hz, 1H), 3.79-3.59 (m, 1H), 3.59-3.48 (m, 1H), 1.38 (d, J = 6.8 Hz, 3H), 0.78-0.53 (m, 4H). | 728 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 15 mL/min; Gradient: 25% B to 25% B in 27.5 min; Wave Length: 220/254 nm |
| 43a | rac-(6R)-N-[[2-(5-aminopyridazin-3-yl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.53 (d, J = 2.7 Hz, 1H), 7.81 (d, J = 1.4 Hz, 1H), 7.80-7.65 (m, 1H), 7.45-7.30 (m, 5H), 7.21-7.05 (m, 3H), 6.80-6.61 (m, 3H), 5.88-4.85 (m, 2H), 4.81-4.40 (m, 3H), 4.40-4.15 (m, 2H), 3.86 (d, J = 12.8 Hz, 1H), 3.79-3.59 (m, 1H), 3.59-3.40 (m, 1H), 1.40 (d, J = 6.9 Hz, 3H), 0.79-0.50 (m, 4H). | 762 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 15 mL/min; Gradient: 25% B to 25% B in 18 min; Wave Length: 220/254 nm |
| 43b | rac-(6S)-N-[[2-(5-aminopyridazin-3-yl)phenyl]methyl]-7-[4-bromo-3-(trifluoromethyl)benzoyl]-2-[4-(cyclopropoxy)phenyl]-6-methyl-3-oxo-6,8-dihydro-5H-imidazo[1,5-a]pyrazine-1-carboxamide | (400 MHz, CDCl₃) δ 8.52 (d, J = 2.6 Hz, 1H), 7.81 (d, J = 1.4 Hz, 1H), 7.75-7.67 (m, 1H), 7.50-7.29 (m, 5H), 7.20-7.02 (m, 3H), 6.82-6.60 (m, 3H), 5.98-4.79 (m, 2H), 4.79-4.40 (m, 3H), 4.35-4.19 (m, 2H), 3.86 (d, J = 12.7 Hz, 1H), 3.79-3.60 (m, 1H), 3.60-3.30 (m, 1H), 1.40 (d, J = 6.9 Hz, 3H), 0.78-0.51 (m, 4H). | 762 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 15 mL/min; Gradient: 25% B to 25% B in 18 min; Wave Length: 220/254 nm |
| 44a | rac-(6R)-7-(4-bromo-3-chloro-benzoyl)-2-[4-(cyclopropoxy)phenyl]-N-[[2-(1H-imidazol-4-yl)phenyl]methyl]-6-methyl-3-oxo-6,8-dihydro-5H-imidazo[1,5-a]pyrazine-1-carboxamide | (400 MHz, CDCl₃) δ 7.70 (d, J = 8.1 Hz, 1H), 7.57 (d, J = 1.9 Hz, 2H), 7.45-7.38 (m, 1H), 7.34-7.29 (m, 1H), 7.28-7.09 (m, 6H), 7.06-6.98 (m, 2H), 5.83-4.25 (m, 5H), 3.86 (d, J = 12.7 Hz, 1H), 3.71 (d, J = 8.6 Hz, 2H), 1.44-1.32 (m, 3H), 0.92-0.69 (m, 4H). | 701 | Column: CHIRALPAK ID, 2*25 cm, 5 μm; Mobile Phase A: Hex: DCM = 3: 1(0.5% 2M NH₃-MeOH)--HPLC, Mobile Phase B: EtOH--HPLC; Flow rate: 20 mL/min; Gradient: 50% B to 50% B in 11 min; Wave Length: 220/254 nm |
| 44b | rac-(6S)-7-(4-bromo-3-chloro-benzoyl)-2-[4-(cyclopropoxy)phenyl]-N-[[2-(1H-imidazol-4- | (400 MHz, CDCl₃) δ 7.70 (d, J = 8.2 Hz, 1H), 7.57 (d, J = 1.9 Hz, 2H), 7.45-7.40 (m, 1H), 7.34-7.29 (m, 1H), 7.28-7.08 | 701 | Column: CHIRALPAK ID, 2*25 cm, 5 μm; Mobile Phase A: Hex: |

TABLE C-continued

| Compound | Name | $^1$H NMR | [M + H]$^+$ | Separation Method |
|---|---|---|---|---|
| | yl)phenyl]methyl]-6-methyl-3-oxo-6,8-dihydro-5H-imidazo[1,5-a]pyrazine-1-carboxamide | (m, 6H), 7.07-6.98 (m, 2H), 5.65-4.24 (m, 5H), 3.86 (d, J = 12.8 Hz, 1H), 3.70 (s, 2H), 1.39 (d, J = 6.9 Hz, 3H), 0.93-0.63 (m, 4H). | | DCM = 3: 1(0.5% 2M NH$_3$-MeOH)--HPLC, Mobile Phase B: EtOH--HPLC; Flow rate: 20 mL/min; Gradient: 50% B to 50% B in 11 min; Wave Length: 220/254 nm |
| 45a | rac-(6R)-7-(4-bromo-3-chloro-benzoyl)-2-[4-(cyclopropoxy)phenyl]-N-[[2-fluoro-6-(5-methyl-1,3,4-oxadiazol-2-yl)phenyl]methyl]-6-methyl-3-oxo-6,8-dihydro-5H-imidazo[1,5-a]pyrazine-1-carboxamide | (300 MHz, CDCl$_3$) δ 7.74-7.62 (m, 2H), 7.56 (d, J = 1.8 Hz 1H), 7.50-7.40 (m, 1H), 7.25-7.18 (m, 2H), 7.03 (d, J = 9.0 Hz, 2H), 6.74 (d, J = 9.0 Hz 2H), 6.60 (t, J = 6.1 Hz 1H), 5.80-4.90 (m, 2H), 4.92-4.80 (m, 1H), 4.75-4.50 (m, 2H), 3.82 (d, J = 12.6 Hz 1H), 3.70-3.50 (m, 2H), 2.63 (s, 3H), 1.36 (d, J = 6.9 Hz 3H), 0.90-0.68 (m, 4H). | 735 | Column: CHIRAL ART Cellulose-SB, 2*25 cm, 5 μm; Mobile Phase A: MtBE(0.5% 2M NH$_3$-MeOH)--HPLC, Mobile Phase B: IPA--HPLC; Flow rate: 45 mL/min; Gradient: 50% B to 50% B in 18 min; Wave Length: 220/254 nm |
| 45b | rac-(6S)-7-(4-bromo-3-chloro-benzoyl)-2-[4-(cyclopropoxy)phenyl]-N-[[2-fluoro-6-(5-methyl-1,3,4-oxadiazol-2-yl)phenyl]methyl]-6-methyl-3-oxo-6,8-dihydro-5H-imidazo[1,5-a]pyrazine-1-carboxamide | (300 MHz, CDCl$_3$) δ 7.76-7.62 (m, 2H), 7.56 (d, J = 1.8 Hz 1H), 7.50-7.36 (m, 1H), 7.25 (s, 1H), 7.20-7.16 (m, 1H), 7.03 (d, J = 9.0 Hz 2H), 6.74 (d, J = 9.0 Hz, 2H), 6.60 (t, J = 6.0 Hz 1H), 5.78-4.92 (m, 2H), 4.90-4.80 (m, 1H), 4.70-4.50 (m, 2H), 3.82 (d, J = 12.3 Hz 1H), 3.78-3.56 (m, 2H), 2.63 (s, 3H), 1.36 (d, J = 6.9 Hz 3H), 0.88-0.70 (m, 4H). | 735 | Column: CHIRAL ART Cellulose-SB, 2*25 cm, 5 μm; Mobile Phase A: MtBE(0.5% 2M NH$_3$-MeOH)--HPLC, Mobile Phase B: IPA--HPLC; Flow rate: 45 mL/min; Gradient: 50% B to 50% B in 18 min; Wave Length: 220/254 nm |
| 46a | rac-(6R)-7-(4-bromo-3-chloro-benzoyl)-6-methyl-2-(2-methyl-1,3-benzoxazol-5-yl)-3-oxo-N-[(2-pyrimidin-4-ylphenyl)methyl]-6,8-dihydro-5H-imidazo[1,5-a]pyrazine-1-carboxamide | (400 MHz, CDCl$_3$) δ 8.70 (d, J = 4.0 Hz, 1H), 8.56 (s, 1H), 7.72-7.70 (m, 1H), 7.59-7.58 (m, 2H), 7.52-7.38 (s, 5H), 7.22-7.19 (m, 1H), 7.13-7.05 (m, 2H), 6.71 (s, 1H), 5.34 (s, 2H), 4.64 (d, J = 8.0 Hz, 1H), 4.38-4.23 (m, 2H), 3.87 (d, J = 6.0 Hz, 1H), 3.72 (d, J = 6.0 Hz, 1H), 2.56 (s, 3H), 1.41 (d, J = 4.0 Hz, 3H). | 712 | Column: CHIRALPAK IF, 2*25 cm, 5 μm; Mobile Phase A: MtBE(0.5% 2M NH$_3$-MeOH)--HPLC, Mobile Phase B: EtOH--HPLC; Flow rate: 12 mL/min; Gradient: 40% B to 40% B in 50 min; Wave Length: 220/254 nm |
| 46b | rac-(6S)-7-(4-bromo-3-chloro-benzoyl)-6-methyl-2-(2-methyl-1,3-benzoxazol-5-yl)-3-oxo-N-[(2-pyrimidin-4-ylphenyl)methyl]-6,8-dihydro-5H-imidazo[1,5-a]pyrazine-1-carboxamide | (400 MHz, CDCl$_3$) δ 8.70 (d, J = 4.0 Hz, 1H), 8.56 (s, 1H), 7.72-7.70 (m, 1H), 7.59-7.58 (m, 2H), 7.52-7.38 (s, 5H), 7.22-7.19 (m, 1H), 7.13-7.05 (m, 2H), 6.71 (s, 1H), 5.34 (s, 2H), 4.64 (d, J = 8.0 Hz, 1H), 4.38-4.23 (m, 2H), 3.87 (d, J = 6.0 Hz, 1H), 3.72 (d, J = 6.0 Hz, 1H), 2.56 (s, 3H), 1.41 (d, J = 4.0 Hz, 3H). | 712 | Column: CHIRALPAK IF, 2*25 cm, 5 μm; Mobile Phase A: MtBE(0.5% 2M NH$_3$-MeOH)--HPLC, Mobile Phase B: EtOH--HPLC; Flow rate: 12 mL/min; Gradient: 40% B to 40% B in 50 min; Wave Length: 220/254 nm |
| 127 | N-benzyl-7-(4-bromo-3-chloro-benzoyl)-2-[2-(methylamino)-1,3-benzoxazol-5-yl]-3-oxo-6,8-dihydro-5H-imidazo[1,5-a]pyrazine-1-carboxamide | (DMSO-d$_6$, 600 MHz, 80° C.): 2.95 (d, J = 5.5 Hz, 3H), 3.7 (t, J = 5.9 Hz, 2H), 3.84 (s, 2H), 4.23 (d, J = 4.6 Hz, 2H), 4.88 (s, 2H), 6.87 (dd, J = 9.1 Hz, 2.8 Hz, 1H), 6.98 (s, 2H), 7.10 (s, 1H), 7.14-7.16 (m, 1H), 7.17-7.21 (m, 3H), 7.31 (d, J = 9.1 Hz, 1H), 7.40 (dd, J = 9.1 Hz, 1.8 Hz, 1H), 7.66 (s, 1H), 7.75 (d J = 1.7 Hz, 1H), 7.85 (d, J = 8.2 Hz) ppm. | 634 | NA |
| 47a | rac-(6R)-7-[4-bromo-3-(trifluoromethyl)benzoyl]-2-[4-(cyclopropoxy)phenyl]-6-methyl-N-[[2-(5-methyl-1,3,4-oxadiazol-2-yl)phenyl]methyl]-3-oxo-6,8-dihydro-5H-imidazo[1,5-a]pyrazine-1-carboxamide | (DMSO-d$_6$, 600 MHz, 80° C.) δ 0.66-0.71 (m, 2H), 0.78-0.83 (m, 2H), 1.29 (s, 3H), 2.57 (s, 3H), 3.63-3.73 (m, 2H), 3.82 (hept, J = 3.1 Hz, 1H), 4.52 (d, J = 18.2 Hz, 1H), 4.58 (br. s, 1H), 4.62 (d, J = 6.2 Hz, 1H), 5.18 (br. s, 1H), 6.98 (d, J = 6.8 Hz, 2H), 7.14 (d, J = 8.8Hz, 3H), 7.28-7.33 (m, 1H), 7.45-7.51 (m, 2H), 7.70 (dd, J = 8.1 Hz, 1.5 Hz, 1H), 7.81-7.87 (m, 1H), 7.91 (d, J = 1.5 Hz, 1H), 7.97 (d, J = 8.1 Hz, 1H) ppm. | 751 | NA |
| 48a | rac-(6R)-7-[4-bromo-3-(trifluoromethyl)benzoyl]-6-methyl-2-(2-methyl-1,3-benzoxazol-5-yl)-3-oxo-N-[(2-pyrimidin-4-ylphenyl)methyl]-6,8-dihydro-5H-imidazo[1,5-a]pyrazine-1-carboxamide | (400 MHz, CDCl$_3$) δ 8.70 (d, J = 2.0 Hz, 1H), 8.54 (s, 1H), 7.82 (d, J = 2.0 Hz, 2H), 7.59-7.37 (m, 7H), 7.13-7.05 (m, 2H), 6.71 (s, 1H), 5.37 (s, 2H), 4.66 (d, J = 8.0 Hz, 1H), 4.37-4.23 (m, 2H), 3.88 (d, J = 6.0 Hz, 1H), 3.73 (d, J = 4.0 Hz, 1H), 2.56 (s, 3H), 1.43 (d, J = 4.0 Hz, 3H). | 746 | Column: CHIRALPAK IE, 2*25 cm, 5 μm Mobile Phase A: MtBE(0.5% 2M NH$_3$-MeOH)--HPLC, Mobile Phase B: EtOH--HPLC; Flow rate: 15 mL/min; Gradient: 50% B to 50% B in 28.5 min; Wave Length: 220/254 nm |

TABLE C-continued

| Compound | Name | ¹H NMR | [M + H]⁺ | Separation Method |
|---|---|---|---|---|
| 48b | rac-(6S)-7-[4-bromo-3-(trifluoromethyl)benzoyl]-6-methyl-2-(2-methyl-1,3-benzoxazol-5-yl)-3-oxo-N-[(2-pyrimidin-4-ylphenyl)methyl]-6,8-dihydro-5H-imidazo[1,5-a]pyrazine-1-carboxamide | (400 MHz, CDCl$_3$) δ 8.70 (d, J = 2.0 Hz, 1H), 8.54 (s, 1H), 7.82 (d, J = 2.0 Hz, 2H), 7.59-7.37 (m, 2H), 7.13-7.05 (m, 2H), 6.71 (s, 1H), 5.37 (s, 2H), 4.66 (d, J = 8.0 Hz, 1H), 4.37-4.23 (m, 2H), 3.88 (d, J = 6.0 Hz, 1H), 3.73 (d, J = 4.0 Hz, 1H), 2.56 (s, 3H), 1.43 (d, J = 4.0 Hz, 3H). | 746 | Column: CHIRALPAK IE, 2*25 cm, 5 μm Mobile Phase A: MtBE(0.5% 2M NH$_3$-MeOH)--HPLC, Mobile Phase B: EtOH--HPLC; Flow rate: 15 mL/min; Gradient: 50% B to 50% B in 28.5 min; Wave Length: 220/254 nm |
| 49a | rac-(6R)-7-(4-bromo-3-chloro-benzoyl)-2-[4-(cyclopropoxy)phenyl]-N-[(2-fluoro-6-pyridazin-3-yl-phenyl)methyl]-6-methyl-3-oxo-6,8-dihydro-5H-imidazo[1,5-a]pyrazine-1-carboxamide | (400 MHz, CDCl$_3$) δ 9.17-9.15 (m, 1H), 7.69-7.56 (m, 4H), 7.45-7.39 (m, 1H), 7.21-7.14 (m, 5H), 6.71 (d, J = 4.0 Hz, 2H), 6.45-6.43 (m, 1H), 5.70-4.85 (m, 2H), 4.63 (d, J = 10.0 Hz, 1H), 4.44-4.39 (m, 1H), 4.27-4.23 (m, 1H), 3.86 (d, J = 8.0 Hz, 1H), 3.71-3.68 (m, 1H), 3.45-3.42 (m, 1H), 1.40 (d, J = 2.0 Hz, 3H), 0.67-0.63 (m, 2H), 0.57-0.49 (m, 2H). | 731 | Column: CHIRALPAK IA, 2*25 cm, 20 um Mobile Phase A: MtBE(0.5% 2M NH$_3$-MeOH)--HPLC, Mobile Phase B: IPA--HPLC; Flow rate: 16 mL/min; Gradient: 50% B to 50% B in 19 min; Wave Length: 220/254 nm |
| 49b | rac-(6S)-7-(4-bromo-3-chloro-benzoyl)-2-[4-(cyclopropoxy)phenyl]-N-[(2-fluoro-6-pyridazin-3-yl-phenyl)methyl]-6-methyl-3-oxo-6,8-dihydro-5H-imidazo[1,5-a]pyrazine-1-carboxamide | (400 MHz, CDCl$_3$) δ 9.17-9.15 (m, 1H), 7.69-7.56 (m, 4H), 7.45-7.39 (m, 1H), 7.21-7.14 (m, 5H), 6.71 (d, J = 4.0 Hz, 2H), 6.45-6.43 (m, 1H), 5.75-4.85 (m, 2H), 4.63 (d, J = 10.0 Hz, 1H), 4.44-4.39 (m, 1H), 4.27-4.23 (m, 1H), 3.87 (d, J = 8.0 Hz, 1H), 3.71-3.68 (m, 1H), 3.45-3.42 (m, 1H), 1.40 (d, J = 2.0 Hz, 3H), 0.70-0.63 (m, 2H), 0.57-0.49 (m, 2H). | 731 | Column: CHIRALPAK IA, 2*25 cm, 20 um Mobile Phase A: MtBE(0.5% 2M NH$_3$-MeOH)--HPLC, Mobile Phase B: IPA--HPLC; Flow rate: 16 mL/min; Gradient: 50% B to 50% B in 19 min; Wave Length: 220/254 nm |
| 50a | rac-(6R)-7-[4-bromo-3-(trifluoromethyl)benzoyl]-2-[4-(cyclopropoxy)phenyl]-N-[(2-fluoro-6-pyridazin-3-yl-phenyl)methyl]-6-methyl-3-oxo-6,8-dihydro-5H-imidazo[1,5-a]pyrazine-1-carboxamide | (400 MHz, CDCl$_3$) δ 9.16-9.15 (m, 1H), 7.83-7.77 (m, 2H), 7.64-7.56 (m, 2H), 7.47-7.39 (m, 2H), 7.21-7.14 (m, 4H), 6.70 (d, J = 4.0 Hz, 2H), 6.46-6.43 (m, 1H), 5.69-4.90 (m, 2H), 4.65 (d, J = 8.0 Hz, 1H), 4.44-4.39 (m, 1H), 4.25-4.22 (m, 1H), 3.87 (d, J = 6.0 Hz, 1H), 3.71 (d, J = 6.0 Hz, 1H), 3.44-3.41 (m Hz, 1H), 1.41 (d, J = 4.0 Hz, 3H), 0.69-0.62 (m, 2H), 0.56-0.49 (m, 2H). | 765 | Column: CHIRALPAK IF, 2*25 cm, 5 μm Mobile Phase A: MtBE(0.5% 2M NH$_3$-MeOH)--HPLC, Mobile Phase B: EtOH--HPLC; Flow rate: 12.5 mL/min; Gradient: 35% B to 35% B in 20 min; Wave Length: 220/254 nm |
| 50b | rac-(6S)-7-[4-bromo-3-(trifluoromethyl)benzoyl]-2-[4-(cyclopropoxy)phenyl]-N-[(2-fluoro-6-pyridazin-3-yl-phenyl)methyl]-6-methyl-3-oxo-6,8-dihydro-5H-imidazo[1,5-a]pyrazine-1-carboxamide | (400 MHz, CDCl$_3$) δ 9.17-9.15 (m, 1H), 7.83-7.77 (m, 2H), 7.64-7.57 (m, 2H), 7.47-7.39 (m, 2H), 7.21-7.14 (m, 4H), 6.71 (d, J = 4.0 Hz, 2H), 6.45-6.42 (m, 1H), 5.69-4.90 (m, 2H), 4.64 (d, J = 10.0 Hz, 1H), 4.44-4.39 (m, 1H), 4.24 (d, J = 4.0 Hz, 1H), 3.88 (d, J = 4.0 Hz, 1H), 3.72 (d, J = 6.0 Hz, 1H), 3.45-3.42 (m Hz, 1H), 1.41 (d, J = 4.0 Hz, 3H), 0.70-0.63 (m, 2H), 0.57-0.49 (m, 2H). | 765 | Column: CHIRALPAK IF, 2*25 cm, 5 μm Mobile Phase A: MtBE(0.5% 2M NH$_3$-MeOH)--HPLC, Mobile Phase B: EtOH--HPLC; Flow rate: 12.5 mL/min; Gradient: 35% B to 35% B in 20 min; Wave Length: 220/254 nm |
| 51a | rac-(6R)-7-(4-bromo-3-chloro-benzoyl)-2-[4-(cyclopropoxy)phenyl]-6-methyl-3-oxo-N-[[2-(1H-pyrazol-3-yl)phenyl]methyl]-6,8-dihydro-5H-imidazo[1,5-a]pyrazine-1-carboxamide | (400 MHz, CDCl$_3$) δ 7.78 (d, J = 8.1 Hz, 1H), 7.73-7.42 (m, 5H), 7.42-7.29 (m, 3H), 7.26-7.17 (m, 3H), 7.13-7.02 (m, 2H), 6.54 (s, 1H), 5.98 (s, 1H), 4.77-4.25 (m, 4H), 3.92 (d, J = 12.8 Hz, 1H), 3.78-3.61 (m, 2H), 1.37 (d, J = 6.8 Hz, 3H), 0.81 (d, J = 7.2 Hz, 4H). | 701 | Column: CHIRALPAK IE, 2*25 cm, 5 μm; Mobile Phase A: MtBE(0.5% 2M NH$_3$-MeOH)--HPLC Mobile Phase B: EtOH--HPLC; Flow rate: 20 mL/min; Gradient: 20% B to 20% B in 26 min; Wave Length: 220/254 nm |
| 51b | rac-(6S)-7-(4-bromo-3-chloro-benzoyl)-2-[4-(cyclopropoxy)phenyl]-6-methyl-3-oxo-N-[[2-(1H-pyrazol-3-yl)phenyl]methyl]-6,8-dihydro-5H-imidazo[1,5-a]pyrazine-1-carboxamide | (400 MHz, CDCl$_3$) δ 7.78 (d, J = 8.2 Hz, 1H), 7.72-7.42 (m, 5H), 7.42-7.29 (m, 3H), 7.26-7.17 (m, 3H), 7.07 (m, J = 8.5 Hz, 2H), 6.54 (s, 1H), 5.99 (s, 1H), 4.50 (m, J = 155.7, 16.0 Hz, 4H), 3.92 (d, J = 12.8 Hz, 1H), 3.77-3.62 (m, 2H), 1.37 (d, J = 6.8 Hz, 3H), 0.81 (d, J = 6.9 Hz, 4H). | 701 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 20% B to 20% B in 26 min; Wave Length: 220/254 nm |

TABLE C-continued

| Compound | Name | ¹H NMR | [M + H]⁺ | Separation Method |
|---|---|---|---|---|
| 52a | rac-(6S)-7-[4-bromo-3-(trifluoromethyl)benzoyl]-6-methyl-3-oxo-N-[(2-pyrimidin-4-ylphenyl)methyl]-2-[4-[(2S)-2-(trifluoromethyl)morpholin-4-yl]phenyl]-6,8-dihydro-5H-imidazo[1,5-a]pyrazine-1-carboxamide | (DMSO-$d_6$, 600 MHz, 80° C.) δ 1.28 (d, J = 6.7 Hz, 3H), 2.67 (t, J = 11.1 Hz, 1H), 2.75 (td, J = 12.0 Hz, 3.1 Hz, 1H), 3.44 (d, J = 11.8 Hz, 1H), 3.59 (d, J = 11.8 Hz, 1H), 3.64-3.72 (m, 2H), 3.75 (td, J = 11.4 Hz, 2.7 Hz, 1H), 4.08 (d, J = 11.0 Hz, 1H), 4.20-4.29 (m, 1H), 4.37 (d, J = 6.0 Hz, 2H), 4.47-4.78 (m, 2H), 5.20 (br. s.' 1H), 6.87 (d, J = 8.9 Hz, 2H), 7.01 (br. s., 1H), 7.11 (d, J = 8.6 Hz, 2H), 7.30 (br. s., 1H), 7.40-7.46 (m, 2H), 7.50-7.55 (m, 1H), 7.66 (dd, J = 5.2 Hz, 0.8 Hz, 1H), 7.70 (dd, J = 8.1 Hz, 1.4 Hz, 1H), 7.91 (d, J = 1.7 Hz, 1H), 7.97 (d, J = 8.0 Hz, 1H), 8.84 (d, J = 5.3 Hz, 1H), 9.05 (d, J = 0.7 Hz, 1H). | 844 | NA |
| 52b | rac-(6R)-7-[4-bromo-3-(trifluoromethyl)benzoyl]-6-methyl-3-oxo-N-[(2-pyrimidin-4-ylphenyl)methyl]-2-[4-[(2S)-2-(trifluoromethyl)morpholin-4-yl]phenyl]-6,8-dihydro-5H-imidazo[1,5-a]pyrazine-1-carboxamide | (DMSO-$d_6$, 600 MHz, 80° C.) δ 1.28 (d, J = 6.8 Hz, 3H), 2.67 (t, J = 11.2 Hz, 1H), 2.72-2.80 (m, 1H), 3.44 (d, J = 12.1 Hz, 1H), 3.59 (d, J = 11.6 Hz, 1H), 3.64-3.71 (m, 2H), 3.72-3.79 (m, 1H), 4.00-4.13 (m, 1H), 4.21-4.30 (m, 1H), 4.37 (d, J = 5.7 Hz, 2H), 4.51 (d, J = 18.2 Hz, 1H), 4.59 (br. s, 1H), 5.20 (br. s, 1H), 6.87 (d, J = 9.0 Hz, 2H), 7.01 (br. s, 1H), 7.11 (d, J = 8.8 Hz, 2H), 7.23-7.32 (m, 1H), 7.37-7.47 (m, 2H), 7.49-7.57 (m, 1H), 7.66 (dd, J = 0.9 Hz, 5.8 Hz, 1H), 7.70 (dd, J = 1.5 Hz, 8.3 Hz, 1H), 7.91 (d, J = 1.5 Hz, 1H), 7.97 (d, J = 8.1 Hz, 1H), 8.83 (d, J = 5.3 Hz, 1H), 9.05 (d, J = 0.7 Hz, 1H). | 844 | NA |
| 53a | rac-(6R)-7-(4-bromo-3-chloro-benzoyl)-6-methyl-2-(2-methyl-1,3-benzoxazol-5-yl)-N-[[2-(5-methyl-1,3,4-oxadiazol-2-yl)phenyl]methyl]-3-oxo-6,8-dihydro-5H-imidazo[1,5-a]pyrazine-1-carboxamide | (300 MHz, $CDCl_3$) δ 7.70 (t, J = 4.2 Hz 2H), 7.68-7.52 (m, 2H), 7.50-7.40 (m, 3H), 7.40-7.30 (m, 1H), 7.22-7.10 (m, 2H), 6.81 (d, J = 5.7 Hz 1H), 5.90-4.78 (m, 2H), 4.70-4.45 (m, 3H), 3.84 (d, J = 12.6 Hz, 1H), 3.75-3.50 (m, 1H), 2.70 (s, 3H), 2.55 (s, 3H), 1.38 (d, J = 6.9 Hz 3H). | 716 | Column: CHIRAL ART Cellulose-SB, 2*25 cm, 5 μm Mobile Phase A: MtBE(0.5% 2M $NH_3$-MeOH)--HPLC, Mobile Phase B: EtOH--HPLC; Flow rate: 20 mL/min; Gradient: 50% B to 50% B in 35 min; Wave Length: 220/254 nm |
| 53b | rac-(6S)-7-(4-bromo-3-chloro-benzoyl)-6-methyl-2-(2-methyl-1,3-benzoxazol-5-yl)-N-[[2-(5-methyl-1,3,4-oxadiazol-2-yl)phenyl]methyl]-3-oxo-6,8-dihydro-5H-imidazo[1,5-a]pyrazine-1-carboxamide | 300 MHz, $CDCl_3$) δ 7.80-7.60 (m, 2H), 7.56 (t, J = 4.6 Hz 2H), 7.50-7.38 (m, 3H), 7.38-7.30 (m, 1H), 7.20-7.10 (m, 2H), 6.82 (s, 1H), 5.90-4.80 (m, 2H), 4.65-4.32 (m, 3H), 3.90-3.59 (m, 2H), 2.70 (s, 3H), 2.55 (s, 3H), 1.38 (d, J = 6.9 Hz 3H). | 716 | Column: CHIRAL ART Cellulose-SB, 2*25 cm, 5 μm Mobile Phase A: MtBE(0.5% 2M $NH_3$-MeOH)--HPLC, Mobile Phase B: EtOH--HPLC; Flow rate: 20 mL/min; Gradient: 50% B to 50% B in 35 min; Wave Length: 220/254 nm |
| 54a | rac-(6R)-7-[4-bromo-3-(trifluoromethyl)benzoyl]-6-methyl-2-(2-methyl-1,3-benzoxazol-5-yl)-N-[[2-(5-methyl-1,3,4-oxadiazol-2-yl)phenyl]methyl]-3-oxo-6,8-dihydro-5H-imidazo[1,5-a]pyrazine-1-carboxamide | (300 MHz, $CDCl_3$) δ 7.80 (d, J = 8.4 Hz 2H), 7.75-7.65 (m, 1H), 7.64-7.38 (m, 5H), 7.36-7.28 (m, 1H), 7.24-7.02 (m, 1H), 6.81 (t, J = 6.0 Hz 1H), 5.90-4.80 (m, 2H), 4.76-4.35 (m, 3H), 3.83 (t, J = 6.3 Hz 1H), 3.78-3.55 (m, 1H), 2.69 (s, 3H), 2.54 (s, 3H), 1.60 (s, 3H). | 750 | Column: CHIRALPAK IA, 2*25 cm, 5 μm Mobile Phase A: MtBE(0.5% 2M $NH_3$-MeOH)--HPLC, Mobile Phase B: EtOH--HPLC; Flow rate: 20 mL/min; Gradient: 30% B to 30% B in 21 min; Wave Length: 220/254 nm |
| 54b | rac-(6S)-7-[4-bromo-3-(trifluoromethyl)benzoyl]-6-methyl-2-(2-methyl-1,3-benzoxazol-5-yl)-N-[[2-(5-methyl-1,3,4-oxadiazol-2-yl)phenyl]methyl]-3-oxo-6,8-dihydro-5H-imidazo[1,5-a]pyrazine-1-carboxamide | (400 MHz, $CDCl_3$) δ 7.81 (d, J = 8.0 Hz 2H), 7.75-7.68 (m, 1H), 7.54 (t, J = 6.0 Hz 1H), 7.52-7.45 (m, 2H), 7.45-7.35 (m, 2H), 7.35-7.28 (m, 1H), 7.20-7.10 (m, 1H), 6.82 (s, 1H), 5.80-4.80 (m, 2H), 4.80-4.40 (m, 3H), 3.85 (d, J = 12.4 Hz 1H), 3.70 (d, J = 9.2 Hz 1H), 2.69 (s, 3H), 2.54 (s, 3H), 1.40 (d, J = 6.8 Hz 3H). | 750 | Column: CHIRALPAK IA, 2*25 cm, 5 μm Mobile Phase A: MtBE(0.5% 2M $NH_3$-MeOH)--HPLC, Mobile Phase B: EtOH--HPLC; Flow rate: 20 mL/min; Gradient: 30% B to 30% B in 21 min; Wave Length: 220/254 nm |
| 128 | N-benzyl-7-(4-bromo-3-chloro-benzoyl)-2-[1-(2-hydroxyethyl)indol-5-yl]-3-oxo-6,8-dihydro-5H-imidazo[1,5-a]pyrazine-1-carboxamide | (DMSO-$d_6$, 600 MHz, 80° C.) δ 3.69-3.71 (m, J = 6.1 Hz, 2H), 3.76-3.79 (m, 2H), 3.85 (br s, 2H), 4.18 (d, J = 6.1 Hz, 2H), 4.24 (t, J = 6.1 Hz, 2H), 4.68 (t, J = 5.4 Hz, 1H), 4.89 (s, 2H), 6.46 (d, J = 3.3 Hz, 1H), 6.80 (br s, 1H), 6.86 (d, J = 7.5 | 650 | NA |

TABLE C-continued

| Compound | Name | ¹H NMR | [M + H]⁺ | Separation Method |
|---|---|---|---|---|
| | | Hz, 2H), 7.02 (dd, J = 8.9 Hz, 1.9 Hz, 1H), 7.10-7.15 (m, 3H), 7.41 (dd, J= 8.4 Hz, 2.3 Hz, 1H), 7.44 (d, J = 3.3 Hz, 1H), 7.48 (s, 1H), 7.49 (s, 1H), 7.75 (d, J = 1.9 Hz, 1H), 7.85 (d, J = 8.4 Hz, 1H) ppm. | | |
| 56a | (6RS)-7-[4-bromo-3-(trifluoromethyl)benzoyl]-2-[4-[(2R)-2-hydroxypropoxy]phenyl]-6-methyl-3-oxo-N-[(2-pyridazin-3-ylphenyl)methyl]-6,8-dihydro-5H-imidazo[1,5-a]pyrazine-1-carboxamide | (400 MHz, CDCl₃) δ 9.12-9.11 (m, 1H), 7.82 (s, 1H), 7.77 (d, J = 4.0 Hz, 1H), 7.64-7.61 (m, 1H), 7.57-7.52 (m, 1H), 7.46-7.44 (m, 4H), 7.40-7.27 (m, 1H), 7.12 (d, J = 4.0 Hz, 2H), 6.84 (d, J = 4.0 Hz, 1H), 6.56 (d, J = 4.0 Hz, 2H), 5.23 (s, 2H), 4.67-4.63 (m, 1H), 4.35-4.25 (m, 2H), 4.08-4.05 (m, 1H), 3.87 (d, J = 6.0 Hz, 1H), 3.72-3.67 (m, 2H), 3.52 (d, J = 4.0 Hz, 1H), 2.28 (s, 1H), 1.41 (d, J = 4.0 Hz, 3H), 1.25-1.22 (m, 3H). | 765 | Column: CHIRAL ART Amylose-SA, 2*25 cm, 5 μm; Mobile Phase A: Hex: DCM = 3: 1(0.5% 2M NH₃-MeOH)--HPLC, Mobile Phase B: IPA--HPLC; Flow rate: 20 mL/min; Gradient: 20% B to 20% B in 12.5 min; Wave Length: 254/220 nm |
| 56b | (6SR)-7-[4-bromo-3-(trifluoromethyl)benzoyl]-2-[4-[(2R)-2-hydroxypropoxy]phenyl]-6-methyl-3-oxo-N-[(2-pyridazin-3-ylphenyl)methyl]-6,8-dihydro-5H-imidazo[1,5-a]pyrazine-1-carboxamide | (400 MHz, CDCl₃) δ 9.12-9.11 (m, 1H), 7.82 (s, 1H), 7.77 (d, J = 4.0 Hz, 1H), 7.64-7.61 (m, 1H), 7.57-7.52 (m, 1H), 7.46-7.44 (m, 4H), 7.40-7.27 (m, 1H), 7.12 (d, J = 4.0 Hz, 2H), 6.84 (d, J = 4.0 Hz, 1H), 6.56 (d, J = 4.0 Hz, 2H), 5.23 (s, 2H), 4.67-4.63 (m, 1H), 4.35-4.25 (m, 2H), 4.08-4.05 (m, 1H), 3.87 (d, J = 6.0 Hz, 1H), 3.72-3.67 (m, 2H), 3.52 (d, J = 4.0 Hz, 1H), 2.28 (s, 1H), 1.41 (d, J = 4.0 Hz, 3H), 1.25-1.22 (m, 3H). | 765 | Column: CHIRAL ART Amylose-SA, 2*25 cm, 5 μm; Mobile Phase A: Hex: DCM = 3: 1(0.5% 2M NH₃-MeOH)--HPLC, Mobile Phase B: IPA--HPLC; Flow rate: 20 mL/min; Gradient: 20% B to 20% B in 12.5 min; Wave Length: 254/220 nm |
| 57a | (6RS)-7-[4-bromo-3-(trifluoromethyl)benzoyl]-2-[4-[(2S)-2-hydroxypropoxy]phenyl]-6-methyl-3-oxo-N-[(2-pyridazin-3-ylphenyl)methyl]-6,8-dihydro-5H-imidazo[1,5-a]pyrazine-1-carboxamide | (400 MHz, CDCl₃) δ 9.12-9.10 (m, 1H), 7.82-7.76 (m, 2H), 7.64 (d, J = 2.0 Hz, 1H), 7.62-7.54 (m, 1H), 7.46-7.38 (m, 5H), 7.12 (d, J = 4.0 Hz, 2H), 6.85-6.82 (m, 1H), 6.62-6.55 (m, 2H), 5.85-4.90 (s 2H), 4.66 (d, J = 10.0 Hz, 1H), 4.36-4.25 (m, 2H), 4.09-4.03 (m, 1H), 3.87 (d, J = 6.0 Hz, 1H), 3.72-3.62 (m, 2H), 3.51-3.47 (m, 1H), 2.50-2.10 (s, 1H), 1.41 (d, J = 4.0 Hz, 3H), 1.25-1.22 (m, 3H). | 765 | Column: CHIRALPAK IF, 2*25 cm, 5 μm; Mobile Phase A: MtBE(0.1% DEA)-HPLC, Mobile Phase B: EtOH--HPLC; Flow rate: 20 mL/min; Gradient: 30% B to 30% B in 16 min; Wave Length: 220/254 nm |
| 57b | (6SR)-7-[4-bromo-3-(trifluoromethyl)benzoyl]-2-[4-[(2S)-2-hydroxypropoxy]phenyl]-6-methyl-3-oxo-N-[(2-pyridazin-3-ylphenyl)methyl]-6,8-dihydro-5H-imidazo[1,5-a]pyrazine-1-carboxamide | (400 MHz, CDCl₃) δ 9.12-9.10 (m, 1H), 7.82-7.76 (m, 2H), 7.64 (d, J = 2.0 Hz, 1H), 7.62-7.54 (m, 1H), 7.46-7.40 (m, 4H),7.39-7.38 (m, 1H), 7.12 (d, J = 4.0 Hz, 2H), 6.85-6.82 (m, 1H), 6.56 (d, J = 4.0 Hz, 2H), 5.85-4.90 (s, 2H), 4.65 (d, J = 10.0 Hz, 1H), 4.35-4.25 (m, 2H), 4.09-4.05 (m, 1H), 3.87 (d, J = 6.0 Hz, 1H), 3.72-3.67 (m, 2H), 3.53-3.48 (m, 1H), 2.28 (s, 1H), 1.41 (d, J = 4.0 Hz, 3H), 1.25-1.22 (m, 3H). | 765 | Column: CHIRALPAK IF, 2*25 cm, 5 μm; Mobile Phase A: MtBE(0.1% DEA)-HPLC, Mobile Phase B: EtOH--HPLC; Flow rate: 20 mL/min; Gradient: 30% B to 30% B in 16 min; Wave Length: 220/254 nm |
| 129 | N-benzyl-7-(4-bromo-3-chlorobenzoyl)-2-[4-(3-hydroxycyclobutoxy)phenyl]-3-oxo-6,8-dihydro-5H-imidazo[1,5-a]pyrazine-1-carboxamide | (DMSO-d₆, 600 MHz, 80° C.) δ 2.32-2.34 (m, 4H), 3.67-3.69 (m, 2H), 3.83 (br s 2H), 4.25 (d, J = 5.4 Hz, 2H), 4.38-4.43 (m, 1H), 4.79-4.93 (m, 4H), 6.82 (d, J = 8.8 Hz, 2H), 7.05 (d, J = 6.5 Hz, 2H), 7.14-7.27 (m, 6H), 7.39 (dd, J = 8.2 Hz, 1.8 Hz, 1H), 7.74 (d, J = 1.7 Hz, 1H), 7.85 (d, J = 8.1 Hz, 1H) ppm. | 652 | NA |
| 58a | (6RS)-7-[4-bromo-3-(trifluoromethyl)benzoyl]-2-[4-[(2S)-2-hydroxypropoxy]phenyl]-6-methyl-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.77-8.74 (m, 2H), 7.82 (d, J = 4.0 Hz, 2H), 7.54-7.41 (m, 6H), 7.15 (d, J = 4.0 Hz, 2H), 6.84-6.81 (m, 1H), 6.64 (d, J = 4.0 Hz, 2H), 5.23 (s, 2H), 4.65(d, J = 8.0 Hz, 1H), 4.45-4.32 (m, 2H), 4.09-3.84 (m, 1H), 3.74-3.69 (m, 1H), 3.58-3.54 (m, 2H), 2.54 (s, 1H), 1.41 (d, J = 4.0 Hz, 3H), 1.26 (d, J = 2.0 Hz, 3H). | 765 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 14 mL/min; Gradient: 20% B to 20% B in 30 min; Wave Length: 220/254 nm |
| 58b | (6SR)-7-[4-bromo-3-(trifluoromethyl)benzoyl]-2-[4-[(2S)-2-hydroxypropoxy]phenyl]-6-methyl-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.77-8.74 (m, 2H), 7.82 (d, J = 4.0 Hz, 2H), 7.54-7.41 (m, 6H), 7.15 (d, J = 4.0 Hz, 2H), 6.84-6.81 (m, 1H), 6.64 (d, J = 4.0 Hz, 2H), 5.23 (s, 2H), 4.65 (d, J = 8.0 Hz, 1H), 4.45-4.32 (m, 2H), 4.09-3.84 (m, 1H), 3.74-3.69 (m, 1H), 3.58-3.54 (m, 2H), 2.54 (s, 1H), 1.41 (d, J = 4.0 Hz, 3H), 1.26 (d, J = 2.0 Hz, 3H). | 765 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 14 mL/min; Gradient: 20% B to 20% B in 30 min; Wave Length: 220/254 nm |

TABLE C-continued

| Compound | Name | ¹H NMR | [M + H]⁺ | Separation Method |
|---|---|---|---|---|
| 59a | rac-(6R)-7-[4-bromo-3-(trifluoromethyl)benzoyl]-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl$_3$) δ 8.61 (d, J = 4.9 Hz, 2H), 8.13 (dd, J = 5.7, 3.6 Hz, 1H), 7.84 (d, J = 7.7 Hz, 2H), 7.47 (ddd, J = 9.3, 6.9, 2.8 Hz, 4H), 7.19 (t, J = 4.9 Hz, 1H), 7.13-6.94 (m, 3H), 6.73 (d, J = 8.7 Hz, 2H), 5.70-4.38 (m, 5H), 3.87 (d, J = 12.8 Hz, 1H), 3.73 (d, J = 13.5 Hz, 1H), 3.45 (dt, J = 6.0, 3.0 Hz, 1H), 1.43 (d, J = 7.0 Hz, 3H), 0.71 (t, J = 6.1 Hz, 2H), 0.60 (t, J = 3.8 Hz, 2H). | 747 | Column: CHIRALPAK IA, 2*25 cm, 20 um; Mobile Phase A: MtBE(0.5% 2M NH$_3$-MeOH)--HPLC, Mobile Phase B: EtOH--HPLC; Flow rate: 16 mL/min; Gradient: 30% B to 30% B in 14 min; Wave Length: 220/254 nm |
| 59b | rac-(6S)-7-[4-bromo-3-(trifluoromethyl)benzoyl]-2-[4-(cyclopropoxy)phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl3) δ 8.61 (d, J = 4.9 Hz, 2H), 8.13 (dd, J = 5.5, 3.6 Hz, 1H), 7.88-7.80 (m, 2H), 7.47 (ddd, J = 9.3, 6.9, 2.8 Hz, 4H), 7.19 (t, J = 4.9 Hz, 1H), 7.14-6.95 (m, 3H), 6.73 (d, J = 8.8 Hz, 2H), 5.53-4.39 (m, 5H), 3.87 (d, J = 12.5 Hz, 1H), 3.73 (d, J = 10.8 Hz, 1H), 3.45 (dt, J = 6.0, 3.1 Hz, 1H), 1.43 (d, J = 7.0 Hz, 3H), 0.78-0.66 (m, 2H), 0.59 (d, J = 2.9 Hz, 2H). | 747 | Column: CHIRALPAK IA, 2*25 cm, 20 um; Mobile Phase A: MtBE(0.5% 2M NH$_3$-MeOH)--HPLC, Mobile Phase B: EtOH--HPLC; Flow rate: 16 mL/min; Gradient: 30% B to 30% B in 14 min; Wave Length: 220/254 nm |
| 60a | (6RS)-7-[4-bromo-3-(trifluoromethyl)benzoyl]-2-[4-[(2R)-2-hydroxypropoxy]phenyl]-6-methyl-3-oxo-N-[[2-(2-pyridyl)phenyl]methyl]-6,8-dihydro-5H-imidazo[1,5-a]pyrazine-1-carboxamide | (300 MHz, CDCl$_3$) δ 8.24 (d, J = 4.6 Hz, 1H), 7.88-7.67 (m, 3H), 7.51-7.35 (m, 6H), 7.25-7.08 (m, 4H), 6.64-6.56 (m, 2H), 5.70-4.82 (m, 2H), 4.68 (d, J = 18.8 Hz, 1H), 4.47-4.15 (m, 2H), 4.06 (s, 1H), 3.92-3.80 (m, 1H), 3.78-3.57 (m, 2H), 3.55-3.43 (m, 1H), 2.19 (s, 1H), 1.43 (d, J = 7.0 Hz, 3H), 1.24 (d, J = 6.4 Hz, 3H) | 764 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 20% B to 20% B in 16 min; Wave Length: 220/254 nm |
| 60b | (6SR)-7-[4-bromo-3-(trifluoromethyl)benzoyl]-2-[4-[(2R)-2-hydroxypropoxy]phenyl]-6-methyl-3-oxo-N-[[2-(2-pyridyl)phenyl]methyl]-6,8-dihydro-5H-imidazo[1,5-a]pyrazine-1-carboxamide | (300 MHz, CDCl$_3$) δ 8.24 (d, J = 4.9 Hz, 1H), 7.87-7.71 (m, 3H), 7.52-7.35 (m, 6H), 7.23-7.09 (m, 4H), 6.64-6.57 (m, 2H), 6.00-4.80 (m, 2H), 4.68 (d, J = 18.8 Hz, 1H), 4.44-4.17 (m, 2H), 4.07 (d, J = 18.8 Hz, 1H), 3.98-3.80 (m, 1H), 3.80-3.58 (m, 2H), 3.55-3.42 (m, 1H), 2.19 (s, 1H), 1.43 (d, J = 7.0 Hz, 3H), 1.24 (d, J = 6.4 Hz, 3H). | 764 | Column: CHIRALPAK IE, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 20% B to 20% B in 16 min; Wave Length: 220/254 nm |
| 61a | (6RS)-7-[4-bromo-3-(trifluoromethyl)benzoyl]-2-[4-[(2S)-2-hydroxypropoxy]phenyl]-6-methyl-3-oxo-N-[[2-(2-pyridyl)phenyl]methyl]-6,8-dihydro-5H-imidazo[1,5-a]pyrazine-1-carboxamide | (300 MHz, CDCl$_3$) δ 8.25 (s, 1H), 7.87-7.71 (m, 3H), 7.52-7.35 (m, 6H), 7.25-7.08 (m, 4H), 6.61 (d, J = 8.7 Hz, 2H), 6.00-4.80 (m, 2H), 4.68 (d, J = 18.7 Hz, 1H), 4.44-4.19 (m, 2H), 4.14-4.00 (m, 1H), 3.94-3.82 (m, 1H), 3.79-3.59 (m, 2H), 3.56-3.42 (m, 1H), 2.18 (s, 1H), 1.43 (d, J = 7.0 Hz, 3H), 1.24 (d, J = 6.4 Hz, 3H). | 764 | Column: CHIRALPAK IF, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 20% B to 20% B in 16 min; Wave Length: 220/254 nm |
| 61b | (6SR)-7-[4-bromo-3-(trifluoromethyl)benzoyl]-2-[4-[(2S)-2-hydroxypropoxy]phenyl]-6-methyl-3-oxo-N-[[2-(2-pyridyl)phenyl]methyl]-6,8-dihydro-5H-imidazo[1,5-a]pyrazine-1-carboxamide | (300 MHz, CDCl$_3$) δ 8.26 (s, 1H), 7.89-7.68 (m, 3H), 7.53-7.34 (m, 6H), 7.25-7.07 (m, 4H), 6.61 (d, J = 8.5 Hz, 2H), 5.90-4.82 (s, 2H), 4.68 (d, J = 18.8 Hz, 1H), 4.47-4.17 (m, 2H), 4.14-3.95 (m, 1H), 3.88 (d, J = 12.8 Hz, 1H), 3.82-3.58 (m, 2H), 3.52 (t, J = 8.4 Hz, 1H), 1.43 (d, J = 7.0 Hz, 3H), 1.24 (d, J = 6.4 Hz, 3H). | 764 | Column: CHIRALPAK IF, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 20% B to 20% B in 16 min; Wave Length: 220/254 nm |
| 62a | (6RS)-7-[4-bromo-3-(trifluoromethyl)benzoyl]-6-methyl-3-oxo-N-[(2-pyrimidin-4-ylphenyl)methyl]-2-[4-[(2R)-3,3,3-trifluoro-2-hydroxy-propoxy]phenyl]-6,8-dihydro-5H-imidazo[1,5-a]pyrazine-1-carboxamide | (400 MHz, CDCl$_3$) δ 8.73 (d, J = 4.0 Hz, 1H), 8.66 (s, 1H), 7.83 (d, J = 4.0 Hz, 2H), 7.59-7.41 (m, 6H), 7.18 (d, J = 6.0 Hz, 2H), 6.76-6.70 (m, 3H), 5.35 (s, 2H), 4.66-4.55(m, 2H), 4.47-4.42 (m, 2H), 4.38-4.31 (m, 1H), 4.12 (d, J = 2.0 Hz, 1H), 3.98-3.93 (m, 1H), 3.85(d, J = 6.0 Hz, 1H), 3.71-3.67 (m, 1H), 1.40 (d, J = 4.0 Hz, 3H). | 819 | Column: CHIRAL ART Cellulose-SB, 2*25 cm, 5 μm; Mobile Phase A: MtBE(0.5% 2M NH$_3$-MeOH)--HPLC, Mobile Phase B: EtOH--HPLC; Flow rate: 20 mL/min; Gradient: 25% B to 25% B in 13 min; Wave Length: 220/254 nm |
| 62b | ((6SR)-7-[4-bromo-3-(trifluoromethyl)benzoyl]-6-methyl-3-oxo-N-[(2-pyrimidin-4-ylphenyl)methyl]-2-[4-[(2R)-3,3,3-trifluoro-2-hydroxy-propoxy]phenyl]- | (400 MHz, CDCl$_3$) δ 8.73 (d, J = 4.0 Hz, 1H), 8.66 (s, 1H), 7.83 (d, J = 4.0 Hz, 2H), 7.59-7.41 (m, 6H), 7.18 (d, J = 6.0 Hz, 2H), 6.76-6.70 (m, 3H), 5.35 (s, 2H), 4.66-4.55 (m, 2H), 4.47-4.42 (m, 2H), | 819 | Column: CHIRAL ART Cellulose-SB, 2*25 cm, 5 μm; Mobile Phase A: MtBE(0.5% 2M NH$_3$-MeOH)--HPLC, Mobile |

TABLE C-continued

| Compound | Name | ¹H NMR | [M + H]⁺ | Separation Method |
|---|---|---|---|---|
| | 6,8-dihydro-5H-imidazo[1,5-a]pyrazine-1-carboxamide | 4.38-4.31 (m, 1H), 4.12 (d, J = 2.0 Hz, 1H), 3.98-3.93 (m, 1H), 3.85 (d, J = 6.0 Hz, 1H), 3.71-3.67 (m, 1H), 1.40 (d, J = 4.0 Hz, 3H). | | Phase B: EtOH--HPLC; Flow rate: 20 mL/min; Gradient: 25% B to 25% B in 13 min; Wave Length: 220/254 nm |
| 63a | (6RS)-7-[4-bromo-3-(trifluoromethyl)benzoyl]-6-methyl-3-oxo-N-[(2-pyrimidin-4-ylphenyl)methyl]-2-4-[(2S)-3,3,3-trifluoro-2-hydroxy-propoxy]phenyl]-6,8-dihydro-5H-imidazo[1,5-a]pyrazine-1-carboxamide | (400 MHz, CDCl₃) δ 8.73 (d, J = 4.0 Hz, 1H), 8.66 (s, 1H), 7.83 (d, J = 4.0 Hz, 2H), 7.59-7.41 (m, 6H), 7.18 (d, J = 6.0 Hz, 2H), 6.76-6.70 (m, 3H), 5.35 (s, 2H), 4.66-4.55 (m, 2H), 4.47-4.42 (m, 2H), 4.38-4.31 (m, 1H), 4.12 (d, J = 2.0 Hz, 1H), 3.98-3.93 (m, 1H), 3.85(d, J = 6.0 Hz, 1H), 3.71-3.67 (m, 1H), 1.40 (d, J = 4.0 Hz, 3H). | 819 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 14 min; Wave Length: 220/254 nm |
| 63b | (6SR)-7-[4-bromo-3-(trifluoromethyl)benzoyl]-6-methyl-3-oxo-N-[(2-pyrimidin-4-ylphenyl)methyl]-2-4-[(2S)-3,3,3-trifluoro-2-hydroxy-propoxy]phenyl]-6,8-dihydro-5H-imidazo[1,5-a]pyrazine-1-carboxamide | (400 MHz, CDCl₃) δ 8.73 (d, J = 4.0 Hz, 1H), 8.66 (s, 1H), 7.83 (d, J = 4.0 Hz, 2H), 7.59-7.41 (m, 6H), 7.18 (d, J = 6.0 Hz, 2H), 6.76-6.70 (m, 3H), 5.35 (s, 2H), 4.66-4.55(m, 2H), 4.47-4.42 (m, 2H), 4.38-4.31 (m, 1H), 4.12 (d, J = 2.0 Hz, 1H), 3.98-3.93 (m, 1H), 3.85(d, J = 6.0 Hz, 1H), 3.71-3.67 (m, 1H), 1.40 (d, J = 4.0 Hz, 3H). | 819 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 14 min; Wave Length: 220/254 nm |
| 64a | (6RS)-7-[4-bromo-3-(trifluoromethyl)benzoyl]-2-[4-[(2R)-2-hydroxypropoxy]phenyl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.62 (d, J = 5.0 Hz, 2H), 8.23-8.12 (m, 1H), 7.85 (d, J = 7.7 Hz, 2H), 7.48 (q, J = 6.3, 4.3 Hz, 4H), 7.20 (t, J = 4.9 Hz, 1H), 7.08 (d, J = 8.5 Hz, 2H), 6.96 (s, 1H), 6.54 (d, J = 8.7 Hz, 2H), 5.32 (s, 1H), 4.73-4.54 (m, 2H), 4.46 (d, J = 13.4 Hz, 1H), 4.12 (td, J = 7.0, 3.0 Hz, 1H), 3.87 (d, J = 12.7 Hz, 1H), 3.79-3.63 (m, 2H), 3.52 (t, J = 8.4 Hz, 1H), 2.09 (s, 1H), 1.43 (d, J = 7.0 Hz, 3H), 1.29 (d, J = 6.4 Hz, 3H). | 765 | Column: CHIRAL ART Cellulose-SB, 2*25 cm, 5 μm; Mobile Phase A: MtBE(0.5% 2M NH3-MeOH)--HPLC, Mobile Phase B: EtOH--HPLC; Flow rate: 20 mL/min; Gradient: 25% B to 25% B in 18.5 min; Wave Length: 220/254 nm |
| 64b | (6SR)-7-[4-bromo-3-(trifluoromethyl)benzoyl]-2-[4-[(2R)-2-hydroxypropoxy]phenyl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.61 (d, J = 4.9 Hz, 2H), 8.23-8.12 (m, 1H), 7.85 (d, J = 6.5 Hz, 2H), 7.59-7.38 (m, 4H), 7.19 (t, J = 4.9 Hz, 1H), 7.08 (d, J = 8.3 Hz, 2H), 6.97 (s, 1H), 6.54 (d, J = 8.3 Hz, 2H), 5.32 (s, 1H), 4.63 (dd, J = 41.9, 15.6 Hz, 2H), 4.50-4.41 (m, 1H), 4.17-4.06 (m, 1H), 3.87 (d, J = 12.9 Hz, 1H), 3.80-3.59 (m, 2H), 3.52 (t, J = 8.5 Hz, 1H), 2.09 (s, 1H), 1.43 (d, J = 6.9 Hz, 3H), 1.29 (d, J = 6.4 Hz, 3H). | 765 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 18.5 min; Wave Length: 220/254 nm |
| 65a | (6RS)-7-[4-bromo-3-(trifluoromethyl)benzoyl]-2-[4-[(2S)-2-hydroxypropoxy]phenyl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.61 (d, J = 4.9 Hz, 2H), 8.18 (dd, J = 6.0, 3.2 Hz, 1H), 7.91-7.78 (m, 2H), 7.49 (dq, J = 12.7, 4.7 Hz, 4H), 7.18 (t, J = 4.9 Hz, 1H), 7.08 (d, J = 8.7 Hz, 2H), 6.97 (s, 1H), 6.58-6.49 (m, 2H), 5.32-4.11 (m, 5H), 3.87 (d, J = 12.8 Hz, 1H), 3.77-3.60 (m, 2H), 3.52 (t, J = 8.3 Hz, 1H), 2.09 (s, 1H), 1.43 (d, J = 6.9 Hz, 3H), 1.29 (d, J = 6.4 Hz, 3H). | 765 | Column:CHIRAL ART 65 Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 19 min; Wave Length: 220/254 nm |
| 65b | (6SR)-7-[4-bromo-3-(trifluoromethyl)benzoyl]-2-[4-[(2S)-2-hydroxypropoxy]phenyl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.62 (d, J = 4.9 Hz, 2H), 8.19 (dd, J = 5.9, 3.4 Hz, 1H), 7.85 (d, J = 7.2 Hz, 2H), 7.59-7.37 (m, 4H), 7.20 (t, J = 4.9 Hz, 1H), 7.08 (d, J = 8.5 Hz, 2H), 6.96 (s, 1H), 6.54 (d, J = 8.5 Hz, 2H), 5.30-4.12 (m, 5H), 3.87 (d, J = 12.7 Hz, 1H), 3.79-3.61 (m, 2H), 3.55-3.47 (m, 1H), 2.09 (s, 1H), 1.43 (d, J = 7.0 Hz, 3H), 1.29 (d, J = 6.4 Hz, 3H). | 765 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 19 min; Wave Length: 220/254 nm |
| 66a | (6RS)-7-[4-bromo-3-(trifluoromethyl)benzoyl]-6-methyl-3-oxo-N-[(2-pyridazin-3-ylphenyl)methyl]-2-[4-[(2R)-3,3,3-trifluoro-2-hydroxy-propoxy]phenyl]-6,8-dihydro-5H-imidazo[1,5-a]pyrazine-1-carboxamide | (300 MHz, CDCl₃) δ 9.08 (d, J = 4.0 Hz, 1H), 7.82-7.76 (m, 2H), 7.63-7.31 (m, 7H), 7.12-7.05 (m, 2H), 6.77 (d, J = 10.0 Hz, 1H), 6.53 (d, J = 6.0 Hz, 2H), 5.46-4.88 (m, 2H), 4.65 (d, J = 12.0 Hz, 1H), 4.47-4.01 (m, 4H), 3.95-3.68 (m, 4H), 1.41 (d, J = 4.0 Hz, 3H). | 819 | Column: CHIRALPAK IE, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 30% B to 30% B in 21 min; Wave Length: 220/254 nm |

TABLE C-continued

| Compound | Name | ¹H NMR | [M + H]⁺ | Separation Method |
|---|---|---|---|---|
| 66b | (6SR)-7-[4-bromo-3-(trifluoromethyl)benzoyl]-6-methyl-3-oxo-N-[(2-pyridazin-3-ylphenyl)methyl]-2-4-[(2R)-3,3,3-trifluoro-2-hydroxy-propoxy]phenyl]-6,8-dihydro-5H-imidazo[1,5-a]pyrazine-1-carboxamide | (300 MHz, CDCl₃) δ 9.09-9.07 (m, 1H), 7.82-7.77 (m, 2H), 7.64-7.35 (m, 7H), 7.10 (d, J = 4.0 Hz, 2H), 6.76-6.72 (m, 1H), 6.55 (d, J = 6.0 Hz, 2H), 5.46-5.06 (m, 2H), 4.68-4.58 (m, 1H), 4.36-3.69 (m, 8H), 1.41 (d, J = 4.0 Hz, 3H). | 819 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 30% B to 30% B in 21 min; Wave Length: 220/254 nm |
| 67a | (6RS)-7-[4-bromo-3-(trifluoromethyl)benzoyl]-6-methyl-3-oxo-N-[(2-pyridazin-3-ylphenyl)methyl]-2-4-[(2S)-3,3,3-trifluoro-2-hydroxy-propoxy]phenyl]-6,8-dihydro-5H-imidazo[1,5-a]pyrazine-1-carboxamide | (300 MHz, CDCl₃) δ 9.09 (d, J = 4.0 Hz, 1H), 7.83-7.74 (m, 2H), 7.65-7.55 (m, 2H), 7.49-7.29 (m, 5H), 7.11 (d, J = 6.0 Hz, 2H), 6.72 (s, 1H), 6.55 (d, J = 6.0 Hz, 2H), 5.10-4.94 (s, 1H), 4.65 (d, J = 12.0 Hz, 1H), 4.36-3.65 (m, 8H), 1.41 (d, J = 4.0 Hz, 3H). | 819 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 11 min; Wave Length: 220/254 nm |
| 67b | (6SR)-7-[4-bromo-3-(trifluoromethyl)benzoyl]-6-methyl-3-oxo-N-[(2-pyridazin-3-ylphenyl)methyl]-2-4-[(2S)-3,3,3-trifluoro-2-hydroxy-propoxy]phenyl]-6,8-dihydro-5H-imidazo[1,5-a]pyrazine-1-carboxamide | (300 MHz, CDCl₃) δ 9.10 (d, J = 4.0 Hz, 1H), 7.83-7.77 (m, 2H), 7.67-7.59 (m, 2H), 7.49-7.35 (m, 5H), 7.24-7.10 (m, 2H), 6.70 (d, J = 2.0 Hz, 1H), 6.55 (d, J = 6.0 Hz, 2H), 5.47-5.02 (s, 1H), 4.65 (d, J = 12.0 Hz, 1H), 4.37-3.68 (m, 8H), 1.41 (m, 3H). | 819 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 11 min; Wave Length: 220/254 nm |
| 68a | (6RS)-7-[4-bromo-3-(trifluoromethyl)benzoyl]-6-methyl-3-oxo-N-[[2-(2-pyridyl)phenyl]methyl]-2-[4-[(2R)-3,3,3-trifluoro-2-hydroxy-propoxy]phenyl]-6,8-dihydro-5H-imidazo[1,5-a]pyrazine-1-carboxamide | (300 MHz, CDCl₃) δ 8.26 (s, 1H), 7.88-7.70 (m, 3H), 7.53-7.34 (m, 6H), 7.23 (s, 1H), 7.17-6.99 (m, 3H), 6.56 (d, J = 8.5 Hz, 2H), 5.34 (s, 2H), 4.68 (d, J = 18.8 Hz, 1H), 4.46-4.30 (m, 1H), 4.28-4.18 (m, 1H), 4.10 (s, 1H), 3.94-3.58 (m, 5H), 1.43 (d, J = 7.0 Hz, 3H). | 818 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 11 min; Wave Length: 220/254 nm; RT1(min) |
| 68b | (6SR)-7-[4-bromo-3-(trifluoromethyl)benzoyl]-6-methyl-3-oxo-N-[[2-(2-pyridyl)phenyl]methyl]-2-[4-[(2R)-3,3,3-trifluoro-2-hydroxy-propoxy]phenyl]-6,8-dihydro-5H-imidazo[1,5-a]pyrazine-1-carboxamide | (300 MHz, CDCl₃) δ 8.26 (s, 1H), 7.89-7.70 (m, 3H), 7.54-7.34 (m, 6H), 7.26-6.98 (m, 4H), 6.56 (d, J = 8.5 Hz, 2H), 6.20-4.80 (m, 1H), 4.68 (d, J = 18.6 Hz, 1H), 4.40-4.30 (m, 1H), 4.29-4.07 (m, 2H), 4.03-3.63 (m, 5H), 1.44 (d, J = 6.9 Hz, 3H). | 818 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 11 min; Wave Length: 220/254 nm; RT1(min) |
| 69a | (6RS)-7-[4-bromo-3-(trifluoromethyl)benzoyl]-6-methyl-3-oxo-N-[[2-(2-pyridyl)phenyl]methyl]-2-[4-[(2S)-3,3,3-trifluoro-2-hydroxy-propoxy]phenyl]-6,8-dihydro-5H-imidazo[1,5-a]pyrazine-1-carboxamide | (300 MHz, CDCl₃) δ 8.26 (s, 1H), 7.88-7.71 (m, 3H), 7.54-7.34 (m, 6H), 7.23 (s, 1H) 7.18-7 09 (m, 2H) 7.04 (d J = 6.3 Hz, 1H) δ.56. (d j = 8.4, Hz 2H) δ.00-4.80 (m, 2H), 4.68 (d, J = 18.8 Hz, 1H), 4.42-4.30 (m, 1H), 4.27-4.03 (m, 2H), 3.96-3.66 (m, 4H), 3.61 (s, 1H), 1.44 (d, J = 7.0 Hz, 3H). | 818 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 12.5 min; Wave Length: 220/254 nm |
| 69b | (6SR)-7-[4-bromo-3-(trifluoromethyl)benzoyl]-6-methyl-3-oxo-N-[[2-(2-pyridyl)phenyl]methyl]-2-[4-[(2S)-3,3,3-trifluoro-2-hydroxy-propoxy]phenyl]-6,8-dihydro-5H-imidazo[1,5-a]pyrazine-1-carboxamide | (300 MHz, CDCl₃) δ 8.23 (s, 1H), 7.89-7.69 (m, 3H), 7.53-7.33 (m, 6H), 7.23 (t, J = 6.4 Hz, 1H), 7.18-7.08 (m, 2H), 7.09-6.99 (m, 1H), 6.56 (d, J = 8.5 Hz, 2H), 6.10-4.90 (m, 2H), 4.68 (d, J = 18.8 Hz, 1H), 4.40-4.30 (m, 1H), 4.29-4.04 (m, 2H), 3.96-3.68 (m, 4H), 3.60 (s, 1H), 1.43 (d, J = 7.0 Hz, 3H). | 818 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 25% B to 25% B in 12.5 min; Wave Length: 220/254 nm |

TABLE C-continued

| Compound | Name | ¹H NMR | [M + H]⁺ | Separation Method |
|---|---|---|---|---|
| 70a | rac-(6R)-7-[4-bromo-3-(trifluoromethyl)benzoyl]-6-methyl-3-oxo-2-[4-(2-oxobutoxy)phenyl]-N-[(2-pyrimidin-2-ylphenyl)methyl]-6,8-dihydro-5H-imidazo[1,5-a]pyrazine-1-carboxamide | (300 MHz, CDCl₃) δ 8.62-8.57 (m, 2H), 8.13-8.10 (m, 1H), 7.83-7.81 (m, 2H), 7.61-7.36 (m, 4H), 7.22-7.19 (m, 1H), 7.10 (d, J = 6.0 Hz, 2H), 6.99 (s, 1H), 6.53 (d, J = 6.0 Hz, 2H), 5.41-5.02 (m, 2H), 4.68-4.39 (m, 3H), 4.32 (d, J = 6.0 Hz, 2H), 3.86-3.67 (m,2H), 2.59-2.50 (m, 2H), 1.40 (d, J = 4.0 Hz, 3H), 1.26-1.14 (m, 3H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 30% B to 30% B in 14 min; Wave Length: 220/254 nm |
| 70b | rac-(6S)-7-[4-bromo-3-(trifluoromethyl)benzoyl]-6-methyl-3-oxo-2-[4-(2-oxobutoxy)phenyl]-N-[(2-pyrimidin-2-ylphenyl)methyl]-6,8-dihydro-5H-imidazo[1,5-a]pyrazine-1-carboxamide | (400 MHz, CDCl₃) δ 8.64-8.59 (m, 2H), 8.13-8.11 (m, 1H), 7.83-7.77 (m, 2H), 7.52-7.29 (m, 4H), 7.25-7.22 (m, 1H), 7.10 (d, J = 6.0 Hz, 2H), 6.99 (d, J = 4.0 Hz, 1H), 6.53 (d, J = 4.0 Hz, 2H), 5.39-5.10 (m, 2H), 4.65 (d, J = 10.0 Hz, 1H), 4.54-4.48 (m, 1H), 4.42 (d, J = 6.0 Hz, 1H), 4.32 (s, 2H), 3.84 (d, J = 6.0 Hz, 1H), 3.70 (d, J = 4.0 Hz, 1H), 2.61-2.51 (m, 2H), 1.41-1.36 (m, 3H), 1.19-1.10 (m, 3H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 30% B to 30% B in 14 min; Wave Length: 220/254 nm |
| 72a | rac-(6R)-7-[4-bromo-3-(trifluoromethyl)benzoyl]-6-methyl-3-oxo-N-[(2-pyrimidin-4-ylphenyl)methyl]-2-[1-(2,2,2-trifluoroethyl)indazol-5-yl]-6,8-dihydro-SH-imidazo[1,5-a]pyrazine-1-carboxamide | (400 MHz, CDCl₃) δ 8.66 (d, J = 5.3 Hz, 1H), 8.56 (s, 1H), 7.86-7.82 (m, 2H), 7.63 (s, 1H), 7.57-7.38 (m, 6H), 7.33 (d, J = 5.4 Hz, 1H), 7.25-7.23 (m, 2H), 7.06 (s, 1H), 5.36 (s, 2H), 4.75-4.73 (m, 3H), 4.38 (s, 1H), 4.27-4.17 (m, 1H), 3.91 (d, J = 12.8 Hz, 1H), 3.78 (d, J = 12.7 Hz, 1H), 1.47 (d, J = 6.9 Hz, 3H). | 813 | Column: Lux Sum Celluloes-3, 2.12*25 cm, 5 μm; Mobile Phase A: CO₂, Mobile Phase B: IPA: ACN = 2:1; Flow rate: 100 mL/min; Gradient: isocratic 40% B; Column Temperature(° C.): 35; Back Pressure(bar): 100; Wave Length: 220 nm |
| 72b | rac-(6S)-7-[4-bromo-3-(trifluoromethyl)benzoyl]-6-methyl-3-oxo-N-[(2-pyrimidin-4-ylphenyl)methyl]-2-[1-(2,2,2-trifluoroethyl)indazol-5-yl]-6,8-dihydro-SH-imidazo[1,5-a]pyrazine-1-carboxamide | (400 MHz, CDCl₃) δ 8.65 (d, J = 5.3 Hz, 1H), 8.55 (s, 1H), 7.96-7.82 (m, 2H), 7.63 (s, 1H), 7.59-7.38 (m, 6H), 7.32 (dd, J = 5.3, 1.4 Hz, 1H), 7.25-7.23 (m, 2H), 7.07 (s, 1H), 5.39 (s, 2H), 4.75-4.73 (m, 3H), 4.36 (d, J = 8.7 Hz, 1H), 4.27-4.17 (m, 1H), 3.91 (d, J = 12.8 Hz, 1H), 3.77 (d, J = 12.8 Hz, 1H), 1.46 (d, J = 7.0 Hz, 3H). | 813 | Column: Lux Sum Celluloes-3, 2.12*25 cm, 5 μm; Mobile Phase A: CO2, Mobile Phase B: IPA: ACN=2: 1; Flow rate: 100 mL/min; Gradient: isocratic 40% B; Column Temperature(° C.): 35; Back Pressure(bar): 100; Wave Length: 220 nm |
| 74a | rac-(6R)-7-[4-bromo-3-(trifluoromethyl)benzoyl]-2-[4-[(1-hydroxycyclopropyl)methoxy]phenyl]-6-methyl-3-oxo-N-[(2-pyrimidin-4-ylphenyl)methyl]-6,8-dihydro-SH-imidazo[1,5-a]pyrazine-1-carboxamide | (400 MHz, CDCl₃) δ 8.77-8.73 (m, 2H), 7.82 (d, J = 4.0 Hz, 2H), 7.57-7.41 (m, 6H), 7.13 (d, J = 4.0 Hz, 2H), 6.81-6.78 (m, 1H), 6.69 (d, J = 6.0 Hz, 2H), 5.80-4.96 (m, 2H), 4.65 (d, J = 10.0 Hz, 1H), 4.47-4.35 (m, 2H), 3.87-3.81 (m, 3H), 3.70 (d, J = 4.0 Hz, 1H), 3.30 (s, 1H), 1.40 (d, J =2.0 Hz, 3H), 0.98-0.90 (m, 2H), 0.74-0.66 (m, 2H). | 777 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 13 mL/min; Gradient: 30% B to 30% B in 30 min; Wave Length: 220/254 nm |
| 74b | rac-(6S)-7-[4-bromo-3-(trifluoromethyl)benzoyl]-2-[4-[(1-hydroxycyclopropyl)methoxy]phenyl]-6-methyl-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.76-8.73 (m, 2H), 7.82 (d, J = 4.0 Hz, 2H), 7.57-7.41 (m, 6H), 7.13 (d, J = 4.0 Hz, 2H), 6.81-6.78 (m, 1H), 6.69 (d, J = 6.0 Hz, 2H), 5.80-4.87 (m, 2H), 4.65 (d, J = 10.0 Hz, 1H), 4.47-4.34 (m, 2H), 3.87-3.81 (m, 3H), 3.70 (d, J = 6.0 Hz, 1H), 3.32 (s, 1H), 1.40 (d, J =2.0 Hz, 3H), 0.97-0.90 (m, 2H), 0.73-0.66 (m, 2H). | 777 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 13 mL/min; Gradient: 30% B to 30% B in 30 min; Wave Length: 220/254 nm |
| 75a | (6RS)-7-[4-bromo-3-(trifluoromethyl)benzoyl]-6-methyl-3-oxo-N-[(2-pyrimidin-2-ylphenyl)methyl]-2-[4-[(2S)-3,3,3-trifluoro-2-hydroxy-propoxy]phenyl]-6,8-dihydro-5H-imidazo[1,5-a]pyrazine-1-carboxamide | (400 MHz, CDCl₃) δ 8.59 (d, J = 4.0 Hz, 2H), 8.16-8.12 (m, 1H), 7.84-7.82 (m, 2H), 7.52-7.43 (m, 4H), 7.18-7.16 (m, 1H), 7.05 (d, J = 4.0 Hz, 2H), 6.84 (s, 1H), 6.47 (d, J = 4.0 Hz, 2H), 5.22 (s, 2H) 4.68-4.55 (m, 2H), 4.48-4.43 (m, 1H; 4.22 (s, 1H), 3.93-3.79 (m, 1H), 3.85-3.81 (m, 2H), 3.71 (d, J = 6.0 Hz, 1H), 3.53 (s, 1H), 1.41 (d, J = 2.0 Hz, 3H). | 819 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 10 min; Wave Length: 220/254 nm |
| 75b | (6SR)-7-[4-bromo-3-(trifluoromethyl)benzoyl]-6-methyl-3-oxo-N-[(2-pyrimidin-2-ylphenyl)methyl]-2-[4-[(2S)-3,3,3- | (400 MHz, CDCl₃) δ 8.59 (d, J = 4.0 Hz, 2H), 8.16-8.12 (m, 1H), 7.84-7.82 (m, 2H), 7.52-7.43 (m, 4H), 7.18-7.16 (m, 1H), 7.05 (d, J = 4.0 Hz, 2H), 6.84 (s, | 819 | Column: CHIRAL ART Amylose-SA, 2*25 cm, 5 μm; Mobile Phase A: MtBE(0.5% 2M NH₃- |

TABLE C-continued

| Compound | Name | ¹H NMR | [M + H]⁺ | Separation Method |
|---|---|---|---|---|
| | trifluoro-2-hydroxy-propoxy]phenyl]-6,8-dihydro-5H-imidazo[1,5-a]pyrazine-1-carboxamide | 1H), 6.47 (d, J = 4.0 Hz, 2H), 5.22 (s, 2H), 4.68-4.55 (m, 2H), 4.48-4.43 (m, 1H), 4.22 (s, 1H), 3.93-3.79 (m, 1H), 3.85-3.81 (m, 2H), 3.71 (d, J = 6.0 Hz, 1H), 3.53 (s, 1H), 1.41 (d, J = 2.0 Hz, 3H). | | MeOH)--HPLC, Mobile Phase B: EtOH--HPLC; Flow rate: 20 mL/min; Gradient: 20% B to 20% B in 10 min; Wave Length: 220/254 nm |
| 76a | rac-(6R)-7-[4-bromo-3-(trifluoromethyl)benzoyl]-6-methyl-2-[4-(6-methyl-2,6-diazaspiro[3.3]heptan-2-yl)phenyl]-3-oxo-N-[(2-pyridazin-3-ylphenyl)methyl]-6,8-dihydro-5H-imidazo[1,5-a]pyrazine-1-carboxamide | (400 MHz, CDCl₃) δ 9.14 (dd, J = 4.8, 1.8 Hz, 1H), 7.82 (s, 1H), 7.78 (d, J = 8.2 Hz, 1H),7.75-7.50 (m, 2H) 7.49-7.35 (m, 5H), 7.09-7.03 (m, 2H), 6.52 (t, J = 6.0 Hz, 1H), 6.15 (d, J = 8.6 Hz, 2H), 5.24 (s, 1H), 4.65 (d, J = 18.7 Hz, 1H), 4.34 (qd, J = 14.2, 5.8 Hz, 2H), 3.89 (d, J = 12.8 Hz, 1H), 3.76 (s, 5H), 3.43 (s, 4H), 2.39 (s, 3H), 1.42 (d, J = 6.9 Hz, 3H). | 801 | Column: (R, R)-WHELK-01-Kromasil, 5*25 cm, 5 μm; Mobile Phase A: Hex: DCM=1:1(0.5% 2M NH₃-MeOH)--HPLC, Mobile Phase B: EtOH--HPLC; Flow rate: 20 mL/min; Gradient: 15% B to 15% B in 16 min; Wave Length: 220/254 nm |
| 76b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[(2-pyridazin-3-ylphenyl)methyl]-6,8-dihydro-5H-imidazo[1,5-a]pyrazine-1-carboxamide | (400 MHz, CDCl₃) δ 9.14 (dd, J = 4.8, 1.8 Hz, 1H), 7.87-7.74 (m, 2H), 7.65-7.53 (m, 2H), 7.49-7.35 (m, 5H), 7.09-7.03 (m, 2H), 6.52 (t, J = 6.0 Hz, 1H), 6.15 (d, J = 8.6 Hz, 2H), 5.24 (s, 1H), 4.65 (d, J = 18.7 Hz, 1H), 4.34 (qd, J = 14.2, 5.8 Hz, 2H), 3.89 (d, J = 12.8 Hz, 1H), 3.76 (s, 5H), 3.43 (s, 4H), 2.39 (s, 3H), 1.42 (d, J = 6.9 Hz, 3H). | 801 | Column: (R,R)-WHELK-01-Kromasil, 5*25 cm, 5 μm; Mobile Phase A: Hex: DCM = 1:1(0.5% 2M NH₃-MeOH)--HPLC, Mobile Phase B: EtOH--HPLC; Flow rate: 20 mL/min; Gradient: 15% B to 15% B in 16 min; Wave Length: 220/254 nm |
| 77a | rac-(6R)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-(2-pyridyl)phenyl]methyl]-6,8-dihydro-5H-imidazo[1,5-a]pyrazine-1-carboxamide | (400 MHz, CDCl₃) δ 8.29 (d, J = 4.8 Hz, 1H), 7.87-7.79 (m, 2H), 7.74 (td, J = 7.7, 1.8 Hz, 1H), 7.50-7.34 (m, 6H), 7.21-7.16 (m, 1H), 7.07-7.00 (m, 2H), 6.92 (t, J = 6.0 Hz, 1H), 6.14 (d, J = 8.7 Hz, 2H) 5.28 (s, 1H), 4.68 (d, J = 19.0 Hz, 1H), 4.45-4.31 (m, 1H), 4.24 (dd, J = 13.7, 5.7 Hz, 1H), 3.88 (d, J = 12.7 Hz, 1H), 3.69 (s, 5H), 3.47 (s, 4H), 2.43 (s, 3H), 1.42 (d, J = 6.9 Hz, 3H). | 800 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 15.5 min; Wave Length: 254/220 nm |
| 77b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-(2-pyridyl)phenyl]methyl]-6,8-dihydro-5H-imidazo[1,5-a]pyrazine-1-carboxamide | (400 MHz, CDCl₃) δ 8.29 (d, J = 4.8 Hz, 1H), 7.87-7.79 (m, 2H), 7.74 (td, J = 7.7, 1.8 Hz, 1H), 7.50-7.34 (m, 6H), 7.21-7.16 (m, 1H), 7.07-7.00 (m, 2H), 6.92 (t, J = 6.0 Hz, 1H), 6.14 (d, J = 8.7 Hz, 2H) 5.28 (s, 1H), 4.68 (d, J = 19.0 Hz, 1H), 4.45-4.31 (m, 1H), 4.24 (dd, J = 13.7, 5.7 Hz, 1H), 3.88 (d, J = 12.7 Hz, 1H), 3.69 (s, 5H), 3.47 (s, 4H), 2.43 (s, 3H), 1.42 (d, J = 6.9 Hz, 3H). | 800 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 15.5 min; Wave Length: 254/220 nm |
| 78a | rac-(6R)-7-[4-bromo-3-(trifluoromethyl)benzoyl]-6-methyl-2-[4-(6-methyl-2,6-diazaspiro[3.3]heptan-2-yl)phenyl]-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.58 (d, J = 4.9 Hz, 2H), 8.14-8.03 (m, 1H), 7.87-7.75 (m, 2H), 7.44 (ddt, J = 9.3, 6.0, 2.9 Hz, 4H), 7.14 (t, J = 4.9 Hz, 1H), 6.93 (dd, J = 7.2, 5.0 Hz, 3H), 5.98 (d, J = 8.6 Hz, 2H), 5.27 (s, 1H), 4.76-4.33 (m, 3H), 3.84 (d, J = 12.8 Hz, 1H), 3.66 (s, 5H), 3.43 (s, 4H), 2.38 (s, 3H), 1.39 (d, J = 7.0 Hz, 3H). | 801 | Column: Lux Sum Celluloes-3, 3*25 cm, 5 μm; Mobile Phase A: CO₂, Mobile Phase B: MeOH(0.2% DEA); Flow rate: 70 mL/min; Gradient: isocratic 40% B; Column Temperature(° C.): 35; Back Pressure(bar): 100; Wave Length: 220 nm |
| 78b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.61 (d, J = 4.8 Hz, 2H), 8.15-8.10 (m, 1H), 7.90-7.81 (m, 2H), 7.52-7.42 (m, 4H), 7.17 (t, J = 4.9 Hz, 1H), 6.99-6.85 (m, 3H), 6.01 (d, J = 8.5 Hz, 2H), 5.32 (s, 1H), 4.74-4.51 (m, 2H), 4.46-4.37 (m, 1H), 3.91-3.83 (m, 1H), 3.77-3.64 (m, 5H), 3.49 (s, 4H), 2.42 (s, 3H), 1.42 (d, J = 7.0 Hz, 3H). | 801 | Column: Lux Sum Celluloes-3, 3*25 cm, 5 μm; Mobile Phase A: CO₂, Mobile Phase B: MeOH(0.2% DEA); Flow rate: 70 mL/min; Gradient: isocratic 40% B; Column Temperature(° C.): 35; Back Pressure(bar): 100; Wave Length: 220 nm |

TABLE C-continued

| Compound | Name | ¹H NMR | [M + H]⁺ | Separation Method |
|---|---|---|---|---|
| 79a | rac-(6R)-7-[4-bromo-3-(trifluoromethyl)benzoyl]-6-methyl-3-oxo-N-[(2-pyrimidin-4-ylphenyl)methyl]-2-[2-(2,2,2-trifluoroethyl)indazol-5-yl]-6,8-dihydro-5H-imidazo[1,5-a]pyrazine-1-carboxamide | (400 MHz, CDCl₃) δ 8.58 (d, J = 2.8 Hz, 1H), 8.47 (s, 1H), 7.90-7.80 (m, 3H), 7.70 (s, 1H), 7.60-7.40 (m, 4H), 7.40-7.28 (m, 2H), 7.22-7.10 (m, 1H), 6.95-6.70 (m, 1H), 5.80-5.00 (m, 2H), 5.00-4.80 (m, 2H), 4.69 (d, J = 9.8 Hz 1H), 4.38 (d, J = 2.6 Hz 1H), 4.30-4.10 (m, 1H), 3.88 (d, J = 6.4 Hz, 1H), 3.75 (d, J = 3.5 Hz, 1H), 1.44 (d, J = 3.4 Hz, 3H). | 813 | Column: CHIRALPAK IA, 3*25 cm, 5 μm Mobile Phase A: CO₂, Mobile Phase B: MeOH(0.2% DEA); Flow rate: 70 mL/min; Gradient: isocratic 40% B; Column Temperature(° C.): 35; Back Pressure(bar): 100; Wave Length: 220 nm |
| 79b | rac-(6S)-7-[4-bromo-3-(trifluoromethyl)benzoyl]-6-methyl-3-oxo-N-[(2-pyrimidin-4-ylphenyl)methyl]-2-[2-(2,2,2-trifluoroethyl)indazol-5-yl]-6,8-dihydro-5H-imidazo[1,5-a]pyrazine-1-carboxamide | (400 MHz, CDCl₃) δ 8.58 (d, J = 2.8 Hz, 1H), 8.47 (s, 1H), 7.90-7.80 (m, 3H), 7.70 (s, 1H), 7.60-7.40 (m, 4H), 7.40-7.28 (m, 2H), 7.22-7.10 (m, 1H), 6.95-6.70 (m, 1H), 5.80-5.00 (m, 2H), 5.00-4.80 (m, 2H), 4.69 (d, J = 9.8 Hz 1H), 4.38 (d, J = 2.6 Hz 1H), 4.30-4.10 (m, 1H), 3.88 (d, J = 6.4 Hz, 1H), 3.75 (d, J = 3.5 Hz, 1H), 1.44 (d, J = 3.4 Hz, 3H). | 813 | Column: CHIRALPAK IA, 3*25 cm, 5 μm Mobile Phase A: CO₂, Mobile Phase B: MeOH(0.2% DEA); Flow rate: 70 mL/min; Gradient: isocratic 40% B; Column Temperature(° C.): 35; Back Pressure(bar): 100; Wave Length: 220 nm |
| 80a | rac-(6R)-7-[4-bromo-3-(trifluoromethyl)benzoyl]-6-methyl-2-[4-(2-methyl-2,7-diazaspiro[3.5]nonan-7-yl)phenyl]-3-oxo-N-[(2-pyrimidin-4-ylphenyl)methyl]-6,8-dihydro-5H-imidazo[1,5-a]pyrazine-1-carboxamide | (300 MHz, CDCl₃) δ 8.79-8.72 (m, 2H), 7.82 (d, J = 6.0 Hz, 2H), 7.51-7.39 (m, 6H), 7.06 (d, J = 6.0 Hz, 2H), 6.86-6.82 (m, 1H), 6.61 (d, J = 6.0 Hz, 2H), 5.69-4.85 (s, 1H), 4.65 (d, J = 12.0 Hz, 1H), 4.44-4.28 (m, 2H), 3.86 (d, J = 10.0 Hz, 1H), 3.73-3.65 (m, 1H), 3.21 (s, 4H), 2.89-2.80 (m, 4H), 2.48 (s, 3H), 1.82-1.79 (m, 4H), 1.42-1.31 (m, 3H). | 829 | Column: CHIRALPAK IE, 2*25 cm, 5 μm; Mobile Phase A: MtBE(0.5% 2M NH₃-MeOH)--HPLC, Mobile Phase B: MeOH--HPLC; Flow rate: 20 mL/min; Gradient: 50% B to 50% B in 25 min; Wave Length: 220/254 nm |
| 80b | rac-(6S)-7-[4-bromo-3-(trifluoromethyl)benzoyl]-6-methyl-2-[4-(2-methyl-2,7-diazaspiro[3.5]nonan-7-yl)phenyl]-3-oxo-N-[(2-pyrimidin-4-ylphenyl)methyl]-6,8-dihydro-5H-imidazo[1,5-a]pyrazine-1-carboxamide | (300 MHz, CDCl₃) δ 8.80 (s, 1H), 8.73 (d, J = 4.0 Hz, 1H), 7.82 (d, J = 6.0 Hz, 2H), 7.50-7.39 (m, 6H), 7.05 (d, J = 6.0 Hz, 2H), 6.86-6.82 (m, 1H), 6.60 (d, J = 6.0 Hz, 2H), 5.85-4.85 (s, 1H), 4.65 (d, J = 12.0 Hz, 1H), 4.44-4.28 (m, 2H), 3.85 (d, J = 10.0 Hz, 1H), 3.70 (d, J = 12.0 Hz, 1H), 3.10 (s, 4H), 2.88-2.85 (m, 4H), 2.47 (s, 3H), 1.87-1.71 (m, 4H), 1.42-1.33 (m, 3H). | 829 | Column: CHIRALPAK IE, 2*25 cm, 5 μm; Mobile Phase A: MtBE(0.5% 2M NH₃-MeOH)--HPLC, Mobile Phase B: MeOH--HPLC; Flow rate: 20 mL/min; Gradient: 50% B to 50% B in 25 min; Wave Length: 220/254 nm |
| 81a | rac-(6R)-7-[4-bromo-3-(trifluoromethyl)benzoyl]-2-[4-[(1-hydroxycyclopropyl)methoxy]phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.66-8.58 (m, 2H), 8.18-8.14 (m, 1H), 7.87-7.77 (m, 2H), 7.49-7.33 (m, 4H), 7.23-7.15 (m 1H), 7.06-7.00 (m, 2H), 6.92 (d, J = 4.0 Hz, 1H), 6.53 (d, J = 6.0 Hz, 1H), 5.79-4.85 (s, 1H), 4.69-4.42 (m, 3H), 3.84 (d, J = 8.0 Hz, 1H), 3.66 (m, d, J = 12.0 Hz, 3H), 3.08-1.82 (m, 1H), 1.40 (d, J = 4.0 Hz, 3H), 0.99-0.89 (m, 2H), 0.69-0.60 (m, 2H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 22 min; Wave Length: 220/254 nm |
| 81b | rac-(6S)-7-[4-bromo-3-(trifluoromethyl)benzoyl]-2-[4-[(1-hydroxycyclopropyl)methoxy]phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.62-8.58 (m, 2H), 8.16-8.13 (m, 1H), 7.82 (d, J = 6.0 Hz, 2H), 7.49-7.42 (m, 4H), 7.18-7.15 (m, 1H), 7.05 (d, J = 6.0 Hz, 2H), 6.96-6.91 (m, 1H), 6.53 (d, J = 6.0 Hz, 2H), 5.40-4.42 (m, 5H), 3.84 (d, J = 8.0 Hz, 1H), 3.70 (s, 3H), 3.04-2.34 (m, 1H), 1.40 (d, J = 4.0 Hz, 3H), 0.99-0.94 (m, 2H), 0.69-0.64 (m, 2H). | 777 | Column: CHIRALPAK IE, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 22 min; Wave Length: 220/254 nm |
| 82a | rac-(6R)-7-[4-bromo-3-(trifluoromethyl)benzoyl]-6-methyl-3-oxo-N-[(2-pyrimidin-4-ylphenyl)methyl]-2-[4-[rac-(2R)-3,3,3-trifluoro-2-hydroxy-2-methyl-propoxy]phenyl]-6,8-dihydro-5H-imidazo[1,5-a]pyrazine-1-carboxamide | (400 MHz, CDCl₃) δ 8.74 (d, J = 2.0 Hz, 2H), 7.83-7.81 (m, 2H), 7.57-7.42 (m, 6H), 7.14 (d, J = 4.0 Hz, 2H), 6.83-6.80 (m, 1H), 6.63 (d, J = 4.0 Hz, 2H), 5.35 (s, 2H), 4.65 (d, J = 8.0 Hz, 1H), 4.45-4.33 (m, 2H), 3.88-3.69 (m, 5H), 1.58-1.40 (m, 6H). | 833 | Column: Lux Sum Cellulose-2, 2.12*25 cm, 5 μm; Mobile Phase A: Hex(0.5% 2M NH₃-MeOH)--HPLC, Mobile Phase B: EtOH--HPLC; Flow rate: 20 mL/min; Gradient: 50% B to 50% B in 52 min; Wave Length: 254/220 nm |
| 82b | rac-(6S)-7-[4-bromo-3-(trifluoromethyl)benzoyl]-6-methyl-3-oxo-N-[(2-pyrimidin-4-ylphenyl)methyl]-2-[4-[rac-(2R)-3,3,3-trifluoro-2-hydroxy-2-methyl- | (400 MHz, CDCl₃) δ 8.74 (d, J = 2.0 Hz, 2H), 7.83-7.81 (m, 2H), 7.57-7.42 (m, 6H), 7.14 (d, J = 4.0 Hz, 2H), 6.83-6.80 (m, 1H), 6.63 (d, J = 4.0 Hz, 2H), 5.35 (s, 2H), 4.65 (d, J = 8.0 Hz, 1H), 4.45-4.33 | 833 | Column: Lux Sum Cellulose-2, 2.12*25 cm, 5 μm; Mobile Phase A: Hex(0.5% 2M NH₃-MeOH)--HPLC, Mobile |

TABLE C-continued

| Compound | Name | ¹H NMR | [M + H]⁺ | Separation Method |
|---|---|---|---|---|
| | propoxy]phenyl]-6,8-dihydro-5H-imidazo[1,5-a]pyrazine-1-carboxamide | (m, 2H), 3.88-3.69 (m, 5H), 1.58-1.40 (m, 6H). | | Phase B: EtOH--HPLC; Flow rate: 20 mL/min; Gradient: 50% B to 50% B in 52 min; Wave Length: 254/220 nm |
| 83a | rac-(6R)-7-[4-bromo-3-(trifluoromethyl)benzoyl]-6-methyl-3-oxo-N-[(2-pyrimidin-4-ylphenyl)methyl]-2-[4-[rac-(2S)-3,3,3-trifluoro-2-hydroxy-2-methyl-propoxy]phenyl]-6,8-dihydro-5H-imidazo[1,5-a]pyrazine-1-carboxamide | (400 MHz, CDCl₃) δ 8.74 (d, J = 2.0 Hz, 2H), 7.83-7.81 (m, 2H), 7.57-7.42 (m, 6H), 7.14 (d, J = 4.0 Hz, 2H), 6.83-6.80 (m, 1H), 6.63 (d, J = 4.0 Hz, 2H), 5.35 (s, 2H), 4.65 (d, J = 8.0 Hz, 1H), 4.45-4.33 (m, 2H), 3.88-3.69 (m, 5H), 1.58-1.40 (m, 6H). | 833 | Column: Lux Sum Cellulose-2, 2.12*25 cm, 5 μm; Mobile Phase A: Hex(0.5% 2M NH₃-MeOH)--HPLC, Mobile Phase B: EtOH--HPLC; Flow rate: 20 mL/min; Gradient: 50% B to 50% B in 47 min; Wave Length: 254/220 nm |
| 84a | rac-(6R)-7-[4-bromo-3-(trifluoromethyl)benzoyl]-6-methyl-2-[4-(1-methyl-1,6-diazaspiro[3.3]heptan-6-yl)phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.83 (s, 1H), 8.76 (d, J = 5.3 Hz, 1H), 7.83 (d, J = 8.2 Hz, 2H), 7.57-7.41 (m, 6H), 7.06 (d, J = 8.6 Hz, 2H), 6.79 (t, J = 6.2 Hz, 1H), 6.31-6.14 (m, 2H), 5.28 (s, 2H), 4.67 (d, J = 18.9 Hz, 1H), 4.39 (qd, J = 13.7, 6.1 Hz, 2H), 3.90 (dd, J = 20.0, 10.4 Hz, 3H), 3.71 (dd, J = 8.5, 2.6 Hz, 3H), 3.25 (s, 2H), 2.40 (s, 5H), 1.42 (d, J = 7.0 Hz, 3H). | 801 | Column: CHIRALPAK IE, 3*25 cm, 5 μm Mobile Phase A: MtBE(0.5% 2M NH₃-MeOH)--HPLC, Mobile Phase B: EtOH--HPLC; Flow rate: 27 mL/min; Gradient: 50% B to 50% B in 50 min; Wave Length: 220/254 nm |
| 84b | rac-(6S)-7-[4-bromo-3-(trifluoromethyl)benzoyl]-6-methyl-2-[4-(1-methyl-1,6-diazaspiro[3.3]heptan-6-yl)phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.83 (s, 1H), 8.76 (d, J = 5.3 Hz, 1H), 7.83 (d, J = 8.2 Hz, 2H), 7.57-7.41 (m, 6H), 7.06 (d, J = 8.6 Hz, 2H), 6.79 (t, J = 6.2 Hz, 1H), 6.31-6.14 (m, 2H), 5.28 (s, 1H), 4.67 (d, J = 18.9 Hz, 1H), 4.39 (qd, J = 13.7, 6.1 Hz, 2H), 3.90 (dd, J = 20.0, 10.4 Hz, 3H), 3.71 (dd, J = 8.5, 2.6 Hz, 3H), 3.25 (s, 2H), 2.40 (s, 5H), 1.42 (d, J = 7.0 Hz, 3H). | 801 | Column: CHIRALPAK IE, 3*25 cm, 5 μm Mobile Phase A: MtBE(0.5% 2M NH₃-MeOH)--HPLC, Mobile Phase B: EtOH--HPLC; Flow rate: 27 mL/min; Gradient: 50% B to 50% B in 50 min; Wave Length: 220/254 nm |
| 83b | rac-(6S)-7-[4-bromo-3-(trifluoromethyl)benzoyl]-6-methyl-3-oxo-N-[(2-pyrimidin-4-ylphenyl)methyl]-2-[4-[rac-(2S)-3,3,3-trifluoro-2-hydroxy-2-methyl-propoxy]phenyl]-6,8-dihydro-5H-imidazo[1,5-a]pyrazine-1-carboxamide | (400 MHz, CDCl₃) δ 8.74 (d, J = 2.0 Hz, 2H), 7.83-7.81 (m, 2H), 7.57-7.42 (m, 6H), 7.14 (d, J = 4.0 Hz, 2H), 6.83-6.80 (m, 1H), 6.63 (d, J = 4.0 Hz, 2H), 5.35 (s, 2H), 4.65 (d, J = 8.0 Hz, 1H), 4.45-4.33 (m, 2H), 3.88-3.69 (m, 5H), 1.58-1.40 (m, 6H). | 833 | Column: Lux Sum Cellulose-2, 2.12*25 cm, 5 μm Mobile Phase A: Hex(0.5% 2M NH₃-MeOH)--HPLC, Mobile Phase B: EtOH--HPLC; Flow rate: 20 mL/min; Gradient: 50% B to 50% B in 47 min; Wave Length: 254/220 nm |
| 87a | (6RS)-7-[4-bromo-3-(trifluoromethyl)benzoyl]-6-methyl-2-[4-[(3S)-4-methyl-3-(trifluoromethyl)piperazin-1-yl]phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.85-8.69 (m, 2H), 7.87-7.76 (m, 2H), 7.60-7.35 (m, 6H), 7.08 (d, J = 8.6 Hz, 2H), 6.99 (t, J = 6.3 Hz, 1H), 6.53 (d, J = 8.6 Hz, 2H), 5.30 (s, 2H), 4.66 (d, J = 18.5 Hz, 1H), 4.44-4.24 (m, 2H), 3.86 (d, J = 12.8 Hz, 1H), 3.71 (d, J = 12.7 Hz, 1H), 3.23 (d, J = 12.4 Hz, 1H), 3.15-2.93 (m, 3H), 2.92-2.72 (m, 2H), 2.57 (s, 4H), 1.41 (d, J = 7.0 Hz, 3H). | 857 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 16 min; Wave Length: 220/254 nm |
| 87b | (6SR)-7-[4-bromo-3-(trifluoromethyl)benzoyl]-6-methyl-2-[4-[(3S)-4-methyl-3-(trifluoromethyl)piperazin-1-yl]phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.86-8.63 (m, 2H), 7.92-7.76 (m, 2H), 7.63-7.34 (m, 6H), 7.08 (d, J = 8.7 Hz, 2H), 6.99 (t, J = 6.3 Hz, 1H), 6.53 (d, J = 8.5 Hz, 2H), 5.50 (s, 2H), 4.66 (d, J = 18.8 Hz, 1H), 4.44-4.23 (m, 2H), 3.86 (d, J = 12.8 Hz, 1H), 3.76-3.63 (m, 1H), 3.23 (d, J = 12.3 Hz, 1H), 3.15-2.91 (m, 3H), 2.91-2.70 (m, 2H), 2.57 (s, 4H), 1.41 (d, J = 6.9 Hz, 3H). | 857 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 16 min; Wave Length: 220/254 nm |
| 88a | rac-(6R)-7-[4-bromo-3-(trifluoromethyl)benzoyl]-6-methyl-2-[4-(2-methyl-2,6-diazaspiro[3.4]octan-6-yl)phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.82 (d, J = 1.3 Hz, 1H), 8.73 (d, J = 5.3 Hz, 1H), 7.90-7.81 (m, 2H), 7.58-7.40 (m, 6H), 7.09-7.02 (m, 2H), 6.77 (t, J = 6.2 Hz, 1H), 6.31 (d, J = 8.7 Hz, 2H), 5.32 (s, 1H), 4.67 (d, J = 19.0 Hz, 1H), 4.52-4.32 (m, 2H), 3.88 (d, J = 12.8 Hz, 1H), 3.72 (d, J = 12.5 Hz, 1H), 3.33 (d, J = 30.9 Hz, 6H), 3.16 (t, J = 6.9 Hz, 2H), 2.47 (s, 3H), 2.19 (t, J = 6.8 Hz, 2H), 1.42 (d, J = 6.9 Hz, 3H). | 815 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 18 min; Wave Length: 220/254 nm |

TABLE C-continued

| Compound | Name | ¹H NMR | [M + H]⁺ | Separation Method |
|---|---|---|---|---|
| 88b | rac-(6S)-7-[4-bromo-3-(trifluoromethyl)benzoyl]-6-methyl-2-[4-(2-methyl-2,6-diazaspiro[3.4]octan-6-yl)phenyl]-3-oxo-N-[(2-pyrimidin-4-ylphenyl)methyl]-6,8-dihydro-5H-imidazo[1,5-a]pyrazine-1-carboxamide | (400 MHz, CDCl₃) δ 8.82 (d, J = 1.3 Hz, 1H), 8.73 (d, J = 5.3 Hz, 1H), 7.90-7.81 (m, 2H), 7.58-7.40 (m, 6H), 7.09-7.02 (m, 2H), 6.77 (t, J = 6.2 Hz, 1H), 6.31 (d, J = 8.7 Hz, 2H), 5.32 (s, 1H), 4.67 (d, J = 19.0 Hz, 1H), 4.52-4.32 (m, 2H), 3.88 (d, J = 12.8 Hz, 1H), 3.72 (d, J = 12.5 Hz, 1H), 3.33 (d, J = 30.9 Hz, 6H), 3.16 (t, J = 6.9 Hz, 2H), 2.47 (s, 3H), 2.19 (t, J = 6.8 Hz, 2H), 1.42 (d, J = 6.9 Hz, 3H). | 815 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 18 min; Wave Length: 220/254 nm |
| 89a | rac-(6R)-7-[4-bromo-3-(trifluoromethyl)benzoyl]-6-methyl-3-oxo-N-[[2-(2-pyridyl)phenyl]methyl]-2-[4-[rac-(2R)-3,3,3-trifluoro-2-hydroxy-2-methyl-propoxy]phenyl]-6,8-dihydro-5H-imidazo[1,5-a]pyrazine-1-carboxamide | (300 MHz, CDCl₃) δ 8.21 (s, 1H), 7.90-7.70 (m, 3H), 7.55-7.35 (m, 6H), 7.22-7.00 (m, 4H), 6.54 (d, J = 8.7 Hz 2H), 5.90-4.80 (m, 2H), 4.66 (d, J = 19.2 Hz 1H), 4.40-4.20 (m, 2H), 3.92-3.50 (m, 4H), 3.10 (s, 1H), 1.41 (d, J =7.2 Hz, 6H). | 832 | Column: Lux Sum Cellulose-2, 2.12*25 cm, 5 μm Mobile Phase A: Hex(0.5% 2M NH₃-MeOH)--HPLC, Mobile Phase B: EtOH--HPLC; Flow rate: 20 mL/min; Gradient: 50% B to 50% B in 43 min; Wave Length: 220/254 nm |
| 89b | rac-(6S)-7-[4-bromo-3-(trifluoromethyl)benzoyl]-6-methyl-3-oxo-N-[[2-(2-pyridyl)phenyl]methyl]-2-[4-[rac-(2R)-3,3,3-trifluoro-2-hydroxy-2-methyl-propoxy]phenyl]-6,8-dihydro-5H-imidazo[1,5-a]pyrazine-1-carboxamide | (300 MHz, CDCl₃) δ 8.21 (s, 1H), 7.90-7.70 (m, 3H), 7.55-7.35 (m, 6H), 7.22-7.00 (m, 4H), 6.54 (d, J = 8.7 Hz 2H), 5.90-4.80 (m, 2H), 4.66 (d, J = 19.2 Hz 1H), 4.45-4.30 (m, 1H), 4.30-4.10 (m, 1H), 3.92-3.50 (m, 4H), 3.10 (s, 1H), 1.41 (d, J =9.0 Hz, 6H). | 832 | Column: Lux Sum Cellulose-2, 2.12*25 cm, 5 μm Mobile Phase A: Hex(0.5% 2M NH₃-MeOH)--HPLC, Mobile Phase B: EtOH--HPLC; Flow rate: 20 mL/min; Gradient: 50% B to 50% B in 43 min; Wave Length: 220/254 nm |
| 90a | rac-(6R)-7-[4-bromo-3-(trifluoromethyl)benzoyl]-6-methyl-3-oxo-N-[[2-(2-pyridyl)phenyl]methyl]-2-[4-[rac-(2S)-3,3,3-trifluoro-2-hydroxy-2-methyl-propoxy]phenyl]-6,8-dihydro-5H-imidazo[1,5-a]pyrazine-1-carboxamide | (300 MHz, CDCl₃) δ 8.21 (s, 1H), 7.90-7.70 (m, 3H), 7.55-7.35 (m, 6H), 7.22-7.00 (m, 4H), 6.54 (d, J = 8.7 Hz 2H), 5.90-4.80 (m, 2H), 4.66 (d, J = 19.2 Hz 1H), 4.45-4.30 (m, 1H), 4.30-4.10 (m, 1H), 3.92-3.50 (m, 4H), 3.10 (s, 1H), 1.41 (d, J =8.1 Hz, 6H). | 832 | Column: Lux Sum Cellulose-2, 2.12*25 cm, 5 μm Mobile Phase A: Hex(0.5% 2M NH₃-MeOH)--HPLC, Mobile Phase B: EtOH--HPLC; Flow rate: 20 mL/min; Gradient: 50% B to 50% B in 43 min; Wave Length: 220/254 nm |
| 90b | rac-(6S)-7-[4-bromo-3-(trifluoromethyl)benzoyl]-6-methyl-3-oxo-N-[[2-(2-pyridyl)phenyl]methyl]-2-[4-[rac-(2S)-3,3,3-trifluoro-2-hydroxy-2-methyl-propoxy]phenyl]-6,8-dihydro-5H-imidazo[1,5-a]pyrazine-1-carboxamide | (300 MHz, CDCl₃) δ 8.21 (s, 1H), 7.90-7.70 (m, 3H), 7.55-7.35 (m, 6H), 7.22-7.00 (m, 4H), 6.54 (d, J = 8.7 Hz 2H), 5.90-4.80 (m, 2H), 4.66 (d, J = 19.2 Hz 1H), 4.40-4.20 (m, 2H), 3.92-3.50 (m, 4H), 3.10 (s, 1H), 1.41 (d, J =7.5 Hz, 6H). | 832 | Column: Lux Sum Cellulose-2, 2.12*25 cm, 5 μm Mobile Phase A: Hex(0.5% 2M NH₃-MeOH)--HPLC, Mobile Phase B: EtOH--HPLC; Flow rate: 20 mL/min; Gradient: 50% B to 50% B in 43 min; Wave Length: 220/254 nm |
| 92a | rac-(6R)-2-(2-amino-1,3-benzoxazol-5-yl)-7-(4-bromo-3-chloro-benzoyl)-6-methyl-3-oxo-N-[(2-pyrimidin-4-ylphenyl)methyl]-6,8-dihydro-5H-imidazo[1,5-a]pyrazine-1-carboxamide | (300 MHz, CDCl₃) δ 8.77-8.62 (m, 2H), 7.82 (d, J = 8.0 Hz, 2H), 7.55-7.34 (m, 6H), 7.22 (d, J = 1.7 Hz, 1H), 6.88 (q, J = 8.5 Hz, 2H), 6.71 (s, 1H), 5.71 (s, 2H), 5.34 (s, 1H), 4.66 (d, J = 19.1 Hz, 1H), 4.14-4.22 (m, 2H), 3.87 (d, J = 12.8 Hz, 1H), 3.73 (d, J = 12.9 Hz, 1H), 1.43 (d, J = 6.9 Hz, 3H). | 713 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 50% B to 50% B in 17 min; Wave Length: 220/254 nm |
| 92b | rac-(6S)-2-(2-amino-1,3-benzoxazol-5-yl)-7-(4-bromo-3-chloro-benzoyl)-6-methyl-3-oxo-N-[(2-pyrimidin-4-ylphenyl)methyl]-6,8-dihydro-5H-imidazo[1,5-a]pyrazine-1-carboxamide | (300 MHz, CDCl₃) δ 8.75-8.57 (m, 2H), 7.71 (d, J = 8.2 Hz, 1H), 7.58 (d, J = 2.0 Hz, 1H), 7.53-7.29 (m, 6H), 7.24-7.15 (m, 2H), 6.92-6.77 (m, 2H), 6.75-6.64 (m, 1H), 5.80 (s, 2H), 5.35 (s, 1H), 4.63 (d, J = 19.1 Hz, 1H), 4.32 (qd, J = 13.7, 6.1 Hz, 2H), 3.86 (d, J = 12.7 Hz, 1H), 3.71 (d, J = 8.7 Hz, 1H), 1.40 (d, J = 7.0 Hz, 3H). | 713 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 17 min; Wave Length: 220/254 nm |
| 94a | (6RS)-7-[4-bromo-3-(trifluoromethyl)benzoyl]-2-[1-[(2S)-2-hydroxypropyl]indazol-5-yl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.29 (d, J = 8.0 Hz, 2H), 8.03-8.01 (m, 1H), 7.90-7.83 (m, 2H), 7.75 (s, 1H), 7.65 (d, J = 8.0 Hz, 1H), 7.50-7.43 (m, 4H), 6.99-6.92 (m, 4H), 5.22 (s, 1H), 4.70 (d, J = 8.0 Hz, 1H), 4.53 (s, 1H), 4.36 (d, J = 6.0 Hz, 1H), 4.22-4.12 (m, 2H), 4.03-3.97 (m, | 789 | Column: CHIRALPAK IF, 2*25 cm, 5 μm; Mobile Phase A: MtBE(0.5% 2M NH₃-MeOH)--HPLC, Mobile Phase B: IPA--HPLC; Flow rate: 12 mL/min; |

TABLE C-continued

| Compound | Name | ¹H NMR | [M + H]⁺ | Separation Method |
|---|---|---|---|---|
| | | 1H), 3.87 (d, J = 6.0 Hz, 1H), 3.74 (d, J = 4.0 Hz, 1H), 2.33 (s, 1H), 1.43 (d, J = 4.0 Hz, 3H), 1.28-1.24 (m, 3H). | | Gradient: 50% B to 50% B in 41 min; Wave Length: 220/254 nm; |
| 94b | (6SR)-7-[4-bromo-3-(trifluoromethyl)benzoyl]-2-[1-[(2S)-2-hydroxypropyl]indazol-5-yl]-6-methyl-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.29 (d, J = 8.0 Hz, 2H), 8.03-8.01 (m, 1H), 7.90-7.83 (m, 2H), 7.75 (s, 1H), 7.65 (d, J = 8.0 Hz, 1H), 7.50-7.43 (m, 4H), 6.99-6.92 (m, 4H), 5.22 (s, 2H), 4.70 (d, J = 8.0 Hz, 1H), 4.53 (s, 1H), 4.36 (d, J = 6.0 Hz, 1H), 4.22-4.12 (m, 2H), 4.03-3.97 (m, 1H), 3.87 (d, J = 6.0 Hz, 1H), 3.74 (d, J = 4.0 Hz, 1H), 3.07 (s, 1H), 1.43 (d, J = 4.0 Hz, 3H), 1.28-1.24 (m, 3H). | 789 | Column: CHIRALPAK IF, 2*25 cm, 5 μm; Mobile Phase A: MtBE(0.5% 2M NH₃-MeOH)--HPLC, Mobile Phase B: IPA--HPLC; Flow rate: 12 mL/min; Gradient: 50% B to 50% B in 41 min; Wave Length: 220/254 nm; |
| 95a | rac-(6R)-7-[4-bromo-3-(trifluoromethyl)benzoyl]-6-methyl-2-[4-[2-(methylamino)propoxy]phenyl]-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.58 (d, J =4.8 Hz, 2H), 8.20-8.00 (m, 1H), 7.90-7.70 (m, 2H), 7.52-7.40 (m, 4H), 7.23-7.10 (m, 1H), 7.10-6.95 (m, 3H), 6.70-6.45 (m, 2H), 5.30 (s, 2H), 4.70-4.30 (m, 3H), 3.90-3.68 (m, 4H), 3.30-3.10 (m, 2H), 2.54 (d, J = 9.3 Hz, 3H), 1.42-1.46 (m, 6H). | 778 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 11 mL/min; Gradient: 50% B to 50% B in 32 min; Wave Length: 220/254 nm |
| 95b | rac-(6S)-7-[4-bromo-3-(trifluoromethyl)benzoyl]-6-methyl-2-[4-[2-(methylamino)propoxy]phenyl]-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.58 (d, J = 4.8 Hz, 2H), 8.20-8.00 (m, 1H), 7.90-7.70 (m, 2H), 7.52-7.40 (m, 4H), 7.23-7.10 (m, 1H), 7.10-6.95 (m, 3H), 6.70-6.45 (m, 2H), 5.30 (s, 2H), 4.70-4.30 (m, 3H), 3.90-3.68 (m, 4H), 3.30-3.10 (m, 2H), 2.54 (d, J =9.3 Hz, 3H), 1.40 (d, J =7.2 Hz, 3H), 1.23 (d, J =6.6 Hz, 3H). | 778 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 11 mL/min; Gradient: 50% B to 50% B in 32 min; Wave Length: 220/254 nm |
| 96a | rac-(6R)-7-[4-bromo-3-(trifluoromethyl)benzoyl]-6-methyl-2-[4-(2-morpholinopropoxy)phenyl]-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.59 (d, J = 4.8 Hz, 2H), 8.24-8.00 (m, 1H), 8.00-7.65 (m, 2H), 7.50-7.38 (m, 4H), 7.24-6.80 (m, 4H), 6.70-6.30 (m, 2H), 5.30 (s, 1H), 4.80-4.26 (m, 3H), 4.10-3.10 (m, 8H), 3.10-2.20 (m, 5H), 1.40 (d, J = 6.9 Hz, 3H), 1.20 (s, 3H). | 834 | Column: CHIRALPAK IF, 2*25 cm, 5 μm; Mobile Phase A: MeOH(0.5% 2M NH₃-MeOH)--HPLC, Mobile Phase B: EtOH--HPLC; Flow rate: 14 mL/min; Gradient: 30% B to 30% B in 17.5 min; Wave Length: 220/254 nm |
| 96b | rac-(6S)-7-[4-bromo-3-(trifluoromethyl)benzoyl]-6-methyl-2-[4-(2-morpholinopropoxy)phenyl]-3-oxo-N-[(2-pyrimidin-2-ylphenyl)methyl]-6,8-dihydro-5H-imidazo[1,5-a]pyrazine-1-carboxamide | (400 MHz, CDCl₃) δ 8.59 (d, J = 2.4 Hz, 2H), 8.20-8.00 (m, 1H), 7.80 (d, J =3.8 2H), 7.56-7.30 (m, 4H), 7.16 (s, 1H), 7.10-6.90 (m, 3H), 6.60-6.40 (m, 2H), 5.40 (s, 2H), 4.80-4.60 (m, 1H), 4.60-4.50 (m, 1H), 4.48-4.40 (m, 1H), 4.40-3.40 (m, 8H), 2.80 (s, 1H), 2.62 (s, 4H), 1.40-1.35 (m, 3H), 1.20 (s, 3H). | 834 | Column: CHIRALPAK IF, 2*25 cm, 5 μm; Mobile Phase A: MeOH(0.5% 2M NH₃-MeOH)--HPLC, Mobile Phase B: EtOH--HPLC; Flow rate: 14 mL/min; Gradient: 30% B to 30% B in 17.5 min; Wave Length: 220/254 nm |
| 97a | rac-(6R)-7-[4-bromo-3-(trifluoromethyl)benzoyl]-2-[4-[2-(dimethylamino)propoxy]phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.58 (d, J = 4.8 Hz, 2H), 8.20-7.90 (m, 1H), 7.90-7.70 (m, 2H), 7.60-7.30 (m, 4H), 7.20-7.10 (m, 1H), 7.10-6.88 (m, 3H), 6.70-6.20 (m, 2H), 5.70-4.90 (m, 1H),4.80-4.20 (m, 3H), 4.00-3.40 (m, 4H), 2.88 (d, J = 5.4 Hz, 1H), 2.36 (s, 6H) , 1.40 (d, J = 6.9 Hz, 3H), 1.12 (d, J = 6.6 Hz, 3H). | 792 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 14.5 mL/min; Gradient: 30% B to 30% B in 17 min; Wave Length: 220/254 nm |
| 97b | rac-(6S)-7-[4-bromo-3-(trifluoromethyl)benzoyl]-2-[4-[2-(dimethylamino)propoxy]phenyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.58 (d, J = 4.8 Hz, 2H), 8.20-7.90 (m, 1H), 7.90-7.70 (m, 2H), 7.60-7.30 (m, 4H), 7.20-7.10 (m, 1H), 7.10-6.88 (m, 3H), 6.70-6.20 (m, 2H), 5.70-4.90 (m, 1H), 4.80-4.20 (m, 3H), 4.00-3.40 (m, 4H), 2.88 (d, J = 5.4 Hz, 1H), 2.36 (s, 6H) , 1.40 (d, J = 6.9 Hz, 3H), 1.13 (d, J = 6.6 Hz, 3H). | 792 | Column: CHIRALPAK IF, 2*25 cm, 5 μm; Mobile Phase A: MtBE(0.5% 2M NH3-MeOH)--HPLC, Mobile Phase B: EtOH--HPLC; Flow rate: 14.5 mL/min; Gradient: 30% B to 30% B in 17 min; Wave Length: 220/254 nm |
| 98a | rac-(6R)-7-[4-bromo-3-(trifluoromethyl)benzoyl]-6-methyl-2-[4-(6-methyl-2,6-diazaspiro[3.3]heptan-2-yl)phenyl]-3- | (300 MHz, CDCl₃) δ 8.75 (d, J = 5.0 Hz, 1H), 8.32 (dd, J = 7.3, 2.8 Hz, 1H), 7.90-7.74 (m, 2H) ,7.46 (dt, J = 7.2, 4.2 Hz, 5H), 6.86 (d, J = 8.6 Hz, 2H), 6.62 (t, | 867 | Column: CHIRAL ART Amylose-SA, 2*25 cm, 5 μm Mobile Phase A: MtBE(0.5% 2M NH₃- |

TABLE C-continued

| Compound | Name | ¹H NMR | [M + H]⁺ | Separation Method |
|---|---|---|---|---|
| | oxo-N-[[2-[4-(trifluoromethyl)pyrimidin-2-yl]phenyl]methyl]-6,8-dihydro-5H-imidazo[1,5-a]pyrazine-1-carboxamide | J = 6.2 Hz, 1H), 5.96-5.75 (m, 2H), 5.33 (s, 1H), 4.75-4.57 (m, 2H), 4.51 (dd, J = 13.8, 5.8 Hz, 1H), 3.83 (d, J = 12.9 Hz, 1H), 3.75-3.60 (m, 5H), 3.41 (s, 4H), 2.37 (s, 3H), 1.39 (d, J = 6.9 Hz, 3H). | | MeOH)--HPLC, Mobile Phase B: EtOH--HPLC; Flow rate: 20 mL/min; Gradient: 30% B to 30% B in 13 min; Wave Length: 220/254 nm |
| 98b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-[4-(trifluoromethyl)pyrimidin-2-yl]phenyl]methyl]-6,8-dihydro-5H-imidazo[1,5-a]pyrazine-1-carboxamide | (300 MHz, CDCl₃) δ 8.75 (d, J = 5.0 Hz, 1H), 8.40-8.24 (m, 1H), 7.89-7.72 (m, 2H), 7.56-7.36 (m, 5H), 7.05-6.80 (m, 2H), 6.62 (t, J = 6.3 Hz, 1H), 5.96-5.75 (m, 2H), 5.31 (s, 1H), 4.70-4.20 (m, 3H), 3.83 (d, J = 12.8 Hz, 1H), 3.57-3.75 (m, 5H), 3.35 (s, 4H), 2.33 (s, 3H), 1.39 (d, J = 6.9 Hz, 3H). | 867 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 30% B to 30% B in 13 min; Wave Length: 220/254 nm |
| 99a | rac-(6R)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-[1-(2,2,2-trifluoroethyl)pyrazol-3-yl]phenyl]methyl]-6,8-dihydro-5H-imidazo[1,5-a]pyrazine-1-carboxamide | (300 MHz, CDCl₃) δ 7.80 (d, J = 6.0 Hz, 2H), 7.61-7.43 (m, 3H), 7.39-7.29 (m, 3H), 6.99 (d, J = 6.0 Hz, 2H), 6.45 (d, J = 2.0 Hz, 1H), 6.24 (s, 1H), 6.12 (d, J = 6.0 Hz, 2H), 5.44-5.16 (m, 1H), 4.66-4.37 (m, 5H), 3.91-3.67 (m, 7H), 3.58 (s, 4H), 2.43 (d, J = 12.0 Hz, 3H), 1.39 (d, J = 6.0 Hz, 3H). | 871 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 20% B to 20% B in 25 min; Wave Length: 220/254 nm |
| 99b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-[1-(2,2,2-trifluoroethyl)pyrazol-3-yl]phenyl]methyl]-6,8-dihydro-5H-imidazo[1,5-a]pyrazine-1-carboxamide | (400 MHz, CDCl₃) δ 7.80 (d, J = 4.0 Hz, 2H), 7.52-7.44 (m, 3H), 7.34-7.28 (m, 3H), 6.99 (d, J = 4.0 Hz, 2H), 6.45 (d, J = 2.0 Hz, 1H), 6.24 (s, 1H), 6.11 (d, J = 4.0 Hz, 2H), 5.35-5.20 (m, 1H), 4.61-4.39 (m, 6H), 3.86-3.76 (m, 5H), 3.71-3.60 (m, 1H), 3.52 (s, 4H), 2.42 (s, 3H), 1.39 (d, J = 4.0 Hz, 3H). | 871 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 20% B to 20% B in 25 min; Wave Length: 220/254 nm |
| 100a | rac-(6R)-7-[4-bromo-3-(trifluoromethyl)benzoyl]-6-methyl-3-oxo-N-[(2-pyrimidin-2-ylphenyl)methyl]-2-[1-(2,2,2-trifluoroethyl)indazol-5-yl]-6,8-dihydro-5H-imidazo[1,5-a]pyrazine-1-carboxamide | (400 MHz, CDCl₃) δ 8.27 (d, J = 4.9 Hz, 2H), 7.95-7.86 (m, 1H), 7.87-7.80 (m, 2H), 7.77 (s, 1H), 7.60 (d, J = 1.9 Hz, 1H), 7.54-7.38 (m, 4H), 7.24-7.19 (m, 1H), 7.16-7.01 (m, 2H), 6.94 (t, J = 4.9 Hz, 1H), 5.49-5.26 (m, 1H), 4.84-4.63 (m, 3H), 4.55-4.39 (m, 1H), 4.38-4.25 (m, 1H), 3.95-3.82 (m, 1H), 3.82-3.65 (m, 1H), 1.43 (d, J = 7.0 Hz, 3H). | 813 | Column: (R,R)-WHELK-01-Kromasil, 5*25 cm, 5 μm Mobile Phase A: MtBE(0.5% 2M NH3-MeOH)--HPLC, Mobile Phase B: EtOH--HPLC; Flow rate: 20 mL/min; Gradient: 25% B to 25% B in 17 min; Wave Length: 220/254 nm |
| 100b | rac-(6S)-7-[4-bromo-3-(trifluoromethyl)benzoyl]-6-methyl-3-oxo-N-[(2-pyrimidin-2-ylphenyl)methyl]-2-[1-(2,2,2-trifluoroethyl)indazol-5-yl]-6,8-dihydro-5H-imidazo[1,5-a]pyrazine-1-carboxamide | (400 MHz, CDCl₃) δ 8.27 (d, J = 4.9 Hz, 2H), 7.95-7.86 (m, 1H), 7.87-7.80 (m, 2H), 7.77 (s, 1H), 7.60 (d, J = 1.9 Hz, 1H), 7.54-7.38 (m, 4H), 7.24-7.19 (m, 1H), 7.16-7.01 (m, 2H), 6.94 (t, J = 4.9 Hz, 1H), 5.49-5.26 (m, 1H), 4.84-4.63 (m, 3H), 4.55-4.39 (m, 1H), 4.38-4.25 (m, 1H), 3.95-3.82 (m, 1H), 3.82-3.65 (m, 1H), 1.43 (d, J = 7.0 Hz, 3H). | 813 | Column: (R,R)-WHELK-01-Kromasil, 5*25 cm, 5 μm Mobile Phase A: MtBE(0.5% 2M NH₃-MeOH)--HPLC, Mobile Phase B: EtOH--HPLC; Flow rate: 20 mL/min; Gradient: 25% B to 25% B in 17 min; Wave Length: 220/254 nm |
| 101a | (6RS)-7-[4-bromo-3-(trifluoromethyl)benzoyl]-6-methyl-3-oxo-N-[(2-pyrimidin-2-ylphenyl)methyl]-2-[1-[(2R)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 20% B to 20% B in 13 min; Wave Length: 220/254 nm |
| 101b | (6SR)-7-[4-bromo-3-(trifluoromethyl)benzoyl]-6-methyl-3-oxo-N-[(2-pyrimidin-2- | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, | 843 | Column: CHIRALPAK IF, 2*25 cm, 5 μm Mobile Phase A: |

TABLE C-continued

| Compound | Name | ¹H NMR | [M + H]⁺ | Separation Method |
|---|---|---|---|---|
| | ylphenyl)methyl]-2-[1-[(2R)-3,3,3-trifluoro-2-hydroxy-propyl]indazol-5-yl]-6,8-dihydro-5H-imidazo[1,5-a]pyrazine-1-carboxamide | 1H), 7.50-7.41 (m, 4H), 7.03-6.95 (m, 3H) δ.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | | MtBE(0.5% 2M NH₃-MeOH)--HPLC, Mobile Phase B: EtOH--HPLC; Flow rate: 20 mL/min; Gradient: 20% B to 20% B in 13 min; Wave Length: 220/254 nm |
| 102a | (6RS)-7-[4-bromo-3-(trifluoromethyl)benzoyl]-6-methyl-3-oxo-N-[(2-pyrimidin-2-ylphenyl)methyl]-2-[1-[(2S)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 12% B to 12% B in 23 min; Wave Length: 220/254 nm |
| 102b | (6SR)-7-[4-bromo-3-(trifluoromethyl)benzoyl]-6-methyl-3-oxo-N-[(2-pyrimidin-2-ylphenyl)methyl]-2-[1-[(2S)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 12% B to 12% B in 23 min; Wave Length: 220/254 nm |
| 103a | rac-(6R)-7-[4-bromo-3-(trifluoromethyl)benzoyl]-6-methyl-3-oxo-N-[(2-pyrimidin-2-ylphenyl)methyl]-2-[1-(2,2,2-trifluoroethyl)benzotriazol-5-yl]-6,8-dihydro-5H-imidazo[1,5-a]pyrazine-1-carboxamide | (300 MHz, CDCl₃) δ 8.42 (s, 2H), 8.12 (d, J = 1.7 Hz, 1H), 7.96-7.87 (m, 1H), 7.87-7.76 (m, 2H), 7.49 (d, J = 8.2 Hz, 3H), 7.22 (s, 1H), 7.11 (s, 2H), 5.36-5.05 (m, 3H), 4.70 (d, J = 18.7 Hz, 1H), 4.54-4.23 (m, 2H), 3.88 (d, J = 12.8 Hz, 1H), 3.74 (d, J = 13.5 Hz, 1H), 2.53 (s, 2H), 1.44 (d, J = 6.9 Hz, 3H). | 814 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 15 mL/min; Gradient: 20% B to 20% B in 19 min; Wave Length: 254/220 nm |
| 103b | rac-(6S)-7-[4-bromo-3-(trifluoromethyl)benzoyl]-6-methyl-3-oxo-N-[(2-pyrimidin-2-ylphenyl)methyl]-2-[1-(2,2,2-trifluoroethyl)benzotriazol-5-yl]-6,8-dihydro-5H-imidazo[1,5-a]pyrazine-1-carboxamide | (300 MHz, CDCl₃) δ 8.42 (s, 2H), 8.12 (d, J = 1.7 Hz, 1H), 7.96-7.87 (m, 1H), 7.87-7.76 (m, 2H), 7.49 (d, J = 8.2 Hz, 3H), 7.22 (s, 1H), 7.11 (s, 2H), 5.36-5.05 (m, 3H), 4.70 (d, J = 18.7 Hz, 1H), 4.54-4.23 (m, 2H), 3.88 (d, J = 12.8 Hz, 1H), 3.74 (d, J = 13.5 Hz, 1H), 2.53 (s, 2H), 1.44 (d, J = 6.9 Hz, 3H). | 814 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 15 mL/min; Gradient: 20% B to 20% B in 19 min; Wave Length: 254/220 nm |
| 104a | rac-(6R)-7-[4-bromo-3-(trifluoromethyl)benzoyl]-N-[(2-chloro-6-fluoro-phenyl)methyl]-6-methyl-3-oxo-2-[1-(2,2,2-trifluoroethyl)indazol-5-yl]-6,8-dihydro-5H-imidazo[1,5-a]pyrazine-1-carboxamide | (300 MHz, CDCl₃) δ 8.02-7.97 (m, 1H), 7.86-7.80 (m, 2H), 7.69-7.64 (m, 1H), 7.52-7.45 (m, 2H), 7.42-7.37 (m, 1H), 7.12-7.04 (m, 1H), 6.90 (d, J = 8.1 Hz, 1H), 6.76 (t, J = 8.7 Hz, 1H), 5.45-4.90 (m, 5H), 4.76-4.59 (m, 1H), 4.55-4.55 (m, 5.9 Hz, 1H), 4.37-4.27 (m, 1H), 3.91-3.84 (m, 1H), 3.79-3.69 (m, 1H), 1.42 (d, J = 7.0 Hz, 3H). | 787 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 20% B to 20% B in 20 min; Wave Length: 220/254 nm |
| 104b | rac-(6S)-7-[4-bromo-3-(trifluoromethyl)benzoyl]-N-[(2-chloro-6-fluoro-phenyl)methyl]-6-methyl-3-oxo-2-[1-(2,2,2-trifluoroethyl)indazol-5-yl]-6,8-dihydro-5H-imidazo[1,5-a]pyrazine-1-carboxamide | (300 MHz, CDCl₃) δ 8.02-7.97 (m, 1H), 7.86-7.80 (m, 2H), 7.69-7.64 (m, 1H), 7.52-7.45 (m, 2H), 7.42-7.37 (m, 1H), 7.12-7.04 (m, 1H), 6.90 (d, J = 8.1 Hz, 1H), 6.76 (t, J = 8.7 Hz, 1H), 5.45-4.90 (m, 5H), 4.76-4.59 (m, 1H), 4.55-4.45 (m, 1H), 4.37-4.27 (m, 1H), 3.91-3.84 (m, 1H), 3.79-3.69 (m, 1H), 1.42 (d, J = 7.0 Hz, 3H). | 787 | Column: CHIRAL ART Amylose-SA, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 20% B to 20% B in 20 min; Wave Length: 220/254 nm |
| 105a | (6RS)-7-[4-bromo-3-(trifluoromethyl)benzoyl]-6-methyl-3-oxo-N-[(2-pyrimidin-2-ylphenyl)methyl]-2-[2-[(2R)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J =12.0 Hz, 1H), 1.43 (d, J = 4.0 Hz, 3H). | 843 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 10 min; Wave Length: 220/254 nm |

TABLE C-continued

| Compound | Name | ¹H NMR | [M + H]⁺ | Separation Method |
|---|---|---|---|---|
| 105b | (6SR)-7-[4-bromo-3-(trifluoromethyl)benzoyl]-6-methyl-3-oxo-N-[(2-pyrimidin-2-ylphenyl)methyl]-2-[2-[(2R)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 10 min; Wave Length: 220/254 nm |
| 106a | rac-(6R)-7-[4-bromo-3-(trifluoromethyl)benzoyl]-N-[(2-chloro-6-fluoro-phenyl)methyl]-6-methyl-2-[4-(6-methyl-2,6-diazaspiro[3.3]heptan-2-yl)phenyl]-3-oxo-6,8-dihydro-5H-imidazo[1,5-a]pyrazine-1-carboxamide | (400 MHz, CDCl₃) δ 7.85-7.78 (m, 2H), 7.48-7.43 (m, 1H), 7.21-7.13 (m, 1H), 7.11-7.04 (m, 3H), 6.96-6.89 (m, 1H), 6.37-6.31 (m, 2H), 5.69-4.92 (m, 2H), 4.72-4.58 (m, 1H), 4.57-4.46 (m, 1H), 4.42-4.29 (m, 1H), 3.94 (s, 4H), 3.88-3.81 (m, 1H), 3.77-3.64 (m, 1H), 3.53 (s, 4H), 2.42 (s, 3H), 1.44-1.33 (m, 3H). | 775 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 21 min; Wave Length: 220/254 nm |
| 106b | rac-(6S)-7-[4-bromo-3-(trifluoromethyl)benzoyl]-N-[(2-chloro-6-fluoro-phenyl)methyl]-6-methyl-2-[4-(6-methyl-2,6-diazaspiro[3.3]heptan-2-yl)phenyl]-3-oxo-6,8-dihydro-5H-imidazo[1,5-a]pyrazine-1-carboxamide | (400 MHz, CDCl₃) δ 7.85-7.78 (m, 2H), 7.48-7.43 (m, 1H), 7.21-7.13 (m, 1H), 7.11-7.04 (m, 3H), 6.96-6.89 (m, 1H), 6.37-6.31 (m, 2H), 5.69-4.92 (m, 2H), 4.72-4.58 (m, 1H), 4.57-4.46 (m, 1H), 4.42-4.29 (m, 1H), 3.94 (s, 4H), 3.88-3.81 (m, 1H), 3.77-3.64 (m, 1H), 3.53 (s, 4H), 2.42 (s, 3H), 1.44-1.33 (m, 3H). | 775 | Column: CHIRAL ART Cellulose-SB, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 50% B to 50% B in 21 min; Wave Length: 220/254 nm |
| 107a | (6RS)-7-[4-bromo-3-(trifluoromethyl)benzoyl]-6-methyl-3-oxo-N-[(2-pyrimidin-2-ylphenyl)methyl]-2-[2-[(2S)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRALPAK IF, 2*25 cm, 5 μm Mobile Phase A: MtBE(0.5% 2M NH₃-MeOH)--HPLC, Mobile Phase B: EtOH--HPLC; Flow rate: 20 mL/min; Gradient: 15% B to 15% B in 14.5 min; Wave Length: 220/254 nm |
| 107b | (6SR)-7-[4-bromo-3-(trifluoromethyl)benzoyl]-6-methyl-3-oxo-N-[(2-pyrimidin-2-ylphenyl)methyl]-2-[2-[(2S)-3,3,3-trifluoro-2-hydroxy-propyl]indazol-5-yl]-6,8-dihydro-5H-imidazo[1,5-a]pyrazine-1-carboxamide | (400 MHz, CDCl₃) δ 8.34 (d, J = 2.0 Hz, 2H), 7.94-7.92 (m, 1H), 7.87-7.83 (m, 2H), 7.60 (s, 1H), 7.50 (d, J = 2.0 Hz, 1H), 7.50-7.41 (m, 4H), 7.03-6.95 (m, 3H), 6.70 (s, 1H), 5.22 (s, 1H), 4.70 (d, J = 8.0 Hz, 1H), 4.53 (s, 1H), 4.45-4.29 (m, 4H), 3.86 (d, J = 8.0 Hz, 1H), 3.73 (d, J = 12.0 Hz, 1H), 1.43 (d, J = 4.0 Hz, 3H). | 843 | Column: CHIRALPAK IF, 2*25 cm, 5 μm Mobile Phase A: MtBE(0.5% 2M NH3-MeOH)--HPLC, Mobile Phase B: EtOH--HPLC; Flow rate: 20 mL/min; Gradient: 15% B to 15% B in 14.5 min; Wave Length: 220/254 nm |
| 108a | rac-(6R)-2-(1,2-benzoxazol-5-yl)-7-[4-bromo-3-(trifluoromethyl)benzoyl]-6-methyl-3-oxo-N-[(2-pyrimidin-2-ylphenyl)methyl]-6,8-dihydro-5H-imidazo[1,5-a]pyrazine-1-carboxamide | (300 MHz, DMSO-d₆) δ 11.24 (s, 1H), 8.86 (s, 2H), 7.95 (s, 3H), 7.80-7.10 (m, 8H), 6.82 (m, J =8.7 Hz 1H), 5.50 (s, 1H), 4.52 (s, 4H), 3.66 (s, 2H), 1.25 (s, 3H). | 732 | Column: CHIRALPAK IE, 2*25 cm, 5 μm Mobile Phase A: Hex: DCM = 3: 1(0.1% FA)--HPLC, Mobile Phase B: IPA--HPLC; Flow rate: 20 mL/min; Gradient: 20% B to 20% B in 25 min; Wave Length: 220/254 nm |
| 108b | rac-(6S)-2-(1,2-benzoxazol-5-yl)-7-[4-bromo-3-(trifluoromethyl)benzoyl]-6-methyl-3-oxo-N-[(2-pyrimidin-2-ylphenyl)methyl]-6,8-dihydro-5H-imidazo[1,5-a]pyrazine-1-carboxamide | (300 MHz, DMSO-d₆) δ 11.24 (s, 1H), 8.86 (s, 2H), 7.95 (s, 3H), 7.80-7.10 (m, 8H), 6.82 (m, J =8.7 Hz 1H), 5.50 (s, 1H), 4.52 (s, 4H), 3.66 (s, 2H), 1.25 (s, 3H). | 732 | Column: CHIRALPAK IE, 2*25 cm, 5 μm; Mobile Phase A: Hex: DCM = 3: 1(0.1% FA)--HPLC, Mobile Phase B: IPA--HPLC; Flow rate: 20 mL/min; Gradient: 20% B to 20% B in 25 min; Wave Length: 220/254 nm |
| 109a | rac-(6R)-2-[1-(azetidin-3-yl)indazol-5-yl]-7-[4-bromo-3-(trifluoromethyl)benzoyl]-6-methyl-3- | (300 MHz, CDCl₃) δ 8.29 (d, J = 2.0 Hz, 2H), 8.00-7.97 (m, 1H), 7.85-7.82 (m, 2H), 7.76 (s, 1H), 7.61 (d, J = 2.0 Hz, | 786 | Column: CHIRAL ART Cellulose-SC, 2*25 cm, 5 μm; Mobile Phase A: |

TABLE C-continued

| Compound | Name | ¹H NMR | [M + H]⁺ | Separation Method |
|---|---|---|---|---|
| | oxo-N-[(2-pyrimidin-2-ylphenyl)methyl]-6,8-dihydro-5H-imidazo[1,5-a]pyrazine-1-carboxamide | 1H), 7.51-7.43 (m, 4H), 7.07-6.87 (m, 4H), 5.51-5.06 (m, 3H), 4.70 (d, J = 14.0 Hz, 1H), 4.54-4.47 (m, 1H), 4.36-4.23 (m, 3H), 4.00-3.71 (m, 4H), 1.43 (d, J = 4.0 Hz, 3H). | | Hex: DCM = 1: 1(0.5% 2M NH₃-MeOH)--HPLC, Mobile Phase B: EtOH--HPLC; Flow rate: 20 mL/min; Gradient: 50% B to 50% B in 21 min; Wave Length: 220/254 nm |
| 109b | rac-(6S)-2-[1-(azetidin-3-yl)indazol-5-yl]-7-[4-bromo-3-(trifluoromethyl)benzoyl]-6-methyl-3-oxo-N-[(2-pyrimidin-2-ylphenyl)methyl]-6,8-dihydro-5H-imidazo[1,5-a]pyrazine-1-carboxamide | (300 MHz, CDCl₃) δ 8.30 (d, J = 2.0 Hz, 2H), 8.00-7.97 (m, 1H), 7.85-7.82 (m, 2H), 7.77 (s, 1H), 7.61 (d, J = 2.0 Hz, 1H), 7.54-7.43 (m, 4H), 7.01-6.87 (m, 4H), 5.53-5.07 (m, 3H), 4.70 (d, J = 14.0 Hz, 1H), 4.54-4.45 (m, 1H), 4.36-4.27 (m, 3H), 4.05-372 (m, 4H), 1.43 (d, J = 4.0 Hz, 3H). | 786 | Column: CHIRAL ART Cellulose-SC, 2*25 cm, 5 μm; Mobile Phase A: Hex: DCM = 1: 1(0.5% 2M NH3-MeOH)--HPLC, Mobile Phase B: EtOH--HPLC; Flow rate: 20 mL/min; Gradient: 50% B to 50% B in 21 min; Wave Length: 220/254 nm |
| 110a | rac-(6R)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-[3-(trifluoromethyl)pyrazol-1-yl]phenyl]methyl]-6,8-dihydro-5H-imidazo[1,5-a]pyrazine-1-carboxamide | (300 MHz, CDCl₃) δ 7.87-7.70 (m, 2H), 7.63 (d, J = 2.0 Hz, 1H), 7.47-7.34 (m, 3H), 7.31 (s, 1H), 7.25-7.19 (m, 1H), 7.08-6.94 (m, 2H), 6.66 (d, J = 2.6 Hz, 1H), 6.19 (d, J = 8.7 Hz, 2H), 5.84 (t, J = 6.0 Hz, 1H), 5.23 (s, 1H), 4.60 (d, J = 18.9 Hz, 1H), 4.33-4.20 (m, 1H), 4.19-4.01 (m, 1H), 3.81 (s, 6H), 3.41 (s, 4H), 2.35 (s, 3H), 1.40 (d, J = 7.0 Hz, 3H). | 857 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 32 min; Wave Length: 220/254 nm |
| 110b | rac-(6S)-7-[4-bromo-3-(trifluoromethyl)benzoyl]-6-methyl-2-[4-(6-methyl-2,6-diazaspiro[3.3]heptan-2-yl)phenyl]-3-oxo-N-[[2-[3-(trifluoromethyl)pyrazol-1-yl]phenyl]methyl]-6,8-dihydro-5H-imidazo[1,5-a]pyrazine-1-carboxamide | (300 MHz, CDCl₃) δ 7.87-7.70 (m, 2H), 7.63 (d, J = 2.0 Hz, 1H), 7.47-7.34 (m, 3H), 7.31 (s, 1H), 7.25-7.19 (m, 1H), 7.08-6.94 (m, 2H), 6.66 (d, J = 2.6 Hz, 1H), 6.19 (d, J = 8.7 Hz, 2H), 5.84 (t, J = 6.0 Hz, 1H), 5.23 (s, 1H), 4.60 (d, J = 18.9 Hz, 1H), 4.33-4.20 (m, 1H), 4.19-4.01 (m, 1H), 3.81 (s, 6H), 3.41 (s, 4H), 2.35 (s, 3H), 1.40 (d, J = 7.0 Hz, 3H). | 857 | Column: CHIRAL ART Amylose-SA, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 20% B to 20% B in 32 min; Wave Length: 220/254 nm |
| 111a | (6RS)-7-[4-bromo-3-(trifluoromethyl)benzoyl]-2-[1-[(2R)-2-hydroxypropyl]indazol-5-yl]-6-methyl-3-oxo-N-[[2-[1-(2,2,2-trifluoroethyl)pyrazol-3-yl]phenyl]methyl]-6,8-dihydro-5H-imidazo[1,5-a]pyrazine-1-carboxamide | (400 MHz, CDCl₃) δ 7.88-7.70 (m, 3H), 7.56 (s, 1H), 7.50-7.43 (m, 1H), 7.40-7.27 (m, 4H), 7.06-6.95 (m, 2H), 6.53 (s, 1H), 6.35-6.26 (m, 1H), 5.55-5.05 (m, 1H), 4.75-4.45 (m, 1H), 4.50-4.26 (m, 4H), 4.25-4.13 (m, 2H), 4.10-4.01 (m, 1H), 3.91-3.81 (m, 1H), 3.78-3.63 (m, 1H), 1.41 (d, J = 6.9 Hz, 3H), 1.30-1.17 (m, 3H). | 859 | Column: (R,R)-WHELK-01-Kromasil, 2.11*25 cm, 5 μm; Mobile Phase A: MtBE(0.5% 2M NH₃-MeOH)--HPLC, Mobile Phase B: EtOH--HPLC; Flow rate: 20 mL/min; Gradient: 40% B to 40% B in 27 min; Wave Length: 220/254 nm |
| 111b | (6SR)-7-[4-bromo-3-(trifluoromethyl)benzoyl]-2-[1-[(2R)-2-hydroxypropyl]indazol-5-yl]-6-methyl-3-oxo-N-[[2-[1-(2,2,2-trifluoroethyl)pyrazol-3-yl]phenyl]methyl]-6,8-dihydro-5H-imidazo[1,5-a]pyrazine-1-carboxamide | (400 MHz, CDCl₃) δ 7.86-7.69 (m, 3H), 7.56 (s, 1H), 7.50-7.43 (m, 1H), 7.40-7.26 (m, 4H), 7.05-6.95 (m, 2H), 6.53 (s, 1H), 6.35-6.26 (m, 1H), 5.55-5.05 (m, 1H), 4.75-4.45 (m, 1H), 4.50-4.26 (m, 4H), 4.24-4.11 (m, 2H), 4.10-4.01 (m, 1H), 3.91-3.81 (m, 1H), 3.78-3.61 (m, 1H), 2.10-1.93 (m, 1H), 1.41 (d, J = 6.9 Hz, 3H), 1.30-1.17 (m, 3H). | 859 | Column: (R, R)-WHELK-01-Kromasil, 2.11*25 cm, 5 μm; Mobile Phase A: MtBE(0.5% 2M NH₃-MeOH)--HPLC, Mobile Phase B: EtOH--HPLC; Flow rate: 20 mL/min; Gradient: 40% B to 40% B in 27 min; Wave Length: 220/254 nm |
| 112a | rac-(6R)-7-[4-bromo-3-(trifluoromethyl)benzoyl]-6-methyl-2-[4-(6-methyl-2,6-diazaspiro[3.3]heptan-2-yl)phenyl]-N-[[2-(1,3,4-oxadiazol-2-yl)phenyl]methyl]-3-oxo-6,8-dihydro-5H-imidazo[1,5-a]pyrazine-1-carboxamide | (300 MHz, CDCl₃) δ 8.37 (s, 1H), 7.88 (m, 1H), 7.85-7.75 (m, 2H), 7.57-7.38 (m, 4H), 6.99-6.89 (m, 2H), 6.56 (s, 1H), 6.25-6.15 (m, 2H), 5.27 (s, 2H), 4.82-4.53 (m, 3H), 3.94 (s, 4H), 3.83 (d, J = 12.8 Hz, 1H), 3.72-3.62 (m, 1H), 3.55 (s, 4H), 2.42 (s, 3H), 1.37 (d, J = 6.9 Hz, 3H). | 791 | Column: CHIRALPAK IF, 2*25 cm, 5 μm; Mobile Phase A: MtBE(0.5% 2M NH₃-MeOH)--HPLC, Mobile Phase B: EtOH--HPLC; Flow rate: 20 mL/min; Gradient: 15% B to 15% B in 14.5 min; Wave Length: 220/254 nm |
| 112b | rac-(6S)-7-[4-bromo-3-(trifluoromethyl)benzoyl]-6-methyl-2-[4-(6-methyl-2,6-diazaspiro[3.3]heptan-2-yl)phenyl]-N-[[2-(1,3,4-oxadiazol-2- | (300 MHz, CDCl₃) δ 8.37 (s, 1H), 7.88 (m, 1H), 7.85-7.75 (m, 2H), 7.57-7.38 (m, 4H), 6.99-6.89 (m, 2H), 6.56 (s, 1H), 6.25-6.15 (m, 2H), 5.27 (s, 2H), 4.82-4.53 (m, 3H), 3.94 (s, 4H), 3.83 (d, J = | 791 | Column: CHIRALPAK IF, 2*25 cm, 5 μm; Mobile Phase A: MtBE(0.5% 2M NH₃-MeOH)--HPLC, Mobile |

TABLE C-continued

| Compound | Name | ¹H NMR | [M + H]⁺ | Separation Method |
|---|---|---|---|---|
| | yl)phenyl]methyl]-3-oxo-6,8-dihydro-5H-imidazo[1,5-a]pyrazine-1-carboxamide | 12.8 Hz, 1H), 3.72-3.62 (m, 1H), 3.55 (s, 4H), 2.42 (s, 3H), 1.37 (d, J = 6.9 Hz, 3H). | | Phase B: EtOH--HPLC; Flow rate: 20 mL/min; Gradient: 15% B to 15% B in 14.5 min; Wave Length: 220/254 nm |
| 113a | rac-(6R)-7-[4-bromo-3-(trifluoromethyl)benzoyl]-6-methyl-2-[4-(6-methyl-2,6-diazaspiro[3.3]heptan-2-yl)phenyl]-N-[[2-(4-methyl-5-oxo-1H-1,2,4-triazol-3-yl)phenyl]methyl]-3-oxo-6,8-dihydro-5H-imidazo[1,5-a]pyrazine-1-carboxamide | (300 MHz, CDCl₃) δ 7.87-7.81 (m, 2H), 7.64-7.56 (m, 1H), 7.50-7.33 (m, 3H), 7.30-7.27 (m, 1H), 7.22-7.11 (m, 2H), 6.62-6.54 (m, 2H), 6.11 (s, 1H), 5.41 (s, 1H), 4.66-4.56 (m, 1H), 4.23 (d, J = 6.2 Hz, 2H), 4.09 (s, 4H), 3.91-3.83 (m, 1H), 3.69 (s, 5H), 3.18 (s, 3H), 2.48 (s, 3H), 1.37 (d, J = 6.9 Hz, 3H). | 820 | Column: CHIRAL ART Amylose-SA, 2*25 cm, 5 μm; Mobile Phase A: MtBE(0.5% IPAmine)--HPLC, Mobile Phase B: EtOH--HPLC; Flow rate: 20 mL/min; Gradient: 40% B to 40% B in 24 min; Wave Length: 220/254 nm |
| 113b | rac-(6S)-7-[4-bromo-3-(trifluoromethyl)benzoyl]-6-methyl-2-[4-(6-methyl-2,6-diazaspiro[3.3]heptan-2-yl)phenyl]-N-[[2-(4-methyl-5-oxo-1H-1,2,4-triazol-3-yl)phenyl]methyl]-3-oxo-6,8-dihydro-5H-imidazo[1,5-a]pyrazine-1-carboxamide | (300 MHz, CDCl₃) δ 7.87-7.81 (m, 2H), 7.64-7.56 (m, 1H), 7.50-7.33 (m, 3H), 7.30-7.27 (m, 1H), 7.22-7.11 (m, 2H), 6.62-6.54 (m, 2H), 6.11 (s, 1H), 5.41 (s, 1H), 4.66-4.56 (m, 1H), 4.23 (d, J = 6.2 Hz, 2H), 4.09 (s, 4H), 3.91-3.83 (m, 1H), 3.69 (s, 5H), 3.18 (s, 3H), 2.48 (s, 3H), 1.37 (d, J = 6.9 Hz, 3H). | 820 | Column: CHIRAL ART Amylose-SA, 2*25 cm, 5 μm; Mobile Phase A: MtBE(0.5% IPAmine)--HPLC, Mobile Phase B: EtOH--HPLC; Flow rate: 20 mL/min; Gradient: 40% B to 40% B in 24 min; Wave Length: 220/254 nm |

TABLE D

| Structure | Cmpd |
|---|---|
| 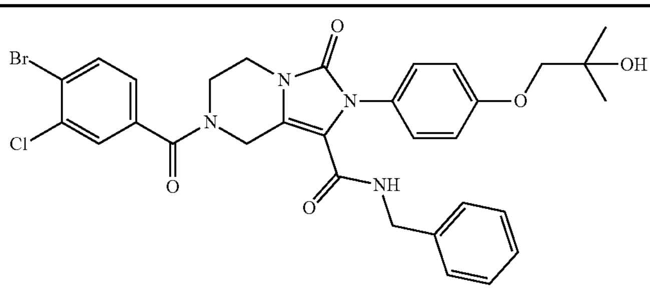 | 114 |
| 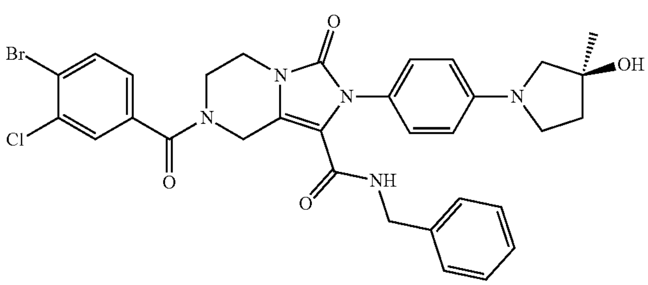 [SMILES: C[C@]1(O)CCN(c2ccc(-n3c(C(=O)NCc4ccccc4)c4n(c3=O)CCN(C(=O)c3ccc(Br)c(Cl)c3)C4)cc2)C1] | 115a |
| 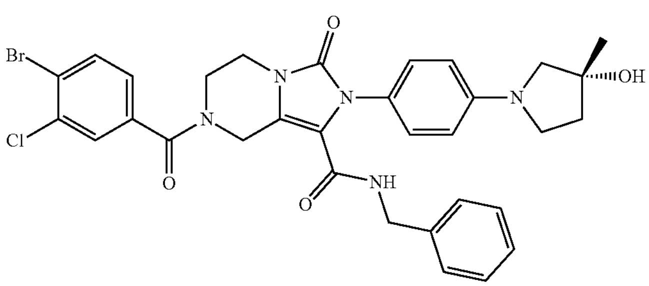 [SMILES: C[C@@]1(O)CCN(c2ccc(-n3c(C(=O)NCc4ccccc4)c4n(c3=O)CCN(C(=O)c3ccc(Br)c(Cl)c3)C4)cc2)C1] | 115b |

TABLE D-continued

| Structure | Cmpd |
|---|---|
| 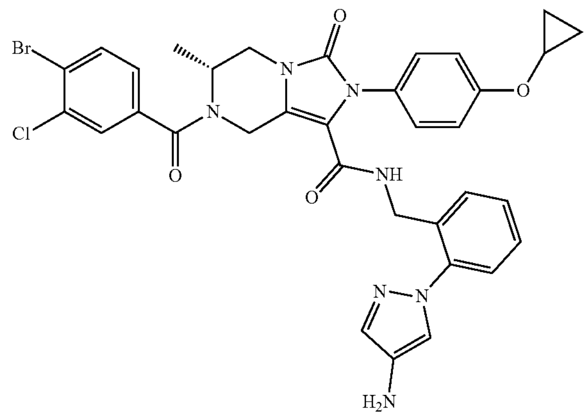 [SMILES: C[C@@H]1Cn2c(c(C(=O)NCc3ccccc3-n3cc(N)cn3)n(-c3ccc(OC4CC4)cc3)c2=O)CN1C(=O)c1ccc(Br)c(Cl)c1] | 19a |
| 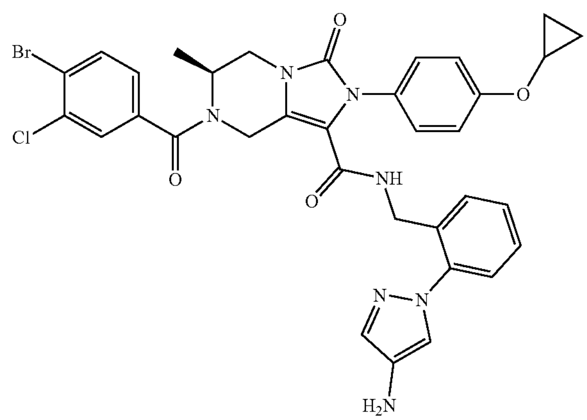 [SMILES: C[C@H]1Cn2c(c(C(=O)NCc3ccccc3-n3cc(N)cn3)n(-c3ccc(OC4CC4)cc3)c2=O)CN1C(=O)c1ccc(Br)c(Cl)c1] | 19b |
| 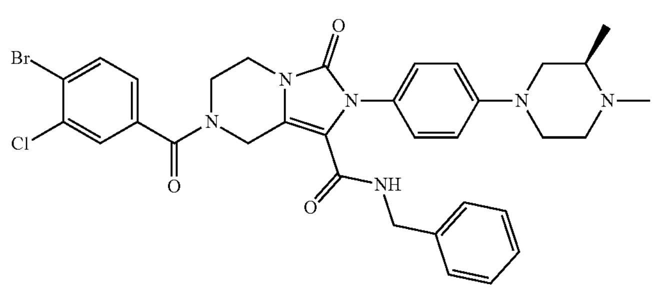 [SMILES: C[C@@H]1CN(c2ccc(-n3c(C(=O)NCc4ccccc4)c4n(c3=O)CCN(C(=O)c3ccc(Br)c(Cl)c3)C4)cc2)CCN1C] | 116 |
| 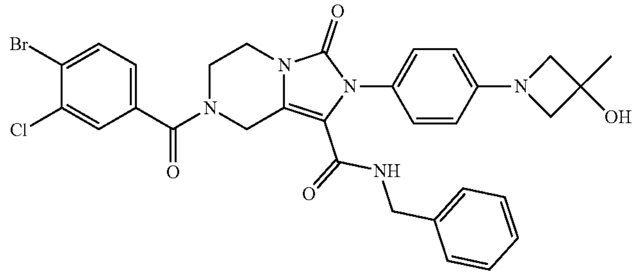 [SMILES: CC1(O)CN(c2ccc(-n3c(C(=O)NCc4ccccc4)c4n(c3=O)CCN(C(=O)c3ccc(Br)c(Cl)c3)C4)cc2)C1] | 117 |

TABLE D-continued

| Structure | Cmpd |
|---|---|
| 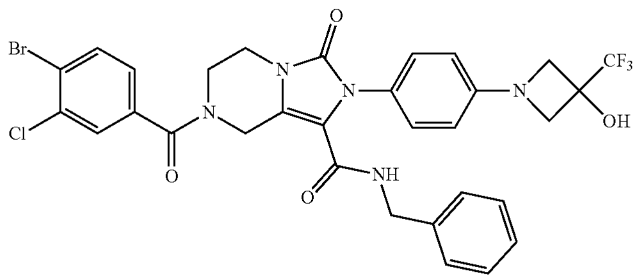 [SMILES: O=C(NCc1ccccc1)c1c2n(c(=O)n1-c1ccc(N3CC(O)(C(F)(F)F)C3)cc1)CCN(C(=O)c1ccc(Br)c(Cl)c1)C2] | 118 |
| 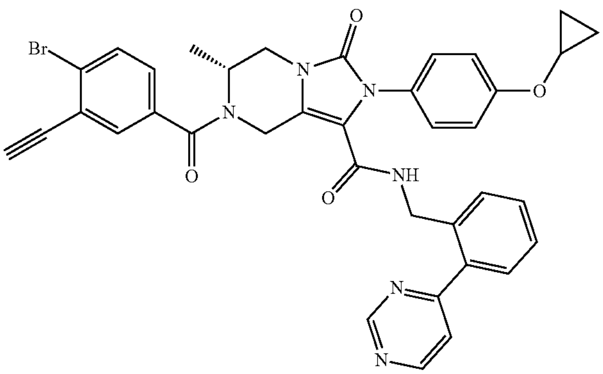 [SMILES: C#Cc1cc(C(=O)N2Cc3c(C(=O)NCc4ccccc4-c4ccncn4)n(-c4ccc(OC5CC5)cc4)c(=O)n3C[C@H]2C)ccc1Br] | 20a |
| 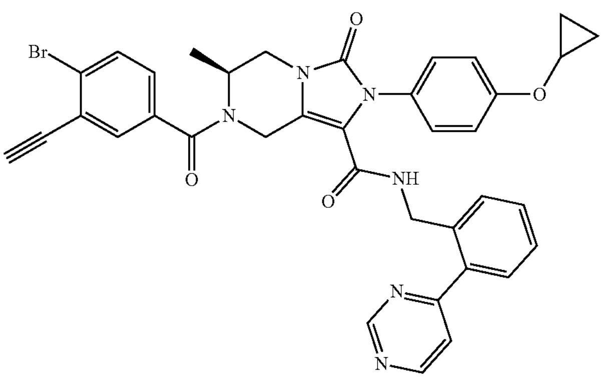 [SMILES: C#Cc1cc(C(=O)N2Cc3c(C(=O)NCc4ccccc4-c4ccncn4)n(-c4ccc(OC5CC5)cc4)c(=O)n3C[C@@H]2C)ccc1Br] | 20b |
| 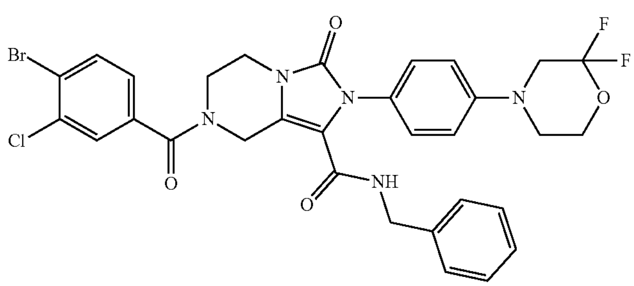 [SMILES: O=C(NCc1ccccc1)c1c2n(c(=O)n1-c1ccc(N3CCOC(F)(F)C3)cc1)CCN(C(=O)c1ccc(Br)c(Cl)c1)C2] | 119 |
| 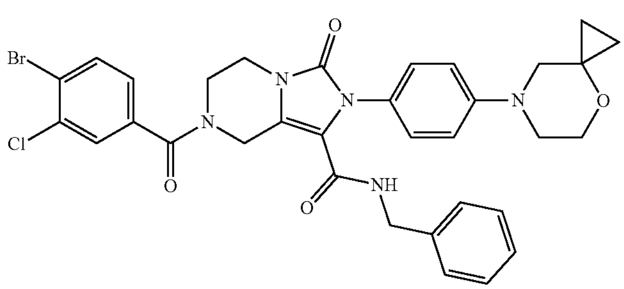 [SMILES: O=C(NCc1ccccc1)c1c2n(c(=O)n1-c1ccc(N3CCOC4(CC4)C3)cc1)CCN(C(=O)c1ccc(Br)c(Cl)c1)C2] | 120 |

TABLE D-continued
| Structure | Cmpd |
|---|---|
| 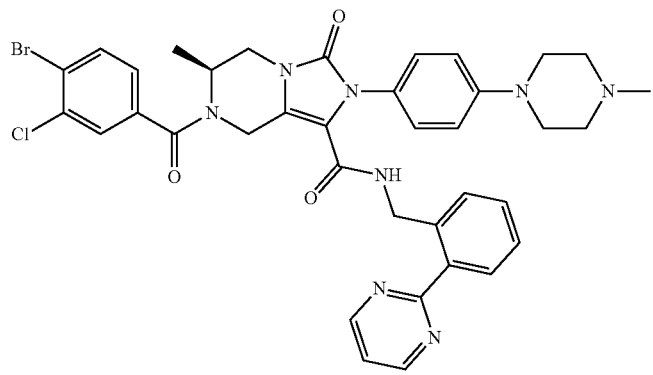 [SMILES: C[C@H]1Cn2c(c(C(=O)NCc3ccccc3-c3ncccn3)n(-c3ccc(N4CCN(C)CC4)cc3)c2=O)CN1C(=O)c1ccc(Br)c(Cl)c1] | 21a |
| 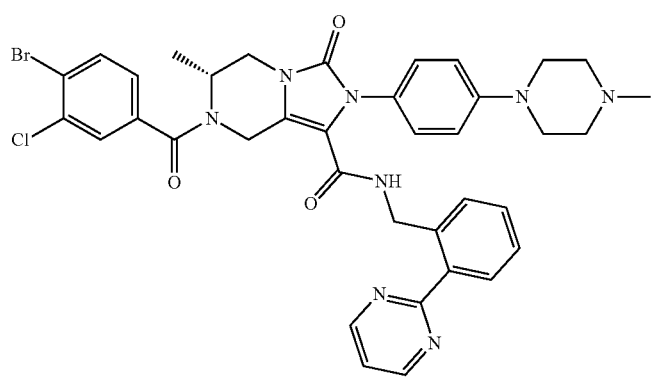 [SMILES: C[C@@H]1Cn2c(c(C(=O)NCc3ccccc3-c3ncccn3)n(-c3ccc(N4CCN(C)CC4)cc3)c2=O)CN1C(=O)c1ccc(Br)c(Cl)c1] | 21b |
| 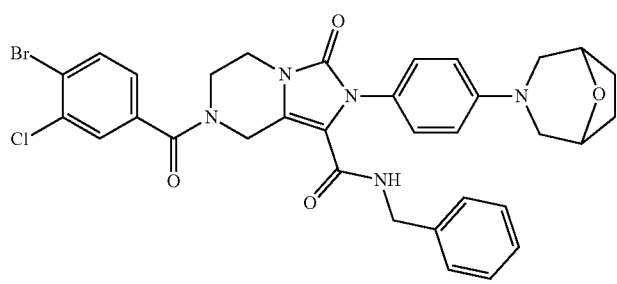 [SMILES: O=C(NCc1ccccc1)c1c2n(c(=O)n1-c1ccc(N3CC4CCC(C3)O4)cc1)CCN(C(=O)c1ccc(Br)c(Cl)c1)C2] | 121 |
| 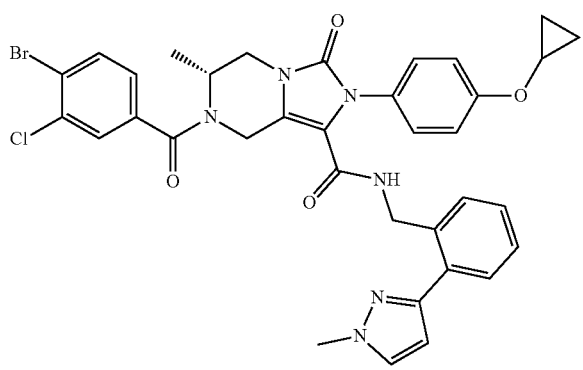 [SMILES: C[C@@H]1Cn2c(c(C(=O)NCc3ccccc3-c3ccn(C)n3)n(-c3ccc(OC4CC4)cc3)c2=O)CN1C(=O)c1ccc(Br)c(Cl)c1] | 22a |

TABLE D-continued

| Structure | Cmpd |
|---|---|
| 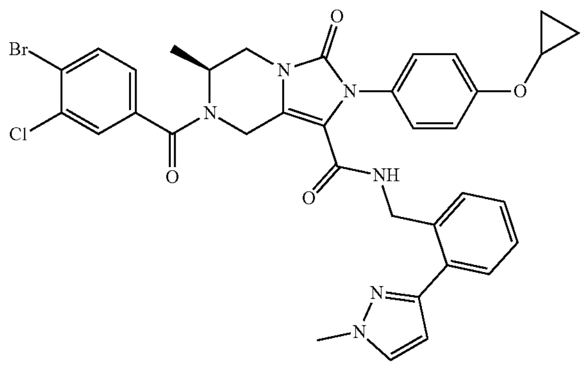 [SMILES: C[C@H]1Cn2c(c(C(=O)NCc3ccccc3-c3ccn(C)n3)n(-c3ccc(OC4CC4)cc3)c2=O)CN1C(=O)c1ccc(Br)c(Cl)c1] | 22b |
| 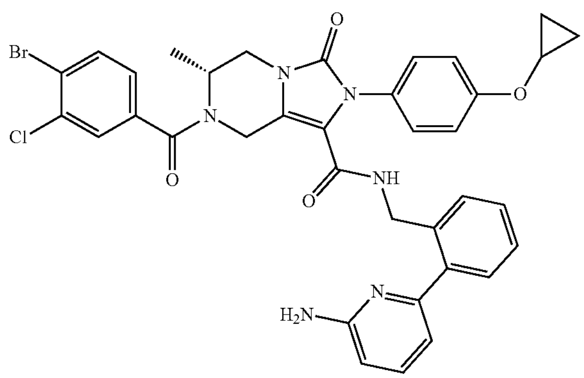 [SMILES: C[C@@H]1Cn2c(c(C(=O)NCc3ccccc3-c3cccc(N)n3)n(-c3ccc(OC4CC4)cc3)c2=O)CN1C(=O)c1ccc(Br)c(Cl)c1] | 23a |
| 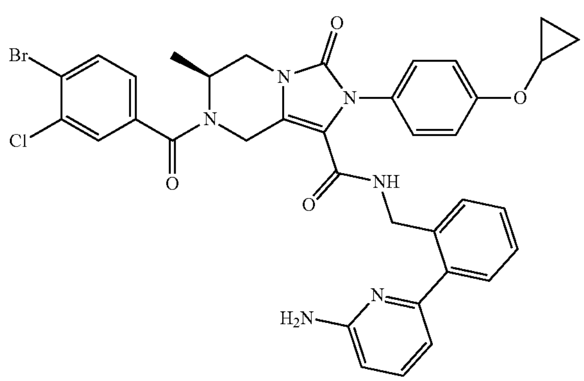 [SMILES: C[C@H]1Cn2c(c(C(=O)NCc3ccccc3-c3cccc(N)n3)n(-c3ccc(OC4CC4)cc3)c2=O)CN1C(=O)c1ccc(Br)c(Cl)c1] | 23b |
| 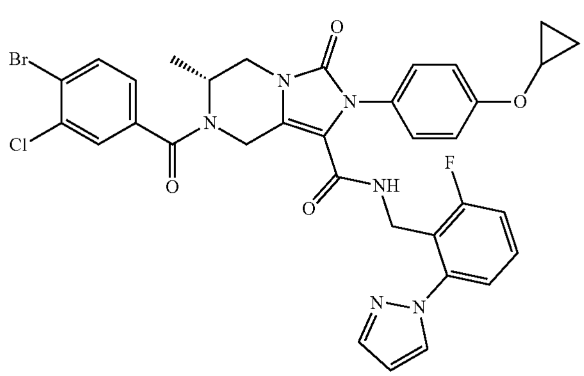 [SMILES: C[C@@H]1Cn2c(c(C(=O)NCc3c(F)cccc3-n3cccn3)n(-c3ccc(OC4CC4)cc3)c2=O)CN1C(=O)c1ccc(Br)c(Cl)c1] | 24a |

TABLE D-continued

| Structure | Cmpd |
|---|---|
| 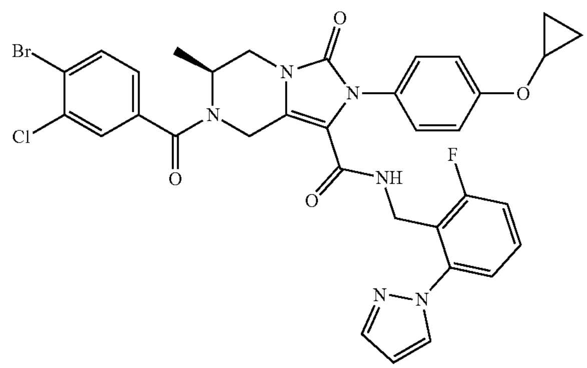 [SMILES: C[C@H]1Cn2c(c(C(=O)NCc3c(F)cccc3-n3cccn3)n(-c3ccc(OC4CC4)cc3)c2=O)CN1C(=O)c1ccc(Br)c(Cl)c1] | 24b |
| 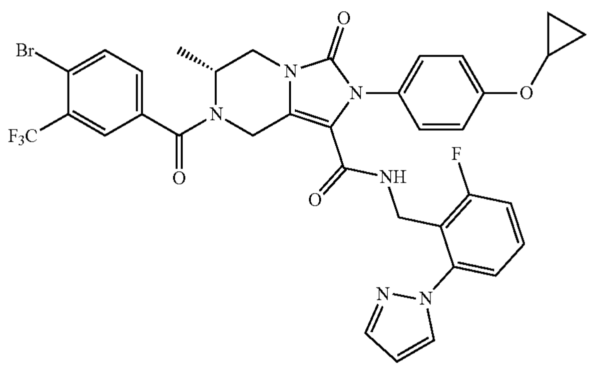 [SMILES: C[C@@H]1Cn2c(c(C(=O)NCc3c(F)cccc3-n3cccn3)n(-c3ccc(OC4CC4)cc3)c2=O)CN1C(=O)c1ccc(Br)c(C(F)(F)F)c1] | 25a |
| 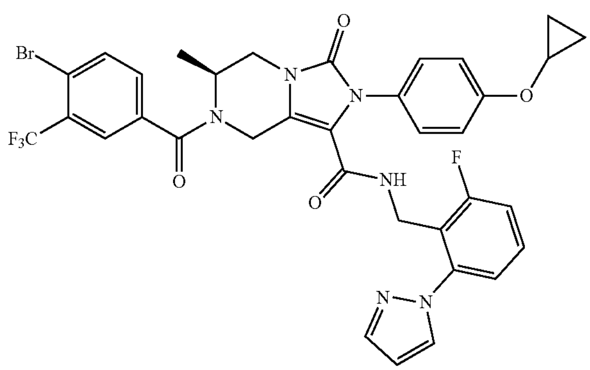 [SMILES: C[C@H]1Cn2c(c(C(=O)NCc3c(F)cccc3-n3cccn3)n(-c3ccc(OC4CC4)cc3)c2=O)CN1C(=O)c1ccc(Br)c(C(F)(F)F)c1] | 25b |
| 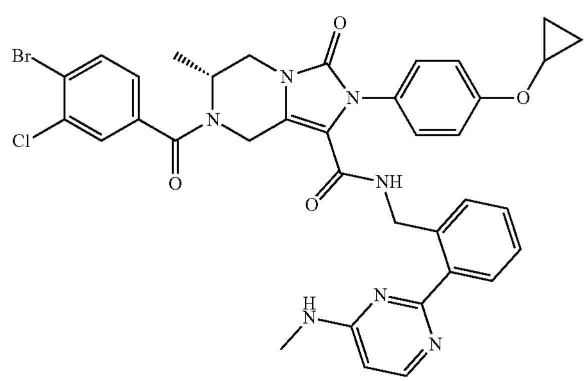 [SMILES: CNc1ccnc(-c2ccccc2CNC(=O)c2c3n(c(=O)n2-c2ccc(OC4CC4)cc2)C[C@@H](C)N(C(=O)c2ccc(Br)c(Cl)c2)C3)n1] | 26a |

TABLE D-continued
| Structure | Cmpd |
|---|---|
| 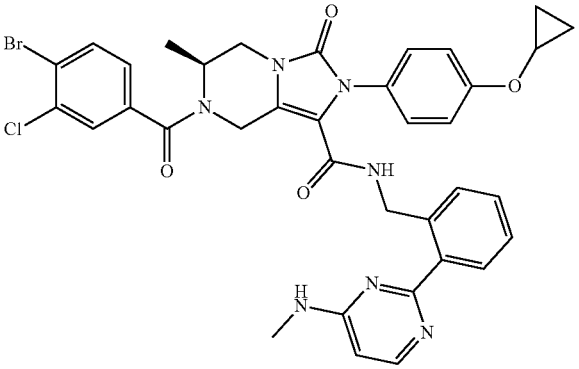 [SMILES: CNc1ccnc(-c2ccccc2CNC(=O)c2c3n(c(=O)n2-c2ccc(OC4CC4)cc2)C[C@H](C)N(C(=O)c2ccc(Br)c(Cl)c2)C3)n1] | 26b |
| 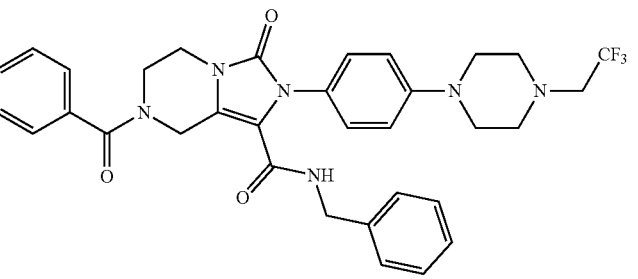 | 122 |
| 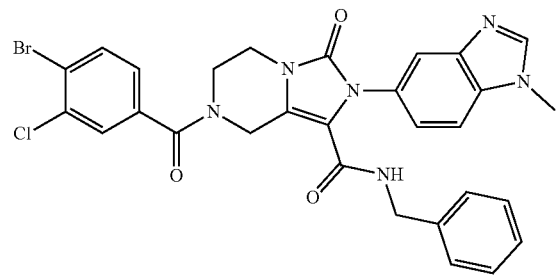 [SMILES: Cn1cnc2cc(-n3c(C(=O)NCc4ccccc4)c4n(c3=O)CCN(C(=O)c3ccc(Br)c(Cl)c3)C4)ccc21] | 123 |
| 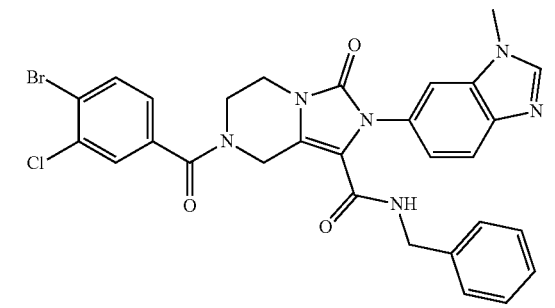 [SMILES: Cn1cnc2ccc(-n3c(C(=O)NCc4ccccc4)c4n(c3=O)CCN(C(=O)c3ccc(Br)c(Cl)c3)C4)cc21] | 124 |
| 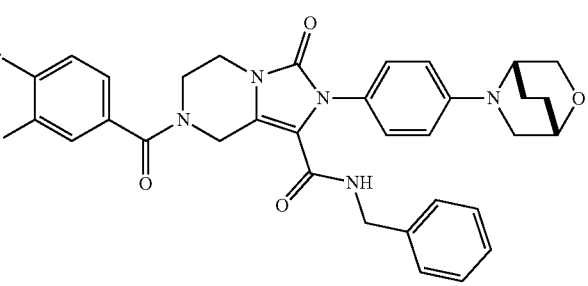 | 125a |

TABLE D-continued
| Structure | Cmpd |
|---|---|
| 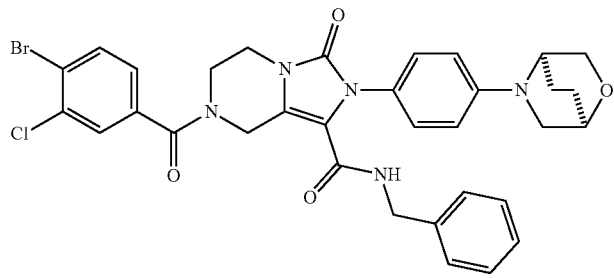 | 125b |
| 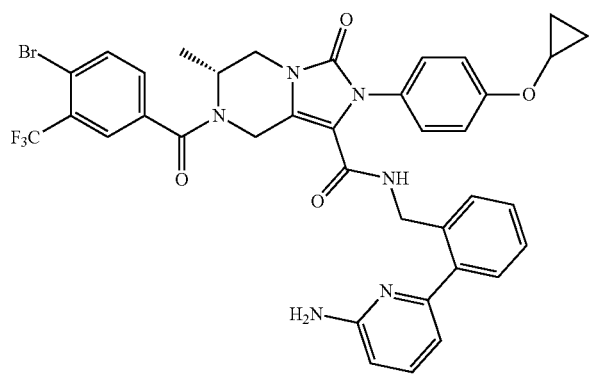 [SMILES: C[C@@H]1Cn2c(c(C(=O)NCc3ccccc3-c3cccc(N)n3)n(-c3ccc(OC4CC4)cc3)c2=O)CN1C(=O)c1ccc(Br)c(C(F)(F)F)c1] | 27a |
| 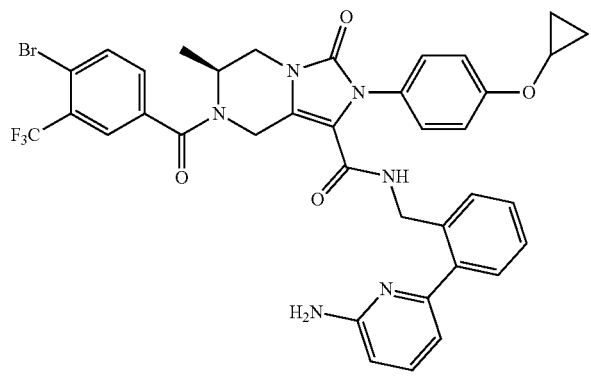 | 27b |
| 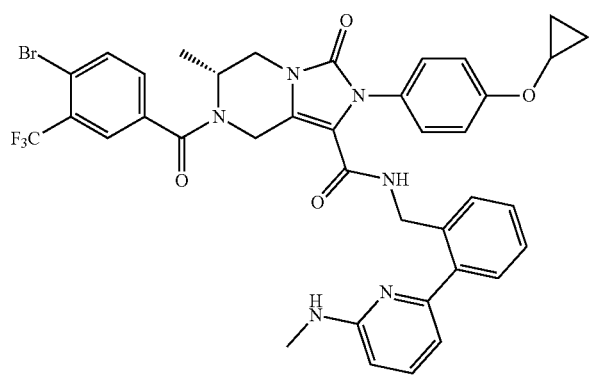 [SMILES: CNc1cccc(-c2ccccc2CNC(=O)c2c3n(c(=O)n2-c2ccc(OC4CC4)cc2)C[C@@H](C)N(C(=O)c2ccc(Br)c(C(F)(F)F)c2)C3)n1] | 28a |

TABLE D-continued
| Structure | Cmpd |
|---|---|
| 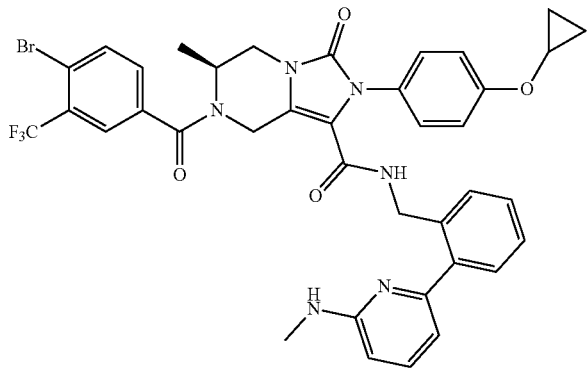 [SMILES: CNc1cccc(-c2ccccc2CNC(=O)c2c3n(c(=O)n2-c2ccc(OC4CC4)cc2)C[C@H](C)N(C(=O)c2ccc(Br)c(C(F)(F)F)c2)C3)n1] | 28b |
| 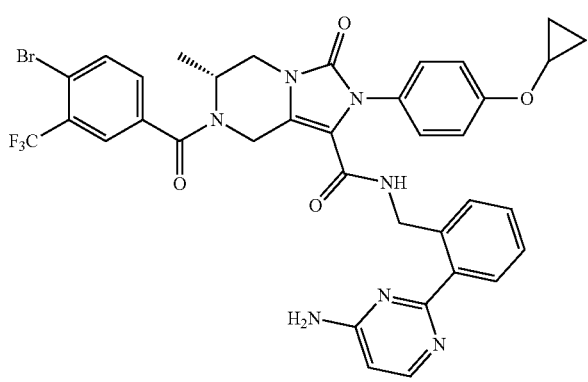 [SMILES: C[C@@H]1Cn2c(c(C(=O)NCc3ccccc3-c3nccc(N)n3)n(-c3ccc(OC4CC4)cc3)c2=O)CN1C(=O)c1ccc(Br)c(C(F)(F)F)c1] | 29a |
| 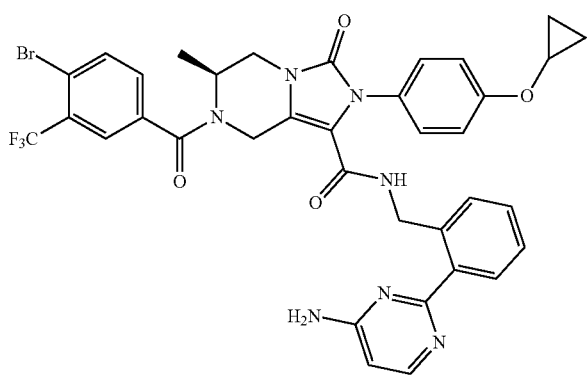 [SMILES: C[C@H]1Cn2c(c(C(=O)NCc3ccccc3-c3nccc(N)n3)n(-c3ccc(OC4CC4)cc3)c2=O)CN1C(=O)c1ccc(Br)c(C(F)(F)F)c1] | 29b |
| 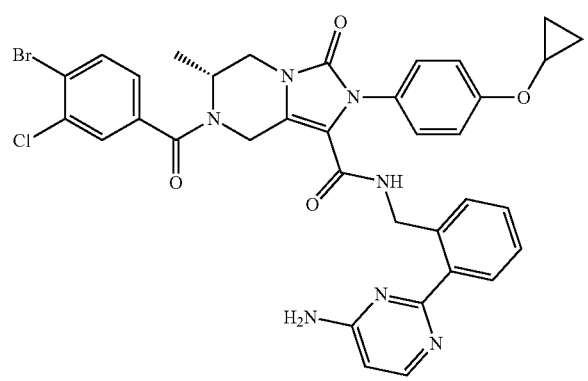 | 30a |

TABLE D-continued

| Structure | Cmpd |
|---|---|
| 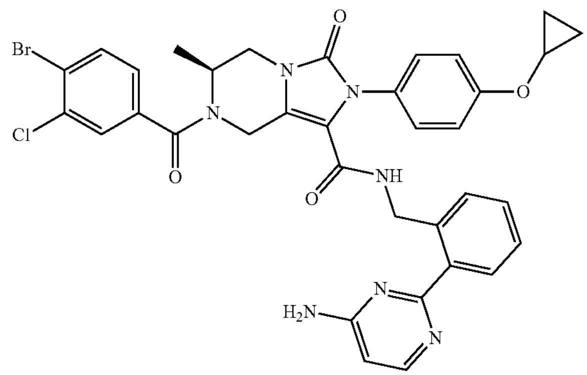 [SMILES: C[C@H]1Cn2c(c(C(=O)NCc3ccccc3-c3nccc(N)n3)n(-c3ccc(OC4CC4)cc3)c2=O)CN1C(=O)c1ccc(Br)c(Cl)c1] | 30b |
| 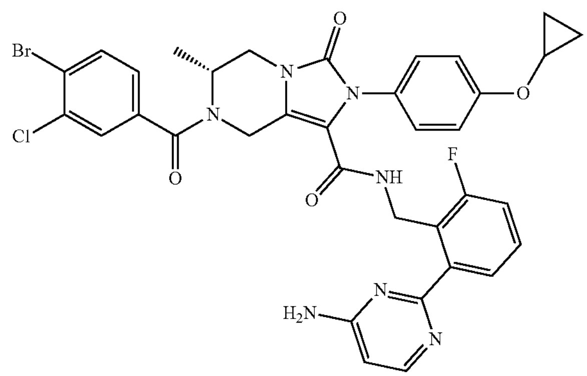 [SMILES: C[C@@H]1Cn2c(c(C(=O)NCc3c(F)cccc3-c3nccc(N)n3)n(-c3ccc(OC4CC4)cc3)c2=O)CN1C(=O)c1ccc(Br)c(Cl)c1] | 31a |
| 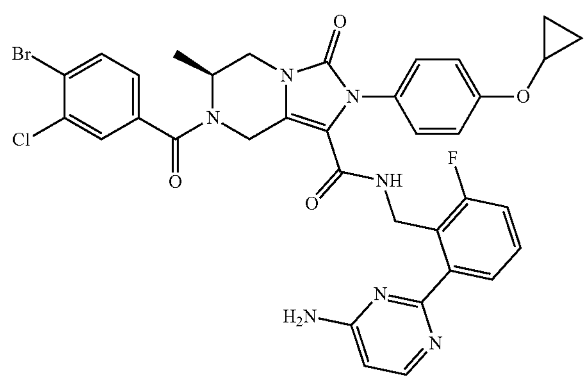 [SMILES: C[C@H]1Cn2c(c(C(=O)NCc3c(F)cccc3-c3nccc(N)n3)n(-c3ccc(OC4CC4)cc3)c2=O)CN1C(=O)c1ccc(Br)c(Cl)c1] | 31b |
| 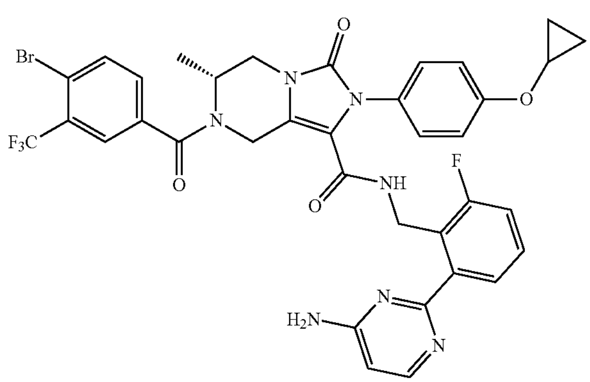 | 32a |

TABLE D-continued

| Structure | Cmpd |
|---|---|
| 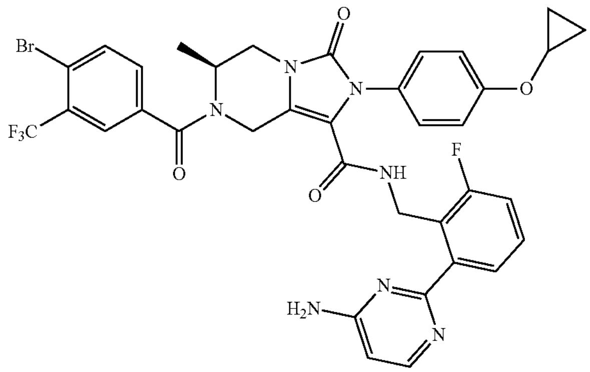 | 32b |
| 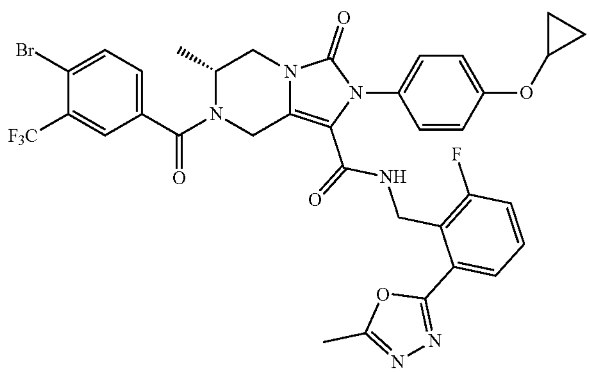 [SMILES: Cc1nnc(-c2cccc(F)c2CNC(=O)c2c3n(c(=O)n2-c2ccc(OC4CC4)cc2)C[C@@H](C)N(C(=O)c2ccc(Br)c(C(F)(F)F)c2)C3)o1] | 33a |
| 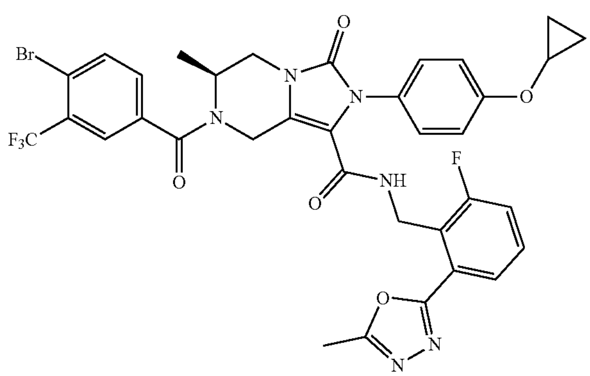 [SMILES: Cc1nnc(-c2cccc(F)c2CNC(=O)c2c3n(c(=O)n2-c2ccc(OC4CC4)cc2)C[C@H](C)N(C(=O)c2ccc(Br)c(C(F)(F)F)c2)C3)o1] | 33b |
| 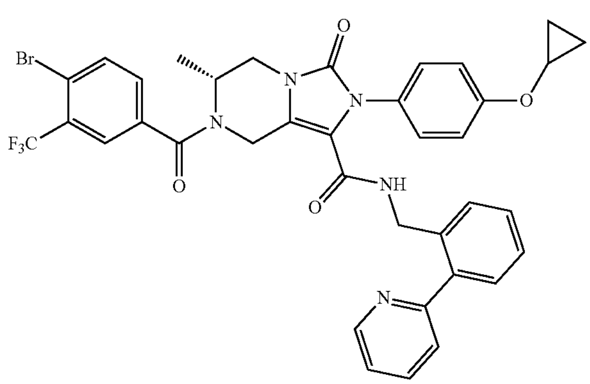 [SMILES: C[C@@H]1Cn2c(c(C(=O)NCc3ccccc3-c3ccccn3)n(-c3ccc(OC4CC4)cc3)c2=O)CN1C(=O)c1ccc(Br)c(C(F)(F)F)c1] | 34a |

TABLE D-continued
| Structure | Cmpd |
|---|---|
| 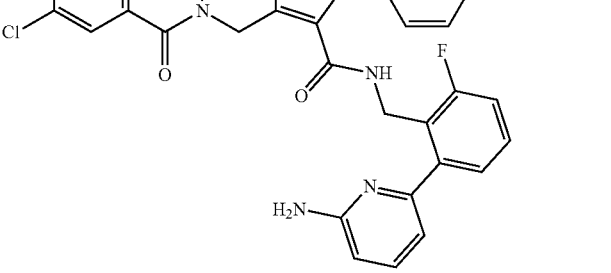 | 35a |
| 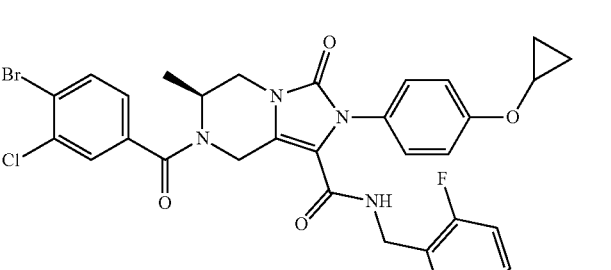 | 35b |
| 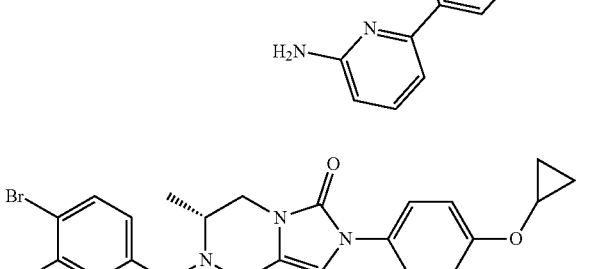 | 36a |
| 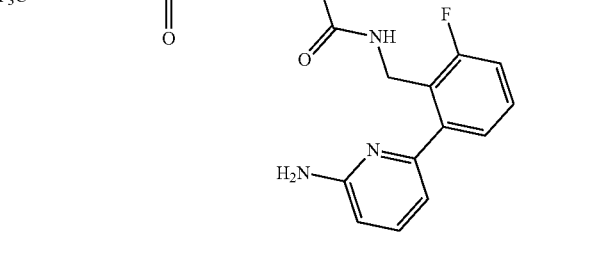 | 36b |

TABLE D-continued

| Structure | Cmpd |
|---|---|
| 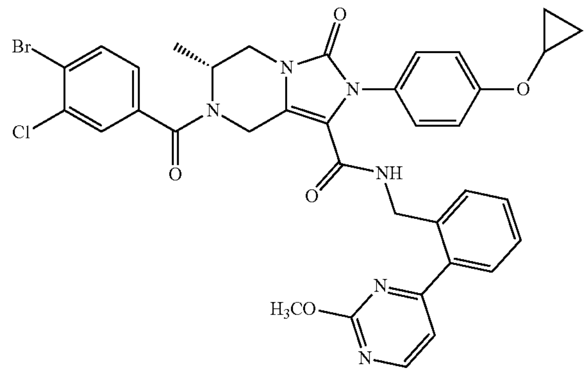 [SMILES: COc1nccc(-c2ccccc2CNC(=O)c2c3n(c(=O)n2-c2ccc(OC4CC4)cc2)C[C@@H](C)N(C(=O)c2ccc(Br)c(Cl)c2)C3)n1] | 37a |
| 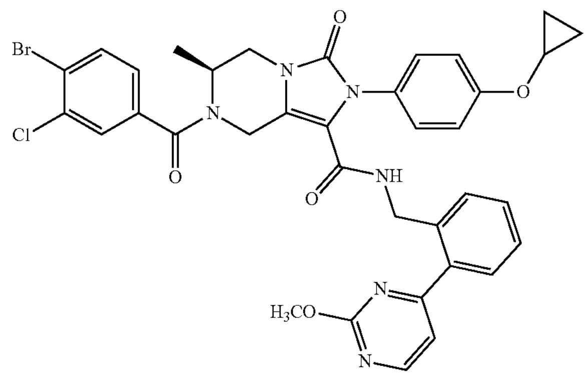 [SMILES: COc1nccc(-c2ccccc2CNC(=O)c2c3n(c(=O)n2-c2ccc(OC4CC4)cc2)C[C@H](C)N(C(=O)c2ccc(Br)c(Cl)c2)C3)n1] | 37b |
| 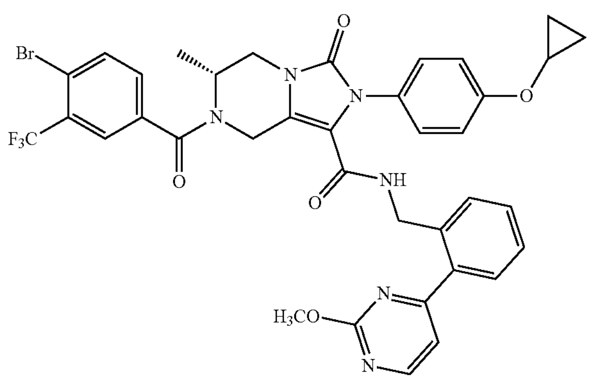 [SMILES: COc1nccc(-c2ccccc2CNC(=O)c2c3n(c(=O)n2-c2ccc(OC4CC4)cc2)C[C@@H](C)N(C(=O)c2ccc(Br)c(C(F)(F)F)c2)C3)n1] | 38a |
| 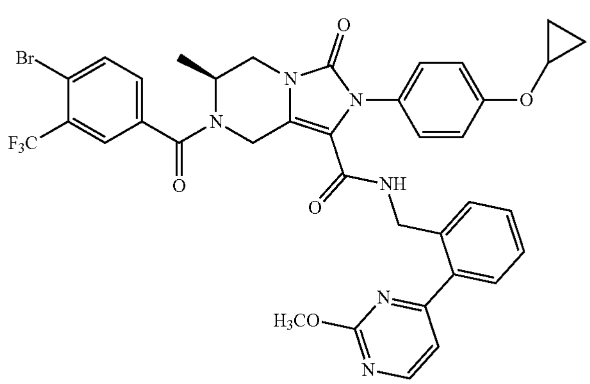 [SMILES: COc1nccc(-c2ccccc2CNC(=O)c2c3n(c(=O)n2-c2ccc(OC4CC4)cc2)C[C@H](C)N(C(=O)c2ccc(Br)c(C(F)(F)F)c2)C3)n1] | 38b |

TABLE D-continued

| Structure | Cmpd |
|---|---|
| 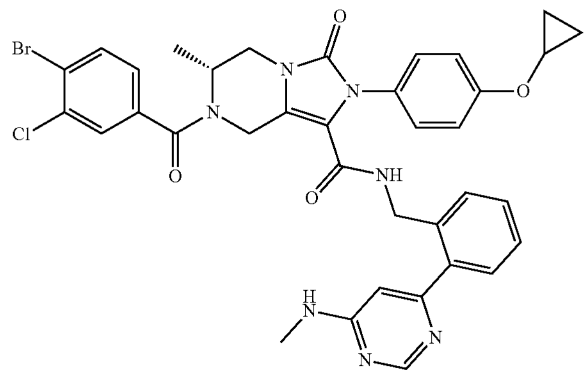 [SMILES: CNc1cc(-c2ccccc2CNC(=O)c2c3n(c(=O)n2-c2ccc(OC4CC4)cc2)C[C@@H](C)N(C(=O)c2ccc(Br)c(Cl)c2)C3)ncn1] | 39a |
| 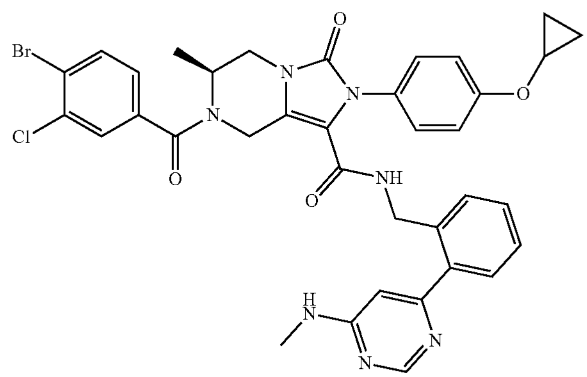 [SMILES: CNc1cc(-c2ccccc2CNC(=O)c2c3n(c(=O)n2-c2ccc(OC4CC4)cc2)C[C@H](C)N(C(=O)c2ccc(Br)c(Cl)c2)C3)ncn1] | 39b |
| 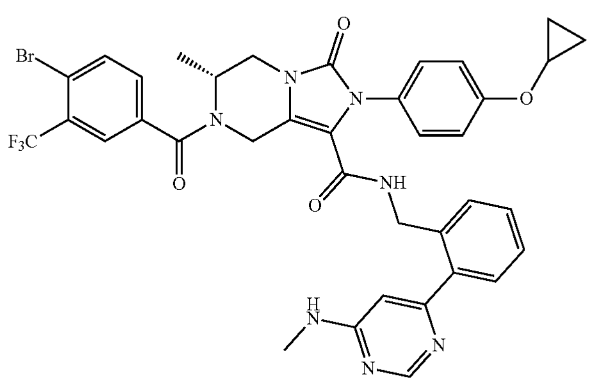 [SMILES: CNc1cc(-c2ccccc2CNC(=O)c2c3n(c(=O)n2-c2ccc(OC4CC4)cc2)C[C@@H](C)N(C(=O)c2ccc(Br)c(C(F)(F)F)c2)C3)ncn1] | 40a |
| 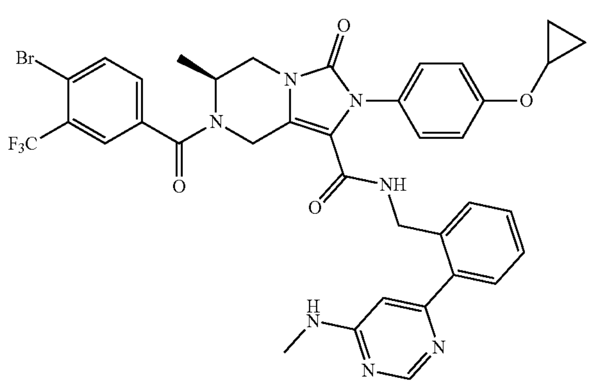 [SMILES: CNc1cc(-c2ccccc2CNC(=O)c2c3n(c(=O)n2-c2ccc(OC4CC4)cc2)C[C@H](C)N(C(=O)c2ccc(Br)c(C(F)(F)F)c2)C3)ncn1] | 40b |

TABLE D-continued
| Structure | Cmpd |
|---|---|
| 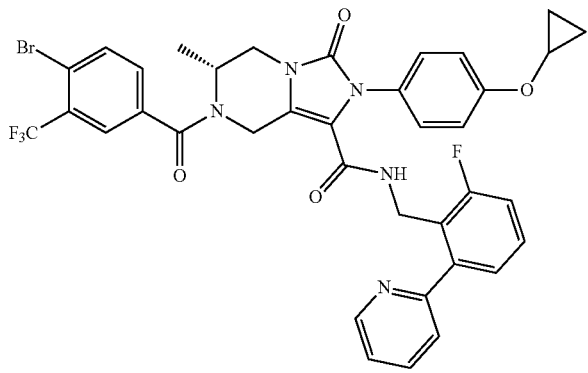 [SMILES: C[C@@H]1Cn2c(c(C(=O)NCc3c(F)cccc3-c3ccccn3)n(-c3ccc(OC4CC4)cc3)c2=O)CN1C(=O)c1ccc(Br)c(C(F)(F)F)c1] | 41a |
| 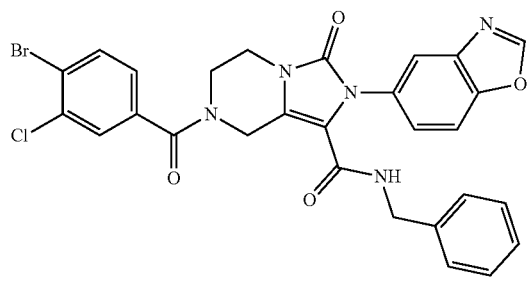 [SMILES: O=C(NCc1ccccc1)c1c2n(c(=O)n1-c1ccc3ocnc3c1)CCN(C(=O)c1ccc(Br)c(Cl)c1)C2] | 126 |
| 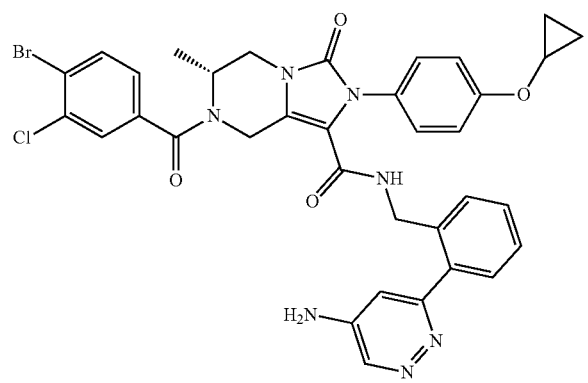 [SMILES: C[C@@H]1Cn2c(c(C(=O)NCc3ccccc3-c3cc(N)cnn3)n(-c3ccc(OC4CC4)cc3)c2=O)CN1C(=O)c1ccc(Br)c(Cl)c1] | 42a |
| 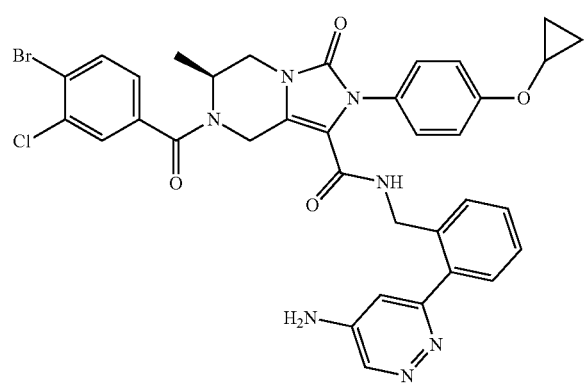 [SMILES: C[C@H]1Cn2c(c(C(=O)NCc3ccccc3-c3cc(N)cnn3)n(-c3ccc(OC4CC4)cc3)c2=O)CN1C(=O)c1ccc(Br)c(Cl)c1] | 42b |

TABLE D-continued
| Structure | Cmpd |
|---|---|
| 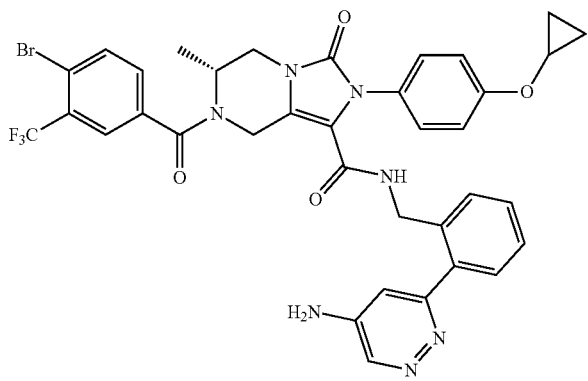 [SMILES: C[C@@H]1Cn2c(c(C(=O)NCc3ccccc3-c3cc(N)cnn3)n(-c3ccc(OC4CC4)cc3)c2=O)CN1C(=O)c1ccc(Br)c(C(F)(F)F)c1] | 43a |
| 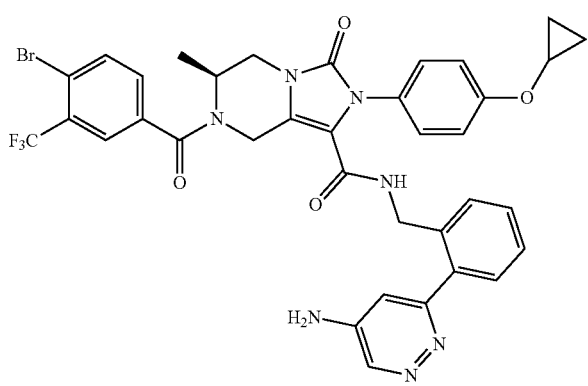 [SMILES: C[C@H]1Cn2c(c(C(=O)NCc3ccccc3-c3cc(N)cnn3)n(-c3ccc(OC4CC4)cc3)c2=O)CN1C(=O)c1ccc(Br)c(C(F)(F)F)c1] | 43b |
| 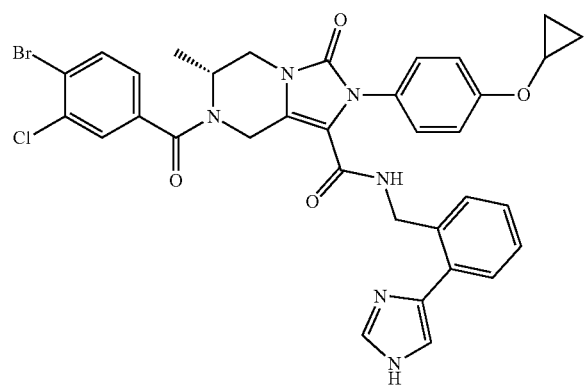 [SMILES: C[C@@H]1Cn2c(c(C(=O)NCc3ccccc3-c3c[nH]cn3)n(-c3ccc(OC4CC4)cc3)c2=O)CN1C(=O)c1ccc(Br)c(Cl)c1] | 44a |
| 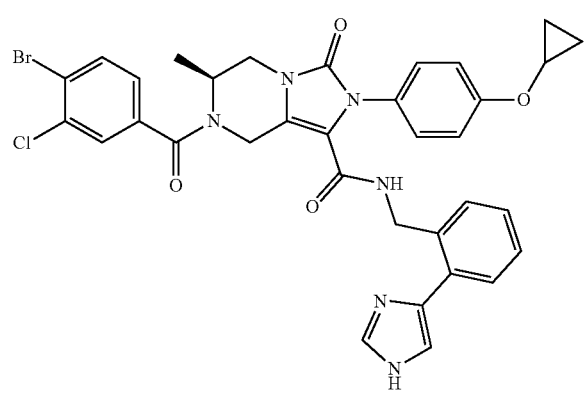 [SMILES: C[C@H]1Cn2c(c(C(=O)NCc3ccccc3-c3c[nH]cn3)n(-c3ccc(OC4CC4)cc3)c2=O)CN1C(=O)c1ccc(Br)c(Cl)c1] | 44b |

TABLE D-continued

| Structure | Cmpd |
|---|---|
| 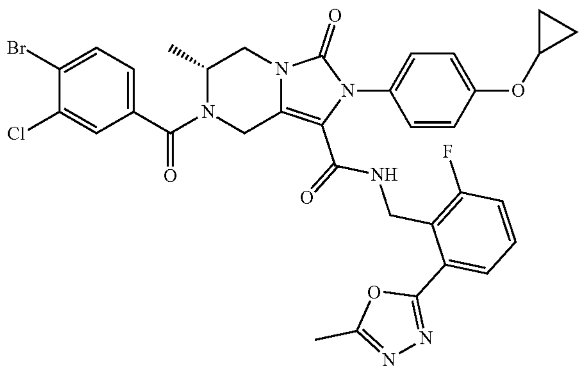 [SMILES: Cc1nnc(-c2cccc(F)c2CNC(=O)c2c3n(c(=O)n2-c2ccc(OC4CC4)cc2)C[C@@H](C)N(C(=O)c2ccc(Br)c(Cl)c2)C3)o1] | 45a |
| 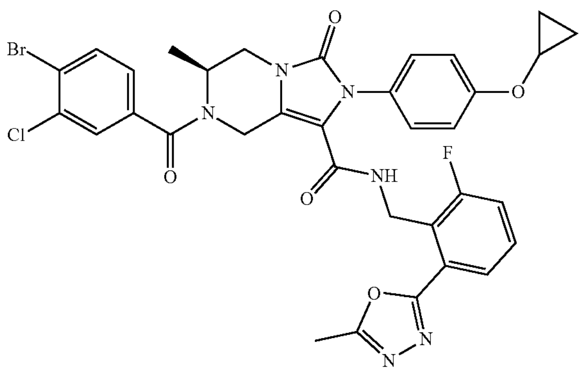 [SMILES: Cc1nnc(-c2cccc(F)c2CNC(=O)c2c3n(c(=O)n2-c2ccc(OC4CC4)cc2)C[C@H](C)N(C(=O)c2ccc(Br)c(Cl)c2)C3)o1] | 45b |
| 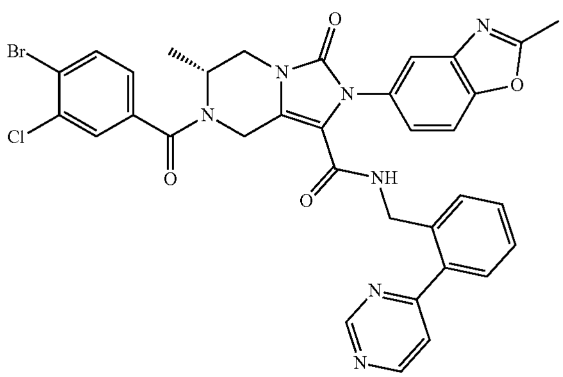 [SMILES: Cc1nc2cc(-n3c(C(=O)NCc4ccccc4-c4ccncn4)c4n(c3=O)C[C@@H](C)N(C(=O)c3ccc(Br)c(Cl)c3)C4)ccc2o1] | 46a |
| 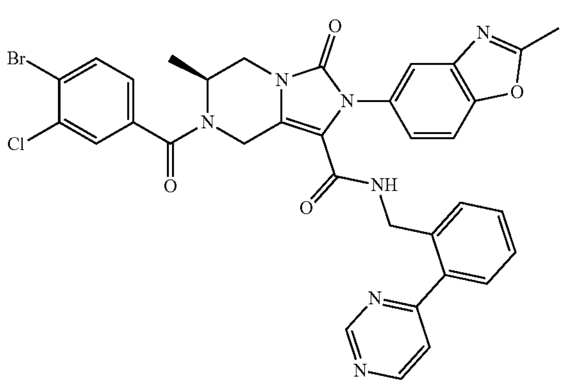 [SMILES: Cc1nc2cc(-n3c(C(=O)NCc4ccccc4-c4ccncn4)c4n(c3=O)C[C@H](C)N(C(=O)c3ccc(Br)c(Cl)c3)C4)ccc2o1] | 46b |

TABLE D-continued
| Structure | Cmpd |
|---|---|
| 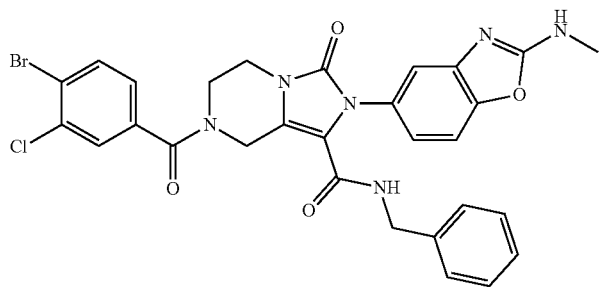 [SMILES: CNc1nc2cc(-n3c(C(=O)NCc4ccccc4)c4n(c3=O)CCN(C(=O)c3ccc(Br)c(Cl)c3)C4)ccc2o1] | 127 |
| 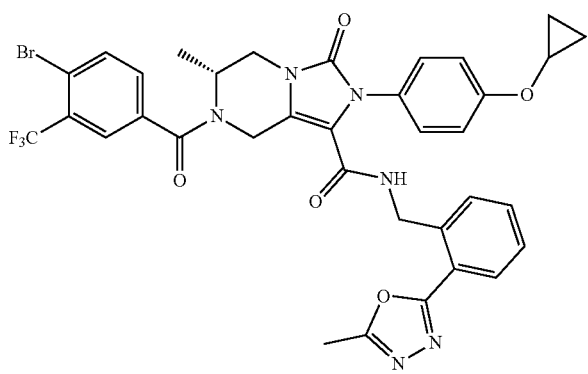 [SMILES: Cc1nnc(-c2ccccc2CNC(=O)c2c3n(c(=O)n2-c2ccc(OC4CC4)cc2)C[C@@H](C)N(C(=O)c2ccc(Br)c(C(F)(F)F)c2)C3)o1] | 47a |
| 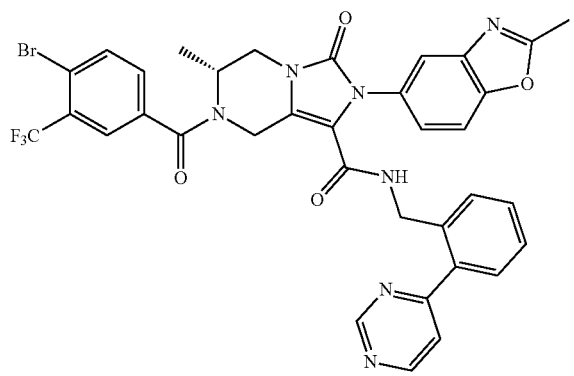 [SMILES: Cc1nc2cc(-n3c(C(=O)NCc4ccccc4-c4ccncn4)c4n(c3=O)C[C@@H](C)N(C(=O)c3ccc(Br)c(C(F)(F)F)c3)C4)ccc2o1] | 48a |
| 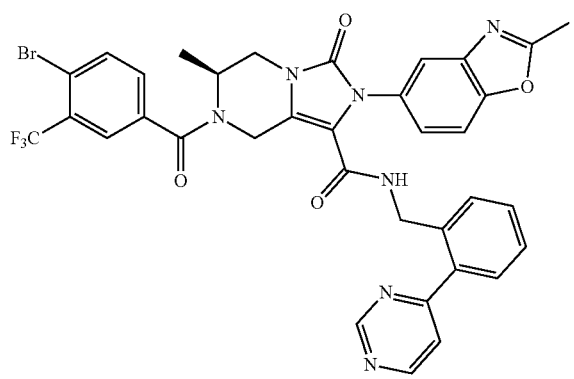 [SMILES: Cc1nc2cc(-n3c(C(=O)NCc4ccccc4-c4ccncn4)c4n(c3=O)C[C@H](C)N(C(=O)c3ccc(Br)c(C(F)(F)F)c3)C4)ccc2o1] | 48b |

TABLE D-continued

| Structure | Cmpd |
|---|---|
| 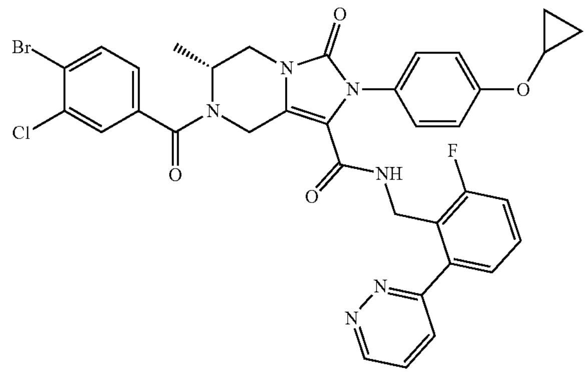 [SMILES: C[C@@H]1Cn2c(c(C(=O)NCc3c(F)cccc3-c3cccnn3)n(-c3ccc(OC4CC4)cc3)c2=O)CN1C(=O)c1ccc(Br)c(Cl)c1] | 49a |
| 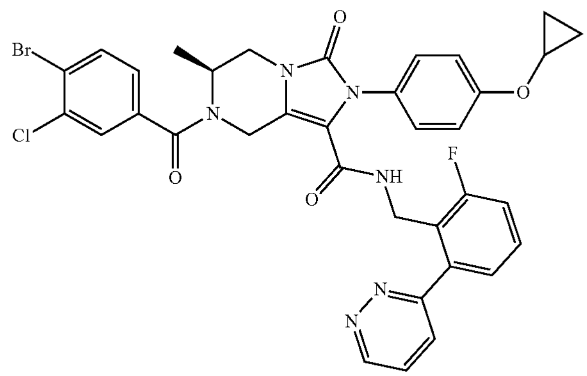 [SMILES: C[C@H]1Cn2c(c(C(=O)NCc3c(F)cccc3-c3cccnn3)n(-c3ccc(OC4CC4)cc3)c2=O)CN1C(=O)c1ccc(Br)c(Cl)c1] | 49b |
| 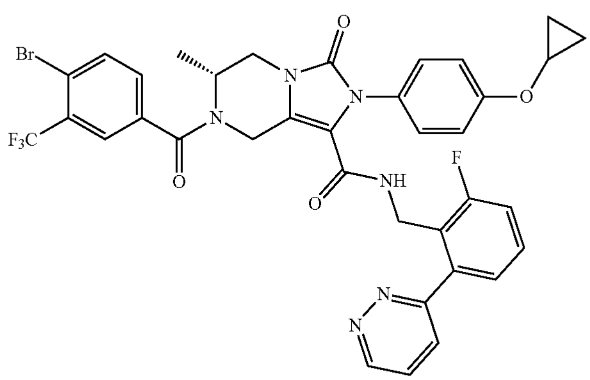 [SMILES: C[C@@H]1Cn2c(c(C(=O)NCc3c(F)cccc3-c3cccnn3)n(-c3ccc(OC4CC4)cc3)c2=O)CN1C(=O)c1ccc(Br)c(C(F)(F)F)c1] | 50a |
| 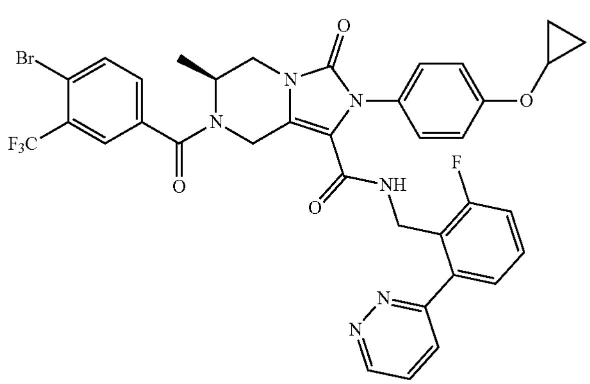 [SMILES: C[C@H]1Cn2c(c(C(=O)NCc3c(F)cccc3-c3cccnn3)n(-c3ccc(OC4CC4)cc3)c2=O)CN1C(=O)c1ccc(Br)c(C(F)(F)F)c1] | 50b |

TABLE D-continued

| Structure | Cmpd |
|---|---|
| 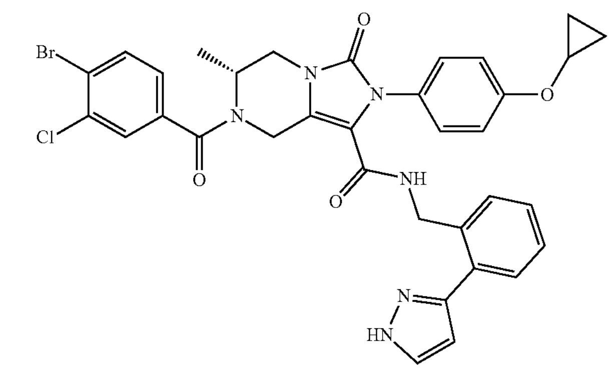 [SMILES: C[C@@H]1Cn2c(c(C(=O)NCc3ccccc3-c3cc[nH]n3)n(-c3ccc(OC4CC4)cc3)c2=O)CN1C(=O)c1ccc(Br)c(Cl)c1] | 51a |
| 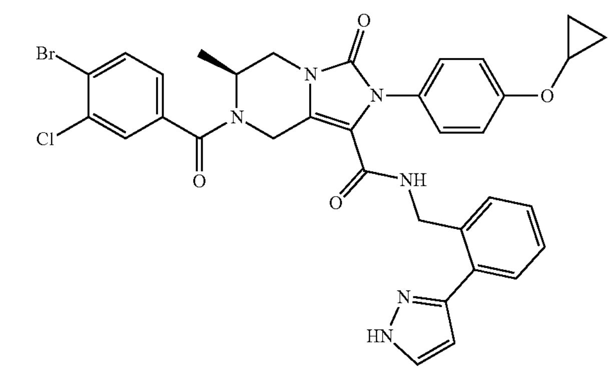 [SMILES: C[C@H]1Cn2c(c(C(=O)NCc3ccccc3-c3cc[nH]n3)n(-c3ccc(OC4CC4)cc3)c2=O)CN1C(=O)c1ccc(Br)c(Cl)c1] | 51b |
| 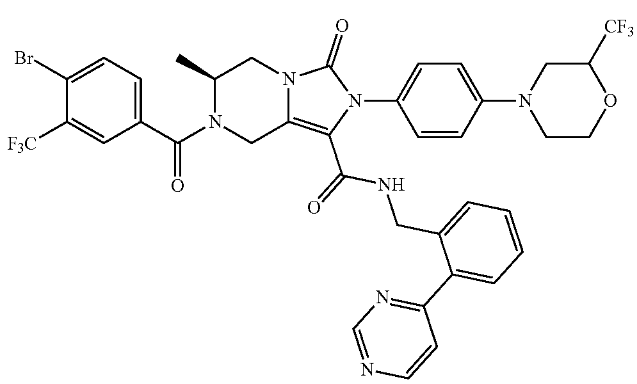 [SMILES: C[C@H]1Cn2c(c(C(=O)NCc3ccccc3-c3ccncn3)n(-c3ccc(N4CCOC(C(F)(F)F)C4)cc3)c2=O)CN1C(=O)c1ccc(Br)c(C(F)(F)F)c1] | 52a |
| 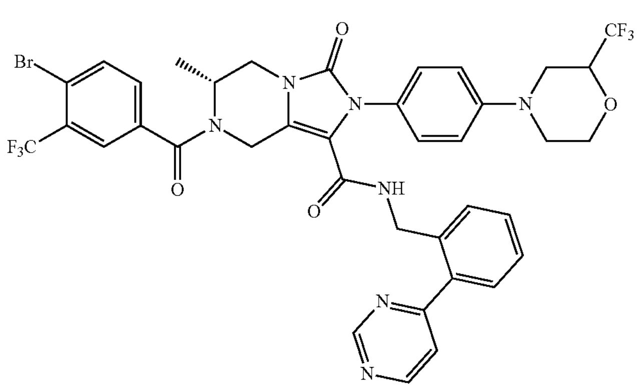 [SMILES: C[C@@H]1Cn2c(c(C(=O)NCc3ccccc3-c3ccncn3)n(-c3ccc(N4CCOC(C(F)(F)F)C4)cc3)c2=O)CN1C(=O)c1ccc(Br)c(C(F)(F)F)c1] | 52b |

TABLE D-continued

| Structure | Cmpd |
|---|---|
| 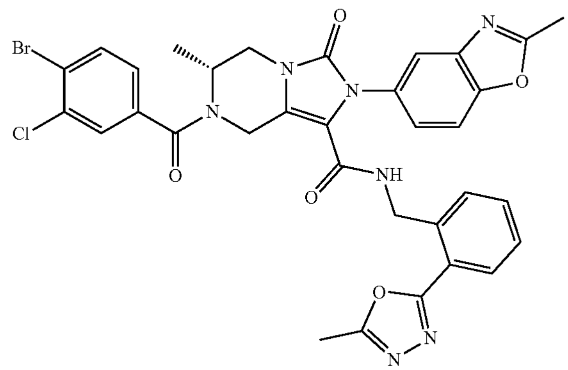 [SMILES: Cc1nnc(-c2ccccc2CNC(=O)c2c3n(c(=O)n2-c2ccc4oc(C)nc4c2)C[C@@H](C)N(C(=O)c2ccc(Br)c(Cl)c2)C3)o1] | 53a |
| 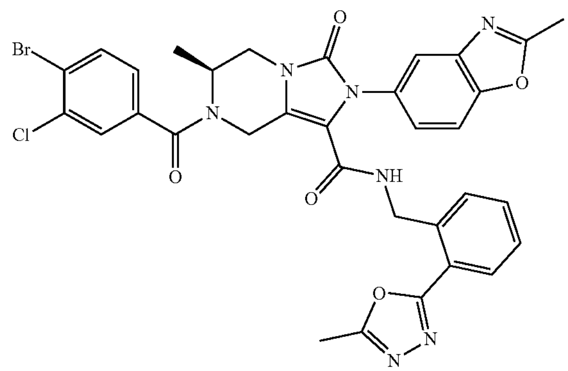 [SMILES: Cc1nnc(-c2ccccc2CNC(=O)c2c3n(c(=O)n2-c2ccc4oc(C)nc4c2)C[C@H](C)N(C(=O)c2ccc(Br)c(Cl)c2)C3)o1] | 53b |
| 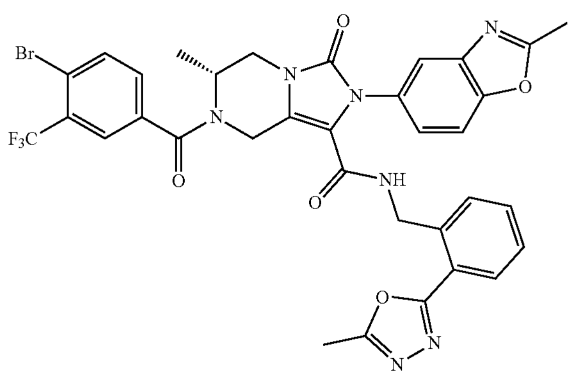 [SMILES: Cc1nnc(-c2ccccc2CNC(=O)c2c3n(c(=O)n2-c2ccc4oc(C)nc4c2)C[C@@H](C)N(C(=O)c2ccc(Br)c(C(F)(F)F)c2)C3)o1] | 54a |
| 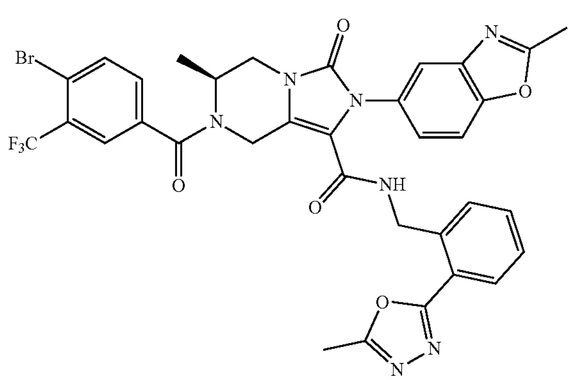 [SMILES: Cc1nnc(-c2ccccc2CNC(=O)c2c3n(c(=O)n2-c2ccc4oc(C)nc4c2)C[C@H](C)N(C(=O)c2ccc(Br)c(C(F)(F)F)c2)C3)o1] | 54b |

TABLE D-continued
| Structure | Cmpd |
|---|---|
| 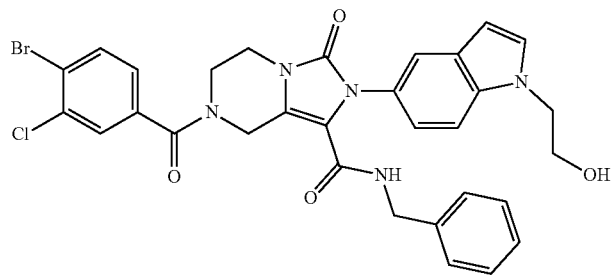 [SMILES: O=C(NCc1ccccc1)c1c2n(c(=O)n1-c1ccc3c(ccn3CCO)c1)CCN(C(=O)c1ccc(Br)c(Cl)c1)C2] | 128 |
| 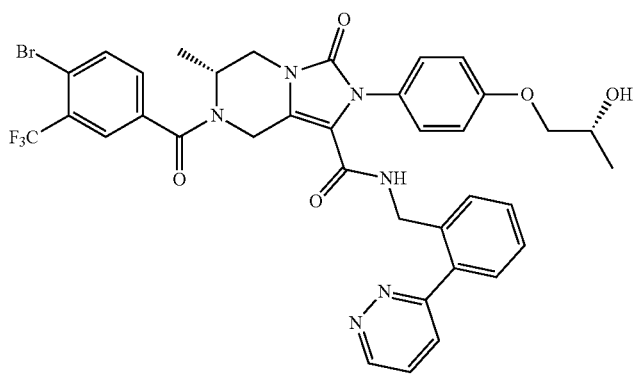 [SMILES: C[C@@H]1Cn2c(c(C(=O)NCc3ccccc3-c3cccnn3)n(-c3ccc(OC[C@@H](C)O)cc3)c2=O)CN1C(=O)c1ccc(Br)c(C(F)(F)F)c1] | 56a |
| 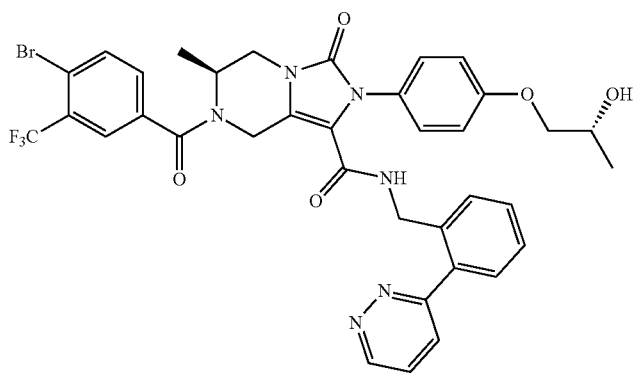 [SMILES: C[C@@H](O)COc1ccc(-n2c(C(=O)NCc3ccccc3-c3cccnn3)c3n(c2=O)C[C@H](C)N(C(=O)c2ccc(Br)c(C(F)(F)F)c2)C3)cc1] | 56b |
| 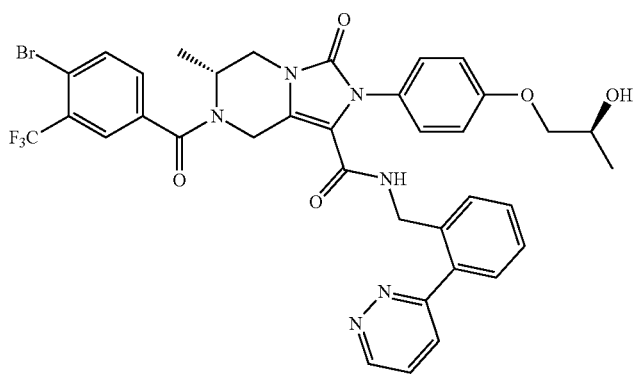 [SMILES: C[C@H](O)COc1ccc(-n2c(C(=O)NCc3ccccc3-c3cccnn3)c3n(c2=O)C[C@@H](C)N(C(=O)c2ccc(Br)c(C(F)(F)F)c2)C3)cc1] | 57a |

TABLE D-continued
| Structure | Cmpd |
|---|---|
| 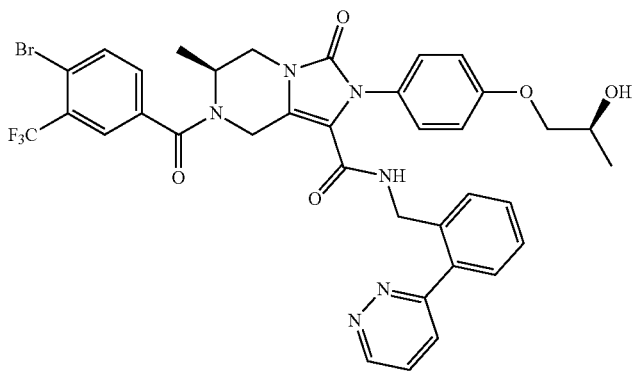 | 57b |
| 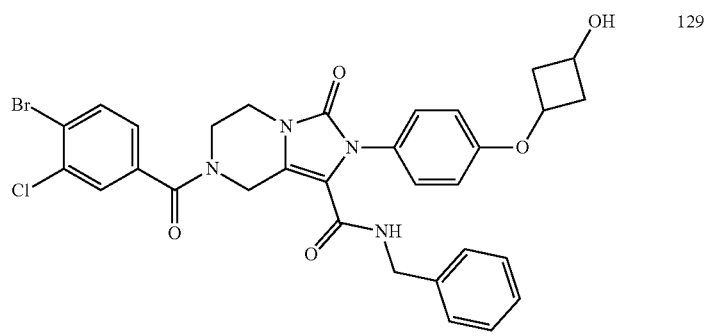 | 129 |
| 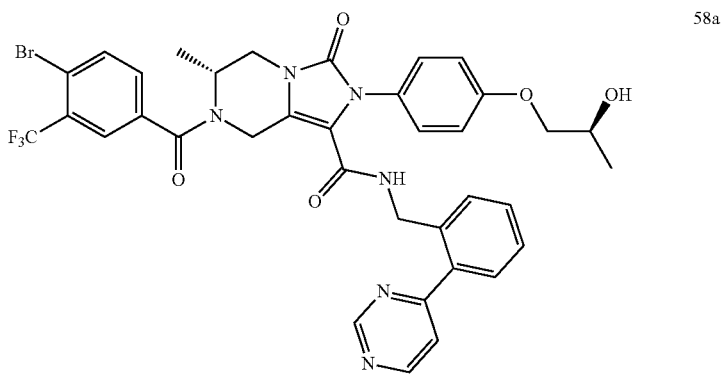 | 58a |
| 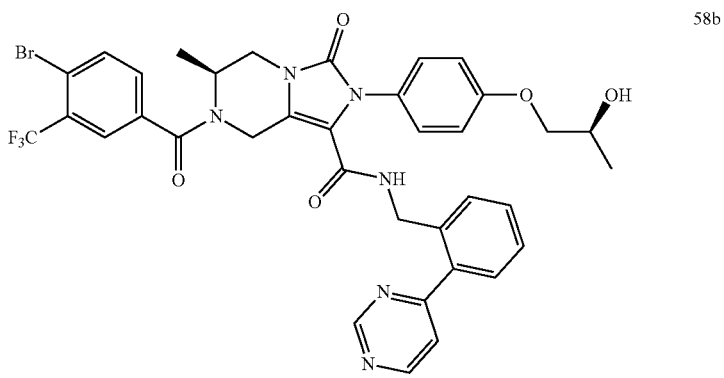 | 58b |

TABLE D-continued

| Structure | Cmpd |
|---|---|
| 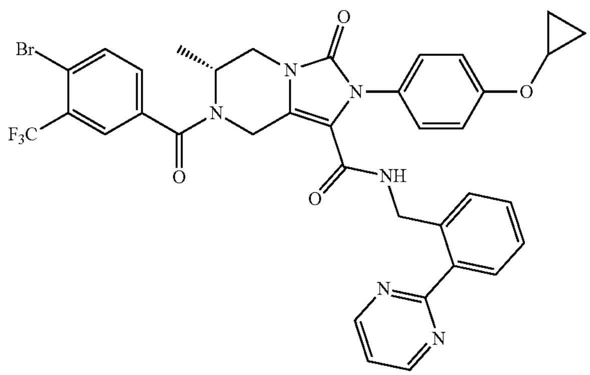 [SMILES: C[C@@H]1Cn2c(c(C(=O)NCc3ccccc3-c3ncccn3)n(-c3ccc(OC4CC4)cc3)c2=O)CN1C(=O)c1ccc(Br)c(C(F)(F)F)c1] | 59a |
| 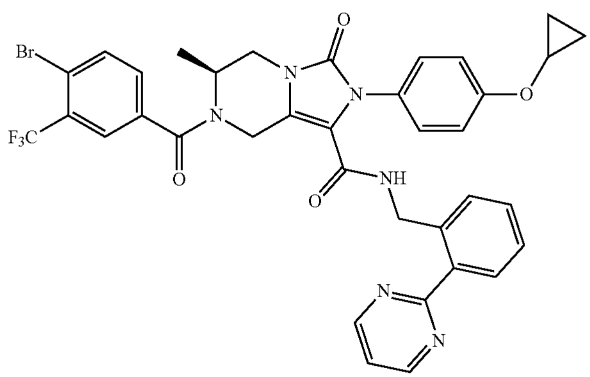 [SMILES: C[C@H]1Cn2c(c(C(=O)NCc3ccccc3-c3ncccn3)n(-c3ccc(OC4CC4)cc3)c2=O)CN1C(=O)c1ccc(Br)c(C(F)(F)F)c1] | 59b |
| 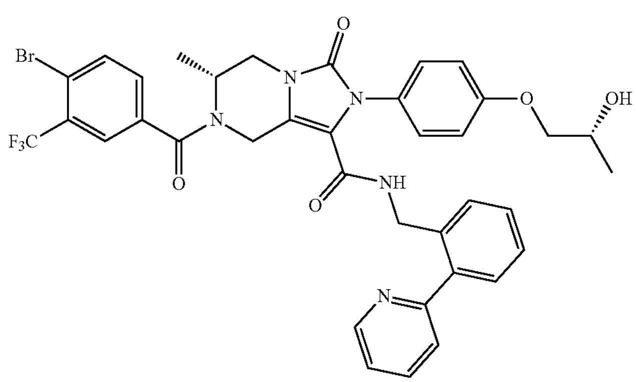 [SMILES: C[C@@H]1Cn2c(c(C(=O)NCc3ccccc3-c3ccccn3)n(-c3ccc(OC[C@@H](C)O)cc3)c2=O)CN1C(=O)c1ccc(Br)c(C(F)(F)F)c1] | 60a |
| 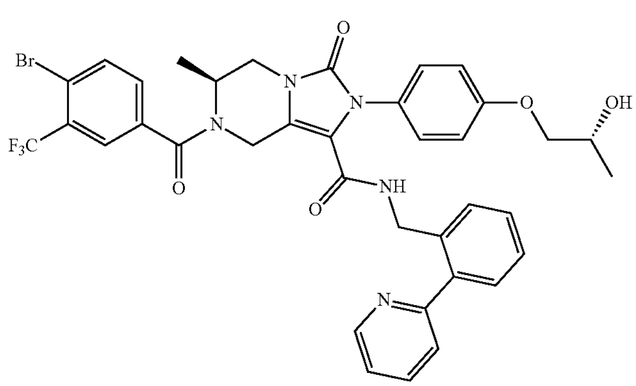 [SMILES: C[C@@H](O)COc1ccc(-n2c(C(=O)NCc3ccccc3-c3ccccn3)c3n(c2=O)C[C@H](C)N(C(=O)c2ccc(Br)c(C(F)(F)F)c2)C3)cc1] | 60b |

TABLE D-continued

| Structure | Cmpd |
|---|---|
| 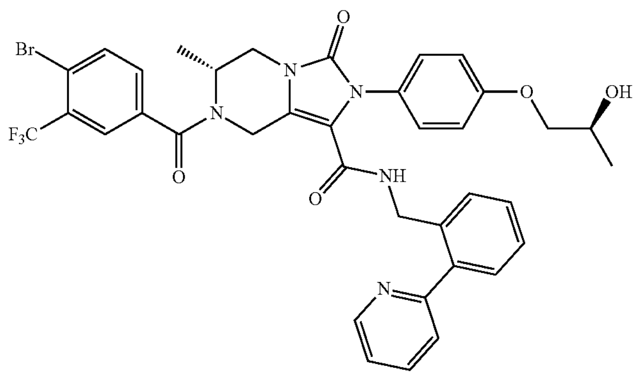 [SMILES: C[C@H](O)COc1ccc(-n2c(C(=O)NCc3ccccc3-c3ccccn3)c3n(c2=O)C[C@@H](C)N(C(=O)c2ccc(Br)c(C(F)(F)F)c2)C3)cc1] | 61a |
| 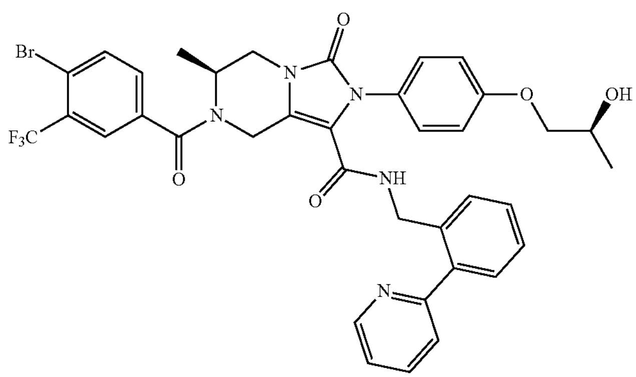 [SMILES: C[C@H](O)COc1ccc(-n2c(C(=O)NCc3ccccc3-c3ccccn3)c3n(c2=O)C[C@H](C)N(C(=O)c2ccc(Br)c(C(F)(F)F)c2)C3)cc1] | 61b |
| 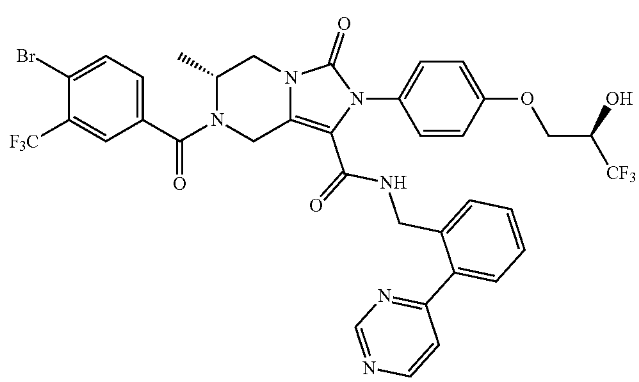 [SMILES: C[C@@H]1Cn2c(c(C(=O)NCc3ccccc3-c3ccncn3)n(-c3ccc(OC[C@@H](O)C(F)(F)F)cc3)c2=O)CN1C(=O)c1ccc(Br)c(C(F)(F)F)c1] | 62a |
| 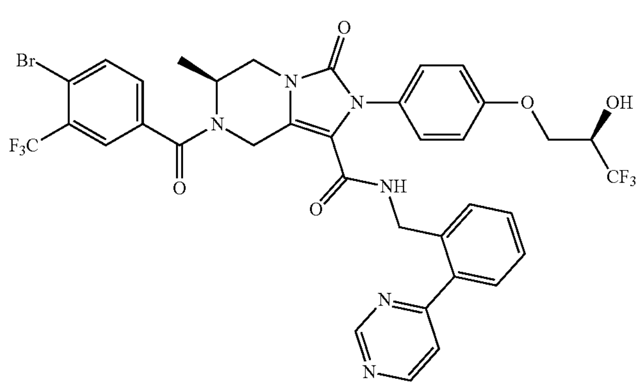 [SMILES: C[C@H]1Cn2c(c(C(=O)NCc3ccccc3-c3ccncn3)n(-c3ccc(OC[C@@H](O)C(F)(F)F)cc3)c2=O)CN1C(=O)c1ccc(Br)c(C(F)(F)F)c1] | 62b |

TABLE D-continued

| Structure | Cmpd |
|---|---|
| 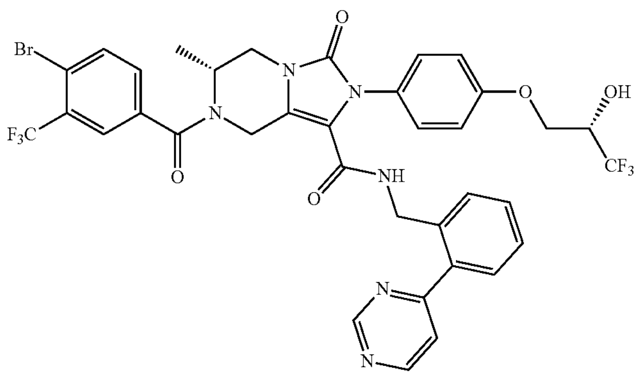 [SMILES: C[C@@H]1Cn2c(c(C(=O)NCc3ccccc3-c3ccncn3)n(-c3ccc(OC[C@H](O)C(F)(F)F)cc3)c2=O)CN1C(=O)c1ccc(Br)c(C(F)(F)F)c1] | 63a |
| 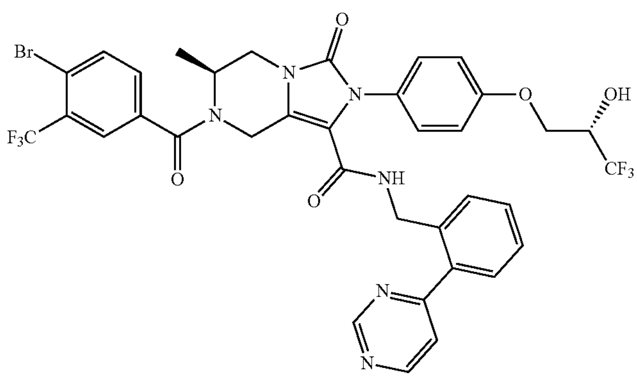 [SMILES: C[C@H]1Cn2c(c(C(=O)NCc3ccccc3-c3ccncn3)n(-c3ccc(OC[C@H](O)C(F)(F)F)cc3)c2=O)CN1C(=O)c1ccc(Br)c(C(F)(F)F)c1] | 63b |
| 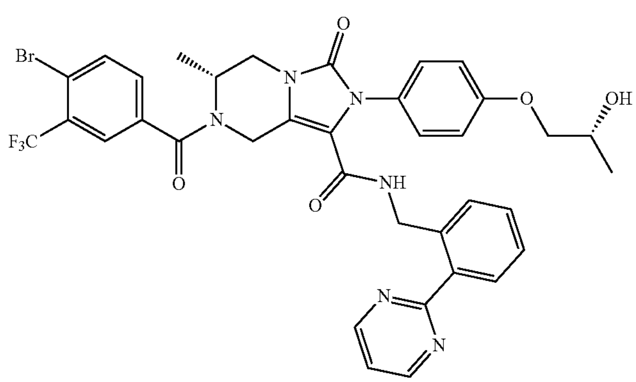 [SMILES: C[C@@H]1Cn2c(c(C(=O)NCc3ccccc3-c3ncccn3)n(-c3ccc(OC[C@@H](C)O)cc3)c2=O)CN1C(=O)c1ccc(Br)c(C(F)(F)F)c1] | 64a |
| 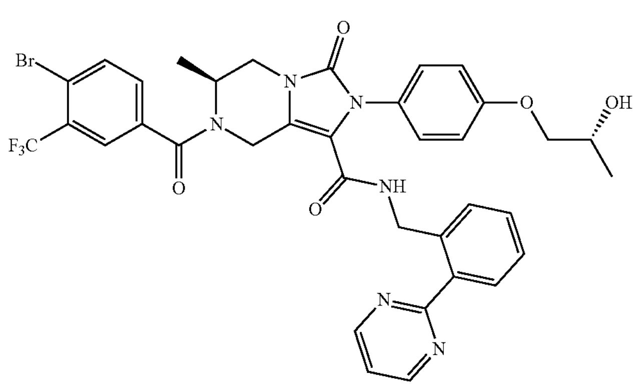 [SMILES: C[C@@H](O)COc1ccc(-n2c(C(=O)NCc3ccccc3-c3ncccn3)c3n(c2=O)C[C@H](C)N(C(=O)c2ccc(Br)c(C(F)(F)F)c2)C3)cc1] | 64b |

TABLE D-continued

| Structure | Cmpd |
|---|---|
| 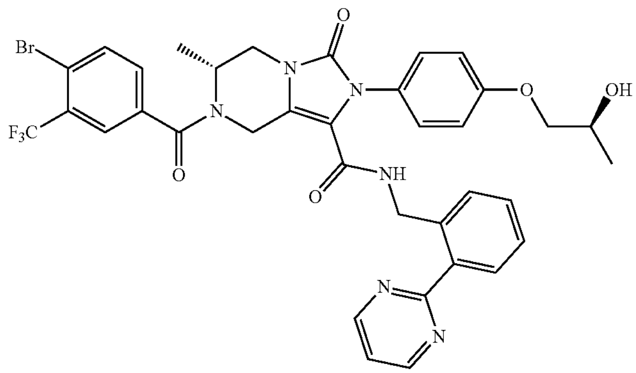 [SMILES: C[C@H](O)COc1ccc(-n2c(C(=O)NCc3ccccc3-c3ncccn3)c3n(c2=O)C[C@@H](C)N(C(=O)c2ccc(Br)c(C(F)(F)F)c2)C3)cc1] | 65a |
| 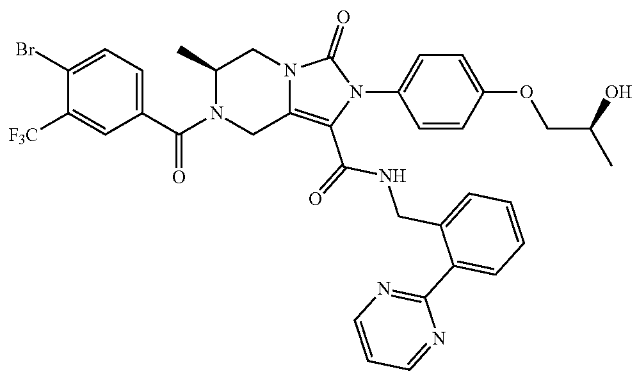 [SMILES: C[C@H](O)COc1ccc(-n2c(C(=O)NCc3ccccc3-c3ncccn3)c3n(c2=O)C[C@H](C)N(C(=O)c2ccc(Br)c(C(F)(F)F)c2)C3)cc1] | 65b |
| 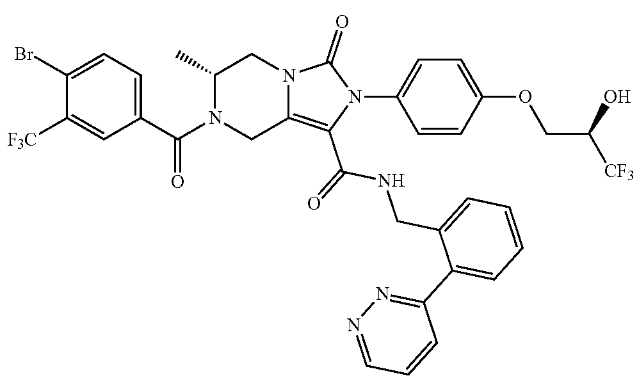 [SMILES: C[C@@H]1Cn2c(c(C(=O)NCc3ccccc3-c3cccnn3)n(-c3ccc(OC[C@@H](O)C(F)(F)F)cc3)c2=O)CN1C(=O)c1ccc(Br)c(C(F)(F)F)c1] | 66a |
| 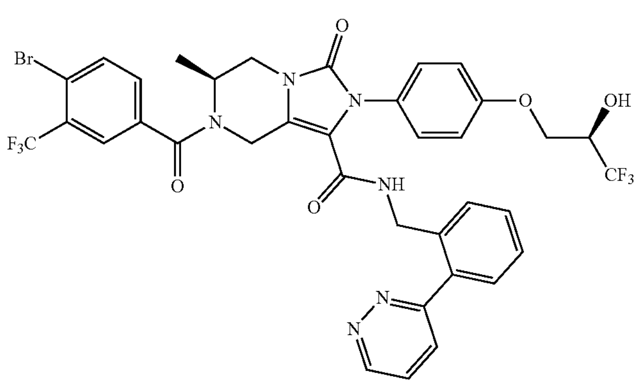 [SMILES: C[C@H]1Cn2c(c(C(=O)NCc3ccccc3-c3cccnn3)n(-c3ccc(OC[C@@H](O)C(F)(F)F)cc3)c2=O)CN1C(=O)c1ccc(Br)c(C(F)(F)F)c1] | 66b |

TABLE D-continued

| Structure | Cmpd |
|---|---|
| 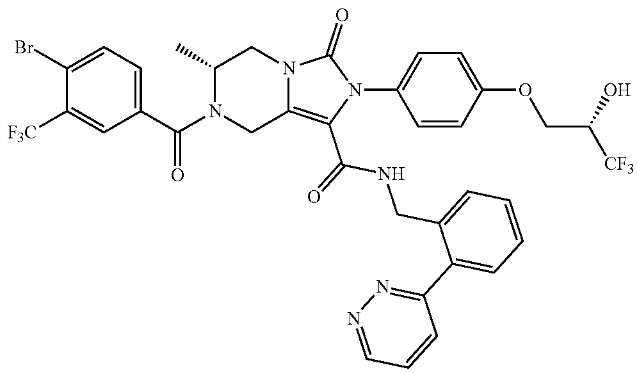 [SMILES: C[C@@H]1Cn2c(c(C(=O)NCc3ccccc3-c3cccnn3)n(-c3ccc(OC[C@H](O)C(F)(F)F)cc3)c2=O)CN1C(=O)c1ccc(Br)c(C(F)(F)F)c1] | 67a |
| 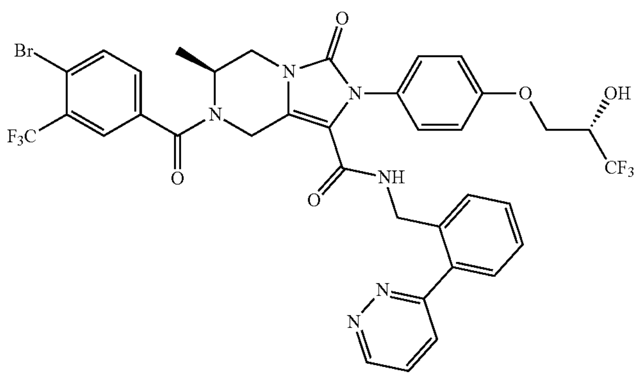 [SMILES: C[C@H]1Cn2c(c(C(=O)NCc3ccccc3-c3cccnn3)n(-c3ccc(OC[C@H](O)C(F)(F)F)cc3)c2=O)CN1C(=O)c1ccc(Br)c(C(F)(F)F)c1] | 67b |
| 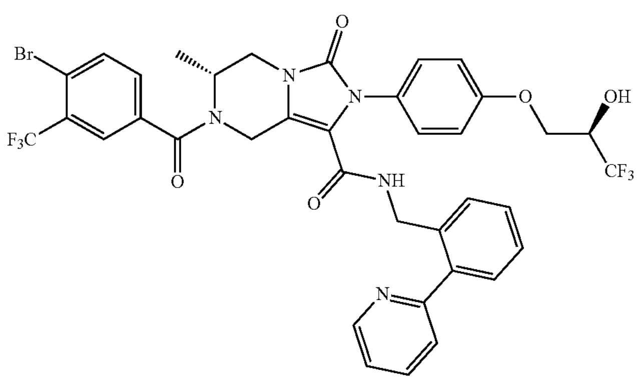 [SMILES: C[C@@H]1Cn2c(c(C(=O)NCc3ccccc3-c3ccccn3)n(-c3ccc(OC[C@@H](O)C(F)(F)F)cc3)c2=O)CN1C(=O)c1ccc(Br)c(C(F)(F)F)c1] | 68a |
| 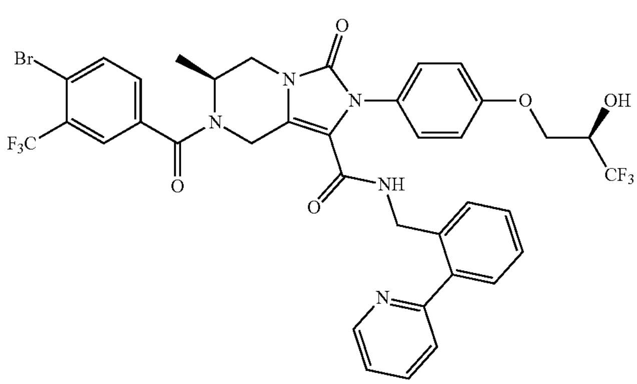 [SMILES: C[C@H]1Cn2c(c(C(=O)NCc3ccccc3-c3ccccn3)n(-c3ccc(OC[C@@H](O)C(F)(F)F)cc3)c2=O)CN1C(=O)c1ccc(Br)c(C(F)(F)F)c1] | 68b |

TABLE D-continued
| Structure | Cmpd |
|---|---|
| 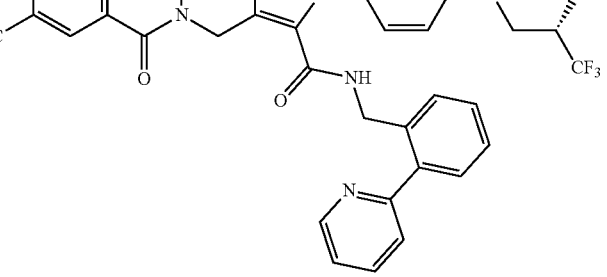 | 69a |
| 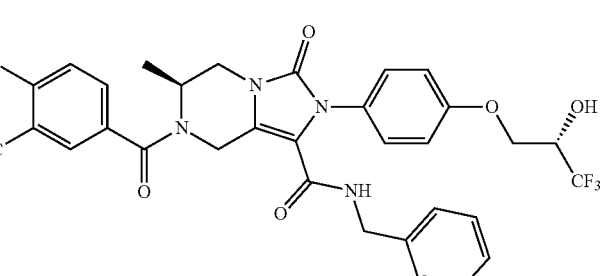 | 69b |
| 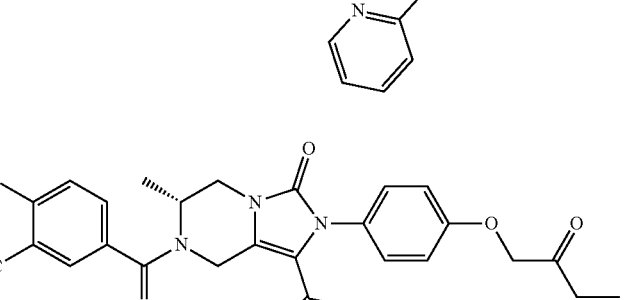 | 70a |
| 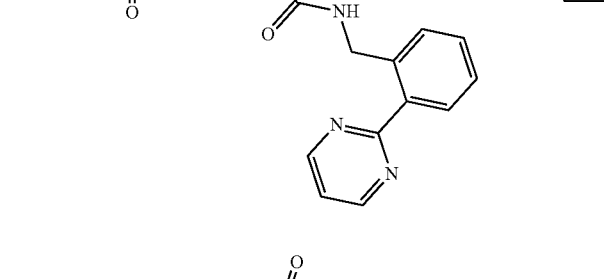 | 70b |

TABLE D-continued

| Structure | Cmpd |
|---|---|
| 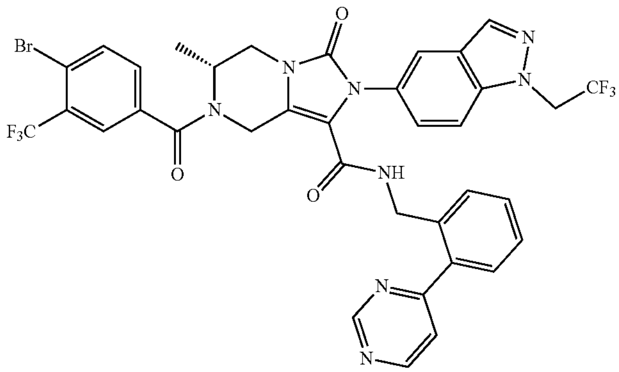 [SMILES: C[C@@H]1Cn2c(c(C(=O)NCc3ccccc3-c3ccncn3)n(-c3ccc4c(cnn4CC(F)(F)F)c3)c2=O)CN1C(=O)c1ccc(Br)c(C(F)(F)F)c1] | 72a |
| 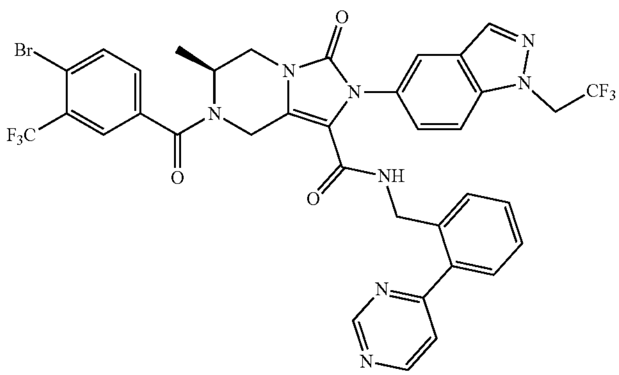 [SMILES: C[C@H]1Cn2c(c(C(=O)NCc3ccccc3-c3ccncn3)n(-c3ccc4c(cnn4CC(F)(F)F)c3)c2=O)CN1C(=O)c1ccc(Br)c(C(F)(F)F)c1] | 72b |
| 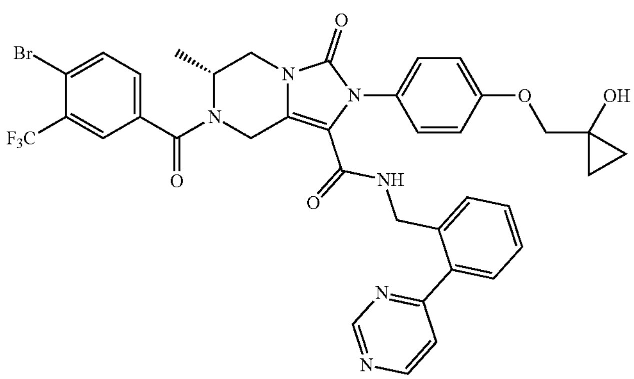 [SMILES: C[C@@H]1Cn2c(c(C(=O)NCc3ccccc3-c3ccncn3)n(-c3ccc(OCC4(O)CC4)cc3)c2=O)CN1C(=O)c1ccc(Br)c(C(F)(F)F)c1] | 74a |
| 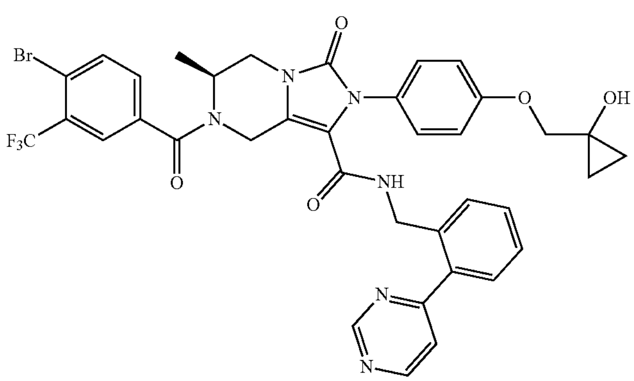 [SMILES: C[C@H]1Cn2c(c(C(=O)NCc3ccccc3-c3ccncn3)n(-c3ccc(OCC4(O)CC4)cc3)c2=O)CN1C(=O)c1ccc(Br)c(C(F)(F)F)c1] | 74b |

TABLE D-continued

| Structure | Cmpd |
|---|---|
| 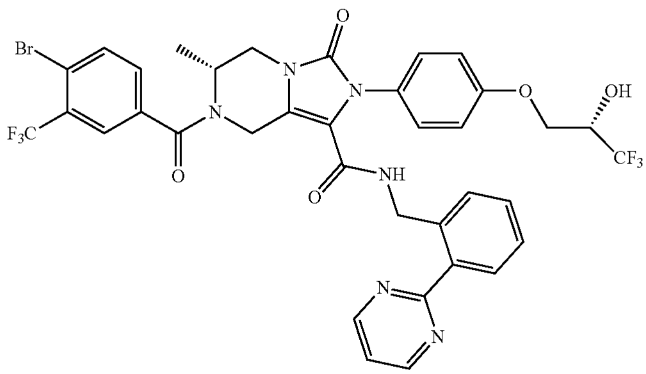 [SMILES: C[C@@H]1Cn2c(c(C(=O)NCc3ccccc3-c3ncccn3)n(-c3ccc(OC[C@H](O)C(F)(F)F)cc3)c2=O)CN1C(=O)c1ccc(Br)c(C(F)(F)F)c1] | 75a |
| 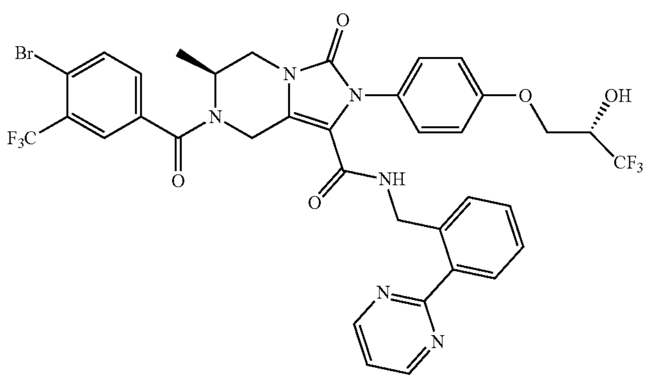 [SMILES: C[C@H]1Cn2c(c(C(=O)NCc3ccccc3-c3ncccn3)n(-c3ccc(OC[C@H](O)C(F)(F)F)cc3)c2=O)CN1C(=O)c1ccc(Br)c(C(F)(F)F)c1] | 75b |
| 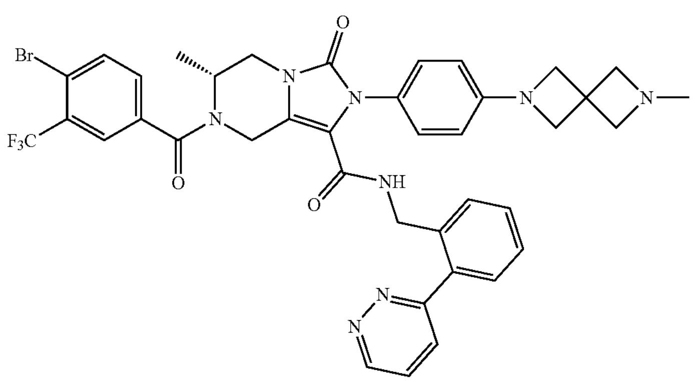 [SMILES: C[C@@H]1Cn2c(c(C(=O)NCc3ccccc3-c3cccnn3)n(-c3ccc(N4CC5(CN(C)C5)C4)cc3)c2=O)CN1C(=O)c1ccc(Br)c(C(F)(F)F)c1] | 76a |
| 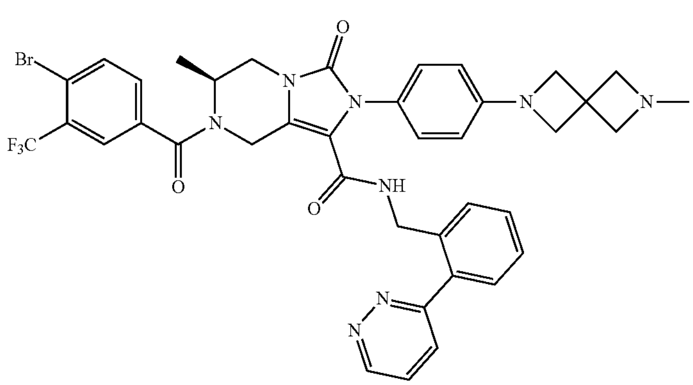 [SMILES: C[C@H]1Cn2c(c(C(=O)NCc3ccccc3-c3cccnn3)n(-c3ccc(N4CC5(CN(C)C5)C4)cc3)c2=O)CN1C(=O)c1ccc(Br)c(C(F)(F)F)c1] | 76b |

TABLE D-continued

| Structure | Cmpd |
|---|---|
| 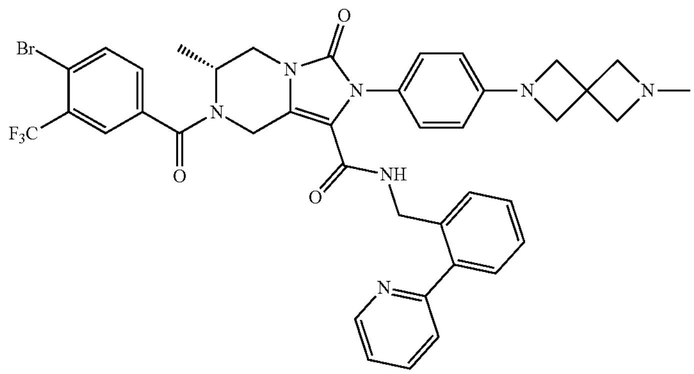 [SMILES: C[C@@H]1Cn2c(c(C(=O)NCc3ccccc3-c3ccccn3)n(-c3ccc(N4CC5(CN(C)C5)C4)cc3)c2=O)CN1C(=O)c1ccc(Br)c(C(F)(F)F)c1] | 77a |
| 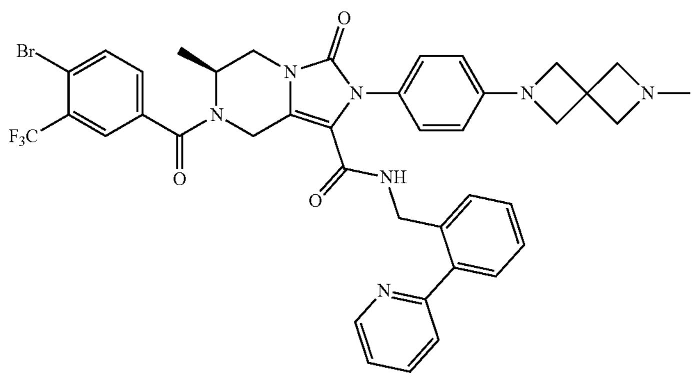 [SMILES: C[C@H]1Cn2c(c(C(=O)NCc3ccccc3-c3ccccn3)n(-c3ccc(N4CC5(CN(C)C5)C4)cc3)c2=O)CN1C(=O)c1ccc(Br)c(C(F)(F)F)c1] | 77b |
| 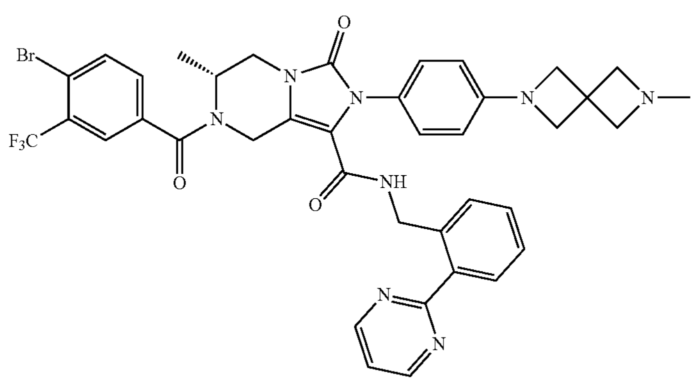 [SMILES: C[C@@H]1Cn2c(c(C(=O)NCc3ccccc3-c3ncccn3)n(-c3ccc(N4CC5(CN(C)C5)C4)cc3)c2=O)CN1C(=O)c1ccc(Br)c(C(F)(F)F)c1] | 78a |
| 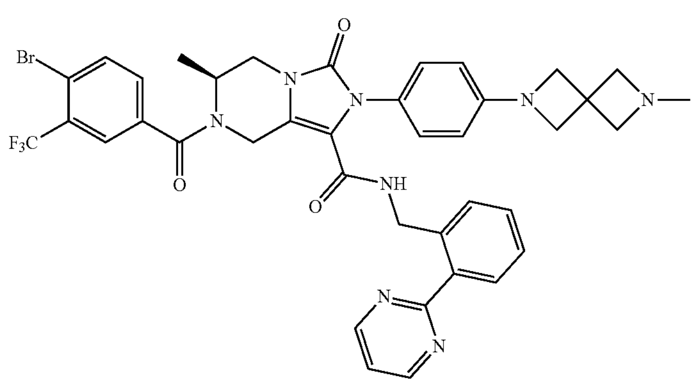 [SMILES: C[C@H]1Cn2c(c(C(=O)NCc3ccccc3-c3ncccn3)n(-c3ccc(N4CC5(CN(C)C5)C4)cc3)c2=O)CN1C(=O)c1ccc(Br)c(C(F)(F)F)c1] | 78b |

TABLE D-continued

| Structure | Cmpd |
|---|---|
| 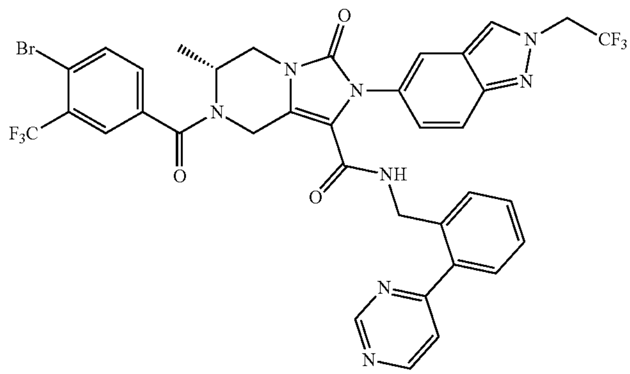 [SMILES: C[C@@H]1Cn2c(c(C(=O)NCc3ccccc3-c3ccncn3)n(-c3ccc4nn(CC(F)(F)F)cc4c3)c2=O)CN1C(=O)c1ccc(Br)c(C(F)(F)F)c1] | 79a |
| 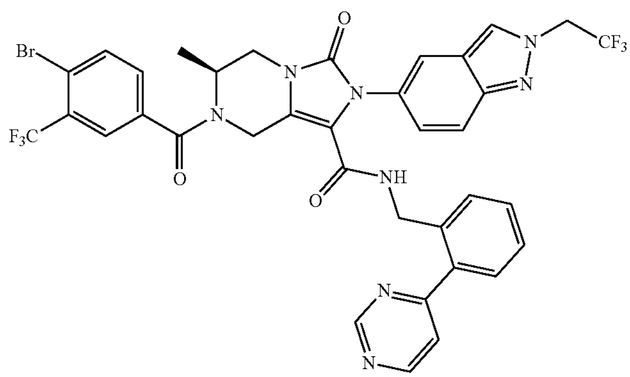 [SMILES: C[C@H]1Cn2c(c(C(=O)NCc3ccccc3-c3ccncn3)n(-c3ccc4nn(CC(F)(F)F)cc4c3)c2=O)CN1C(=O)c1ccc(Br)c(C(F)(F)F)c1] | 79b |
| 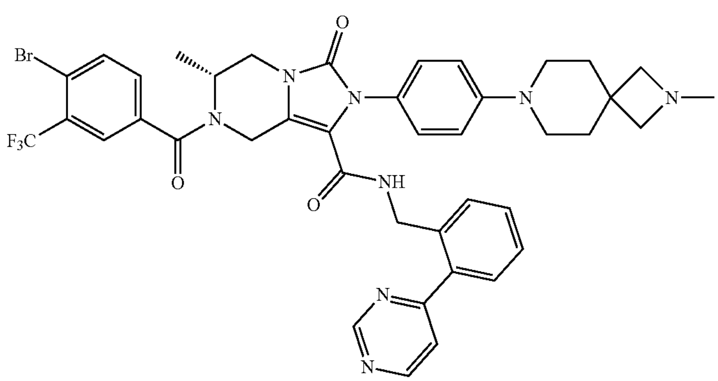 [SMILES: C[C@@H]1Cn2c(c(C(=O)NCc3ccccc3-c3ccncn3)n(-c3ccc(N4CCC5(CC4)CN(C)C5)cc3)c2=O)CN1C(=O)c1ccc(Br)c(C(F)(F)F)c1] | 80a |
| 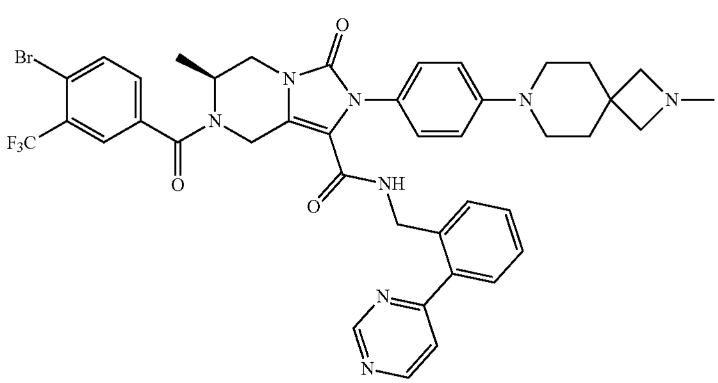 [SMILES: C[C@H]1Cn2c(c(C(=O)NCc3ccccc3-c3ccncn3)n(-c3ccc(N4CCC5(CC4)CN(C)C5)cc3)c2=O)CN1C(=O)c1ccc(Br)c(C(F)(F)F)c1] | 80b |

TABLE D-continued

| Structure | Cmpd |
|---|---|
| 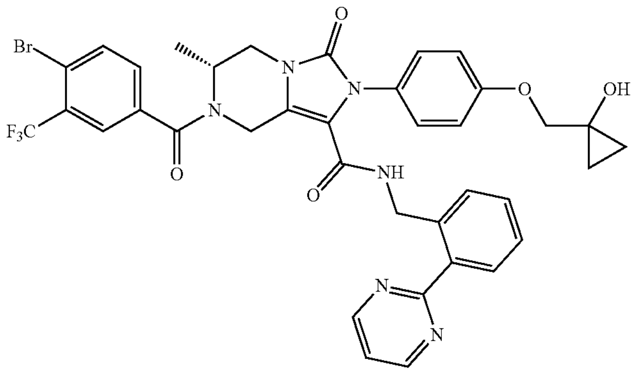 [SMILES: C[C@@H]1Cn2c(c(C(=O)NCc3ccccc3-c3ncccn3)n(-c3ccc(OCC4(O)CC4)cc3)c2=O)CN1C(=O)c1ccc(Br)c(C(F)(F)F)c1] | 81a |
| 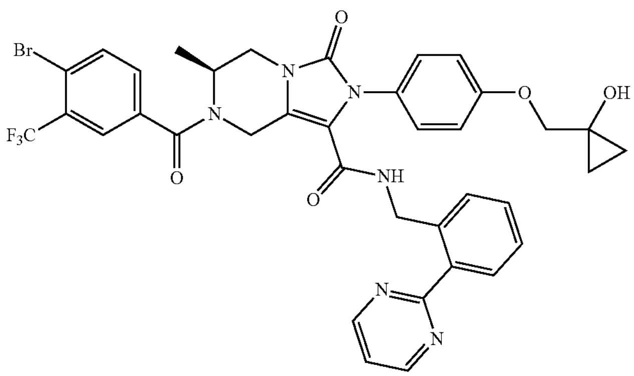 [SMILES: C[C@H]1Cn2c(c(C(=O)NCc3ccccc3-c3ncccn3)n(-c3ccc(OCC4(O)CC4)cc3)c2=O)CN1C(=O)c1ccc(Br)c(C(F)(F)F)c1] | 81b |
| 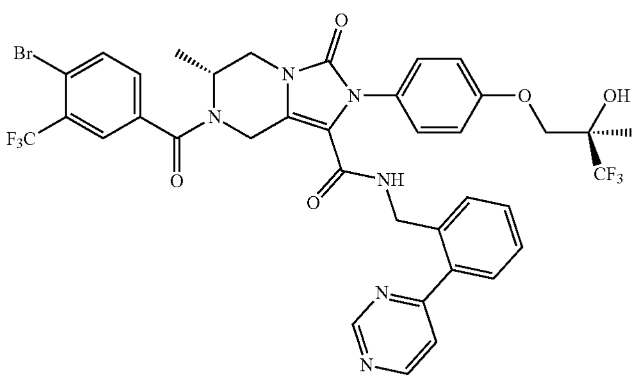 [SMILES: C[C@@H]1Cn2c(c(C(=O)NCc3ccccc3-c3ccncn3)n(-c3ccc(OC[C@@](C)(O)C(F)(F)F)cc3)c2=O)CN1C(=O)c1ccc(Br)c(C(F)(F)F)c1] | 82a |
| 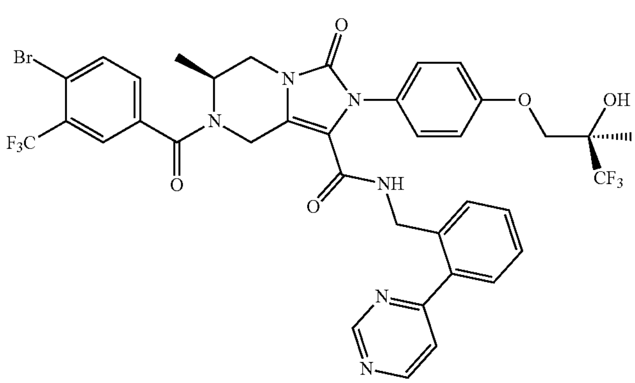 [SMILES: C[C@H]1Cn2c(c(C(=O)NCc3ccccc3-c3ccncn3)n(-c3ccc(OC[C@@](C)(O)C(F)(F)F)cc3)c2=O)CN1C(=O)c1ccc(Br)c(C(F)(F)F)c1] | 82b |

TABLE D-continued

| Structure | Cmpd |
|---|---|
| 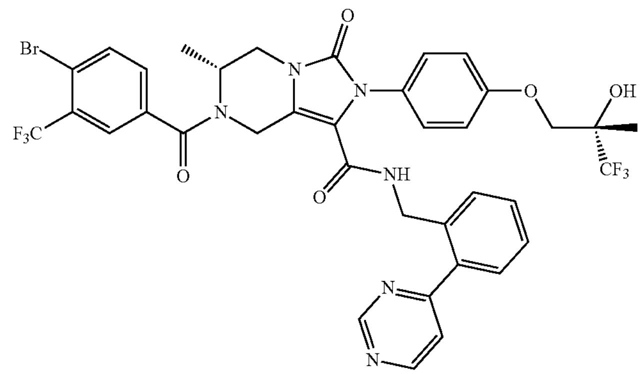 [SMILES: C[C@@H]1Cn2c(c(C(=O)NCc3ccccc3-c3ccncn3)n(-c3ccc(OC[C@](C)(O)C(F)(F)F)cc3)c2=O)CN1C(=O)c1ccc(Br)c(C(F)(F)F)c1] | 83a |
| 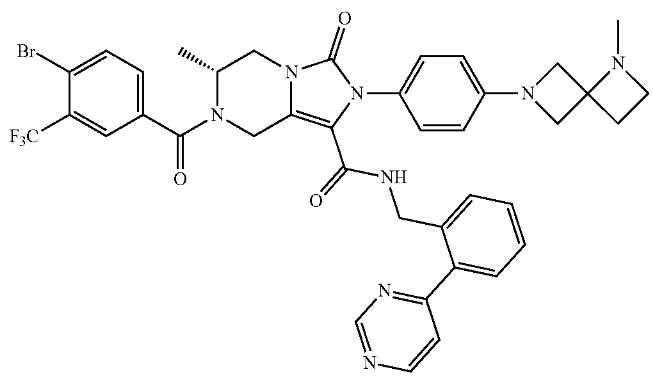 [SMILES: C[C@@H]1Cn2c(c(C(=O)NCc3ccccc3-c3ccncn3)n(-c3ccc(N4CC5(CCN5C)C4)cc3)c2=O)CN1C(=O)c1ccc(Br)c(C(F)(F)F)c1] | 84a |
| 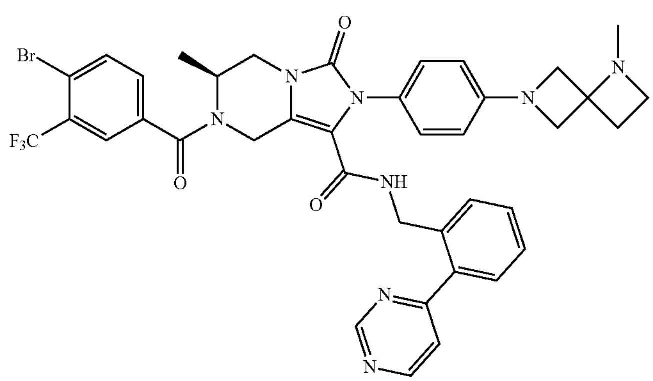 [SMILES: C[C@H]1Cn2c(c(C(=O)NCc3ccccc3-c3ccncn3)n(-c3ccc(N4CC5(CCN5C)C4)cc3)c2=O)CN1C(=O)c1ccc(Br)c(C(F)(F)F)c1] | 84b |
| 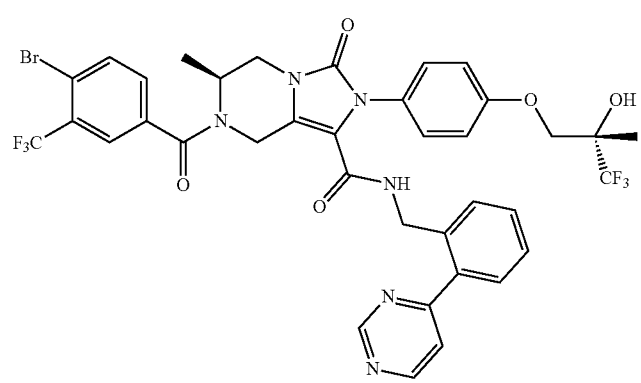 [SMILES: C[C@H]1Cn2c(c(C(=O)NCc3ccccc3-c3ccncn3)n(-c3ccc(OC[C@](C)(O)C(F)(F)F)cc3)c2=O)CN1C(=O)c1ccc(Br)c(C(F)(F)F)c1] | 83b |

TABLE D-continued

| Structure | Cmpd |
|---|---|
| 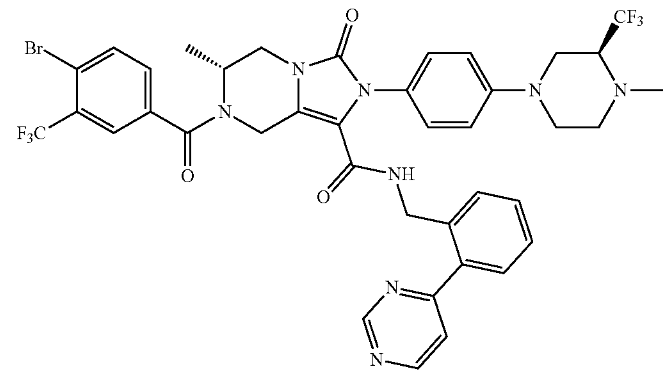 [SMILES: C[C@@H]1Cn2c(c(C(=O)NCc3ccccc3-c3ccncn3)n(-c3ccc(N4CCN(C)[C@H](C(F)(F)F)C4)cc3)c2=O)CN1C(=O)c1ccc(Br)c(C(F)(F)F)c1] | 87a |
| 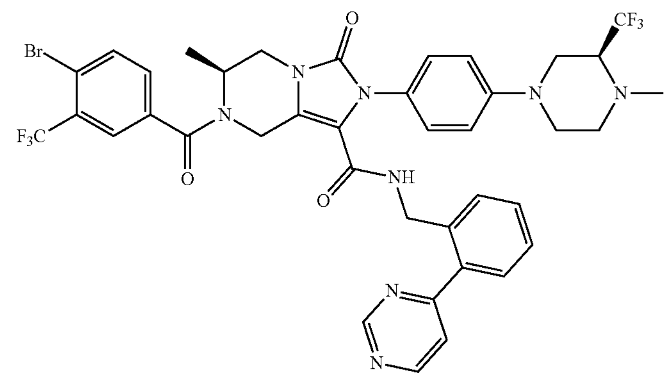 [SMILES: C[C@H]1Cn2c(c(C(=O)NCc3ccccc3-c3ccncn3)n(-c3ccc(N4CCN(C)[C@H](C(F)(F)F)C4)cc3)c2=O)CN1C(=O)c1ccc(Br)c(C(F)(F)F)c1] | 87b |
| 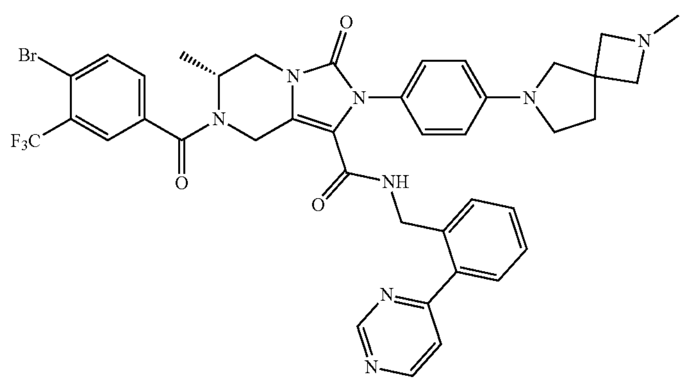 [SMILES: C[C@@H]1Cn2c(c(C(=O)NCc3ccccc3-c3ccncn3)n(-c3ccc(N4CCC5(CN(C)C5)C4)cc3)c2=O)CN1C(=O)c1ccc(Br)c(C(F)(F)F)c1] | 88a |
| 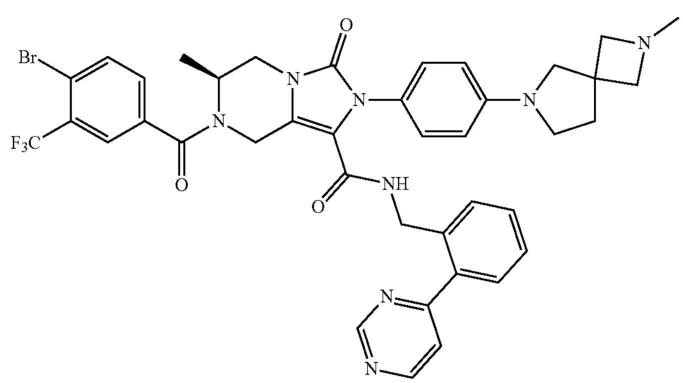 [SMILES: C[C@H]1Cn2c(c(C(=O)NCc3ccccc3-c3ccncn3)n(-c3ccc(N4CCC5(CN(C)C5)C4)cc3)c2=O)CN1C(=O)c1ccc(Br)c(C(F)(F)F)c1] | 88b |

TABLE D-continued

| Structure | Cmpd |
|---|---|
| 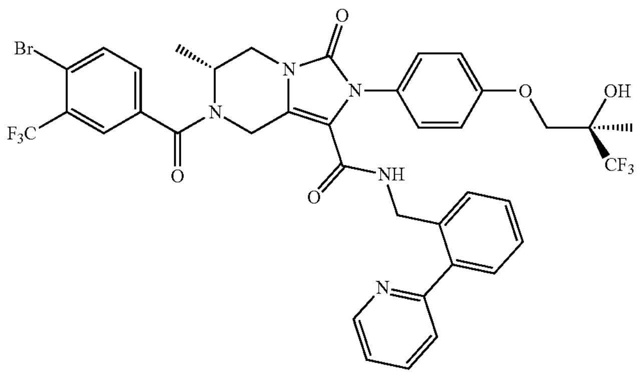 [SMILES: C[C@@H]1Cn2c(c(C(=O)NCc3ccccc3-c3ccccn3)n(-c3ccc(OC[C@@](C)(O)C(F)(F)F)cc3)c2=O)CN1C(=O)c1ccc(Br)c(C(F)(F)F)c1] | 89a |
| 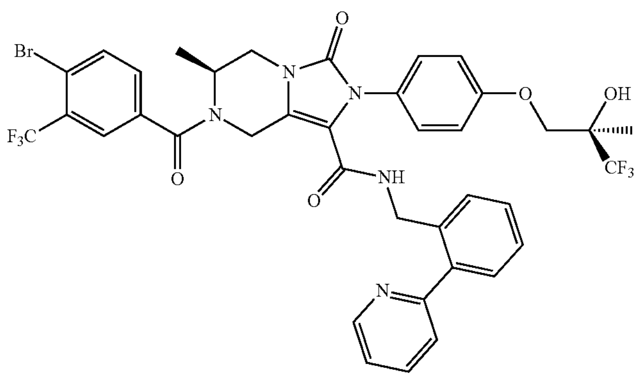 [SMILES: C[C@H]1Cn2c(c(C(=O)NCc3ccccc3-c3ccccn3)n(-c3ccc(OC[C@@](C)(O)C(F)(F)F)cc3)c2=O)CN1C(=O)c1ccc(Br)c(C(F)(F)F)c1] | 89b |
| 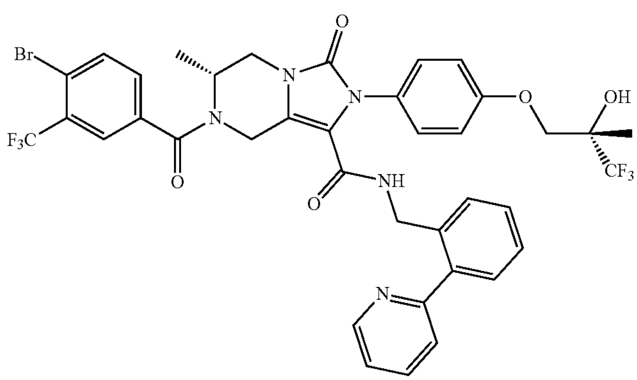 [SMILES: C[C@@H]1Cn2c(c(C(=O)NCc3ccccc3-c3ccccn3)n(-c3ccc(OC[C@](C)(O)C(F)(F)F)cc3)c2=O)CN1C(=O)c1ccc(Br)c(C(F)(F)F)c1] | 90a |
| 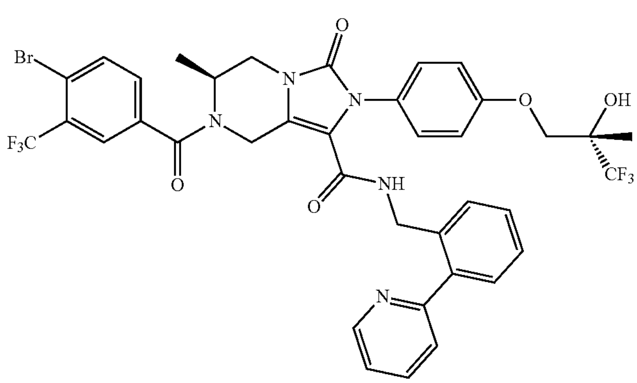 [SMILES: C[C@H]1Cn2c(c(C(=O)NCc3ccccc3-c3ccccn3)n(-c3ccc(OC[C@](C)(O)C(F)(F)F)cc3)c2=O)CN1C(=O)c1ccc(Br)c(C(F)(F)F)c1] | 90b |

TABLE D-continued

| Structure | Cmpd |
|---|---|
| 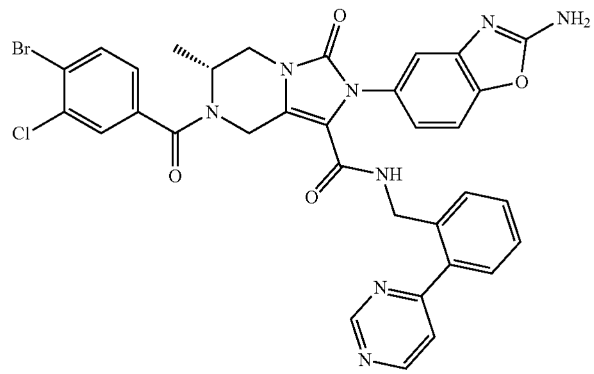 [SMILES: C[C@@H]1Cn2c(c(C(=O)NCc3ccccc3-c3ccncn3)n(-c3ccc4oc(N)nc4c3)c2=O)CN1C(=O)c1ccc(Br)c(Cl)c1] | 92a |
| 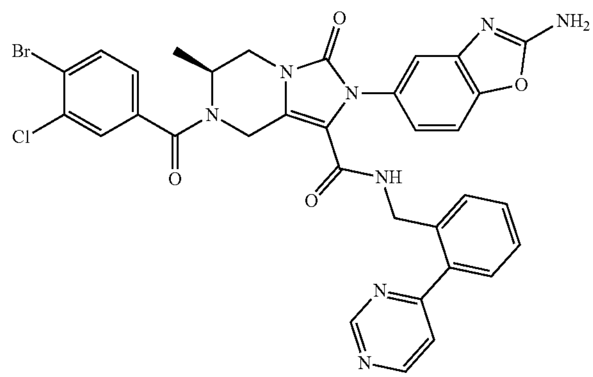 [SMILES: C[C@H]1Cn2c(c(C(=O)NCc3ccccc3-c3ccncn3)n(-c3ccc4oc(N)nc4c3)c2=O)CN1C(=O)c1ccc(Br)c(Cl)c1] | 92b |
| 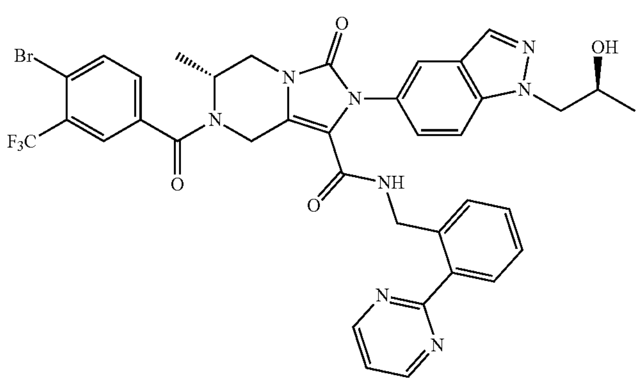 [SMILES: C[C@H](O)Cn1ncc2cc(-n3c(C(=O)NCc4ccccc4-c4ncccn4)c4n(c3=O)C[C@@H](C)N(C(=O)c3ccc(Br)c(C(F)(F)F)c3)C4)ccc21] | 94a |
| 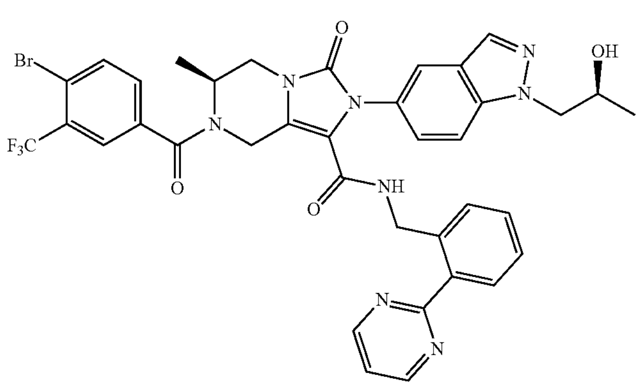 [SMILES: C[C@H](O)Cn1ncc2cc(-n3c(C(=O)NCc4ccccc4-c4ncccn4)c4n(c3=O)C[C@H](C)N(C(=O)c3ccc(Br)c(C(F)(F)F)c3)C4)ccc21] | 94b |

TABLE D-continued
| Structure | Cmpd |
|---|---|
| 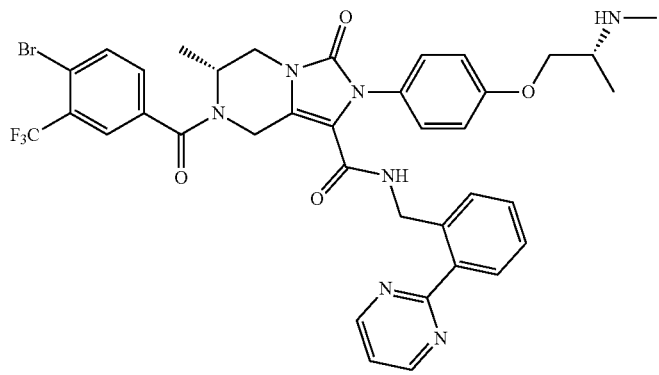 [SMILES: CN[C@H](C)COc1ccc(-n2c(C(=O)NCc3ccccc3-c3ncccn3)c3n(c2=O)C[C@@H](C)N(C(=O)c2ccc(Br)c(C(F)(F)F)c2)C3)cc1] | 95a |
| 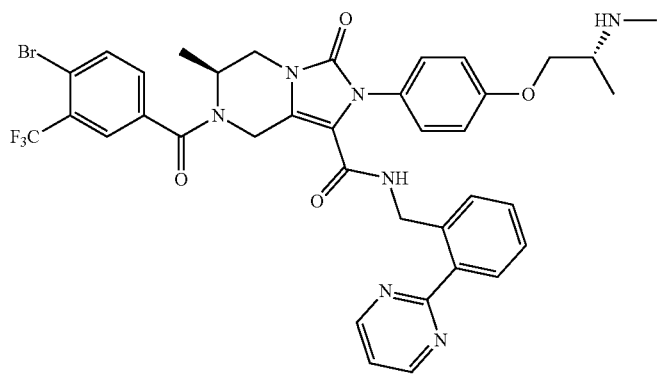 [SMILES: CN[C@H](C)COc1ccc(-n2c(C(=O)NCc3ccccc3-c3ncccn3)c3n(c2=O)C[C@H](C)N(C(=O)c2ccc(Br)c(C(F)(F)F)c2)C3)cc1] | 95b |
| 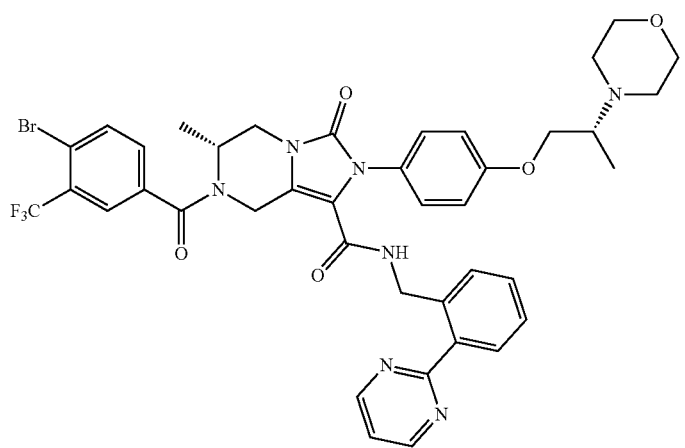 [SMILES: C[C@H](COc1ccc(-n2c(C(=O)NCc3ccccc3-c3ncccn3)c3n(c2=O)C[C@@H](C)N(C(=O)c2ccc(Br)c(C(F)(F)F)c2)C3)cc1)N1CCOCC1] | 96a |

TABLE D-continued
| Structure | Cmpd |
|---|---|
| 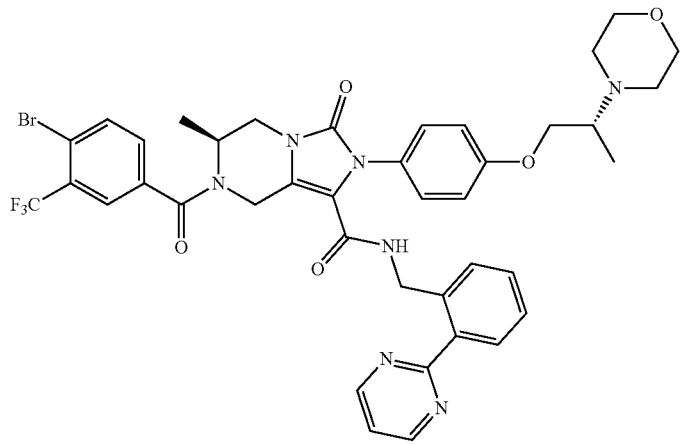 [SMILES: C[C@H](COc1ccc(-n2c(C(=O)NCc3ccccc3-c3ncccn3)c3n(c2=O)C[C@H](C)N(C(=O)c2ccc(Br)c(C(F)(F)F)c2)C3)cc1)N1CCOCC1] | 96b |
| 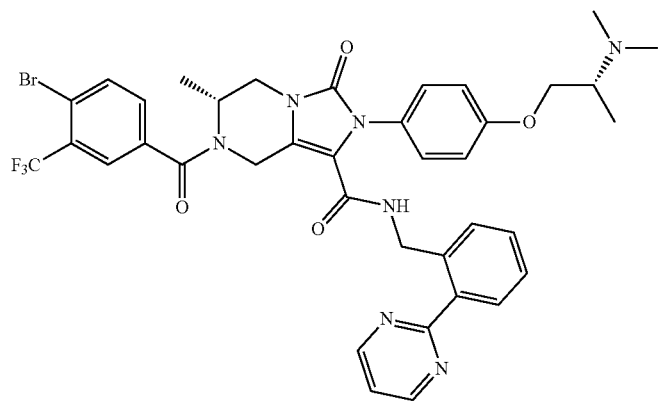 [SMILES: C[C@H](COc1ccc(-n2c(C(=O)NCc3ccccc3-c3ncccn3)c3n(c2=O)C[C@@H](C)N(C(=O)c2ccc(Br)c(C(F)(F)F)c2)C3)cc1)N(C)C] | 97a |
| 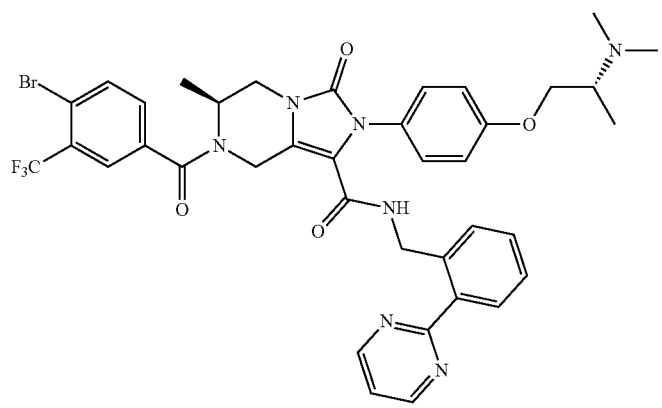 [SMILES: C[C@H](COc1ccc(-n2c(C(=O)NCc3ccccc3-c3ncccn3)c3n(c2=O)C[C@H](C)N(C(=O)c2ccc(Br)c(C(F)(F)F)c2)C3)cc1)N(C)C] | 97b |

TABLE D-continued

| Structure | Cmpd |
|---|---|
| 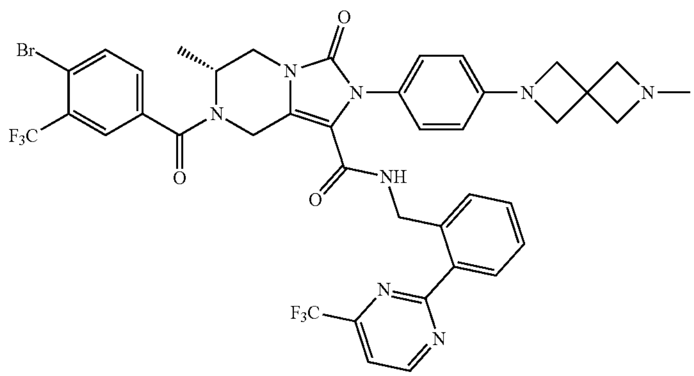 [SMILES: C[C@@H]1Cn2c(c(C(=O)NCc3ccccc3-c3nccc(C(F)(F)F)n3)n(-c3ccc(N4CC5(CN(C)C5)C4)cc3)c2=O)CN1C(=O)c1ccc(Br)c(C(F)(F)F)c1] | 98a |
| 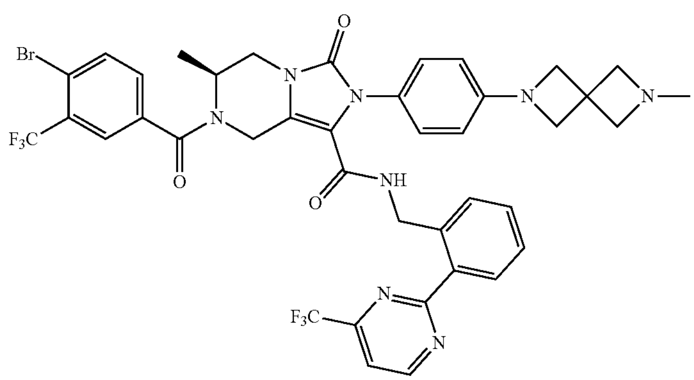 [SMILES: C[C@H]1Cn2c(c(C(=O)NCc3ccccc3-c3nccc(C(F)(F)F)n3)n(-c3ccc(N4CC5(CN(C)C5)C4)cc3)c2=O)CN1C(=O)c1ccc(Br)c(C(F)(F)F)c1] | 98b |
| 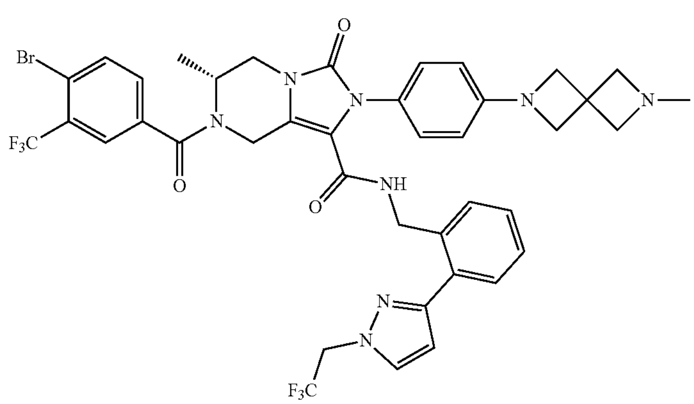 [SMILES: C[C@@H]1Cn2c(c(C(=O)NCc3ccccc3-c3ccn(CC(F)(F)F)n3)n(-c3ccc(N4CC5(CN(C)C5)C4)cc3)c2=O)CN1C(=O)c1ccc(Br)c(C(F)(F)F)c1] | 99a |
| 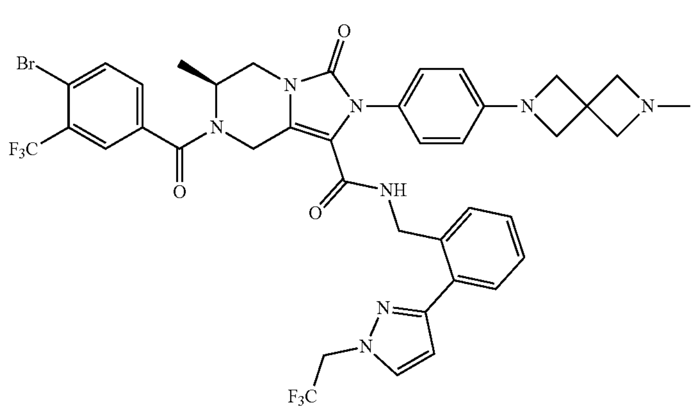 [SMILES: C[C@H]1Cn2c(c(C(=O)NCc3ccccc3-c3ccn(CC(F)(F)F)n3)n(-c3ccc(N4CC5(CN(C)C5)C4)cc3)c2=O)CN1C(=O)c1ccc(Br)c(C(F)(F)F)c1] | 99b |

TABLE D-continued
| Structure | Cmpd |
|---|---|
| 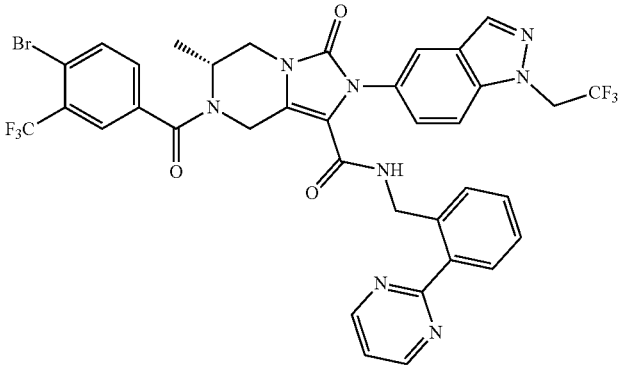 [SMILES: C[C@@H]1Cn2c(c(C(=O)NCc3ccccc3-c3ncccn3)n(-c3ccc4c(cnn4CC(F)(F)F)c3)c2=O)CN1C(=O)c1ccc(Br)c(C(F)(F)F)c1] | 100a |
| 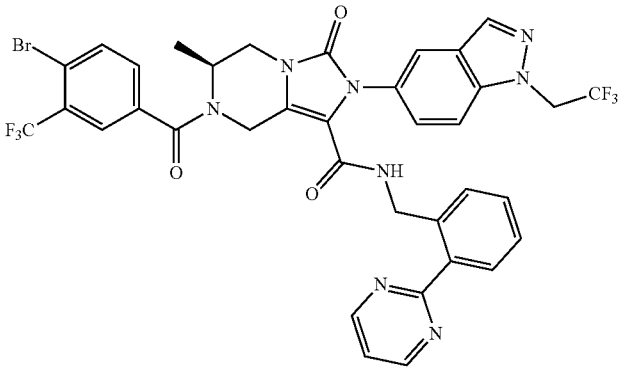 [SMILES: C[C@H]1Cn2c(c(C(=O)NCc3ccccc3-c3ncccn3)n(-c3ccc4c(cnn4CC(F)(F)F)c3)c2=O)CN1C(=O)c1ccc(Br)c(C(F)(F)F)c1] | 100b |
| 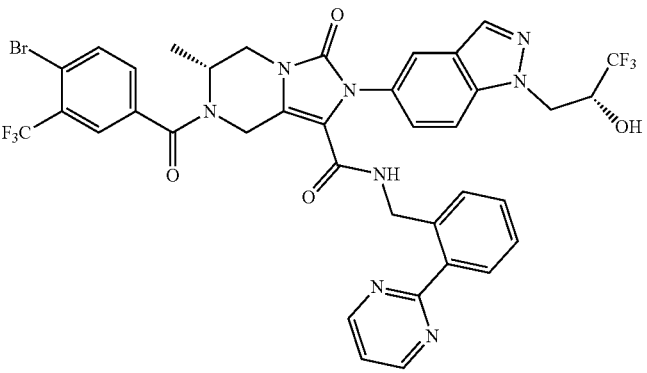 [SMILES: C[C@@H]1Cn2c(c(C(=O)NCc3ccccc3-c3ncccn3)n(-c3ccc4c(cnn4C[C@@H](O)C(F)(F)F)c3)c2=O)CN1C(=O)c1ccc(Br)c(C(F)(F)F)c1] | 101a |
| 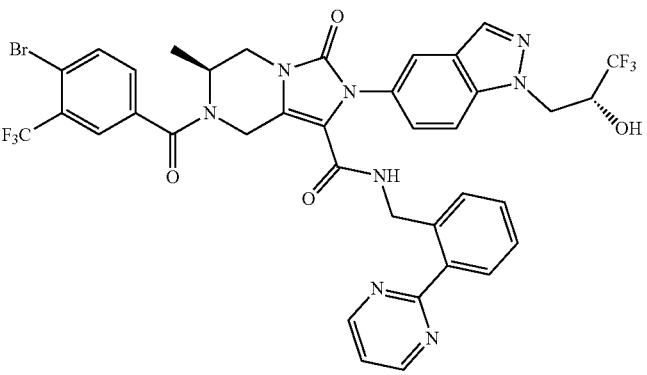 [SMILES: C[C@H]1Cn2c(c(C(=O)NCc3ccccc3-c3ncccn3)n(-c3ccc4c(cnn4C[C@@H](O)C(F)(F)F)c3)c2=O)CN1C(=O)c1ccc(Br)c(C(F)(F)F)c1] | 101b |

TABLE D-continued
| Structure | Cmpd |
|---|---|
| 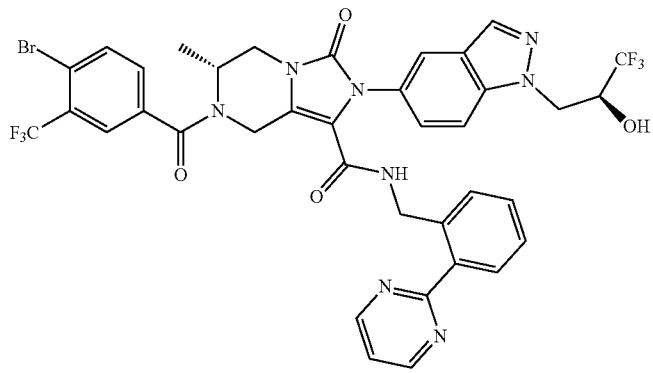 [SMILES: C[C@@H]1Cn2c(c(C(=O)NCc3ccccc3-c3ncccn3)n(-c3ccc4c(cnn4C[C@H](O)C(F)(F)F)c3)c2=O)CN1C(=O)c1ccc(Br)c(C(F)(F)F)c1] | 102a |
| 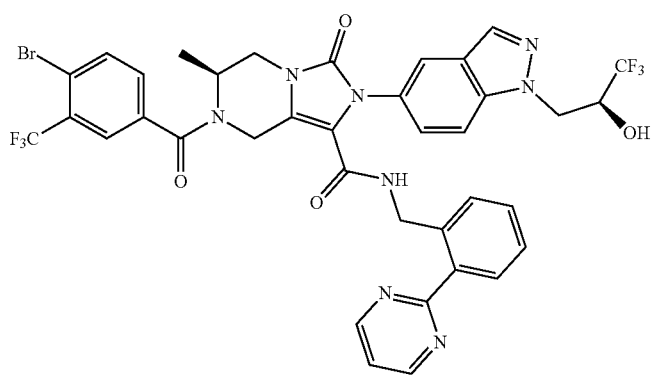 [SMILES: C[C@H]1Cn2c(c(C(=O)NCc3ccccc3-c3ncccn3)n(-c3ccc4c(cnn4C[C@H](O)C(F)(F)F)c3)c2=O)CN1C(=O)c1ccc(Br)c(C(F)(F)F)c1] | 102b |
| 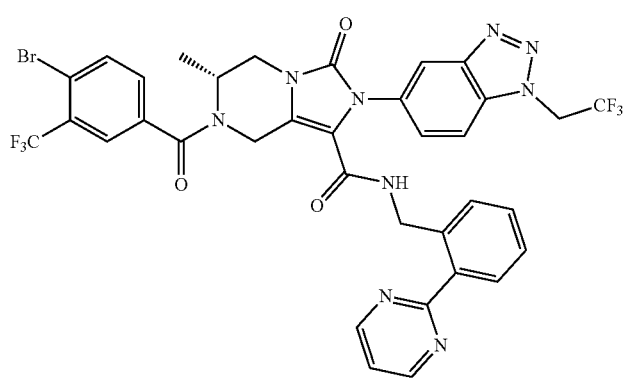 [SMILES: C[C@@H]1Cn2c(c(C(=O)NCc3ccccc3-c3ncccn3)n(-c3ccc4c(c3)nnn4CC(F)(F)F)c2=O)CN1C(=O)c1ccc(Br)c(C(F)(F)F)c1] | 103a |
| 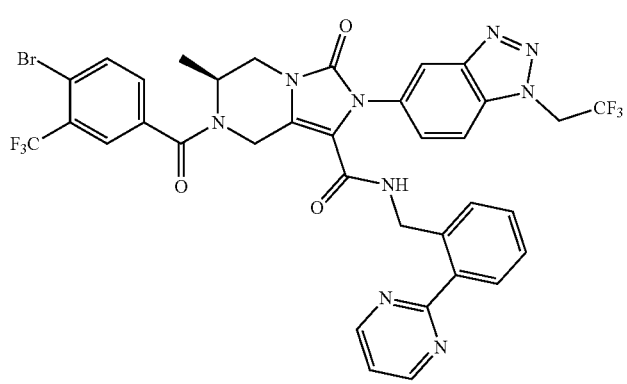 [SMILES: C[C@H]1Cn2c(c(C(=O)NCc3ccccc3-c3ncccn3)n(-c3ccc4c(c3)nnn4CC(F)(F)F)c2=O)CN1C(=O)c1ccc(Br)c(C(F)(F)F)c1] | 103b |

TABLE D-continued
| Structure | Cmpd |
|---|---|
| 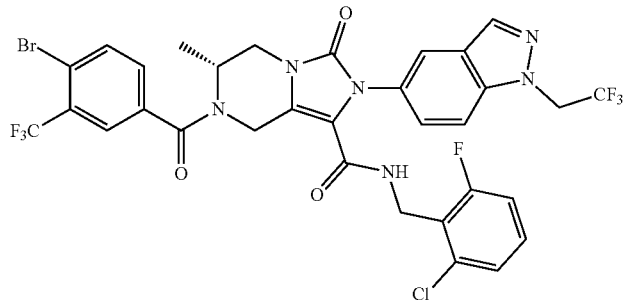 [SMILES: C[C@@H]1Cn2c(c(C(=O)NCc3c(F)cccc3Cl)n(-c3ccc4c(cnn4CC(F)(F)F)c3)c2=O)CN1C(=O)c1ccc(Br)c(C(F)(F)F)c1] | 104a |
| 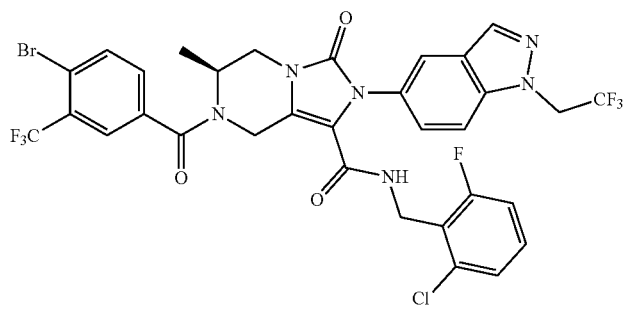 [SMILES: C[C@H]1Cn2c(c(C(=O)NCc3c(F)cccc3Cl)n(-c3ccc4c(cnn4CC(F)(F)F)c3)c2=O)CN1C(=O)c1ccc(Br)c(C(F)(F)F)c1] | 104b |
| 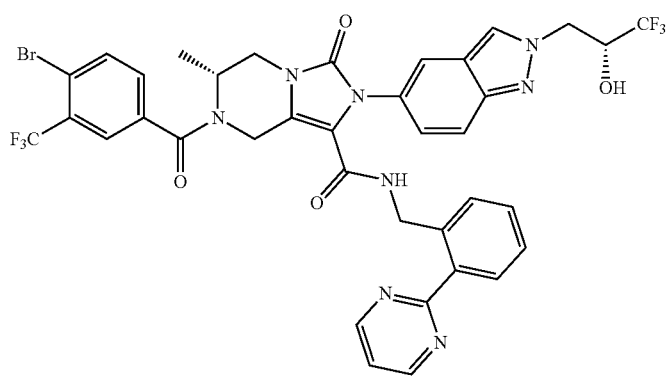 [SMILES: C[C@@H]1Cn2c(c(C(=O)NCc3ccccc3-c3ncccn3)n(-c3ccc4nn(C[C@@H](O)C(F)(F)F)cc4c3)c2=O)CN1C(=O)c1ccc(Br)c(C(F)(F)F)c1] | 105a |
| 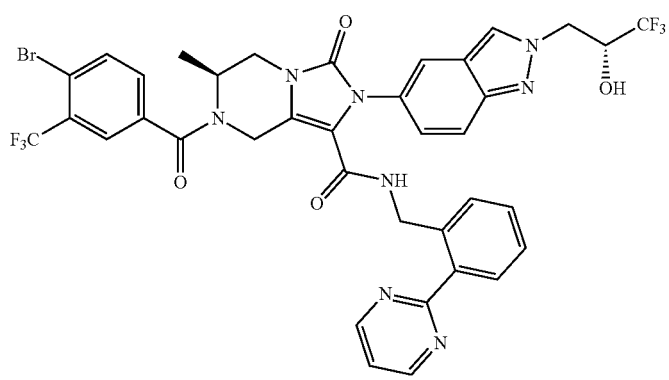 [SMILES: C[C@H]1Cn2c(c(C(=O)NCc3ccccc3-c3ncccn3)n(-c3ccc4nn(C[C@@H](O)C(F)(F)F)cc4c3)c2=O)CN1C(=O)c1ccc(Br)c(C(F)(F)F)c1] | 105b |

TABLE D-continued
| Structure | Cmpd |
|---|---|
| 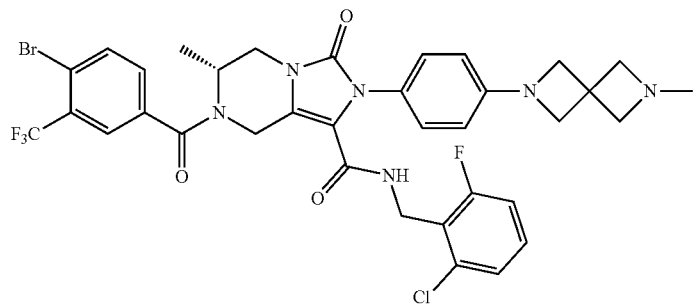 [SMILES: C[C@@H]1Cn2c(c(C(=O)NCc3c(F)cccc3Cl)n(-c3ccc(N4CC5(CN(C)C5)C4)cc3)c2=O)CN1C(=O)c1ccc(Br)c(C(F)(F)F)c1] | 106a |
| 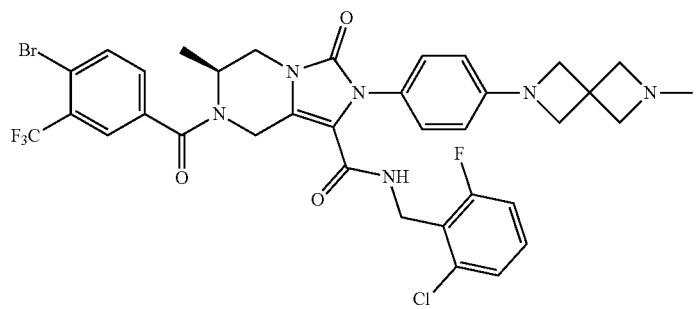 [SMILES: C[C@H]1Cn2c(c(C(=O)NCc3c(F)cccc3Cl)n(-c3ccc(N4CC5(CN(C)C5)C4)cc3)c2=O)CN1C(=O)c1ccc(Br)c(C(F)(F)F)c1] | 106b |
| 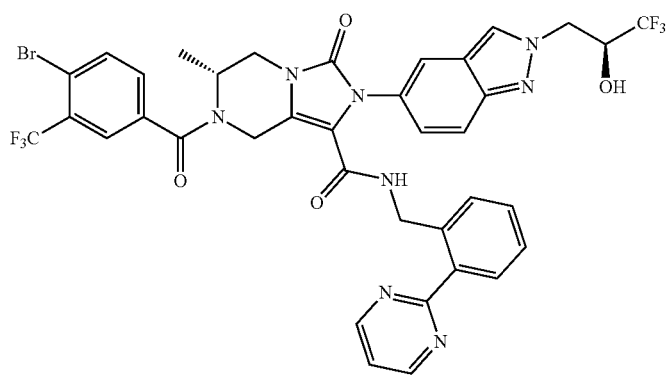 [SMILES: C[C@@H]1Cn2c(c(C(=O)NCc3ccccc3-c3ncccn3)n(-c3ccc4nn(C[C@H](O)C(F)(F)F)cc4c3)c2=O)CN1C(=O)c1ccc(Br)c(C(F)(F)F)c1] | 107a |
| 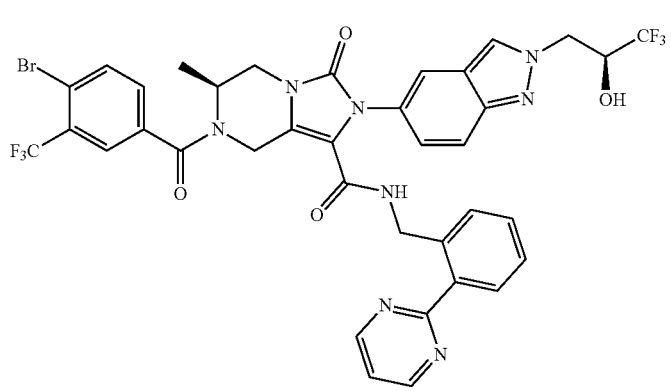 [SMILES: C[C@H]1Cn2c(c(C(=O)NCc3ccccc3-c3ncccn3)n(-c3ccc4nn(C[C@H](O)C(F)(F)F)cc4c3)c2=O)CN1C(=O)c1ccc(Br)c(C(F)(F)F)c1] | 107b |

TABLE D-continued

| Structure | Cmpd |
|---|---|
| 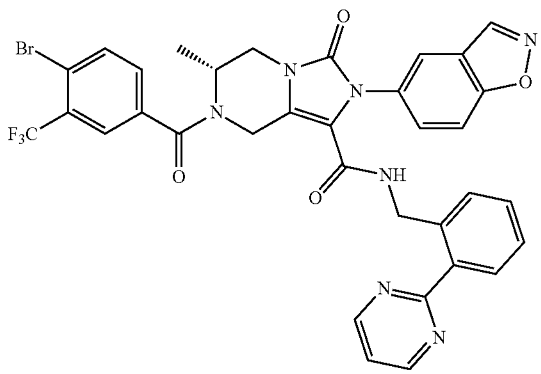 [SMILES: C[C@@H]1Cn2c(c(C(=O)NCc3ccccc3-c3ncccn3)n(-c3ccc4oncc4c3)c2=O)CN1C(=O)c1ccc(Br)c(C(F)(F)F)c1] | 108a |
| 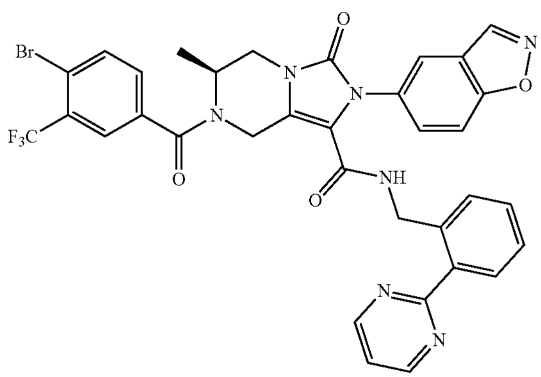 [SMILES: C[C@H]1Cn2c(c(C(=O)NCc3ccccc3-c3ncccn3)n(-c3ccc4oncc4c3)c2=O)CN1C(=O)c1ccc(Br)c(C(F)(F)F)c1] | 108b |
| 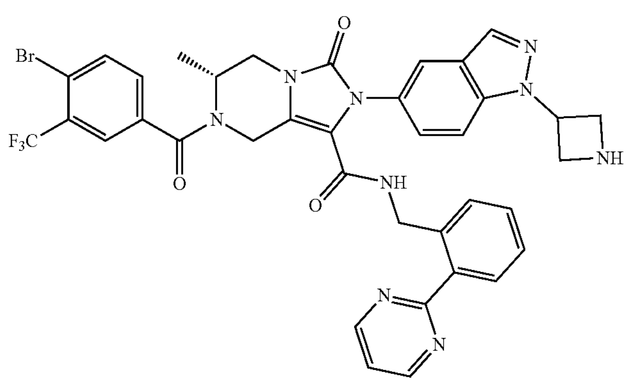 [SMILES: C[C@@H]1Cn2c(c(C(=O)NCc3ccccc3-c3ncccn3)n(-c3ccc4c(cnn4C4CNC4)c3)c2=O)CN1C(=O)c1ccc(Br)c(C(F)(F)F)c1] | 109a |
| 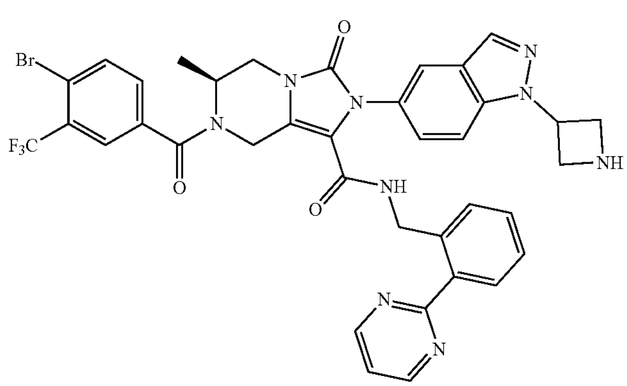 [SMILES: C[C@H]1Cn2c(c(C(=O)NCc3ccccc3-c3ncccn3)n(-c3ccc4c(cnn4C4CNC4)c3)c2=O)CN1C(=O)c1ccc(Br)c(C(F)(F)F)c1] | 109b |

TABLE D-continued
| Structure | Cmpd |
|---|---|
| 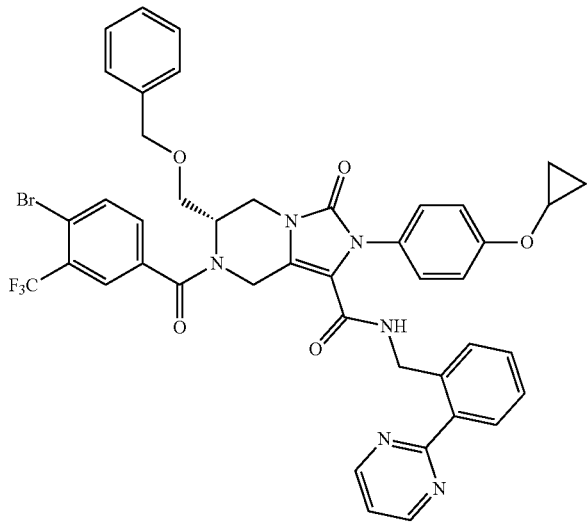 [SMILES: O=C(NCc1ccccc1-c1ncccn1)c1c2n(c(=O)n1-c1ccc(OC3CC3)cc1)C[C@@H](COCc1ccccc1)N(C(=O)c1ccc(Br)c(C(F)(F)F)c1)C2] | 130 |
| 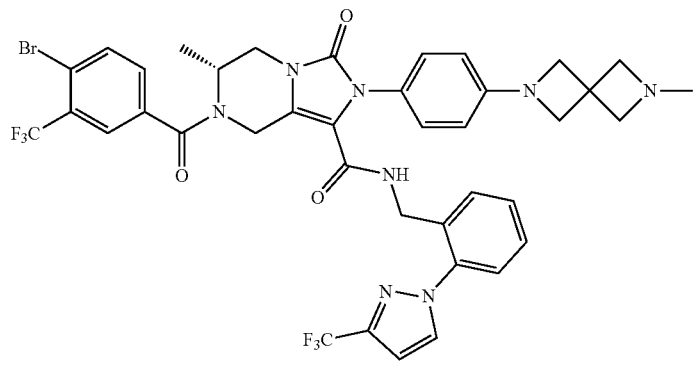 [SMILES: C[C@@H]1Cn2c(c(C(=O)NCc3ccccc3-n3ccc(C(F)(F)F)n3)n(-c3ccc(N4CC5(CN(C)C5)C4)cc3)c2=O)CN1C(=O)c1ccc(Br)c(C(F)(F)F)c1] | 110a |
| 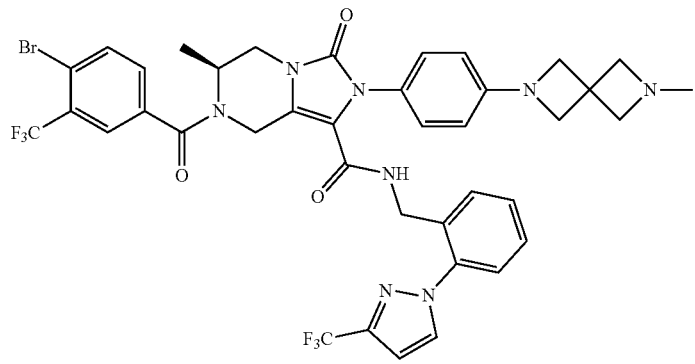 [SMILES: C[C@H]1Cn2c(c(C(=O)NCc3ccccc3-n3ccc(C(F)(F)F)n3)n(-c3ccc(N4CC5(CN(C)C5)C4)cc3)c2=O)CN1C(=O)c1ccc(Br)c(C(F)(F)F)c1] | 110b |

TABLE D-continued
| Structure | Cmpd |
|---|---|
| 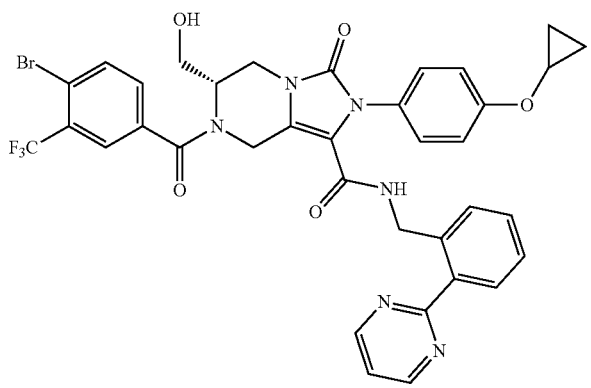 [SMILES: O=C(NCc1ccccc1-c1ncccn1)c1c2n(c(=O)n1-c1ccc(OC3CC3)cc1)C[C@@H](CO)N(C(=O)c1ccc(Br)c(C(F)(F)F)c1)C2] | 131 |
| 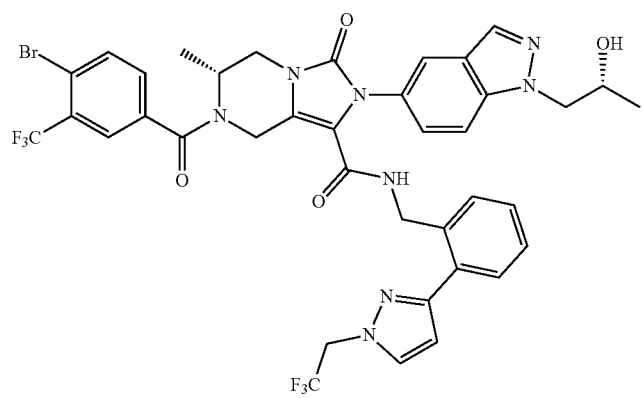 [SMILES: C[C@@H]1Cn2c(c(C(=O)NCc3ccccc3-c3ccn(CC(F)(F)F)n3)n(-c3ccc4c(cnn4C[C@@H](C)O)c3)c2=O)CN1C(=O)c1ccc(Br)c(C(F)(F)F)c1] | 111a |
| 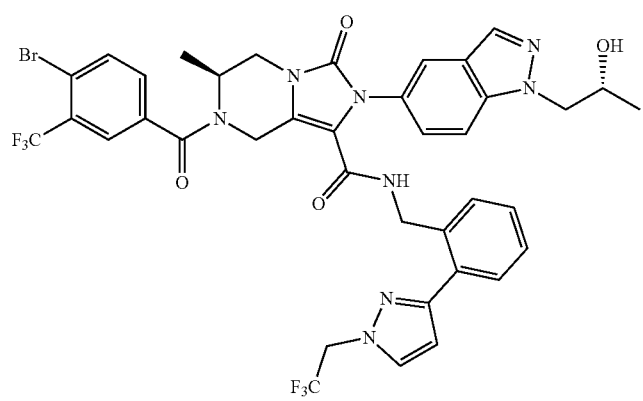 [SMILES: C[C@@H](O)Cn1ncc2cc(-n3c(C(=O)NCc4ccccc4-c4ccn(CC(F)(F)F)n4)c4n(c3=O)C[C@H](C)N(C(=O)c3ccc(Br)c(C(F)(F)F)c3)C4)ccc21] | 111b |

TABLE D-continued
| Structure | Cmpd |
|---|---|
| 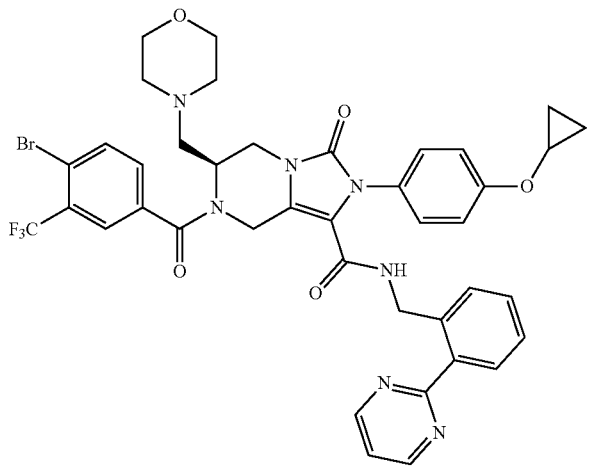 [SMILES: O=C(NCc1ccccc1-c1ncccn1)c1c2n(c(=O)n1-c1ccc(OC3CC3)cc1)C[C@H](CN1CCOCC1)N(C(=O)c1ccc(Br)c(C(F)(F)F)c1)C2] | 132a |
| 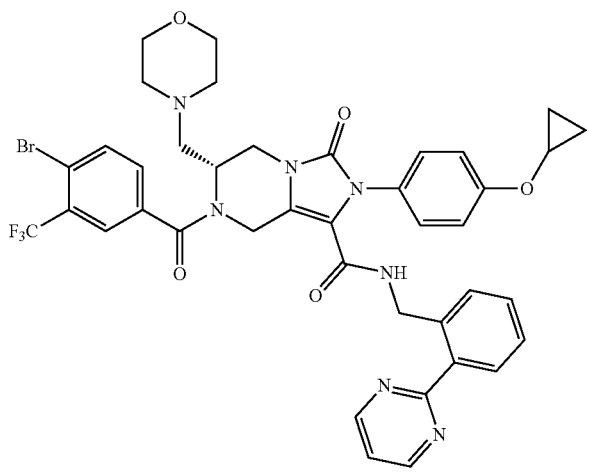 [SMILES: O=C(NCc1ccccc1-c1ncccn1)c1c2n(c(=O)n1-c1ccc(OC3CC3)cc1)C[C@@H](CN1CCOCC1)N(C(=O)c1ccc(Br)c(C(F)(F)F)c1)C2] | 132b |
| 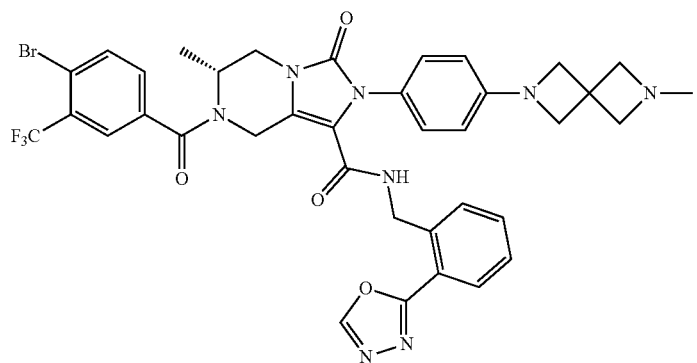 [SMILES: C[C@@H]1Cn2c(c(C(=O)NCc3ccccc3-c3nnco3)n(-c3ccc(N4CC5(CN(C)C5)C4)cc3)c2=O)CN1C(=O)c1ccc(Br)c(C(F)(F)F)c1] | 112a |

TABLE D-continued

| Structure | Cmpd |
|---|---|
| 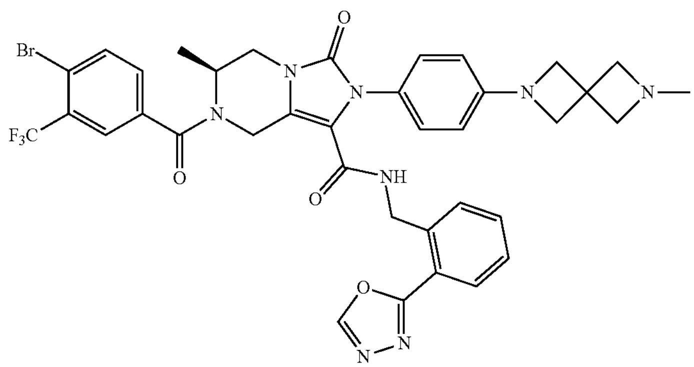 [SMILES: C[C@H]1Cn2c(c(C(=O)NCc3ccccc3-c3nnco3)n(-c3ccc(N4CC5(CN(C)C5)C4)cc3)c2=O)CN1C(=O)c1ccc(Br)c(C(F)(F)F)c1] | 112b |
| 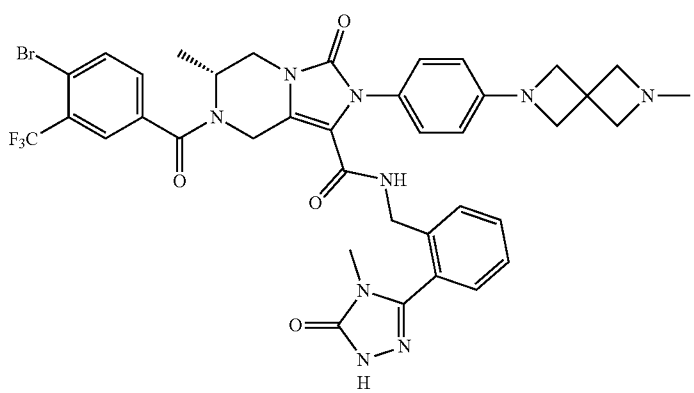 | 113a |
| 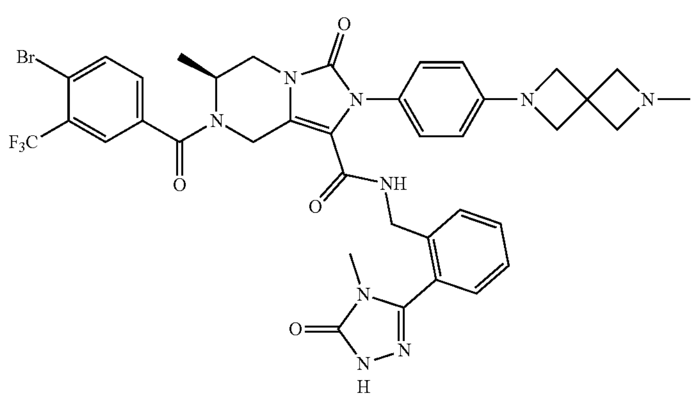 | 113b |
| 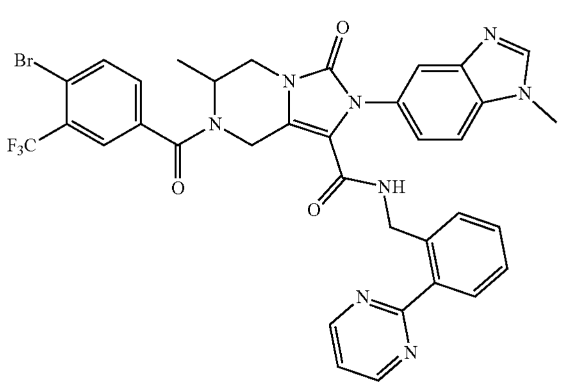 [SMILES: CC1Cn2c(c(C(=O)NCc3ccccc3-c3ncccn3)n(-c3ccc4c(c3)ncn4C)c2=O)CN1C(=O)c1ccc(Br)c(C(F)(F)F)c1] | 133 |

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using ATPlite (Perkin Elmer).

On day 0, HepG2.117 cells (which are maintained in routine cell culture with doxycycline present in the medium at a final concentration of 1 μg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycyline and 100 μL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for ATPlite measurement). The cells were incubated at 37° C. and 5% $CO_2$ for 3 days. The plate map of compound treatment is shown in FIG. 1.

On day 4, cell viability was assessed using ATPlite and cell lysates were prepared for HBV DNA extraction and subsequent quantification by qPCR.

HBV DNA Quantification by qPCR

Medium was removed from each well and 100 μL of 0.33% NP-40 in $H_2O$ was added to each well. Plates were sealed, incubated at 4° C. for 5 mins, vortexed extensively and centrifuged briefly. Next, 35 μL of lysate was added to 65 μL QuickExtract DNA Extraction Solution (Epicentre) in a PCR plate for each well. PCR plate was incubated at 65° C. for 6 mins, 98° C. for 2 mins and finally cooled to 4° C. HBV DNA was then quantified by qPCR with HBV-specific primers and probes as specified in Table 1 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 1

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 1) |
|  | HBV-reverse | GACAAACGGGCAACATACCTT (SEQ ID NO: 2) |
| HBV Probe | HBV probe | FAM/CCTCTKCAT/ZEN/CCTGCTGCTATGCCTCATC/3IABkFQ/ (SEQ ID NO: 3) |

A DNA standard was prepared by dilution of an IDT gBlock corresponding to the amplicon with concentrations ranging from 10^2 to 10^8 copies/input (i.e. per 4 μL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by ATPlite according to the manufacturer's manual. In brief, 50 μL of cell lysis solution was added to the culture plates and shaken for 5', followed by addition of 50 μL substrate into each well and further shaking. The plates were incubated at room temperature for 10 mins and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The $CC_{50}$, $EC_{50}$ and $EC_{90}$ values were determined by dose-response curves fitted using non-linear regression.

As shown in Table 2, compounds of Formula (I) are active against HBV, where 'A' indicates an $EC_{50} \leq 50$ nM, 'B' indicates an $EC_{50} > 50$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 2

| Compound | $EC_{50}$ |
|---|---|
| 1a | B |
| 1b | A |
| 2a | B |
| 2b | A |
| 3a | A |
| 3b | B |
| 4a | B |
| 4h | A |
| 5a | C |
| 6a | B |
| 6b | A |
| 7a | B |
| 7b | A |
| 8a | B |
| 8b | A |
| 9a | B |
| 9b | A |
| 10a | C |
| 10b | B |
| 11a | A |
| 11b | B |
| 12a | B |
| 12b | A |
| 13a | B |
| 13b | A |
| 14a | B |
| 14b | A |
| 15a | B |
| 15b | A |
| 16a | B |
| 16b | A |
| 17a | B |
| 17b | A |
| 18a | B |
| 18b | A |
| 19a | C |
| 19b | B |
| 20a | C |
| 20b | B |
| 21a | A |
| 21b | B |
| 22a | B |
| 22b | A |
| 23a | B |

TABLE 2-continued

| Compound | EC$_{50}$ |
|---|---|
| 23b | A |
| 24a | B |
| 24b | A |
| 25a | B |
| 25b | A |
| 26a | A |
| 26b | A |
| 27a | A |
| 27b | A |
| 28a | A |
| 28b | A |
| 29a | A |
| 29b | A |
| 30a | B |
| 30b | A |
| 31a | B |
| 31b | A |
| 32a | A |
| 32b | A |
| 33a | B |
| 33b | A |
| 34a | A |
| 35a | B |
| 35b | A |
| 36a | A |
| 36b | A |
| 37a | B |
| 37b | A |
| 38a | A |
| 38b | A |
| 39a | B |
| 39b | A |
| 40a | A |
| 40b | A |
| 41a | A |
| 42a | C |
| 42b | B |
| 43a | C |
| 43b | B |
| 44a | B |
| 44b | A |
| 45a | B |
| 45b | B |
| 46a | B |
| 46b | A |
| 47a | A |
| 48a | B |
| 48b | A |
| 49a | B |
| 49b | B |
| 50a | B |
| 50b | A |
| 51a | B |
| 51b | A |
| 52a | B |
| 52b | A |
| 53a | B |
| 53b | B |
| 54a | A |
| 54b | B |
| 55a | B |
| 55b | A |
| 56a | C |
| 56b | B |
| 57a | B |
| 57b | B |
| 58a | B |
| 58b | A |
| 59a | A |
| 59b | A |
| 60a | B |
| 60b | A |
| 61a | A |
| 61b | A |
| 62a | A |
| 62b | B |
| 63a | A |
| 63b | B |

TABLE 2-continued

| Compound | EC$_{50}$ |
|---|---|
| 64a | A |
| 64b | B |
| 65a | A |
| 65b | B |
| 66a | B |
| 66b | B |
| 67a | B |
| 67b | A |
| 68a | A |
| 68b | A |
| 69a | A |
| 69b | B |
| 70a | B |
| 70b | A |
| 71a | A |
| 71b | B |
| 72a | A |
| 72b | B |
| 73a | C |
| 73b | B |
| 74a | B |
| 74b | A |
| 75a | A |
| 75b | B |
| 76a | C |
| 76b | C |
| 77a | A |
| 77b | B |
| 78a | A |
| 78b | B |
| 79a | B |
| 79b | A |
| 80a | B |
| 80b | B |
| 81a | B |
| 81b | A |
| 82a | B |
| 82b | A |
| 83a | B |
| 83b | B |
| 84a | B |
| 84b | A |
| 85a | B |
| 85b | B |
| 85c | B |
| 85d | B |
| 87a | B |
| 87b | A |
| 88a | A |
| 88b | B |
| 89a | A |
| 89b | A |
| 90a | B |
| 90b | B |
| 91a | B |
| 91b | B |
| 92a | C |
| 92b | C |
| 93a | C |
| 93b | B |
| 94a | B |
| 94b | B |
| 95a | B |
| 95b | B |
| 96a | A |
| 96b | A |
| 97a | B |
| 97b | A |
| 98a | B |
| 98b | C |
| 99a | B |
| 99b | B |
| 100a | A |
| 100b | A |
| 101a | B |
| 101b | A |
| 102a | B |
| 102b | A |

TABLE 2-continued

| Compound | EC$_{50}$ |
|---|---|
| 103a | B |
| 103b | A |
| 104a | A |
| 104b | B |
| 105a | A |
| 105b | B |
| 106a | B |
| 106b | B |
| 107a | B |
| 107b | B |
| 108a | C |
| 108b | C |
| 109a | C |
| 109b | C |
| 110a | B |
| 110b | B |
| 111a | B |
| 111b | B |
| 112a | C |
| 112b | C |
| 113a | nd |
| 113b | nd |
| 114 | B |
| 115a | B |
| 115b | B |
| 116 | B |
| 117 | B |
| 118 | B |
| 119 | B |
| 120 | B |
| 121 | B |
| 122 | B |
| 123 | C |
| 124 | C |
| 125a | B |
| 125b | B |
| 126 | C |
| 127 | C |
| 128 | B |
| 129 | B |
| 130 | C |
| 131 | C |
| 132a | C |
| 132b | C | nd = no data

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I) having the structure:

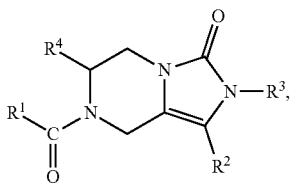

or a pharmaceutically acceptable salt or a stereoisomer thereof, wherein:

$R^1$ is a 3,4-disubstituted phenyl, wherein the 3,4-disubstituted phenyl is substituted with 2 substituents independently selected from the group consisting of —F, —Cl, —Br, —CHF$_2$, —CF$_3$, —CH$_3$, —CN and —C≡CH, or a trisubstituted phenyl, wherein the trisubstituted phenyl is substituted with 3 substituents independently selected from the group consisting of —F, —Cl, —Br, —CHF$_2$, —CF$_3$, —CH$_3$, —CN and —C≡CH;

$R^2$ is —C(═O) $R^5$;

$R^3$ is selected from the group consisting of a substituted phenyl, a substituted monocyclic heteroaryl a substituted bicyclic heteroaryl and

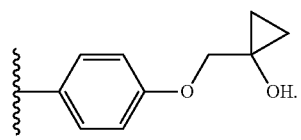 [SMILES: *c1ccc(OCC2(O)CC2)cc1]

wherein the phenyl, the monocyclic heteroaryl and the bicyclic heteroaryl are substituted with one or more substituents selected from the group consisting of halogen; hydroxy; —NH$_2$; —NH (an unsubstituted C$_{1-4}$ alkyl); —N(an unsubstituted C$_{1-4}$ alkyl)$_2$; an unsubstituted C$_{1-4}$ alkyl; an unsubstituted methoxy; an unsubstituted ethoxy; an unsubstituted n-propoxy; an unsubstituted isopropoxy; an unsubstituted n-butoxy; an unsubstituted iso-butoxy; an unsubstituted sec-butoxy; an unsubstituted tert-butoxy; an unsubstituted cyclopropoxy; an unsubstituted cyclobutoxy; an unsubstituted C$_{1-4}$ haloalkyl; an unsubstituted C$_{1-4}$ haloalkoxy; hydroxy-substituted methoxy; hydroxy-substituted ethoxy; hydroxy-substituted n-propoxy; hydroxy-substituted isopropoxy; hydroxy-substituted n-butoxy; hydroxy-substituted iso-butoxy; hydroxy-substituted sec-butoxy; hydroxy-substituted tert-butoxy; hydroxy-substituted cyclopropoxy; hydroxy-substituted cyclobutoxy; methoxy substituted by an amine-mono (an unsubstituted C$_{1-4}$ alkyl); ethoxy substituted by an amine-mono(an unsubstituted C$_{1-4}$ alkyl); n-propoxy substituted by an amine-mono(an unsubstituted C$_{1-4}$ alkyl); isopropoxy substituted by an amine-mono(an unsubstituted C$_{1-4}$ alkyl); n-butoxy substituted by an amine-mono(an unsubstituted C$_{1-4}$ alkyl); iso-butoxy substituted by an amine-mono(an unsubstituted C$_{1-4}$ alkyl); sec-butoxy substituted by an amine-mono(an unsubstituted C$_{1-4}$ alkyl); tert-butoxy substituted by an amine-mono(an unsubstituted C$_{1-4}$ alkyl); methoxy substituted by an amine-di(an unsubstituted C$_{1-4}$ alkyl); ethoxy substituted by an amine-di(an unsubstituted C$_{1-4}$ alkyl); n-propoxy substituted by an amine-di(an unsubstituted C$_{1-4}$ alkyl); isopropoxy substituted by an amine-di(an unsubstituted C$_{1-4}$ alkyl); n-butoxy substituted by an amine-di(an unsubstituted C$_{1-4}$ alkyl); iso-butoxy substituted by an amine-di(an unsubstituted C$_{1-4}$ alkyl); sec-butoxy substituted by an amine-di(an unsubstituted C$_{1-4}$ alkyl); tert-butoxy substituted by an amine-di(an unsubstituted C$_{1-4}$ alkyl); methoxy substituted by a monocyclic heterocyclyl; ethoxy substituted by a monocyclic heterocyclyl; n-propoxy substituted by a monocyclic heterocyclyl; isopropoxy substituted by a monocyclic heterocyclyl; n-butoxy substituted by a monocyclic heterocyclyl; iso-butoxy substituted by a monocyclic heterocyclyl; sec-butoxy substituted by a monocyclic heterocyclyl; tert-butoxy substituted by a monocyclic heterocyclyl; an unsubstituted C$_{1-4}$ hydroxyalkyl; C$_{1-4}$ alkyl substituted by hydroxy and halogen; G methoxy substituted by hydroxy and halogen; ethoxy substituted by hydroxy and halogen; n-propoxy substituted by hydroxy and halogen; isopropoxy substituted by hydroxy and halogen; n-butoxy substituted by hydroxy and halogen; iso-butoxy substituted by hydroxy and halogen; tert-butoxy substituted by hydroxy and halogen; cyclopropoxy substituted by hydroxy and halogen; cyclobutoxy substituted by hydroxy and halogen; methoxy substituted by hydroxy and —NR$^{Z1}$R$^{Z2}$; ethoxy substituted by hydroxy and —NR$^{Z1}$R$^{Z2}$; n-propoxy substituted by hydroxy and —NR$^{Z1}$R$^{Z2}$; isopropoxy substituted by hydroxy and —NR$^{Z1}$R$^{Z2}$; n-butoxy; substituted by hydroxy and —NR$^{Z1}$R$^{Z2}$; iso-butoxy substituted by hydroxy and —NR$^{Z1}$R$^{Z2}$; tert-butoxy substituted by hydroxy and —NR$^{Z1}$R$^{Z2}$; cyclopropoxy substituted by hydroxy and —NR$^{Z1}$R$^{Z2}$; cyclobutoxy substituted by hydroxy and —NR$^{Z1}$R$^{Z2}$; —O—CH$_2$—C(=O)-(an unsubstituted C$_{1-4}$ alkyl); an unsubstituted monocyclic heterocyclyl; a substituted monocyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted fused-bicyclic heterocyclyl; a substituted fused-bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted sprio-bicyclic heterocyclyl; a substituted sprio-bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted monocyclic heteroaryl; a substituted monocyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted bicyclic heteroaryl and a substituted bicyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; and wherein each R$^{Z1}$ and each R$^{Z2}$ are independently H or an unsubstituted C$_{1-4}$ alkyl; or wherein each R$^{Z1}$ and each R$^{Z2}$ are taken together along with the N to which each R$^{Z1}$ and each R$^{Z2}$ are attached to form a monocyclic heterocyclyl;

R$^4$ is selected from the group consisting of —CHF$_2$, —CH$_3$, -cyclopropyl, —(CH$_2$)$_{1-4}$-(hydroxy), —CH$_2$—O—CH$_2$-(an unsubstituted phenyl) and —CH$_2$-(an unsubstituted heterocyclyl), wherein the unsubstituted heterocyclyl of the —CH$_2$-(an unsubstituted heterocyclyl) is an unsubstituted monocyclic heterocyclyl;

(i) R$^5$ is

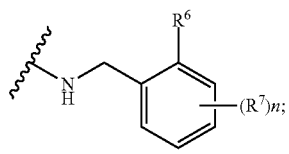

R$^6$ is an unsubstituted 5- or 6-membered monocyclic heteroaryl or a substituted 5- or 6-membered monocyclic heteroaryl,
wherein the unsubstituted monocyclic heteroaryl contains 1, 2 or 3 N (nitrogens, and optionally 1 or 2 additional heteroatoms independently selected from the group consisting of oxygen and sulfur; and wherein the substituted 5- or 6-membered monocyclic heteroaryl contains 1, 2 or 3 N (nitrogen), and optionally 1 or 2 additional heteroatoms independently selected from the group consisting of oxygen and sulfur, and is substituted with one or more substituents independently selected from the group consisting of halogen, an unsubstituted C$_{1-4}$ alkyl, an unsubstituted C$_{1-4}$ haloalkyl, an unsubstituted methoxy, an unsubstituted ethoxy, an unsubstituted n-propoxy, an unsubstituted isopropoxy, an unsubstituted n-butoxy, an unsubstituted iso-butoxy, an unsubstituted sec-butoxy, an unsubstituted tert-butoxy, —NH$_2$ and —NH (an unsubstituted C$_{1-6}$ alkyl);

R$^7$ is selected from the group consisting of halogen, an unsubstituted C$_{1-4}$ alkyl, an unsubstituted methoxy, an unsubstituted ethoxy, an unsubstituted n-propoxy, an unsubstituted isopropoxy, an unsubstituted n-butoxy, an unsubstituted iso-butoxy, an unsubstituted sec-butoxy and an unsubstituted tert-butoxy; and n is 0 or 1; or (ii) R$^5$ is

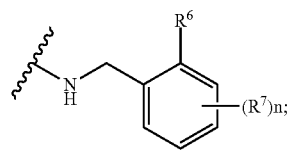

R$^6$ is halogen;
R$^7$ is halogen; and
n is 1; and
provided that the compound of Formula (I) cannot be selected from the group consisting of:

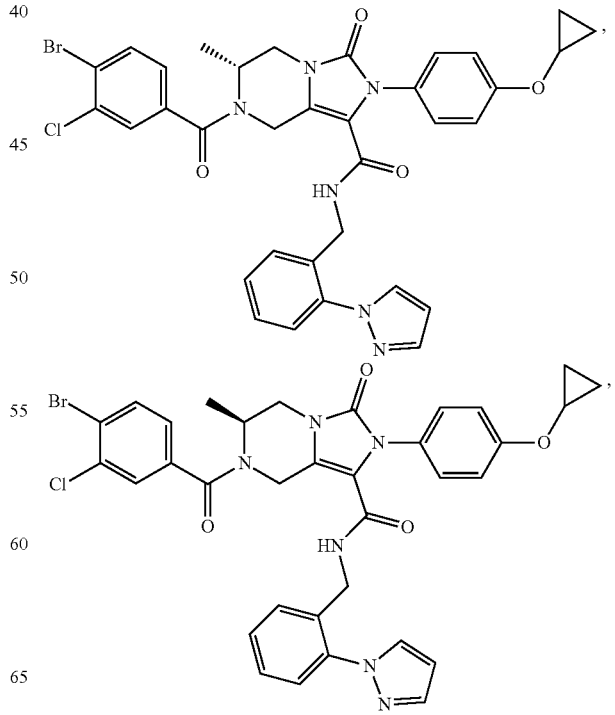

387
-continued
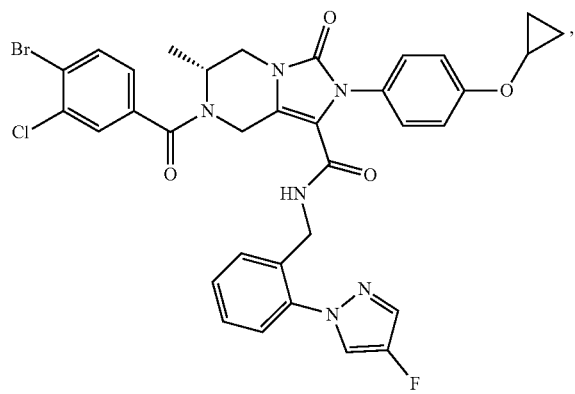
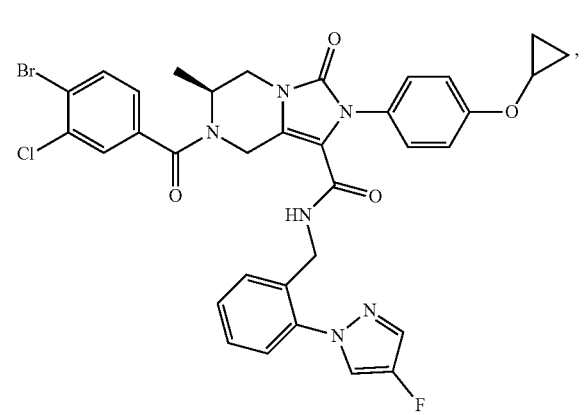
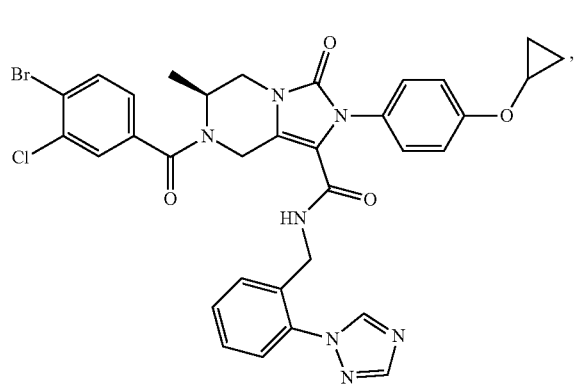
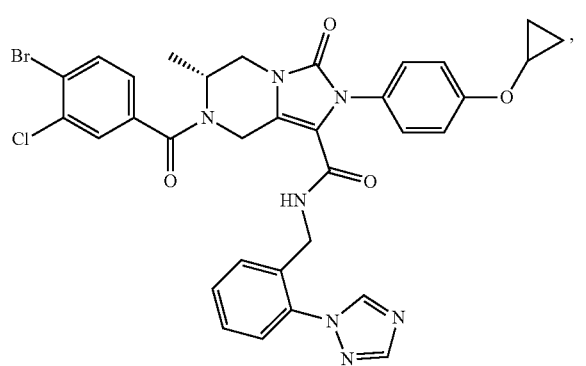
388
-continued
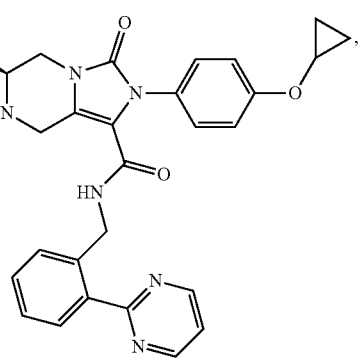
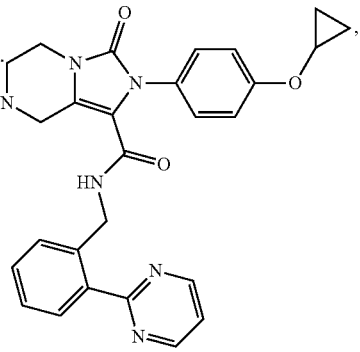
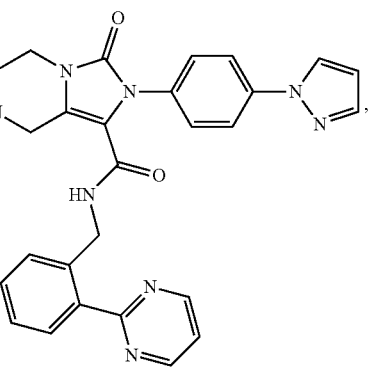
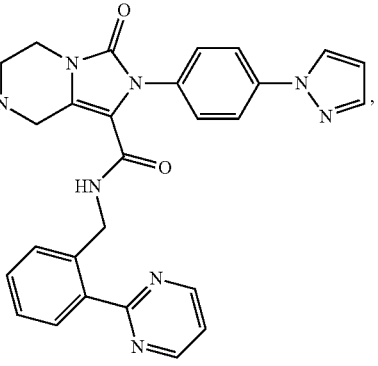

-continued

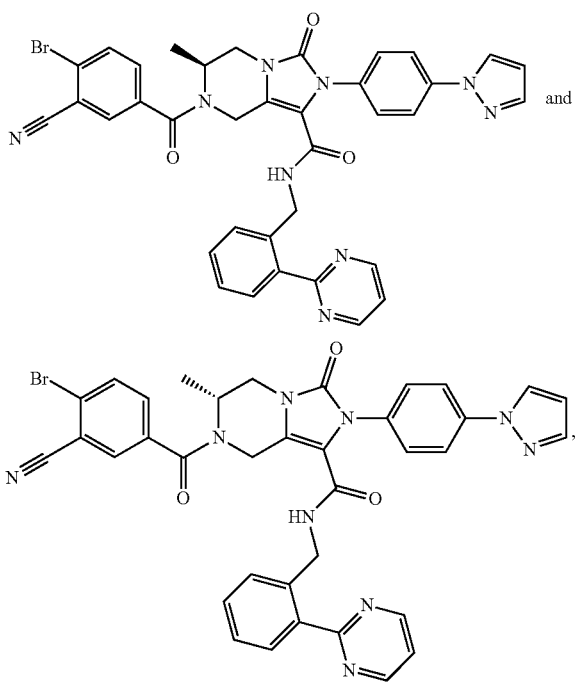

and

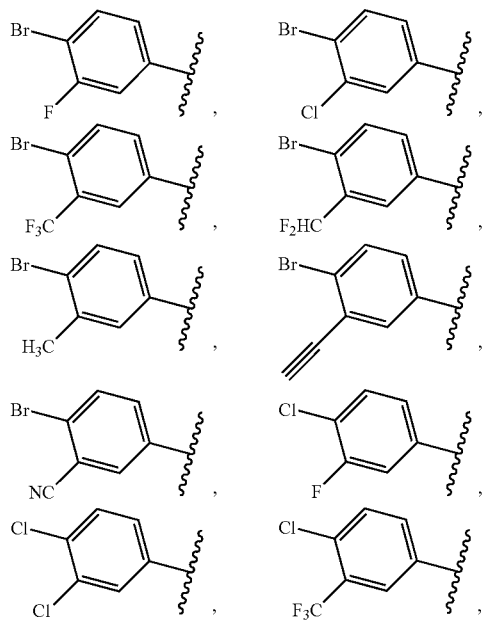

or a pharmaceutically acceptable salt or a stereoisomer thereof.

2. The compound of claim 1, or a pharmaceutically acceptable salt or a stereoisomer thereof, wherein $R^1$ is a 3,4-disubstituted phenyl, wherein the 3,4-disubstituted phenyl is substituted with 2 substituents independently selected from the group consisting of —F, —Cl, —Br, —CHF$_2$, —CF$_3$, —CH$_3$, —CN and —C≡CH.

3. The compound of claim 1, or a pharmaceutically acceptable salt or a stereoisomer thereof, wherein $R^1$ is selected from the group consisting of:

-continued

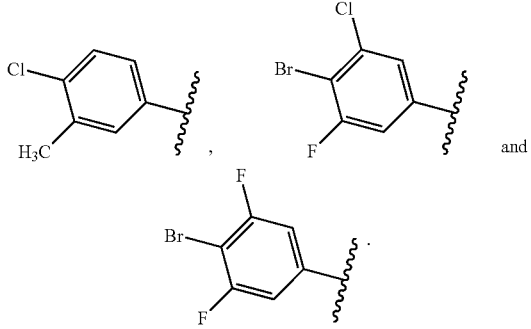

4. The compound of claim 1, or a pharmaceutically acceptable salt or a stereoisomer thereof, wherein $R^1$ is a trisubstituted phenyl, wherein the trisubstituted phenyl is substituted with 3 substituents selected from the group consisting of —F, —Cl, —Br, —CHF$_2$, —CF$_3$, —CH$_3$, —CN and —C≡CH.

5. The compound of claim 1, or a pharmaceutically acceptable salt or a stereoisomer thereof, wherein $R^3$ is a substituted phenyl, wherein the phenyl is substituted with one or more substituents selected from the group consisting of halogen; hydroxy; —NH$_2$; —NH (an unsubstituted C$_{1-4}$ alkyl); —N(an unsubstituted C$_{1-4}$ alkyl)$_2$; an unsubstituted C$_{1-4}$ alkyl; an unsubstituted methoxy; an unsubstituted ethoxy; an unsubstituted n-propoxy; an unsubstituted isopropoxy; an unsubstituted n-butoxy; an unsubstituted iso-butoxy; an unsubstituted sec-butoxy; an unsubstituted tert-butoxy; an unsubstituted cyclopropoxy; an unsubstituted cyclobutoxy; an unsubstituted C$_{1-4}$ haloalkyl; an unsubstituted C$_{1-4}$ haloalkoxy; hydroxy-substituted methoxy; hydroxy-substituted ethoxy; hydroxy-substituted n-propoxy; hydroxy-substituted isopropoxy; hydroxy-substituted n-butoxy; hydroxy-substituted iso-butoxy; hydroxy-substituted sec-butoxy; hydroxy-substituted tert-butoxy; hydroxy-substituted cyclopropoxy; hydroxy-substituted cyclobutoxy; methoxy substituted by an amine-mono(an unsubstituted C$_{1-4}$ alkyl); ethoxy substituted by an amine-mono(an unsubstituted C$_{1-4}$ alkyl); n-propoxy substituted by an amine-mono(an unsubstituted C$_{1-4}$ alkyl); isopropoxy substituted by an amine-mono(an unsubstituted C$_{1-4}$ alkyl); n-butoxy substituted by an amine-mono(an unsubstituted C$_{1-4}$ alkyl); iso-butoxy substituted by an amine-mono(an unsubstituted C$_{1-4}$ alkyl); sec-butoxy substituted by an amine-mono(an unsubstituted C$_{1-4}$ alkyl); tert-butoxy substituted by an amine-mono(an unsubstituted C$_{1-4}$ alkyl); methoxy substituted by an amine-di(an unsubstituted C$_{1-4}$ alkyl); ethoxy substituted by an amine-di(an unsubstituted C$_{1-4}$ alkyl); n-propoxy substituted by an amine-di(an unsubstituted C$_{1-4}$ alkyl); isopropoxy substituted by an amine-di (an unsubstituted C$_{1-4}$ alkyl); n-butoxy substituted by an amine-di(an unsubstituted C$_{1-4}$ alkyl); iso-butoxy substituted by an amine-di(an unsubstituted C$_{1-4}$ alkyl); sec-butoxy substituted by an amine-di(an unsubstituted C$_{1-4}$ alkyl); tert-butoxy substituted by an amine-di(an unsubstituted C$_{1-4}$ alkyl); methoxy substituted by a monocyclic heterocyclyl; ethoxy substituted by a monocyclic heterocyclyl; n-propoxy substituted by a monocyclic heterocyclyl; isopropoxy substituted by a monocyclic heterocyclyl; n-butoxy substituted by a monocyclic heterocyclyl; iso-butoxy substituted by a monocyclic heterocyclyl; sec-butoxy substituted by a monocyclic heterocyclyl; tert-butoxy substituted by a monocyclic heterocyclyl; an unsubstituted C$_{1-4}$ hydroxyalkyl; C$_{1-4}$ alkyl substituted by hydroxy and halogen; G methoxy substituted by hydroxy and halogen; ethoxy substituted by hydroxy and halogen; n-propoxy substituted by hydroxy and halogen; isopropoxy substituted by hydroxy and halogen; n-butoxy substituted by hydroxy and halogen; iso-butoxy substituted by hydroxy and halogen; tert-butoxy substituted by hydroxy and halogen; cyclopropoxy substituted by hydroxy and halogen; cyclobutoxy substituted by hydroxy and halogen; methoxy substituted by hydroxy and —NR$^{Z1}$R$^{Z2}$; ethoxy substituted by hydroxy and —NR$^{Z1}$R$^{Z2}$; n-propoxy substituted by hydroxy and —NR$^{Z1}$R$^{Z2}$; iso-propoxy substituted by hydroxy and —NR$^{Z1}$R$^{Z2}$; n-butoxy substituted by hydroxy and —NR$^{Z1}$R$^{Z2}$; iso-butoxy substituted by hydroxy and —NR$^{Z1}$R$^{Z2}$; tert-butoxy substituted by hydroxy and —NR$^{Z1}$R$^{Z2}$; cyclopropoxy substituted by hydroxy and —NR$^{Z1}$R$^{Z2}$; cyclobutoxy substituted by hydroxy and —NR$^{Z1}$R$^{Z2}$; —O—CH$_2$—C(=O)-(an unsubstituted C$_{1-4}$ alkyl); an unsubstituted monocyclic heterocyclyl; a substituted monocyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted fused-bicyclic heterocyclyl; a substituted fused-bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted sprio-bicyclic heterocyclyl; a substituted sprio-bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted monocyclic heteroaryl; a substituted monocyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted bicyclic heteroaryl and a substituted bicyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; and wherein each R$^{Z1}$ and each R$^{Z2}$ are independently H or an unsubstituted C$_{1-4}$ alkyl; or wherein each R$^{Z1}$ and each R$^{Z2}$ are taken together along with the N (nitrogen) to which each R$^{Z1}$ and each R$^{Z2}$ are attached to form a monocyclic heterocyclyl.

6. The compound of claim 1, or a pharmaceutically acceptable salt or a stereoisomer thereof, wherein R$^3$ is a substituted bicyclic heteroaryl, wherein the substituted bicyclic heteroaryl is substituted with one or more substituents selected from the group consisting of halogen; hydroxy; —NH$_2$; —NH (an unsubstituted C$_{1-4}$ alkyl); —N(an unsubstituted C$_{1-4}$ alkyl)$_2$; an unsubstituted C$_{1-4}$ alkyl; an unsubstituted methoxy; an unsubstituted ethoxy; an unsubstituted n-propoxy; an unsubstituted isopropoxy; an unsubstituted n-butoxy; an unsubstituted iso-butoxy; an unsubstituted sec-butoxy; an unsubstituted tert-butoxy; an unsubstituted cyclopropoxy; an unsubstituted cyclobutoxy; an unsubstituted C$_{1-4}$ haloalkyl; an unsubstituted C$_{1-4}$ haloalkoxy; hydroxy-substituted methoxy; hydroxy-substituted ethoxy; hydroxy-substituted n-propoxy; hydroxy-substituted iso-propoxy; hydroxy-substituted n-butoxy; hydroxy-substituted iso-butoxy; hydroxy-substituted sec-butoxy; hydroxy-substituted tert-butoxy; hydroxy-substituted cyclopropoxy; hydroxy-substituted cyclobutoxy; methoxy substituted by an amine-mono(an unsubstituted C$_{1-4}$ alkyl); ethoxy substituted by an amine-mono(an unsubstituted C$_{1-4}$ alkyl); n-propoxy substituted by an amine-mono(an unsubstituted C$_{1-4}$ alkyl); isopropoxy substituted by an amine-mono(an unsubstituted C$_{1-4}$ alkyl); n-butoxy substituted by an amine-mono(an unsubstituted C$_{1-4}$ alkyl); iso-butoxy substituted by an amine-mono(an unsubstituted C$_{1-4}$ alkyl); sec-butoxy substituted by an amine-mono(an unsubstituted C$_{1-4}$ alkyl); tert-butoxy substituted by an amine-mono(an unsubstituted C$_{1-4}$ alkyl); methoxy substituted by an amine-di(an unsubstituted C$_{1-4}$ alkyl); ethoxy substituted by an amine-di(an unsubstituted C$_{1-4}$ alkyl); n-propoxy substituted by an amine-di(an unsubstituted C$_{1-4}$ alkyl); isopropoxy substituted by an amine-di(an unsubstituted C$_{1-4}$ alkyl); n-butoxy substituted by an amine-di(an unsubstituted C$_{1-4}$ alkyl); iso-butoxy substituted by an amine-di(an unsubstituted C$_{1-4}$ alkyl); sec-butoxy substituted by an amine-di(an unsubstituted C$_{1-4}$ alkyl); tert-butoxy substituted by an amine-di(an unsubstituted C$_{1-4}$ alkyl); methoxy substituted by a monocyclic heterocyclyl; ethoxy substituted by a monocyclic heterocyclyl; n-propoxy substituted by a monocyclic heterocyclyl; isopropoxy substituted by a monocyclic heterocyclyl; n-butoxy substituted by a monocyclic heterocyclyl; iso-butoxy substituted by a monocyclic heterocyclyl; sec-butoxy substituted by a monocyclic heterocyclyl; tert-butoxy substituted by a monocyclic heterocyclyl; an unsubstituted C$_{1-4}$ hydroxyalkyl; C$_{1-4}$ alkyl substituted by hydroxy and halogen; methoxy substituted by hydroxy and halogen; methoxy substituted by hydroxy and halogen; n-propoxy substituted by hydroxy and halogen; isopropoxy substituted by hydroxy and halogen; n-butoxy substituted by hydroxy and halogen; iso-butoxy substituted by hydroxy and halogen; tert-butoxy substituted by hydroxy and halogen; cyclopropoxy substituted by hydroxy and halogen; cyclobutoxy substituted by hydroxy and halogen; methoxy substituted by hydroxy and —NR$^{Z1}$R$^{Z2}$; ethoxy substituted by hydroxy and —NR$^{Z1}$R$^{Z2}$; n-propoxy substituted by hydroxy and —NR$^{Z1}$R$^{Z2}$; isopropoxy substituted by hydroxy and —NR$^{Z1}$R$^{Z2}$; n-butoxy; substituted by hydroxy and —NR$^{Z1}$R$^{Z2}$; iso-butoxy substituted by hydroxy and —NR$^{Z1}$R$^{Z2}$; tert-butoxy substituted by hydroxy and —NR$^{Z1}$R$^{Z2}$; cyclopropoxy substituted by hydroxy and —NR$^{Z1}$R$^{Z2}$; cyclobutoxy substituted by hydroxy and —NR$^{Z1}$R$^{Z2}$; —O—CH$_2$—C(=O)-(an unsubstituted C$_{1-4}$ alkyl); an unsubstituted monocyclic heterocyclyl; a substituted monocyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted fused-bicyclic heterocyclyl; a substituted fused bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted sprio-bicyclic heterocyclyl; a substituted sprio-bicyclic heterocyclyl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted monocyclic heteroaryl; a substituted monocyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; an unsubstituted bicyclic heteroaryl and a substituted bicyclic heteroaryl substituted by 1, 2 or 3 moieties selected from the group consisting of halogen, hydroxy, an unsubstituted C$_{1-4}$ alkyl and an unsubstituted C$_{1-4}$ haloalkyl; and wherein each R$^{Z1}$ and each R$^{Z2}$ are independently H or an unsubstituted C$_{1-4}$ alkyl; or wherein each R$^{Z1}$ and each R$^{Z2}$ are taken together along with the N (nitrogen) to which each R$^{Z1}$ and each R$^{Z2}$ are attached to form a monocyclic heterocyclyl.

7. The compound of claim 1, or a pharmaceutically acceptable salt or a stereoisomer thereof, wherein R$^3$ is selected from the group consisting of:

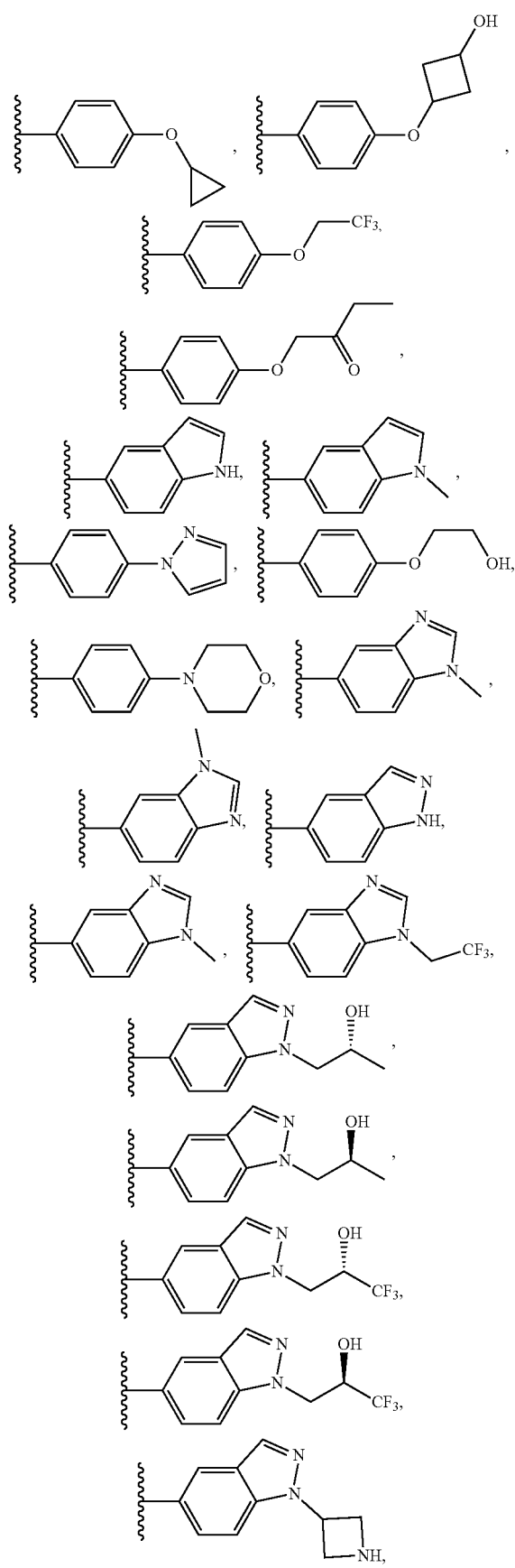
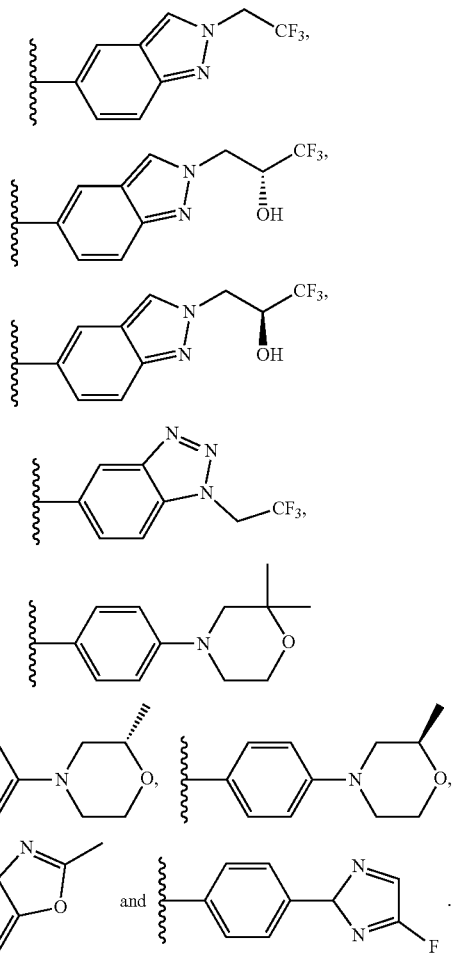
8. The compound of claim 1, or a pharmaceutically acceptable salt or a stereoisomer thereof, wherein $R^3$ is selected from the group consisting of:

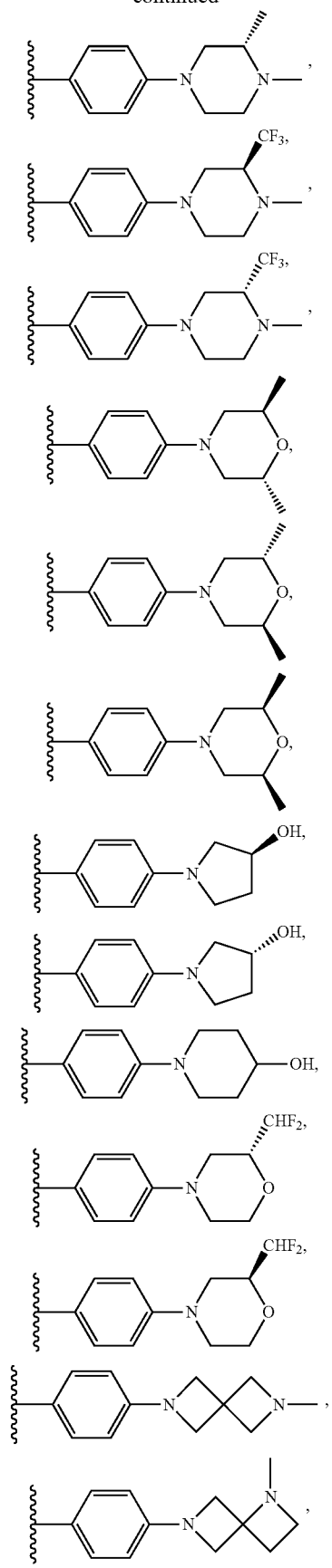
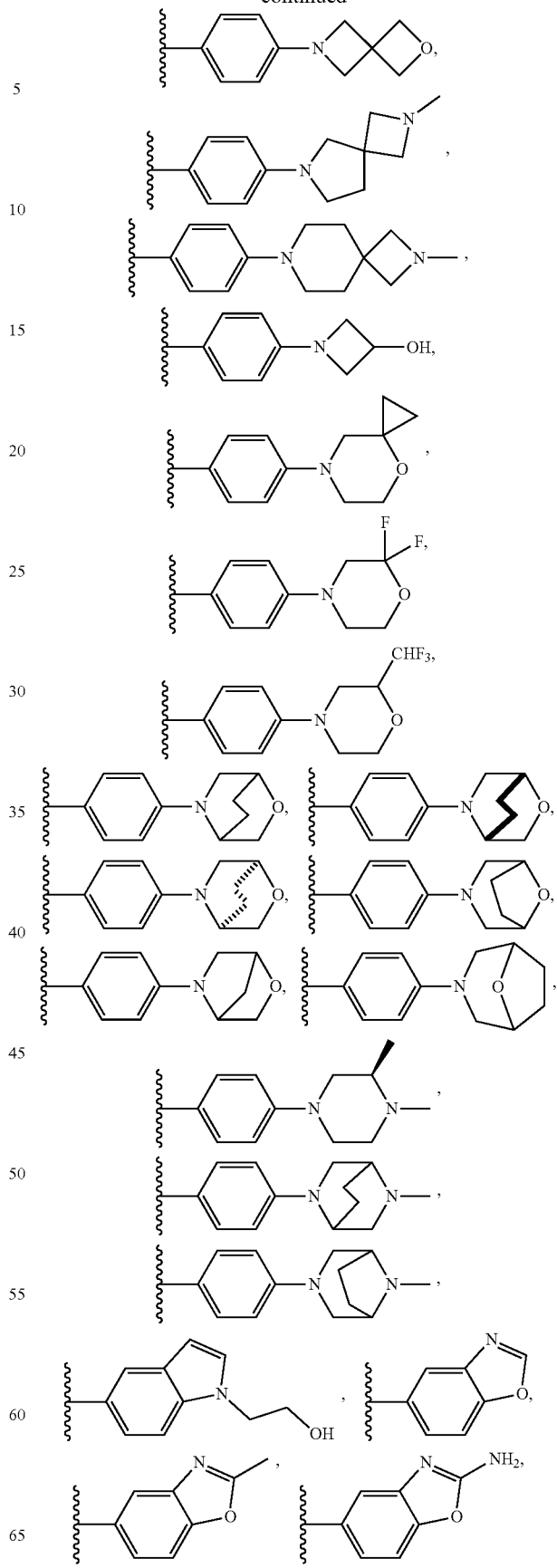

397
-continued
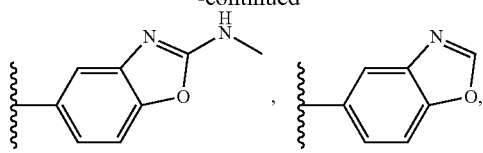
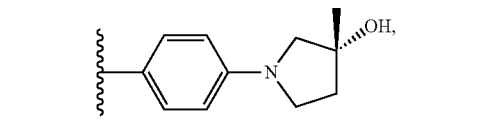
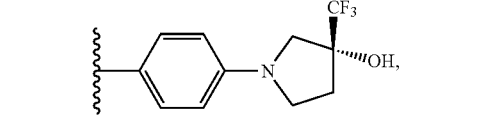
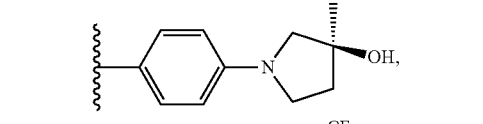
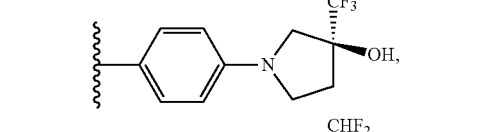
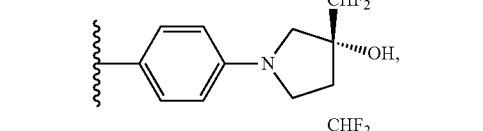
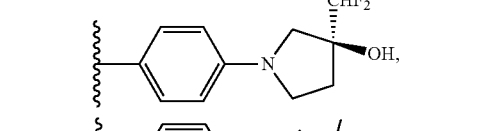
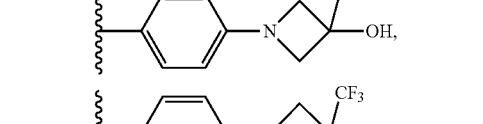
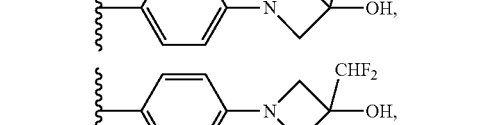
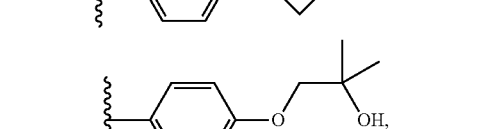
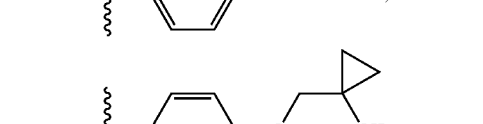
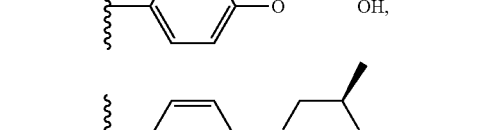
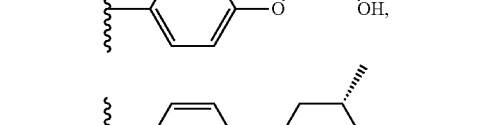
398
-continued
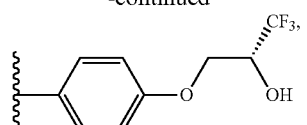
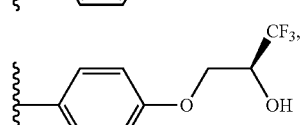
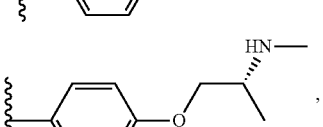
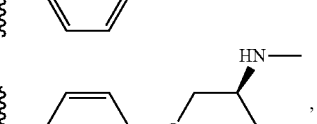
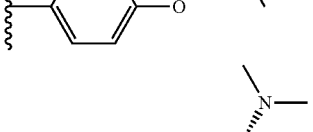
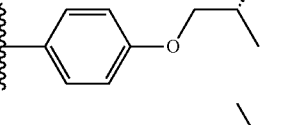
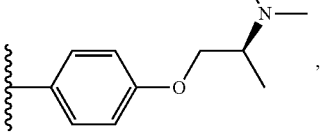
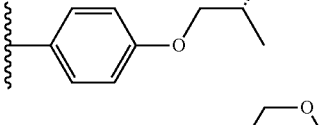
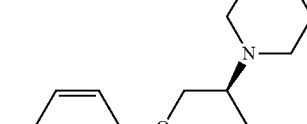
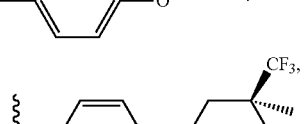
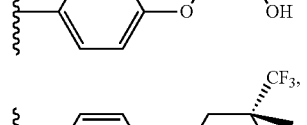
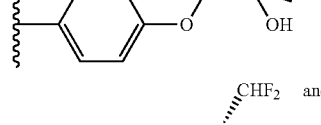
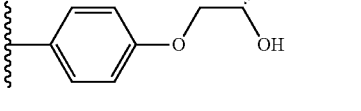

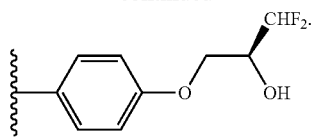

9. The compound of claim 1, or a pharmaceutically acceptable salt or a stereoisomer thereof, wherein $R^4$ is —CH$_3$.

10. The compound of claim 1, or a pharmaceutically acceptable salt or a stereoisomer thereof, wherein $R^5$ is

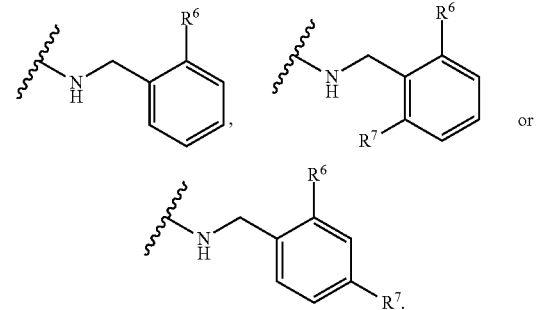

11. The compound of claim 1, or a pharmaceutically acceptable salt or a stereoisomer thereof, wherein $R^5$ is

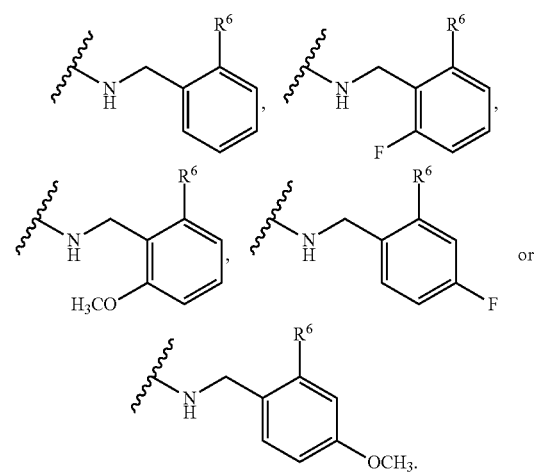

12. The compound of claim 1, or a pharmaceutically acceptable salt or a stereoisomer thereof, wherein $R^5$ is selected from the group consisting of:

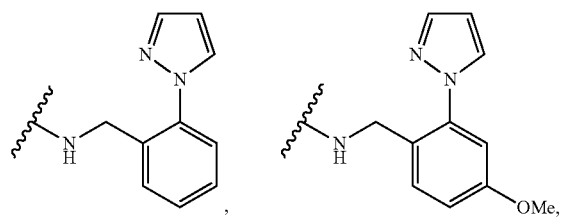
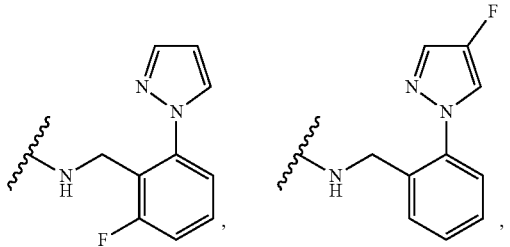
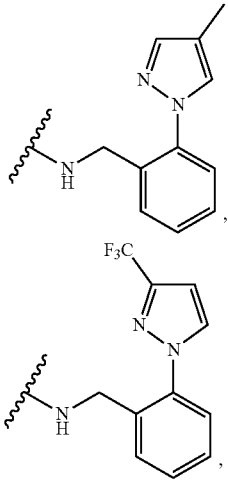
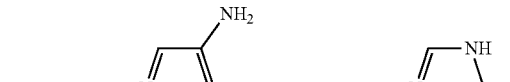
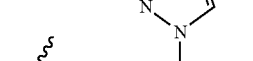
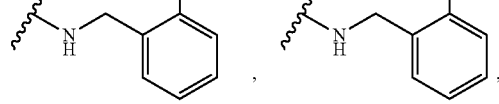
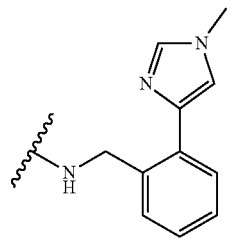
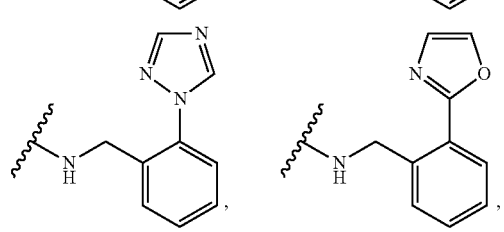
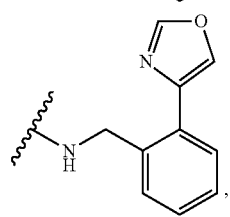

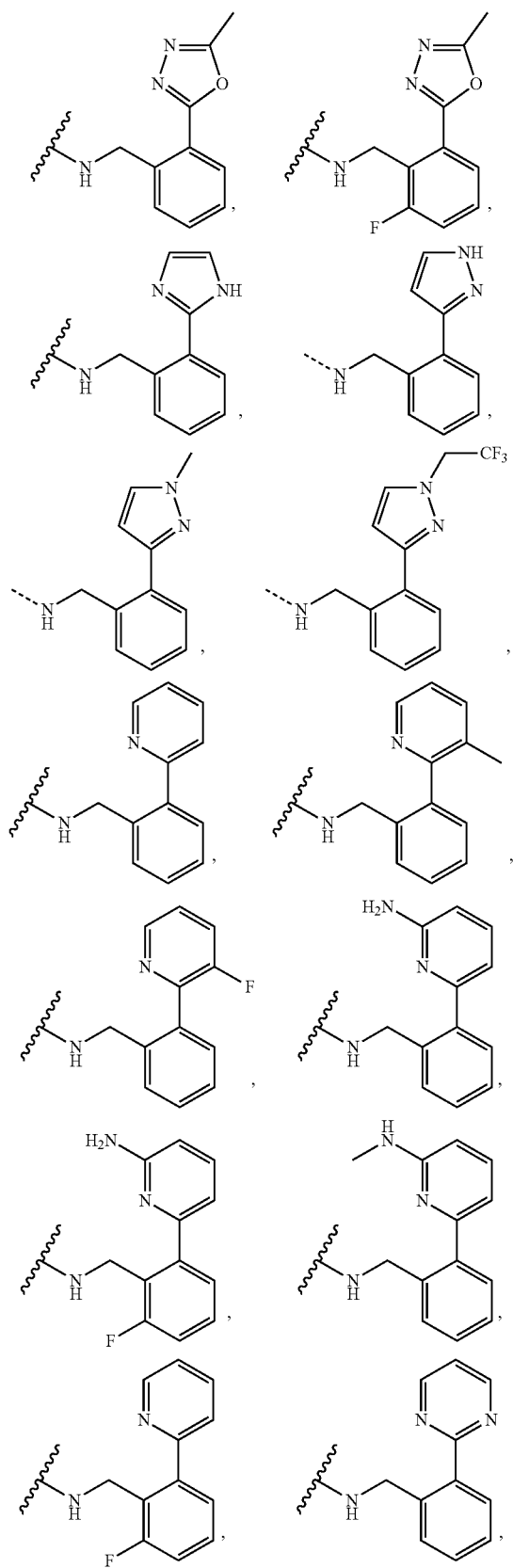
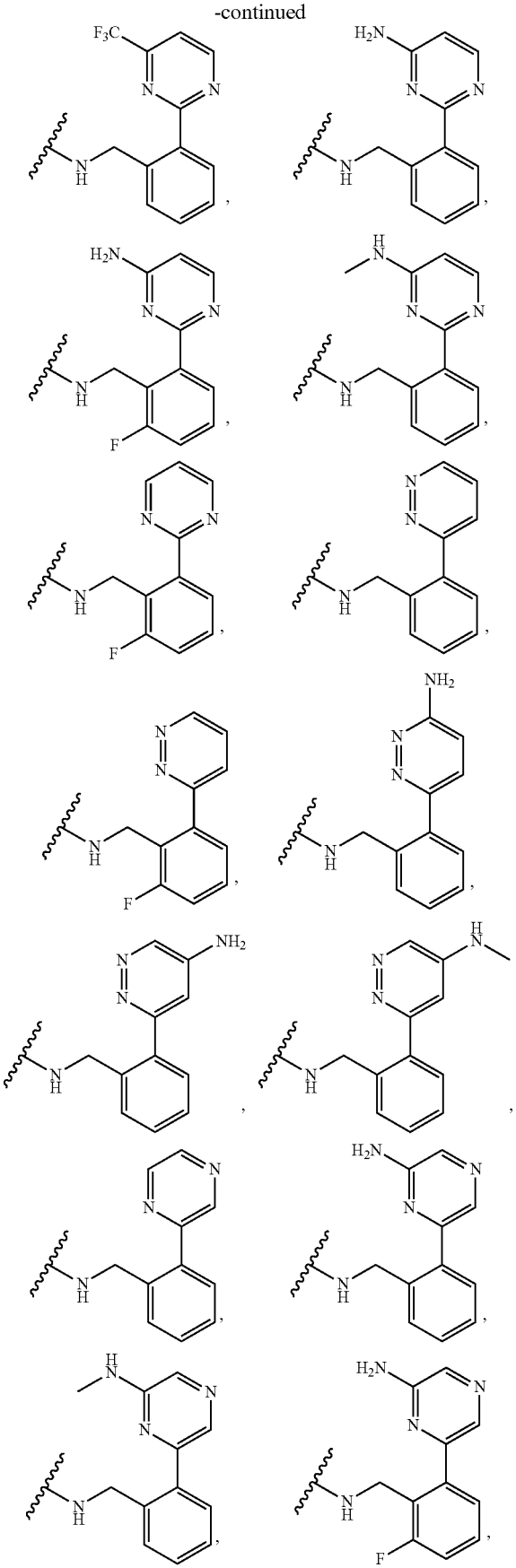

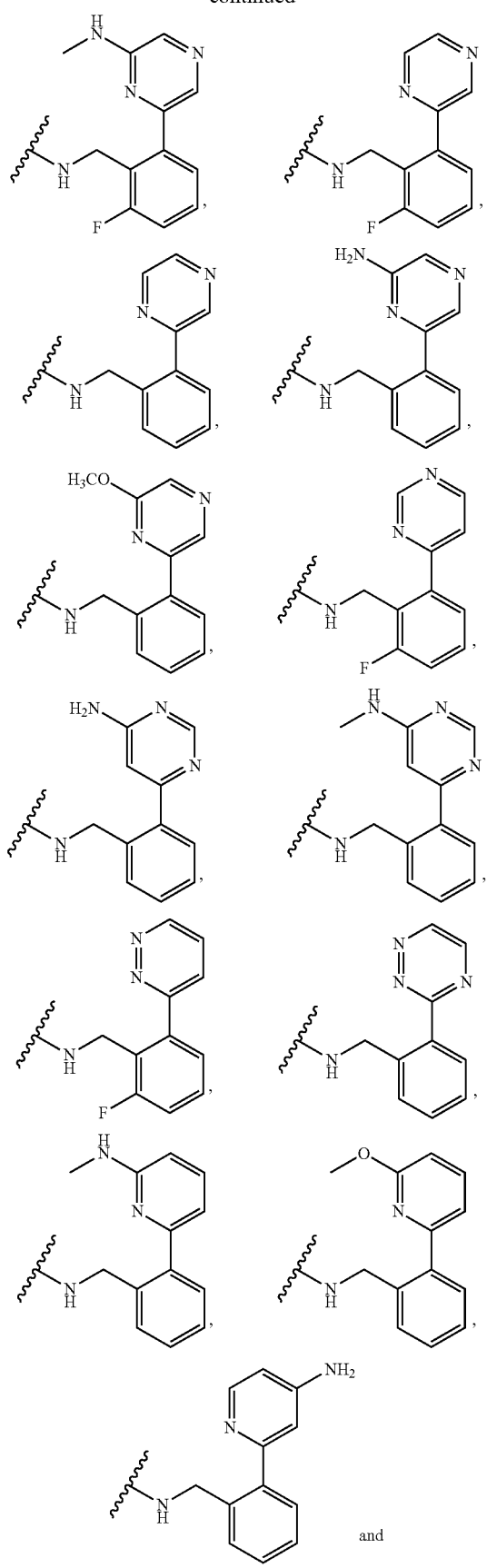

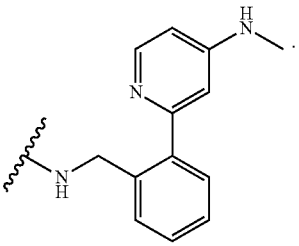

13. The compound of claim 1, or a pharmaceutically acceptable salt or a stereoisomer thereof, wherein $R^6$ is selected from the group consisting of an unsubstituted or a substituted pyrazolyl, an unsubstituted or a substituted imidazolyl, an unsubstituted or a substituted oxazolyl, an unsubstituted or a substituted 1,3,4-oxadiazolyl, an unsubstituted or a substituted pyridinyl, an unsubstituted or a substituted pyrimidinyl, an unsubstituted or a substituted pyrazinyl, an unsubstituted or a substituted pyridazinyl and an unsubstituted or a substituted 1,2,4-triazinyl, wherein is the substituted pyrazolyl, the substituted imidazolyl, the substituted oxazolyl, the substituted 1,3,4-oxadiazolyl, the substituted pyridinyl, the substituted pyrimidinyl, the substituted pyrazinyl, the substituted pyridazinyl and the substituted 1,2,4-triazinyl are independently substituted with one or more substituents selected from the group consisting of halogen, an unsubstituted $C_{1-4}$ alkyl, an unsubstituted $C_{1-4}$ haloalkyl, an unsubstituted methoxy, an unsubstituted ethoxy, an unsubstituted n-propoxy, an unsubstituted isopropoxy, an unsubstituted n-butoxy, an unsubstituted isobutoxy, an unsubstituted sec-butoxy, an unsubstituted tert-butoxy, —$NH_2$ and —NH (an unsubstituted $C_{1-6}$ alkyl).

14. The compound of claim 1, or a pharmaceutically acceptable salt or a stereoisomer thereof, wherein $R^6$ is halogen; $R^7$ is halogen; and n is 1.

15. A pharmaceutical composition comprising a pharmaceutically acceptable excipient and an effective amount of a compound of claim 1, or a pharmaceutically acceptable salt or a stereoisomer thereof.

16. A method for treating hepatitis B in a subject, wherein the method comprises administering to the subject suffering from hepatitis B an effective amount of a compound of claim 1, or a pharmaceutically acceptable salt or a stereoisomer thereof.

17. The method of claim 16, wherein the method further comprises administering to the subject suffering from hepatitis B an effective amount of an additional agent, wherein the additional agent is selected from the group consisting of an interferon, a nucleoside analog, a nucleotide analog, a sequence specific oligonucleotide, a nucleic acid polymer, an entry inhibitor and a small molecule immunomodulator.

18. A method for treating hepatitis D in a subject, wherein the method comprises administering to the subject suffering from hepatitis D an effective amount of a compound of claim 1, or a pharmaceutically acceptable salt or a stereoisomer thereof.

19. A selected from the group consisting of:
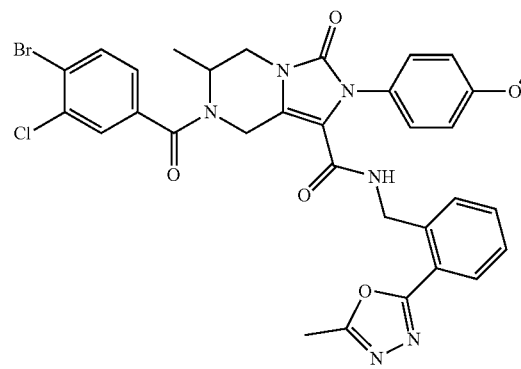
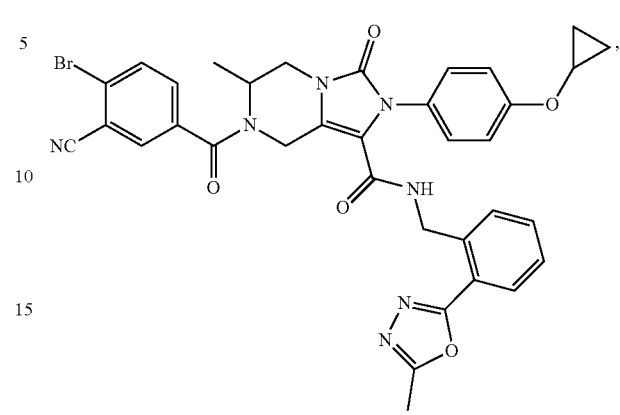
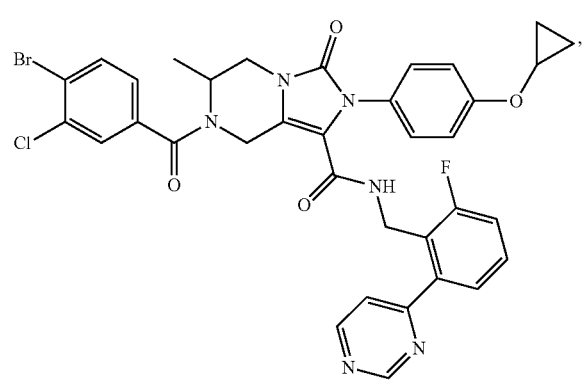
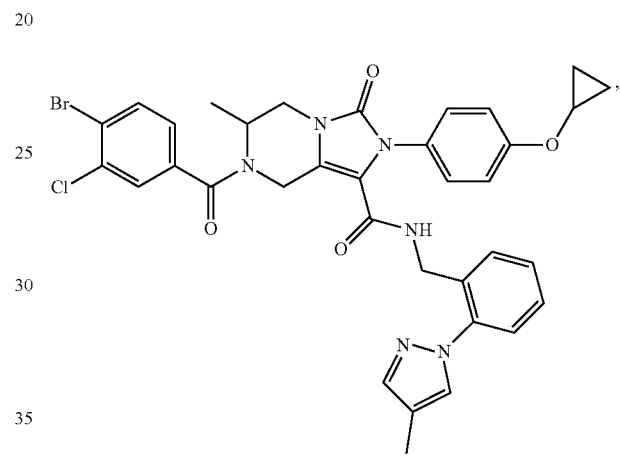
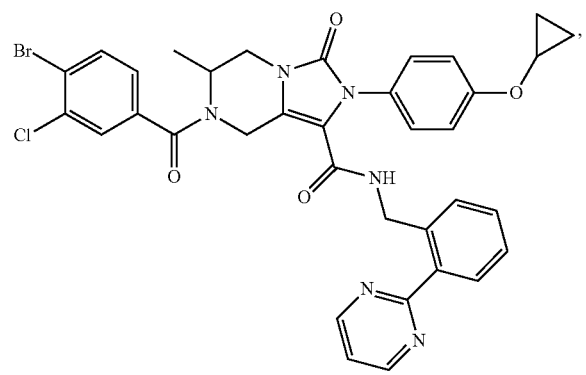
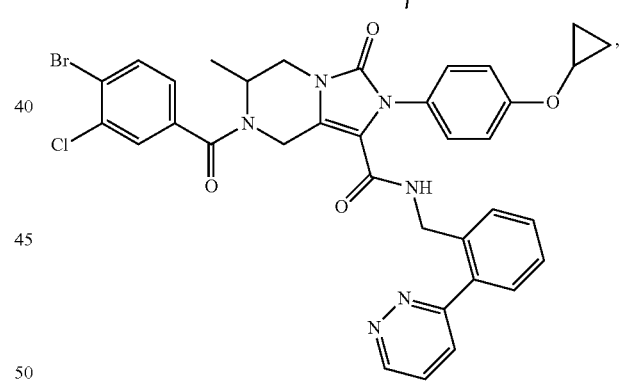
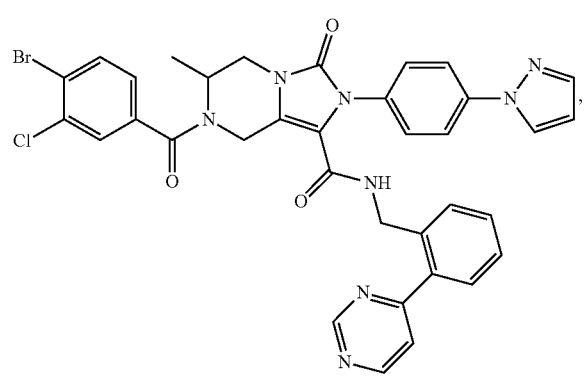
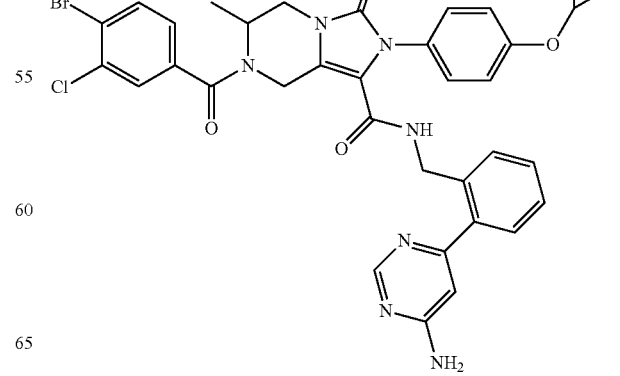

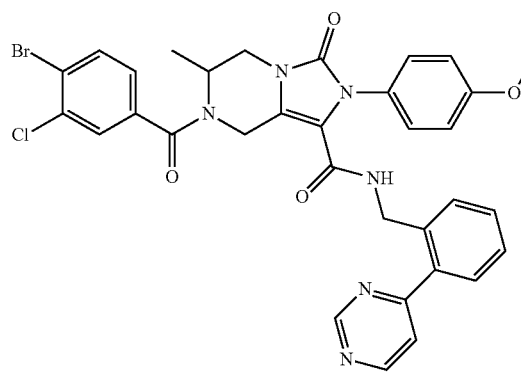
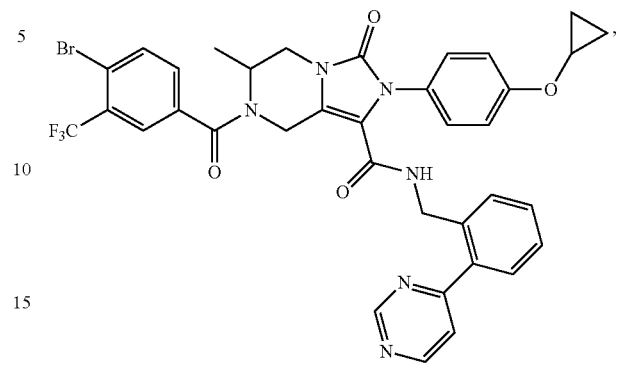
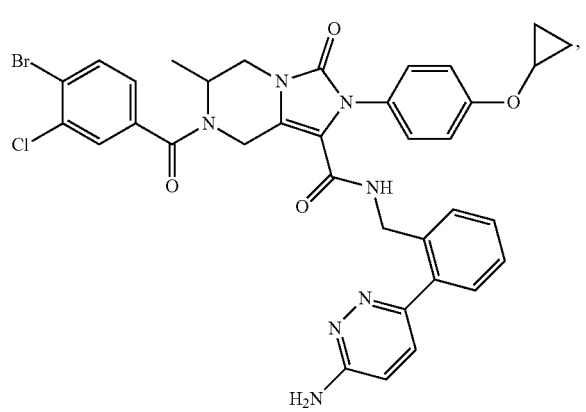
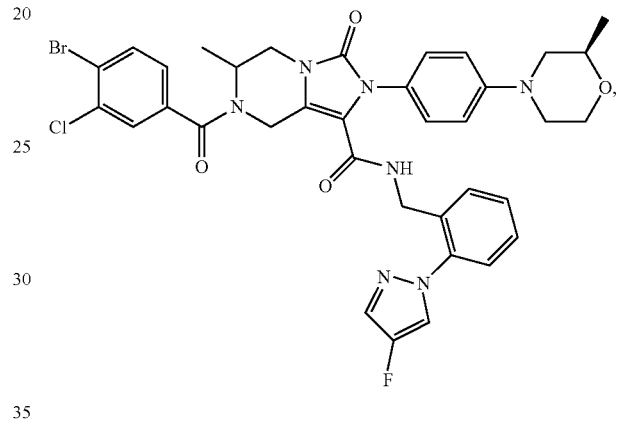
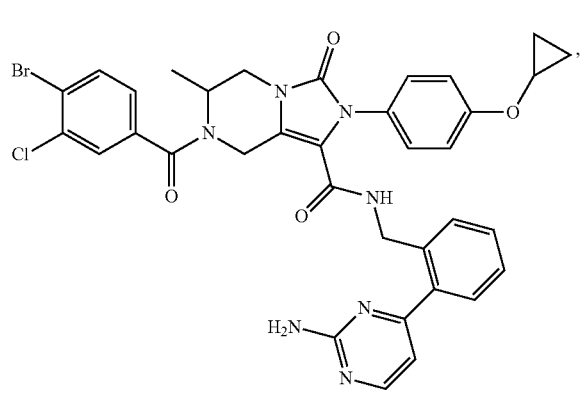
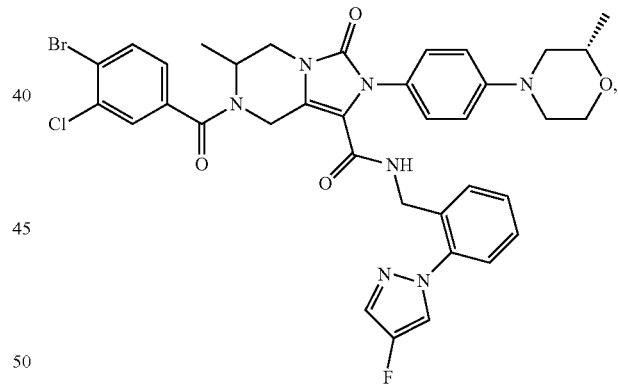
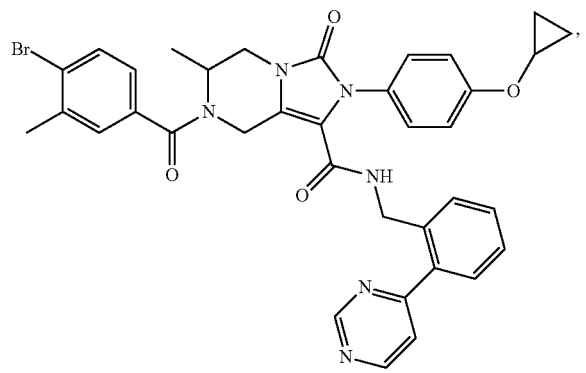
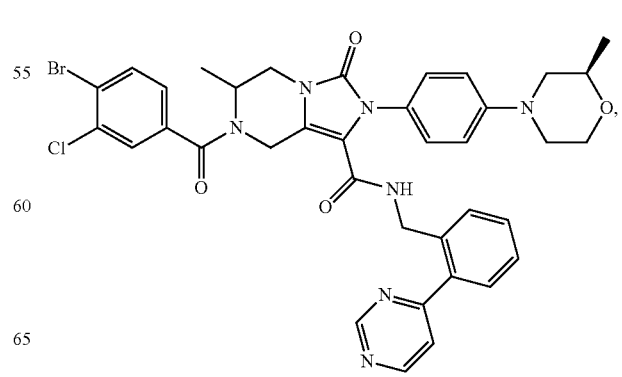

409
-continued
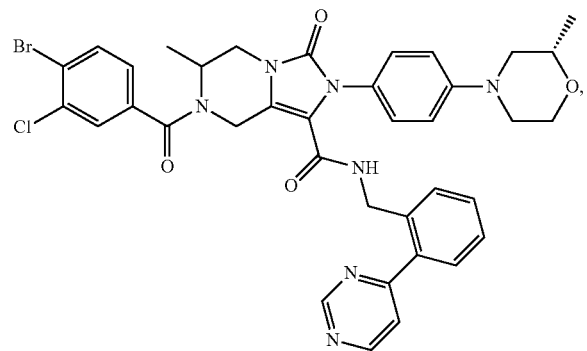
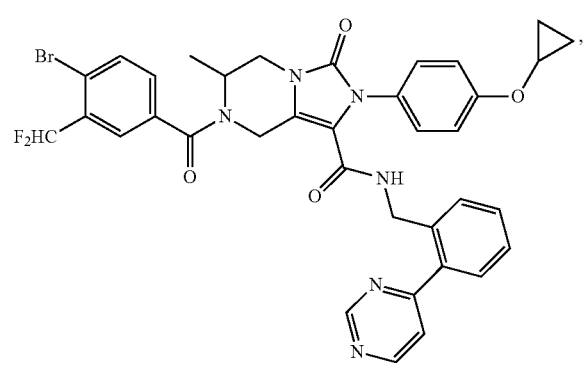
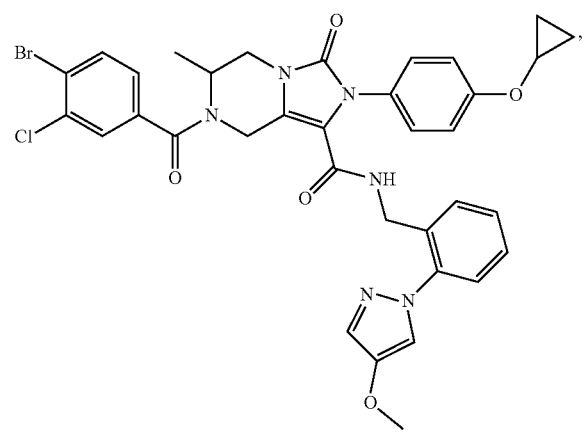
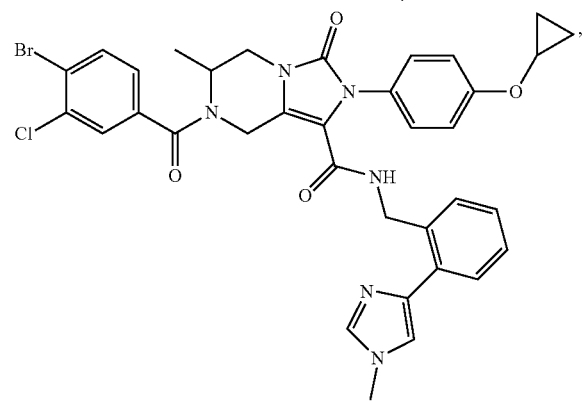
410
-continued
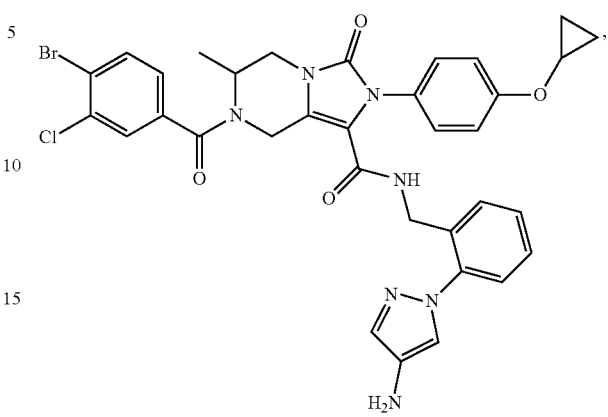
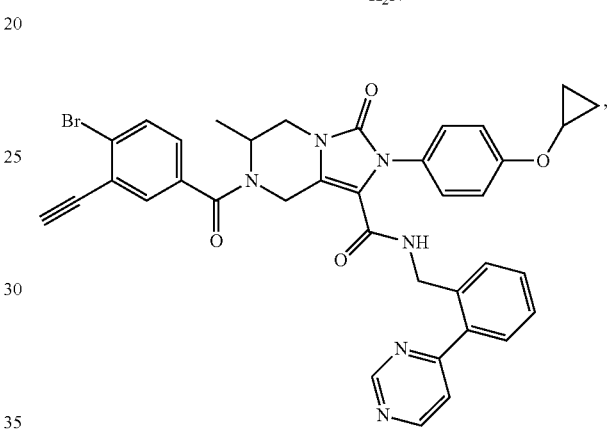
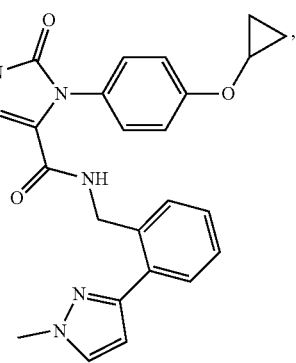

411
-continued
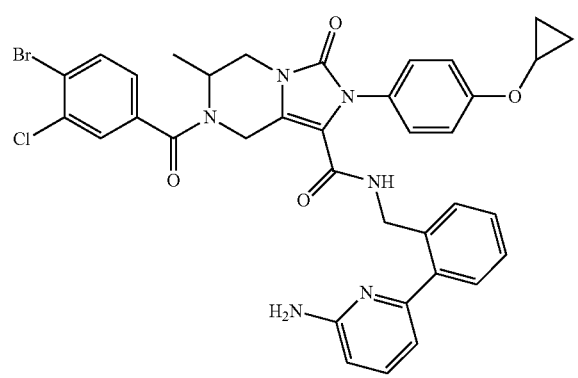
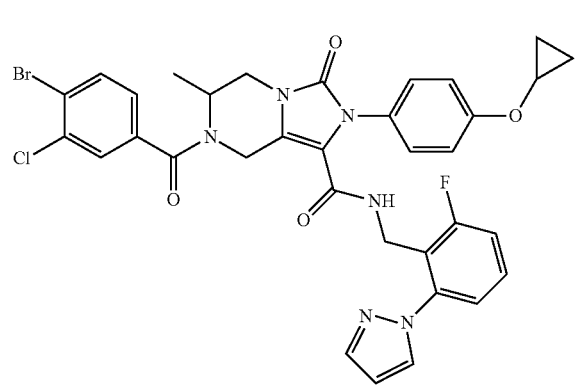
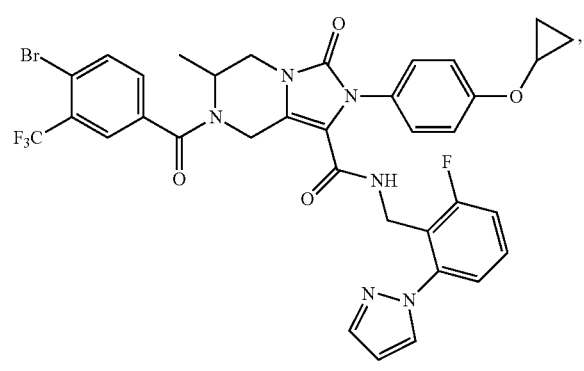
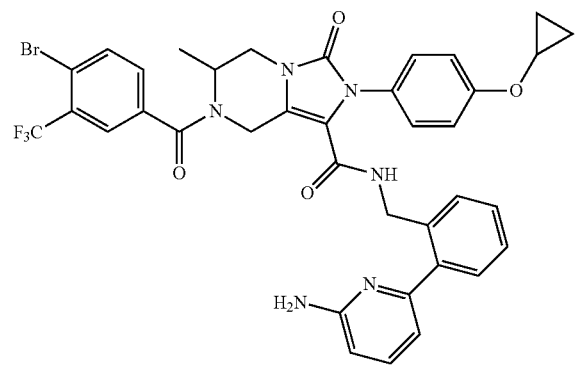
412
-continued
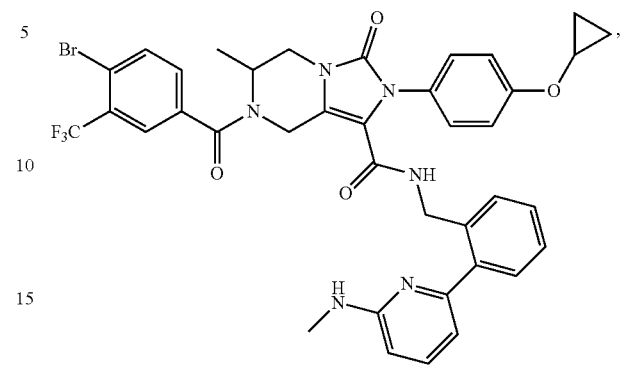
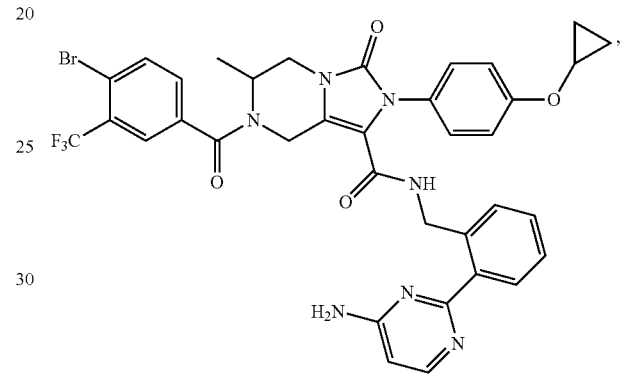
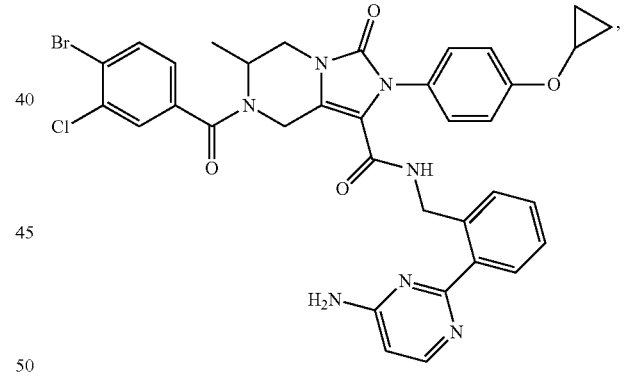
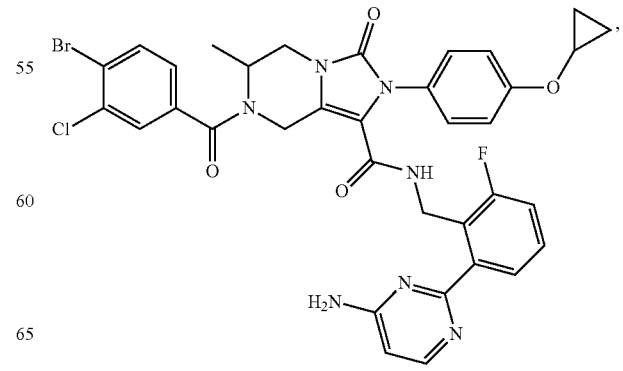

413
-continued
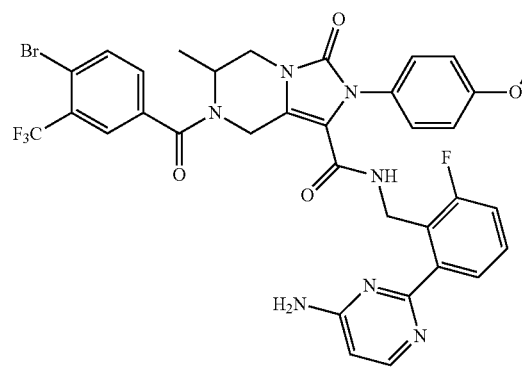
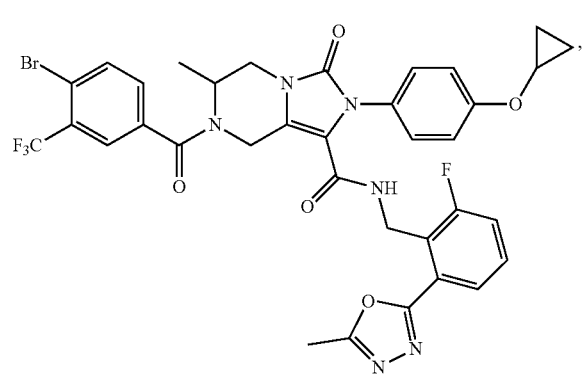
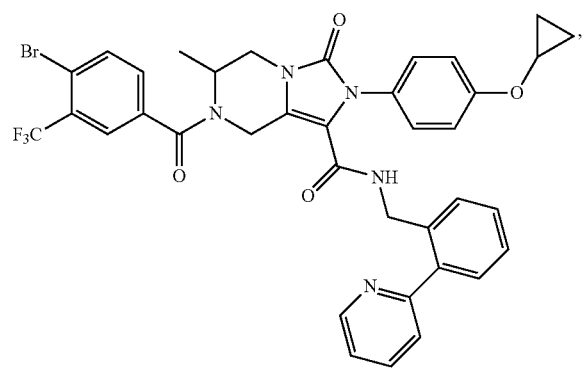
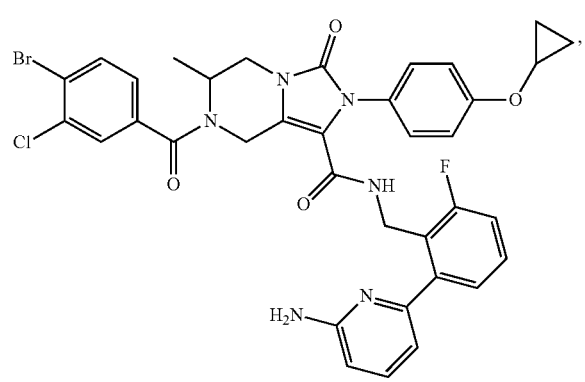
414
-continued
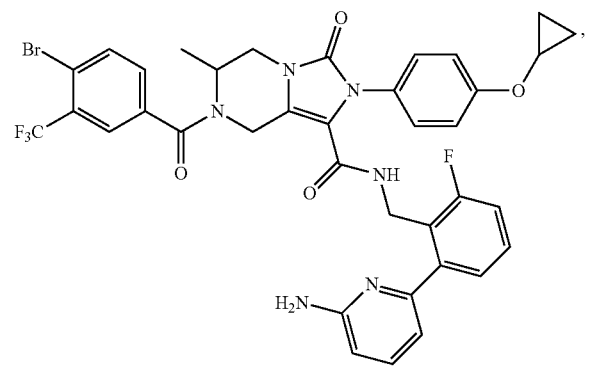
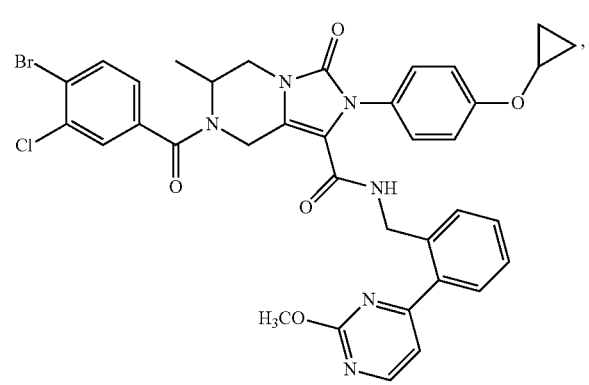
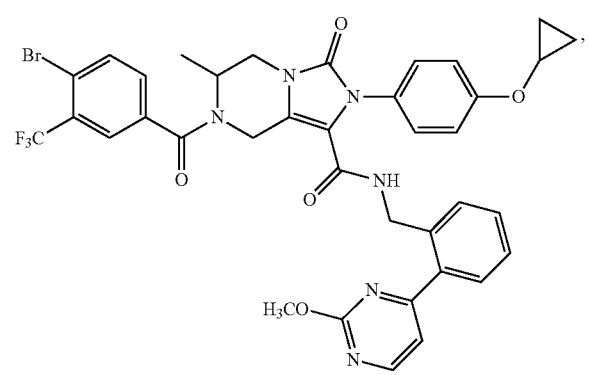
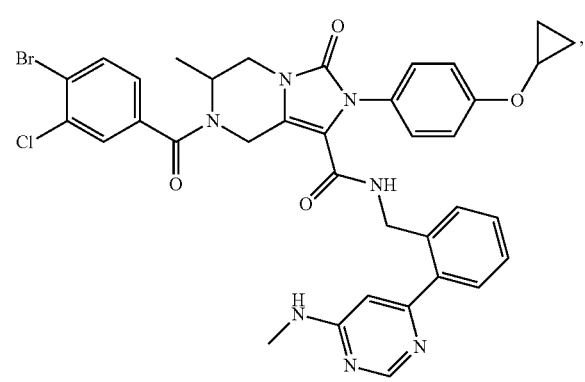

415
-continued
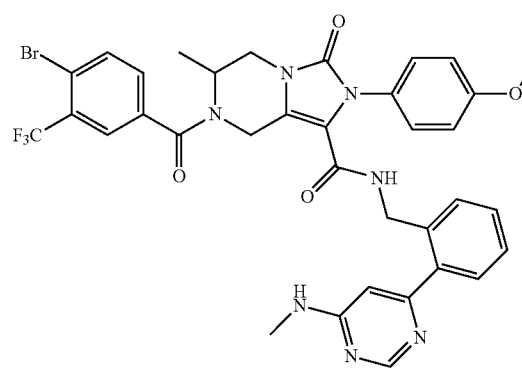
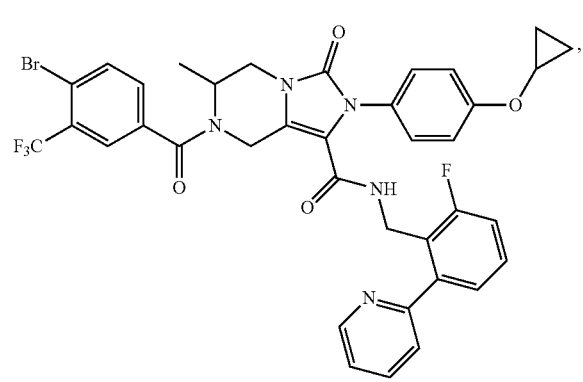
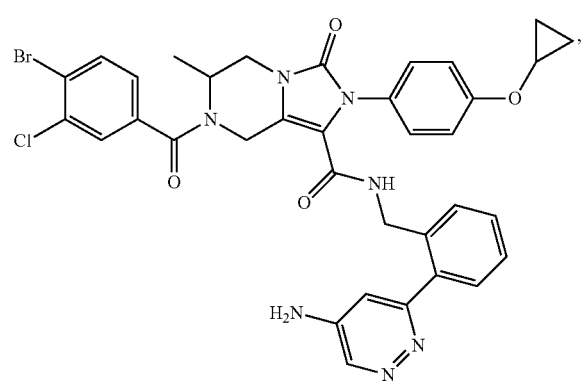
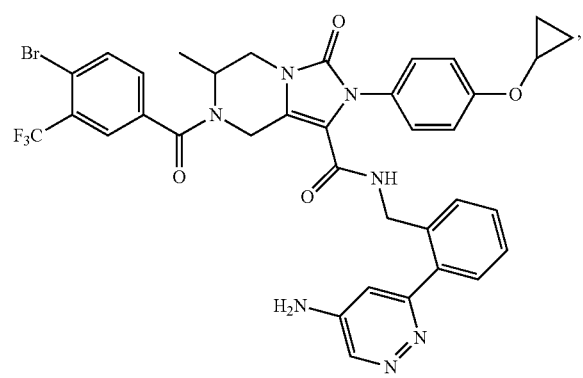
416
-continued
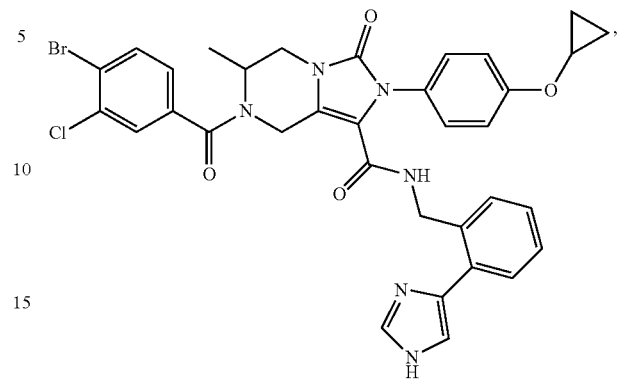
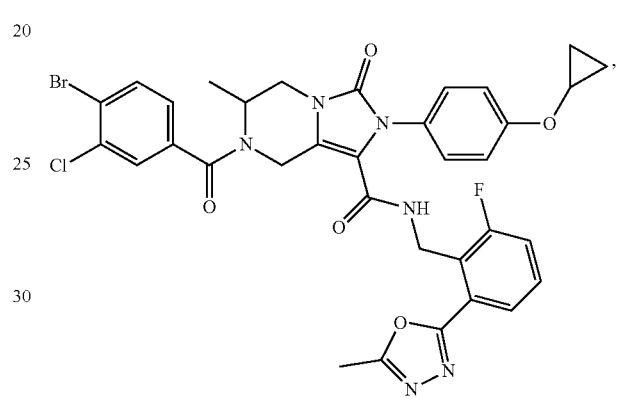
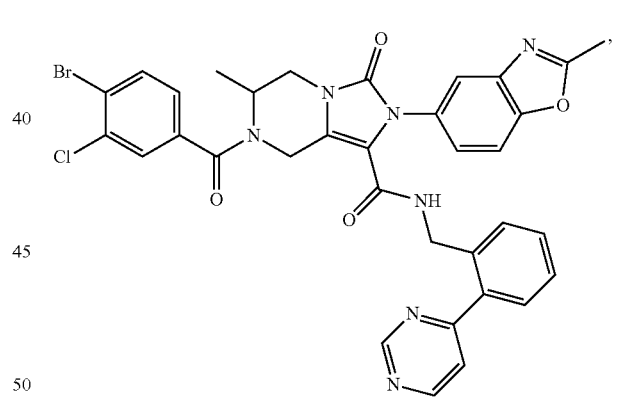
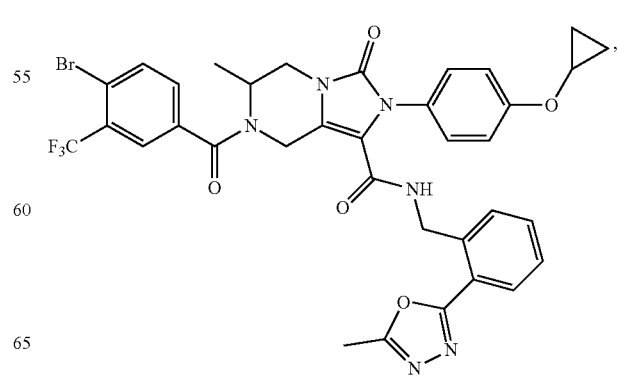

417
-continued
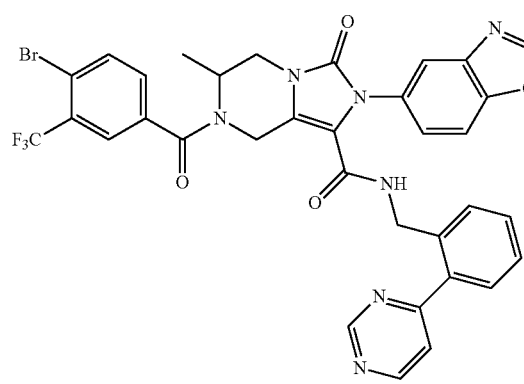
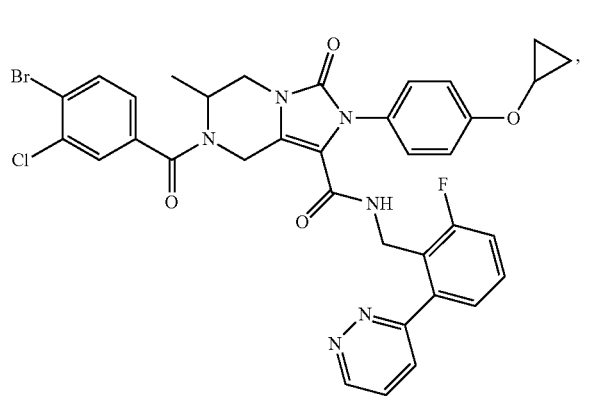
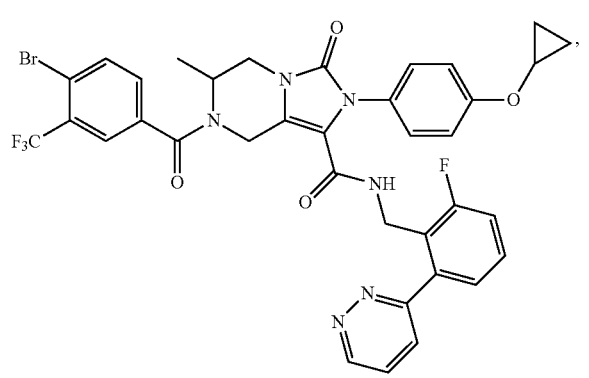
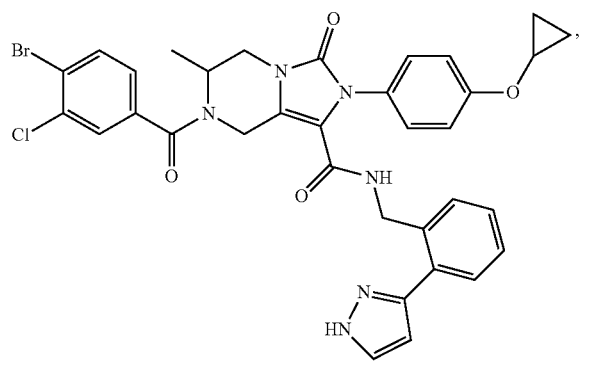
418
-continued
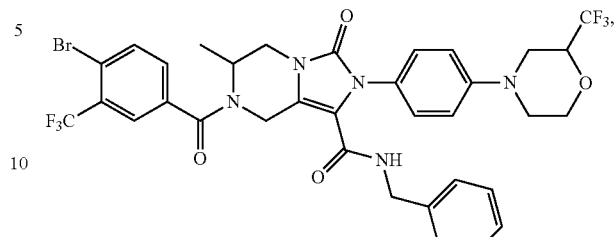
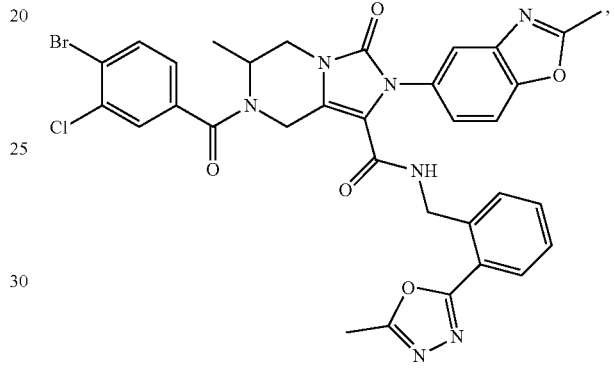
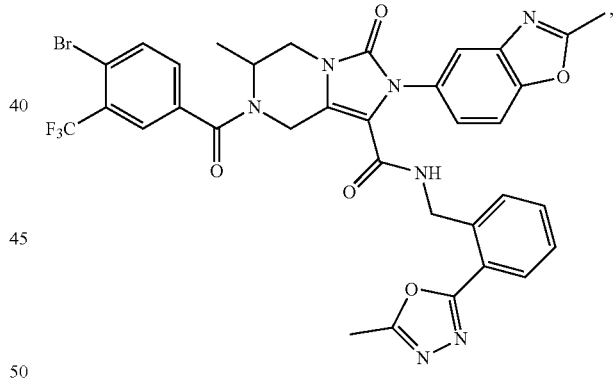
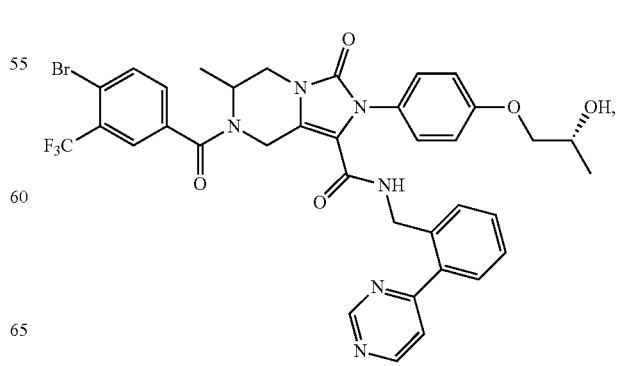

419
-continued
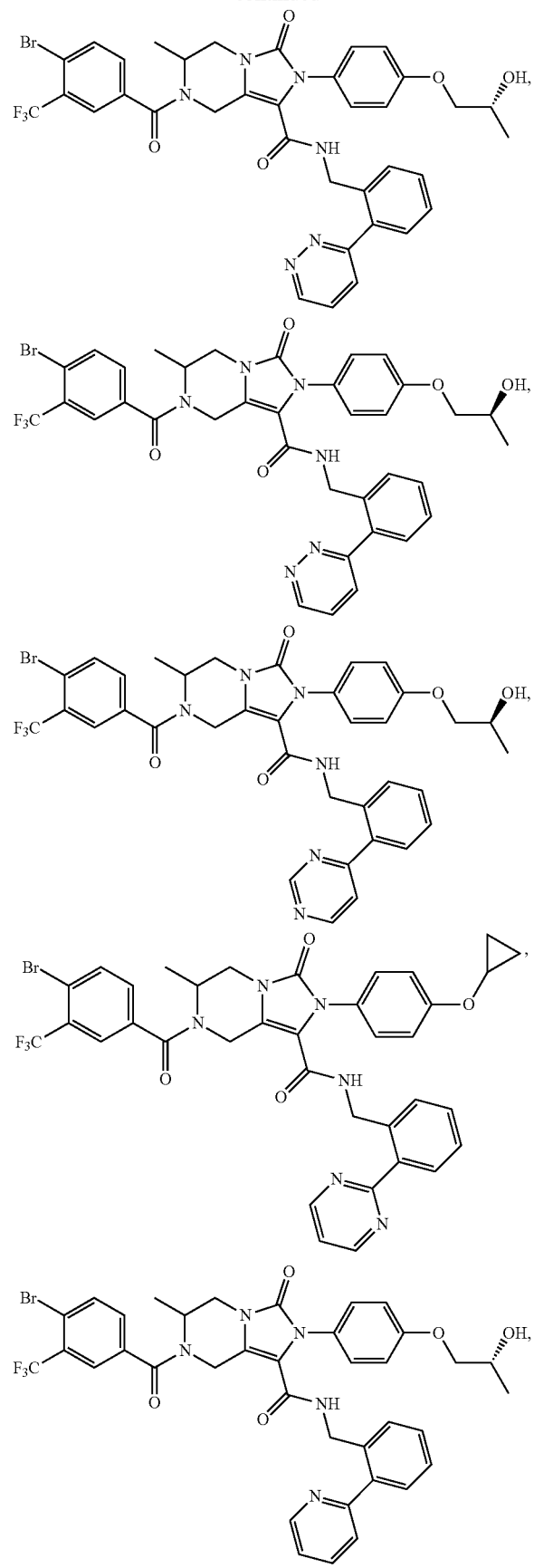
420
-continued
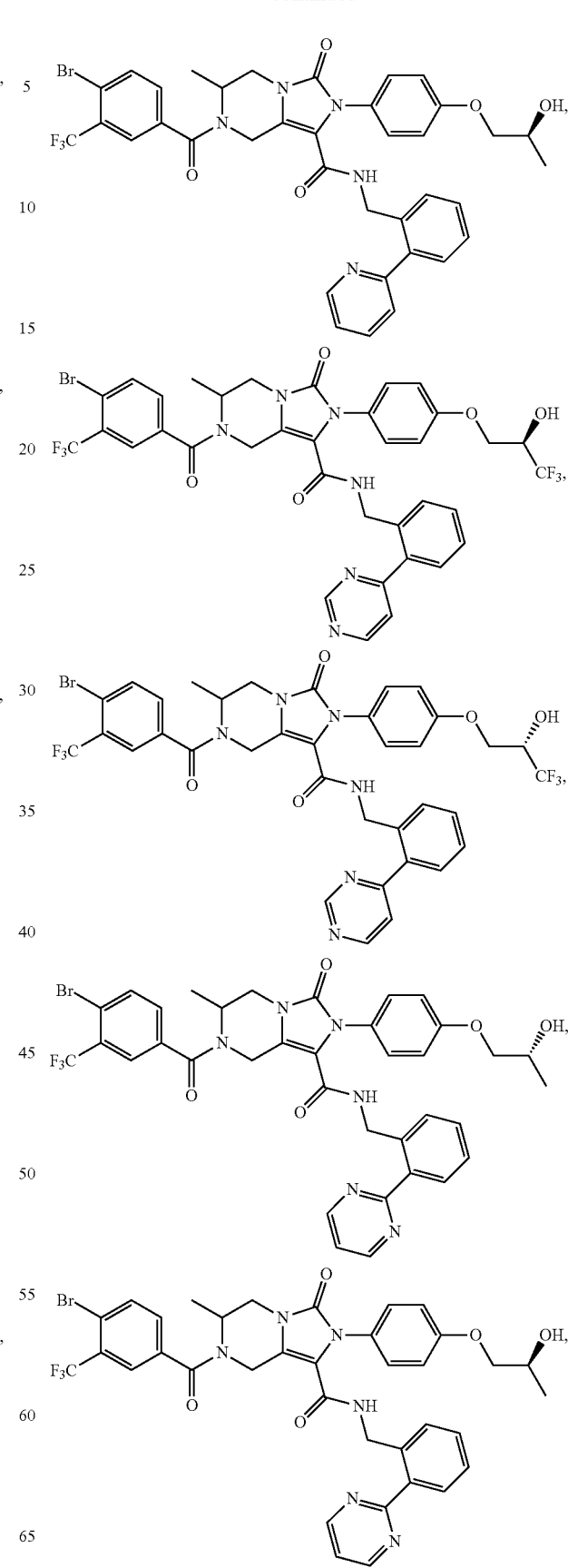

421
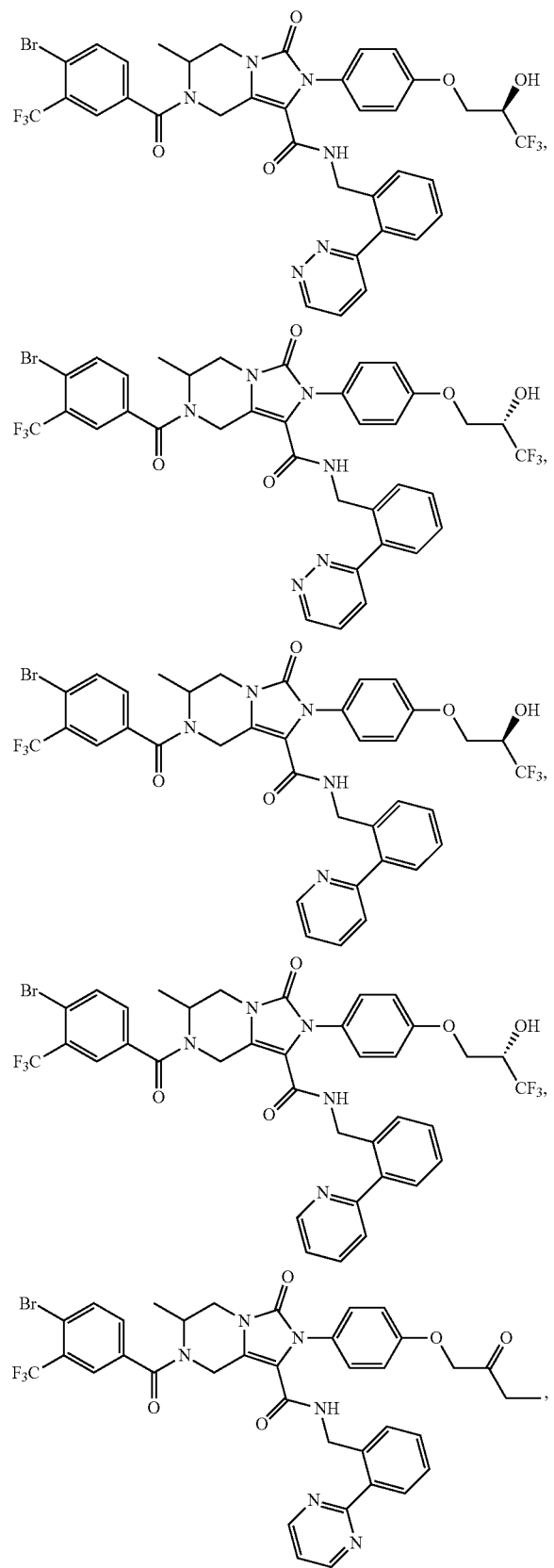
422
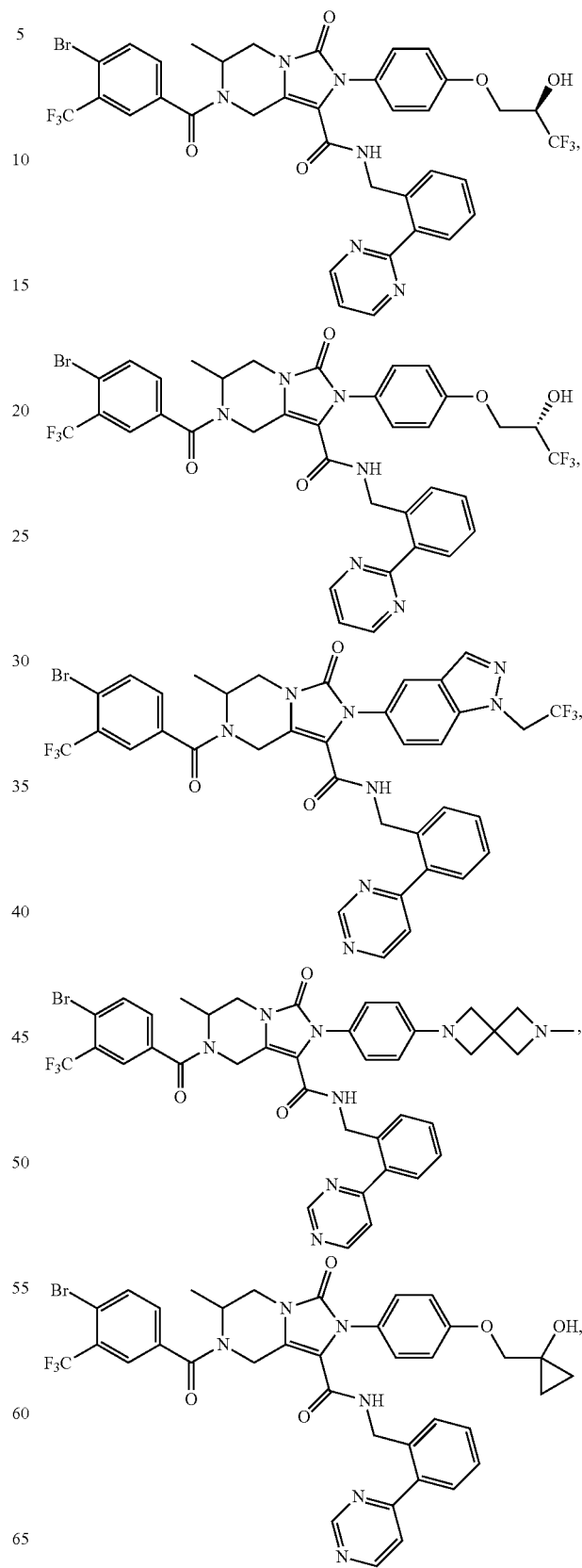

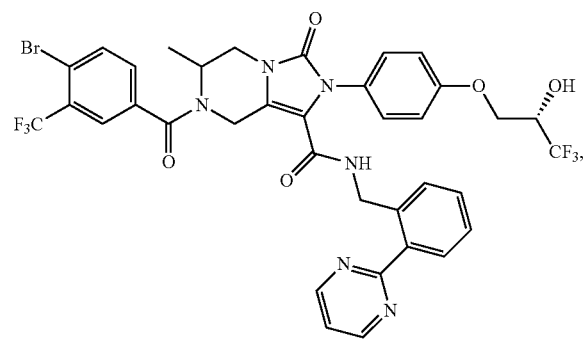
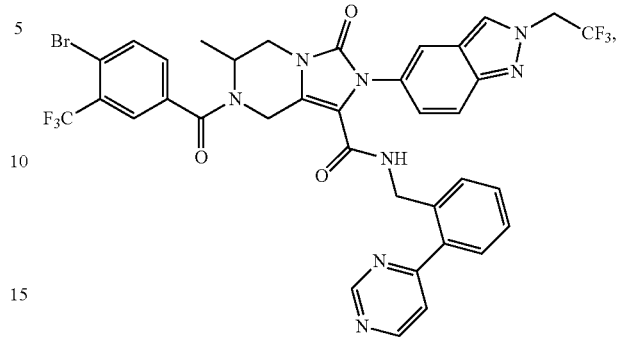
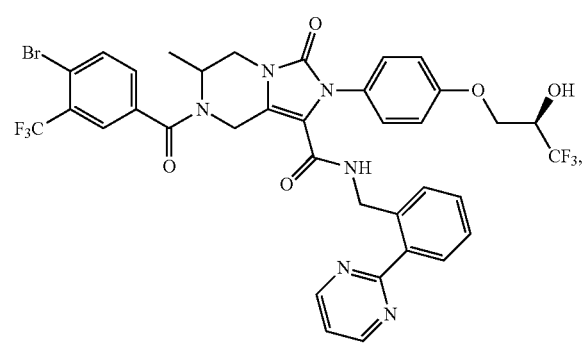
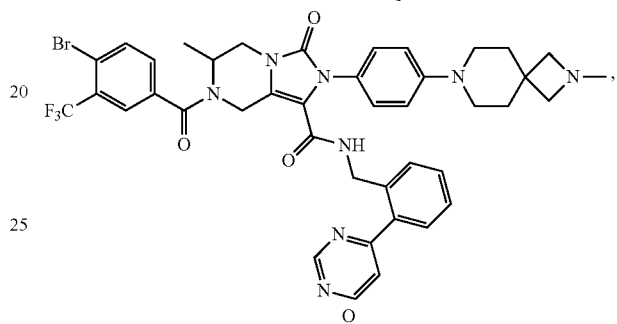
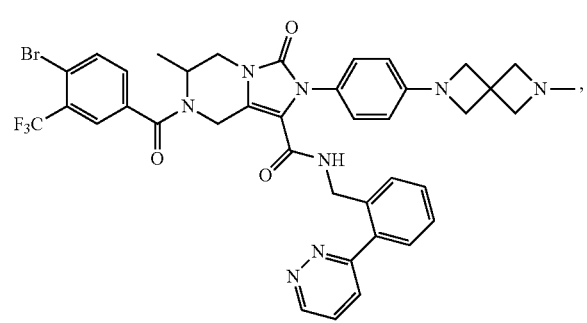
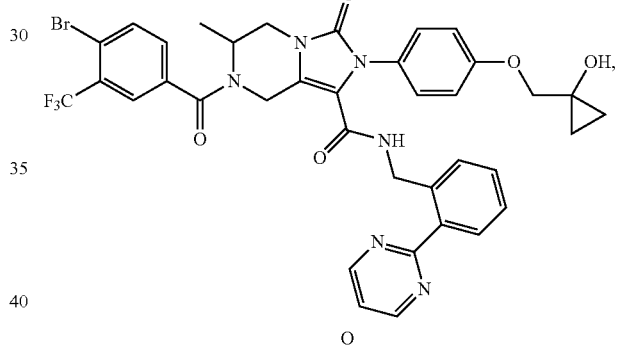
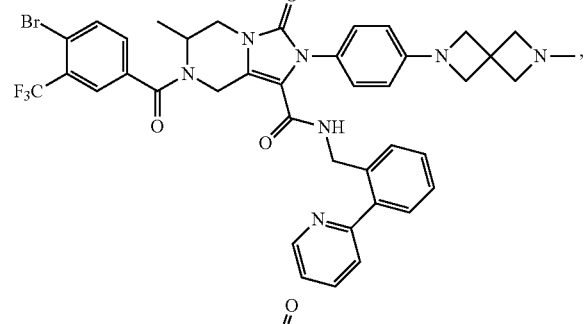
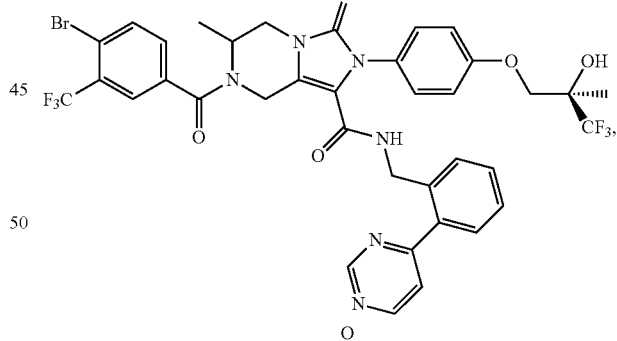
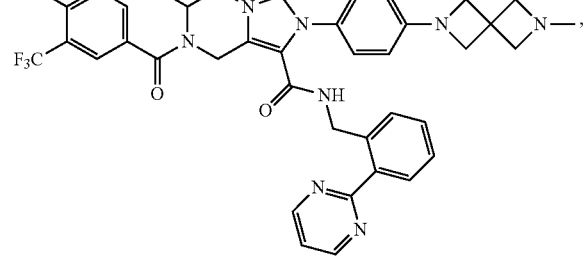
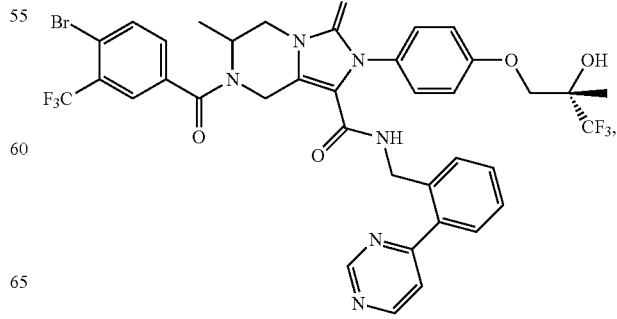

425
-continued
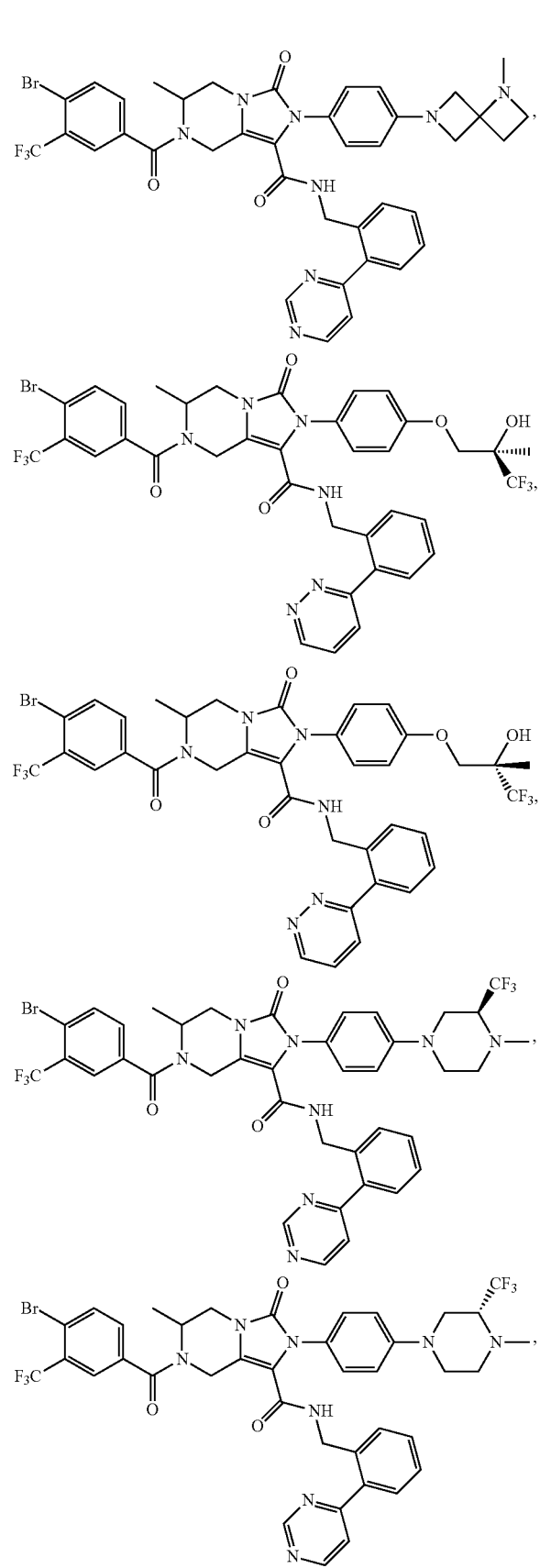
426
-continued
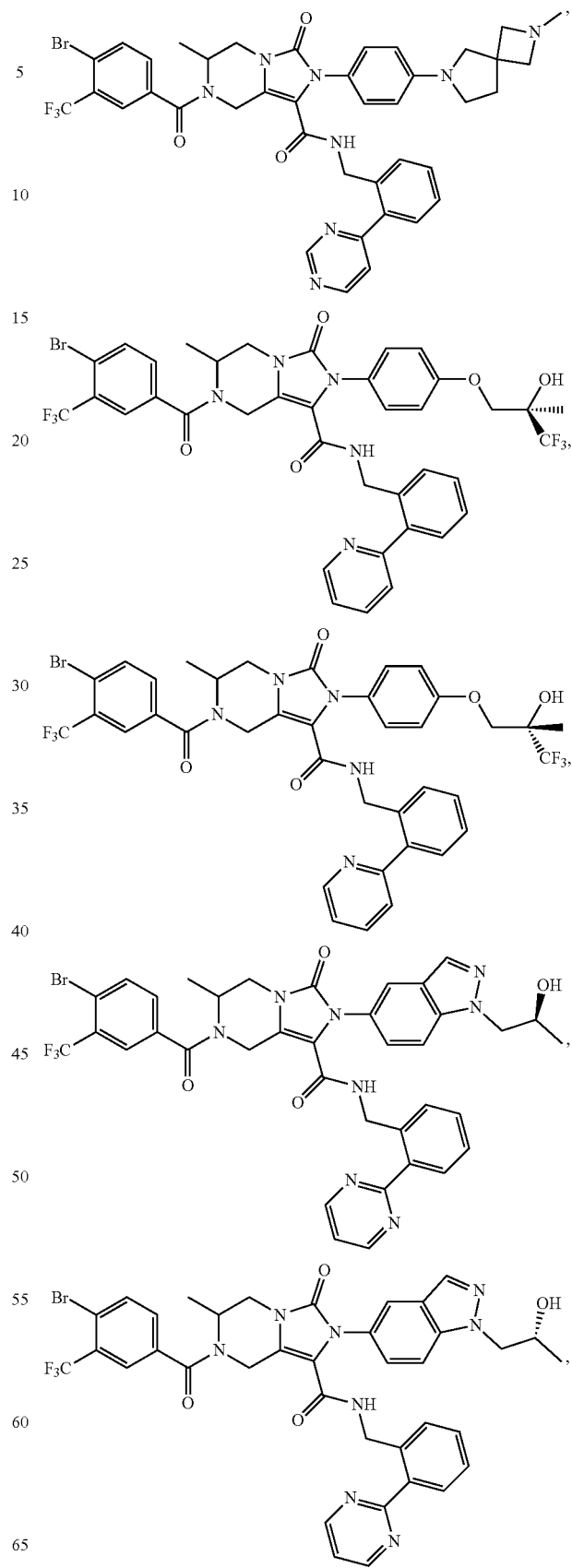

427
-continued
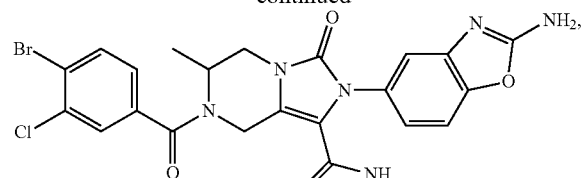
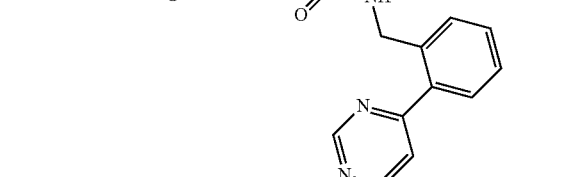
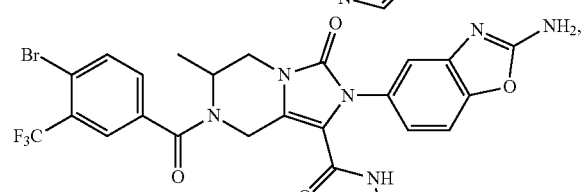
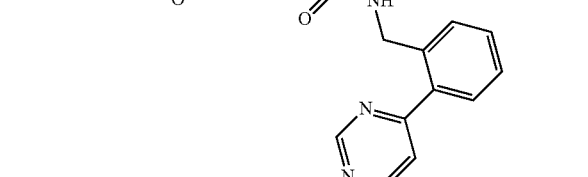
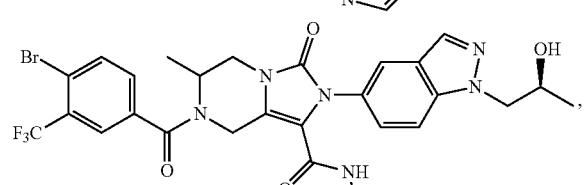
428
-continued
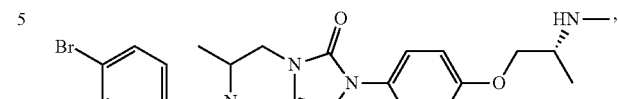
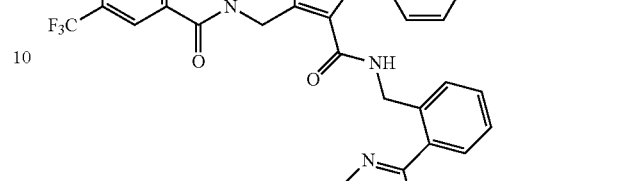
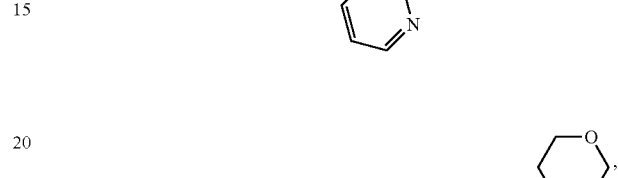
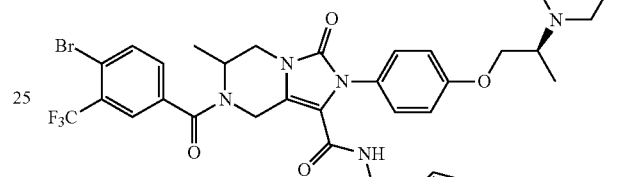
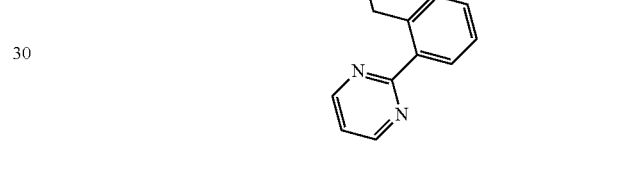

429
-continued
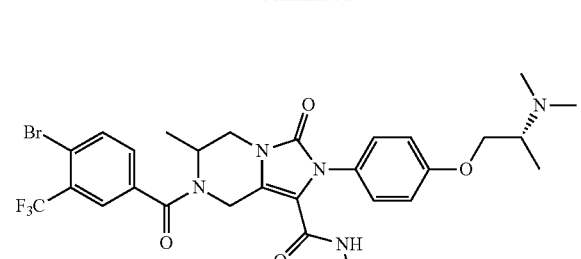
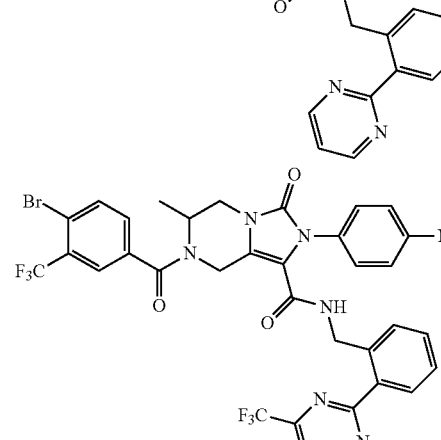
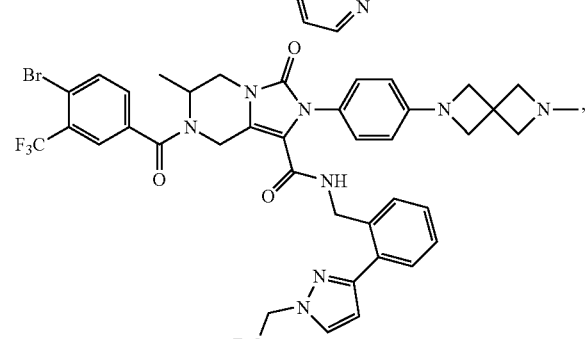
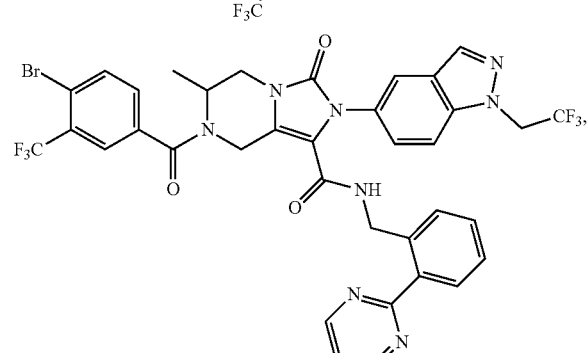
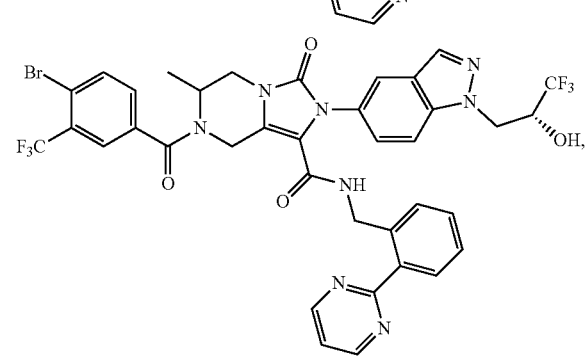
430
-continued
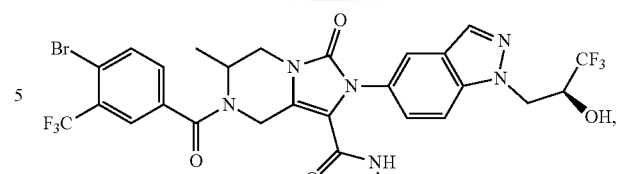
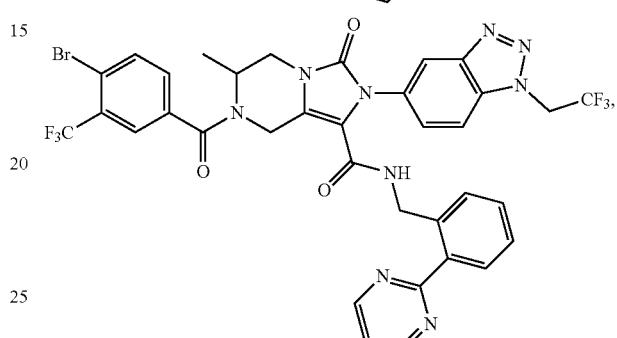
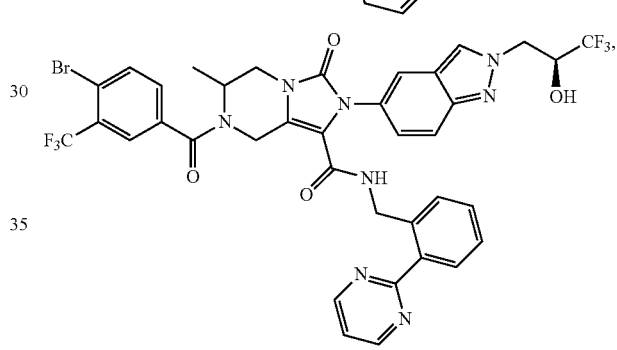
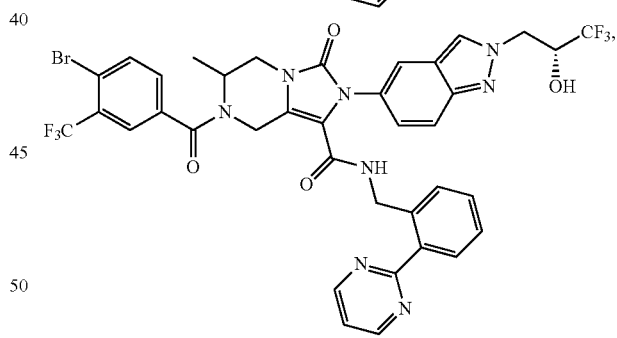
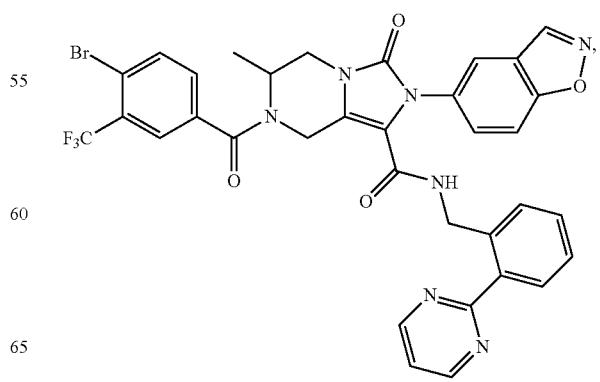

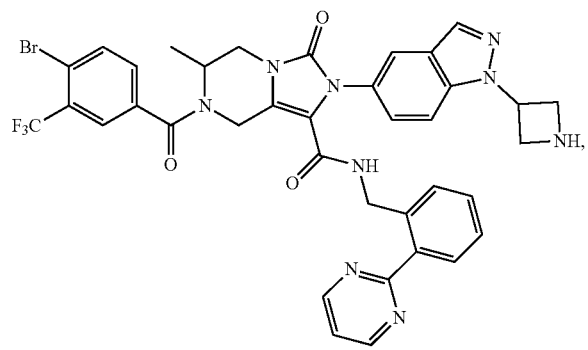
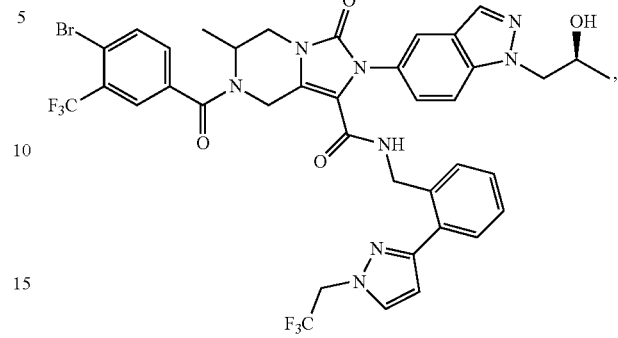
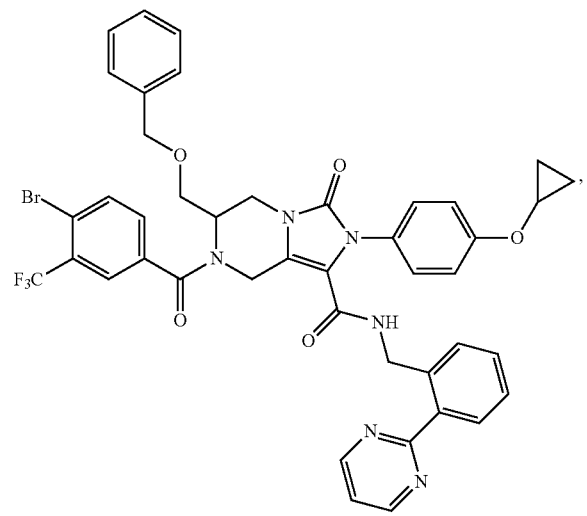
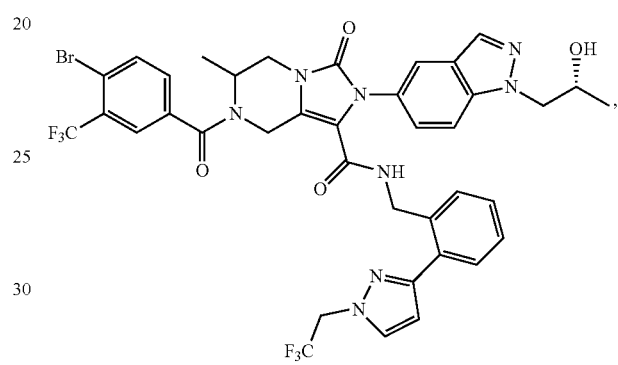
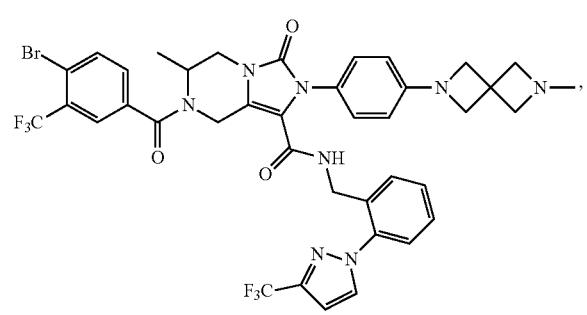
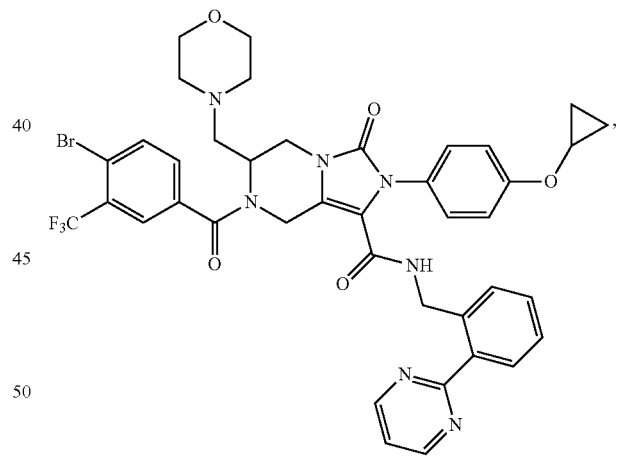
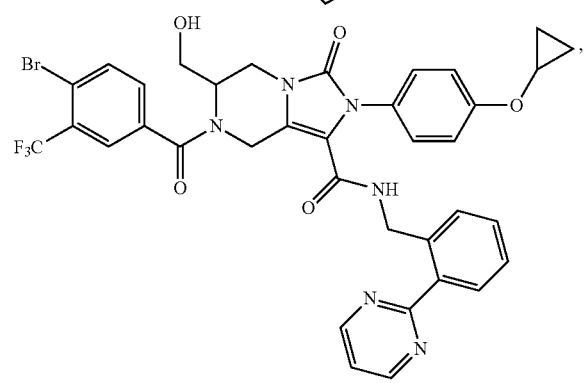

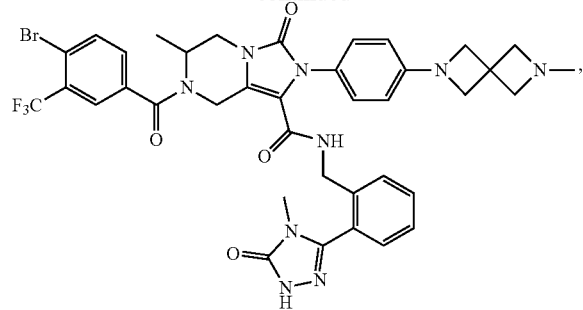
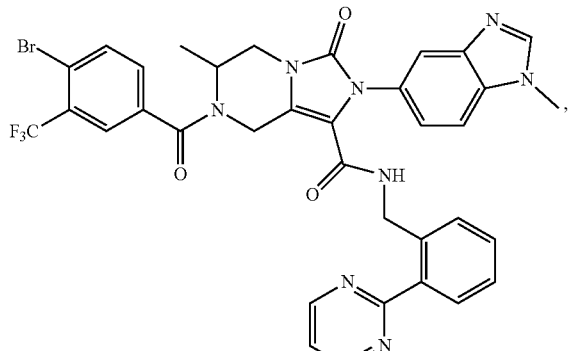
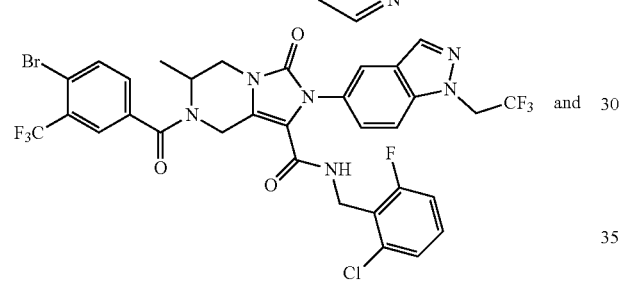
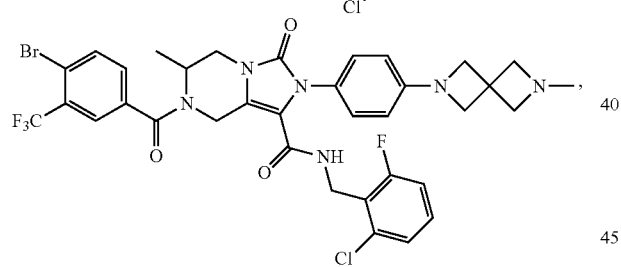
and
or a pharmaceutically acceptable salt or stereoisomer thereof.
20. A selected from the group consisting of:
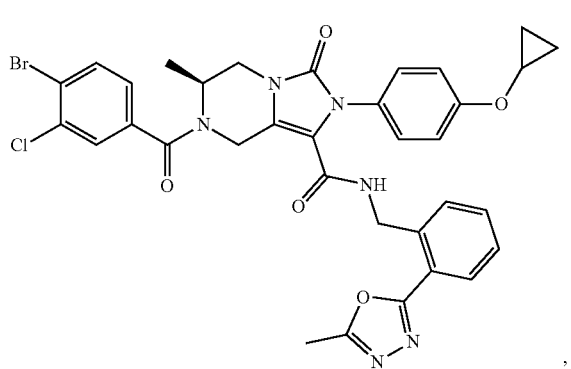
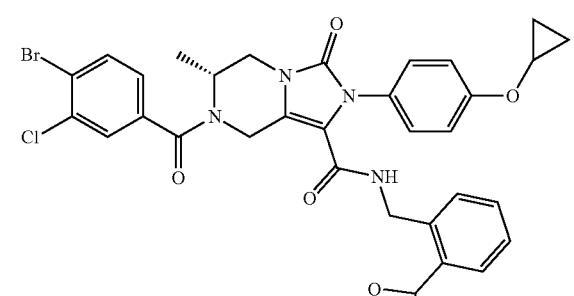
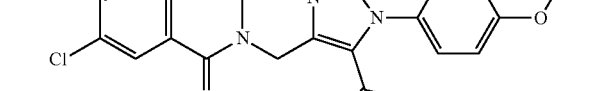

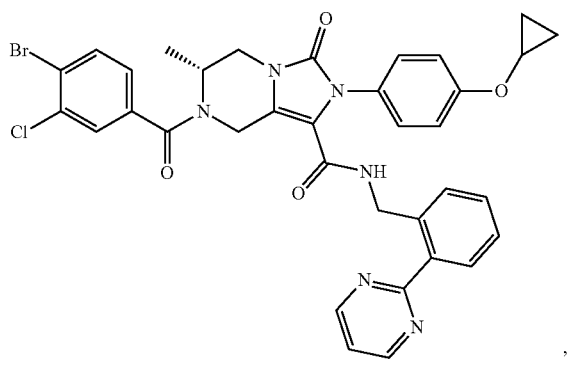
,
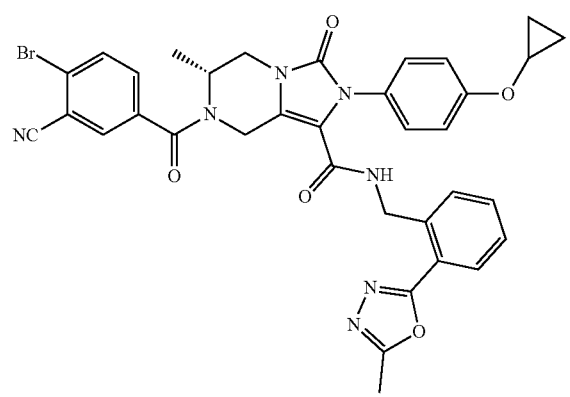
,
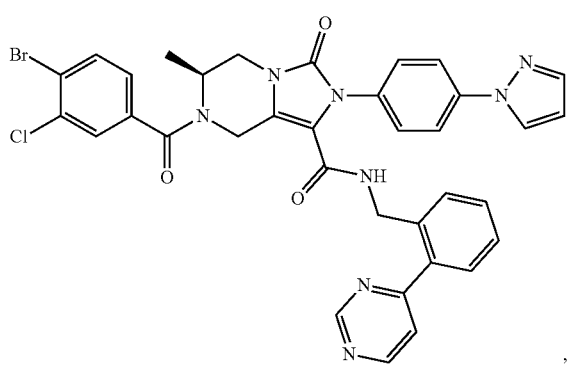
,
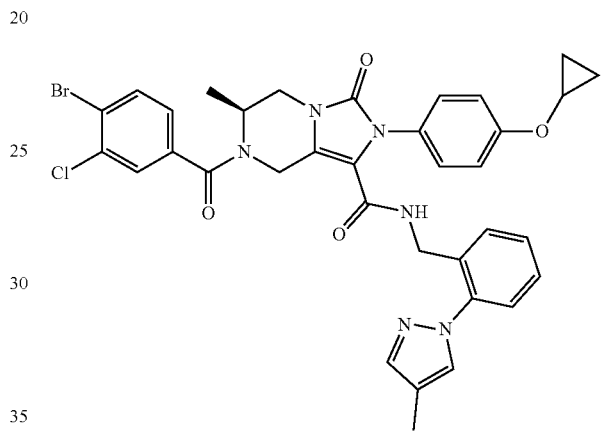
,
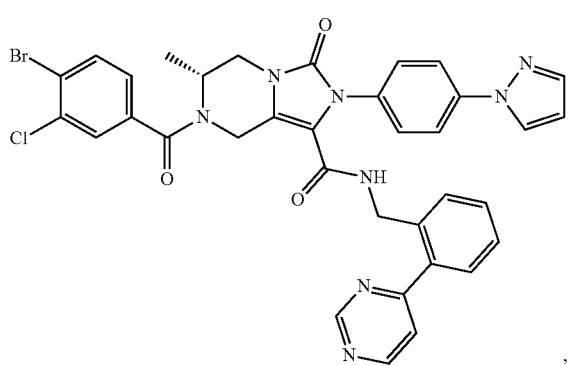
,
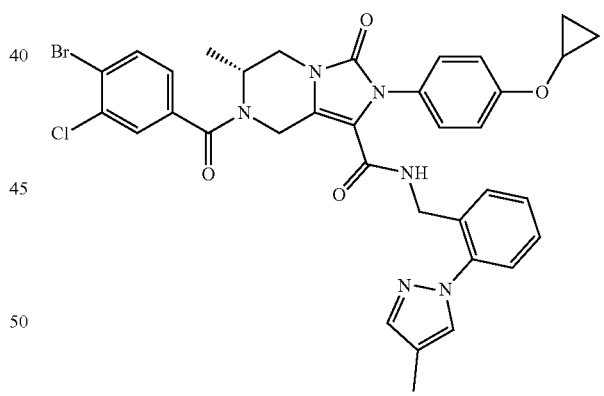
,
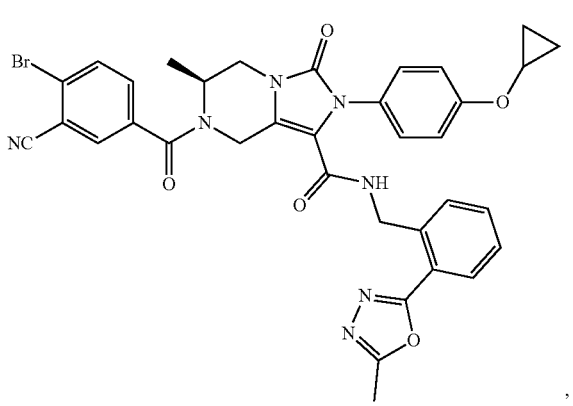
,
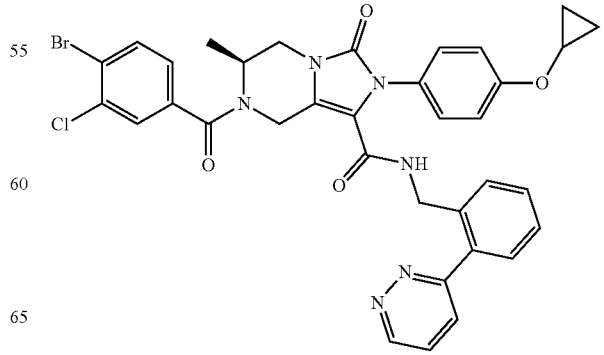
, 437
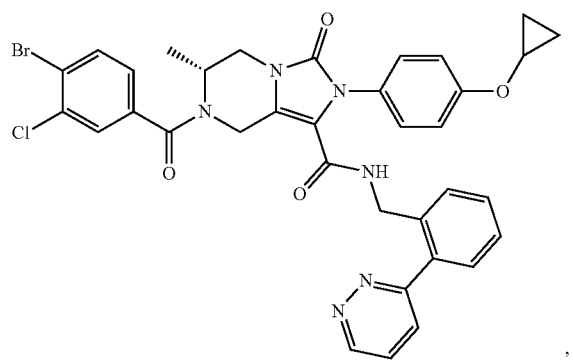
438
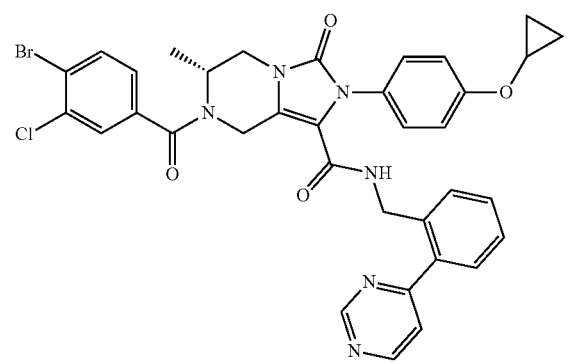
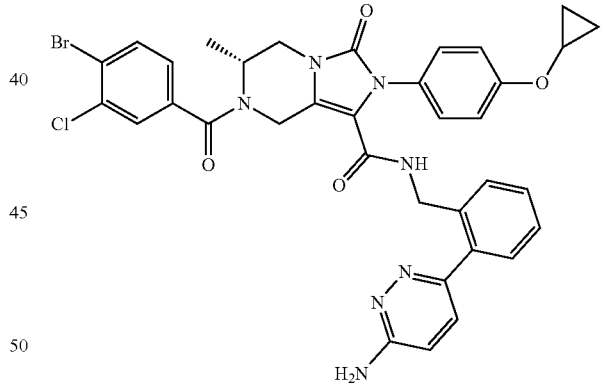
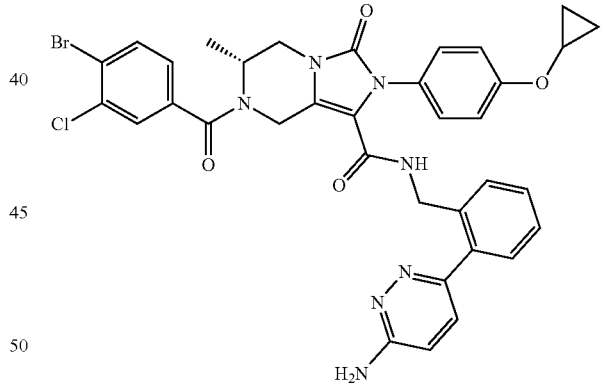
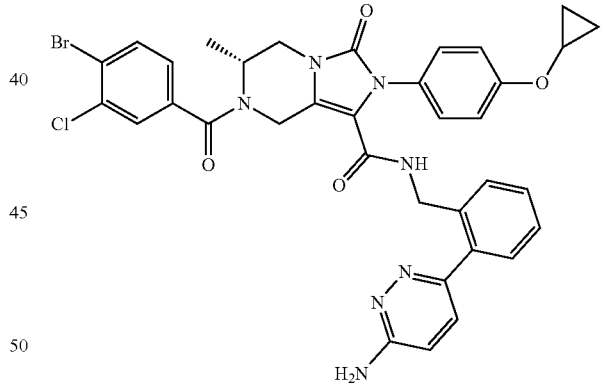

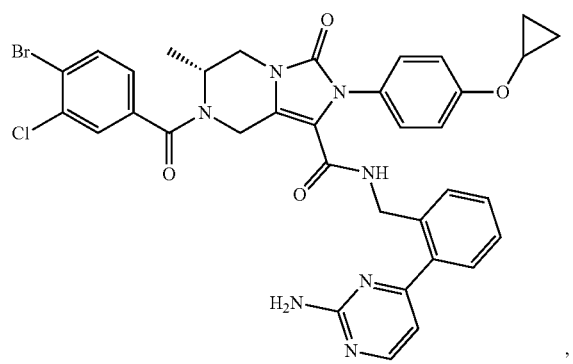
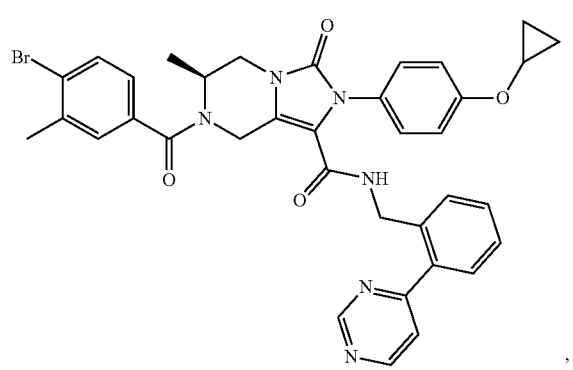
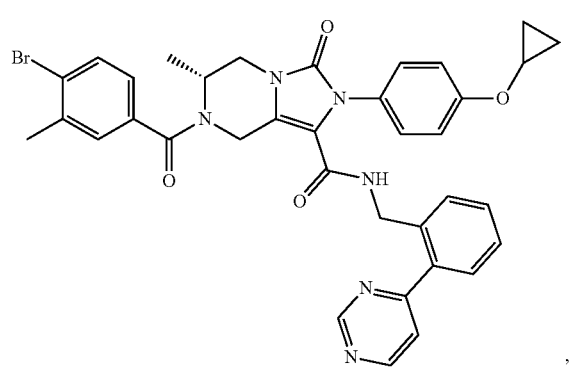
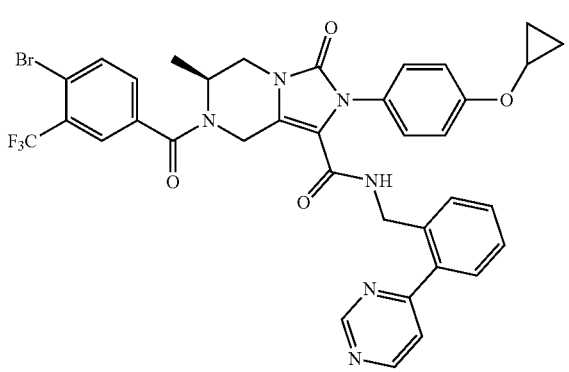
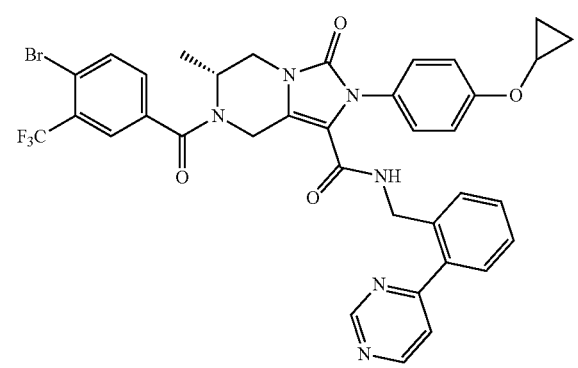
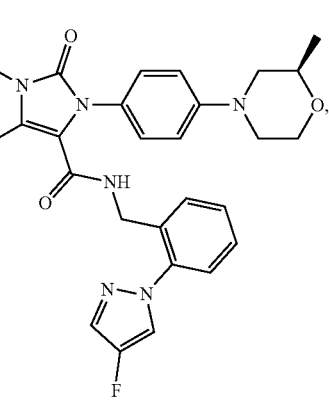
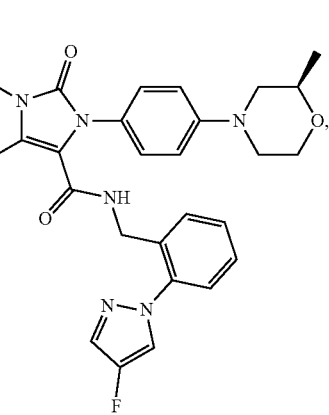
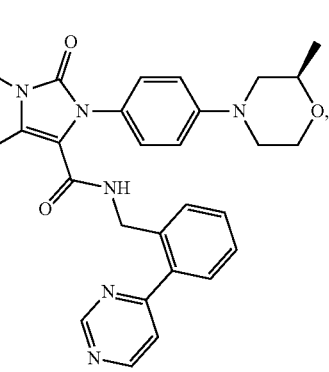

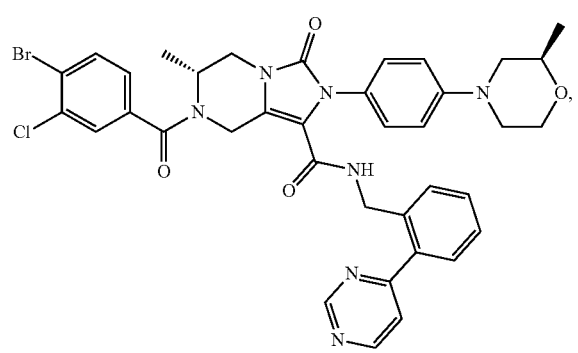
,
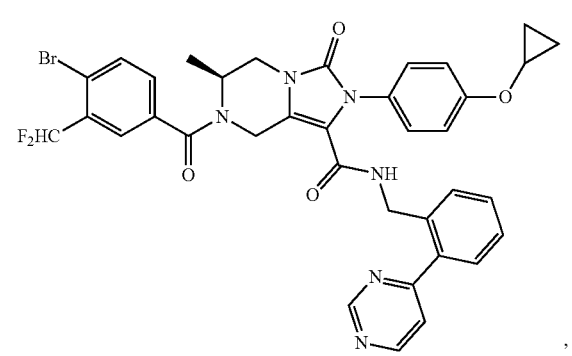
,
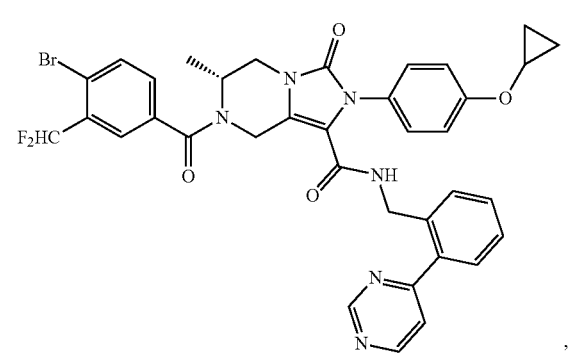
,
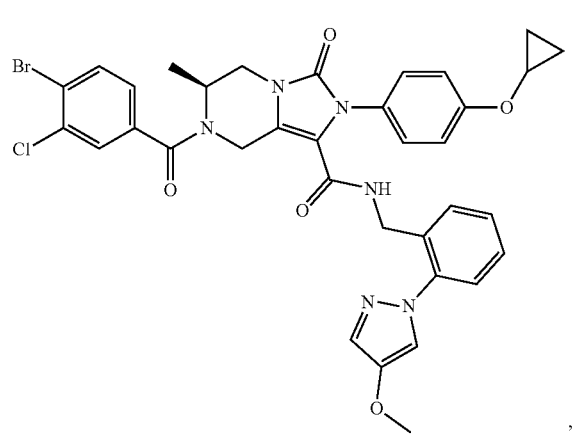
,
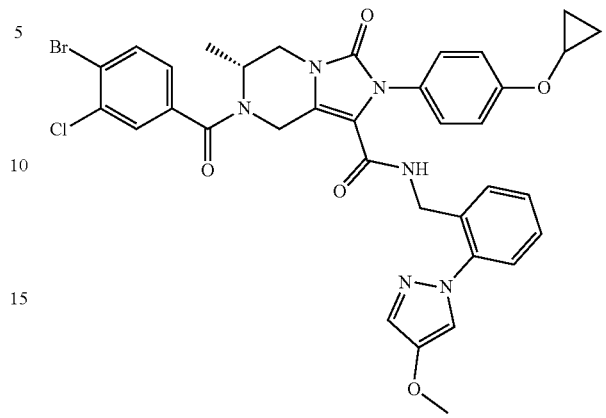
,
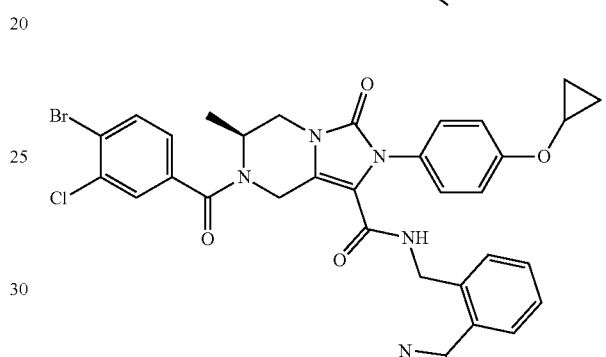
,
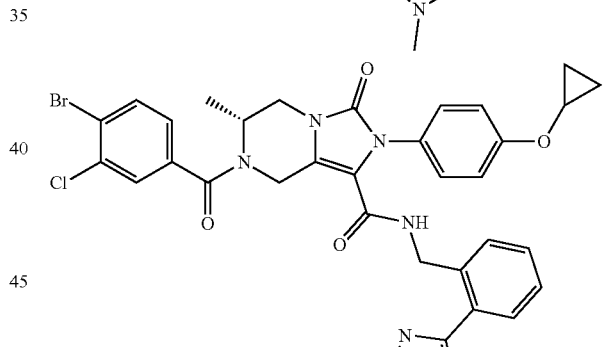
,
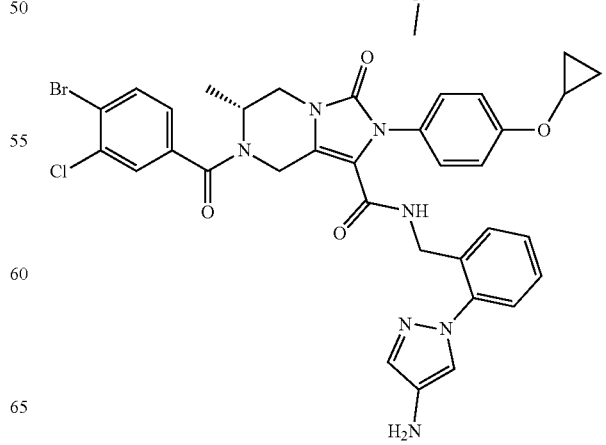
, 443
-continued
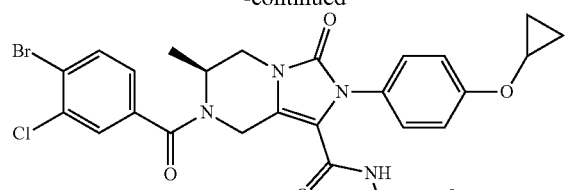
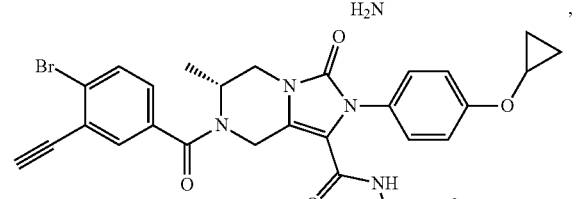
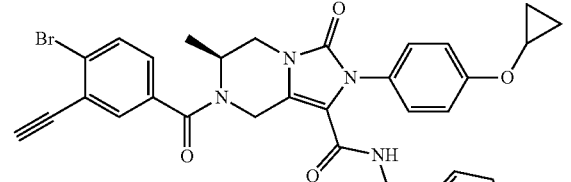
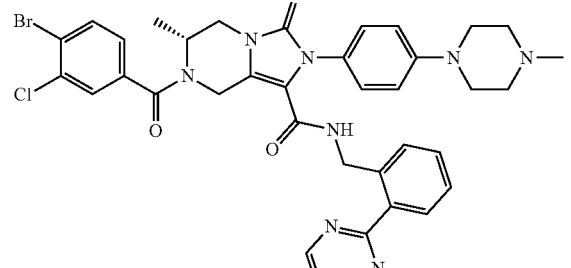
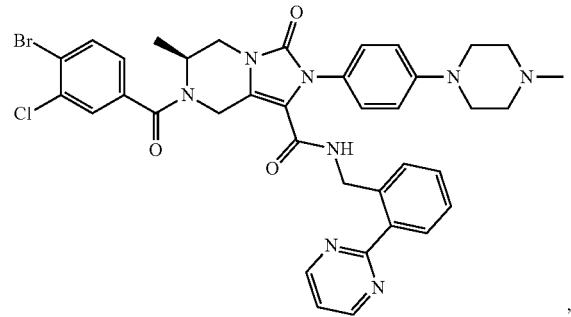
444
-continued
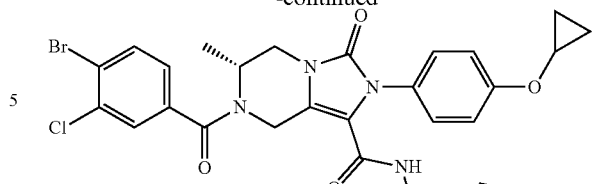
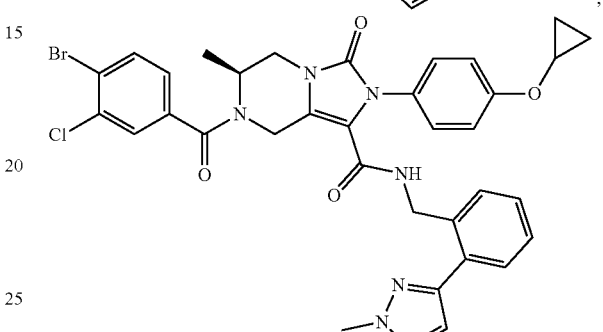
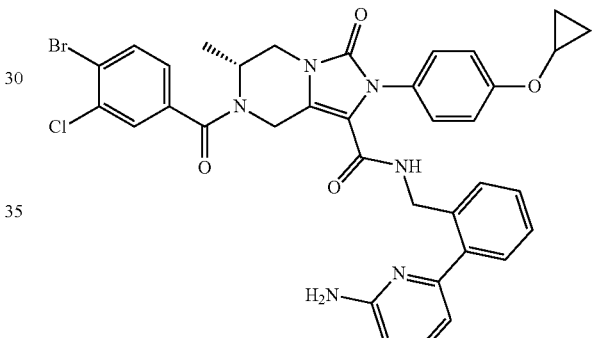
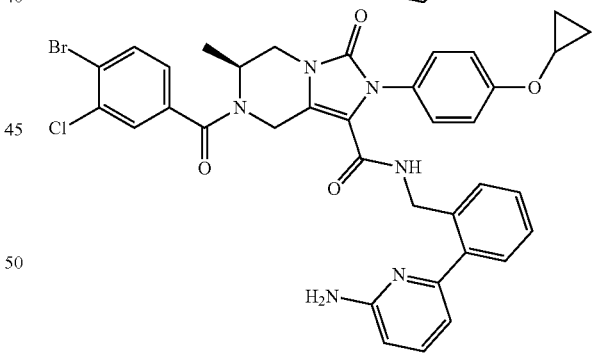
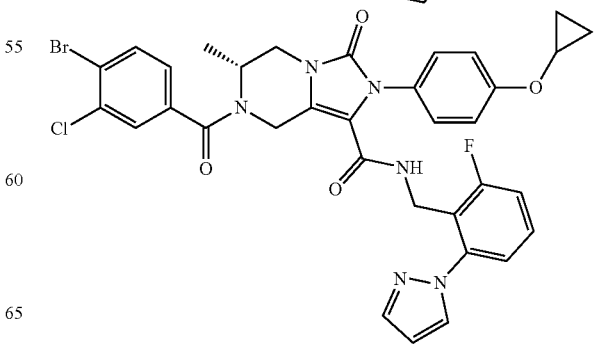

445
-continued
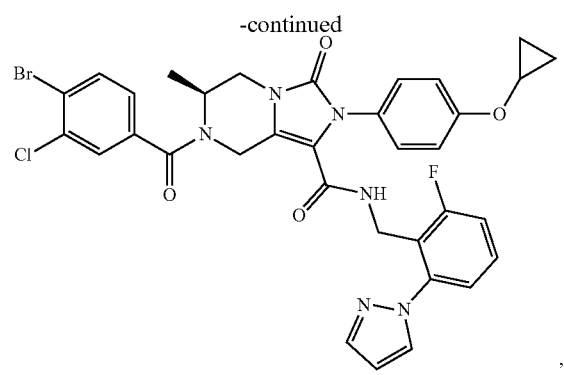
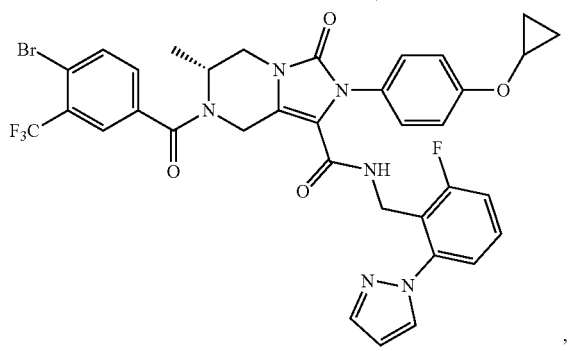
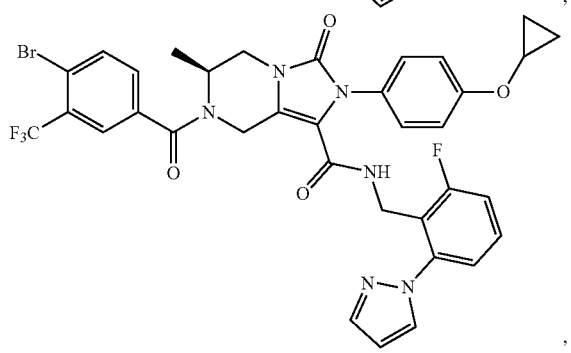
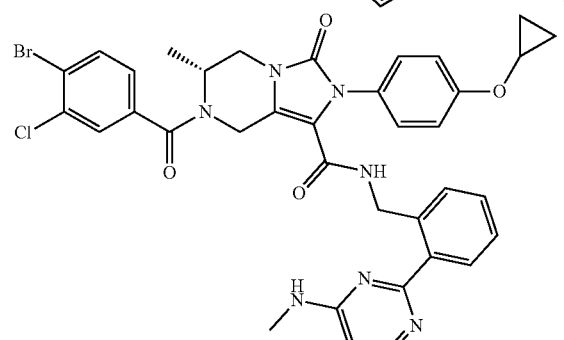
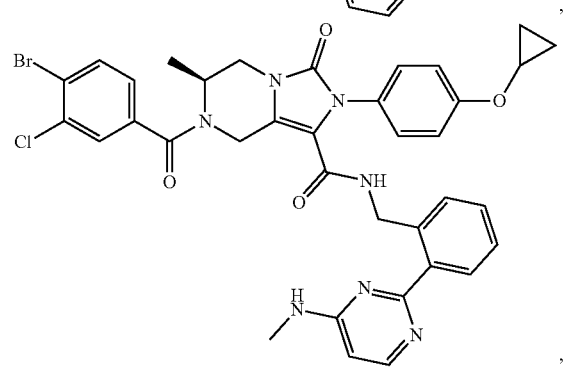
446
-continued
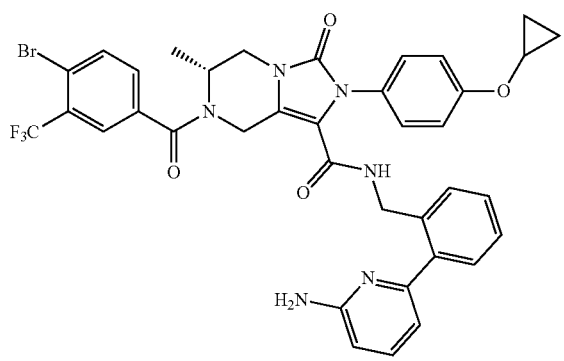
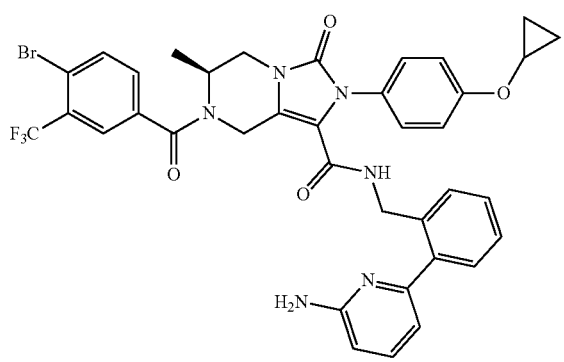
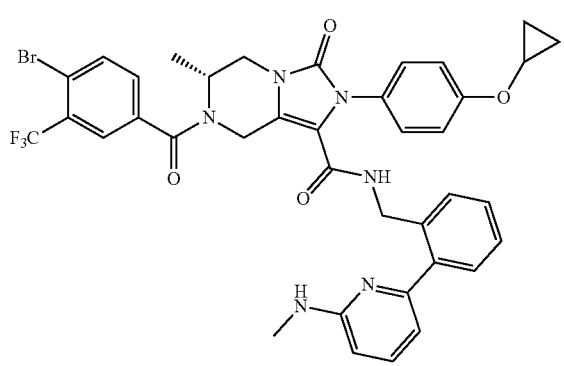
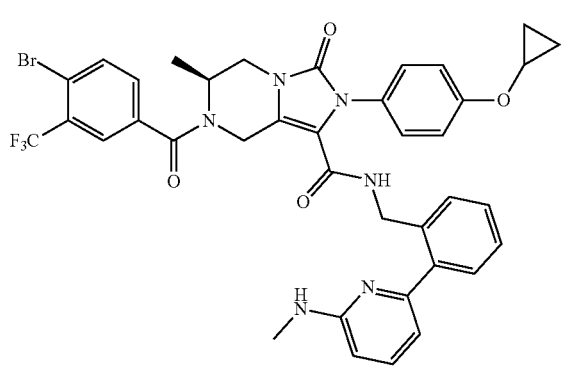

447
-continued
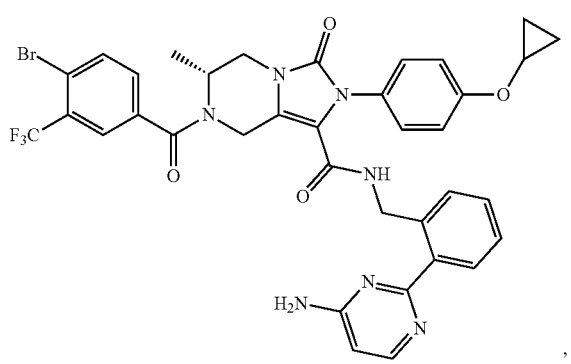
,
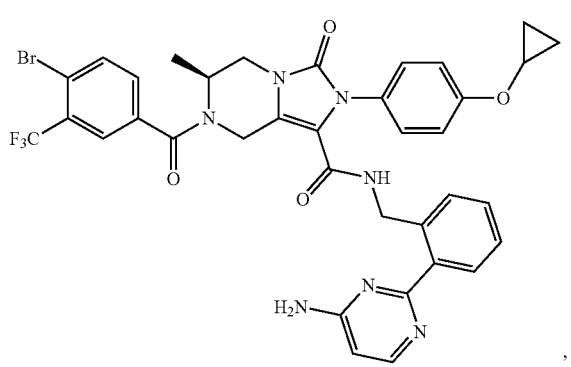
,
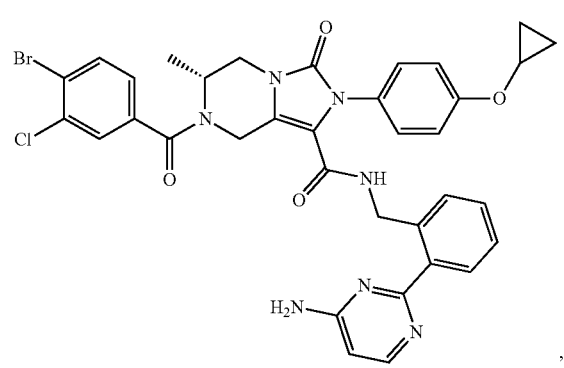
,
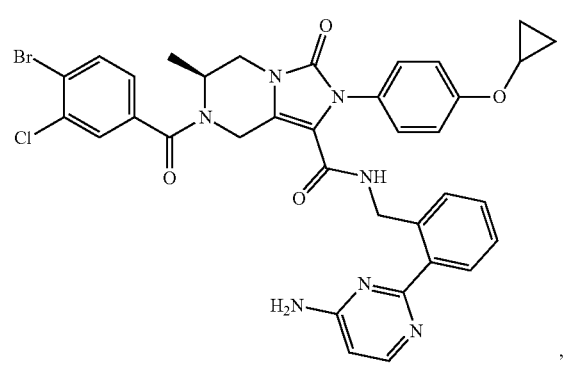
,
448
-continued
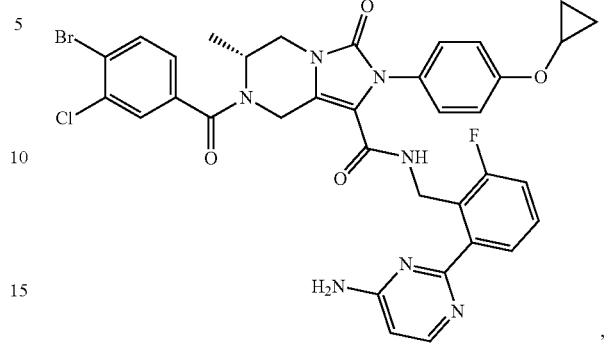
,
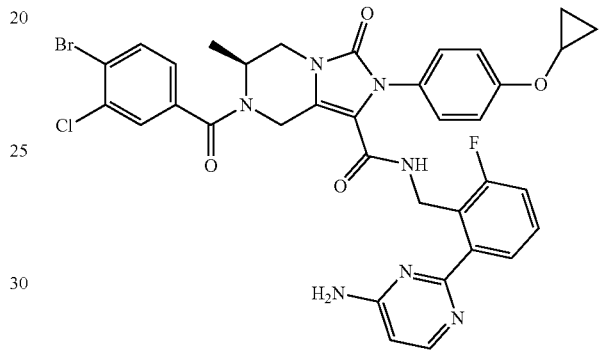
,
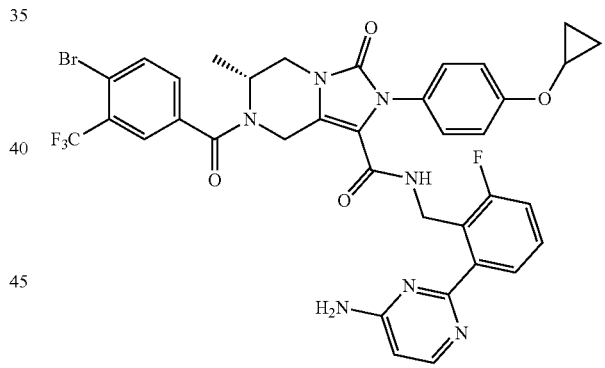
,
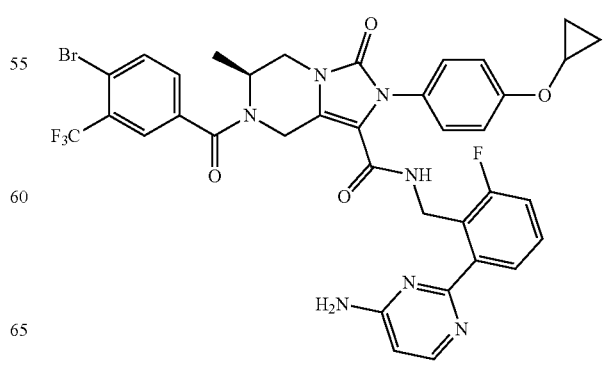
, 449
-continued
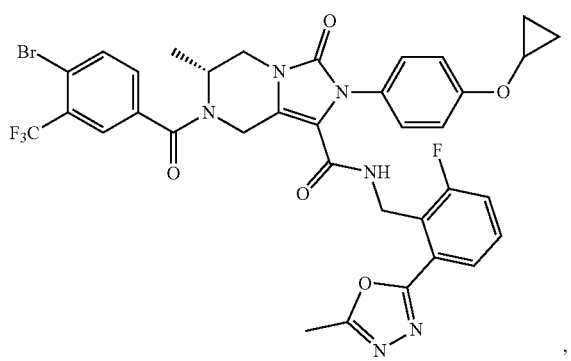
,
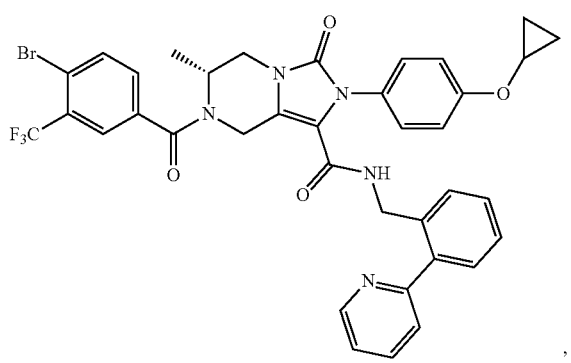
,
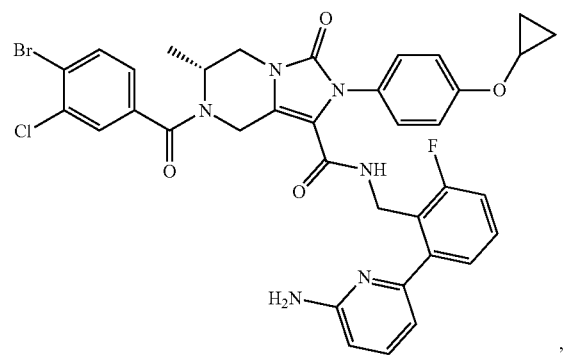
,
450
-continued
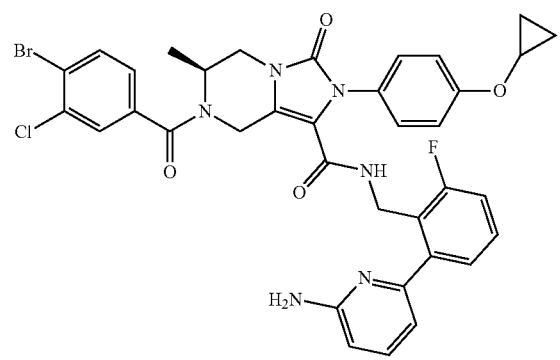
,
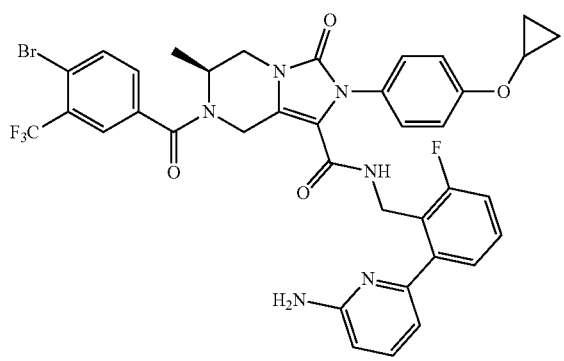
,
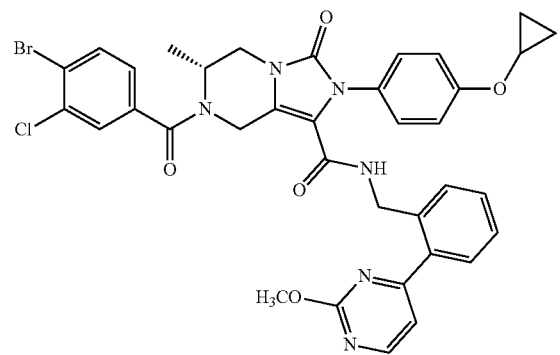
, 451
-continued
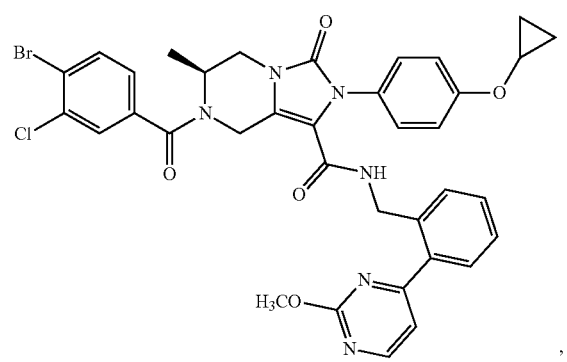
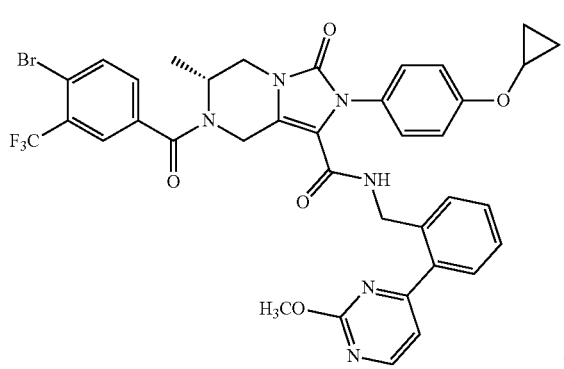
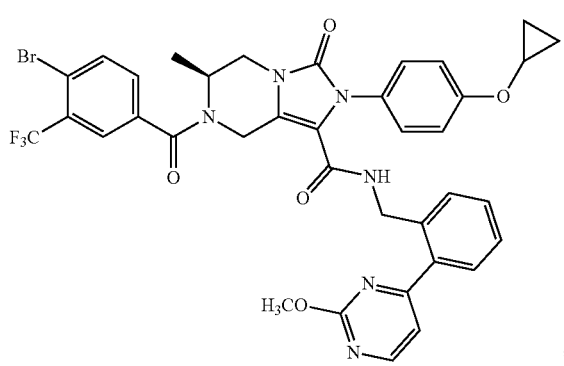
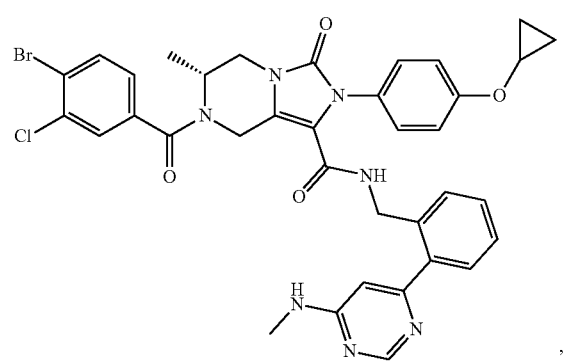
452
-continued
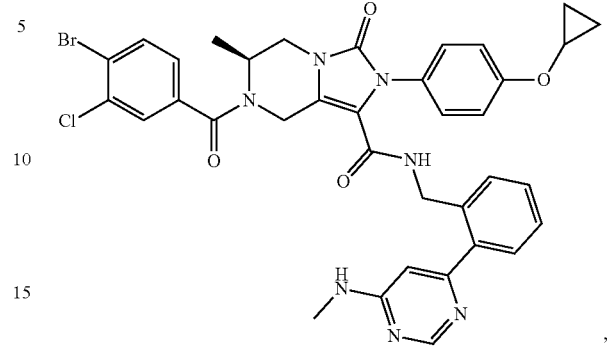
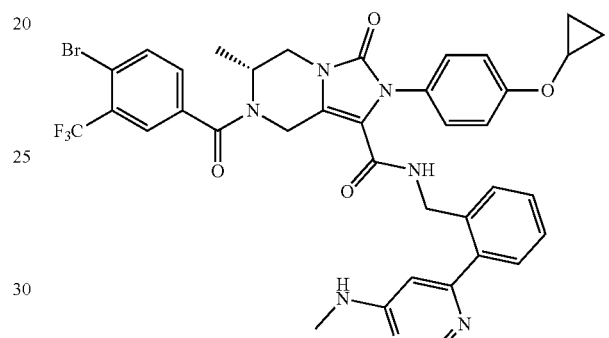
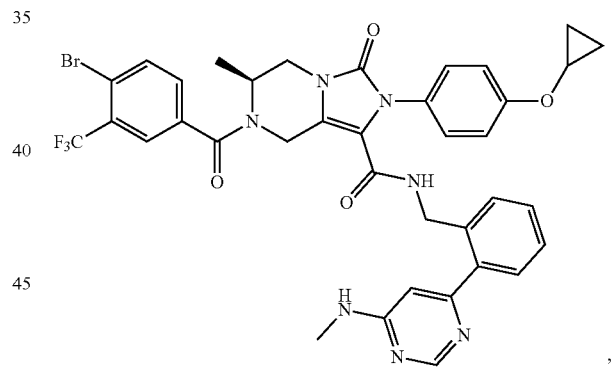
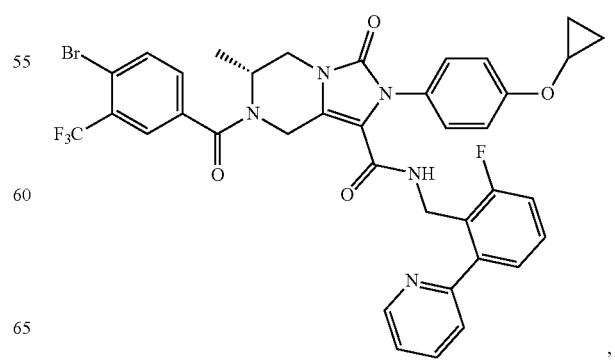

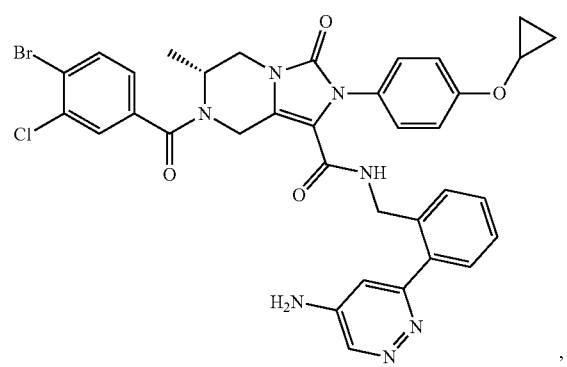
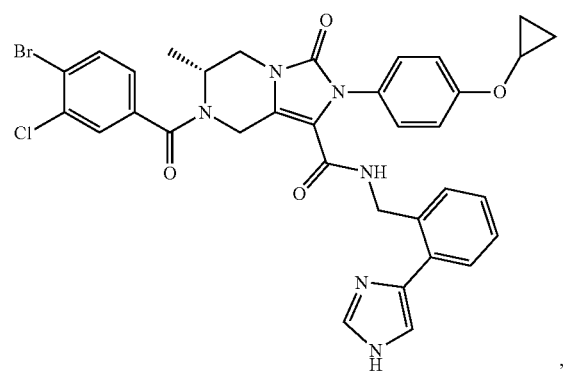
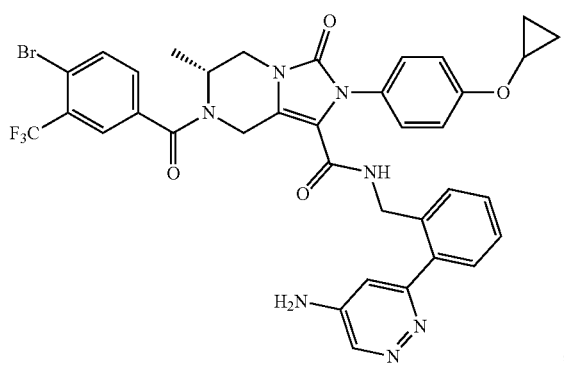
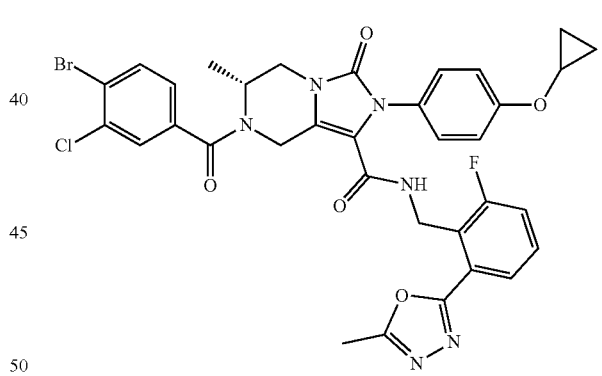
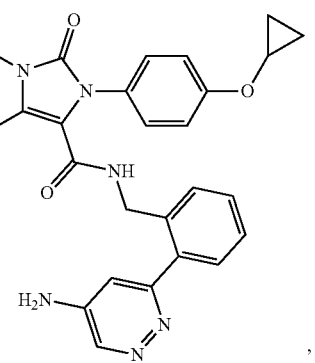
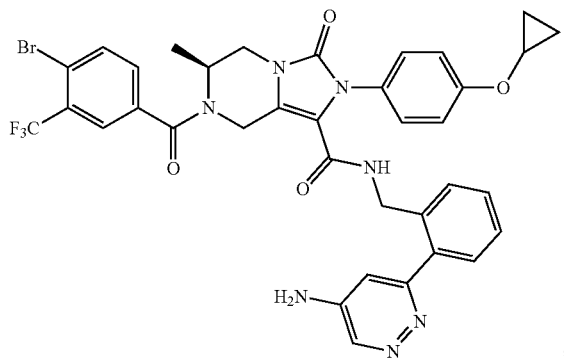
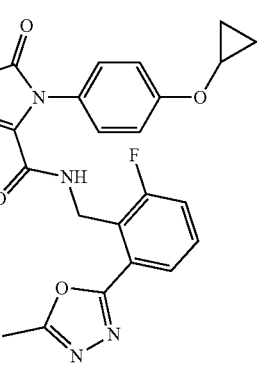

455
-continued
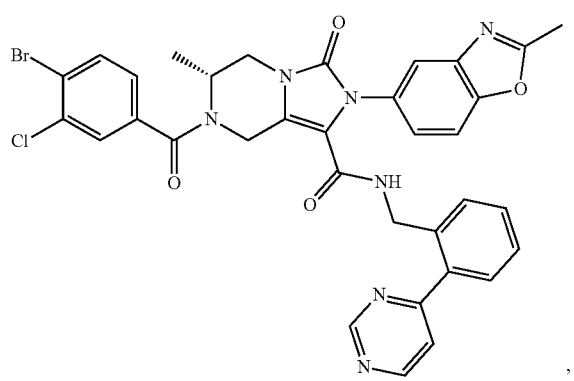
,
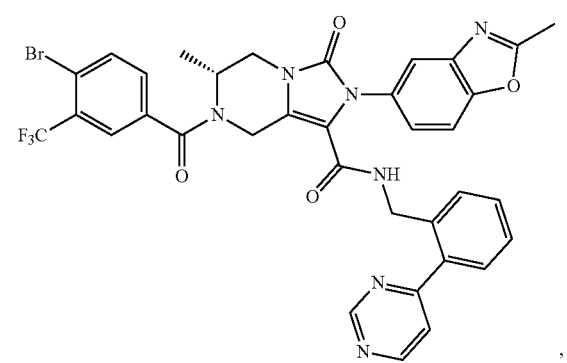
,
456
-continued
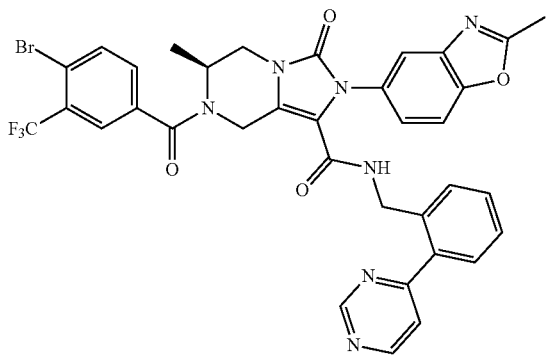
,
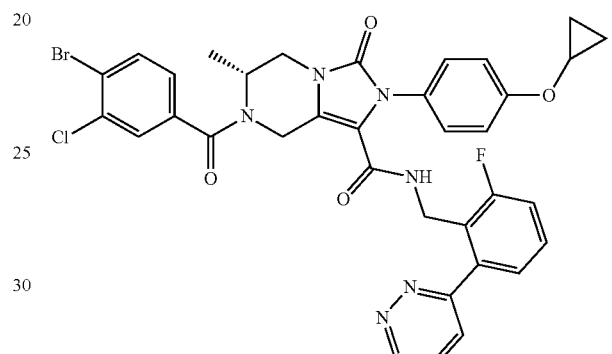
,
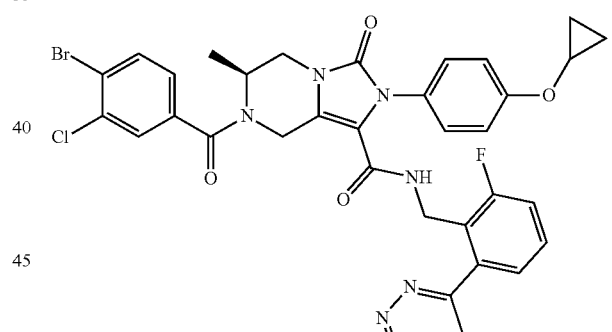
,
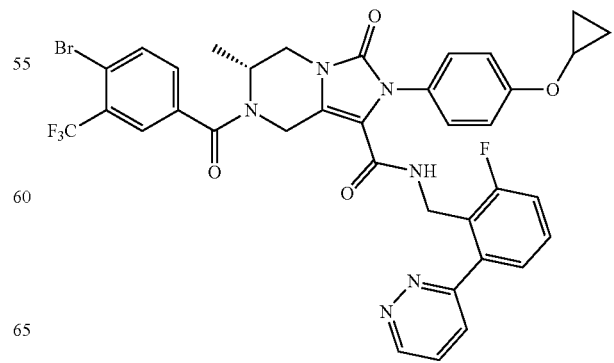
, 457
-continued
458
-continued
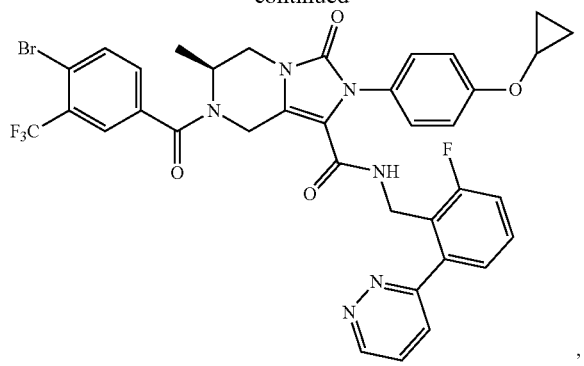
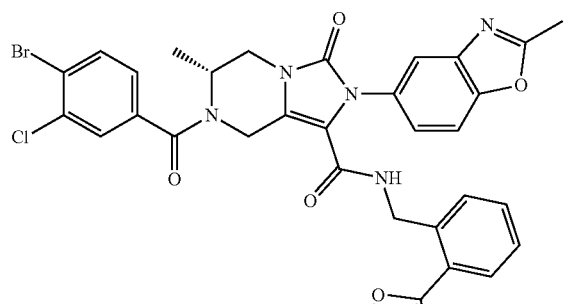
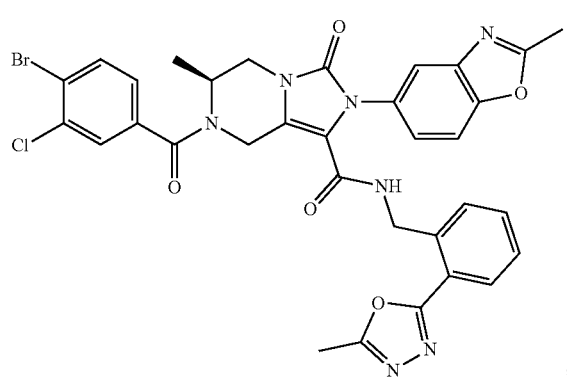
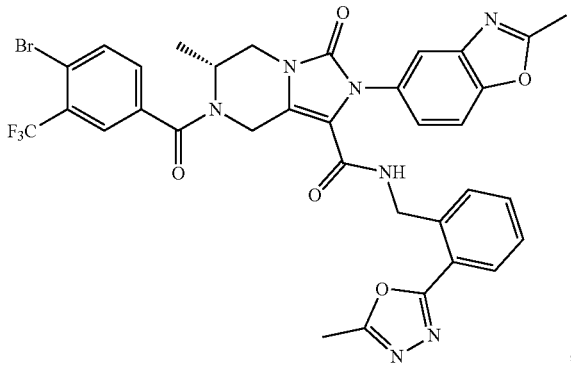
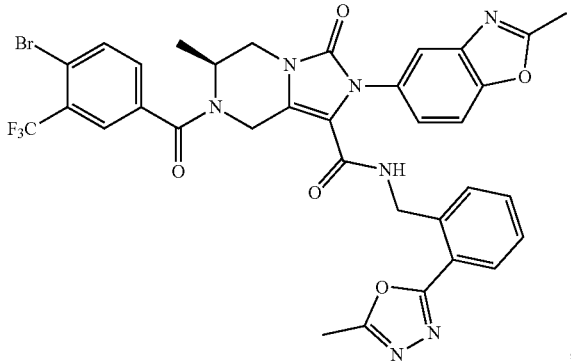

459
-continued
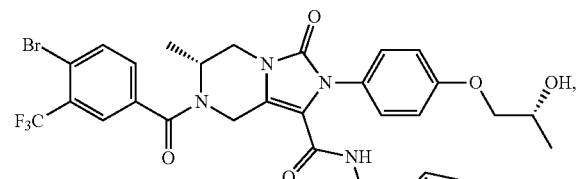
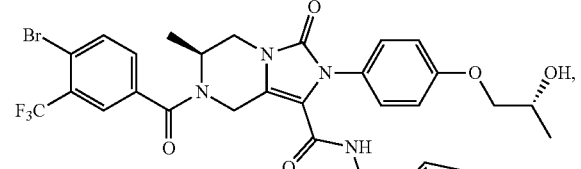
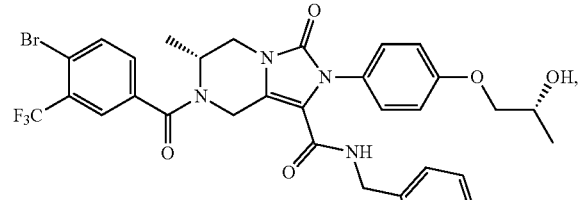
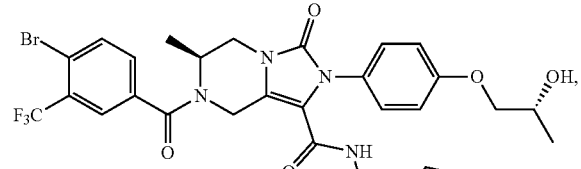
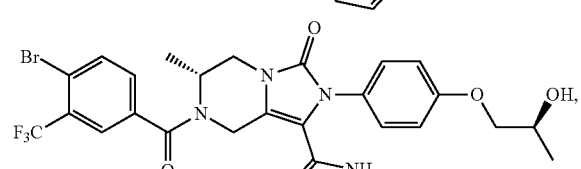
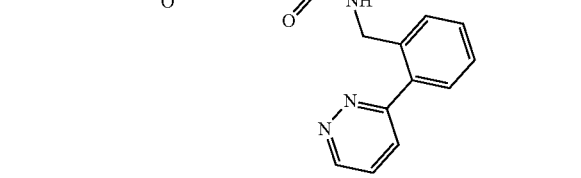
460
-continued
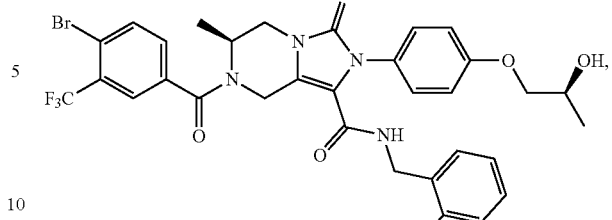
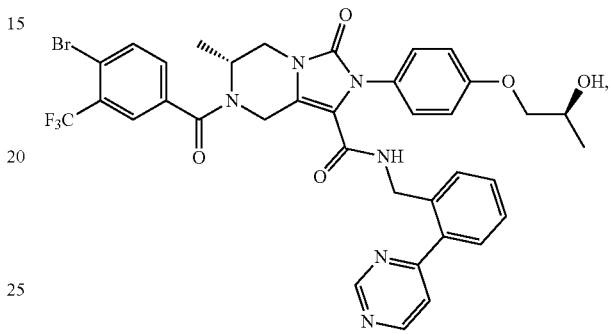
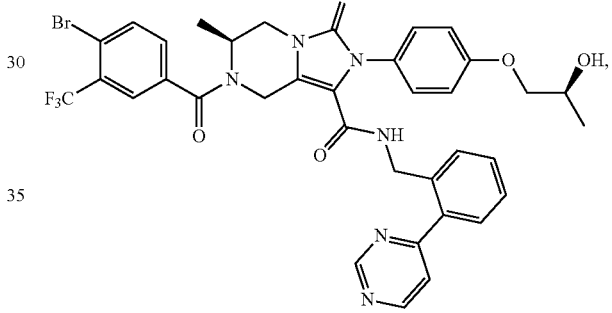
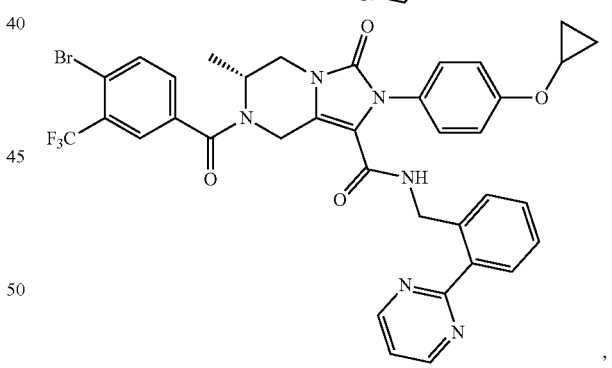
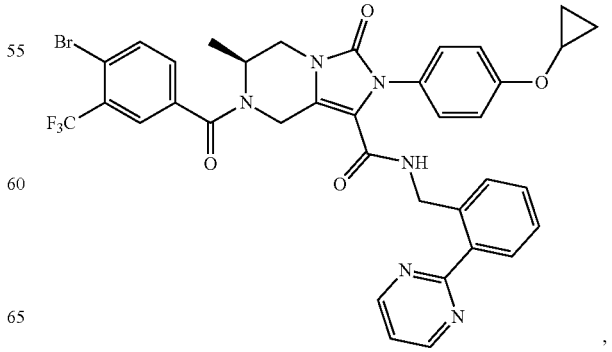

461
-continued
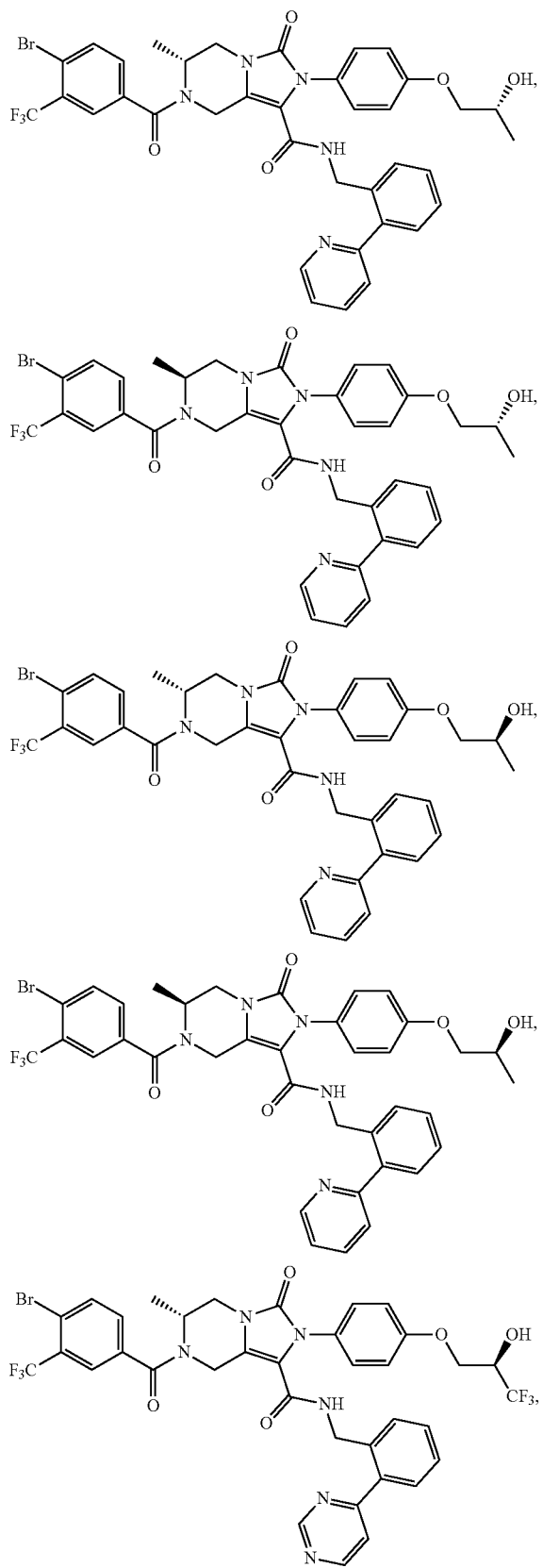
462
-continued
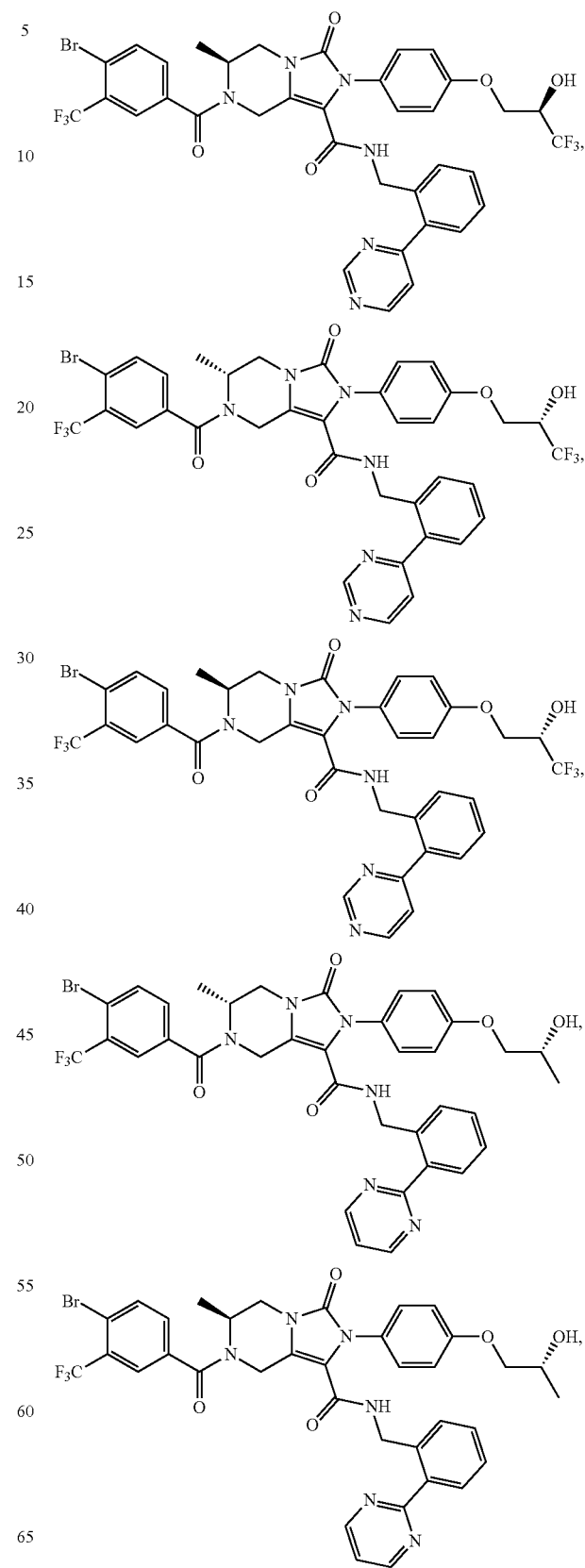

463
-continued
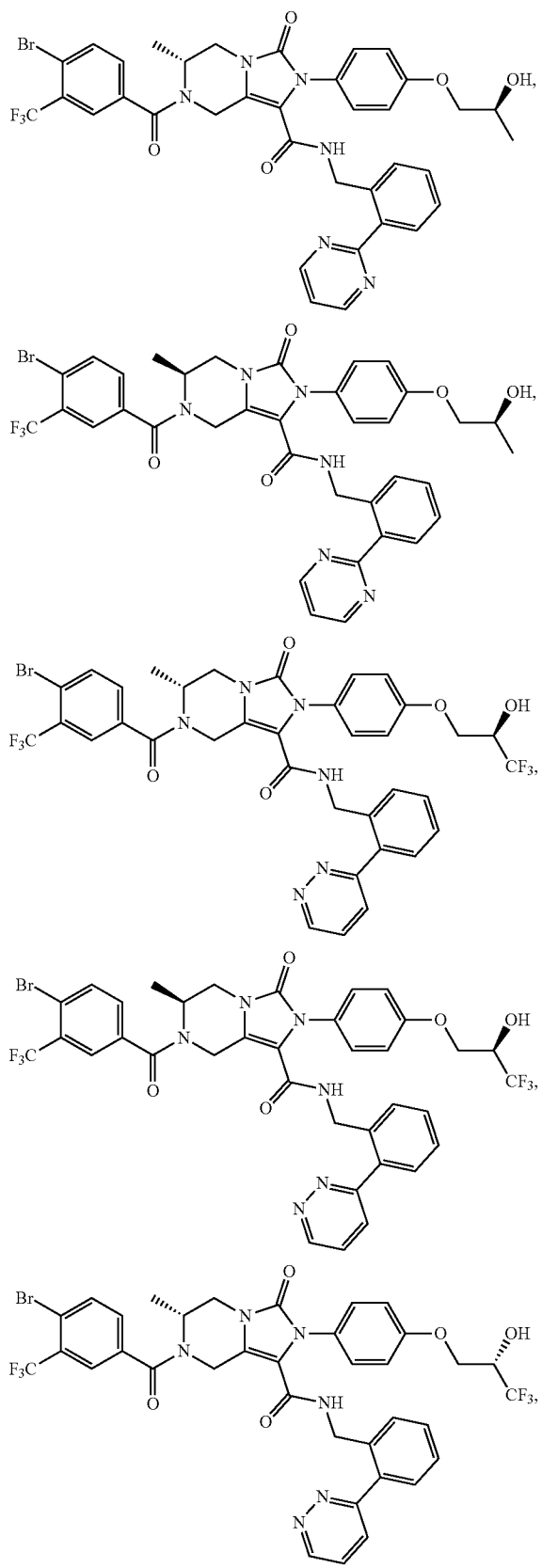
464
-continued
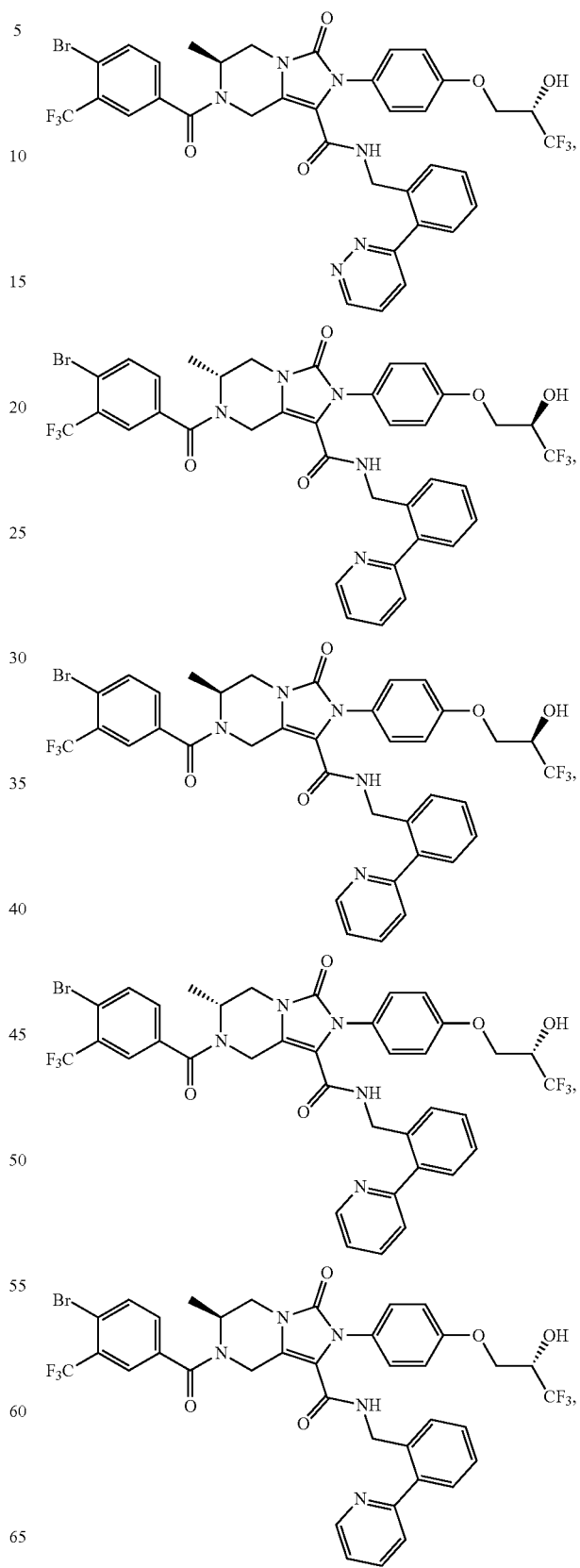

465
-continued
466
-continued
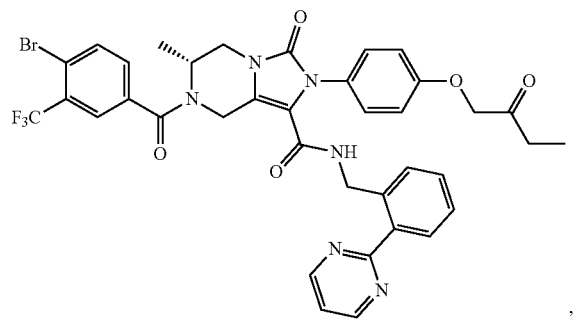
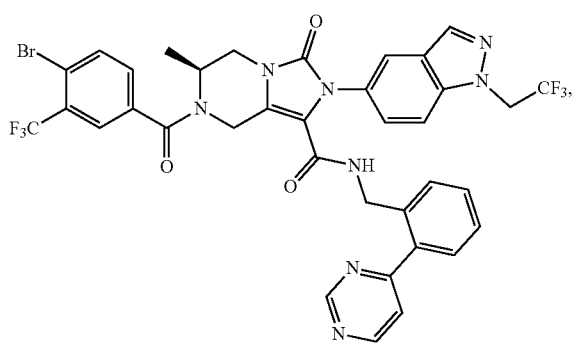
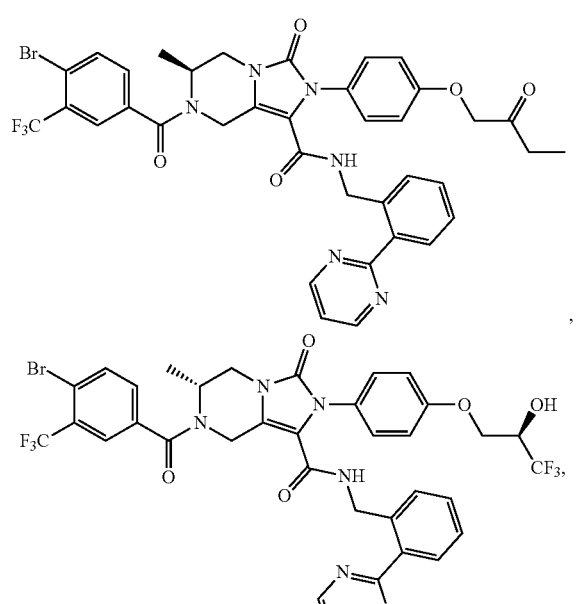
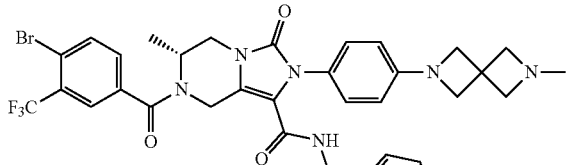
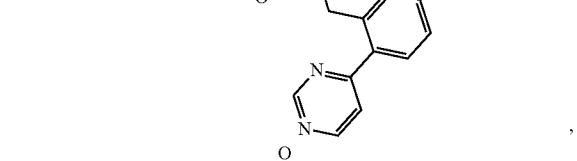
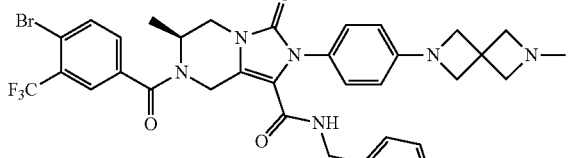
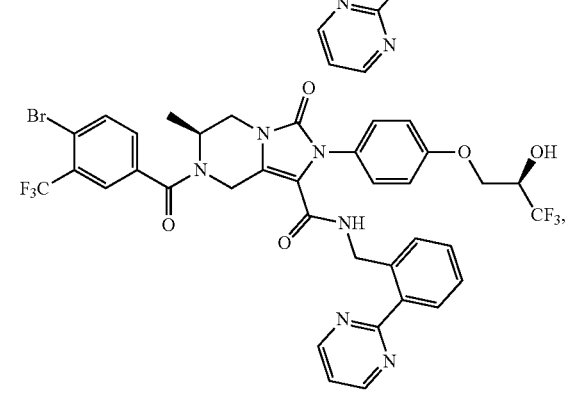
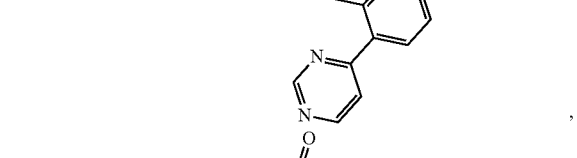
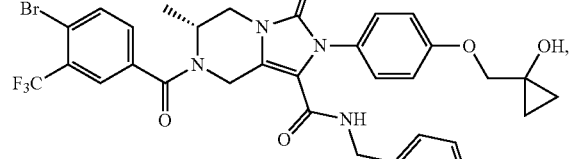
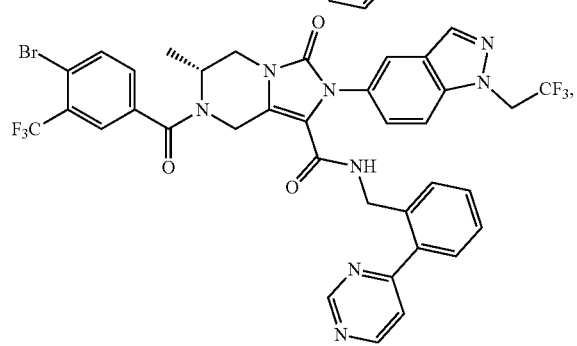
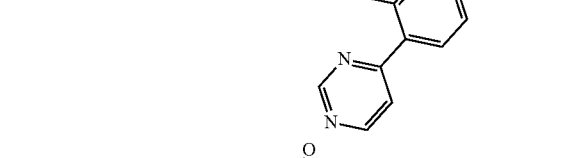
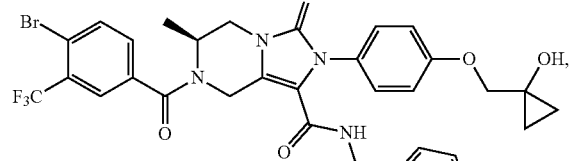
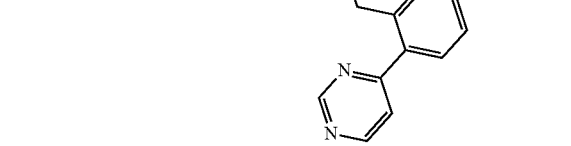

467
-continued
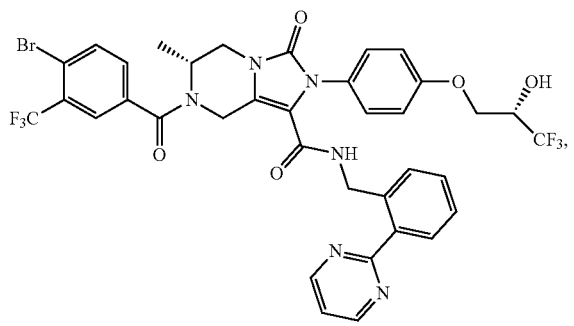
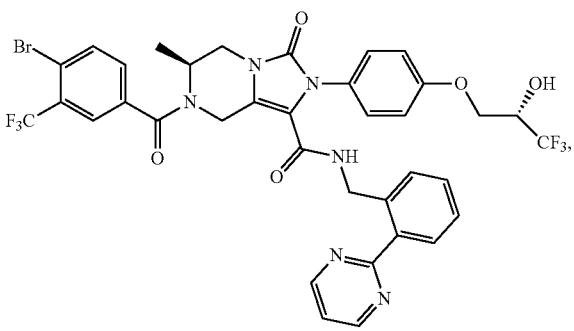
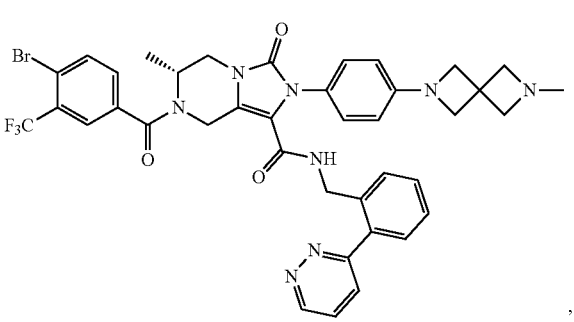
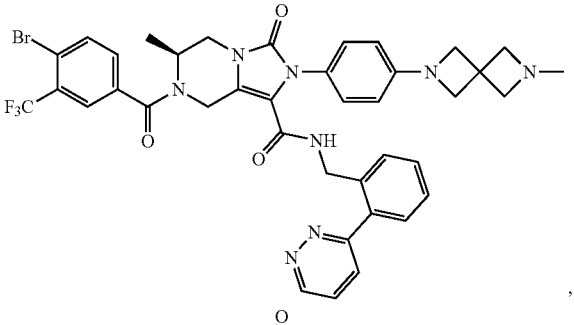
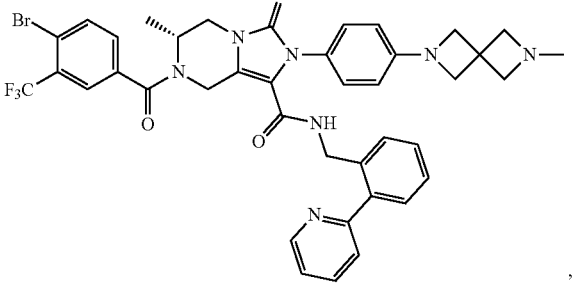
468
-continued
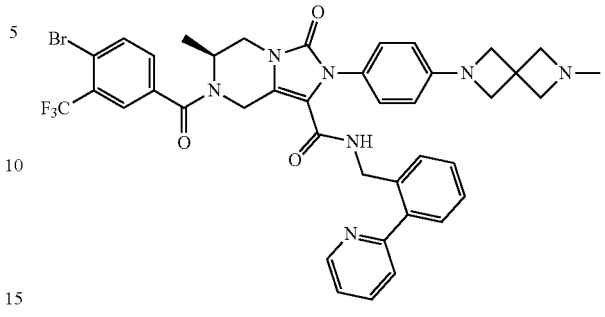
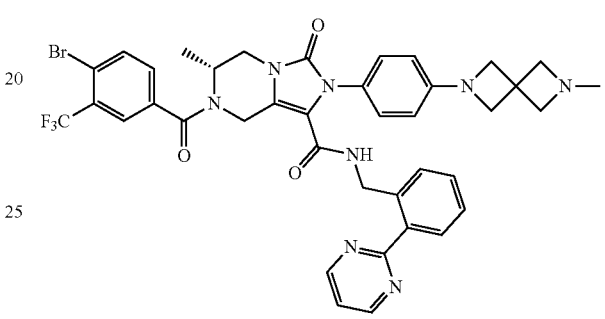
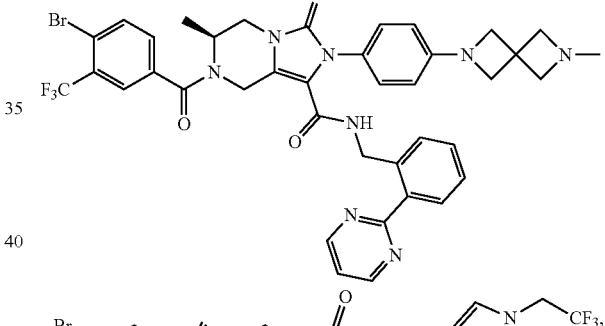
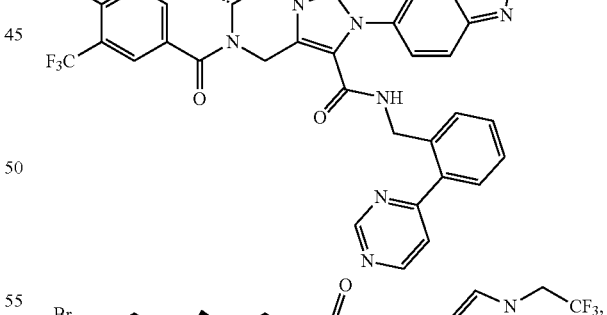
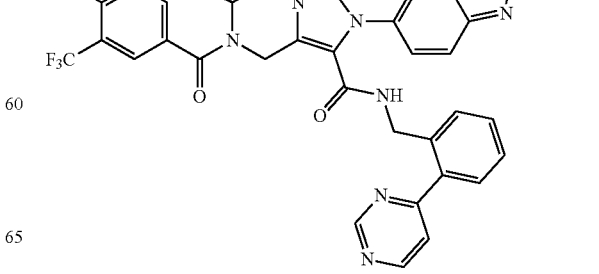

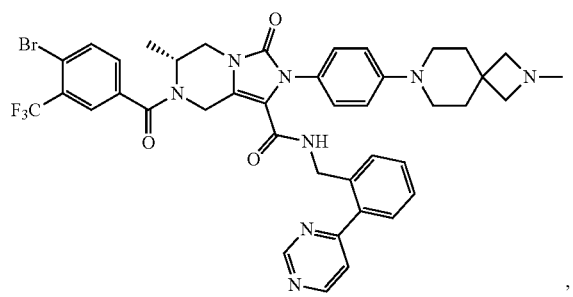
,
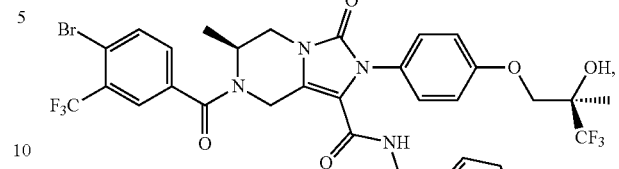
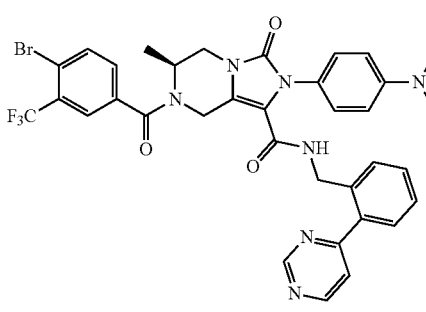
,
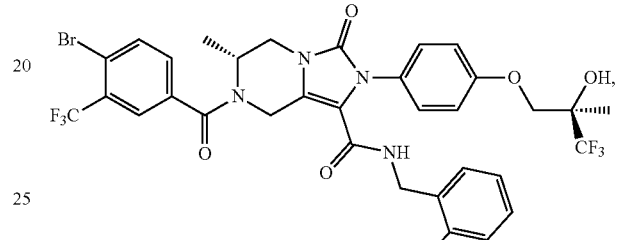
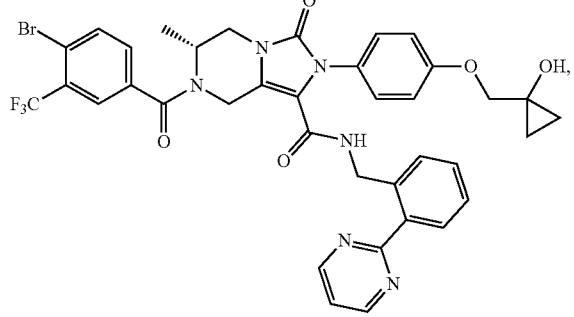
,
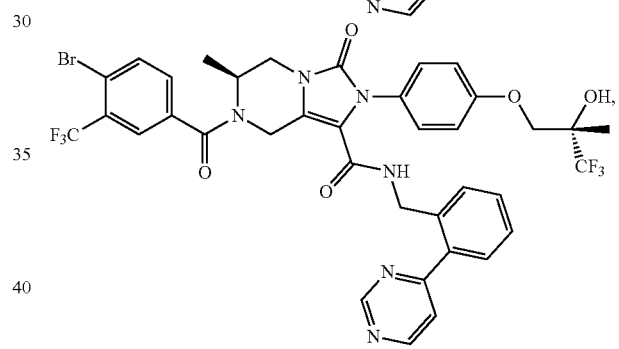
,
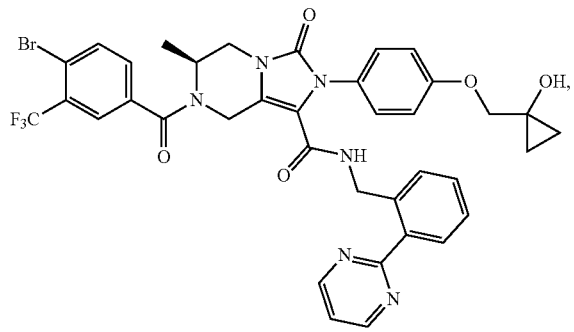
,
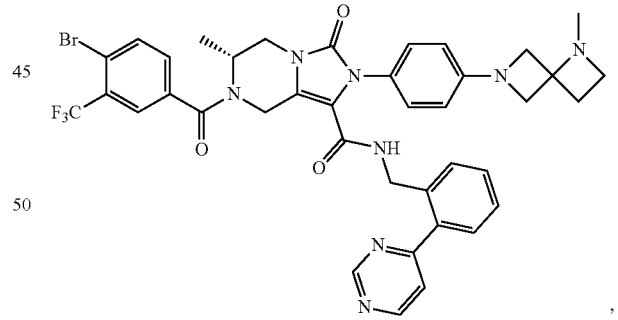
,
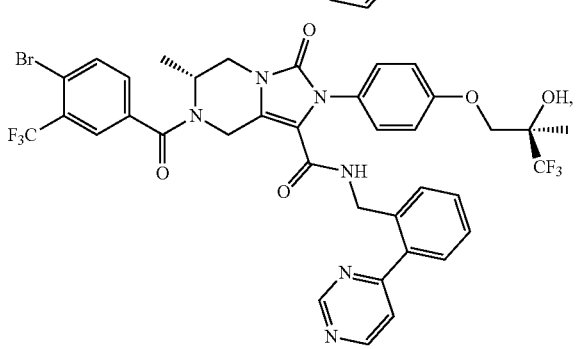
,
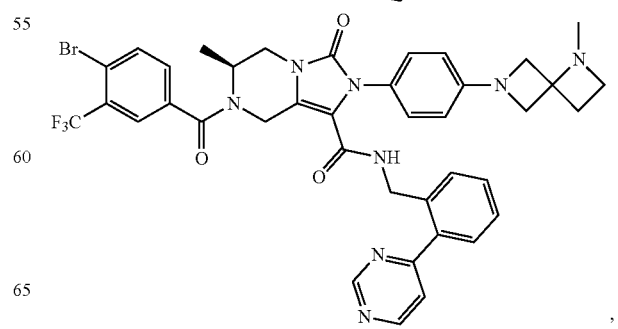
, 471
-continued
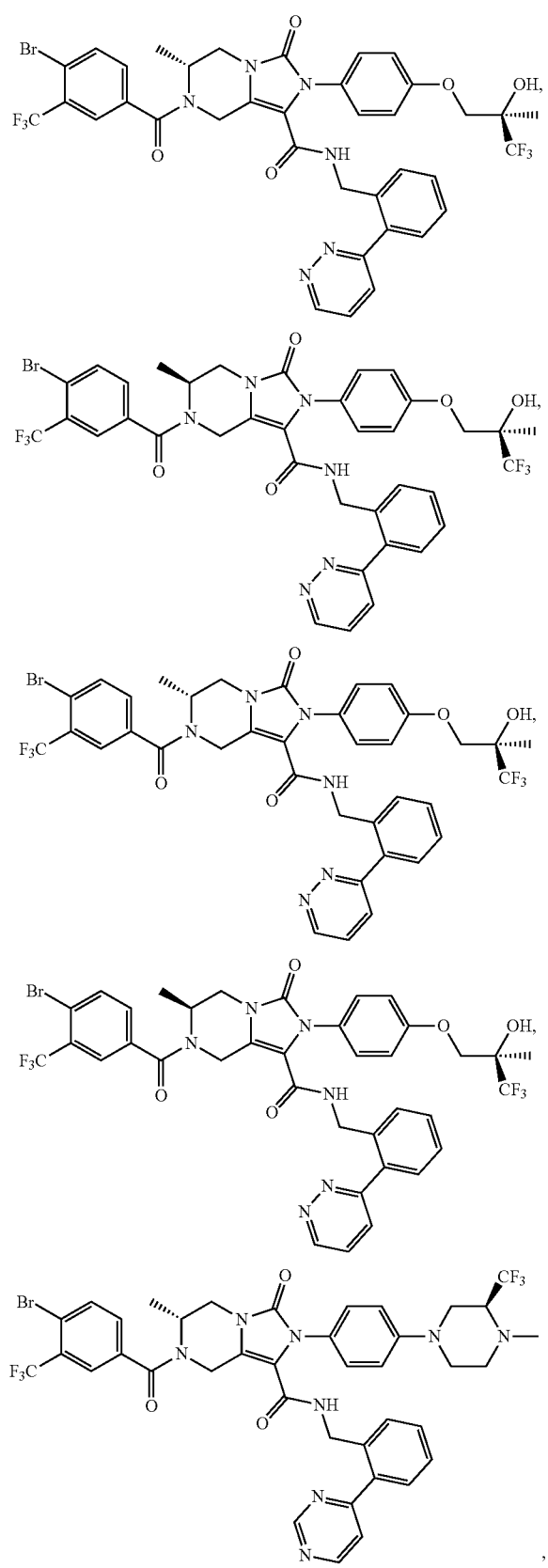
472
-continued
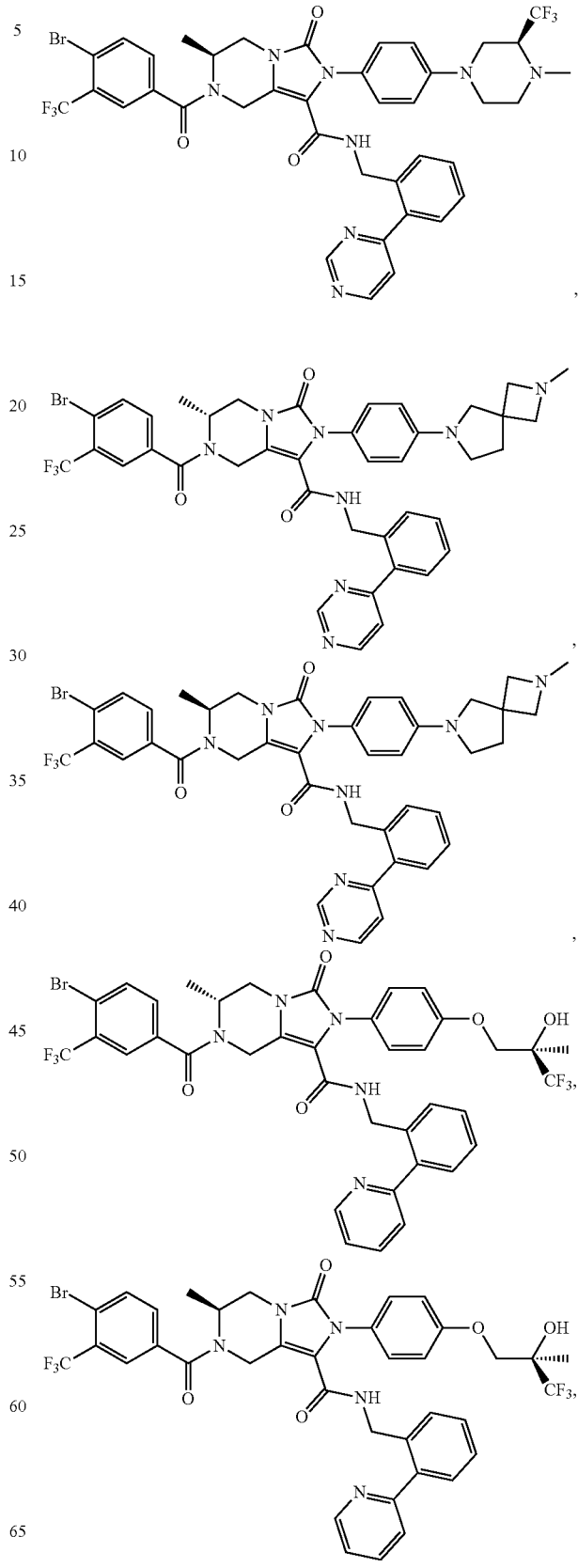

473
-continued
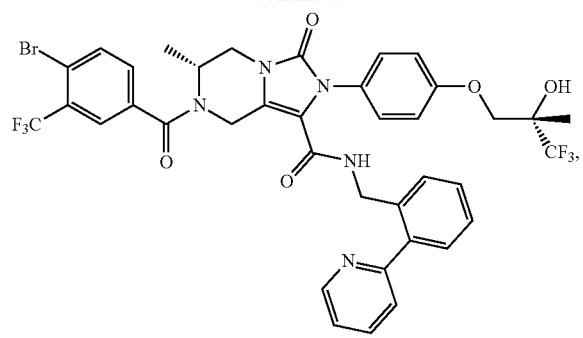
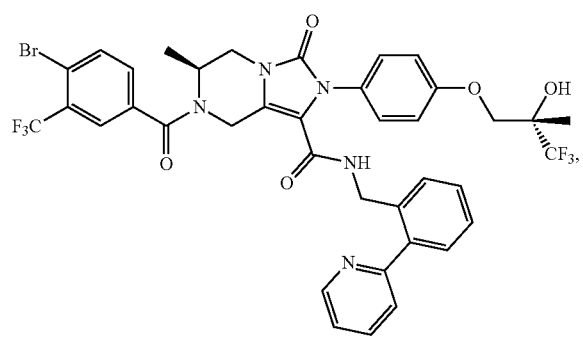
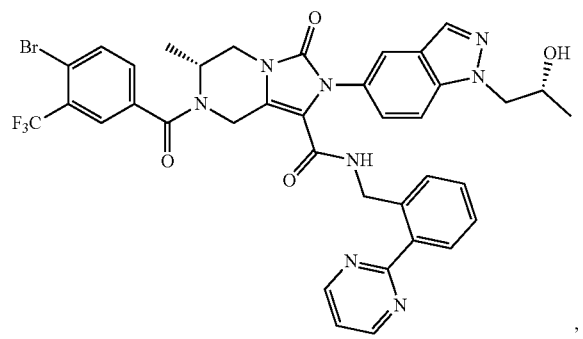
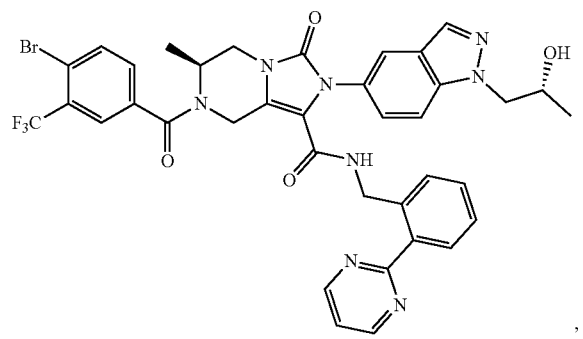
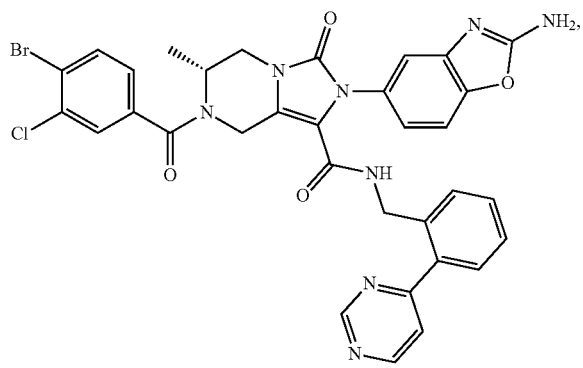
474
-continued
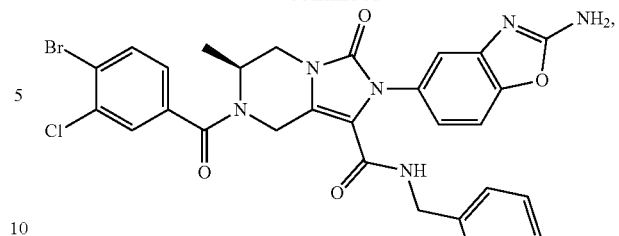
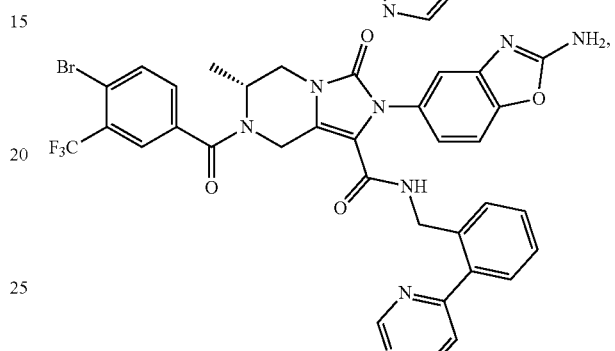
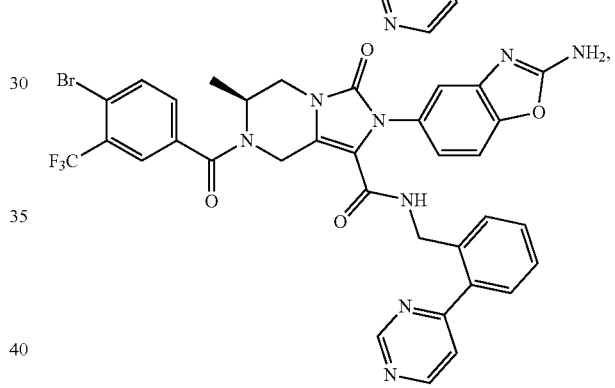
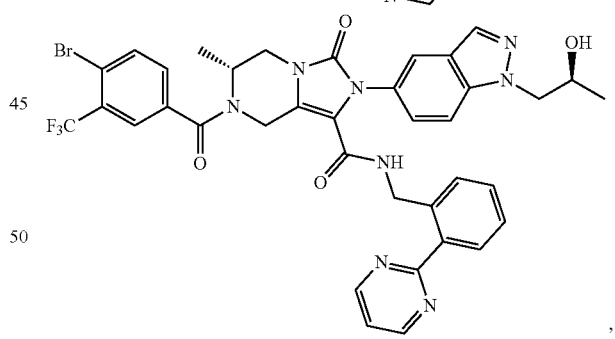
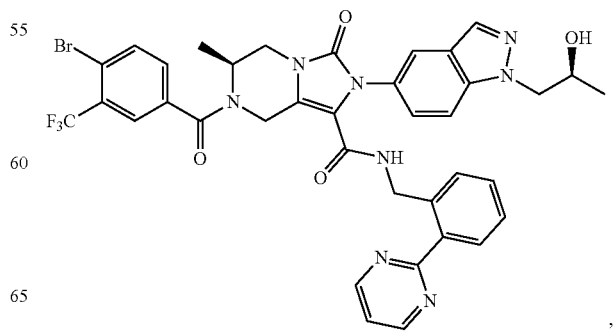

475
-continued
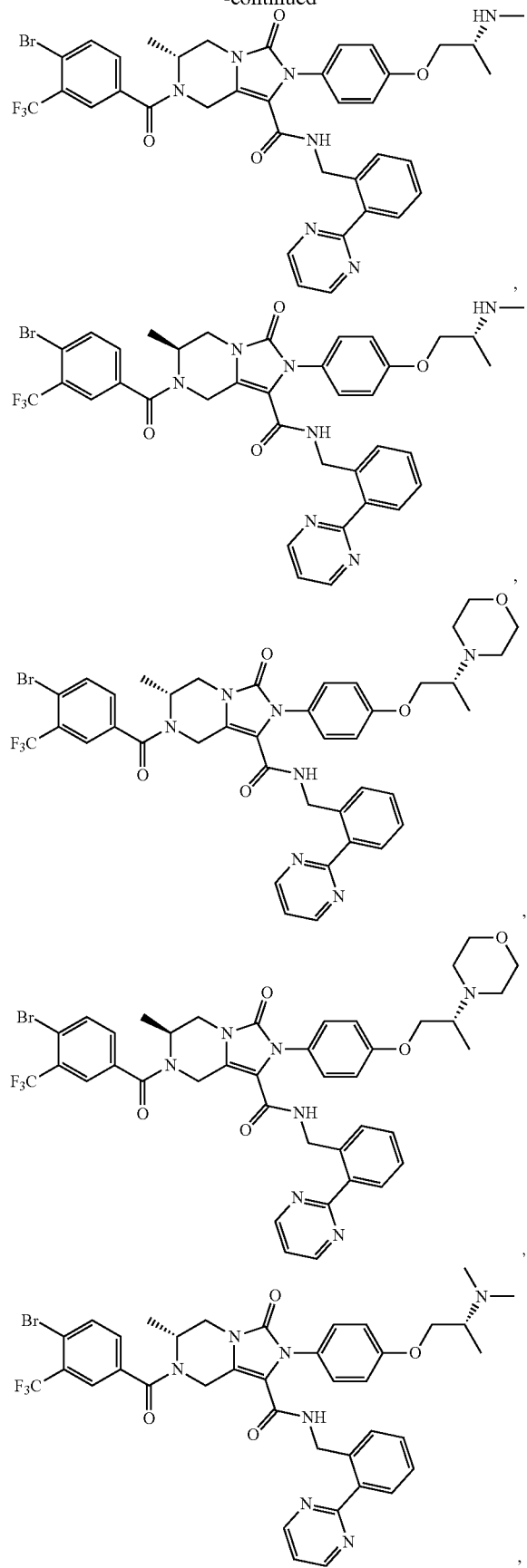
476
-continued
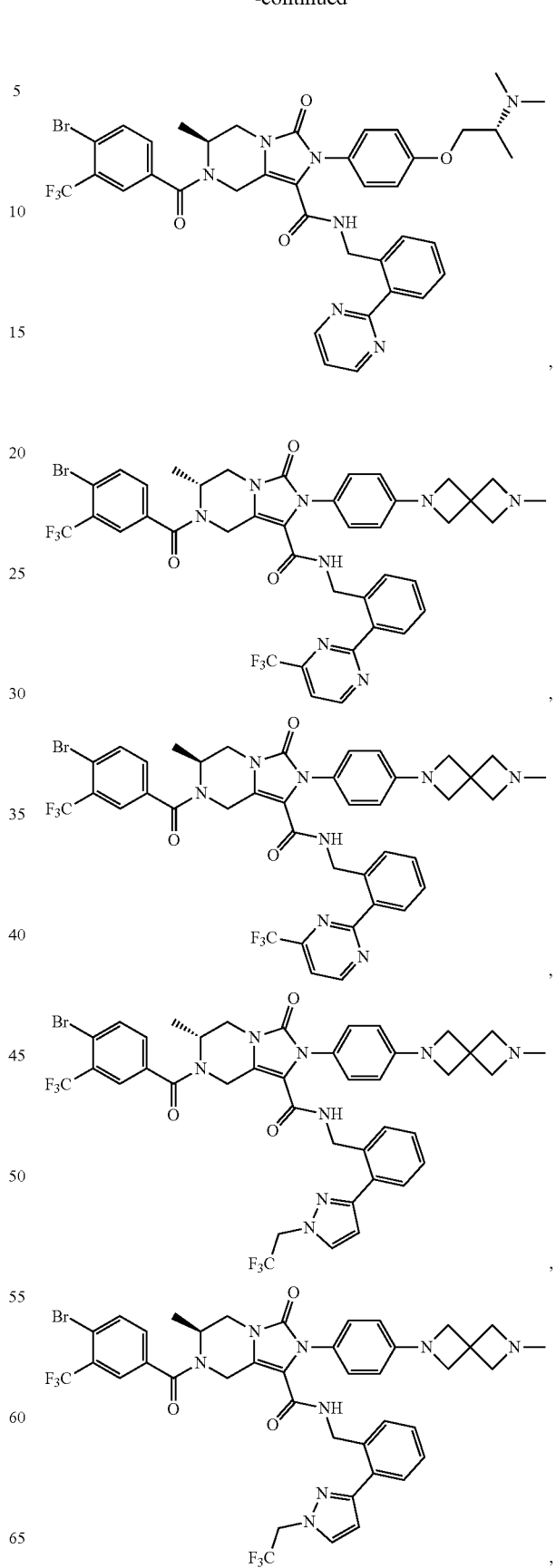

477
-continued
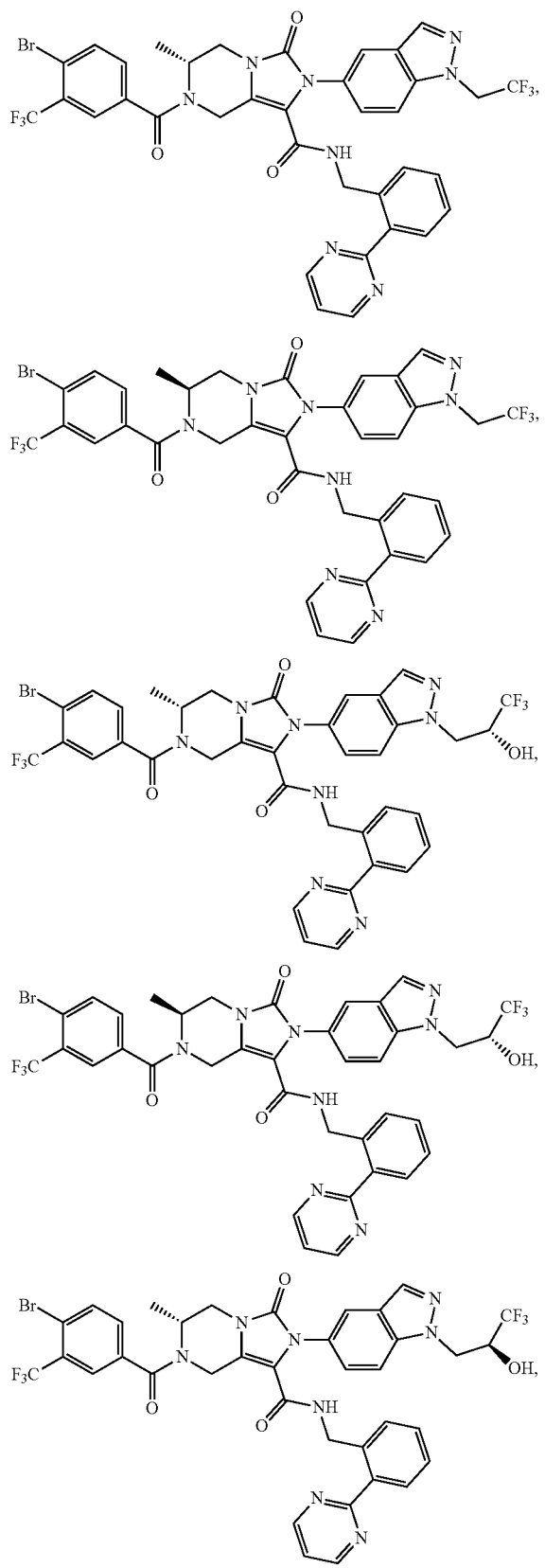
478
-continued
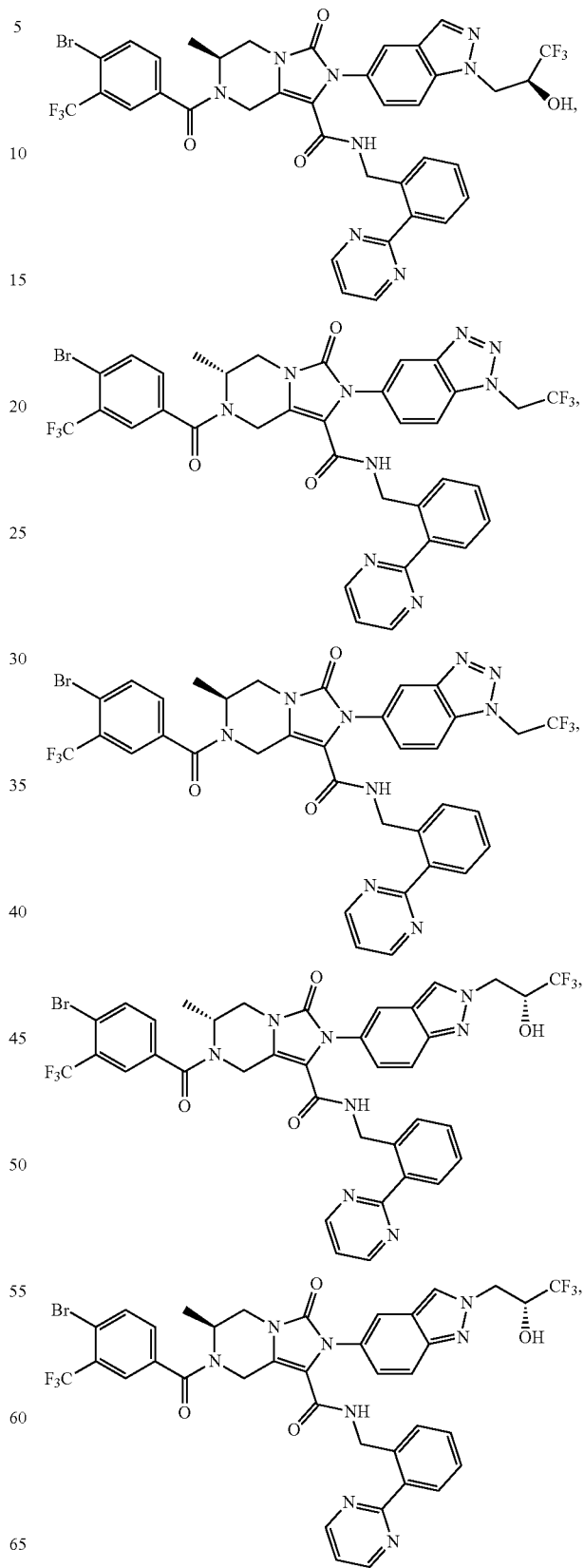

479
-continued
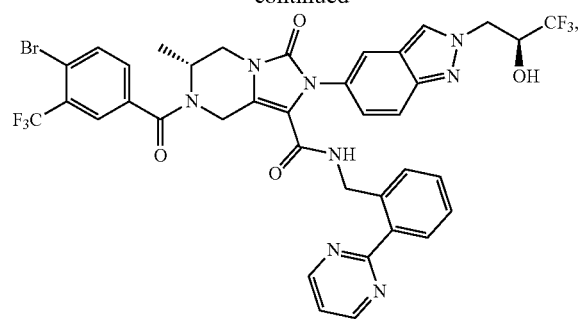
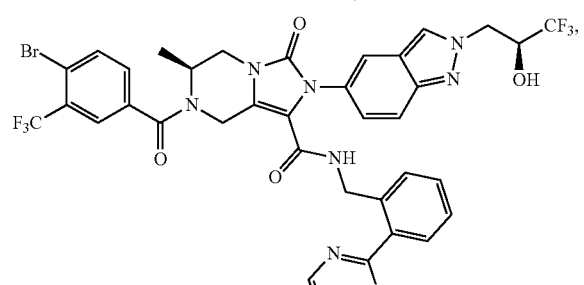
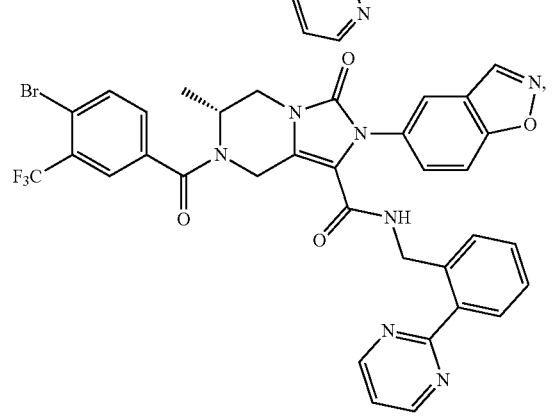
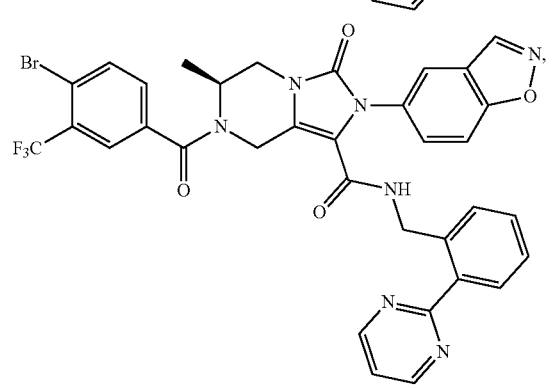
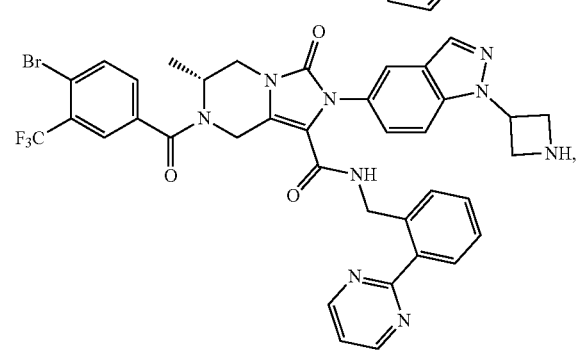
480
-continued
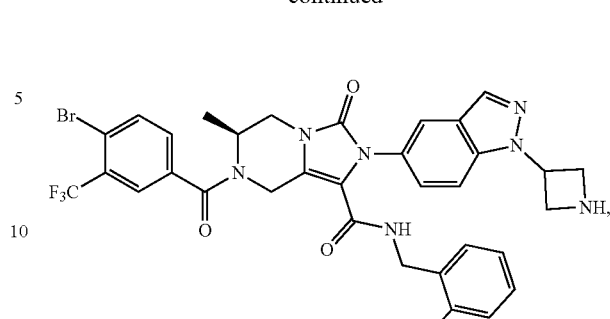
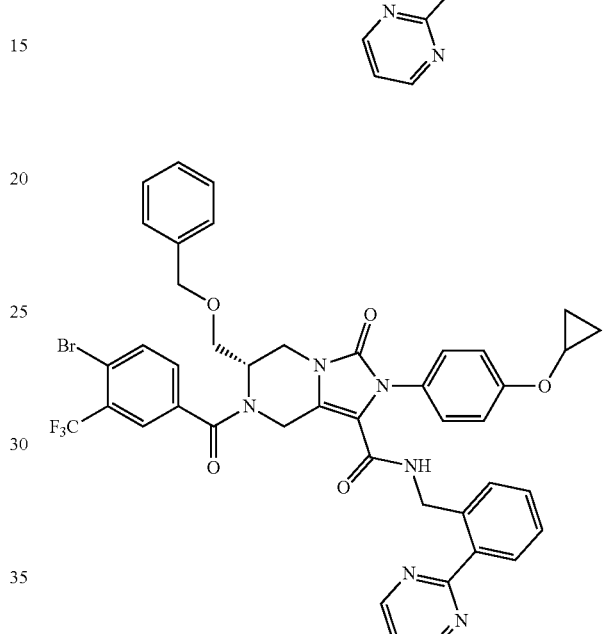
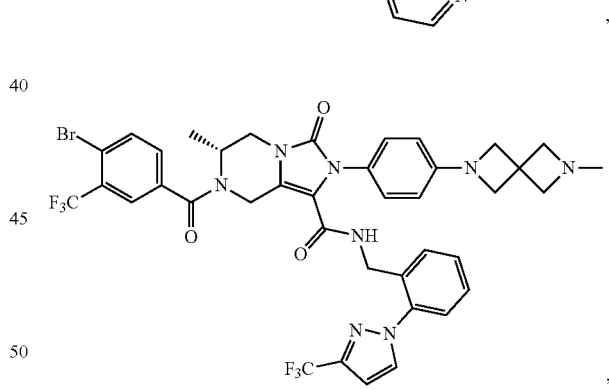
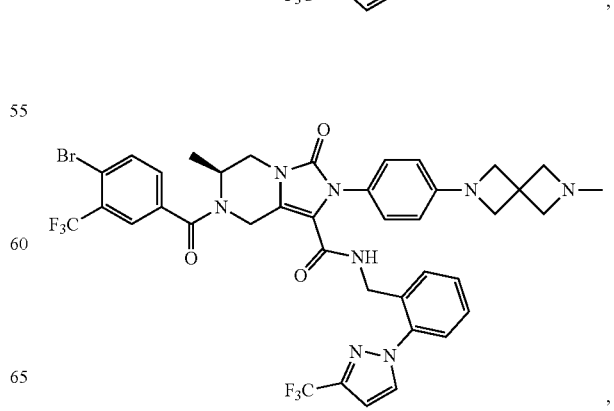

481
-continued
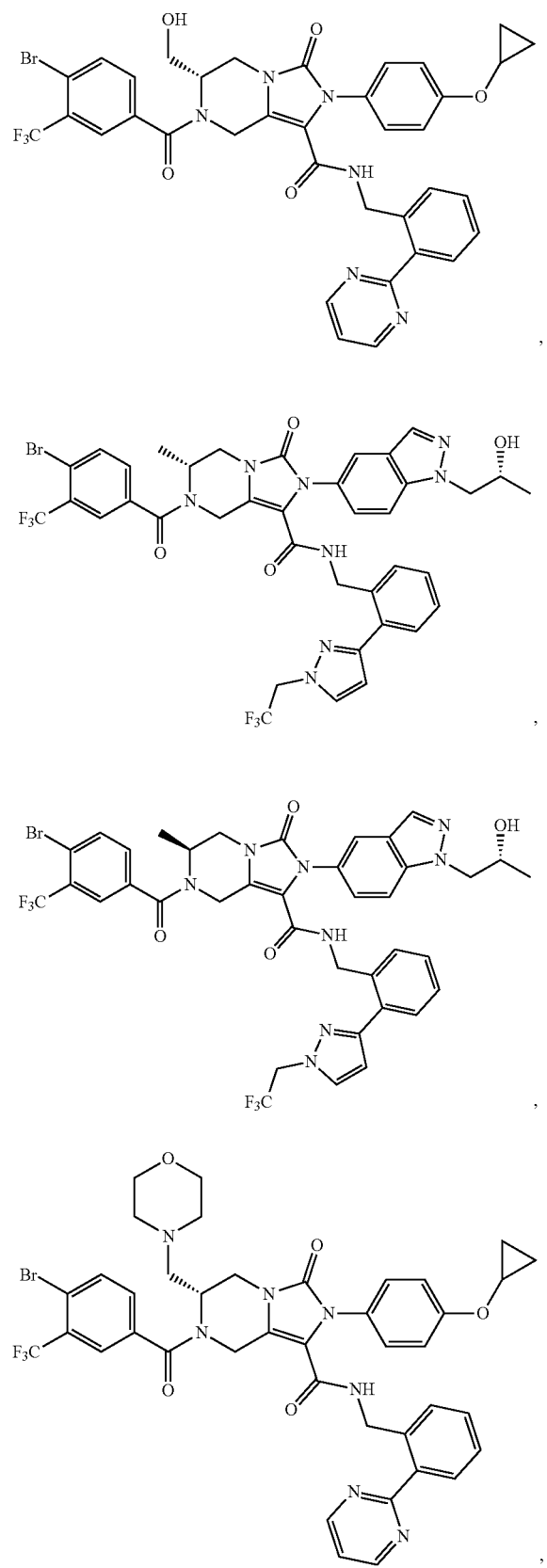
482
-continued
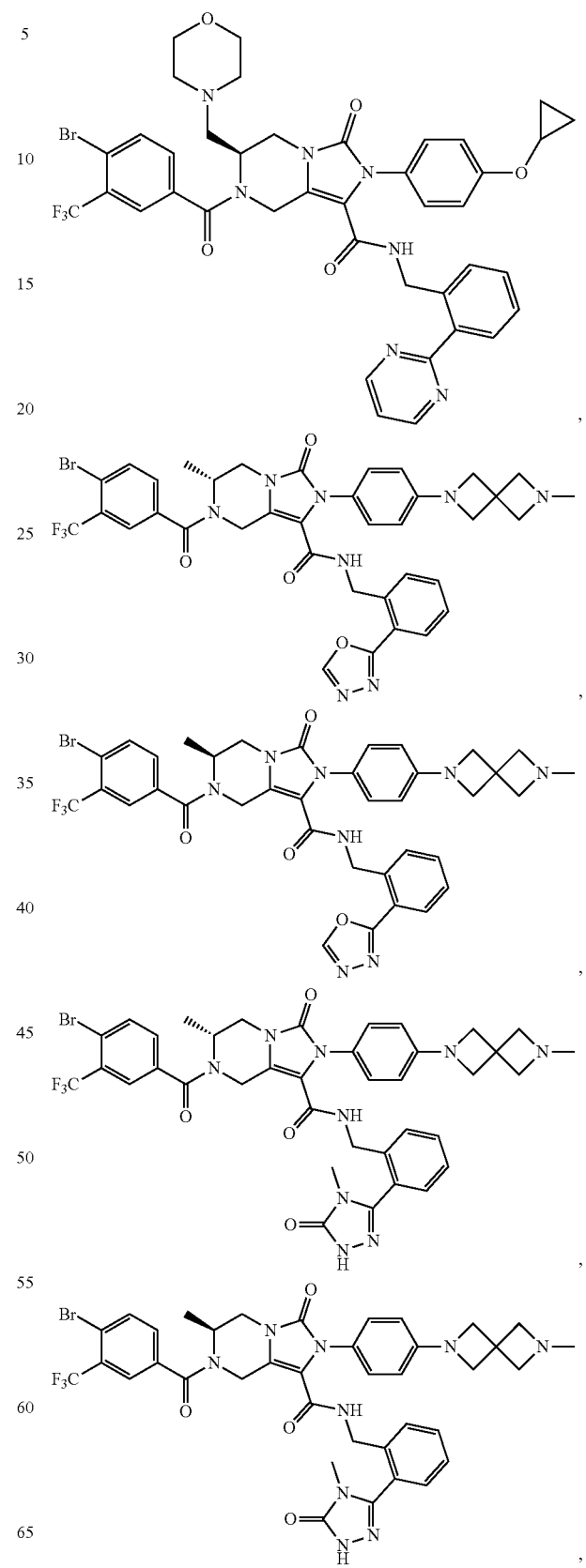

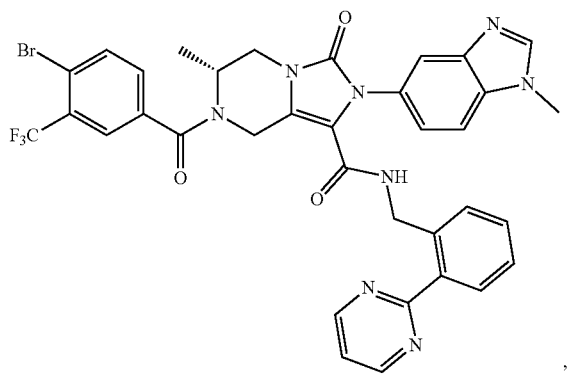
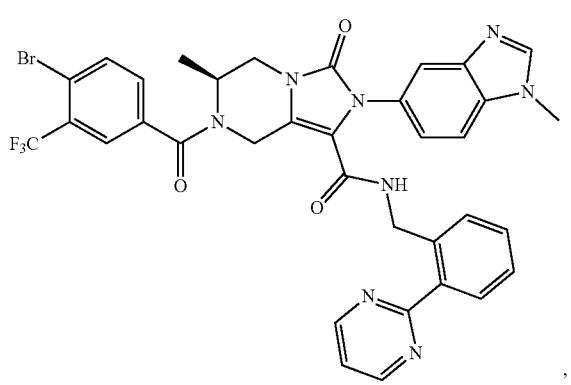
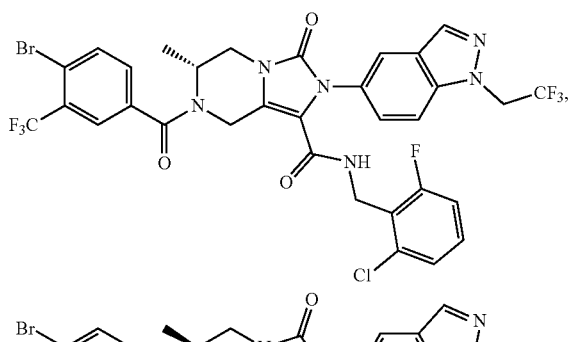
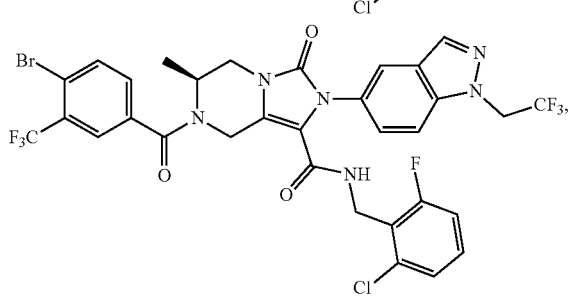
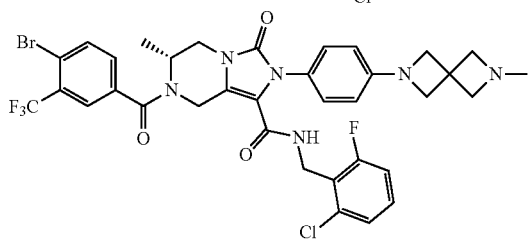
and
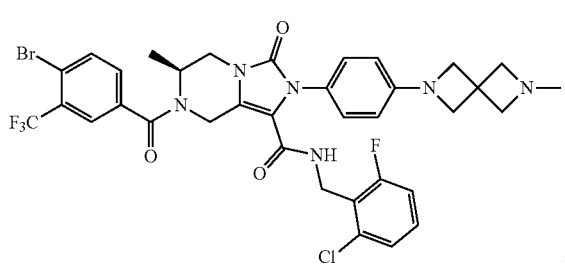
or a pharmaceutically acceptable salt thereof.
21. A compound selected from the group consisting of:
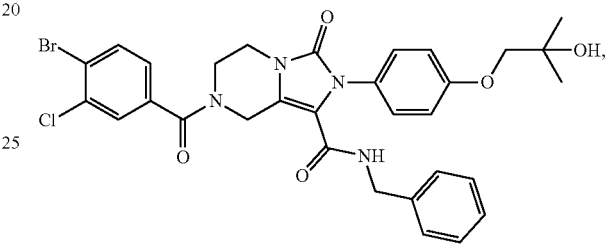
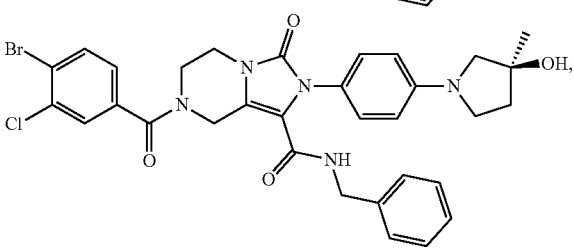
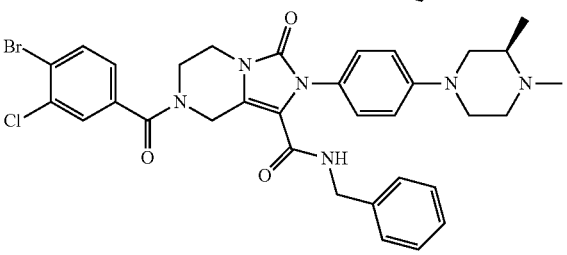
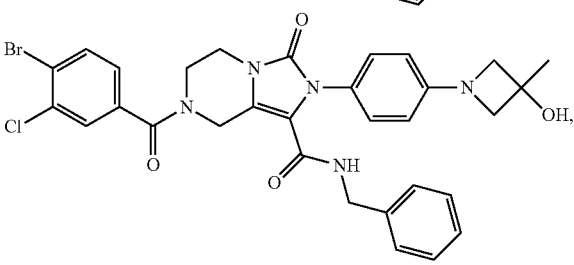

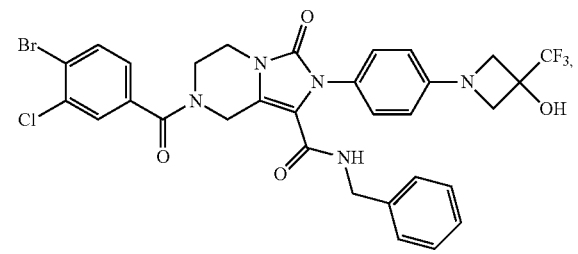
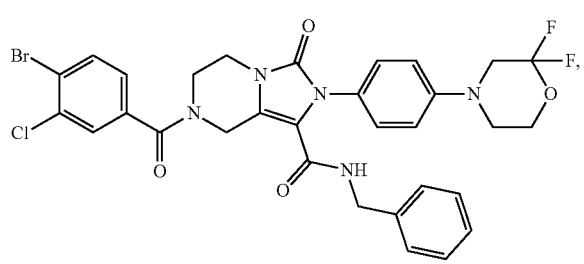
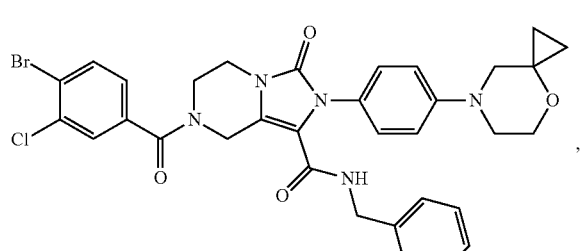
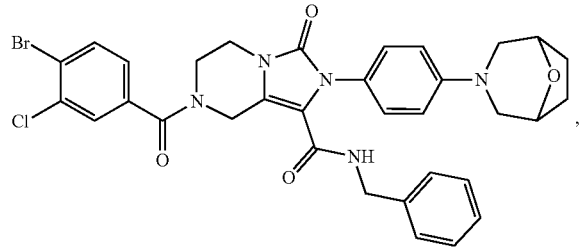
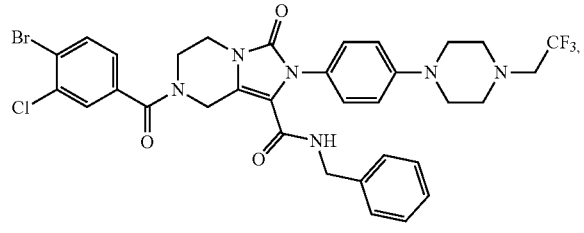
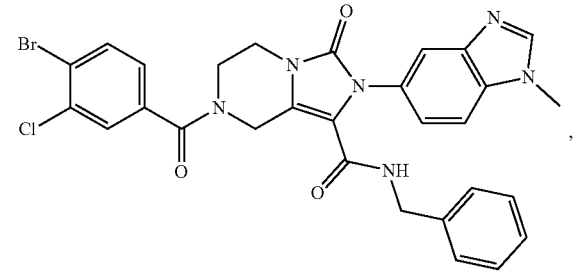
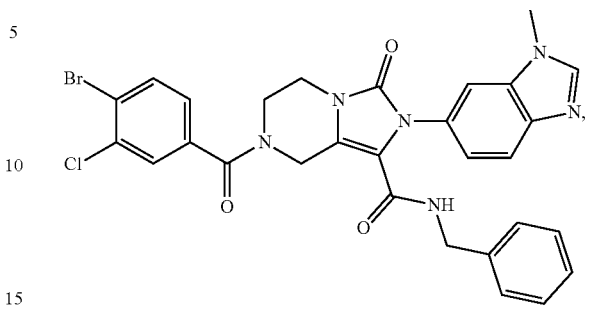
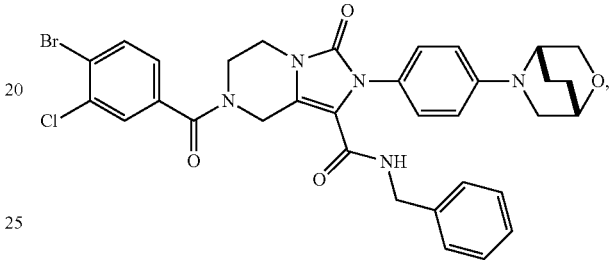
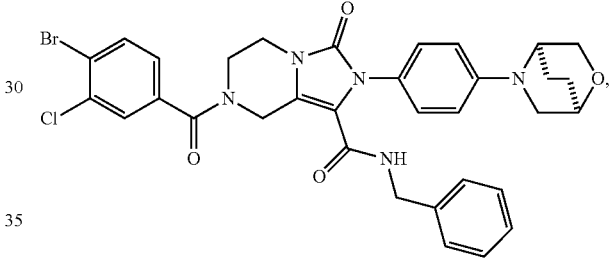
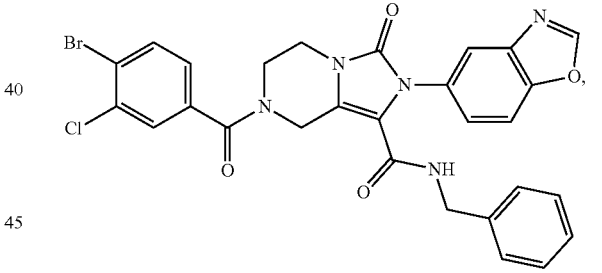
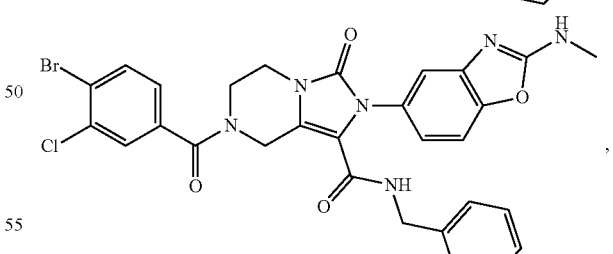
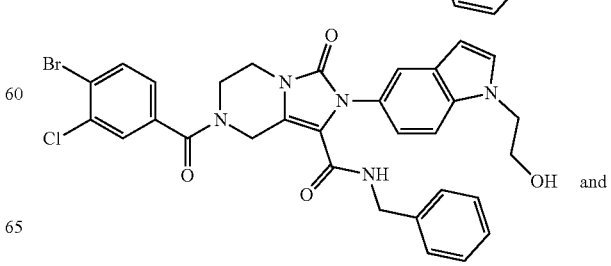
and

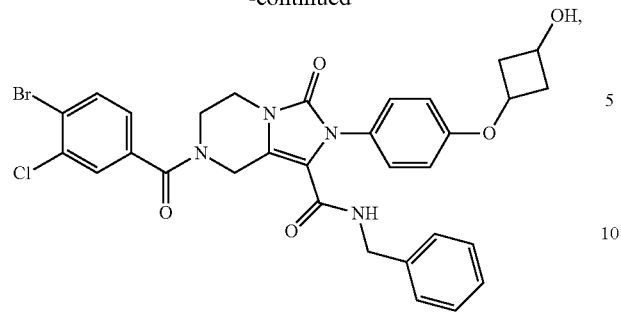
or a pharmaceutically acceptable salt thereof.

UNITED STATES PATENT AND TRADEMARK OFFICE
CERTIFICATE OF CORRECTION

PATENT NO. : 11,845,752 B2
APPLICATION NO. : 17/450808
DATED : December 19, 2023
INVENTOR(S) : Sandrine Vendeville et al.

Page 1 of 14

It is certified that error appears in the above-identified patent and that said Letters Patent is hereby corrected as shown below:

In the Specification

In Column 15, Lines 49-57 (Approx.), delete

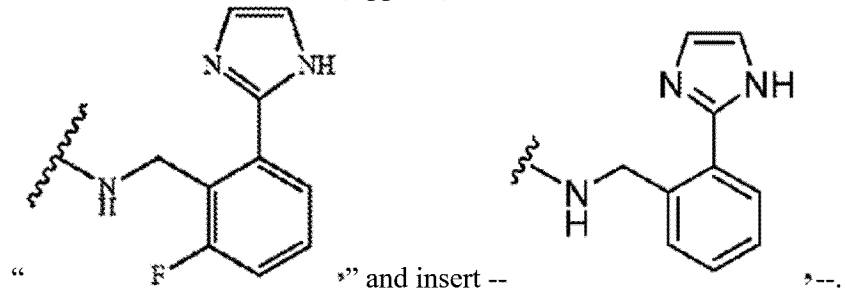

" and insert --                 ---.

In Column 19, Lines 12-20 (Approx.), delete

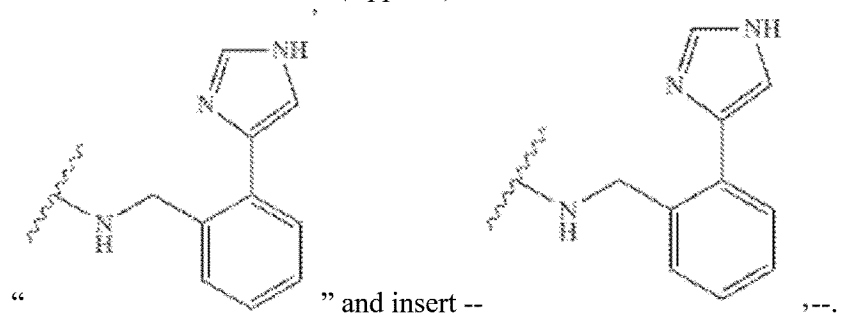

" and insert --                 ,---.

In Column 24, Lines 37-41 (Approx.), delete

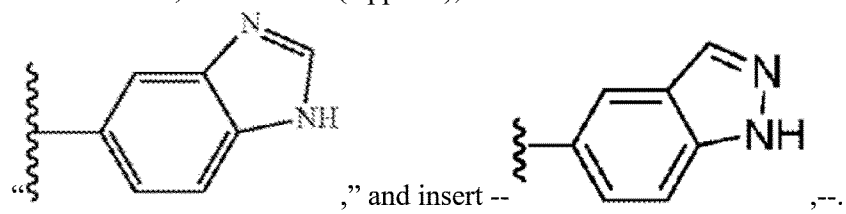

," and insert --                 ,---.

Signed and Sealed this
Eleventh Day of March, 2025

Coke Morgan Stewart
*Acting Director of the United States Patent and Trademark Office*

CERTIFICATE OF CORRECTION (continued)
U.S. Pat. No. 11,845,752 B2

In Column 47, Lines 5-18 (Approx.), delete " 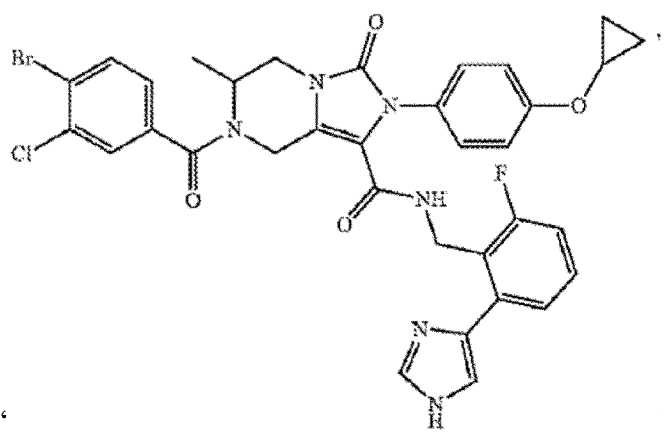 "

and insert -- 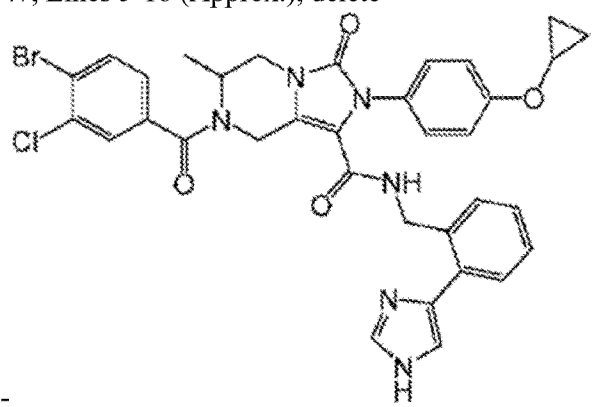 ,--.

In Column 49, Lines 2-14 (Approx.), delete

" 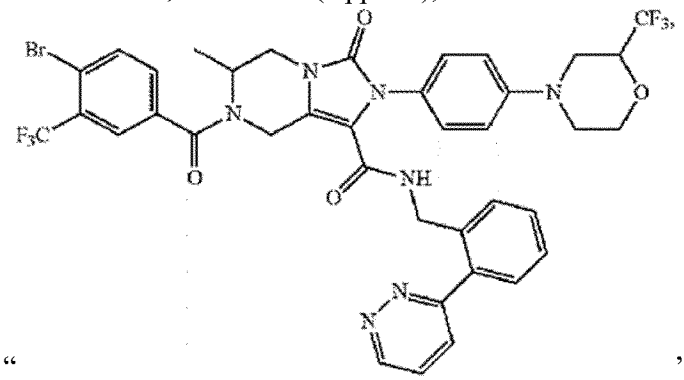 " and insert

CERTIFICATE OF CORRECTION (continued)
U.S. Pat. No. 11,845,752 B2

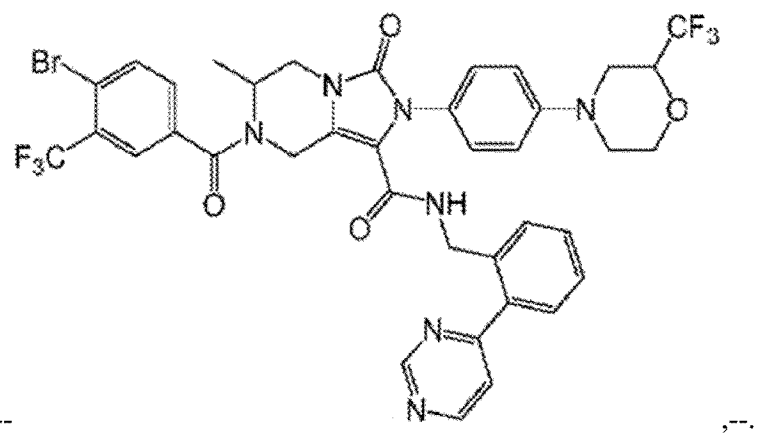

-- ,--.

In Column 63, Lines 41-66 (Approx.), delete

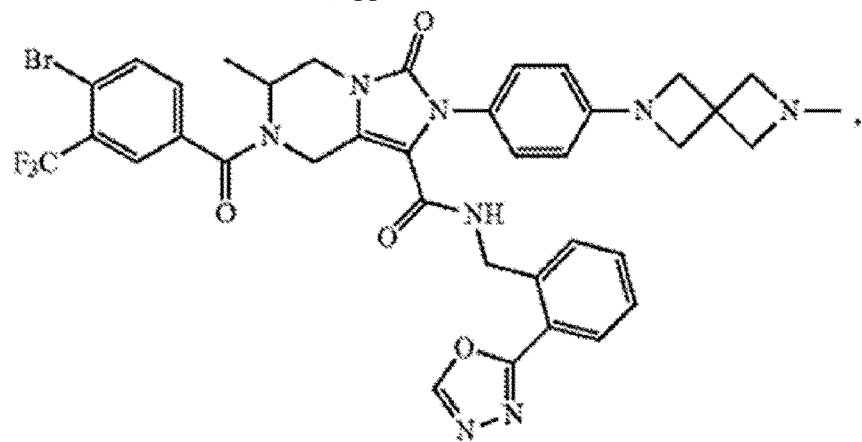

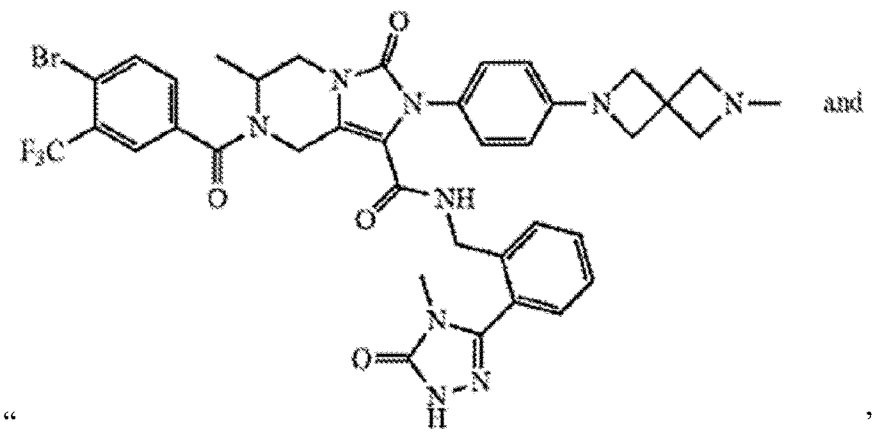

" " and insert

CERTIFICATE OF CORRECTION (continued)
U.S. Pat. No. 11,845,752 B2

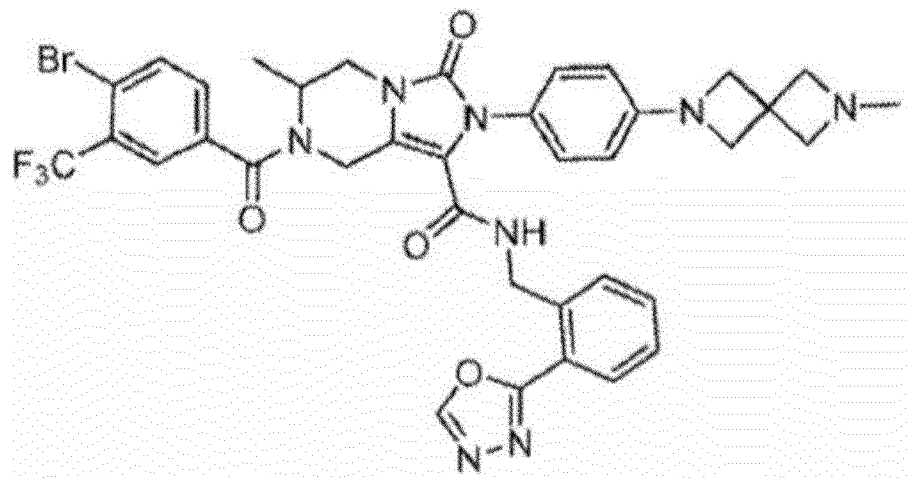

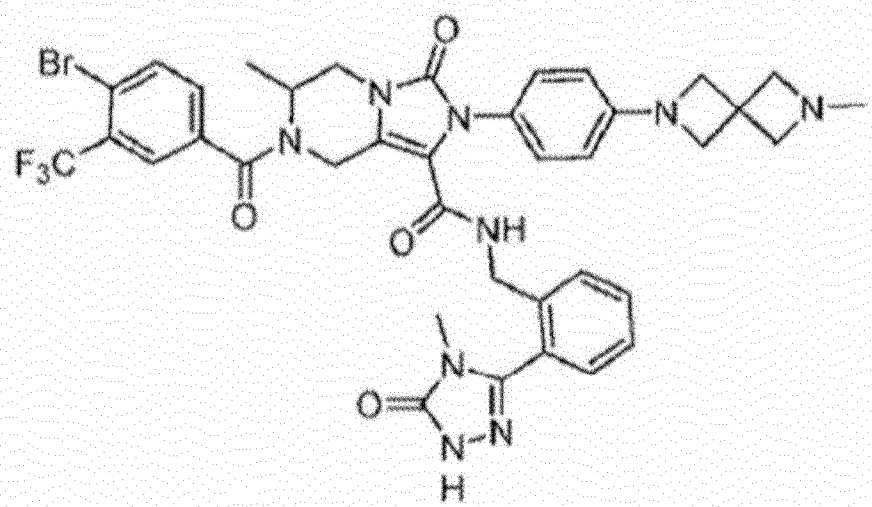

-- and --.

In Column 96, Lines 5-16 (Approx.), delete

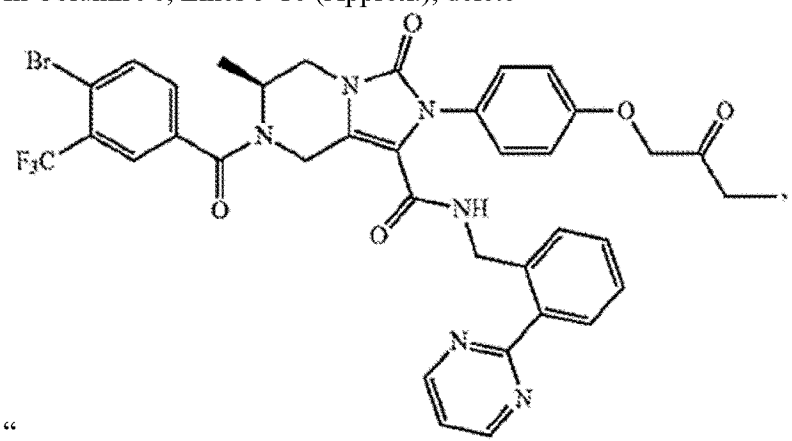

" " and insert

CERTIFICATE OF CORRECTION (continued)
U.S. Pat. No. 11,845,752 B2

Page 5 of 14

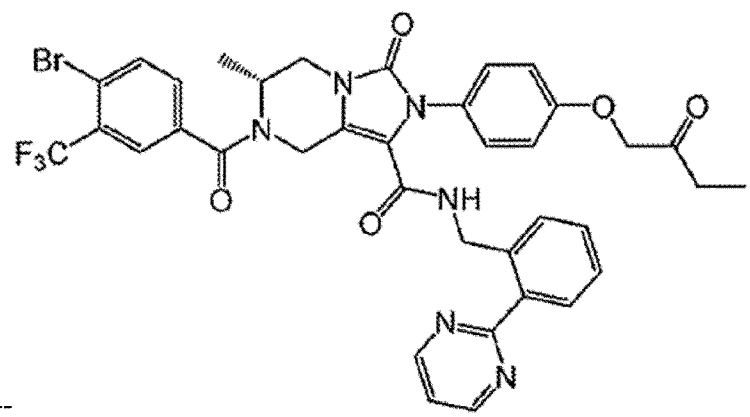

--

,--.

In Column 112, Lines 20-48 (Approx.), delete

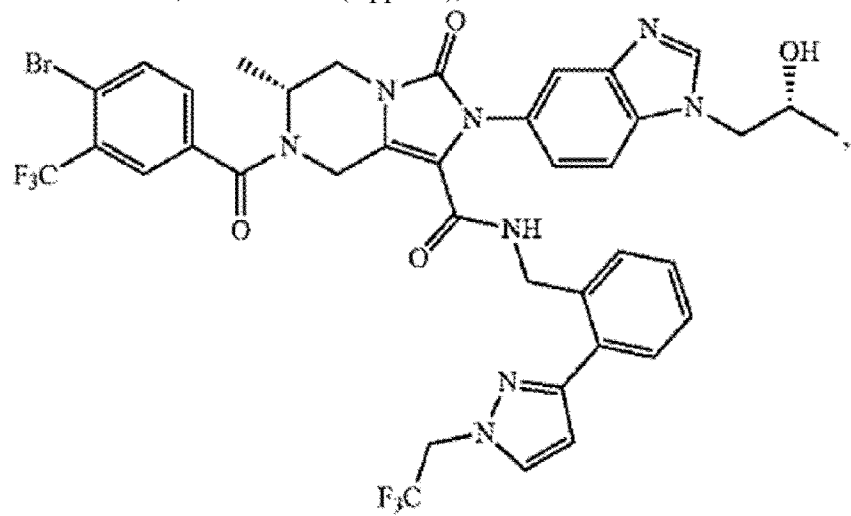

"

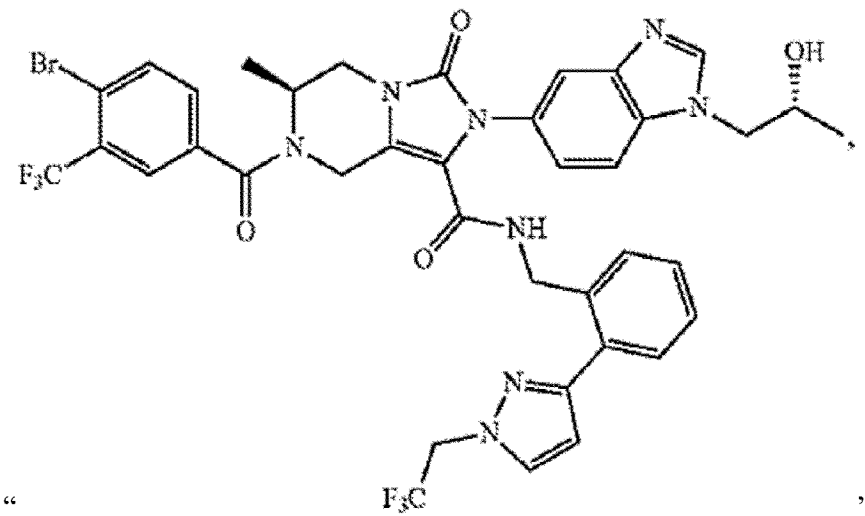

" and insert

CERTIFICATE OF CORRECTION (continued)
U.S. Pat. No. 11,845,752 B2

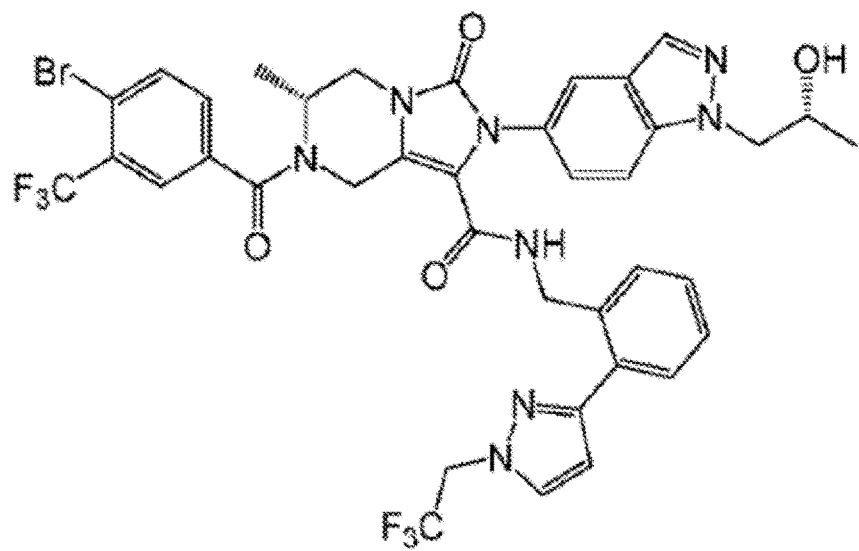

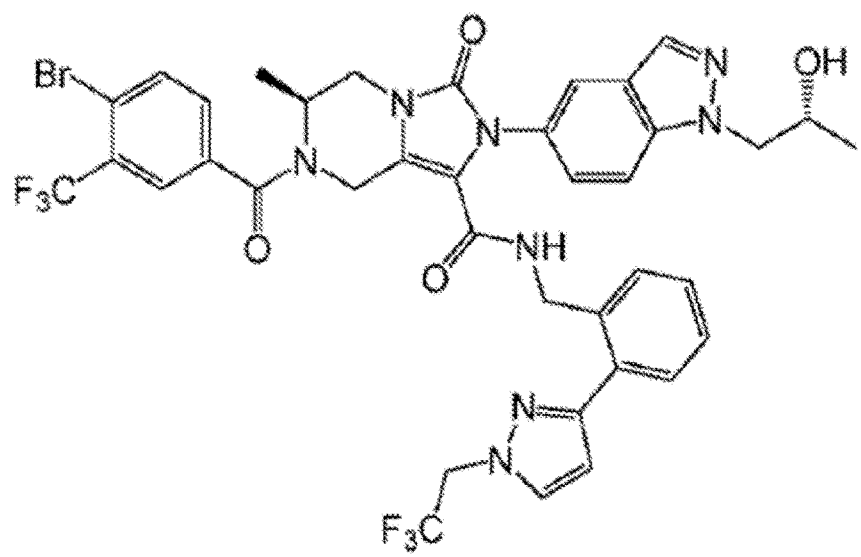

--                                                                         --.

In Column 118, Lines 31-43 (Approx.), delete

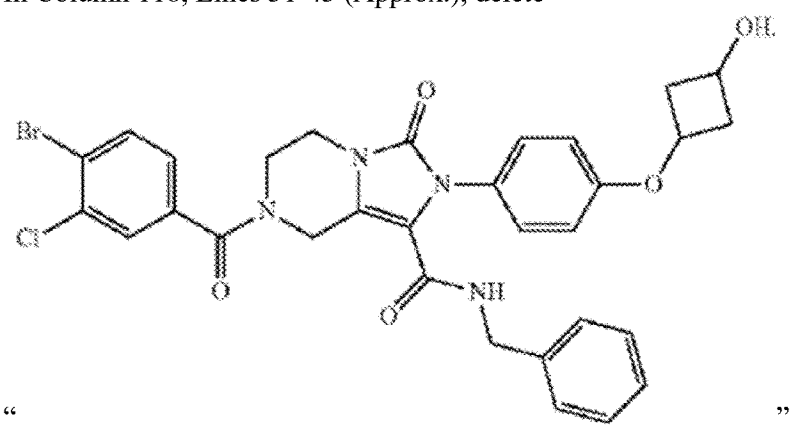

"                                                            " and insert

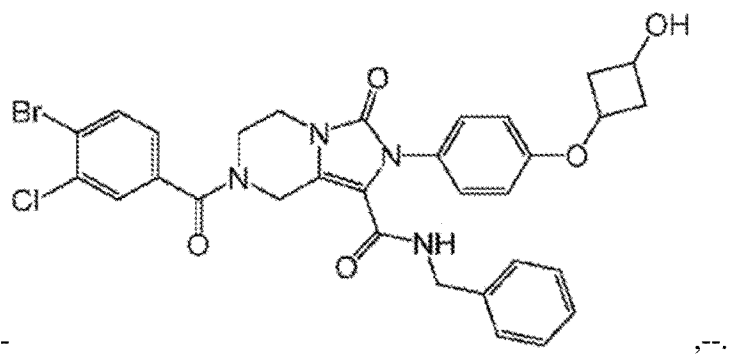

--                                    ,--.

In Column 122, Lines 53-61 (Approx.), delete

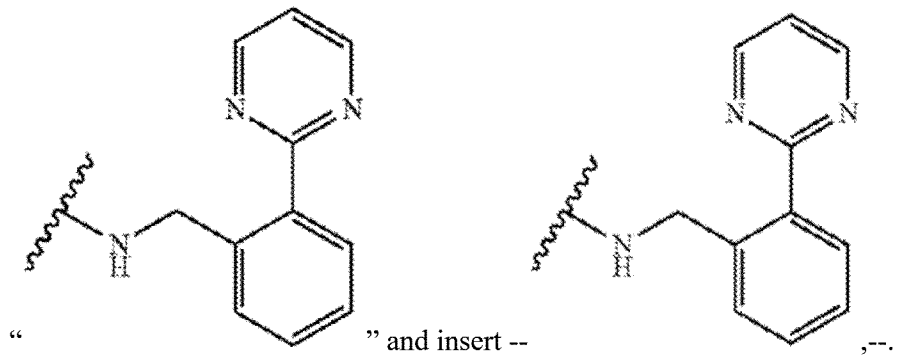

"                " and insert --                    ,--.

In Column 122, Lines 61-65 (Approx.), delete " 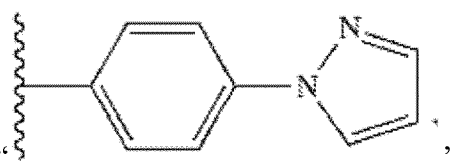 ".

In Column 125, Line 65, delete "triphosgen" and insert --triphosgene--.

In Column 131, Line 28, delete "log 10" and insert --log10--.

In Column 132, Line 45, delete "CpsrA psln" and insert --CpsrApsln--.

In Column 136, Line 48 (Approx.), delete "isochratic" and insert --isocratic--.

In Column 147, Line 29 (Approx.), delete "isochratic" and insert --isocratic--.

In Column 148, Line 67, delete "[M+H]$^{+\cdot}$" and insert --[M+H]$^{+}$.--.

In Column 151, Line 38, delete "6H, 8H" and insert --6H,8H--.

In Column 152, Line 36 (Approx.), delete "hydroxypropoxyl]" and insert --hydroxypropoxy]--.

In Column 168, Lines 5-12 (Approx.), delete

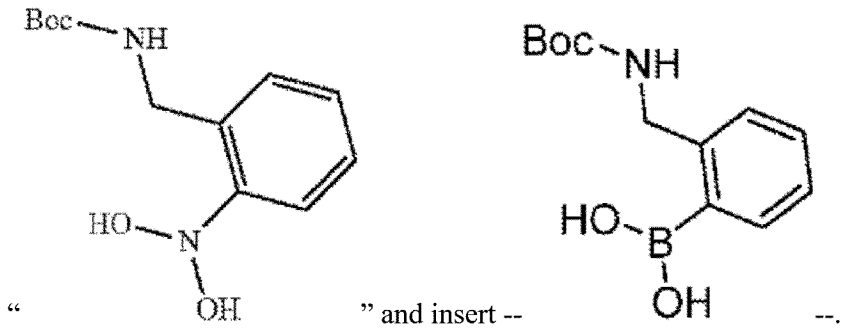

" and insert -- --.

In Column 172, Line 42, delete "products" and insert --products.--.

In Column 172, Line 58, delete "Sum" and insert --5 μm--.

In Column 181, Line 44 (Approx.), delete "C18" and insert --$C_{18}$--.

In Column 183, Line 1, delete "6H, 8H" and insert --6H,8H--.

In Column 183, Line 47 (Approx.), delete "6H, 8H" and insert --6H,8H--.

In Column 184, Line 39 (Approx.), delete "6H, 8H" and insert --6H,8H--.

In Column 193, Line 26, delete "6H, 8H" and insert --6H,8H--.

In Column 194, Line 53 (Approx.), delete "C18" and insert --$C_{18}$--.

In Column 197, Line 65, delete "6H, 8H" and insert --6H,8H--.

In Column 198, Line 8 (Approx.), delete "6H, 8H" and insert --6H,8H--.

In Column 204, Line 43, delete "C18" and insert --$C_{18}$--.

In Columns 221-222 (TABLE C), Line 13 (Approx.), delete "isochratic" and insert --isocratic--.

In Columns 221-222 (TABLE C), Line 16 (Approx.), delete "Hz, 2H)" and insert --Hz, 2H),--.

In Columns 221-222 (TABLE C), Line 25 (Approx.), delete "isochratic" and insert --isocratic--.

In Columns 221-222 (TABLE C), Line 28 (Approx.), delete "Hz, 2H)" and insert --Hz, 2H),--.

In Columns 223-224 (TABLE C-continued), Line 50 (Approx.), delete "isochratic" and insert --isocratic--.

In Columns 223-224 (TABLE C-continued), Line 59 (Approx.), delete "isochratic" and insert --isocratic--.

In Columns 225-226 (TABLE C-continued), Line 47 (Approx.), delete "NH3" and insert --NH$_3$--.

In Columns 227-228 (TABLE C-continued), Line 15 (Approx.), delete "2[4" and insert --2-[4--.

In Columns 227-228 (TABLE C-continued), Line 25 (Approx.), delete "(4rac" and insert --rac--.

In Columns 227-228 (TABLE C-continued), Line 26 (Approx.), delete "2[4" and insert --2-[4--.

In Columns 227-228 (TABLE C-continued), Line 64 (Approx.), delete "isochratic" and insert --isocratic--.

In Columns 229-230 (TABLE C-continued), Line 5 (Approx.), delete "isochratic" and insert --isocratic--.

In Columns 231-232 (TABLE C-continued), Line 4 (Approx.), delete "n;" and insert --μm;--.

In Columns 231-232 (TABLE C-continued), Line 59 (Approx.), delete "μm" and insert --μm;--.

In Columns 233-234 (TABLE C-continued), Line 4 (Approx.), delete "μm" and insert --μm;--.

In Columns 233-234 (TABLE C-continued), Line 59 (Approx.), delete "μm" and insert --μm;--.

In Columns 235-236 (TABLE C-continued), Line 59 (Approx.), delete "μm" and insert --μm;--.

In Columns 239-240 (TABLE C-continued), Line 21 (Approx.), delete "2[4" and insert --2-[4--.

In Columns 239-240 (TABLE C-continued), Line 71 (Approx.), delete "μm" and insert --μm;--.

In Columns 241-242 (TABLE C-continued), Line 4 (Approx.), delete "μm" and insert --μm;--.

In Columns 241-242 (TABLE C-continued), Line 14 (Approx.), delete "um" and insert --μm;--.

In Columns 241-242 (TABLE C-continued), Line 24 (Approx.), delete "um" and insert --μm;--.

In Columns 241-242 (TABLE C-continued), Line 34 (Approx.), delete "μm" and insert --μm;--.

In Columns 241-242 (TABLE C-continued), Line 44 (Approx.), delete "μm" and insert --μm;--.

In Columns 243-244 (TABLE C-continued), Line 10 (Approx.), delete "s.'" and insert --s.,--.

In Columns 243-244 (TABLE C-continued), Line 36 (Approx.), delete "μm" and insert --μm;--.

In Columns 243-244 (TABLE C-continued), Line 46 (Approx.), delete "μm" and insert --μm;--.

In Columns 243-244 (TABLE C-continued), Line 55 (Approx.), delete "μm" and insert --μm;--.

In Columns 243-244 (TABLE C-continued), Line 65 (Approx.), delete "μm" and insert --μm;--.

In Columns 247-248 (TABLE C-continued), Line 4 (Approx.), delete "um;" and insert --μm;--.

In Columns 247-248 (TABLE C-continued), Line 14 (Approx.), delete "um;" and insert --μm;--.

In Columns 249-250 (TABLE C-continued), Line 31, delete "NH3" and insert --NH$_3$--.

In Columns 249-250 (TABLE C-continued), Line 71 (Approx.), delete "μm" and insert --μm;--.

In Columns 253-254 (TABLE C-continued), Line 24 (Approx.), delete "Sum" and insert --5 μm--.

In Columns 253-254 (TABLE C-continued), Line 25 (Approx.), delete "Celluloes" and insert --Cellulose--.

In Columns 253-254 (TABLE C-continued), Line 35 (Approx.), delete "Sum" and insert --5 μm--.

In Columns 253-254 (TABLE C-continued), Line 36 (Approx.), delete "Celluloes" and insert --Cellulose--.

In Columns 253-254 (TABLE C-continued), Line 71 (Approx.), delete "2H) 4.68" and insert --2H), 4.68--.

In Columns 253-254 (TABLE C-continued), Line 72 (Approx.), delete "1H;" and insert --1H),--.

In Columns 255-256 (TABLE C-continued), Line 51 (Approx.), delete "Sum" and insert --5 μm--.

In Columns 255-256 (TABLE C-continued), Line 52 (Approx.), delete "Celluloes" and insert --Cellulose--.

In Columns 255-256 (TABLE C-continued), Line 62 (Approx.), delete "Sum" and insert --5 μm--.

In Columns 255-256 (TABLE C-continued), Line 63 (Approx.), delete "Celluloes" and insert --Cellulose--.

In Columns 257-258 (TABLE C-continued), Line 4 (Approx.), delete "μm" and insert --μm;--.

In Columns 257-258 (TABLE C-continued), Line 15 (Approx.), delete "μm" and insert --μm;--.

In Columns 257-258 (TABLE C-continued), Line 26 (Approx.), delete "μm" and insert --μm;--.

In Columns 257-258 (TABLE C-continued), Line 63 (Approx.), delete "Sum" and insert --5 μm--.

In Columns 257-258 (TABLE C-continued), Line 73 (Approx.), delete "Sum" and insert --5 μm--.

In Columns 259-260 (TABLE C-continued), Line 8 (Approx.), delete "Sum" and insert --5 μm--.

In Columns 259-260 (TABLE C-continued), Line 19 (Approx.), delete "μm" and insert --μm;--.

In Columns 259-260 (TABLE C-continued), Line 29 (Approx.), delete "μm" and insert --μm;--.

In Columns 259-260 (TABLE C-continued), Line 38 (Approx.), delete "Sum" and insert --5 μm--.

In Columns 259-260 (TABLE C-continued), Line 40 (Approx.), delete "μm" and insert --μm;--.

In Columns 261-262 (TABLE C-continued), Line 13 (Approx.), delete "Sum" and insert --5 μm--.

In Column 261-262 (TABLE C-continued), Line 15 (Approx.), delete "μm" and insert --μm;--.

In Columns 261-262 (TABLE C-continued), Line 23 (Approx.), delete "Sum" and insert --5 μm--.

In Columns 261-262 (TABLE C-continued), Line 25 (Approx.), delete "μm" and insert --μm;--.

In Columns 261-262 (TABLE C-continued), Line 33 (Approx.), delete "Sum" and insert --5 μm--.

In Columns 261-262 (TABLE C-continued), Line 35 (Approx.), delete "μm" and insert --μm;--.

In Columns 261-262 (TABLE C-continued), Line 43 (Approx.), delete "Sum" and insert --5 μm--.

In Columns 261-262 (TABLE C-continued), Line 45 (Approx.), delete "μm" and insert --μm;--.

In Columns 261-262 (TABLE C-continued), Line 55 (Approx.), delete "μm" and insert --μm;--.

In Columns 263-264 (TABLE C-continued), Line 69 (Approx.), delete "NH3" and insert --$NH_3$--.

In Columns 263-264 (TABLE C-continued), Line 78 (Approx.), delete "μm" and insert --μm;--.

In Columns 265-266 (TABLE C-continued), Line 11 (Approx.), delete "μm" and insert --μm;--.

In Columns 265-266 (TABLE C-continued), Line 21 (Approx.), delete "μm" and insert --μm;--.

In Columns 265-266 (TABLE C-continued), Line 31 (Approx.), delete "μm" and insert --μm;--.

In Columns 265-266 (TABLE C-continued), Line 32 (Approx.), delete "NH3" and insert --$NH_3$--.

In Columns 265-266 (TABLE C-continued), Line 41, delete "μm" and insert --μm;--.

In Columns 265-266 (TABLE C-continued), Line 43 (Approx.), delete "NH3" and insert --$NH_3$--.

In Columns 265-266 (TABLE C-continued), Line 52 (Approx.), delete "μm" and insert --μm;--.

In Columns 265-266 (TABLE C-continued), Line 62 (Approx.), delete "μm" and insert --μm;--.

CERTIFICATE OF CORRECTION (continued)
U.S. Pat. No. 11,845,752 B2

In Columns 265-266 (TABLE C-continued), Line 72 (Approx.), delete "µm" and insert --µm;--.

In Columns 267-268 (TABLE C-continued), Line 11 (Approx.), delete "µm" and insert --µm;--.

In Columns 267-268 (TABLE C-continued), Line 13 (Approx.), delete "NH3" and insert --NH$_3$--.

In Columns 267-268 (TABLE C-continued), Line 21 (Approx.), delete "µm" and insert --µm;--.

In Columns 267-268 (TABLE C-continued), Line 31 (Approx.), delete "µm" and insert --µm;--.

In Columns 267-268 (TABLE C-continued), Line 41 (Approx.), delete "µm" and insert --µm;--.

In Columns 267-268 (TABLE C-continued), Line 52 (Approx.), delete "µm" and insert --µm;--.

In Columns 267-268 (TABLE C-continued), Line 62 (Approx.), delete "µm" and insert --µm;--.

In Columns 269-270 (TABLE C-continued), Line 34 (Approx.), delete "µm" and insert --µm;--.

In Columns 269-270 (TABLE C-continued), Line 44 (Approx.), delete "µm" and insert --µm;--.

In Columns 269-270 (TABLE C-continued), Line 46 (Approx.), delete "NH3" and insert --NH$_3$--.

In Columns 269-270 (TABLE C-continued), Line 54, delete "µm" and insert --um;--.

In Columns 271-272 (TABLE C-continued), Line 13 (Approx.), delete "NH3" and insert --NH$_3$--.

In Column 274 (TABLE C-continued), Line 11 (Approx.), delete "IPAmine" and insert --IPA--.

In Column 274 (TABLE C-continued), Line 21 (Approx.), delete "IPAmine" and insert --IPA--.

In Column 373, Line 21, delete "doxcycyline" and insert --doxycycline--.

In the Claims

In Column 383, Line 50 (Approx.), In Claim 1, delete "—C(=O) R$^5$;" and insert -- —C(=O)R$^5$;--.

In Column 383, Line 52 (Approx.), In Claim 1, delete "a substituted monocyclic heteroaryl" and insert --a substituted monocyclic heteroaryl,--.

In Column 383, Claim 1, Lines 55-60 (Approx.), delete

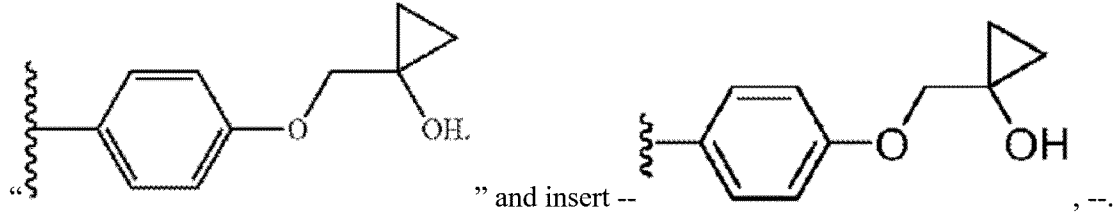

In Column 384, Claim 1, Line 67, before "methoxy", delete "G".

In Column 385, Claim 1, Line 9, delete "—NR$^{Z1}$R$^{Z2}$" and insert -- —NR$^{Z1}$R$^{Z2}$;--.

In Column 385, Claim 1, Line 27, delete "sprio" and insert --spiro--.

In Column 385, Claim 1, Line 28, delete "sprio" and insert --spiro--.

In Column 385, Claim 1, Line 65, delete "(nitrogens," and insert --(nitrogens),--.

In Column 391, Claim 5, Line 1, before "methoxy", delete "G".

In Column 391, Claim 5, Line 25, delete "sprio" and insert --spiro--.

In Column 391, Claim 5, Line 26, delete "sprio" and insert --spiro--.

In Column 392, Claim 6, Line 23, delete "methoxy" and insert --ethoxy--.

In Column 392, Claim 6, Line 48, delete "sprio" and insert --spiro--.

In Column 392, Claim 6, Line 49, delete "sprio" and insert --spiro--.

In Column 394, Claim 7, Lines 28-33 (Approx.), delete

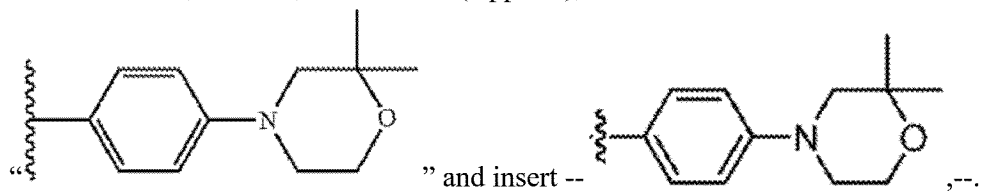

In Column 394, Claim 7, Lines 34-38 (Approx.), delete

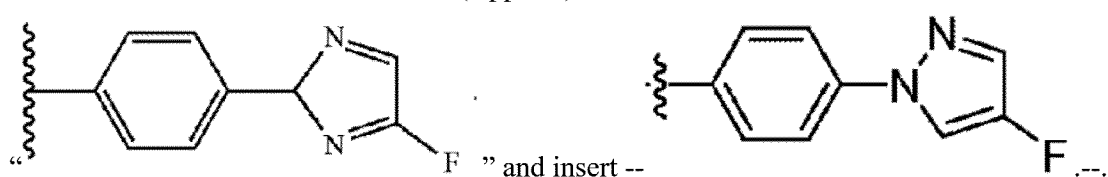

In Column 397, Claim 8, Lines 2-7 (Approx.), delete

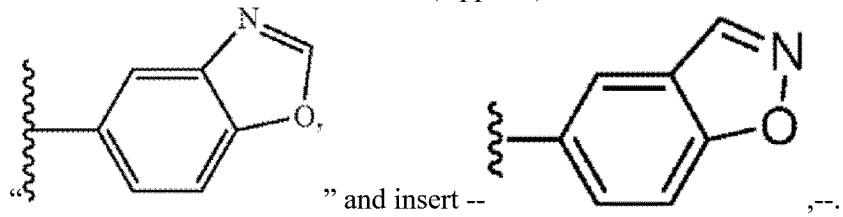

CERTIFICATE OF CORRECTION (continued)
U.S. Pat. No. 11,845,752 B2

In Column 403, Claim 12, Lines 12-19 (Approx.), delete

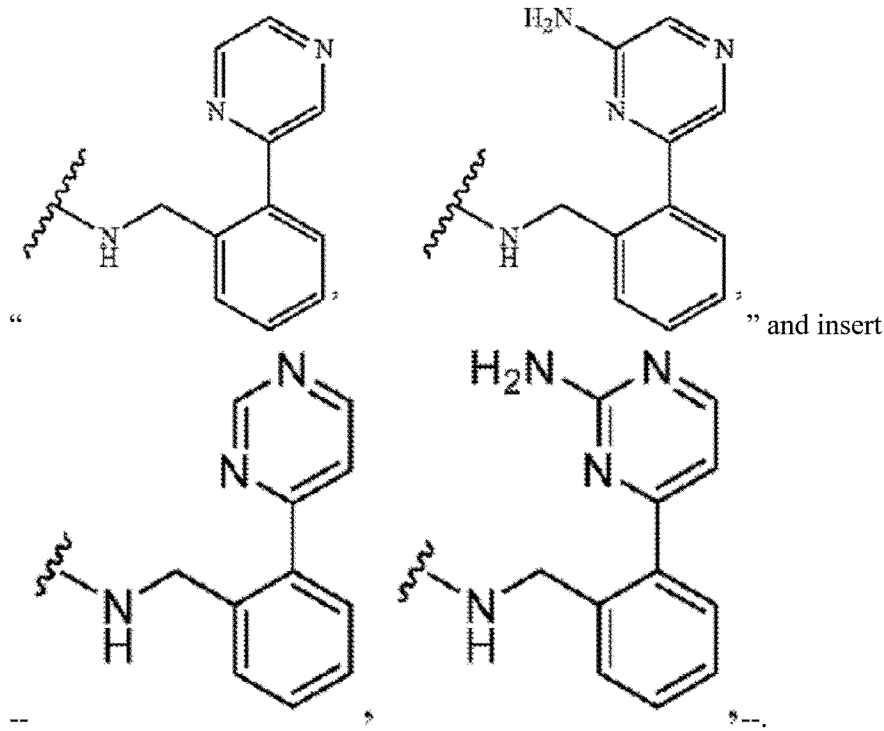

" and insert -- , --.

In Column 403, Claim 12, Lines 21-29 (Approx.), delete

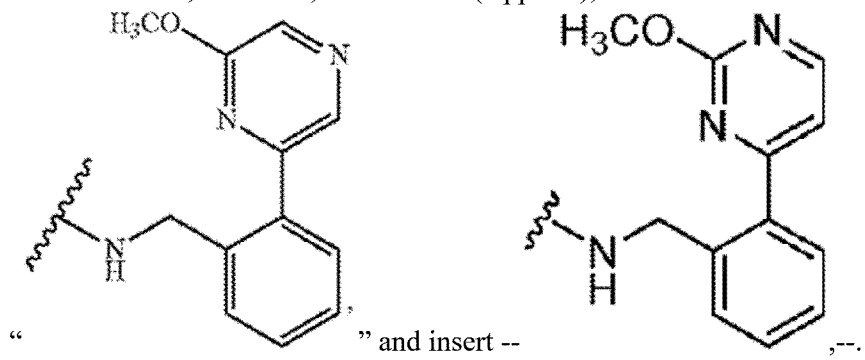

" and insert -- , --.

In Column 405, Claim 19, Line 1, before "selected" insert --compound--.

In Column 433, Claim 20, Line 1, before "selected" insert --compound--.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 1
gtgtctgcgg cgttttatca                                           20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                         21

<210> SEQ ID NO 3
<211> LENGTH: 28
<212> TYPE: DNA
<213> ORGANISM: Artificial Sequence
<220> FEATURE:
<223> OTHER INFORMATION: Synthetic HBV-probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
<221> NAME/KEY: modified_base
```

<222> LOCATION: 28
<223> OTHER INFORMATION: N=C-3IABkFQ

<400> SEQUENCE: 3
nctctkcanc ctgctgctat gcctcatn                                              28

<210> SEQ ID NO 4
<211> LENGTH: 40
<212> TYPE: DNA
<213> ORGANISM: Artificial Sequence
<220> FEATURE:
<223> OTHER INFORMATION: Modified Oligonucleotide
<220> FEATURE:
<221> NAME/KEY: modified_base
<222> LOCATION: (1)...(40)
<223> OTHER INFORMATION: Phosphorothioate linkage
<220> FEATURE:
<221> NAME/KEY: modified_base
<222> LOCATION: (1)...(1)
<223> OTHER INFORMATION: 2'-OMe-nucleotide
<220> FEATURE:
<221> NAME/KEY: modified_base
<222> LOCATION: (2)...(2)
<223> OTHER INFORMATION: locked 5-methyl-nucleotide
<220> FEATURE:
<221> NAME/KEY: modified_base
<222> LOCATION: (3)...(3)
<223> OTHER INFORMATION: 2'-OMe-nucleotide
<220> FEATURE:
<221> NAME/KEY: modified_base
<222> LOCATION: (4)...(4)
<223> OTHER INFORMATION: locked 5-methyl-nucleotide
<220> FEATURE:
<221> NAME/KEY: modified_base
<222> LOCATION: (5)...(5)
<223> OTHER INFORMATION: 2'-OMe-nucleotide
<220> FEATURE:
<221> NAME/KEY: modified_base
<222> LOCATION: (6)...(6)
<223> OTHER INFORMATION: locked 5-methyl-nucleotide
<220> FEATURE:
<221> NAME/KEY: modified_base
<222> LOCATION: (7)...(7)
<223> OTHER INFORMATION: 2'-OMe-nucleotide
<220> FEATURE:
<221> NAME/KEY: modified_base
<222> LOCATION: (8)...(8)
<223> OTHER INFORMATION: locked 5-methyl-nucleotide
<220> FEATURE:
<221> NAME/KEY: modified_base
<222> LOCATION: (9)...(9)
<223> OTHER INFORMATION: 2'-OMe-nucleotide
<220> FEATURE:
<221> NAME/KEY: modified_base
<222> LOCATION: (10)...(10)
<223> OTHER INFORMATION: locked 5-methyl-nucleotide
<220> FEATURE:
<221> NAME/KEY: modified_base
<222> LOCATION: (11)...(11)
<223> OTHER INFORMATION: ribo-nucleotide
<220> FEATURE:
<221> NAME/KEY: modified_base
<222> LOCATION: (12)...(12)
<223> OTHER INFORMATION: locked 5-methyl-nucleotide
<220> FEATURE:
<221> NAME/KEY: modified_base
<222> LOCATION: (13)...(13)
<223> OTHER INFORMATION: 2'-OMe-nucleotide
<220> FEATURE:
<221> NAME/KEY: modified_base
<222> LOCATION: (14)...(14)
<223> OTHER INFORMATION: locked 5-methyl-nucleotide
<220> FEATURE:
<221> NAME/KEY: modified_base
<222> LOCATION: (15)...(15)
<223> OTHER INFORMATION: 2'-OMe-nucleotide
<220> FEATURE:

```
<221> NAME/KEY: modified_base
<222> LOCATION: (16)...(16)
<223> OTHER INFORMATION: locked 5-methyl-nucleotide
<220> FEATURE:
<221> NAME/KEY: modified_base
<222> LOCATION: (17)...(17)
<223> OTHER INFORMATION: ribo-nucleotide
<220> FEATURE:
<221> NAME/KEY: modified_base
<222> LOCATION: (18)...(18)
<223> OTHER INFORMATION: locked 5-methyl-nucleotide
<220> FEATURE:
<221> NAME/KEY: modified_base
<222> LOCATION: (19)...(19)
<223> OTHER INFORMATION: 2'-OMe-nucleotide
<220> FEATURE:
<221> NAME/KEY: modified_base
<222> LOCATION: (20)...(20)
<223> OTHER INFORMATION: locked 5-methyl-nucleotide
<220> FEATURE:
<221> NAME/KEY: modified_base
<222> LOCATION: (21)...(21)
<223> OTHER INFORMATION: 2'-OMe-nucleotide
<220> FEATURE:
<221> NAME/KEY: modified_base
<222> LOCATION: (22)...(22)
<223> OTHER INFORMATION: locked 5-methyl-nucleotide
<220> FEATURE:
<221> NAME/KEY: modified_base
<222> LOCATION: (23)...(23)
<223> OTHER INFORMATION: ribo-nucleotide
<220> FEATURE:
<221> NAME/KEY: modified_base
<222> LOCATION: (24)...(24)
<223> OTHER INFORMATION: locked 5-methyl-nucleotide
<220> FEATURE:
<221> NAME/KEY: modified_base
<222> LOCATION: (25)...(25)
<223> OTHER INFORMATION: 2'-OMe-nucleotide
<220> FEATURE:
<221> NAME/KEY: modified_base
<222> LOCATION: (26)...(26)
<223> OTHER INFORMATION: locked 5-methyl-nucleotide
<220> FEATURE:
<221> NAME/KEY: modified_base
<222> LOCATION: (27)...(27)
<223> OTHER INFORMATION: 2'-OMe-nucleotide
<220> FEATURE:
<221> NAME/KEY: modified_base
<222> LOCATION: (28)...(28)
<223> OTHER INFORMATION: locked 5-methyl-nucleotide
<220> FEATURE:
<221> NAME/KEY: modified_base
<222> LOCATION: (29)...(29)
<223> OTHER INFORMATION: ribo-nucleotide
<220> FEATURE:
<221> NAME/KEY: modified_base
<222> LOCATION: (30)...(30)
<223> OTHER INFORMATION: locked 5-methyl-nucleotide
<220> FEATURE:
<221> NAME/KEY: modified_base
<222> LOCATION: (31)...(31)
<223> OTHER INFORMATION: 2'-OMe-nucleotide
<220> FEATURE:
<221> NAME/KEY: modified_base
<222> LOCATION: (32)...(32)
<223> OTHER INFORMATION: locked 5-methyl-nucleotide
<220> FEATURE:
<221> NAME/KEY: modified_base
<222> LOCATION: (33)...(33)
<223> OTHER INFORMATION: 2'-OMe-nucleotide
<220> FEATURE:
<221> NAME/KEY: modified_base
<222> LOCATION: (34)...(34)
<223> OTHER INFORMATION: locked 5-methyl-nucleotide
<220> FEATURE:
<221> NAME/KEY: modified_base
<222> LOCATION: (35)...(35)
<223> OTHER INFORMATION: ribo-nucleotide
```

```
<220> FEATURE:
<221> NAME/KEY: modified_base
<222> LOCATION: (36)...(36)
<223> OTHER INFORMATION: locked 5-methyl-nucleotide
<220> FEATURE:
<221> NAME/KEY: modified_base
<222> LOCATION: (37)...(37)
<223> OTHER INFORMATION: 2'-OMe-nucleotide
<220> FEATURE:
<221> NAME/KEY: modified_base
<222> LOCATION: (38)...(38)
<223> OTHER INFORMATION: locked 5-methyl-nucleotide
<220> FEATURE:
<221> NAME/KEY: modified_base
<222> LOCATION: (39)...(39)
<223> OTHER INFORMATION: 2'-OMe-nucleotide
<220> FEATURE:
<221> NAME/KEY: modified_base
<222> LOCATION: (40)...(40)
<223> OTHER INFORMATION: locked 5-methyl-nucleotide

<400> SEQUENCE: 4
acacacacac acacacacac acacacacac acacacacac                           40
```